(12) United States Patent
Ishibashi et al.

(10) Patent No.: US 7,465,731 B2
(45) Date of Patent: Dec. 16, 2008

(54) HDAC INHIBITOR

(75) Inventors: Naoki Ishibashi, Tokyo (JP); Yuki Sawada, Tokyo (JP); Yasuharu Urano, Tokyo (JP); Shigeki Satoh, Tokyo (JP); Yoshikazu Inoue, Tokyo (JP); Yoshiteru Eikyu, Osaka (JP); Koichiro Mukoyoshi, Tokyo (JP); Kazunori Kamijo, Tokyo (JP); Fumiyuki Shirai, Tokyo (JP); Hisashi Takasugi, Sakai (JP)

(73) Assignee: Astellas Pharma Inc., Tokyo (JP)

( * ) Notice: Subject to any disclaimer, the term of this patent is extended or adjusted under 35 U.S.C. 154(b) by 371 days.

(21) Appl. No.: 11/199,453

(22) Filed: Aug. 9, 2005

(65) Prior Publication Data

US 2006/0052599 A1    Mar. 9, 2006

(30) Foreign Application Priority Data

Aug. 9, 2004   (AU) ............................... 2004904487
Dec. 20, 2004  (AU) ............................... 2004907228

(51) Int. Cl.
*C07D 401/12* (2006.01)
*C07D 403/12* (2006.01)
*A61K 31/497* (2006.01)
*A61K 31/506* (2006.01)
*A61K 31/501* (2006.01)

(52) U.S. Cl. ........................... 514/252.03; 514/252.05; 514/255.05; 514/256

(58) Field of Classification Search ................. 544/238, 544/322, 405; 514/252.03, 252.05, 255.05, 514/256

See application file for complete search history.

(56) References Cited

U.S. PATENT DOCUMENTS 7,135,493 B2    11/2006   Urano et al.
2006/0052599 A1  3/2006   Ishibashi et al.

*Primary Examiner*—Kahsay T Habte
(74) *Attorney, Agent, or Firm*—Oblon, Spivak, McClelland, Maier & Neustadt, P.C.

(57) ABSTRACT

A compound having the formula (I):

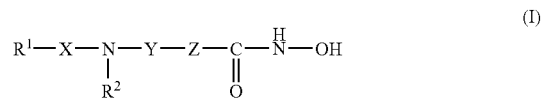

wherein $R^1$ is hydrogen, lower alkyl, lower alkenyl, lower or higher alkynyl, cyclo(lower)alkyl, cyclo(higher)alkyl, cyclo(lower)alkyl(lower)alkyl, cyclo(higher)alkyl(lower)alkyl, cyclo(lower)alkenyl(lower)alkyl, aryl-fused cyclo(lower)alkyl, lower alkoxy, acyl, aryl, ar(lower)alkoxy, ar(lower)alkyl, heteroar(lower)alkyl, amino, heteroaryl, heterocyclyl or heterocyclyl(lower)alkyl, which may be substituted with one or more suitable substituent(s), $R^2$ is hydrogen or lower alkyl, X is arylene, heterorarylene, cycloalkylene, heterocycloalkylene or aryl-fused cycloalkene, Y is arylene, heteroarylene, which may be substituted with one or more suitable substituent(s), Z lower alenylene, which may be substituted with lower alkyl or halogen, or a salt thereof. The compound is useful as a histone deacetylase inhibitor.

18 Claims, No Drawings

HDAC INHIBITOR

CROSS REFERENCES TO RELATED APPLICATIONS

This application claims priority to Australian Patent Application No. 2004904487, filed on Aug. 9, 2004, and Australian Patent Application No. 2004907228, filed on Dec. 20, 2004.

TECHNICAL FIELD

The present invention relates to a compound useful as a medicament, and to a pharmaceutical composition comprising the same.

BACKGROUND ART

Histone deacetylase (hereinafter also referred as HDAC) is known to play an essential role in the transcriptional machinery for regulating gene expression, induce histone hyperacetylation and to affect the gene expression. Therefore, it is useful as a therapeutic or prophylactic agent for diseases caused by abnormal gene expression such as inflammatory disorders, diabetes, diabetic complications, homozygous thalassemia, fibrosis, cirrhosis, acute promyelocytic leukaemia (APL), organ transplant rejections, autoimmune diseases, protozoal infections, tumors, etc.

WO 01/38322 discloses an inhibitor of histone deacetylase represented by the following formula:

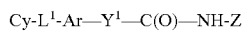

wherein
Cy is cycloalkyl, aryl, heteroaryl or heterocyclyl, each of which is optionally substituted;
$L^1$ is —$(CH_2)_m$—W— wherein m is an integer of 0 to 4, and W is selected from the group consisting of —C(O)NH—, —$S(O)_2NH$—, etc.;
Ar is optionally substituted arylene, which is optionally fused to an aryl, heteroaryl ring, etc.;
$Y^1$ is a chemical bond or a straight- or branched-chain saturated alkylene, wherein said alkylene is optionally substituted; and
Z is selected from the group consisting of anilinyl, pyridyl, thiadiazolyl and —O-M wherein M is H or a pharmaceutically acceptable cation.

WO 02/22577 discloses the following hydroxamate compound as a deacetylase inhibitor:

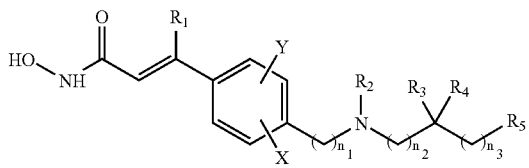

wherein
$R_1$ is H, halo or a straight chain $C_1$-$C_6$ alkyl;
$R_2$ is selected from H, $C_1$-$C_{10}$ alkyl, $C_4$-$C_9$ cycloalkyl, $C_4$-$C_9$ heterocycloalkyl, $C_4$-$C_9$ heterocycloalkylalkyl, cycloalkylalkyl, aryl, heteroaryl, etc.;
$R_3$ and $R_4$ are the same or different and independently H, $C_1$-$C_6$ alkyl, acyl or acylamino, or
$R_3$ and $R_4$ together with the carbon to which they are bound to represent C=O, C=S, etc., or
$R_2$ together with the nitrogen to which it is bound and $R_3$ together with the carbon to which it is bound to form a $C_4$-$C_9$ heterocycloalkyl, a heteroaryl, a polyheteroaryl, a non-aromatic polyheterocycle, or a mixed aryl and non-aryl polyheterocycle ring;
$R_5$ is selected from H, $C_1$-$C_6$ alkyl, etc.;
n, $n_1$, $n_2$ and $n_3$ are the same or different and independently selected from 0-6, when $n_1$ is 1-6, each carbon atom can be optionally and independently substituted with $R_3$ and/or $R_4$;
X and Y are the same or different and independently selected from H, halo, $C_1$-$C_4$ alkyl, etc.;
or a pharmaceutically acceptable salt thereof.

SUMMARY OF THE INVENTION

The present invention relates to a novel compound useful as a medicament, and to a pharmaceutical composition comprising the same.

More particularly, the present invention relates to a compound having a potent inhibitory effect on the activity of histone deacetylase.

The inventors of the present invention have also found that histone deacetylase inhibitors, such as a compound of the formula (I) (hereinafter compound (I)), have a potent immunosuppressive effect and potent antitumor effect. Therefore, a histone deacetylase inhibitors such as compound (I) is useful as an active ingredient for an immunosuppressant and an antitumor agent, and useful as an active ingredient for a therapeutic or prophylactic agent for diseases such as inflammatory disorders, diabetes, diabetic complications, homozygous thalassemia, fibrosis, cirrhosis, acute promyelocytic leukaemia (APL), organ transplant rejections, autoimmune diseases, protozoal infections, tumors, etc.

Accordingly, one object of the present invention is to provide a compound having biological activities for treating or preventing the diseases as stated above.

A further object of the present invention is to provide a pharmaceutical composition containing the compound (I) as an active ingredient.

A yet further object of the present invention is to provide use of the histone deacetylase inhibitors, such as compound (I), for treating and preventing the diseases as stated above.

A yet further object of the present invention is to provide a commercial package comprising the pharmaceutical composition containing the compound (I) and a written matter associated therewith, the written matter stating that the pharmaceutical composition may or should be used for treating or preventing the diseases as stated above.

Thus, the present invention provides A compound having the following formula (I):

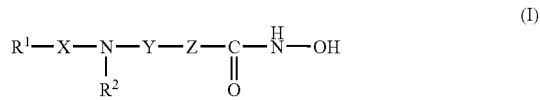

wherein
$R^1$ is hydrogen, lower alkyl, lower alkenyl, lower or higher alkynyl, cyclo(lower)alkyl, cyclo(higher)alkyl, cyclo(lower)alkyl(lower)alkyl, cyclo(higher)alkyl(lower)alkyl, cyclo(lower)alkenyl(lower)alkyl, aryl-fused cyclo(lower)alkyl, lower alkoxy, acyl, aryl, ar(lower)alkoxy, ar(lower)alkyl, heteroar(lower)alkyl, amino, heteroaryl, heterocyclyl or heterocyclyl(lower)alkyl, which may be substituted with one or more suitable substituent(s), $R^2$ is hydrogen or lower alkyl, X is arylene, heteroarylene, cycloalkylene, heterocycloalkylene or aryl-fused cycloalkylene, Y is arylene or heteroarylene, which may be substituted with one or more suitable substituent(s), Z is lower alkenylene, which may be substituted with lower alkyl or halogen, or a salt thereof.

The above-mentioned compound or a salt thereof can be prepared by the processes as illustrated in the following reaction schemes or by the methods disclosed in the Preparations and Examples.

In the above and subsequent descriptions of the present specification, suitable examples and illustration of the various definitions which the present invention intends to include within the scope thereof are explained in detail as follows.

Process A

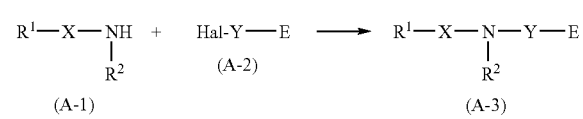

Process B

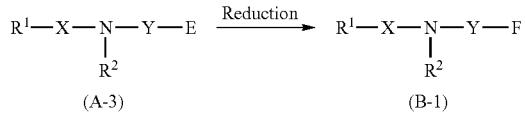

Process C

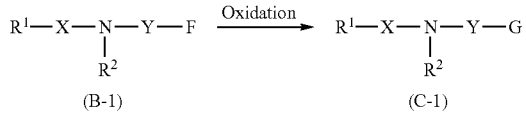

Process D

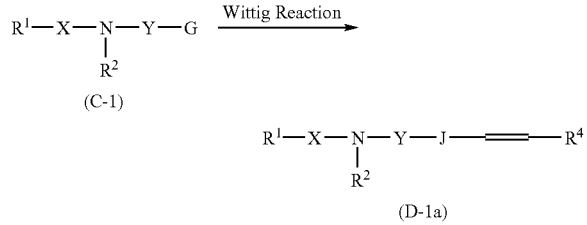

Process E

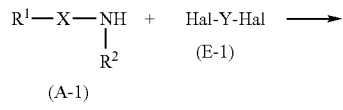

Process F

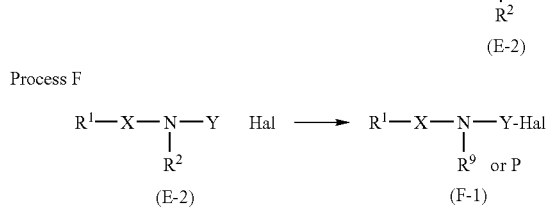

Process G

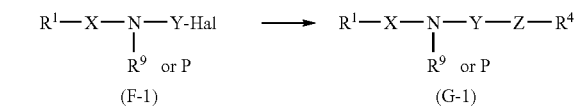

Process H

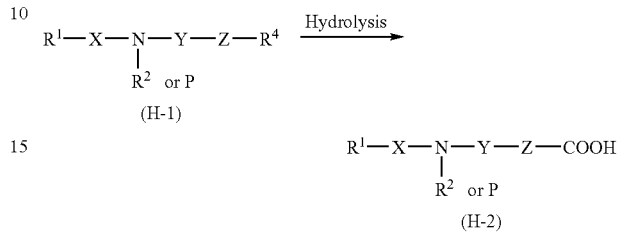

Process I

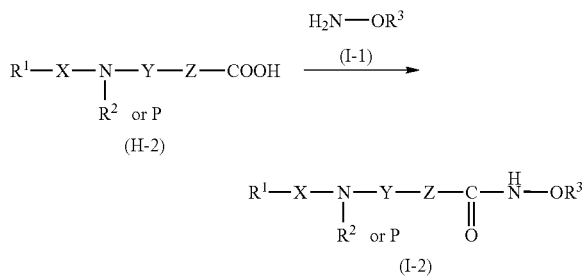

Process J

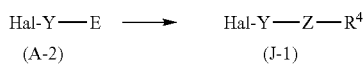

Process K

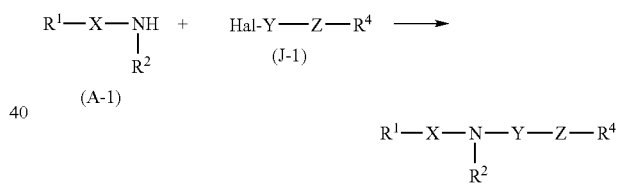

Process L

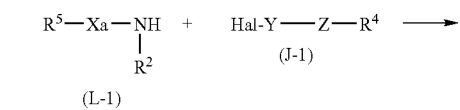

Process M

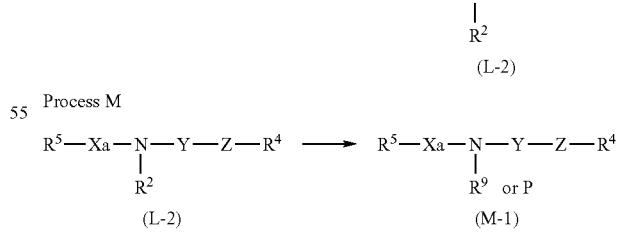

Process N

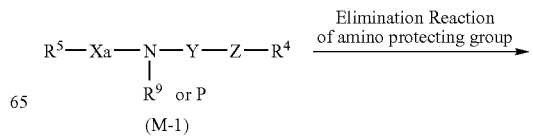

-continued

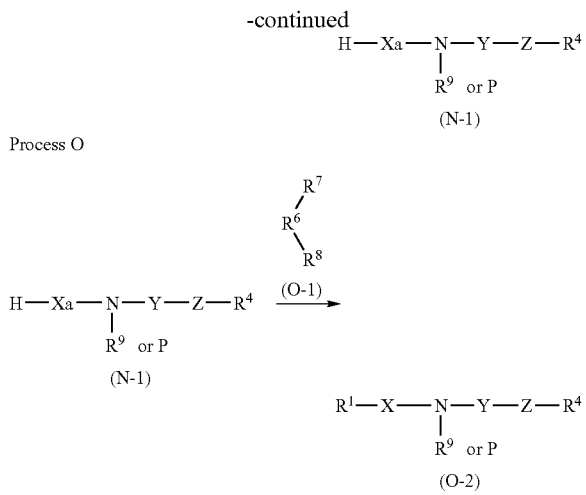

Process O wherein
$R^1$, $R^2$, X, Y and Z are as defined above,
Hal is halogen,
E is protected carboxy or protected carboxy(lower)alkyl,
F is hydroxy(lower)alkyl,
G is formyl or formyl(lower)alkyl,
$R^3$ is hydroxy protecting group,
$R^4$ is protected carboxy,
J is a single bond or lower alkylene,
$R^5$ and P is amino protecting group,
Xa is divalent saturated 3 to 8-membered heteromonocyclic ring containing one nitrogen atom,
$R^1$a is cyclo(lower)alkyl or lower alkyl substituted with cyclo(lower)alkyl,
$R^6$ is cyclo(lower)alkylidene or cyclo(lower)alkylene, and
$R^7$ is hydrogen,
$R^8$ is formyl(lower)alkyl, or
$R^7$ and $R^8$ are taken together to form oxo,
$R^9$ is lower alkyl.

In the above-mentioned Processes A, B, C, D, E, F, G, H, I, J, K, L, M, N and O, each of the starting compounds can be prepared, for example, according to the procedures as illustrated in Preparations in the present specification or in a manner similar thereto.

The compound (I) of the present invention is obtained from compound [I-2], for example, according to the following processes or methods disclosed in the Examples.

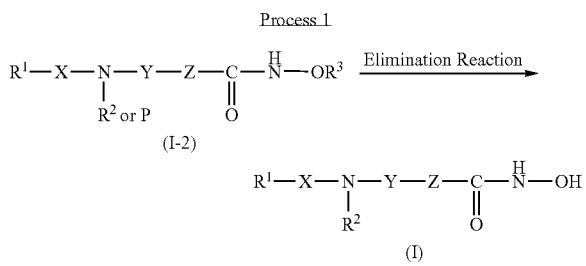

wherein
$R^1$, $R^2$, $R^3$, X, Y, P and Z are as defined above.

Process 1

The compound (I) is obtained by subjecting the compound (F-2) to the elimination reaction of hydroxy protecting group in the presence of an acid.

The acid includes such as hydrogen chloride solution (e.g. hydrogen chloride in solvent such as methanol, dioxane, ethyl acetate, diethyl ether, etc.), acetic acid, p-toluenesulfonic acid, boric acid, etc.

Optionally, one or more suitable solvent(s) for the deprotection is(are) used. Such solvent includes such as methanol, ethanol, ethyl acetate, dioxane, diethyl ether, acetic acid, etc.

The temperature of the reaction is not critical, and the reaction is usually carried out from under cooling to heating.

The compound (I) may be a salt, which is also encompassed in the scope of the present invention. For example, when a basic group such as an amino group is present in a molecule, the salt is exemplified by an acid addition salt (e.g. salt with an inorganic acid such as hydrochloric acid, hydrobromic acid, sulfuric acid, etc., salt with an organic acid such as methanesulfonic acid, benzenesulfonic acid, 4-toluenesulfonic acid, camphorsulfonic acid (e.g., [(1S,4R)-7,7-dimethyl-2-oxobicyclo[2.2.1]hept-1-yl]methanesulfonic acid or an enantiomer thereof, etc.), fumaric acid, maleic acid, mandelic acid, citric acid, salicylic acid, malonic acid, glutaric acid, succinic acid, etc.), etc., and when an acidic group such as carboxyl group is present, the salt is exemplified by a basic salt (e.g. salt with a metal such as lithium, sodium, potassium, calcium, magnesium, aluminium, etc., a salt with amino acid such as lysine, etc.), etc.

In addition, solvates (e.g. hydrate, ethanolate, etc.), anhydrous forms and other polymorphic forms or pharmaceutically acceptable salts of the compound (I) are also encompassed in the scope of the present invention.

When the compound (I) has stereoisomers based on asymmetric carbon atom(s) or double bond(s), such as an optically active form, a geometric isomer and the like, such isomers and mixtures thereof are also encompassed in the scope of the present invention.

In the above and subsequent descriptions of the present specification, suitable examples and illustration of the various definitions which the present invention intends to include within the scope thereof are explained in detail as follows.

Each of the terms "halogen", "halo" and "Hal" may include fluorine, chlorine, bromine and iodine.

The term "lower" used in the description is intended to mean 1 to 6 carbon atom(s) unless otherwise indicated.

The term "higher" used in the description is intended to mean 7 to 11 carbon atom(s) unless otherwise indicated.

Suitable "one or more" may include the number of 1 to 6, preferably 1 to 3.

Suitable "lower alkyl" and "lower alkyl" moiety may include straight or branched alkyl having 1 to 6 carbon atom(s) such as methyl, ethyl, propyl, isopropyl, butyl, isobutyl, sec-butyl, tert-butyl, pentyl, tert-pentyl, neopentyl, hexyl, isohexyl, etc.

Suitable "lower alkenyl" and "lower alkenyl" moiety may include straight or branched alkenyl having 2 to 6 carbon atom(s) such as vinyl, allyl, isopropenyl, pentenyl, hexenyl, 1-propenyl, 2-butenyl, 2-methyl-2-butenyl, etc.

Suitable "lower alkynyl" and "lower alkynyl" moiety may include straight or branched alkynyl having 2 to 6 carbon atom(s) such as ethynyl, propargyl, 3-methyl-1-pentynyl, etc.

Suitable "higher alkynyl" and "heigher alkynyl" moiety may include straight or branched alkynyl having 7 to 11 carbon atom(s) such as heptynyl, octynyl, etc.

Suitable "cyclo(lower)alkyl" and "cyclo(lower)alkyl" moiety may include cycloalkyl having 3 to 6 carbon atoms such as cyclopropyl, cyclobutyl, cyclopentyl, cyclohexyl, etc.

Suitable "cyclo(higher)alkyl" and "cyclo(higher)alkyl" moiety may include cycloalkyl having 7 to 11 carbon atoms such as cycloheptyl, cyclooctyl, adamantyl, etc.

Suitable "cyclo(lower)alkenyl" and "cyclo(lower)alkenyl" moiety may include cycloalkenyl having 3 to 6 carbon atoms such as cyclopropenyl, cyclobutenyl, cyclopentenyl, cyclohexenyl, etc.

Suitable "aryl-fused cyclo(lower)alkyl" and "aryl-fused cyclo(lower)alkyl" moiety may include aryl-fused cycloalkyl having 8 to 12 carbon atoms such as tetrahydronaphthyl, indanyl, benzocyclobutanyl, etc.

Suitable "lower alkoxy" and "lower alkoxy" moiety may include straight or branched alkoxy having 1 to 6 carbon atom(s) such as methoxy, ethoxy, propoxy, isopropoxy, butoxy, isobutoxy, sec-butoxy, tert-butoxy, pentyloxy, tert-pentyloxy, neopentyloxy, hexyloxy, isohexyloxy, etc.

Suitable "halo(lower)alkyl" may include lower alkyl substituted with 1 to 3 halogen atom(s) such as monochloromethyl, dichloromethyl, trichloromethyl, monofluoromethyl, difluoromethyl, trifluoromethyl, monobromomethyl, dibromomethyl, tribromomethyl, monochloroethyl, dichloroethyl, trichloroethyl, monofluoroethyl, difluoroethyl, trifluoroethyl, etc.

Suitable "halo(lower)alkoxy" may include lower alkoxy substituted with 1 to 3 halogen atom(s) such as monochloromethoxy, dichloromethoxy, trichloromethoxy, monofluoromethoxy, difluoromethoxy, trifluoromethoxy, monobromomethoxy, dibromomethoxy, tribromomethoxy, monochloroethoxy, dichloroethoxy, trichloroethoxy, monofluoroethoxy, difluoroethoxy, trifluoroethoxy, etc.

Suitable "lower alkenylene" may include straight or branched alkenylene having 2 to 6 carbon atom(s) such as vinylene, 1-methylvinylene, 2-methylvinylene, 1-propenylene, 2-propenylene, 2-methyl-1-propenylene, 2-methyl-2-propenylene, 1-butenylene, 2-butenylene, 3-butenylene, 1-pentenylene, 2-pentenylene, 3-pentenylene, 4-pentenylene, 1-hexenylene, 2-hexenylene, 3-hexenylene, 4-hexenylene, 5-hexenylene, etc. Suitable lower alkenylene for Z may be, for example, vinylene, 1-methylvinylene, 2-methylvinylene, etc.

Suitable "aryl" or "aryl" moiety described below may include $C_6$-$C_{16}$ aryl such as phenyl, naphthyl, anthryl, pyrenyl, phenanthryl, azulenyl, etc., and this "aryl" or "aryl" moiety described below may be substituted with one or more substituent(s) selected from the group consisting of lower alkyl, halogen, lower alkoxy, amino, hydroxy, cyano, aryl, aryloxy, acyl, cyclo(lower)alkyl, heteroaryl, halo(lower)alkyl or halo(lower)alkoxy.

Suitable "aryloxy" may include $C_6$-$C_{16}$ aryloxy such as phenoxy, naphthyloxy, anthryloxy, pyrenyloxy, phenanthryloxy, azulenyloxy, etc.

Suitable "ar(lower)alkyl" may include phenyl($C_1$-$C_6$)alkyl such as benzyl, phenethyl, phenylpropyl, phenylbutyl, phenylhexyl, etc., naphthyl($C_1$-$C_6$)alkyl such as naphthylmethyl, naphthylethyl, naphthylpropyl, naphthylbutyl, naphthylpentyl, naphtylhexyl, etc.

Suitable "ar(lower)alkoxy" may include phenyl($C_1$-$C_6$) alkoxy such as benzyloxy, phenethyloxy, phenylpropoxy, phenylbutoxy, phenylhexyloxy, etc., naphthyl($C_1$-$C_6$)alkoxy such as naphthylmethoxy, naphthylethoxy, naphthylpropoxy, naphthylbutoxy, naphthylpentyloxy, naphthylhexyloxy, etc.

The "acyl" as used herein includes for example, alkanoyl [e.g., formyl, lower alkyl-carbonyl (e.g., acetyl, propanoyl, butanoyl, 2-methylpropanoyl, pentanoyl, pivaloyl, 2,2-dimethylpropanoyl, hexanoyl and the like), heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl and the like];

alkoxycarbonyl [e.g., lower alkoxycarbonyl (e.g., methoxycarbonyl, ethoxycarbonyl, propoxycarbonyl, isopropoxycarbonyl, butoxycarbonyl, t-butoxycarbonyl, pentyloxycarbonyl and the like) and the like];

lower alkyl-carbonyloxy(lower)alkylcarbonyl (e.g. acetyloxyacetyl, ethylcarbonyloxyacetyl and the like);

arylcarbonyl [e.g., $C_{6-10}$ arylcarbonyl (e.g., benzoyl, toluoyl, naphthoyl, fluorenylcarbonyl and the like)];

arylalkanoyl [e.g., phenyl(lower)alkanoyl (e.g., phenylacetyl, phenylpropanoyl, phenylbutanoyl, phenylisobutanoyl, phenylpentanoyl, phenylhexanoyl and the like), naphthyl(lower)alkanoyl (e.g., naphthylacetyl, naphthylpropanoyl, naphthylbutanoyl and the like) and the like];

arylalkenoyl [e.g., aryl($C_3$-$C_6$) alkenoyl (e.g., phenylpropenoyl, phenylbutenoyl, phenylmethacryloyl, phenylpentenoyl, phenylhexenoyl and the like) and the like)];

naphthylalkenoyl [e.g., naphthyl($C_3$-$C_6$)alkenoyl (e.g., naphthylpropenoyl, naphthylbutenoyl, naphthylmethacryloyl, naphthylpentenoyl, naphthylhexenoyl and the like) and the like];

arylalkoxycarbonyl [e.g., aryl(lower)alkoxycarbonyl such as phenyl(lower)alkoxycarbonyl (e.g., benzyloxycarbonyl and the like), fluorenyl(lower)alkoxycarbonyl (e.g., fluorenylmethyloxycarbonyl and the like) and the like];

aryloxycarbonyl (e.g., phenoxycarbonyl, naphthyloxycarbonyl and the like);

aryloxyalkanoyl [e.g., aryloxy(lower)alkanoyl (e.g., phenoxyacetyl, phenoxypropionyl and the like) and the like];

heterocyclic acyl (e.g., heterocycliccarbonyl and the like);

heterocyclicalkanoyl [e.g., heterocyclic(lower)alkanoyl (e.g., heterocyclicacetyl, heterocyclicpropanoyl, heterocyclicbutanoyl, heterocyclicpentanoyl, heterocyclichexanoyl and the like) and the like]; heterocyclicalkenoyl [e.g., heterocyclic(lower)alkenoyl (e.g., heterocyclicpropenoyl, heterocyclicbutenoyl, heterocyclicpentenoyl, heterocyclichexenoyl and the like)];

carbamoyl;

alkylcarbamoyl [e.g., lower alkylcarbamoyl (e.g., methylcarbamoyl, ethylcarbamoyl and the like)];

alkoxycarbamoyl [e.g., lower alkoxycarbamoyl (e.g., methoxycarbamoyl, ethoxycarbamoyl and the like)] and the like;

arylcarbamoyl [e.g., $C_{6-10}$ arylcarbamoyl (e.g., phenylcarbamoyl, naphthylcarbamoyl and the like) and the like];

arylthiocarbamoyl [e.g., $C_{6-10}$ arylthiocarbamoyl (e.g., phenylthiocarbamoyl, naphthylthiocarbamoyl and the like) and the like];

alkylsulfonyl [e.g., lower alkylsulfonyl (e.g., methylsulfonyl, ethylsulfonyl and the like)];

alkoxysulfonyl [e.g., lower alkoxysulfonyl (e.g., methoxysulfonyl, ethoxysulfonyl and the like)] and the like;

arylsulfonyl (e.g., phenylsulfonyl and the like);

arylglyoxyloyl [e.g., $C_{6-10}$ arylglyoxyloyl (e.g., phenylglyoxyloyl, naphthylglyoxyloyl and the like) and the like];

heterocyclicglyoxyloyl; and the like. Each of these acyl is optionally substituted by one or more suitable substituent(s).

Suitable "lower alkanoyl" may include formyl and alkanoyl in which the alkyl portion is straight or branched alkyl having 1 to 6 carbon atom(s) such as acetyl, ethylcarbonyl, propylcarbonyl, isopropylcarbonyl, butylcarbonyl, isobutylcarbonyl, sec-butylcarbonyl, tert-butylcarbonyl, pentylcarbonyl, tert-pentylcarbonyl, neopentylcarbonyl, hexylcarbonyl, isohexylcarbonyl, etc.

Suitable "cyclo(lower) alkylcarbonyl" may include cycloalkylcarbonyl, in which the cycloalkyl portion is cycloalkyl having 3 to 6 carbon atoms, such as cyclopropylcarbonyl, cyclobutylcarbonyl, cyclopentylcarbonyl, cyclohexylcarbonyl, etc.

Suitable "lower alkoxycarbonyl" may include alkoxycarbonyl in which the alkyl portion is straight or branched alkyl having 1 to 6 carbon atom(s) such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, tert-pentyloxycarbonyl, neopentyloxycarbonyl, hexyloxycarbonyl, isohexyloxycarbonyl, etc.

Suitable "arylcarbonyl" may include arylcarbonyl in which the aryl portion is $C_6$-$C_{16}$ aryl such as phenylcarbonyl (benzoyl), naphthylcarbonyl, anthrylcarbonyl, pyrenylcarbonyl, phenanthrylcarbonyl, azulenylcarbonyl, etc.

Suitable "carbamoyl optionally mono- or di-substituted with lower alkyl(s)"includes carbamoyl; N-(lower)alkylcarbamoyl in which the alkyl portion is alkyl having 1 to 6 carbon atom(s) such as N-methylcarbamoyl, N-ethylcarbamoyl, N-propylcarbamoyl, N-butylcarbamoyl, N-isobutylcarbamoyl, N-tert-butylcarbamoyl, N-pentylcarbamoyl, N-neopentylcarbamoyl, N-isopentylcarbamoyl, N-hexylcarbamoyl, etc.; N,N-di(lower)alkylcarbamoyl in which the alkyl portions are each alkyl having 1 to 6 carbon atom(s) such as N,N-dimethylcarbamoyl, N,N-diethylcarbamoyl, N,N-dipropylcarbamoyl, N,N-dibutylcarbamoyl, N,N-diisobutylcarbamoyl, N,N-di-tert-butylcarbamoyl, N,N-dipentylcarbamoyl, N,N-dineopentylcarbamoyl, N,N-diisopentylcarbamoyl, N,N-dihexylcarbamoyl, N-ethyl-N-methylcarbamoyl, N-methyl-N-propylcarbamoyl, N-butyl-N-methylcarbamoyl, N-methyl-N-isobutylcarbamoyl, etc. Each of these carbamoyl is optionally substituted by one or more suitable substituent(s).

Suitable "arylcarbamoyl" may include arylcarbamoyl in which the aryl portion is $C_6$-$C_{16}$ aryl such as phenylcarbamoyl, naphthylcarbamoyl, anthrylcarbamoyl, pyrenylcarbamoyl, phenanthrylcarbamoyl, azulenylcarbamoyl, etc.

Suitable "aryl(lower)alkenyl" may include phenyl($C_2$-$C_6$) alkenyl such as styryl, phenylpropenyl, phenylbutenyl, phenylhexenyl, etc., naphthyl($C_2$-$C_6$)alkenyl such as naphthylvinyl, naphthylpropenyl, naphthylbutenyl, naphthylpentenyl, naphtylhexenyl, etc.

Suitable "amino" may include unsubstituted amino, and amino mono- or di-substituted with substituent(s) selected from lower alkyl, lower alkanoyl, lower alkylsulfonyl and cycloalkyl such as N-($C_1$-$C_6$ alkyl)amino (e.g., N-methylamino, N-ethylamino, N-propylamino, N-(n-butyl)amino, N-isobutylamino, N-(t-butyl)amino, etc.), N-($C_1$-$C_6$ alkanoyl)amino (e.g., N-acetylamino, N-ethylcarbonylamino, N-propylcarbonylamino, N-(n-butylcarbonyl) amino, N-isobutylcarbonylamino, N-(t-butylcarbonyl) amino, etc.), N-($C_1$-$C_6$) alkylsulfonylamino(e.g., N-methanesulfonylamino, N-ethanesulfonylamino, N-buthylsulfonylamino, etc.), N-($C_3$-$C_6$ cycloalkyl)amino (e.g., N-cyclopropylamino, N-cyclobutylamino, N-cyclopentylamino, N-cyclohexylamino, etc.), N,N-di($C_1$-$C_6$ alkyl) amino (e.g., N,N-dimethylamino, N,N-diethylamino, N-ethyl-N-methylamino, etc.), etc.

Suitable example of "heteroaryl" and "heteroar" moiety may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, oxadiazolyl 20 (e.g., 1,2,4-oxadiazolyl, 1,3,4-oxadiazolyl, 1,2,5-oxadiazolyl, etc.), etc.;

unsaturated condensed heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

unsaturated 3 to 8-membered (more preferably 5 or 6-membered) heteromonocyclic group containing 1 or 2 sulfur atom(s), for example, thienyl, dihydrodithiinyl, dihydrodithionyl, etc.;

unsaturated condensed heterocyclic group containing 1 or 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 or 6-membered) heteromonocyclic group containing an oxygen atom, for example, furyl etc.;

unsaturated condensed heterocyclic group containing an oxygen atom, for example, benzofuranyl or benzotetrahydrofuranyl, etc.;

unsaturated 3 to 8-membered (more preferably 5 or 6-membered) heteromonocyclic group containing an oxygen atom and 1 or 2 sulfur atom(s), for example, dihydrooxathiinyl, etc.;

unsaturated condensed heterocyclic group containing 1 or 2 sulfur atom(s), for example benzothienyl, benzodithiinyl, etc.;

unsaturated condensed heterocyclic group containing an oxygen atom and 1 or 2 sulfur atom(s), for example, benzoxathiinyl, etc.

Suitable example of "heterocyclyl" or "heterocyclyl" moiety may include saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, azetidinyl, etc.;

saturated 3 to 8-membered (more preferably 5 or 6-membered) heteromonocyclic group containing 1 or 2 oxygen atom(s) and 1 to 3 nitrogen atom(s), for example, morpholino, etc.;

saturated 3 to 8-membered (more preferably 5 or 6-membered) heteromonocyclic group containing 1 or 2 sulfur atom(s) and 1 to 3 nitrogen atom(s), for example thiazolidinyl, thiomorpholinyl, thiomorpholino, etc.;

saturated 3 to 8-membered (more preferably 5 or 6-membered) heteromonocyclic group containing 1 or 2 oxygen atom(s), for example, tetrahydrofuranyl, tetrahydropyranyl, dioxacyclopentanyl, dioxacyclohexanyl, etc.;

saturated condensed heterocyclic group containing 1 to 3 nitrogen atom(s), for example, hexahydropyrrolopyrazinyl, etc.; and the like, and this "heterocyclic group" may have one or more suitable substituent(s) selected from the group consisting of halogen, lower alkyl and aryl.

The term "arylene" refers to the diradical group derived from aryl (including substituted aryl) as defined above and is exemplified by 1,2-phenylene, 1,3-phenylene, 1,4-phenylene, 1,2-naphthylene and the like.

The term "heteroarylene" refers to the diradical group derived from heteroaryl (including substituted heteroaryl) as defined above and is exemplified by the groups 2,6-pyridylene, 3,6-pyridazinylene, 2,5-pyrazinylene, 2,5-pyrimidinylene, 1,2-quinolinylene, 1,8-quinolinylene, 1,4-benzofuranylene, 2,5-prudinylene, 2,5-indolenyl, and the like.

The term "cycloalkylene" refers to the diradical group derived from cycloalkyl (including substituted cycloalkyl) as defined above and is exemplified by the groups 1,4-cyclohexylene, 1,3-cyclopentylene, 1,3-cyclobutylene, and the like.

The term "heterocycloalkylene" refers to the diradical group derived from heterocyclyl (including substituted heterocyclyl) as defined above and is exemplified by the groups piperidine, pyrrolidine, piperidone, pyrrolidone and the like.

The term "aryl-fused cycloalkylene" refers to the diradical group derived from aryl-fused cyclo(lower)alkyl (including substituted aryl-fused cyclo(lower)alkyl) as defined above and is exemplified by the groups indanyl, tetrahydronaphthalene and the like.

Suitable "suitable substituent" may include lower alkyl, aryl, cyclo(lower)alkyl, cyclo(lower)alkenyl, heterocyclic group, and the like.

Suitable "protected carboxy" or "protected carboxy" moiety in the "protected carboxy(lower)alkyl" may be a conventional protecting group such as an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxyethyl ester, 2-propionyloxyethyl ester, hexanoyloxymethyl ester, etc.], lower alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.]; higher alkyl ester [e.g. heptyl ester, octyl ester, 3,5-dimethyloctyl ester, 3,7-dimethyloctyl ester, nonyl ester, decyl ester, undecyl ester, dodecyl ester, tridecyl ester, tetradecyl ester, pentadecyl ester, hexadecyl ester, heptadecyl ester, octadecyl ester, nonadecyl ester, adamantyl ester, etc.];
lower alkenyl ester [e.g. ($C_2$-$C_6$)alkenyl ester (e.g. vinyl ester, allyl ester, etc.)];
lower alkynyl ester [e.g. ($C_2$-$C_6$)alkynyl ester (e.g. ethynyl ester, propynyl ester, etc.)];
ar(lower)alkyl ester which may have one or more suitable substituent(s) [e.g. phenyl(lower)alkyl ester which may have 1 to 4 lower alkoxy, halogen, nitro, hydroxy, lower alkyl, phenyl, or halo(lower)alkyl (e.g. benzyl ester,
4-methoxybenzyl ester, 4-chlorobenzyl ester, 4-nitrobenzyl ester, phenethyl ester, trityl ester, benzhydryl ester,
bis(methoxyphenyl)methyl ester, 3,4-dimethoxybenzyl ester,
4-hydroxy-3,5-di-tert-butylbenzyl ester,
4-trifluoromethylbenzyl ester, etc.)];

aryl ester which may have one or more suitable substituent(s) [e.g. phenyl ester which may have 1 to 4 lower alkyl, or halogen (e.g. phenyl ester, 4-chlorophenyl ester, tolyl ester, 4-tert-butylphenyl ester, xylyl ester, mesityl ester, cumenyl ester, etc.)];
cycloalkyloxycarbonyloxy(lower)/allyl ester which may have lower alkyl (e.g., cyclopentyloxycarbonyloxymethyl ester, cyclohexyloxycarbonyloxymethyl ester,
cycloheptyloxycarbonyloxymethyl ester,
1-methylcyclohexyloxycarbonyloxymethyl ester,
1-(or 2-)[cyclopentyloxycarbonyloxy]ethyl ester,
1-(or 2-)[cyclohexyloxycarbonyloxy]ethyl ester, 1-(or 2-)-[cycloheptyloxycarbonyloxy]ethyl ester, etc.), etc.];
(5-(lower)alkyl-2-oxo-1,3-dioxol-4-yl)(lower)alkyl ester [e.g., (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)methyl ester, 1-(or 2-)(5-methyl-2-oxo-1,3-dioxol-4-yl)ethyl ester, 1-(or 2-)(5-ethyl-2-oxo-1,3-dioxol-4-yl)ethyl ester, 1-(or 2-)(5-propyl-2-oxo-1,3-dioxol-4-yl)ethyl ester, etc.]; and the like,
in which the preferred one may be lower alkyl ester, lower alkanoyloxy(lower)alkyl ester, ar(lower)alkyl ester which may have one or more suitable substituent(s),
cycloalkyloxycarbonyloxy(lower)alkyl ester which may have lower alkyl, higher alkyl ester, and [5-(lower)alkyl-2-oxo-1,3-dioxol-4-yl](lower)alkyl ester;
and the more preferred one may be methyl ester, ethyl ester, isobutyl ester, butyl ester, pentyl ester, hexyl ester, benzyl ester; 4-trifluoromethylbenzyl ester, 4-chlorobenzyl ester, adamantyl ester, (5-methyl-2-oxo-1,3-dioxol-4-yl)methyl ester, (1-cyclohexyloxycarbonyloxy)ethyl ester and pivaloyloxymethyl ester, and the like, in which the preferred one may be ($C_1$-$C_4$)alkyl ester, and the most preferred one may be ethyl ester.

Suitable "amino protecting group" may include a conventional protective group such as ar(lower)alkoxycarbonyl and lower alkoxycarbonyl, in which the preferred one may be phenyl($C_1$-$C_4$)alkoxycarbonyl and fluorenyl($C_1$-$C_4$)alkoxycarbonyl and ($C_1$-$C_4$)alkoxycarbonyl, and the most preferred one may be benzyloxycarbonyl, fluorenylmethoxycarbonyl and tert-butoxycarbonyl.

Suitable "hydroxy(lower)alkyl" may included hydroxymethyl, hydroxyethyl, hydroxypropyl, hydroxyisopropyl, hydroxybutyl, hydroxypentyl, hydroxyhexyl, and the like.

Suitable "formyl(lower)alkyl" may include formylmethyl, formylethyl, formylpropyl, formylisopropyl, formylbutyl, formylpentyl, formylhexyl, and the like.

Suitable "hydroxy protecting group" is as follows: lower alkyl (e.g., methyl, ethyl, propyl, isopropyl, butyl, isobutyl, t-butyl, pentyl, hexyl, etc.), preferably methyl;
lower alkoxy(lower)alkyl (e.g. methoxymethyl, etc.);
lower alkoxy(lower)alkoxy(lower)alkyl (e.g. 2-methoxyethoxymethyl, etc.);
ar(lower)alkyl in which the aryl portion is optionally substituted with one or more suitable substituent(s) (e.g. benzyl (Bn), p-methoxybenzyl, m,p-dimethoxybenzyl, etc.), preferably benzyl;
ar(lower)alkoxy(lower)alkyl in which the aryl portion is optionally substituted with one or more suitable substituent(s) (e.g. benzyloxymethyl, p-methoxybenzyloxymethyl, etc.);
(lower)alkylthio(lower)alkyl (e.g. methylthiomethyl, ethylthiomethyl, propylthiomethyl, isopropylthiomethyl, butylthiomethyl, isobutylthiomethyl, hexylthiomethyl, etc.), etc., preferably methylthiomethyl;

trisubstituted silyl such as tri(lower)alkylsilyl (e.g. trimethylsilyl, triethylsilyl, tributylsilyl, tert-butyldimethylsilyl, tri-tert-butylsilyl, etc.), lower alkyldiarylsilyl (e.g. methyldiphenylsilyl, ethyldiphenylsilyl, propyldiphenylsilyl, tert-butyldiphenylsilyl (TBDPS), etc.), etc., preferably tert-butyldimethylsilyl (TBDMS) and tert-butyldiphenylsilyl;

heterocyclic group (e.g. tetrahydropyranyl, etc.);

acyl as described below [e.g. aliphatic acyl such as lower alkanoyl (e.g. acetyl, propanoyl, pivaloyl, etc.); aromatic acyl (e.g. benzoyl (Bz), toluoyl, naphthoyl, fluorenylcarbonyl, etc.);

lower alkoxy-carbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, etc.), etc.;

ar(lower)alkoxycarbonyl in which the aryl portion is optionally substituted with one or more suitable substituent(s) (e.g. benzyloxycarbonyl, bromobenzyloxycarbonyl, etc.);

lower alkylsulfonyl (e.g. methylsulfonyl, ethylsulfonyl, etc.);

lower alkoxysulfonyl (e.g. methoxysulfonyl, ethoxysulfonyl, etc.);

ar(lower)alkanoyl (e.g. phenylacetyl, phenylpropanoyl, phenylbutanoyl, phenylisobutanoyl, phenylpentanoyl, phenylhexanoyl, naphthylacetyl, naphthylpropanoyl, naphthylbutanoyl, naphthylisobutanoyl, naphthylpentanoyl, naphthylhexanoyl, etc.);

ar(lower)alkenoyl such as ar($C_3$-$C_6$)alkenoyl (e.g. phenylpropenoyl, phenylbutenoyl, phenylmethacryloyl, phenylpentenoyl, phenylhexenoyl, naphthylpropenoyl, naphthylbutenoyl, naphthylmethacryloyl, naphthylpentenoyl, naphthylhexenoyl, etc.), etc.];

lower alkenyl (e.g. vinyl, allyl, etc.); etc.

The preferable hydroxy protecting group for the present invention is, for example, tetrahydropyranyl, trimethylsilyl, t-butyldimethylsilyl, etc.

The following abbreviations are also used in the present specification: Boc (t-butyloxycarbonyl); HOBT or HOBt (1-hydroxybenzotriazole); WSCD (1-ethyl-3-(3'-dimethylaminopropyl)carbodiimide); WSCD.HCl or EDCI (1-ethyl-3-(3'-dimethylaminopropyl)carbodiimide hydrochloride); DMF (N,N-dimethylformamide); aq. (aqueous solution); Me (methyl); MeOH (methanol); MeCN (acetonitrile); Et (ethyl); $Et_3N$ (triethylamine); EtOH (ethanol); IPE (diisopropyl ether); tBu (t-butyl); TsCl (p-toluenesulfonyl chloride); Ac (acetyl); AcOH (acetic acid); AcOEt (ethyl acetate); $AcONH_4$ (ammonium acetate); Ph (phenyl); DIEA (diisopropylethylamine); THP (tetrahydropyranyl); THF (tetrahydrofuran) and TFA or TFAOH (trifluoroacetic acid).

Test Method

In order to show the usefulness of the compound (I) of the invention, the pharmacological test result of the representative compound of the present invention is shown in the following.

Test 1: Determination of Histone Deacetylase Inhibitor Activity

The partial purification of human histone deacetylase, the preparation of [$^3$H] acetyl histones, and the assay for histone deacetylase activity were performed basically according to the method as proposed by Yoshida et al. as follows.

Partial Purification of Human Histone Deacetylase

The human histone deacetylase was partially purified from human T cell leukemia Jurkat cells. Jurkat cells ($5\times10^8$ cells) were suspended in 40 mL of the HDA buffer consisting of 15 mM potassium phosphate, pH 7.5, 5% glycerol and 0.2 mM EDTA. After homogenization, nuclei were collected by centrifugation (35,000×g, 10 min) and homogenized in 20 mL of the same buffer supplemented with 1 M $(NH_4)_2SO_4$. The viscous homogenate was sonicated and clarified by centrifugation (35,000×g, 10 min), and the deacetylase was precipitated by raising the concentration of $(NH_4)_2SO_4$ to 3.5 M. The precipitated protein was dissolved in 10 mL of the HDA buffer and dialyzed against 4 liters of the same buffer. The dialyzate was then loaded onto a DEAE-cellulose (Whatman DE52) column (25×85 mm) equilibrated with the same buffer and eluted with 300 mL of a linear gradient (0-0.6 M) of NaCl. A single peak of histone deacetylase activity appeared between 0.3 and 0.4 M NaCl.

Preparation of [$^3$H] Acetyl Histone

To obtain [$^3$H] acetyl-labeled histone as the substrate for the histone deacetylase assay, $1\times10^8$ cells of Jurkat in 20 mL of RPMI-1640 medium (supplemented with 10% FBS, penicillin (50 units/mL) and streptomycin (50 µg/mL)) were incubated with 300 MBq [$^3$H] sodium acetate in the presence of 5 mM sodium butyrate for 30 minutes in 5% $CO_2$-95% air atmosphere at 37° C. in a 75 $cm^2$ flask, harvested into a centrifuge tube (50 mL), collected by centrifugation at 1000 rpm for 10 minutes, and washed once with phosphate-buffered saline. The washed cells were suspended in 15 mL of ice-cold lysis buffer (10 mM Tris-HCl, 50 mM sodium bisulfite, 1% Triton X-100, 10 mM $MgCl_2$, 8.6% sucrose, pH 6.5). After Dounce homogenization (30 stroke), the nuclei were collected by centrifugation at 1000 rpm for 10 minutes, washed 3 times with 15 mL of the lysis buffer, and once with 15 mL of ice-cooled washing buffer (10 mM Tris-HCl, 13 mM EDTA, pH 7.4) successively. The pellet was suspended in 6 mL of ice-cooled water using a mixer, and 68 µl of $H_2SO_4$ was added to the suspension to give a concentration of 0.4 N. After incubation at 4° C. for 1 hour, the suspension was centrifuged for 5 minutes at 15,000 rpm, and the supernatant was taken and mixed with 60 mL of acetone. After overnight incubation at −20° C., the coagulated material was collected by microcentrifugation, air-dried, and stored at −80° C.

Assay for Histone Deacetylase Activity

For the standard assay, 10 µl of [$^3$H] acetyl-labeled histones were added to 90 µl of the enzyme fraction, and the mixture was incubated at 25° C. for 30 minutes. The reaction was stopped by addition of 10 µl of HCl. The released [$^3$H] acetic acid was extracted with 1 mL of ethyl acetate, and 0.9 mL of the solvent layer was taken into 10 mL of toluene scintillation solution for determination of radioactivity.

Test 2: Determination of T-Cell Growth Inhibitor Activity

The T lymphocyte blastogenesis test was performed in microtiter plates with each well containing $1.5\times10^5$ splenic cells of Lewis rats in 0.1 mL RPMI-1640 medium supplemented with 10% fetal bovine serum (FBS), 50 mM 2-mercaptoethanol, penicilln (100 units/mL) and streptomycin (100 µg/mL), to which Concanavalin A (1 µg/mL) was added. The cells were incubated at 37° C. in a humidified atmosphere of 5% $CO_2$ for 72 hours. After the culture period, suppressive activities of the test compounds in T lymphocyte blastogenesis were quantified by AlamarBlue (trademark) Assay. The test samples were dissolved in DMSO and further diluted with RPMI-1640 medium and added to the culture. The activities of the test compounds were expressed as $IC_{50}$.

The results of those tests are shown in the Table 1.

TABLE 1

HDAC inhibitory activity and T-cell growth inhibitory activity of the compound of the present invention

| Examples | Test 1: HDAC inhibitory activity IC$_{50}$ (nM) | Test 2: T-cell growth inhibitory activity IC$_{50}$ (nM) |
| --- | --- | --- |
| Example 3 | <10 | <25 |
| Example 60 | <10 | <25 |
| Example 74 | <10 | <25 |
| Example 76 | <10 | <25 |
| Example 82 | <10 | <25 |
| Example 116 | <10 | <25 |
| Example 119 | <10 | <25 |
| Example 123 | <10 | <25 |
| Example 174 | <10 | <25 |
| Example 189 | <10 | <25 |

The pharmaceutical composition of the present invention comprising histone deacetylase inhibitor such as the compound (I) is useful as a therapeutic or prophylactic agent for diseases caused by abnormal gene expression, such as inflammatory disorders, diabetes, diabetic complications, homozygous thalassemia, fibrosis, cirrhosis, acute promyelocytic leukaemia (APL), protozoal infection, etc. Furthermore, it is useful as an antitumor agent or immunosuppressant, which prevents an organ transplant rejection and autoimmune diseases as exemplified below:

rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation; autoimmune diseases such as rheumatoid arthritis, systemic lupus erythematosus, Hashimoto's thyroiditis, multiple sclerosis, myasthenia gravis, type I diabetes, etc.; and infections caused by pathogenic microorganisms (e.g. *Aspergillus fumigatus, Fusarium oxysporum, Trichophyton asteroides*, etc.).

Furthermore, pharmaceutical preparations of the histone deacetylase inhibitor, such as the compound (I), are useful for the therapy or prophylaxis of the following diseases.

Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, alopecia areata, etc.);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, dust asthma, etc.), particularly chronic or inveterate asthma (e.g. late asthma, airway hyper-responsiveness, etc.), bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases, etc.);

intestinal inflammations/allergies (e.g. coeliac diseases, proctitis, eosinophilic gastroenteritis, mastocytosis, Crohn's disease, ulcerative colitis, etc.);

food-related allergic diseases with symptomatic manifestation remote from the gastrointestinal tract (e.g. migrain, rhinitis, eczema, etc.);

renal diseases (e.g. intestitial nephritis, Goodpasture's syndrome, hemolytic uremic syndrome, diabetic nephropathy, etc.);

nervous diseases (e.g. multiple myositis, Guillain-Barre syndrome, Meniere's disease, multiple neuritis, solitary neuritis, cerebral infarction, Alzheimer's disease, Parkinson's disease, amyotrophic lateral sclerosis (ALS), radiculopathy, etc.);

cerebral ischemic diseases (e.g., head injury, hemorrhage in brain (e.g., subarachnoid hemorrhage, intracerebral hemorrhage, etc.), cerebral thrombosis, cerebral embolism, cardiac arrest, stroke, transient ischemic attack (TIA), hypertensive encephalopathy, etc.);

endocrine diseases (e.g. hyperthyroidism, Basedow's disease, etc.);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, etc.);

bone diseases (e.g. osteoporosis, etc.);

respiratory diseases (e.g. sarcoidosis, pulmonary fibrosis, idiopathic interstitial pneumonia, etc.);

skin diseases (e.g. dermatomyositis, leukoderma vulgaris, ichthyosis vulgaris, photosensitivity, cutaneous T-cell lymphoma, etc.);

circulatory diseases (e.g. arteriosclerosis, atherosclerosis, aortitis syndrome, polyarteritis nodosa, myocardosis, etc.);

collagen diseases (e.g. scleroderma, Wegener's granuloma, Sjögren's syndrome, etc.);

adiposis;

eosinophilic fasciitis;

periodontal diseases (e.g. damage to gingiva, periodontium, alveolar bone or substantia ossea dentis, etc.);

nephrotic syndrome (e.g. glomerulonephritis, etc.);

male pattern alopecia, alopecia senile;

muscular dystrophy;

pyoderma and Sezary syndrome;

chromosome abnormality-associated diseases (e.g. Down's syndrome, etc.);

Addison's disease;

active oxygen-mediated diseases {e.g. organ injury [e.g. ischemic circulation disorders of organs (e.g. heart, liver, kidney, digestive tract, etc.) associated with preservation, transplantation, ischemic diseases (e.g. thrombosis, cardial infarction, etc.), etc.];

intestinal diseases (e.g. endotoxin shock, pseudomembranous colitis, drug- or radiation-induced colitis, etc.);

renal diseases (e.g. ischemic acute renal insufficiency, chronic renal failure, etc.);

pulmonary diseases (e.g. toxicosis caused by pulmonary oxygen or drugs (e.g. paracort, bleomycin, etc.), lung cancer, pulmonary emphysema, etc.);

ocular diseases (e.g. cataracta, iron-storage disease (siderosis bulbi), retinitis, pigmentosa, senile plaques, vitreous scarring, corneal alkali burn, etc.);

dermatitis (e.g. erythema multiforme, linear immunoglobulin A bullous dermatitis, cement dermatitis, etc.); and other diseases (e.g. gingivitis, periodontitis, sepsis, pancreatitis, diseases caused by environmental pollution (e.g. air pollution, etc.), aging, carcinogen, metastasis of carcinoma, hypobaropathy, etc.)};

diseases caused by histamine release or leukotriene C4 release; restenosis of coronary artery following angioplasty and prevention of postsurgical adhesions;

autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans, etc.), polychondritis, etc.); Human Immunodeficiency Virus (HIV) infection, AIDS;

allergic conjunctivitis;

hypertrophic cicatrix, keloid due to trauma, burn or surgery, etc.

Therefore, the pharmaceutical composition of the present invention is useful for the therapy and prophylaxis of liver diseases [e.g. immunogenic diseases (e.g. chronic autoimmune liver diseases such as autoimmune hepatic diseases, primary biliary cirrhosis, sclerosing cholangitis, etc.), partial liver resection, acute liver necrosis (e.g. necrosis caused by toxins, viral hepatitis, shock, anoxia, etc.), hepatitis B, non-A non-B hepatitis, hepatocirrhosis, hepatic failure (e.g. fulminant hepatitis, late-onset hepatitis, "acute-on-chronic" liver failure (acute liver failure on chronic liver diseases, etc.), etc.), etc.].

The pharmaceutical composition of the present invention can be used in the form of pharmaceutical preparation, for example, in a solid, semisolid or liquid form, which contains the histone deacetylase inhibitor, such as the compound (I), as an active ingredient in admixture with an organic or inorganic carrier or excipient suitable for external, enteral or parenteral administrations. The active ingredient may be compounded, for example, with the usual non-toxic, pharmaceutically acceptable carriers for tablets, pellets, capsules, suppositories, solutions, emulsions, suspensions, injections, ointments, liniments, eye drops, lotion, gel, cream, and any other form suitable for use.

The carriers those can be used for the present invention include water, glucose, lactose, gum acacia, gelatin, mannitol, starch paste, magnesium trisilicate, talc, corn starch, keratin, colloidal silica, potato starch, urea and other carriers suitable for use in manufacturing preparations in a solid, semisolid, or liquid form. Furthermore, auxiliary, stabilizing, thickening, solubilizing and coloring agents and perfumes may be used.

For applying the composition to human, it is preferable to apply it by intravenous, intramuscular, topical or oral administration, or by a vascular stent impregnated with the compound (I). While the dosage of therapeutically effective amount of the histone deacetylase inhibitor, such as the compound (I), varies from and also depends upon the age and condition of each individual patient to be treated, when an individual patient is to be treated, in the case of intravenous administration, a daily dose of 0.01-10 mg of the histone deacetylase inhibitor, such as the compound (I), per kg weight of human being, in the case of intramuscular administration, a daily dose of 0.1-10 mg of the histone deacetylase inhibitor, such as the compound of the formula (I), per kg weight of human being, and in the case of oral administration, a daily dose of 0.5-50 mg of the histone deacetylase inhibitor, such as the compound (I), per kg weight of human being, is generally given for treatment.

During the preparation of the above-mentioned pharmaceutical administration forms, the compound (I) or a salt thereof can also be combined together with other immunosuppressive substances, for example rapamycin, mycophenolic acid, cyclosporin A, tacrolimus or brequinar sodium.

Hereinafter the reactions in each Preparations and Examples for preparing the compound (I) of the present invention are explained in more detail. The invention should not be restricted by the following Preparations and Examples in any way.

Preparation 1

A mixture of methyl 6-chloronicotinate (5.0 g), 1-benzyl-3-aminopyrrolidine (6.16 g) and $K_2CO_3$ (4.83 g) in DMF (20 ml) was stirred at 100°C. for 10 hours under atmospheric pressure of nitrogen. The reaction mixture was poured into a mixture of AcOEt and water and the organic layer was washed with brine and dried over $MgSO_4$. The solvent was evaporated in vacuo and the residue was chromatographed on silicagel eluting with AcOEt-MeOH (97:3). The eluted fractions containing the desired product were collected and evaporated in vacuo to give methyl 6-[(1-benzylpyrrolidin-3-yl)amino]nicotinate (4.17 g)

NMR (DMSO-$d_6$, δ): 1.58-1.71 (1H, m), 2.17-2.34 (1H, m), 2.37-2.89 (4H, m), 3.51 (2H, s), 3.65 (2H, s), 4.39 (1H, m), 6.42 (1H, d, J=8.80 Hz), 7.19-7.33 (5H, m), 7.59 (1H, d, J=6.78 Hz), 7.80 (1H, dd, J=2.20 Hz and 8.80 Hz), 8.56 (1H, d, J=2.20 Hz)

The following compounds were obtained according to a similar manner to that of Preparation 1.

Preparation 2

Methyl 6-[N-(1-benzylpyrrolidin-3-yl)-N-methylamino]nicotinate

NMR (DMSO-$d_6$, δ): 173-1.76 ((1H, m), 2.23-2.44 (2H, m), 2.48-2.67 (2H, m), 2.81-2.85 (11H, m), 2.85 (3H, s), 3.53, 3.63 (2H, ABq, J=13.02 Hz), 3.66 (3H, s), 5.34-5.39 (1H, m), 6.66 (1H, d, J=90.6 Hz), 7.20-7.34 (5H, m), 7.92 (1H, dd, J=2.06 Hz, 9.06 Hz), 8.63 (1H, d, J=2.06 Hz)

Preparation 3

Methyl 6-[[1-(tert-butoxycarbonyl)piperidin-4-yl]amino]nicotinate

NMR (CDCl$_3$, δ): 1.47(9H, s), 1.15-2.08(4H, m), 2.79-3.02 (2H, m), 3.90(3H, s), 3.96-4.10(2H, m), 4.95(1H, d, J=7.7 Hz), 6.35(1H, d, J=8.8 Hz), 7.98(1H, dd, J=2.0, 8.8 Hz), 8.73(1H, d, J=2.0 Hz)

Mass (APCI): 358 (M+H)+

Preparation 4

Benzyl 6-[1-(tert-butoxycarbonyl)-4-piperidylamino]-5-chloronicotinate

NMR (DMSO-$d_6$, δ): 1.40(9H, s), 1.48-1.60(2H, m), 1.70-1.90(2H, m), 2.60-2.90(2H, m), 3.85-4.01(2H, m), 4.10-4.40 (1H, m), 5.30(2H, s), 7.05(1H, d, J=8.2 Hz), 7.30-7.47(5H, m), 7.97(1H, d, J=2.0 Hz), 8.60(1H, d, J=2.0 Hz)

Mass (APCI): 445(M+Na)+

Preparation 5

Methyl 6-[[1-(tert-butoxycarbonyl)-4-piperidyl](methyl)amino]-nicotinate

NMR (DMSO-$d_6$, δ): 1.41(9H, s), 1.50-1.80(4H, m), 2.65-2.85(2H, m), 2.89(3H, s), 3.78(3H, s), 4.05-4.20(2H, m), 4.60-4.80(1H, m), 6.72(1H, d, J=8.8 Hz), 7.94(1H, dd, J=2.0, 8.8 Hz), 8.64(1H, d, J=2.0 Hz)

Mass (APCI): 372(M+Na)+

Preparation 6

Lithium aluminium hydride (256 mg) was added to absolution of methyl 6-[(1-benzyl-3-pyrrolidinyl)amino]nicotinate (1.4 g) in THF (50 ml) with stirring at 5-10' under atmospheric pressure of nitrogen, and the reaction mixture was stirred at 5-20° C. for 4 hours. The reaction mixture was cooled at 5° C. and water (0.26 ml), 15% NaOH solution (0.26 ml) and water (0.72 ml) was added, the resultant mixture was stirred at ambient temperature for 20 minutes. The reaction mixture was filtrated and the filtrate was dried over $MgSO_4$. The solvent was evaporated in vacuo and the residue was chromatographed on silicagel eluting with AcOEt-MeOH (85:15). The eluted fractions containing the desired product were collected and evaporated in vacuo to give {6-[(1-benzyl-3-pyrrolidinyl)amino]-3-pyridyl}methanol (0.96 g)

NMR (DMSO-$d_6$, δ): 1.58-1.65 (1H, m), 2.06-2.52 (3H, m), 2.59-2.81 (2H, m), 3.42 (2H, s), 4.18-4.37 (1H, m), 4.26 (2H, d, J=5.28 Hz), 4.87 (1H, t, J=5.28 Hz), 6.43 (1H, d, J=8.54 Hz), 6.53 (1H, d, J=6.80 Hz), 7.18-7.36 (6H, m), 7.85 (1H, d, J=2.10 Hz)

The following compounds were obtained according to a similar manner to that of Preparation 6.

Preparation 7

(6-[(1-Benzyl-3-pyrrolidinyl)(methyl)amino]-3-pyridyl)methanol

NMR (DMSO-$d_6$, δ): 1.67-1.73 (1H, m), 2.07-2.11 (1H, m), 2.24-2.33 (1H, m), 2.43-2.58 (2H, m), 2.76-2.83 (1H, m), 2.90 (3H, s), 3.52, 3.63 (2H, ABq, J=13.08 Hz), 4.32 (2H, d, J=4.78 Hz), 4.94 (1H, t, J=4.78 Hz), 5.18-5.29 (1H, m), 6.58 (1H, d, J=8.74 Hz), 7.21-7.47 (5H, m), 7.44 (1H, dd, J=2.22 Hz, 8.74 Hz), 7.98 (1H, d, J=2.22 Hz)

Preparation 8

(6-{[(3R)-1-Benzyl-3-pyrrolidinyl]amino}-3-pyridyl)methanol

NMR (DMSO-$d_6$, δ): 1.59-1.65 (1H, m), 2.09-2.51 (3H, m), 2.59-2.63 (1H, m), 2.73-2.81 (1H, m), 3.53, 3.59 (2H, ABq, J=12.98 Hz), 4.23 (2H, d, J=5.34 Hz), 4.18-4.28 (1H, m), 4.88 (1H, t, J=5.34 Hz), 6.44 (1H, d, J=8.52 Hz), 6.53 (1H, d, J=6.84 Hz), 7.16-7.36 (6H, m), 7.85 (1H, d, J=2.10 Hz)

Preparation 9

(6-{[(3S)-1-Benzyl-3-pyrrolidinyl]amino}-3-pyridyl)methanol

NMR (DMSO-$d_6$, δ): 1.59-1.66 (1H, m), 2.16-2.55 (3H, m), 2.56-2.60 (1H, m), 2.63-2.81 (1H, m), 3.44-3.63 (2H, m), 4.19-4.35 (3H, m), 4.89 (1H, brs), 6.44 (1H, d, J=8.50 Hz), 6.54 (1H, d, J=6.82 Hz), 7.18-7.34 (6H, m), 7.87 (1H, d, J=2.04 Hz)

Preparation 10 tert-Butyl 4-{[5-(hydroxymethyl)-2-pyridyl]amino}-1-piperidinecarboxylate

NMR (CDCl$_3$, δ): 1.20-1.40(2H, m), 1.47(9H, s), 1.98-2.06 (2H, m), 2.84-3.01(2H, m), 3.76-4.00(1H, m), 4.00-4.39(2H, m), 4.40(1H, d, J=15.8 Hz), 4.52(2H, s), 6.38(1H, d, J=8.8 Hz), 7.46(1H, dd, J=2.0, 8.8 Hz), 8.01(1H, d, J=2.0 Hz)

Mass (APCI): 308(M+H)+

Preparation 11 tert-Butyl 4-{[3-chloro-5-(hydroxymethyl)-2-pyridyl]amino}-1-piperidinecarboxylate Mass (APCI): 343(M+H)+

Preparation 12 tert-Butyl 4-[[5-(hydroxymethyl)-2-pyridyl](methyl)amino]-1-piperidinecarboxylate NMR (DMSO-$d_6$, δ): 1.41(9H, s), 1.54-1.63(4H, m), 2.78 (3H, s), 2.75-2.99(2H, m), 4.01-4.20(2H, m), 4.32(2H, d, J=5.3 Hz), 4.50-4.80(1H, m), 4.90-4.96(1H, m), 6.61(1H, d, J=8.8 Hz), 7.46(1H, dd, J=2.0, 8.8 Hz), 8.00(1H, d, J=2.0 Hz)

Mass (APCI): 344(M+Na)+

Preparation 13

A mixture of (6-[(1-benzyl-3-pyrrolidinyl)amino]-3-pyridyl)methanol (0.96 g) and MnO$_2$ (2.951 g) in AcOEt (50 ml) was refluxed under stirring for 1.5 hour. After removal of the insoluble material, and the solvent was evaporated in vacuo to give 6-[(1-benzyl-3-pyrrolidinyl)amino]nicotinaldehyde (0.75 g)

NMR (DMSO-$d_6$, δ): 1.66-1.72 (1H, m), 2.06-2.52 (3H, m), 2.62-2.82 (2H, m), 3.60 (2H, s), 4.39-4.45 (1H, m), 6.58 (1H, d, J=8.80 Hz), 7.16-7.32 (5H, m), 7.73 (1H, dd, J=2.18 Hz, 8.80 Hz), 7.93 (1H, d, J=5.52 Hz), 8.47 (1H, d, J=2.18 Hz), 9.66 (1H, s)

The following compounds were obtained according to a similar manner to that of Preparation 13.

Preparation 14

6-{[(3R)-1-Benzyl-3-pyrrolidinyl]amino}nicotinaldehyde

NMR (DMSO-$d_6$, δ): 1.66-1.99 (1H, m), 2.23-2.38 (1H, m), 2.41-2.52 (2H, m), 2.61-2.82 (2H, m), 3.52 (2H, s), 4.39-4.45 (1H, m), 6.58 (1H, d, J=8.84 Hz), 7.16-7.33 (5H, m), 7.73 (1H, dd, J=2.20 Hz, 8.84 Hz), 7.90 (1H, d, J=6.64 Hz), 8.47 (1H, d, J=2.20 Hz), 9.66 (1H, s)

Preparation 15

6-{[(3S)-1-Benzyl-3-pyrrolidinyl]amino}nicotinaldehyde

NMR (DMSO-$d_6$, δ): 1.66-2.00 (1H, m), 2.21-2.26 (1H, m), 2.38-2.52 (2H, m), 2.61-2.82 (2H, m), 3.52 (2H, s), 4.45 (1H, m), 6.58 (1H, d, J=8.88 Hz), 7.16-7.33 (5H, m), 7.73 (1H, dd, J=2.18 Hz, 8.88 Hz), 7.90 (1H, d, J=6.72 Hz), 8.47 (1H, d, J=2.18 Hz), 9.66 (1H, s)

Preparation 16

6-{[(3R)-1-Benzyl-3-pyrrolidinyl]amino}-5-chloronicotinaldehyde

NMR (DMSO-$d_6$, δ): 1.86-1.96 (1H, m), 2.00-2.26 (1H, m), 2.43-2.61 (3H, m), 2.61-2.68 (1H, m), 3.60 (2H, s), 4.60-4.67 (1H, m), 7.19-7.37 (5H, m), 7.91 (1H, d, J=1.88 Hz), 8.52 (1H, d, J=1.88 Hz), 9.72 (1H, s)

Preparation 17

6-{[(3S)-1-Benzyl-3-pyrrolidinyl]amino}-5-chloronicotinaldehyde

NMR (DMSO-d$_6$, δ): 1.78-1.99 (1H, m), 2.18-2.30 (1H, m), 2.42-2.68 (3H, m), 2.82-2.90 (1H, m), 3.60 (2H, s), 4.59-4.64 (1H, m), 7.19-7.37 (6H, m), 7.91 (1H, d, J=1.96 Hz), 8.52 (1H, d, J=1.96 HZ), 9.72 (1H, s)

Preparation 18

6-[(1-Benzyl-3-pyrrolidinyl)(methyl)amino]-nicotinaldehyde

NMR (DMSO-d$_6$, δ): 1.65-1.78 (1H, m), 2.20-2.31 (2H, m), 2.45-2.54 (2H, m), 2.63-2.70 (1H, m), 2.82-2.89 (1H, m), 3.07 (3H, s), 3.55, 3.64 (2H, ABq, J=13.04 Hz), 5.40-5.42 (1H, m), 6.76 (1H, d, J=9.10 Hz), 7.23-7.35)$_5$H, m), 7.76 (1H, dd, J=2.24 Hz, 9.10 Hz), 8.56 (1H, d, J=2.24 Hz), 9.74 (1H, s)

Preparation 19 tert-Butyl 4-[(5-formyl-2-pyridyl)amino]-1-piperidinecarboxylate

NMR (CDCl$_3$, δ): 1.2-1.47(11H, m), 2.0-2.10(2H, m), 2.88-3.21(2H, m), 3.92-4.23(3H, m), 5.04(1H, d, J=15.8 Hz), 6.42 (1H, d, J=8.8 Hz), 7.88(1H, dd, J=2.0, 8.8 Hz), 8.51(1H, d, J=2.0 Hz), 9.77(1H, s)

Mass (APCI): 328(M+Na)+

Preparation 20 tert-Butyl 4-[(3-chloro-5-formyl-2-pyridyl)amino]-1-piperidinecarboxylate

NMR (DMSO-d$_6$, δ): 1.40(9H, s), 1.48-1.60(2H, m), 1.70-1.90(2H, m), 2.60-2.90(2H, m), 3.85-4.01(2H, m), 4.10-4.40 (1H, m), 7.26(1H, d, J=8.2 Hz), 7.93(1H, d, J=2.0 Hz), 8.54 (1H, d, J=2.0 Hz), 9.72(1H, s)

Mass (APCI): 362(M+Na)+

Preparation 21 tert-Butyl 4-[(5-formyl-2-pyridyl)(methyl)amino]-1-piperidinecarboxylate

NMR (DMSO-d$_6$, δ): 1.42(9H, s), 1.56-1.75(4H, m), 2.70-2.80(2H, m), 2.94(3H, s), 4.03-4.20(2H, m), 4.70-4.90(1H, m), 6.82(1H, d, J=8.8 Hz), 7.88(1H, dd, J=2.0, 8.8 Hz), 8.59 (1H, d, J=2.0 Hz), 9.72(1H, s)

Mass (APCI): 342(M+Na)+

Preparation 22

5-Chloro-6-{[(3R)-1-(4-fluorobenzyl)-3-pyrrolidinyl]amino}-nicotinaldehyde

Mass (ESI): 334(M+H)+

Preparation 23

5-Chloro-6-{[(3R)-1-(4-methylbenzyl)-3-pyrrolidinyl]amino}-nicotinaldehyde

NMR (DMSO-d$_6$, δ): 1.72-1.85(1H, m), 2.08-2.85(5H, m), 2.27(3H, s), 3.52(2H, s), 4.51-4.64(1H, m), 7.10(2H, d, J=8.8 Hz), 7.19(2H, d, J=8.8 Hz), 7.28(1H, d, J=7.0 Hz), 7.91(1H, d, J=2.0 Hz), 8.52(1H, d, J=2.0 Hz), 9.72(1H, s)

Mass (APCI): 330(M+H)+

Preparation 24

5-Chloro-6-{[(3R)-1-(4-methoxybenzyl)-3-pyrrolidinyl]amino}nicotinaldehyde

Mass (ESI): 346(M+H)+

Preparation 25

A solution of diethylphosphonoacetic acid ethyl ester (896 mg) in THF (10 ml) was added dropwise to a mixture of 60% sodium hydride in oil (170 mg) in THF (20 mL) with stirring at 10-20° C. under atmospheric pressure of nitrogen, and the reaction mixture was stirred at ambient temperature for 30 minutes. A solution of 6-[(1-benzyl-3-pyrrolidinyl)amino] nicotinaldehyde (0.75 g) in THF (10 ml) solution was added the above mixture, and resultant mixture was stirred at ambient temperature for 1.5 hour. The reaction mixture was poured into a mixture of AcOEt-H$_2$O and the organic layer was washed with brine and dried over MgSO$_4$. The solvent was evaporated in vacuo and the residue was chromatographed on silicagel eluting with AcOEt-MeOH (95:5). The eluted fractions containing the desired product were collected and evaporated in vacuo to give ethyl (2E)-3-{6-[(1-benzyl-3-pyrrolidinyl)amino]-3-pyridyl}acrylate (0.83 g).

NMR (DMSO-d$_6$, δ): 1.24 (3H, t, J=7.06 Hz), 1.50-1.73 (1H, m), 2.36-2.52 (3H, m), 2.73-2.77 (2H, m), 3.57 (2H, s), 4.14 (2H, q, J=7.06 Hz), 4.30 (1H, m), 6.31 (1H, d, J=15.80 Hz), 6.52 (1H, d, J=8.86 Hz), 7.18-7.36 (5H, m), 7.49 (1H, d, J=15.80 Hz), 7.77 (1H, dd, J=2.10 Hz, 8.86 Hz), 8.20 (1H, d, J=2.10 Hz)

The following compounds were obtained according to a similar manner to that of Preparation 25.

Preparation 26

Ethyl (2E)-3-{6-[(1-benzyl-3-pyrrolidinyl)(methyl)amino]-3-pyridyl}acrylate

NMR (DMSO-d$_6$, δ): 1.24 (3H, t, J=7.06 Hz), 1.56-1.82 (1H, m), 2.27-2.61 (4H, m), 2.83-2.84 (1H, m), 3.00 (3H, s), 3.58 and 3.63 (2H, ABq, J=13.02 Hz), 5.25-5.39 (1H, m), 6.38 (1H, d, J=15.94 Hz), 6.67 (1H, d, J=9.06 Hz), 7.19-7.34 (5H, m), 7.53 (1H, d, J=15.94 Hz), 7.90 (1H, dd, J=2.26 Hz, 9.06 Hz), 8.30 (1H, d, J=2.26 Hz)

Preparation 27

Ethyl (2E)-3-(6-{[(3R)-1-benzyl-3-pyrrolidinyl]amino}-3-pyridyl)acrylate

NMR (DMSO-d$_6$, δ): 125 (3H, t, J=7.06 Hz), 1.56-1.78 (1H, m), 2.10-2.20 (1H, m), 2.34-2.52 (2H, m), 2.52-2.78 (2H, m), 3.57 (2H, s), 4.15 (2H, q, J=7.06 Hz), 4.36 (1H, m), 6.41 (1H, d, J=15.92 Hz), 6.52 (1H, d, J=8.82 Hz), 7.18-7.37 (6H, m), 7.50 (1H, d, J=15.92 Hz), 7.78 (1H, dd, J=2.10 Hz, 8.82 Hz), 8.20 (1H, d, J=2.10 Hz)

Preparation 28

Ethyl (2E)-3-(6-{[(3S)-1-benzyl-3-pyrrolidinyl]amino}-3-pyridyl)acrylate

NMR (DMSO-d$_6$, δ): 1.24 (3H, t, J=7.06 Hz), 1.56-1.73 (1H, m), 2.21-2.37 (1H, m), 2.39-2.52 (2H, m), 2.73-2.78 (2H, m), 3.57 (2H, s), 4.15 (2H, q, J=7.06 Hz), 4.36 (1H, m), 6.31 (1H, d, J=15.90 Hz), 6.52 (1H, d, J=8.86 Hz), 7.18-7.36 (5H, m), 7.50 (1H, d, J=15.90 Hz), 7.77 (1H, dd, J=2.14 Hz, 8.86 Hz), 8.20 (1H, d, J=2.14 Hz)

Preparation 29

Ethyl (2E)-3-(6-{[(3R)-1-benzyl-3-pyrrolidinyl] amino}-5-chloro-3-pyridyl)acrylate NMR (DMSO-$d_6$, δ): 1.24 (3H, t, J=7.06 Hz), 1.84-1.97 (1H, m), 2.00-2.30 (1H, m), 2.39-2.53 (2H, m), 2.62-2.78 (1H, m), 2.79-2.87 (1H, m), 3.59 (2H, s), 4.16 (2H, q, J=7.06 Hz), 4.49-4.56 (1H, m), 6.49 (1H, d, J=15.96 Hz), 6.73 (1H, d, J=6.90 Hz), 7.19-7.32 (5H, m), 7.51 (1H, d, J=15.96 Hz), 8.10 (1H, d, J=1.88 Hz), 8.26 (1H, d, J=1.88 Hz)

Preparation 30

Ethyl (2E)-3-(6-{[(3S)-1-benzyl-3-pyrrolidinyl] amino}-5-chloro-3-pyridyl)acrylate NMR (DMSO-$d_6$, δ): 1.24 (3H, t, J=7.06 Hz), 1.84-1.99 (1H, m), 2.16-2.30 (1H, m), 2.39-2.46 (2H, m), 2.62-2.66 (1H, m), 2.79-2.88 (1H, m), 3.58 (2H, s), 4.16 (2H, q, J=7.06 Hz), 4.49-4.56 (1H, m), 6.49 (1H, D, J=15.98 Hz), 6.72 (1H, d, J=6.92 Hz), 7.18-7.36 (5H, m), 7.51 (1H, d, J=15.98 Hz), 8.10 (1H, d, J=1.96 Hz), 8.26 (1H, d, J=1.96 Hz)

Preparation 31 tert-Butyl 4-({5-[(1E)-3-ethoxy-3-oxo-1-propen-1-yl]-2-pyridyl}amino)-1-piperidinecarboxylate NMR (DMSO-$d_6$, δ): 1.33(3H, t, J=7.1 Hz), 1.36-1.42(2H, m), 1.47(9H, s), 2.00-2.08(2H, m), 2.88-3.02(2H, m), 3.80-4.00(1H, m), 4.03-4.20(2H, m), 4.24(2H, q), 4.6(1H, m), 6.22(1H, d, J=16.0 Hz), 6.38(1H, d, J=8.7 Hz), 7.57(1H, d, J=16.0 Hz), 7.61(1H, dd, J=2.4, 8.7 Hz), 8.19(1H, d, J=2.4 Hz)

Mass (APCI): 398(M+H)+

Preparation 32 tert-Butyl 4-({3-chloro-5-[(1E)-3-ethoxy-3-oxo-1-propen-1-yl]-2-pyridyl}amino)-1-piperidinecarboxylate Mass (ESI): 410(M+H)+

Preparation 33 tert-Butyl 4-[{5-[(1E)-3-ethoxy-3-oxo-1-propen-1-yl]-2-pyridyl}-(methyl)amino]-1-piperidinecarboxylate Mass (ESI): 390(M+H)+

Preparation 34

Ethyl (2E)-3-(5-chloro-6-{[(3R)-1-(4-fluorobenzyl)-3-pyrrolidinyl]amino}-3-pyridyl)acrylate Mass (ESI): 404(M+H)+

Preparation 35

Ethyl (2E)-3-(5-chloro-6-{[(3R)-1-(4-methylbenzyl)-3-pyrrolidinyl]amino}-3-pyridyl)acrylate NMR (DMSO-$d_6$, δ): 1.24(3H, t, J=7.4 Hz), 1.70-1.95(1H, m), 2.10-2.29(1H, m), 2.27(3H, s), 2.35-2.84(4H, m), 3.53 (2H, s), 4.15(2H, q, J=7.4 Hz), 4.44-4.54(1H, m), 6.48(1H, d, J=16.0 Hz), 6.72(1H, d, J=7.0 Hz), 7.10(2H, d, J=8.8 Hz), 7.18(2H, d, J=8.8 Hz), 7.50(1H, d, J=16.0 Hz), 8.10(1H, d, J=2.0 Hz), 8.26(1H, d, J=2.0 Hz)

Mass (APCI): 400(M+H)+

Preparation 36

Ethyl (2E)-3-(5-chloro-6-{[(3R)-1-(4-methoxybenzyl)-3-pyrrolidinyl]amino}-3-pyridyl)acrylate NMR (DMSO-$d_6$, δ): 1.45-1.85(9H, m), 1.90-2.10(2H, m), 2.70-2.85(2H, m), 3.44(2H, s), 3.45-3.58(1H, m), 3.85-4.15 (2H, m), 4.90(1H, s), 6.32(1H, d, J=16.0 Hz), 6.51(1H, d, J=7.0 Hz), 7.10-7.478(5H, m), 7.84(1H, s), 8.21(1H, s), 11.09 (1H, brs)

Preparation 37

A mixture of ethyl (2E)-3-{6-[(1-benzyl-3-pyrrolidinyl) amino]-3-pyridyl}-acrylate (830 mg) and 1N NaOH solution (4.7 ml) in MeOH (20 ml) was stirred at 70-75° C. for 2 hours. The reaction mixture was evaporated in vacuo, and the residue was dissolved with saturated NaCl solution (20 ml). The solution was adjusted to pH6.0 with aq. HCl, and the precipitate was collected by filtration to give (2E)-3-{6-[(1-benzyl-3-pyrrolidinyl)amino]-3-pyridyl}-acrylic acid (700 mg)

NMR (DMSO-$d_6$, δ): 1.92-2.01 (1H, m), 2.30-2.43 (1H, m), 2.94-3.52 (4H, m), 4.29 (2H, s), 4.53-4.56 (1H, m), 6.28 (1H, d, J=15.82 Hz), 6.62 (1H, d, J=8.78 Hz), 7.39-7.64 (6H, m), 7.75-7.83 (2H, m), 8.20 (1H, d, J=2.00 Hz), 11.92 (1H, m)

The following compounds were obtained according to a similar manner to that of Preparation 37.

Preparation 38

(2E)-3-{6-[(1-Benzyl-3-pyrrolidinyl)(methyl) amino]-3-pyridyl}acrylic acid

NMR (DMSO-$d_6$, δ): 2.08-2.16 (1H, m), 2.80-3.60 (5H, m), 4.23 (2H, brs), 5.54-5.61 (1H, m), 6.35 (1H, d, J=15.92 Hz), 6.72 (1H, d, J=9.02 Hz), 7.39-7.62 (6H, m), 7.92 (1H, dd, J=2.04 Hz, 9.06 Hz), 8.32 (1H, d, J=2.04 Hz)

Preparation 39

(2E)-3-(6-{[(3R)-1-Benzyl-3-pyrrolidinyl]amino}-3-pyridyl)acrylic acid

NMR (DMSO-$d_6$, δ): 1.87-1.93 (1H, m), 2.28-2.38 (1H, m), 2.83-3.37 (4H, m), 4.15 (2H, s), 6.29 (1H, d, J=15.92 Hz), 6.62 (1H, d, J=8.88 Hz), 7.32-7.43 (3H, m), 7.51-7.58 (2H, m), 7.77-7.81 (2H, m), 8.20 (1H, d, J=1.94 Hz)

Preparation 40

(2E)-3-(6-{[(3S)-1-Benzyl-3-pyrrolidinyl]amino}-3-pyridyl)acrylic acid

NMR (DMSO-$d_6$, δ): 1.98-2.04 (1H, m), 2.31-2.38 (1H, m), 2.95-3.56 (4H, m), 4.35 (2H, s), 4.55-4.58 (1H, m), 6.29 (1H, d, J=15.86 Hz), 6.63 (1H, d, J=8.82 Hz), 7.40-7.67 (6H, m), 8.10 (1H, dd, J=2.08 Hz, 8.82 Hz), 7.92 (1H, brs), 8.20 (1H, d, J=2.08 Hz)

Preparation 41

(2E)-3-(6-{[(3R)-1-Benzyl-3-pyrrolidinyl]amino}-5-chloro-3-pyridyl)acrylic acid

NMR (DMSO-$d_6$, δ): 1.76-1.99 (1H, m), 2.19-2.24 (1H, m), 2.48-2.77 (3H, m), 2.91-2.96 (1H, m), 3.60 (2H, s), 4.49-4.56 (1H, m), 6.39 (1H, d, J=15.88Hz), 6.74 (1H, d, J=6.88Hz), 7.21-7.35 (5H, m), 7.45 (1H, d, J=15.88Hz), 8.07 (1H, d, J=1.82Hz), 8.24 (1H, d, J=1.82Hz)

Preparation 42

(2E)-3-(6-{[(3S)-1-Benzyl-3-pyrrolidinyl]amino}-5-chloro-3-pyridyl)acrylic acid

NMR (DMSO-d$_6$, δ): 1.89-1.99 (1H, m), 2.19-2.27 (1H, m), 2.58-3.07 (4H, m), 3.74 (2H, s), 4.44-4.59 (1H, m), 6.40 (1H, d, J=15.96 Hz), 6.82 (1H, d, J=6.88 Hz), 7.25-7.40 (5H, m), 7.46 (1H, d, J=15.96 Hz), 8.08 (1H, d, J=1.82 Hz), 8.24 (1H, d, J=1.82 Hz)

Preparation 43

(2E)-3-(6-{[(3R)-1-(4-Methoxybenzyl)-3-pyrrolidinyl]amino}-3-pyridyl)acrylic acid NMR (DMSO-d$_6$, δ): 1.60-1.95 (1H, m), 2.10-2.40 (1H, m), 2.50-4.00 (6H, m), 3.74 (3H, s), 4.30-4.60 (1H, m), 6.24 (1H, d, J=6 Hz), 6.54 (1H, d, J=8.8 Hz), 6.92 (2H, d, J=8.5 Hz), 7.30-7.60 (4H, m), 7.78 (1H, dd, J=2.1 Hz, J=8.8 Hz), 8.18 (1H, d, J=2.1 Hz), 11.80 (1H, br)

MASS(API-ES); 354 (M+H)+

Preparation 44

(2E)-3-(6-{[(3R)-1-(4-Fluorobenzyl)-3-pyrrolidinyl]amino}-3-pyridyl)acrylic acid NMR (DMSO-d$_6$, δ): 1.50-1.80 (1H, m), 2.05-2.90 (5H, m), 3.50-3.70 (2H, m), 4.20-4.50 (1H, m), 6.22 (1H, d, J=16 Hz), 6.53 (1H, d, J=8.8 Hz), 7.05-7.18 (2H, m), 7.30-7.40 (3H, m), 7.43 (1H, d, J=6 Hz), 7.74 (1H, dd, J=2.1 and 8.8 Hz), 8.15 (1H, d, J=2.1 Hz)

MASS(API-ES, Nega); 340 (M−H)+

Preparation 45

(2E)-3-(6-{[(3R)-1-(4-Chlorobenzyl)-3-pyrrolidinyl]amino}-3-pyridyl)acrylic acid NMR (DMSO-d$_6$, δ): 1.60-1.85 (1H, m), 2.10-3.00 (5H, m), 3.10-3.90 (2H, m), 4.25-4.50 (1H, m), 6.23 (1H, d, J=16 Hz), 6.53 (1H, d, J=8.8 Hz), 7.30-7.55 (6H, m), 7.75 (1H, dd, J=2.1 Hz, J=8.8 Hz), 8.17 (1H, d, J=2.1 Hz)

MASS(API-ES); 358 (M+H)+360

Preparation 46

(2E)-3-(6-{[(3R)-1-(4-Methylbenzyl)-3-pyrrolidinyl]amino}-3-pyridyl)acrylic acid NMR (DMSO-d$_6$, δ): 1.60-1.90 (1H, m), 2.10-3.15 (5H, m), 2.28 (3H, s), 3.50-3.95 (2H, m), 4.25-4.50 (1H, m), 6.24 (1H, d, J=16 Hz), 6.54 (1H, d, J=8.8 Hz), 7.15 (2H, d, J=7.8 Hz), 7.29 (2H, d, J=7.8 Hz), 7.44 (1H, d, J=16 Hz), 7.48(1H, m), 7.76 (1H, dd, J=2.1 Hz, J=8.8 Hz), 8.17 (1H, d, J=2.1 Hz)

MASS(API-ES); 338 (M+H)+

Preparation 47

(2E)-3-(6-{[(3R)-1-(Cyclopropylmethyl)-3-pyrrolidinyl]-amino}-3-pyridyl)acrylic acid NMR (DMSO-d$_6$, δ): 0.05-0.25 (2H, m), 0.40-0.60 (2H, m), 0.80-1.05 (1H, m), 1.60-1.85 (1H, m), 2.10-3.90 (7H, m), 4.25-4.55 (1H, m), 6.24 (1H, d, J=16 Hz), 6.55 (1H, d, J=8.8 Hz), 7.44 (1H, d, J=16 Hz), 7.47 (1H, d, J=6.1 Hz), 7.77 (1H, dd, J=2.1 Hz, J=8.8 Hz), 8.19 (1H, d, J=2.1 Hz)

MASS(API-ES); 288 (M+H)+

Preparation 48

(2E)-3-(6-{[(3R)-1-Benzoyl-3-pyrrolidinyl]amino}-5-chloro-3-pyridyl)acrylic acid NMR (DMSO-d$_6$, δ): 1.90-2.40 (2H, m), 3.20-4.00 (4H, m), 4.40-4.80 (1H, m), 6.30-6.50 (1H, m), 6.95-7.10 (1H, m), 7.35-7.60 (6H, m), 8.05-8.15 (1H, m), 8.20-8.35 (1H, m), 12.26 (1H, br)

MASS(API-ES); 372 (M+H)+, 374

Preparation 49

(2E)-3-(5-Chloro-6-{[(3R)-1-(cyclopropylcarbonyl)-3-pyrrolidinyl]amino}-3-pyridyl)acrylic acid NMR (DMSO-d$_6$, δ): 0.60-0.80 (4H, m), 1.60-1.85 (1H, m), 1.87-2.40 (2H, m), 3.20-4.10 (4H, m), 4.45-4.80 (1H, m), 6.42 (1H, d, J=16 Hz), 6.90-7.05 (1H, m), 7.48 (1H, d, J=16 Hz), 8.07-8.14 (1H, m), 8.25-8.32 (1H, m), 12.21 (1H, br)

MASS(API-ES, Nega); 334 (M−H)−

Preparation 50

(2E)-3-{6-[(1-Benzoyl-4-piperidyl)amino]-3-pyridyl}-acrylic acid

NMR (DMSO-d$_6$, δ): 1.20-1.60(2H, m), 1.70-2.10(2H, m), 3.00-3.60(3H, m), 4.00-4.20(1H, m), 4.20-4.60(1H, m), 6.23 (1H, d, J=16.0 Hz), 6.53(1H, d, J=8.8 Hz), 7.10-7.30(1H, m), 7.35-7.48(6H, m), 7.78(1H, dd, J=2.0, 8.8 Hz), 8.19(1H, d, J=2.0 Hz)

Mass (APCI): 352(M+H)+

Preparation 51

(2E)-3-(6-{[1-(4-Fluorobenzoyl)-4-piperidyl]amino}-3-pyridyl)acrylic acid

NMR (DMSO-d$_6$, δ): 1.30-1.55(2H, m), 1.85-2.10(2H, m), 3.00-3.30(2H, m), 3.58(1H, brs), 4.05-4.11(1H, m), 4.33(1H, brs), 6.22(H, d), 6.22(1H, d, J=8.4 Hz), 6.52(1H, d, J=8.8 Hz), 7.17(1H, brs), 7.26-7.30(2H, m), 7.42-7.48(3H, m), 7.77(1H, dd, J=2.2, 8.8 Hz), 8.19(1H, d, J=2.2 Hz), 12.06(1H, brs)

Mass (APCI): 392(M+Na)+

Preparation 52

(2E)-3-(6-{[1-(4-Methylbenzoyl)-4-piperidyl]amino}-3-pyridyl)acrylic acid

NMR (DMSO-d$_6$, δ): 1.20-1.60(2H, m), 1.80-2.10(2H, m), 2.34(3H, s), 3.03-4.40(6H, m), 6.22(1H, d, J=16.0 Hz), 6.50 (1H, d, J=8.8 Hz), 7.14(1H, d, J=7.4 Hz), 7.21-7.31(4H, m), 7.44(1H, d, J=16.0 Hz), 7.76(1H, dd, J=2.0, 8.8 Hz), 8.18(1H, d, J=2.0 Hz).

Mass (APCI): 383(M+Na)+

Preparation 53

(2E)-3-(6-{[1-(4-Methoxybenzoyl)-4-piperidyl]amino}-3-pyridyl)acrylic acid

NMR (DMSO-d$_6$, δ): 1.31-1.16(2H, m), 1.80-2.00(2H, m), 3.00-3.20(2H, m), 3.82(3H, s), 4.00-4.20(2H, m), 6.24(1H, d, J=16.0 Hz), 6.55(1H, d, J=8.8 Hz), 6.99(2H, d, J=8.8 Hz), 7.27(1H, brs), 7.36(2H, d, J=8.8 Hz), 7.44(1H, d, J=16.0 Hz), 7.78(1H, dd, J=2.1, 8.8 Hz), 8.19(1H, d, J=2.1 Hz), 12.13(1H, brs)

Mass (APCI): 404(M+Na)+

Preparation 54

(2E)-3-[6-({1-[4-(1H-Pyrrol-1-yl)benzoyl]-4-piperidyl}-amino)-3-pyridyl]acrylic acid NMR (DMSO-d$_6$, δ): 1.35-1.60(2H, m), 1.85-2.10(2H, m), 3.10-3.40(2H, m), 3.50-4.50(3H, m), 6.28-6.33(3H, m), 6.54(1H, d, J=8.8 Hz), 7.23(1H, d, J=7.4 Hz), 7.42-7.50(6H, m), 7.66(2H, d, J=8.6 Hz), 7.77(1H, dd, J=2.0, 8.8 Hz), 8.20(1H, d, J=2.0 Hz), 12.13(1H, brs)

Preparation 55

(2E)-3-(6-[(1-{[(4-Chlorophenyl)amino]carbonyl)-4-piperidyl)amino]-3-pyridyl}acrylic acid NMR (DMSO-d$_6$, δ): 1.29-1.45(2H, m), 1.80-2.05(2H, m), 2.85-3.10(2H, m), 3.80-4.20(3H, m), 6.25(1H, d, J=16.0 Hz), 6.75(1H, d, J=8.8 Hz), 7.20-7.60(6H, m), 7.82(1H, dd, J=2.0, 8.8 Hz), 8.20d(1H, d, J=2.0 Hz), 8.69(1H, s), 12.09(1H, brs).

Mass (APCI): 399(M−H)−

Preparation 56

(2E)-3-{6-[(1-{[(4-Methylphenyl)amino]carbonyl}-4-piperidyl)amino]-3-pyridyl}acrylic acid NMR (DMSO-d$_6$, δ): 1.23-1.43(2H, m), 1.89-2.10(2H, m), 2.22(3H, s), 2.84-3.01(2H, m), 4.02-7.10(3H, m), 6.23(1H, d, J=16.0 Hz), 6.52(1H, d, J=8.8 Hz), 7.02(2H, d, J=8.8 Hz), 7.18(1H, d, J=7.0 Hz), 7.34(2H, d, J=8.8 Hz), 7.45(1H, d, J=16.0 Hz), 7.76(1H, dd, J=2.0, 8.8 Hz), 8.20(1H, d, J=2.0 Hz), 8.43(1H, s), 12.04(1H, brs)

Mass (APCI): 403(M+Na)+

Preparation 57

(2E)-3-(6-[(1-{[(4-Methoxyphenyl)amino]carbonyl)-4-piperidyl)amino]-3-pyridyl}acrylic acid NMR (DMSO-d$_6$, δ): 1.28-1.43(2H, m), 1.76-1.94(2H, m), 2.89-3.01(2H, m), 3.70(3H, s), 4.01-4.08(3H, m), 6.23(1H, d, J=16.0 Hz), 6.52(1H, d, J=8.8 Hz), 6.81(2H, d, J=8.8 Hz), 7.18-7.22(1H, m), 7.34(2H, d, J=8.8 Hz), 7.45(1H, d, J=16.0 Hz), 7.77(1H, dd, J=2.0, 8.8 Hz), 8.20(1H, d, J=2.0 Hz), 8.36(1H, s), 12.04(1H, brs)

Mass (APCI): 419(M+Na)+

Preparation 58

(2E)-3-{6-[(1-Benzoyl-4-piperidyl)amino]-5-chloro-3-pyridyl}acrylic acid

NMR (DMSO-d$_6$, δ): 1.50-2.01(4H, m), 2.60-3.80(4H, m), 4.2-4.7(2H, m), 6.38(1H, d, J=16.0 Hz), 6.70(1H, d, J=8.0 Hz), 7.35-7.49(6H, m), 8.08(1H, d, J=2.0 Hz), 8.26(1H, d, J=2.0 Hz)

Mass (APCI): 408(M+Na)+

Preparation 59

(2E)-3-(5-Chloro-6-{[1-(4-chlorobenzoyl)-4-piperidyl]amino}-3-pyridyl)acrylic acid NMR (DMSO-d$_6$, δ): 1.50-2.01(4H, m), 2.60-3.80(4H, m), 4.2-4.7(2H, m), 6.38(1H, d, J=16.0 Hz), 6.70(1H, d, J=8.0 Hz), 7.35-7.57(5H, m), 8.08(1H, d, J=2.0 Hz), 8.26(1H, d, J=2.0 Hz)

Mass (APCI): 442(M+Na)+

Preparation 60

(2E)-3-(5-Chloro-6-{[1-(4-phenoxybenzoyl)-4-piperidyl]amino}-3-pyridyl)acrylic acid NMR (DMSO-d$_6$, δ): 1.45-1.75(2H, m), 1.75-2.10(2H, m), 2.70-4.70(6H, m), 6.37(1H, d, J=16.0 Hz), 6.61(1H, d, J=8.0 Hz), 7.07-7.47(9H, m), 7.99(1H, s), 8.19(1H, s)

Mass (APCI): 476(M−H)−

Preparation 61

(2E)-3-(5-Chloro-6-{[1-(4-fluorobenzyl)-4-piperidyl]amino}-3-pyridyl)acrylic acid NMR (DMSO-d$_6$, δ): 1.80-2.20(4H, m), 2.90-3.24(2H, m), 4.10-4.40(3H, m), 6.38(1H, d, J=16.0 Hz), 6.98(1H, d, J=7.8 Hz), 7.26-7.35(2H, m), 7.46(1H, d, J=16.0 Hz), 7.67-7.73(2H, m), 8.09(1H, s), 8.23(1H, s), 10.98(1H, brs), 12.21(1H, brs)

Preparation 62

A mixture of (2E)-3-{6-[(1-benzyl-3-pyrrolidinyl)amino]-3-pyridyl}acrylic acid (400 mg), O-(tetrahydro-2H-pyran-2-yl)hydroxylamine (159 mg), HOBt (175 mg) and EDCI (202 mg) in DMF (10 ml) was stirred at ambient temperature for 15 hours. The reaction mixture was poured into a mixture of AcOEt-H$_2$O and the organic layer was washed with brine and dried over MgSO$_4$. The solvent was evaporated in vacuo and the residue was chromatographed on silicagel eluting with AcOEt-MeOH (9:1). The eluted fractions containing the desired product were collected and evaporated in vacuo to give (2E)-3-{6-[(1-benzyl-3-pyrrolidinyl)amino]-3-pyridyl)-N-(tetrahydro-2H-pyran-2-yloxy)acrylamide (170 mg)

NMR (DMSO-d$_6$, δ): 1.52-1.68 (7H, m), 2.09-2.50 (3H, m), 2.61-2.81 (2H, m), 3.34 (2H, s), 3.34-3.57 (2H, m), 3.92-3.98 (1H, m), 4.32-4.33 (1H, m), 4.87 (1H, s), 6.20 (1H, d, J=15.20 Hz), 6.53 (1H, d, J=8.82 Hz), 7.20-7.37 (7H, m), 7.58 (1H, d, J=7.90 Hz), 8.11 (1H d, J=1.84 Hz), 11.03 (1H, brs)

The following compounds were obtained according to a similar manner to that of Preparation 62.

Preparation 63

(2E)-3-(6-[(1-Benzyl-3-pyrrolidinyl)(methyl)amino]-3-pyridyl}-N-(tetrahydro-2H-pyran-2-yloxy)acrylamide NMR (DMSO-$d_6$, δ): 1.17-1.76 (7H, m), 1.99-2.44 (2H, m), 2.49-3.00 (3H, m), 2.99 (3H, s), 3.49-3.69 (4H, m), 3.93-4.01 (1H, m), 4.89 (1H, s), 5.29-5.33 (1H, m), 6.28 (1H, d, J=15.44 Hz), 6.69 (1H, d, J=9.02 Hz), 7.19-7.42 (6H, m), 7.71 (1H, d, J=9.02 Hz), 8.24 (1H, s), 11.05 (1H, s)

Preparation 64

(2E)-3-(6-{[(3R)-1-Benzyl-3-pyrrolidinyl]amino}-3-pyridyl)-N-(tetrahydro-2H-pyran-2-yloxy)acrylamide NMR (DMSO-$d_6$, δ): 1.52-1.99 (7H, m), 2.22-2.50 (3H, m), 2.62-2.89 (2H, m), 3.57 (2H, s), 3.34-3.57 (2H, m), 3.98-4.05 (1H, m), 4.30 (1H, m), 8.47 (1H, brs), 6.30 (1H, d, J=15.90 Hz), 6.52 (1H, d, J=8.80 Hz), 7.20-7.37 (7H, m), 7.58 (1H, d, J=8.80 Hz), 8.11 (1H, s), 11.03 (1H, s)

Preparation 65

(2E)-3-(6-{[(3S)-1-Benzyl-3-pyrrolidinyl]amino}-3-pyridyl)-N-(tetrahydro-2H-pyran-2-yloxy)acrylamide NMR (DMSO-$d_6$, δ): 1.52-1.99 (7H, m), 2.22-2.45 (3H, m), 2.62-2.81 (2H, m), 3.51 (2H, s), 3.34-3.57 (2H, m), 3.92-4.00 (1H, m), 4.31 (1H, m), 4.87 (1H, s), 6.20 (1H, d, J=16.10 Hz), 6.52 (1H, d, J=8.84 Hz), 7.20-7.37 (7H, m), 7.58 (1H, d, J=7.76 Hz), 8.11 (1H, d, J=1.92 Hz), 11.03 (1H, s)

Preparation 66

(2E)-3-(6-{[(3R)-1-Benzyl-3-pyrrolidinyl]amino}-5-chloro-3-pyridyl)-N-(tetrahydro-2H-pyran-2-yloxy)acrylamide NMR (DMSO-$d_6$, δ): 1.53-2.00 (7H, m), 2.00-2.30 (1H, m), 2.30-2.78 (3H, m), 2.82-2.89 (1H, m), 3.59 (2H, s), 3.36-3.59 (2H, m), 3.96-4.01 (1H, m), 4.41-4.55 (1H, m), 4.89 (1H, s), 6.32 (1H, d, J=15.68 Hz), 6.42 (1H, d, J=6.88 Hz), 7.19-7.40 (6H, m), 7.84 (1H, s), 8.20 (1H, s), 11.08 (1H, brs)

Preparation 67

(2E)-3-(6-{[(3S)-1-Benzyl-3-pyrrolidinyl]amino}-5-chloro-3-pyridyl)-N-(tetrahydro-2H-pyran-2-yloxy)acrylamide NMR (DMSO-$d_6$, δ): 1.53-2.00 (7H, m), 2.10-2.32 (1H, m), 2.39-2.53 (2H, m), 2.63-2.67 (1H, m), 2.74-2.89 (1H, m), 3.56 (2H, s), 3.50-3.59 (2H, m), 3.96-4.05 (1H, m), 4.48-4.53 (1H, m), 4.90 (1H, s), 6.33 (1H, d, J=15.74 Hz), 6.94 (1H, d, J=6.88 Hz), 7.19-7.33 (6H, m), 7.85 (1H, s), 7.99 (1H, s), 8.20 (1H, s), 11.09 (1H, brs)

Preparation 68

(2E)-3-(6-{[(3R)-1-(4-Methoxybenzyl)-3-pyrrolidinyl]amino}-3-pyridyl)-N-(tetrahydro-2H-pyran-2-yloxy)acrylamide NMR (DMSO-$d_6$, δ): 1.40-1.80 (7H, m), 2.05-2.90 (5H, m), 3.40-3.60 (3H, m), 3.72 (3H, s), 3.80-4.05 (1H, m), 4.20-4.45 (1H, m), 4.87 (1H, s), 6.20 (1H, d, J=16 Hz), 6.51 (1H, d, J=8.8 Hz), 6.86 (2H, d, J=8.5 Hz), 7.21 (2H, d, J=8.5 Hz), 7.20-7.30 (1H, m), 7.33 (1H, d, J=16 Hz), 7.58 (1H, dd, J=1.9 Hz, J=8.8 Hz), 8.11 (1H, d, J=1.9 Hz), 11.03 (1H, br)

MASS(API-ES); 453 (M+H)+

Preparation 69

(2E)-3-(6-{[(3R)-1-(4-Fluorobenzyl)-3-pyrrolidinyl]amino}-3-pyridyl)-N-(tetrahydro-2H-pyran-2-yloxy)acrylamide NMR (DMSO-$d_6$, δ): 1.45-1.80 (7H, m), 2.05-3.00 (5H, m), 3.20-3.65 (3H, m), 3.80-4.05 (1H, m), 4.20-4.45 (1H, m), 4.87 (1H, s), 6.20 (1H, d, J=16 Hz), 6.51 (1H, d, J=8.8 Hz), 7.05-7.40 (6H, m), 7.59 (1H, dd, J=1.8 Hz, J=8.8 Hz), 8.12 (1H, d, J=1.8 Hz), 11.05 (1H, br)

MASS(API-ES); 441 (M+H)+

Preparation 70

(2E)-3-(6-{[(3R)-1-(4-Chlorobenzyl)-3-pyrrolidinyl]amino}-3-pyridyl)-N-(tetrahydro-2H-pyran-2-yloxy)acrylamide NMR (DMSO-$d_6$, δ): 1.40-1.80 (7H, m), 2.05-2.90 (5H, m), 3.40-3.65 (3H, m), 3.80-4.05 (1H, m), 4.20-4.50 (1H, m), 4.87 (1H, s), 6.20 (1H, d, J=16 Hz), 6.52 (1H, d, J=8.8 Hz), 7.22 (1H, d, J=6.6 Hz), 7.27-7.45 (5H, m), 7.59 (1H, dd, J=1.9 Hz, J=8.8 Hz), 8.12 (1H, d, J=1.9 Hz), 11.04 (1H, br)

MASS(API-ES); 457 (M+H)+459

Preparation 71

(2E)-3-(6-{[(3R)-1-(4-Methylbenzyl)-3-pyrrolidinyl]amino}-3-pyridyl)-N-(tetrahydro-2H-pyran-2-yloxy)acrylamide NMR (DMSO-$d_6$, δ): 1.40-1.80 (7H, m), 2.05-2.85 (5H, m), 2.27 (3H, s), 3.40-3.65 (3H, m), 3.80-4.05 (1H, m), 4.20-4.45 (1H, m), 4.87 (1H, s), 6.20 (1H, d, J=16 Hz), 6.51 (1H, d, J=8.8 Hz), 7.05-7.25 (5H, m), 7.33 (1H, d, J=16 Hz), 7.58 (1H, dd, J=1.9 and 8.8 Hz), 8.11 (1H, d, J=1.9 Hz), 11.03 (1H, br)

MASS(API-ES); 437 (M+H)+

Preparation 72

(2E)-3-(6-{[(3R)-1-(Cyclopropylmethyl)-3-pyrrolidinyl]amino}-3-pyridyl)-N-(tetrahydro-2H-pyran-2-yloxy)acrylamide NMR (DMSO-$d_6$, δ): 0.00-0.15 (2H, m), 0.35-0.50 (2H, m), 0.70-0.95 (1H, m), 1.40-1.85 (7H, m), 2.08-2.53 (5H, m), 2.55-2.82 (2H, m), 3.40-3.60 (1H, m), 3.80-4.10 (1H, m), 4.20-4.50 (1H, m), 4.87 (1H, s), 6.21 (1H, d, 3=16 Hz), 6.52 (1H, d, J=8.8 Hz), 7.23 (1H, d, J=6.8 Hz), 7.34 (1H, d, J=16 Hz), 7.59 (1H, dd, J=1.9 and 8.8 Hz), 8.14 (1H, d, J=1.9 Hz), 11.04 (1H, br)

MASS(API-ES); 387 (M+H)+

Preparation 73

(2E)-3-(6-{[(3R)-1-Benzoyl-3-pyrrolidinyl]amino}-5-chloro-3-pyridyl)-N-(tetrahydro-2H-pyran-2-yloxy)acrylamide NMR (DMSO-$d_6$, δ): 1.40-1.80 (6H, m), 1.90-2.40 (2H, m), 3.10-4.10 (6H, m), 4.40-4.85 (1H, m), 4.89 (1H, s), 6.20-6.50

(1H, m), 6.90-7.05 (1H, m), 7.25-7.60 (6H, m), 7.80-7.95 (1H, m), 8.15-8.30 (1H, m), 11.10 (1H, br)

MASS(API-ES); 471 (M+H)+, 473

Preparation 74

(2E)-3-(5-Chloro-6-{[(3R)-1-(cyclopropylcarbonyl)-3-pyrrolidinyl]amino}-3-pyridyl)-N-(tetrahydro-2H-pyran-2-yloxy)acrylamide NMR (DMSO-$d_6$, δ): 0.60-0.80 (4H, m), 1.40-1.85 (7H, m), 1.90-2.40 (2H, m), 3.15-4.10 (6H, m), 4.40-4.85 (1H, m), 4.89 (1H, s), 6.35 (1H, d, J=16 Hz), 6.85-7.00 (1H, m), 7.38 (1H, d, J=16 Hz), 7.88 (1H, s), 8.25 (1H, s), 11.09 (1H, br)

MASS(API-ES); 435 (M+H)+, 437

Preparation 75

(2E)-3-(5-Chloro-6-{[1-(4-phenoxybenzoyl)-4-piperidyl]amino}-3-pyridyl)-N-(tetrahydro-2H-pyran-2-yloxy)acrylamide Mass (APCI): 599(M+Na)+

Preparation 76

(2E)-3-(5-Chloro-6-{[1-(4-chlorobenzyl)-4-piperidyl]amino}-3-pyridyl)-N-(tetrahydro-2H-pyran-2-yloxy)acrylamide NMR (DMSO-$d_6$, δ): 1.45-1.90(9H, m), 1.95-2.15(2H, m), 2.70-2.82(2H, m), 3.46(2H, s), 3.46-3.55(1H, m), 3.85-4.10 (2H, m), 4.88(1H, s), 6.30(1H, d, J=16.0 Hz), 6.51(1H, d, J=7.0 Hz), 7.29-7.46(5H, m), 7.83(1H, s), 8.20(1H, s), 11.08 (1H, brs)

Preparation 77

(2E)-3-(5-Chloro-6-{[1-(4-fluorobenzyl)-4-piperidyl]amino}-3-pyridyl)-N-(tetrahydro-2H-pyran-2-yloxy)acrylamide NMR (DMSO-$d_6$, δ): 1.50-2.10(10H, m), 2.80-3.60(2H, m), 3.80-4.20(2H, m), 4.88(1H, s), 6.32(1H, d, J=16.0 Hz), 6.80 (1H, brs), 7.10-60(4H, m), 7.36(1H, d, J=16.0 Hz), 7.86(1H, s), 8.20(1H, s), 11.09(1H, s), Preparation 78

A mixture of methyl 6-chloronicotinate (8.0 g), (3R)-(−)-1-benzyl-3-aminopyrrolidine (9.86 g), CuO (371 mg) and $K_2CO_3$ (8.38 g) in DMF (60 ml) was stirred at 100° C. for 10 hours under atmospheric pressure of nitrogen. The reaction mixture was poured into a mixture of AcOEt and water and the organic layer was washed with brine and dried over $MgSO_4$. The solvent was evaporated in vacuo and the residue was chromatographed on silicagel eluting with AcOEt-MeOH (97:3). The eluted fractions containing the desired product were collected and evaporated in vacuo to give methyl 6-{[(3R)-1-benzyl-3-pyrrolidinyl]amino}nicotinate (9.9 g).

NMR (DMSO-$d_6$, δ): 1.60-1.67 (1H, m), 2.19-2.36 (1H, m), 2.38-2.89 (2H, m), 2.62-2.81 (2H, m), 3.56 (2H, s), 3.58 (3H, s), 4.38 (1H, m), 6.51 (1H, d, J=8.84 Hz), 7.18-7.33 (5H, m), 7.58 (1H, d, J=6.78 Hz), 8.00 (1H, dd, J=2.22 Hz, 8.84 Hz), 8.55 (1H, d, J=2.22 Hz)

The following compounds were obtained according to a similar manner to that of Preparation 78.

Preparation 79

Methyl 6-{[(3S)-1-benzyl-3-pyrrolidinyl]amino}nicotinate

NMR (DMSO-$d_6$, δ): 1.58-1.68 (1H, m), 2.17-2.24 (1H, m), 2.37-2.44 (2H, m), 2.62-2.82 (2H, m), 3.51 (2H, s), 3.76 (3H, s), 4.39 (1H, m), 6.53 (1H, d, J=8.96 Hz), 7.19-7.33 (5H, m), 7.59 (1H, d, J=6.80 Hz), 7.81 (1H, dd, J=2.20 Hz, 8.96 Hz), 8.56 (1H, d, J=2.20 Hz)

Preparation 80

A mixture of ethyl 5,6-dichloronicotinate (10.0 g), (3R)-(−)-1-benzyl-3-aminopyrrolidine (9.61 g), $K_2CO_3$ (8.38 g) and CuO (371 mg) in DMF (60 ml) was stirred at 100° C. for 10 hours under atmospheric pressure of nitrogen. The reaction mixture was poured into a mixture of AcOEt and water and the organic layer was washed with brine and dried over $MgSO_4$. The solvent was evaporated in vacuo and the residue was chromatographed on silicagel eluting with AcOEt-n-Hexane (7:3). The eluted fractions containing the desired product were collected and evaporated in vacuo to give ethyl 6-{[(3R)-1-benzyl-3-pyrrolidinyl]amino}-5-chloronicotinate (15.95 g)

NMR (DMSO-$d_6$, δ): 1.29 (3H, t, J=7.08 Hz), 1.87-2.01 (1H, m), 2.17-2.21 (1H, m), 2.41-2.53 (2H, m), 2.67-2.87 (2H, m), 3.59 (2H, s), 4.25 (2H, q, J=7.08 Hz), 4.54-4.59 (1H, m), 7.02 (1H, d, J=6.98 Hz), 7.19-7.33 (5H, m), 7.92 (1H, d, J=1.96 Hz), 8.53 (1H, d, J=1.96 Hz)

The following compounds were obtained according to a similar manner to that of Preparation 80.

Preparation 81

Ethyl (2E)-3-(6-{[(3R)-1-benzyl-3-pyrrolidinyl]amino}-5-chloro-3-pyridyl)acrylate NMR (DMSO-$d_6$, δ): 1.28 (3H, t, J=7.08 Hz), 1.87-1.96 (1H, m), 2.00-2.16 (2H, m), 2.40-2.67 (3H, m), 2.80-2.87 (1H, m), 3.59 (2H, s), 4.25 (2H, q, J=7.08 Hz), 4.54-4.58 (1H, m), 7.03 (1H, d, J=6.98 Hz), 7.19-7.33 (5H, m), 7.92 (1H, d, J=1.96 Hz), 8.53 (1H, d, J=1.96 Hz)

Preparation 82

A diisobutylaluminium hydride in toluene solution (15.7 ml) was dropwise added to a solution of ethyl 6-{[(3R)-1-benzyl-3-pyrrolidinyl]amino}-5-chloronicotinate (4.7 g) in toluene (50 ml) with stirring at −30∼−50° C. under atmospheric pressure of nitrogen, and the reaction mixture was stirred at −20∼−40° C. for 2 hours. A MeOH (5 ml) was added to a reaction mixture at −40° C. and saturated sodium potassium tartrate aqueous solution (10 ml) and $MgSO_4$ (10 g) and the resultant mixture was stirred at ambient temperature for 20 minutes. The reaction mixture was filtrated and the filtrate was dried over $MgSO_4$. The solvent was evaporated in vacuo and the residue was chromatographed on silicagel eluting with AcOEt-MeOH (9:1). The eluted fractions containing the desired product were collected and evaporated in vacuo to give (6-{[(3R)-1-benzyl-3-pyrrolidinyl]amino}-5-chloro-3-pyridyl)methanol (1.87 g).

NMR (DMSO-$d_6$, δ): 1.77-1.99 (1H, m), 2.16-2.35 (1H, m), 2.36-2.52 (2H, m), 2.77-2.85 (2H, m), 3.58 (2H, s), 4.32 (2H, s), 4.42-4.49 (1H, m), 5.10 (1H, m), 6.00 (1H, d, J=6.98 Hz), 7.18-7.32 (5H, m), 7.53 (1H, d, J=1.90 Hz), 7.91 (1H, d, J=1.90 Hz)

The following compounds were obtained according to a similar manner to that of Preparation 82.

Preparation 83

(6-{[(3S)-1-Benzyl-3-pyrrolidinyl]amino}-5-chloro-3-pyridyl)methanol

NMR (DMSO-$d_6$, δ): 1.76-1.99 (1H, m), 2.08-2.33 (1H, m), 2.34-2.52 (2H, m), 2.62-2.76 (1H, m), 2.80-2.84 (1H, m), 3.57 (2H, s), 4.32 (2H, d, J=4.76 Hz), 4.41-4.45 (1H, m), 5.06 (1H, t, J=4.76 Hz), 6.03 (1H, d, J=6.96 Hz), 7.18-7.36 (5H, m), 7.53 (1H, d, J=1.94 Hz), 7.90 (1H, d, J=1.94 Hz)

Preparation 84

(5-Chloro-6-{[(3R)-1-(4-fluorobenzyl)-3-pyrrolidinyl]amino}-3-pyridyl)methanol

NMR (DMSO-$d_6$, δ): 1.70-1.89(1H, m), 2.15-2.29(1H, m), 2.34-2.86(4H, m), 3.56(2H, s), 4.31(2H, d, J=5.5 Hz), 4.32-4.48(1H, m), 5.06(1H, t, J=5.5 Hz), 6.04(1H, d, J=7.0 Hz), 7.08-7.34(4H, m), 7.54(1H, d, J=2.0 Hz), 7.91(1H, d, J=2.0 Hz).

Mass (APCI): 336(M+H)+

Preparation 85

(5-Chloro-6-{[(3R)-1-(4-methylbenzyl)-3-pyrrolidinyl]amino}-3-pyridyl)methanol

NMR (DMSO-$d_6$, δ): 1.72-1.85(1H, m), 2.08-2.85(5H, m), 2.27(3H, s), 3.52(2H, s), 4.31(2H, d, J=5.5 Hz), 4.32-4.47 (1H, m), 5.05(1H, t, J=5.5 Hz), 6.02(1H, d, J=7.0 Hz), 7.10 (2H, d, J=8.8 Hz), 7.18(2H, d, J=8.8 Hz), 7.53(1H, d, J=2.0 Hz), 7.90(1H, d, J=2.0 Hz)

Mass (APCI): 332(M+H)+

Preparation 86

(5-Chloro-6-{[(3R)-1-(4-methoxybenzyl)-3-pyrrolidinyl]amino}-3-pyridyl)methanol

Mass (ESI): 348(M+H)+

Preparation 87

A mixture of methyl 6-chloronicotinate (5.14 g), 1-benzyl-4-aminopiperidine (6.84 g) and $K_2CO_3$ (5.38 g) in DMF (30 ml) was stirred at 100° C. for 12 hours under atmospheric pressure of nitrogen. The reaction mixture was poured into a mixture of AcOEt and water and the organic layer was washed with brine and dried over $MgSO_4$. The solvent was evaporated in vacuo and the residue was chromatographed on silicagel eluting with AcOEt-MeOH (98:2). The eluted fractions containing the desired product were collected and evaporated in vacuo to give methyl 6-[(1-benzyl-4-piperidyl)amino] nicotinate (4.77 g)

NMR (DMSO-$d_6$, δ): 1.35-1.52 (2H, m), 1.84-1.89 (2H, m), 1.99-2.11 (2H, m), 1.73-2.81 (2H, m), 3.46 (2H, s), 3.75 (3H, s), 3.75-3.79 (1H, m), 6.48 (1H, d, J=8.80 Hz), 7.19-7.36 (6H, m), 7.79 (1H, dd, J=2.28 Hz, 8.80 Hz), 8.55 (1H, d, J=2.28 Hz)

Preparation 88

Lithium aluminium hydride (304 mg) was added to a solution of methyl 6-[(1-benzyl-4-piperidyl)amino]nicotinate (1.3 g) in THF (20 ml) with stirring at 5-10° C. under atmospheric pressure of nitrogen, and the reaction mixture was stirred at 5-20° C. for 4 hours. The reaction mixture was cooled at 5° C. and water (0.3 ml), 15% NaOH solution (0.3 ml) and water (0.9 ml) was added, the resultant mixture was stirred at ambient temperature for 20 minutes. The reaction mixture was filtrated and the filtrate was dried over $MgSO_4$. The solvent was evaporated in vacuo and the residue was chromatographed on silicagel eluting with AcOEt-MeOH (9:1). The eluted fractions containing the desired product were collected and evaporated in vacuo to give {6-[(1-benzyl-4-piperidyl)amino]-3-pyridyl}methanol (670 mg)

NMR (DMSO-$d_6$, δ): 1.32-1.50 (2H, m), 1.84-1.89 (2H, m), 2.00-2.10 (2H, m), 2.74-2.80 (2H, m), 3.46-3.74 (1H, m), 3.41 (2H, s), 4.22 (2H, d, J=5.44 Hz), 4.87 (1H, t, J=5.44 Hz), 6.28 (1H, d, J=8.52 Hz), 6.42 (1H, d, J=8.52 Hz), 7.19-7.36 (6H, m), 7.85 (1H, s)

The following compound(s) were obtained according to a similar manner to that of Preparation 88.

Preparation 89

(6-{[1-(4-Chlorobenzoyl)-4-piperidyl]amino}-3-pyridyl)methanol

NMR (DMSO-$d_6$, δ): 1.42-1.49 (2H, m), 1.84-1.89 (2H, m), 2.00-2.11 (2H, m), 2.72-2.78 (2H, m), 3.63-3.73 (1H, m), 4.26 (2H, d, J=5.26 Hz), 4.86 (1H, d, J=5.26 Hz), 6.28 (1H, d, J=7.60 Hz), 6.42 (1H, d, J=8.50 Hz), 7.27-7.40 (5H, m), 7.85 (1H, d, J=2.08 Hz)

Preparation 90

4-{[5-(Hydroxymethyl)-2-pyridyl]amino}-N-phenyl-1-piperidinecarboxamide

NMR (DMSO-$d_6$, δ): 1.36-1.43 (2H, m), 1.89-1.94 (2H, m), 2.92-3.03 (2H, m), 3.90-4.08 (3H, m), 4.28 (2H, d, J=5.52 Hz), 4.88 (1H, t, J=5.52 Hz), 6.37 (2H, m), 6.88-6.96 (1H, m), 7.18-7.36 (3H, m), 7.45 (1H, dd, J=2.02 Hz, 8.38 Hz), 7.88 (1H, d, J=2.02 Hz), 8.50 (1H, s)

Preparation 91

A mixture of methyl 6-[(1-benzyl-4-piperidyl)amino] nicotinate (4.2 g) in MeOH (50 ml) was hydrogenated over 10% palladium-carbon (1.5 g) under an atmospheric pressure of hydrogen at ambient temperature under stirring for 15 hours. After removal of the catalyst and solvent was evaporated in vacuo and the residue was triturated with AcOEt and IPE. The precipitate was collected by filtration to give methyl 6-(4-piperidylamino)nicotinate (1.77 g).

NMR (DMSO-$d_6$, δ): 1.18-1.41 (2H, m), 1.81-1.87 (2H, m), 2.60-2.64 (2H, m), 2.99-3.14 (2H, m), 3.46 (3H, s), 3.46-3.76 (1H, m), 6.49 (1H, d, J=8.84 Hz), 7.28-7.39 (2H, m), 7.78 (1H, dd, J=2.26 Hz, 8.84 Hz), 8.55 (1H, d, J=2.26 Hz)

Preparation 92

A mixture of {6-[(1-benzyl-4-piperidyl)amino]-3-pyridyl}methanol (670 mg) and $MnO_2$ (2.94 g) in AcOEt (30 ml) was refluxed under stirring for 2 hours. After removal of the insoluble material, and the solvent was evaporated in vacuo to give 6-[(1-benzyl-4-piperidyl)amino]nicotinaldehyde (560 mg)

NMR (DMSO-$d_6$, δ): 1.39-1.56 (2H, m), 1.86-1.91 (2H, m), 1.99-2.12 (2H, m), 2.76-2.82 (2H, m), 3.47 (2H, s), 3.87 (1H, m), 6.55 (1H, d, J=8.90 Hz), 7.29-7.37 (5H, m), 7.65-7.74 (2H, m), 8.47 (1H, d, J=1.4 Hz), 9.65 (1H, s)

The following compounds were obtained according to a similar manner to that of Preparation 92.

Preparation 93

6-{[1-(4-Chlorobenzoyl)-4-piperidyl]amino}nicotinaldehyde

NMR (DMSO-d$_6$, δ): 1.37-1.56 (2H, m), 1.86-1.91 (2H, m), 2.02-2.13 (2H, m), 2.74-2.80 (2H, m), 3.86 (1H, m), 6.51 (1H, d, J=8.06 Hz), 7.30-7.41 (3H, m), 7.92-7.96 (2H, m), 8.47 (1H, d, J=2.06 Hz), 9.65 (1H, s)

Preparation 94

4-[(5-Formyl-2-pyridyl)amino]-N-phenyl-1-piperidinecarboxamide

NMR (DMSO-d$_6$, δ): 1.31-1.50 (2H, m), 1.91-1.99 (2H, m), 2.94-3.05 (2H, m), 3.98-4.12 (3H, m), 6.75 (1H, d, J=8.86 Hz), 6.89-6.96 (1H, m), 7.19-7.26 (2H, m), 7.44-7.49 (2H, m), 7.73-7.77 (2H, m), 8.50-8.54 (2H, m), 9.67 (1H, s)

Preparation 95

A solution of diethylphosphonoacetic acid ethyl ester (850 mg) in THF (10 ml) was added dropwise to a mixture of 60% sodium hydride in oil (167 mg) in THF (15 mL) with stirring at 10-20° C. under atmospheric pressure of nitrogen, and the reaction mixture was stirred at ambient temperature for 30 minutes. A solution of to the above mixture and resultant mixture was stirred at ambient temperature for 1.5 hour. The reaction mixture was poured into a mixture of AcOEt-H$_2$O and the organic layer was washed with brine and dried over MgSO$_4$. The solvent was evaporated in vacuo and the residue was crystallized with IPE and n-hexane to give ethyl (2E)-3-{6-[(1-benzyl-4-piperidyl)amino]-3-pyridyl}acrylate (450 mg).

NMR (DMSO-d$_6$, δ): 1.23 (3H, t, J=7.06 Hz), 1.36-1.53 (2H, m), 1.84-1.90 (2H, m), 1.99-2.10 (2H, m), 2.75-2.81 (2H, m), 3.46 (2H, s), 3.75-3.79 (1H, m), 4.15 (2H, q, J=7.06 Hz), 6.30 (1H, d, J=15.90 Hz), 6.49 (1H, d, J=8.86 Hz), 7.11 (1H, d=7.52 Hz), 7.19-7.37 (5H, m), 7.49 (1H, d, J=15.90 Hz), 7.76 (1H, dd, J=2.10 Hz, 8.86 Hz), 8.20 (1H, d, J=2.10 Hz)

The following compounds were obtained according to a similar manner to that of Preparation 95.

Preparation 96

A solution of diethylphosphonoacetic acid ethyl ester (274 mg) in THF (10 ml) was added dropwise to a mixture of 60% sodium hydride in oil (55 mg) in THF (10 mL) with stirring at 10-20° C. under atmospheric pressure of nitrogen, and the reaction mixture was stirred at ambient temperature for 30 minutes. A solution of 6-{[1-(4-chlorobenzoyl)-4-piperidyl]amino}nicotinaldehyde (210 mg) in THF (10 ml) solution was added to the above mixture and resultant mixture was stirred at ambient temperature for 1.5 hour. The reaction mixture was poured into a mixture of AcOEt-H$_2$O and the organic layer was washed with brine and dried over MgSO$_4$. The solvent was evaporated in vacuo and the residue was chromatographed on silicagel eluting with AcOEt-MeOH (95:5). The eluted fractions containing the desired product were collected and evaporated in vacuo to give ethyl (2E)-3-(6-{[1-(4-chlorobenzoyl)-4-piperidyl]amino}-3-pyridyl)acrylate (190 mg)

NMR (DMSO-d$_6$, δ): 1.23 (3H, t, J=7.06 Hz), 1.41-1.51 (2H, m), 1.84-1.90 (2H, m), 2.01-2.11 (2H, m), 2.73-2.79 (2H, m), 3.78 (1H, m), 4.14 (2H, q, J=7.06 Hz), 6.30 (1H, d, J=15.86 Hz), 6.48 (1H, d, J=8.88 Hz), 7.11 (1H, d, J=7.48 Hz), 7.30-7.41 (4H, m), 7.49 (1H, d, J=15.86 Hz), 7.76 (1H, dd, J=2.04 Hz, 8.88 Hz), 8.19 (1H, d, J=2.04 Hz)

The following compounds were obtained according to a similar manner to that of Preparation 96.

Preparation 97

Ethyl (2E)-3-(6-{[1-(anilinocarbonyl)-4-piperidyl]amino}-3-pyridyl)acrylate

NMR (DMSO-d$_6$, δ): 1.23 (3H, t, J=7.06 Hz), 1.35-1.45 (2H, m), 1.90-1.95 (2H, m), 2.92-3.05 (2H, m), 3.97-4.20 (4H, m), 6.32 (1H, d, J=15.90 Hz), 6.51 (1H, d, J=8.80 Hz), 6.88-6.96 (1H, m), 7.17-7.26 (2H, m), 7.44-7.55 (3H, m), 8.23 (1H, d, J=2.08 Hz), 8.53 (1H, s)

Preparation 98

A mixture of ethyl (2E)-3-{6-[(1-benzyl-4-piperidyl)amino]-3-pyridyl}acrylate (470 mg) and 1N NaOH solution (2.6 ml) in MeOH (15 ml) was stirred at 65-70° C. for 2 hours. The reaction mixture was evaporated in vacuo and the residue was dissolved with AcOEt and H$_2$O. The aqueous solution was adjusted to PH6.0 with aq.HCl and evaporated in vacuo. The residue was chromatographed on silicagel eluting with AcOEt-MeOH (85:15). The eluted fractions containing the desired product were collected and evaporated in vacuo to give (2E)-3-{6-[(1-benzyl-4-piperidyl)amino]-3-pyridyl}acrylic acid (430 mg).

NMR (DMSO-d$_6$, δ): 1.91-2.13 (4H, m), 2.80-3.60 (2H, m), 3.39-3.49 (2H, m), 3.67 (2H, brs), 4.30-4.50 (1H, m), 6.27 (1H, d, J=15.85 Hz), 6.70 (1H, m), 7.39-7.47 (4H, m), 7.67-7.79 (4H, m), 8.51 (1H, s)

Preparation 99

A mixture of methyl 6-(4-piperidylamino)nicotinate (1.0 g), 4-chlorobenzoic acid (699 mg), HOBt (603 mg) and EDCI (693 mg) in DMF (20 ml) was stirred at ambient temperature for 15 hours. The reaction mixture was poured into a mixture of AcOEt-H$_2$O and the organic layer was washed with brine and dried over MgSO$_4$. The solvent was evaporated in vacuo and the residue was chromatographed on silicagel eluting with AcOEt-n-hexane (7:3). The eluted fractions containing the desired product were collected and evaporated in vacuo to give methyl 6-{[1-(4-chlorobenzoyl)-4-piperidyl]amino}nicotinate (1.21 g)

NMR (DMSO-d$_6$, δ): 1.42 (2H, m), 1.92-1.99 (2H, m), 2.94-3.34 (4H, m), 3.76 (3H, s), 4.09-4.13 (1H, m), 6.52 (1H, d, J=8.84 Hz), 7.40-7.54 (5H, m), 7.81 (1H, dd, J=2.26 Hz, 8.84 Hz), 8.56 (1H, d, J=2.26 Hz)

Preparation 100

A mixture of (2E)-3-{6-[(1-benzyl-4-piperidyl)amino]-3-pyridyl)acrylic acid (430 mg), O-(tetrahydro-2H-pyran-2-yl)hydroxylamine (157 mg), HOBt (181 mg) and EDCI (208 mg) in DMF (20 ml) was stirred at ambient temperature for 15 hours. The reaction mixture was poured into a mixture of AcOEt-H$_2$O and the organic layer was washed with brine and dried over MgSO$_4$. The solvent was evaporated in vacuo and the residue was chromatographed on silicagel eluting with AcOEt-MeOH (9:1-8:2). The eluted fractions containing the desired product were collected and evaporated in vacuo to give (2E)-3-(6-[(1-benzyl-4-piperidyl)amino]-3-pyridyl}-N-(tetrahydro-2H-pyran-2-yloxy)acrylamide (180 mg).

NMR (DMSO-d$_6$, δ): 1.35-1.68 (8H, m), 1.84-1.90 (2H, m), 1.99-2.10 (2H, m), 2.73-2.89 (2H, m), 3.54 (2H, s), 3.73-3.79 (4H, m), 3.42-3.98 (1H, m), 4.87 (1H, s), 6.20 (1H, d, J=14.96

Hz), 6.50 (1H, d, J=8.82 Hz), 7.00 (1H, d, J=7.54 Hz), 7.21-7.37 (6H, m), 7.58 (1H, d, J=8.82 Hz), 8.12 (1H, s), 11.02 (1H, s)

The following compounds were obtained according to a similar manner to that of Preparation 100.

Preparation 101

4-[(5-{(1E)-3-Oxo-3-[(tetrahydro-2H-pyran-2-yloxy)amino]-1-propen-1-yl}-2-pyridyl)amino]-N-phenyl-1-piperidinecarboxamide NMR (DMSO-$d_6$, δ): 1.29-1.68 (8H, m), 1.90-1.99 (2H, m), 2.89-3.04 (2H, m), 3.56-3.60 (1H, m), 3.95-4.10 (4H, m), 4.88 (1H, s), 6.22 (1H, d, J=15.18 Hz), 6.52 (1H, d, J=8.78 Hz), 6.86-6.96 (1H, m), 7.18-7.48 (5H, m), 7.59-8.15 (1H, m), 8.16 (1H, s), 8.51 (1H, s), 11.03 (1H, s)

Preparation 102

(2E)-3-(6-{[1-(4-Chlorobenzoyl)-4-piperidyl]amino}-3-pyridyl)-N-(tetrahydro-2H-pyran-2-yloxy)acrylamide NMR (DMSO-$d_6$, δ): 1.36-1.83 (10H, m), 1.90-2.12 (4H, m), 2.52-2.73 (2H, m), 3.54 (1H, m), 3.93 (1H, m), 4.87 (1H, brs), 6.12-6.22) 1H, m), 6.49 (1H, d, J=8.82 Hz), 6.95-7.00 (1H, m), 7.30-7.41 (4H, m), 7.53-7.62 (1H, m), 8.12 (1H, s), 11.00 (1H, s)

Preparation 103

A mixture of methyl 6-(4-piperidylamino)nicotinate (0.73 g) and phenyl isocyanate (388 mg) in THF (30 ml) was stirred at ambient temperature for 12 hours. IPE (30 ml) was added to a reaction mixture and the precipitate was collected by filtration to give methyl 6-{[1-(anilinocarbonyl)-4-piperidyl]amino}nicotinate (0.72 g)

NMR (DMSO-$d_6$, δ): 1.27-1.48 (2H, m), 1.90-1.95 (2H, m), 2.93-3.04 (2H, m), 3.77 (3H, s), 4.04-4.11 (3H, m), 6.51 (1H, d, J=8.88 Hz), 6.88-6.96 (2H, m), 7.12-7.26 (2H, m), 7.40-7.49 (3H, m), 7.81 (1H, dd, J=8.88 Hz), 8.53 (1H, s), 8.57 (1H, d, J=2.26 Hz)

Preparation 104

A mixture of ethyl (2E)-3-(6-{[1-(4-chlorobenzoyl)-4-piperidyl]amino}-3-pyridyl)acrylate (190 mg) and 1N NaOH solution (1.0 ml) in MeOH (20 ml) was stirred at 70-75° C. for 2 hours. The reaction mixture was evaporated in vacuo and the residue was dissolved in a mixture of AcOEt and water. The aqueous solution was adjusted to PH4.5 and extract with AcOEt and THF. The organic layer was washed with brine and dried over MgSO$_4$. The solvent was concentrated in vacuo and the precipitate was collected by filtration to give (2E)-3-(6-{[1-(4-chlorobenzoyl)-4-piperidyl]amino}-3-pyridyl)acrylic acid (85 mg)

NMR (DMSO-$d_6$, δ): 1.36-2.23 (6H, m), 2.92-3.03 (2H, m), 4.17 (1H, m), 6.24 (1H, d, J=15.88 Hz), 6.54 (1H, d, J=7.94 Hz), 7.34-7.60 (4H, m), 7.76 (1H, dd, J=1.82 Hz, 7.94 Hz), 8.18 (1H, d, J=1.82 Hz), 12.02 (1H, m)

The following compounds were obtained according to a similar manner to that of Preparation 104.

Preparation 105

(2E)-3-(6-{[1-(Anilinocarbonyl)-4-piperidyl]amino}-3-pyridyl)acrylic acid

NMR (DMSO-$d_6$, δ): 1.35-1.45 (2H, m), 1.91-1.95 (2H, m), 3.03-3.05 (2H, m), 3.96-4.10 (3H, m), 6.22 (1H, d, J=15.92 Hz), 6.51 (1H, d, J=8.80 Hz), 6.88-6.96 (1H, m), 7.13-7.26 (3H, m), 7.41-7.49 (3H, m), 7.76 (1H, dd, J=2.08 Hz, 8.80 Hz), 8.19 (1H, d, J=2.08 Hz), 8.52 (1H, s), 12.05 (1H, s)

Preparation 106

(2E)-3-(5-Chloro-6-{[1-(4-chlorobenzyl)-4-piperidyl]amino}-3-pyridyl)acrylic acid NMR (DMSO-$d_6$, δ): 1.50-2.20(6H, m), 2.65-2.85(2H, m), 3.45(2H, s), 4.88-4.22(1H, m), 6.37(1H, d, J=16.0 Hz), 6.49 (1H, d, J=8.0 Hz), 7.29-7.52(5H, m), 8.00(1H, d, J=2.0 Hz), 8.20(1H, d, J=2.0 Hz)

Preparation 107

To a solution of ethyl (2E)-3-(6-{[(3R)-1-benzyl-3-pyrrolidinyl]amino}-3-pyridyl)acrylate (4.74 g) and 4-(Dimethylamino)pyridine (41.2 mg) in tetrahydrofuran (70 ml) was added di-tert-butyldicarbonate (5.89 g) at 20° C. and then stirred at 60° C. for 14 hours. The mixture was concentrated under reduced pressure. The resulting residue was purified by column chromatography on silica gel (70 g) using a mixed solvent of dichloromethane and methanol (60:1 to 15:1). The fractions containing the objective compound were collected and evaporated under reduced pressure. Ethyl (2E)-3-{6-[[(3R)-1-benzyl-3-pyrrolidinyl](tert-butoxycarbonyl)amino]-3-pyridyl}acrylate (5.49 g) was obtained as colorless oil.

NMR (DMSO-$d_6$, δ): 1.27 (3H, t, J=6.8 Hz), 1.41 (9H, s), 1.80-2.20 (2H, m), 2.40-2.80 (4H, m), 3.44, 3.55 (2H, ABq, J=13 Hz), 4.21(2H, q, J=6.8 Hz), 4.60-4.90 (1H, m), 6.78 (1H, d, J=16 Hz), 7.00-7.30 (5H, m), 7.34 (1H, d, J=8.5 Hz), 7.71(1H, d, J=16 Hz), 8.20 (1H, dd, J=2.4 Hz, J=8.5 Hz), 8.73 (1H, d, J=2.4 Hz),

MASS (API-ES); 452 (M+H)+.

Preparation 108

To a solution of ethyl (2E)-3-{6-[[(3R)-1-benzyl-3-pyrrolidinyl](tert-butoxycarbonyl) amino]-3-pyridyl}acrylate (5.45 g) in toluene (55 ml) was added 1-chloroethyl chloroformate (2.59 g) at room temperature and stirred at 20° C. for 1 hour. 1-Chloroethyl chloroformate (795 mg) and N,N-diisopropylethylamine (0.736 ml) was added to the mixture, and the solution was stirred at 20° C. for 15 minutes. After it was concentrated under reduced pressure, the resulting residue was dissolved in EtOH (70 ml). The mixture was stirred at 65° C. for 30 minutes, and concentrated under reduced pressure. The residue was poured into a mixture of aq NaHCO$_3$ solution (80 ml) and dichloromethane (100 ml). The organic layer was separated and dried over sodium sulfate, and evaporated under reduced pressure to give crude oil. The oil was purified by column chromatography (silica gel 125 g, dichloromethane/MeOH (60/1 to 15/1) to give ethyl (2E)-3-(6-{(tert-butoxycarbonyl)[(3R)-3-pyrrolidinyl]amino}-3-pyridyl)acrylate as oil (2.0 g).

NMR (DMSO-$d_6$, δ): 1.26 (3H, t, J=7.1 Hz), 1.31-1.40 (9H, m), 1.60-2.10 (2H, m), 2.30-3.20 (4H, m), 4.20 (2H, q, J=7.1 Hz), 4.50-4.80 (1H, m), 6.76 (1H, d, J=16 Hz), 7.36 (1H, d, J 8.5 Hz), 7.6.8 (1H, d, J=16 Hz), 8.19 (1H, dd, J=2.4 Hz, J=8.5 Hz), 8.72 (1H, d, J=2.4 Hz

MASS(API-ES); 362 (M+H)+

Preparation 109

To a mixture of ethyl (2E)-3-(6-{(tert-butoxycarbonyl)[(3R)-3-pyrrolidinyl]amino}-3-pyridyl)acrylate (350 mg) and 4-methoxybenzaldehyde (145 mg) in dichloromethane (5 ml) was added sodium triacetoxyborohydride (410 mg) at 20°

C., and then it was stirred at the same temperature for 18 hours. The reaction was quenched with saturated aq NaHCO₃ solution, and the mixture was extracted with dichloromethane. The organic layer was dried over sodium sulfate, and concentrated in vacuo. The residue was purified by column chromatography on silica gel (11 g) using a mixed solvent of dichloromethane and MeOH (100:1 to 35:1). The fractions containing the objective compound were collected and evaporated under reduced pressure. ethyl (2E)-3-(6-{(tert-butoxycarbonyl)[(3R)-1-(4-methoxybenzyl)-3-pyrrolidinyl]amino}-3-pyridyl)acrylate (362 mg) was obtained as colorless syrup.

NMR (DMSO-$d_6$, δ): 1.27 (3H, t, J=7.1 Hz), 1.35 (9H, s), 1.80-2.20 (2H, m), 2.30-2.90 (4H, m), 3.36, 3.48 (2H, ABq, J=13 Hz), 3.71 (3H, s), 4.21(H, q, J=7.1 Hz), 4.60-4.85 (1H, m), 6.78 (1H, d, J=16 Hz), 6.81 (2H, d, J=8.6 Hz, 7.06 (2H, d, J=8.6 Hz), 7.33 (1H, d, J=8.4 Hz), 7.71(1H, d, J=16 Hz), 8.20 (1H, dd, J=2.4 Hz, J=8.4 Hz), 8.72 (1H, d, J=2.4 Hz)

MASS(API-ES); 482 (M+H)+

The following compounds were obtained according to a similar manner to that of Preparation 109.

Preparation 110

Ethyl (2E)-3-(6-{(tert-butoxycarbonyl)[(3R)-1-(4-fluorobenzyl)-3-pyrrolidinyl]amino}-3-pyridyl)acrylate NMR (DMSO-$d_6$, δ): 1.27 (3H, t, J=7.1 Hz), 1.36 (9H, s), 1.80-2.20 (2H, m), 2.25-2.90 (4H, m), 3.42, 3.54 (2H, ABq, J=13 Hz), 4.21(2H, q, J=7.1 Hz), 4.60-4.90 (1H, m), 6.78 (1H, d, J=16 Hz), 7.00-7.25 (4H, m), 7.34 (1H, d, J=8.4 Hz), 7.71(1H, d, J 16 Hz), 8.20 (1H, dd, J=2.4 Hz, J=8.4 Hz), 8.73 (1H, d, J=2.4 Hz)

MASS(API-ES); 470 (M+H)+

Preparation 111

Ethyl (2E)-3-(6-{(tert-butoxycarbonyl)[(3R)-1-(4-chlorobenzyl)-3-pyrrolidinyl]amino}-3-pyridyl)acrylate NMR (DMSO-$d_6$, δ): 1.27 (3H, t, J=7.1 Hz), 1.35 (9H, s), 1.85-2.25 (2H, m), 2.30-2.90 (4H, m), 3.42, 3.55 (2H, ABq, J=13 Hz), 4.22 (2H, q, J=7.1 Hz), 4.60-4.90 (1H, m), 6.78 (1H, d, J=16 Hz), 7.17 (2H, d, J=8.4 Hz), 7.31 (2H, d, J=8.4 Hz), 7.34 (1H, d, J=8.5 Hz), 7.71(1H, d, J=16 Hz), 8.20 (1H, dd, J=2.3 and 8.5 Hz), 8.73 (1H, d, J=2.3 Hz)

MASS(API-ES); 486 (M+H)+488

Preparation 112

Ethyl (2E)-3-(6-{(tert-butoxycarbonyl)[(3R)-1-(4-methylbenzyl)-3-pyrrolidinyl]amino}-3-pyridyl)acrylate NMR (DMSO-$d_6$, δ): 1.27 (3H, t, J=7.1 Hz, 1.35 (9H, s), 1.75-2.24 (2H, m), 2.26 (3H, s), 2.30-2.85 (4H, m), 3.38, 3.50 (2H, ABq, J=13 Hz), 4.21 (2H, q, J=7.1 Hz), 4.60-4.85 (1H, m), 6.77 (1H, d, J=16 Hz), 6.95-7.10 (4H, m), 7.33 (1H, d, J=8.4 Hz), 7.70 (1H, d, J=16 Hz), 8.19 (1H, dd, J=2.4 Hz, J=8.4 Hz), 8.71 (1H, d, J=2.4 Hz)

MASS(API-ES); 466 (M+H)+

Preparation 113

To an ice-cooled solution of ethyl (2E)-3-(6-{(tert-butoxycarbonyl)[(3R)-1-(4-methoxybenzyl)-3-pyrrolidinyl] amino}-3-pyridyl)acrylate (360 mg) in dichloromethane (2 ml) was added anisole (11.0 ml) and TFA (2.0 ml), the mixture was stirred at 20° C. for 1 hour. The mixed solution was poured into a mixture of water (20 ml) and AcOEt (20 ml). The pH of the aqueous layer was adjusted to ca.9 with NaHCO₃. The organic layer was separated, washed with brine, dried over sodium sulfate and evaporated under reduced pressure to give ethyl (2E)-3-(6-{[(3R)-1-(4-methoxybenzyl)-3-pyrrolidinyl]amino}-3-pyridyl)acrylate as syrup (295 mg).

NMR (DMSO-$d_6$, δ): 1.24 (3H, t, J=7.1 Hz), 1.60-2.00 (1H, m), 2.10-3.65 (7H, m), 3.74 (3H, s), 4.15 (2H, q, J=7.1 Hz), 4.25-4.55 (1H, m), 6.35 (1H, d, J=16 Hz), 6.53 (1H, d, J=8.8 Hz), 6.93 (2H, d, J=8.5 Hz), 7.25-7.43 (3H, m), 7.51(1H, d, J=16 Hz), 7.82 (1H, dd, J=2.0 and 8.8 Hz), 8.22 (1H, d, J=2.0 Hz)

MASS(API-ES); 382 (M+H)+

The following compounds were obtained according to a similar manner to that of Preparation 113.

Preparation 114

Ethyl (2E)-3-(6-{[(3R)-1-(4-fluorobenzyl)-3-pyrrolidinyl]amino}-3-pyridyl)acrylate NMR (DMSO-$d_6$, δ): 1.23 (3H, t, J=7.1 Hz), 1.50-1.80 (1H, m), 2.10-2.90 (5H, m), 3.58 (2H, br), 4.14 (2H, q, J=7.1 Hz), 4.20-4.50 (1H, m), 6.31 (1H, d, J=16 Hz), 6.51 (1H, d, J=8.8 Hz), 7.05-7.40 (5H, m), 7.49 (1H, d, J=16 Hz), 7.78 (1H, dd, J=2.1 and 8.8 Hz), 8.20 (1H, d, J=2.1 Hz)

MASS(API-ES); 370 (M+H)+

Preparation 115

Ethyl (2E)-3-(6-{[(3R)-1-(4-chlorobenzyl)-3-pyrrolidinyl]amino}-3-pyridyl)acrylate NMR (DMSO-$d_6$, δ): 1.23 (3H, t, J=7.1 Hz), 1.50-1.85 (1H, m), 2.10-3.00 (5H, m), 3.20-3.90 (2H, m), 4.14 (2H, q, J=7.1 Hz), 4.20-4.50 (1H, m), 6.32 (1H, d, J=16 Hz), 6.51 (1H, d, J=8.8 Hz), 7.30-7.45 (5H, m), 7.49 (1H, d, J=16 Hz), 7.79 (1H, dd, J=2.1 Hz, J=8.8 Hz), 8.20 (1H, d, J=2.1 Hz)

MASS(API-ES); 386 (M+H)+388

Preparation 116

Ethyl (2E)-3-(6-{[(3R)-1-(4-methylbenzyl)-3-pyrrolidinyl]amino}-3-pyridyl)acrylate NMR (DMSO-$d_6$, δ): 1.23 (3H, t, J=7.1 Hz), 1.55-1.85 (1H, m), 2.10-3.10 (5H, m), 2.29 (3H, s), 3.20-4.00 (2H, m), 4.14 (2H, q, J=7.1 Hz), 4.25-4.50 (1H, m), 6.33 (1H, d, J=16 Hz), 6.52 (1H, d, J=8.8 Hz), 7.10-7.30 (4H, m), 7.40 (1H, d, J=6.5 Hz), 7.50 (1H, d, J=16 Hz), 7.80 (1H, dd, J=2.1 and 8.8 Hz), 8.21 (1H, d, J=2.1 Hz)

MASS(API-ES); 366 (M+H)+

Preparation 117

Ethyl (2E)-3-(6-{[(3R)-1-(cyclopropylmethyl)-3-pyrrolidinyl]amino}-3-pyridyl)acrylate NMR (DMSO-$d_6$, δ): 0.00-0.20 (2H, m), 0.40-0.60 (2H, m), 0.75-1.00 (1H, m), 1.24 (3H, t, J=7.1 Hz), 1.55-1.80 (1H, m), 2.10-3.60 (7H, m), 4.15 (2H, q, J=7.1 Hz), 4.25-4.50 (1H, m), 6.33 (1H, d, J=16 Hz), 6.53 (1H, d, J=8.8 Hz), 7.39 (1H, d, J=6.5 Hz), 7.51 (1H, d, J=16 Hz), 7.80 (1H, dd, J=2.2 Hz, J=8.8 Hz), 8.23 (1H, d, J=2.2 Hz)

MASS(API-ES); 316 (M+H)+

Preparation 118

To a solution of ethyl (2E)-3-(6-{(tert-butoxycarbonyl)[(3R)-3-pyrrolidinyl]amino}-3-pyridyl)acrylate (310 mg) and cyclopropylmethyl bromide (116 mg) in acetonitrile (7 ml) was added potassium hydrogencarbonate (85.9 mg) and potassium iodide (28.5 mg) at 20 and then the mixture was stirred at 50° C. for 3 hours. The mixed solution was poured into a mixture of water (20 ml) and AcOEt (20 ml). The pH of the aqueous layer was adjusted to ca.9 with NaHCO$_3$. The organic layer was separated, washed with brine, dried over sodium sulfate and evaporated under reduced pressure.

The resulting residue was purified by column chromatography on silica gel (8 g) using a mixed solvent of dichloromethane and MeOH (40:1 to 20:1). The fractions containing the objective compound were collected and evaporated under reduced pressure. Ethyl (2E)-3-(6-{(tert-butoxycarbonyl)[(3R)-1-(cyclopropylmethyl)-3-pyrrolidinyl]amino}-3-pyridyl)acrylate (170 mg) was obtained as colorless syrup.

NMR (DMSO-d$_6$, δ): 0.00-0.10 (2H, m), 0.30-0.50 (2H, m), 0.65-0.90 (1H, m), 1.27 (3H, t, J=7.1 Hz), 1.39 (9H, s), 1.80-3.40 (8H, m), 4.21(2H, q, J=7.1 Hz), 4.60-4.90 (1H, m), 6.76 (1H, d, J=16 Hz), 7.37 (1H, d, J=8.5 Hz), 7.69 (1H, d, J=16 Hz), 8.20 (1H, dd, J=2.3 and 8.5 Hz), 8.73 (1H, d, J=2.3 Hz)

MASS(API-ES); 416 (M+H)+

Preparation 119

To a stirred suspension of ethyl (2E)-3-(6-{(tert-butoxycarbonyl) [(3R)-1-(4-tert-butylbenzyl)-3-pyrrolidinyl]amino}-3-pyridyl)acrylate (430 mg) in dichloromethane (2 mL) was added trifluoroacetic acid (2 mL) and the resulting mixture was stirred at ambient temperature for 2 hours. The mixture was concentrated in vacuo. The residue was dissolved in ethanol (5 mL) and to this solution was added 1N sodium hydroxide aqueous solution (50.1 mL) and the mixture was stirred at fifty degree for 12 hours. The mixture was allowed to cool to ambient temperature. To the mixture was added concentrated hydrogen chloride in an ice bath until pH of the mixture became neutral. The mixture was concentrated in vacuo. The mixture was dissolved in DMF (5 mL) and to the resulting solution was added O-(tetrahydro-2H-pyran-2-yl)hydroxylamine (129 mg), 1-hydroxybenzotriazole (149 mg) and EDCI hydrochloride (211 mg). After stirring at ambient temperature for 2 hours, the mixture was cooled in an ice bath and to this was added saturated aqueous sodium bicarbonate (5 mL) and water (5 mL). The precipitate was filtered, washed with water and dried to afford (2E)-3-(6-{[(3R)-1-(4-tert-butylbenzyl)-3-pyrrolidinyl]amino}-3-pyridyl)-N-(tetrahydro-2H-pyran-2-yloxy)acrylamide (280 mg) as a pale tan solid.

NMR (DMSO-d$_6$, δ): 1.26 (9H, s), 1.42-1.78 (6H, m), 2.07-2.82 (6H, m), 3.28-3.41 (1H, m), 3.49 (1H, d, J=13.9. Hz), 3.55 (1H, d, J=13.9 Hz), 3.84-4.01 (1H, m), 4.24-4.39 (1H, m), 4.85 (1H, brs), 6.20 (1H, br.d, J=16.5 Hz), 6.50 (1H, d, J=8.6 Hz), 7.14-7.29 (1H, m), 7.22 (2H, d, J=8.4 Hz), 7.32 (2H, d, J=8.4 Hz), 7.57 (1H, br.d, J=8.6 Hz), 8.09 (1H, brs)

MS (ES+) m/z 479.36

Preparation 120 tert-Butyl (5-{(1E)-3-oxo-3-[(tetrahydro-2H-pyran-2-yloxy)amino]-1-propen-1-yl}-2-pyridyl){(3R)-1-[4-(trifluoromethyl)benzyl]-3-pyrrolidinyl}carbamate NMR (DMSO-d$_6$, δ): 1.35 (9H, s), 1.45-1.79 (6H, m), 1.87-2.23 (2H, m), 2.44-2.67 (3H, m), 2.72-2.82 (1H, m), 3.48-3.59 (1H, m), 3.54 (1H, d, J=13.6 Hz), 3.65 (1H, d, J=13.6 Hz), 3.88-4.04 (1H, m), 4.68-4.83 (1H, m), 4.92 (1H, brs), 6.60 (1H, d, J=16.1 Hz), 7.35 (1H, d, J=8.1 Hz), 7.39 (2H, d, J=8.4 Hz), 7.55 (1H, d, J=16.1 Hz), 7.63 (2H, d, J=8.4 Hz), 8.02 (1H, br.d, J=8.1 Hz), 8.63 (1H, brs)

MS (ES+) m/z 591.28(M+1).

Preparation 121 tert-Butyl (5-{(1E)-3-oxo-3-[(tetrahydro-2H-pyran-2-yloxy)amino]-1-propen-1-yl}-2-pyridyl){(3R)-1-[4-(trifluoromethoxy)benzyl]-3-pyrrolidinyl}carbamate NMR (DMSO-d$_6$, δ): 1.35 (9H, s), 1.46-1.81 (6H, m), 1.86-2.20 (2H, m), 2.45-2.65 (3H, m), 2.71-2.81 (1H, m), 3.43-3.65 (3H, m); 3.90-4.06 (1H, m), 4.66-4.84 (1H, m), 4.92 (1H, brs), 6.59 (1H, d, J=15.8 Hz), 7.25 (2H, d, J=8.8 Hz), 7.29 (2H, d, J=8.8 Hz), 7.34 (1H, d, J=8.1 Hz), 7.55 (1H, d, J=15.8 Hz), 8.02 (1H, brd, J=8.1 Hz), 8.63 (1H, brs)

MS (ES+) m/z 607.29(M+1)

Preparation 122 tert-Butyl [(3R)-1-(cyclohexylmethyl)-3-pyrrolidinyl](5-{(1E)-3-oxo-3-[(tetrahydro-2H-pyran-2-yloxy)amino]-1-propen-1-yl})-2-pyridyl)carbamate NMR (DMSO-d$_6$, δ): 0.59-1.77 (17H, m), 1.37 (9H, s), 1.85-2.22 (4H, m), 2.23-2.78 (4H, m), 3.47-3.59 (1H, m), 3.88-4.04 (1H, m), 4.64-4.84 (1H, m), 4.92 (1H, brs), 6.58 (1H, d, J=16.5 Hz), 7.35 (1H, d, J=8.1 Hz), 7.53 (1H, d, J=16.5 Hz), 8.01 (1H, br.d, J=8.1 Hz), 8.63 (1H, brs)

MS (ES+) m/z 529.44(M+1)

Preparation 123 tert-Butyl [(3R)-1-(1-cyclohexen-1-ylmethyl)-3-pyrrolidinyl](5-{(1E)-3-oxo-3-[(tetrahydro-2H-pyran-2-yloxy)amino]-1-propen-1-yl}-2-pyridyl)carbamate NMR (DMSO-d$_6$, δ): 1.14-2.20 (16H, m), 1.36 (9H, s), 2.33-2.50 (3H, m), 2.56-2.73 (2H, m), 2.78-2.88 (1H, m), 3.49-3.61 (1H, m), 3.90-4.04 (1H, m), 4.64-4.79 (1H, m), 4.92 (1H, brs), 5.43 (1H, brs), 6.58 (1H, d, J=16.1 Hz), 7.33 (1H, d, J=8.4 Hz), 7.53 (1H, d, J=16.1 Hz), 8.00 (1H, br.d, J=8.4 Hz), 8.63 (1H, brs)

MS (ES+) m/z 527.54(M+1)

Preparation 124

The mixture of 1-chloro-3-(triphenylphosphoranylidene)acetone (6.6 g) and ethyl glyoxylate (50% in toluene, 4.6 g) in dioxane (66 mL) was stirred at 80' for 1.5 hour. The solvent was removed by concentration. The residue was purified by column chromatography on silica gel using a mixture of chloroform and hexane (1:1 v/v) as an eluent. The eluted fractions containing the desired product were collected and evaporated in vacuo to give ethyl (2E)-5-chloro-4-oxo-2-pentenoate (1.58 g).

NMR(DMSO-d$_6$, δ): 1.25(3H, t, J=7.1 Hz), 4.22(2H, q, J=7.1 Hz), 4.85(2H, s), 6.78(1H, d, J=16.1 Hz), 7.07(1H, d, J=16.1 Hz)

Preparation 125

The mixture of ethyl (2E)-5-chloro-4-oxo-2-pentenoate (0.5 g) and N-[1-(4-chlorobenzoyl)-3-pyrrolidinyl]thiourea (0.8 g) in acetonitrile (10 mL) was stirred at 70° C. for 3 hours, and the mixture was evaporated in vacuo. To the residue was added a solution of AcOEt and water, and the mixture was adjusted to pH 8 with 20% aqueous potassium carbonate. The separated organic layer was washed with water, dried over magnesium sulfate and evaporated in vacuo. The residue was purified by column chromatography on silica gel using AcOEt as an eluent. The eluted fractions containing the desired product were collected and evaporated in vacuo to give ethyl (2E)-3-(2-{[1-(4-chlorobenzoyl)-3-pyrrolidinyl] amino}-1,3-thiazol-4-yl)acrylate (1.0 g).

NMR (DMSO-d$_6$, δ): 1.24(3H, t, J=7.1 Hz), 1.88-2.28(2H, m), 3.29-3.72(3H, m), 3.74-3.87(1H, m), 4.07-4.40(3H, m), 6.27 and 6.49(total 1H, each d, J=15.3 Hz), 7.16 and 7.21 (total 1H, each s), 7.31 and 7.37(total 1H, each d, J=15.3 Hz), 7.44-7.62(4H, m), 8.07 and 8.11 (total 1H, each d, J=6.0 Hz)

(+)ESI-MS: 406(M+H)+, 428(M+Na)+

The following compounds were obtained according to a similar manner to that of Preparation 125.

Preparation 126

Ethyl (2E)-3-{2-[(1-benzyl-4-piperidyl)amino]-1,3-thiazol-4-yl}acrylate

NMR(DMSO-d$_6$, δ): 1.23(3H, t, J=7.1 Hz), 1.35-1.58(2H, m), 1.85-2.16(4H, m), 2.68-2.83(2H, m), 3.42-3.62(1H, m), 3.46(2H, s), 4.15(2H, q, J=7.1 Hz), 6.32(1H, d, J=15.2 Hz), 7.12(1H, s), 7.20-7.37(6H, m), 7.76(1H, d, J=7.1 Hz)

(+)ESI-MS: 372(M+H)+

Preparation 127

The mixture of ethyl (2E)-3-(2-{[1-(4-chlorobenzoyl)-3-pyrrolidinyl]amino}-1,3-thiazol-4-yl)acrylate (0.9 g) and 1N-NaOH (4.4 mL) in MeOH (14 mL) was stirred at 50° C. for 3 hours and the mixture was evaporated in vacuo. To the residue was added a solution of AcOEt, THF and water, and the mixture was adjusted to pH 4 with 1N-HCl. The separated organic layer was washed with water, dried over magnesium sulfate and evaporated in vacuo to give (2E)-3-(2-{[1-(4-chlorobenzoyl)-3-pyrrolidinyl]amino}-1,3-thiazol-4-yl) acrylic acid (0.64 g).

NMR(DMSO-d$_6$, δ): 1.84-2.32(2total 1H, m), 3.27-3.71(3H, m), 3.72-3.88(1H, m), 4.20-4.40(1H, m), 6.24 and 6.34(total 1H, each d, J=15.3 Hz), 7.11 and 7.16(total 1H, each s), 7.25 and 7.31(total 1H, each d, J=15.3 Hz), 7.45-7.62(4H, m), 8.02-8.15(1H, m), 12.27(1H, s)

(+)ESI-MS: 400(M+Na)+

The following compounds were obtained according to a similar manner to that of Preparation 127.

Preparation 128

(2E)-3-{2-[(1-Benzyl-4-piperidyl)amino]-1,3-thiazol-4-yl}acrylic acid

NMR(DMSO-d$_6$, δ): 1.38-1.60(2H, m), 1.87-2.04(2H, m), 2.04-2.26(2H, m), 2.72-2.87(2H, m), 3.46-3.63(3H, m), 6.27 (1H, d, J=15.1 Hz), 7.07(1H, s), 7.20-7.36(6H, m), 7.77(1H, d, J=7.2 Hz)

Preparation 129

(2E)-3-(2-{[1-(4-Chlorobenzoyl)-4-piperidyl] amino}-1,3-thiazol-4-yl)acrylic acid NMR(DMSO-d$_6$, δ): 1.31-1.56(2H, m), 1.88-2.13(2H, m), 3.05-3.29(2H, m), 3.46-3.67(1H, m), 3.75-3.93(1H, m), 4.14-4.36(1H, m), 6.29(1H, d, J=15.3 Hz), 7.10(1H, s), 7.27(1H, d, J=15.3 Hz), 7.42(2H, d, J=8.5 Hz), 7.52(2H, d, J=8.5 Hz), 7.84(1H, d, J=6.9 Hz), 12.26(1H, s)

(+)ESI-MS: 414(M+Na)+

Preparation 130

EDCI (0.30 g) was added to the solution of (2E)-3-(2-{[1-(4-chlorobenzoyl)-3-pyrrolidinyl]amino}-1,3-thiazol-4-yl) acrylic-acid (0.6 g), O-(tetrahydro-2H-pyran-2-yl)hydroxylamine (0.22 g), and HOBT (0.26 g) in DMF (10 ml) under ice-cooling and the mixture was stirred at ambient temperature for 20 hours. The reaction mixture was poured into a mixture of AcOEt and water. The separated organic layer was washed with water, dried over magnesium sulfate and evaporated in vacuo to give (2E)-3-(2-{[1-(4-chlorobenzoyl)-3-pyrrolidinyl]amino}-1,3-thiazol-4-yl)-N-(tetrahydro-2H-pyran-2-yloxy)acrylamide (0.66 g).

NMR(DMSO-d$_6$, δ): 1.44-1.75(6H, m), 1.90-2.29(2H, m), 3.27-3.68(4H, m), 3.69-4.05(2H, m), 4.20-4.38(1H, m), 4.85-4.94(1H, m), 6.39 and 6.47(total 1H, each d, J=15.2 Hz), 7.01 and 7.06(total 1H, each s), 7.16 and 7.21(total 1H, each d, J=15.2 Hz), 7.46-7.61(4H, m), 7.99-8.08(1H, m), 11.18 and 11.24(total 1H, each s)

(+)ESI-MS: 477(M+H)+, 499(M+Na)+

The following compounds were obtained according to a similar manner to that of Preparation 130.

Preparation 131

(2E)-3-{2-[(1-Benzyl-4-piperidyl)amino]-1,3-thiazol-4-yl)-N-(tetrahydro-2H-pyran-2-yloxy)acrylamide NMR(DMSO-d$_6$, δ): 1.39-1.76(8H, m), 1.85-2.20(4H, m), 2.68-2.84(2H, m), 3.42-3.64(2H, m), 3.47(2H, s), 3.86-4.02 (1H, m), 4.85-4.92(1H, m), 6.40(1H, d, J=15.1 Hz), 6.96(1H, s), 7.17(1H, d, J=15.1 Hz), 7.22-7.35(5H, m), 7.68(1H, d, J=7.2 Hz), 11.20(1H, s)

(+)ESI-MS: 443(M+H)+

Preparation 132

(2E)-3-(2-([1-(4-Chlorobenzoyl)-4-piperidyl] amino}-1,3-thiazol-4-yl)-N-(tetrahydro-2H-pyran-2-yloxy)acrylamide NMR(DMSO-d$_6$, δ): 1.33-1.76(8H, m), 1.89-2.11(2H, m), 3.05-3.26(2H, m), 3.44-3.64(2H, m), 3.74-4.02(2H, m), 4.14-4.35(1H, m), 4.84-4.92(1H, m), 6.41(1H, d, J=15.1 Hz), 7.00 (1H, s), 7.18(1H, d, J=15.1 Hz), 7.42(2H, d, J=8.5 Hz), 7.53 (2H, d, J=8.5 Hz), 7.79(1H, d, J=7.2 Hz), 11.21(1H, s)

Preparation 133

1-Chloroethyl chloroformate (1.88 mL) was added a mixture of ethyl (2E)-3-(2-[(1-benzyl-4-piperidyl)amino]-1,3-thiazol-4-yl)acrylate (2.7 g) in dichloromethane (40 mL) at ambient temperature and the mixture was stirred at same temperature for 1.5 hour. The solvent was removed by concentration. To the residue was added an EtOH (42.7 mL) and the mixture was stirred at 70° C. for 2 hours. The reaction mixture was added 2N-ethanolic hydrogen chloride (7.3 mL) at ambient temperature and the mixture was stirred at same temperature for 20 hours. The isolated precipitate was collected by filtration to give ethyl (2E)-3-[2-(4-piperidylamino)-1,3-thiazol-4-yl]acrylate dihydrochloride (1.44 g).

NMR(DMSO-$d_6$, δ): 1.24(3H, t, J=7.1 Hz), 1.66-1.88(2H, m), 2.04-2.21(2H, m), 2.88-3.11(2H, m), 3.21-3.38(2H, m), 4.05-4.24(1H, m), 4.17(2H, q, J=7.1 Hz), 6.67(1H, d, J=15.6 Hz), 7.32(1H, s), 7.61(1H, d, J=15.6 Hz), 9.14(4H, br s)

(+)ESI-MS: 282(M+H)+

Preparation 134

4-Chlorobenzoyl chloride (0.19 mL) was added to a mixture of ethyl (2E)-3-[2-(4-piperidylamino)-1,3-thiazol-4-yl]acrylate dihydrochloride (0.5 g) and triethylamine (0.63 mL) in DMF (10 ml) under ice-cooling and the mixture was stirred at same temperature for 4.5 hours. The reaction mixture was poured into saturated aqueous sodium hydrogen carbonate and the mixture was extracted with an AcOEt. The extract layer was washed with water, dried over magnesium sulfate and evaporated in vacuo to give ethyl (2E)-3-(2-{[1-(4-chlorobenzoyl)-4-piperidyl]amino}-1,3-thiazol-4-yl)acrylate (0.48 g).

NMR(DMSO-$d_6$, δ): 1.24(3H, t, J=7.1 Hz), 1.32-1.56(2H, m), 1.87-2.13(2H, m), 3.05-3.29(2H, m), 3.44-3.65(1H, m), 3.76-3.95(1H, m), 4.07-4.35(1H, m), 4.15(2H, q, J=7.1 Hz), 6.34(1H, d, J=15.2 Hz), 7.16(1H, s), 7.34(1H, d, J=15.2 Hz), 7.42(2H, d, J=8.5 Hz), 7.52(2H, d, J=8.5 Hz), 7.86(1H, d, J=7.0 Hz)

(+)ESI-MS: 442(M+Na)+

Preparation 135

To a solution of ethyl (2E)-3-(6-{[(3R)-1-benzyl-3-pyrrolidinyl]amino}-5-chloro-3-pyridyl)acrylate (770 mg) in toluene (14 ml) was added 1-chloroethyl chloroformate (713 mg) at 23° C. and stirred at the same temperature for 1 hour. N,N-Diisopropylethylamine (0.348 ml) was added to the mixture, and the solution was stirred at 23° C. for 15 minutes. After it was concentrated under reduced pressure, the resulting residue was dissolved in EtOH (15 ml). The mixture was stirred at 65° C. for 30 minutes, and concentrated under reduced pressure. The residue was dissolved into EtOH (15 ml), and mixed with 2N-hydrogen chloride in EtOH solution (2 ml). The mixture was stirred at 86° C. for 5 hours. After it was concentrated under reduced pressure, the resulting residue was triturated with IPE (15 ml). Ethyl (2E)-3-{5-chloro-6-[(3R)-3-pyrrolidinylamino]-3-pyridyl}acrylate dihydrochloride (1.1 g) was obtained as brown syrup.

NMR (DMSO-$d_6$, δ): 1.29 (3H, t, J=6.9 Hz), 1.90-2.35 (2H, m), 3.00-4.10 (4H, m), 4.17 (2H, q, J=6.9 Hz), 4.30-4.85 (1H, m), 6.55 (1H, d, J=16 Hz), 7.55 (1H, d, J=16 Hz), 8.15-8.20 (1H, m), 8.30-8.40 (1H, m), 9.56 (4H, br)

MASS(API-ES); 296 (M+H)+Free, 298

Preparation 136

To an ice-cooled solution of ethyl (2E)-3-{5-chloro-6-[(3R)-3-pyrrolidinylamino]-3-pyridyl}acrylate dihydrochloride (330 mg) and Et$_3$N (0.437 ml) in dichloromethane (8 ml) was added benzoyl chloride (132 mg), the mixture was stirred at 23° C. for 1 hour. The mixed solution was poured into a mixture of water (20 ml) and DCM (15 ml). The organic layer was separated, washed with brine, dried over sodium sulfate and evaporated under reduced pressure. The resulting residue was purified by column chromatography on silica gel (12 g) using a mixed solvent of dichloromethane and MeOH (100:1 to 40:1). The fractions containing the objective compound were collected and evaporated under reduced pressure. ethyl (2E)-3-(6-{[(3R)-1-benzoyl-3-pyrrolidinyl]amino}-5-chloro-3-pyridyl)acrylate (245 mg) was obtained as colorless syrup.

NMR (DMSO-$d_6$, δ): 1.18-1.32 (3H, m), 1.90-2.40 (2H, m), 3.20-4.10 (4H, m), 4.11-4.25 (2H, m), 4.40-4.80 (1H, m), 6.40-6.60 (1H, m), 7.00-7.15 (1H, m), 7.35-7.65 (6H, m), 8.10-8.20 (1H, m), 8.22-8.40 (1H, m)

MASS(API-ES); 400 (M+H)+

The following compounds were obtained according to a similar manner to that of Preparation 136.

Preparation 137

Ethyl (2E)-3-(5-chloro-6-{[(3R)-1-(cyclopropylcarbonyl)-3-pyrrolidinyl]amino}-3-pyridyl)acrylate NMR (DMSO-$d_6$, δ): 0.60-0.80 (4H, m), 1.24 (3H, t, J=7.1 Hz), 1.60-1.85 (1H, m), 1.87-2.40 (2H, m), 3.20-4.10 (4H, m), 4.16 (2H, q, J=7.1 Hz), 4.40-4.80 (1H, m), 6.52 (1H, d, J=16 Hz), 6.95-7.10 (1H, m), 7.53 (1H, d, J=16 Hz), 8.10-8.20 (1H, m), 8.30-8.40 (1H, m)

MASS(API-ES); 364 (M+H)+

Preparation 138

To a stirred solution of ethyl (2E)-3-(6-{(tert-butoxycarbonyl)[(3R)-3-pyrrolidinyl]amino}-3-pyridyl)acrylate (330 mg) in dimethylformamide (6 mL) was added potassium carbonate (158 mg) and 1,1'-(bromomethylene)dibenzene (225 mg), and the mixture was stirred at 60° C. for 2 hours. The resulting mixture was poured into water and extracted with ethyl acetate. The organic phase was washed with brine, dried over sodium sulfate, and concentrated in vacuo. The residue was purified by chromatography (hexane:ethyl acetate=4:1 then chloroform:methanol=20:1) to give ethyl (2E)-3-(6-{(tert-butoxycarbonyl)[(3R)-1-(diphenylmethyl)-3-pyrrolidinyl]amino}-3-pyridyl)acrylate (210 mg) as an oil.

NMR (DMSO-$d_6$, δ): 1.36 (3H, t, J=7 Hz), 1.42 (3×3H, s), 2.02-2.30 (2H, m), 2.42-2.61 (2H, m), 2.64 (1H, dd, J=9.5, 7 Hz), 2.78 (1H, dd, J=9.5, 8 Hz), 4.17 (1H, s), 4.29 (2H, q, J=7 Hz), 4.91 (1H, m), 6.49 (1H, d, J=16 Hz), 7.08-7.38 (11H, m), 7.69 (1H, d, J=16 Hz), 7.83 (1H, dd, J=8.5, 2 Hz), 8.57 (1H, d, J=2 Hz)

MS (ES+) m/z 528.

Preparation 139

To a stirred solution of ethyl (2E)-3-(6-{(tert-butoxycarbonyl)[(3R)-1-(diphenylmethyl)-3-pyrrolidinyl]amino}-3-pyridyl)acrylate (205 mg) in methanol (5 mL) was added 1N-NaOH solution (0.8 mL). The mixture was stirred at ambient temperature for 12 hours. Methanol was evaporated in vacuo and the aqueous layer was washed with diisopropyl ether. The aqueous layer was acidified by hydrochloric acid to pH 4, and the precipitate was collected and washed with water to give (2E)-3-(6-{(tert-butoxycarbonyl)[(3R)-1-(diphenylmethyl)-3-pyrrolidinyl]amino}-3-pyridyl)acrylic acid (161 mg) as a white powder.

NMR (DMSO-$d_6$, δ): 1.34 (3×3H, br-s), 1.97-2.74 (6H, m), 4.17 (1H, br), 4.75 (1H, br), 6.70 (1H, br-d, J=16 Hz), 7.12-7.90 (12H, m), 8.23 (1H, m), 8.76 (1H, s)

MS (ES+) m/z 500

Preparation 140

To a stirred solution of (2E)-3-(6-{(tert-butoxycarbonyl)[(3R)-1-(diphenylmethyl)-3-pyrrolidinyl]amino}-3-pyridyl)acrylic acid (142 mg) in DMF (3 mL) was added O-(tetrahydro-2H-pyran-2-yl)hydroxylamine (67 mg), HOBT (77 mg), and EDCI hydrochloride (109 mg), and the resulting mixture was stirred at ambient temperature for 7 hours. The reaction mixture was diluted with ethyl acetate and washed successively with water, saturated NaHCO$_3$ solution, and brine. The organic phase was dried over Na$_2$SO$_4$ and concentrated in vacuo. The residue was purified by preparative thin layer chromatography (chloroform:methanol=5:1) to give tert-butyl [(3R)-1-(diphenylmethyl)-3-pyrrolidinyl](5-{(1E)-3-oxo-3-[(tetrahydro-2H-pyran-2-yloxy)amino]-1-propen-1-yl}-2-pyridyl)carbamate (100 mg) as a pale yellow oil.

NMR (DMSO-d$_6$, δ): 1.34 (3×3H, s), 1.46-1.76 (6H, m), 1.93-2.21 (2H, m), 2.25-2.64 (4H, m), 3.54 (1H, m), 3.97 (1H, m), 4.17 (1H, s), 4.75 (1H, m), 4.93 (1H, m), 6.64 (1H, d, J=16 Hz), 7.07-7.43 (11H, m), 7.59 (1H, d, J=16 Hz), 8.08 (1H, m), 8.68 (1H, d, J=1.5 Hz), 11.34 (1H, s)

MS (ES+) m/z 599.

Preparation 141

To a mixture of ethyl (2E)-3-(6-{(tert-butoxycarbonyl)[(3R)-3-pyrrolidinyl]amino}-3-pyridyl)acrylate dihydrochloride (150 mg), [4-(bromomethyl)phenyl](phenyl)methanone (143 mg), and THF (3.5 mL) was added Et$_3$N (0.168 mL). After stirring for 2 hours at room temperature, the reaction mixture was partitioned between ethyl acetate and water. The organic layer was washed with brine, dried over MgSO$_4$, filtered, and evaporated in vacuo. The residue was purified by column chromatography on silica gel to give ethyl (2E)-3-{6-[[(3R)-1-(4-benzoylbenzyl)-3-pyrrolidinyl](tert-butoxycarbonyl)amino]-3-pyridyl}acrylate (149 mg)

NMR (CDCl$_3$, δ): 1.35 (3H, t, J=7 Hz), 1.45 (9H, s), 2.03-2.32 (2H, m), 2.61-3.05 (4H, m), 3.61-3.76 (2H, m), 4.28 (2H, q, J=7 Hz), 4.87-5.00 (1H, m), 6.46 (1H, d, J=16 Hz), 7.30 (1H, d, J=8 Hz), 7.37 (2H, d, J=8 Hz), 7.45-7.51 (2H, m), 7.56-7.62 (1H, m), 7.66 (1H, d, J=16 Hz), 7.74 (2H, d, J=8 Hz), 7.77-7.83 (3H, m), 8.54 (1H, d, J=2 Hz)

MS (ES+) m/z 556 (M+1)

Preparation 142

To a mixture of ethyl (2E)-3-(6-{(tert-butoxycarbonyl)[(3R)-3-pyrrolidinyl]amino}-3-pyridyl)acrylate dihydrochloride (110 mg), 4-(chloromethyl)-2-phenyl-1,3-thiazole (53.1 mg), and DMF (2.5 mL) was added K$_2$CO$_3$ (123 mg). After stirring for 2 hours at 60° C., the reaction mixture was partitioned between ethyl acetate and water. The organic layer was washed with brine, dried over MgSO$_4$, filtered, and evaporated in vacuo to give ethyl (2E)-3-[6-((tert-butoxycarbonyl){(3R)-1-[(2-phenyl-1,3-thiazol-4-yl)methyl]-3-pyrrolidinyl}amino)-3-pyridyl]acrylate (133 mg).

NMR (DMSO-d$_6$, δ): 1.35 (3H, t, J=7 Hz), 1.44 (9H, s), 2.01-2.36 (2H, m), 2.70-3.16 (4H, m), 3.77-3.92 (2H, m), 4.28 (2H, q, J=7 Hz), 4.90-5.01 (1H, m), 6.42 (1H, d, J=16 Hz), 7.07 (1H, s), 7.31 (1H, d, J=8 Hz), 7.40-7.45 (3H, m), 7.62 (1H, d, J=16 Hz), 7.78 (1H, dd, J=2, 8 Hz), 7.91-7.95 (2H, m), 8.51 (1H, d, J=2 Hz)

MS (ES+) m/z 535 (M+1)

Preparation 143

To a mixture of 2,3-dihydro-1-benzofuran-5-ylmethanol (95.1 mg), Et$_3$N (0.120 mL), and THF (3 mL) was added methanesulfonyl chloride (0.053 mL) at 4° C. The reaction mixture was stirred for 3 hours, and added ethyl (2E)-3-(6-{(tert-butoxycarbonyl)[(3R)-3-pyrrolidinyl]amino}-3-pyridyl)acrylate dihydrochloride (250 mg) and Et$_3$N (0.281 mL). After stirring for 2 hours at 60° C., the resulting mixture was partitioned between ethyl acetate and water. The organic layer was washed with brine, dried over MgSO$_4$, filtered, and evaporated in vacuo. The residue was purified by column chromatography on silica gel to give ethyl (2E)-3-(6-{(tert-butoxycarbonyl)[(3R)-1-(2,3-dihydro-1-benzofuran-5-ylmethyl)-3-pyrrolidinyl]amino}-3-pyridyl)acrylate (134 mg)

NMR (CDCl$_3$, δ): 1.35 (3H, t, J=7 Hz), 1.44 (9H, s), 1.98-2.27 (2H, m), 2.51-3.00 (4H, m), 3.16 (2H, t, J=9 Hz), 3.44-3.57 (2H, m), 4.28 (2H, q, J=7 Hz), 4.55 (2H, t, J=9 Hz), 4.83-4.96 (1H, m), 6.46 (1H, d, J=16 Hz), 6.68 (1H, d, J=8 Hz), 6.95 (1H, d, J=8 Hz), 7.08 (1H, s), 7.29 (1H, d, J=8 Hz), 7.66 (1H, d, J=16 Hz), 7.80 (1H, dd, J=2, 8 Hz), 8.53 (1H, d, J=2 Hz)

MS (ES+) m/z 494 (M+1)

Preparation 144

To a solution of ethyl (2E)-3-{6-[[(3R)-1-(4-benzoylbenzyl)-3-pyrrolidinyl](tert-butoxycarbonyl)amino]-3-pyridyl}acrylate (111 mg) in dioxane (2 mL) was added 1N sodium hydroxide (0.6 mL). After stirring at 60° C. for 2 hours, the reaction mixture was added H$_2$O (10 mL) and acidified with 1N hydrochloric acid (to pH 1). A resulting mixture was extracted with CHCl$_3$, and the organic layer was dried over MgSO$_4$, filtered, and evaporated in vacuo to give (2E)-3-{6-[[(3R)-1-(4-benzoylbenzyl)-3-pyrrolidinyl](tert-butoxycarbonyl)amino]-3-pyridyl}acrylic acid dihydrochloride (97 mg).

NMR (DMSO-d$_6$, δ): 1.46 (9H, s), 2.37-2.77 (2H, m), 3.51-3.99 (4H, m), 4.38-4.47 (2H, m), 5.12-5.24 (1H, m), 6.41 (1H, d, J=16 Hz), 7.30 (1H, d, J=8 Hz), 7.47-7.65 (4H, m), 7.78-7.90 (7H, m), 8.42-8.49 (1H, m)

MS (ES+) m/z 528 (M+1)

The following compounds were obtained according to a similar manner to that of Preparation 144.

Preparation 145

(2E)-3-[6-((tert-Butoxycarbonyl){(3R)-1-[(2-phenyl-1,3-thiazol-4-yl)methyl]-3-pyrrolidinyl}amino)-3-pyridyl]acrylic acid dihydrochloride NMR (CDCl$_3$, δ): 1.44 (9H, s), 2.28-2.68 (2H, m), 3.47-4.00 (4H, m), 4.51-4.56 (2H, m), 5.18-5.32 (1H, m), 6.38 (1H, d, J=16 Hz), 7.33 (1H, d, J=8 Hz), 7.42-7.48 (3H, m), 7.52 (1H, d, J=16 Hz), 7.78 (1H, dd, J=2 and 8 Hz), 7.89-7.96 (3H, m), 8.42-8.47 (1H, m)

MS (ES+) m/z 507 (M+1)

Preparation 146

(2E)-3-(6-{(tert-Butoxycarbonyl)[(3R)-1-(2,3-dihydro-1-benzofuran-5-ylmethyl)-3-pyrrolidinyl]amino}-3-pyridyl)acrylic acid dihydrochloride NMR (DMSO-d$_6$, δ): 1.46 (9H, s), 2.27-2.79 (2H, m), 3.24 (2H, t, J=9 Hz), 3.39-3.94 (4H, m), 4.20-4.26 (2H, m), 4.60 (2H, t, J=9 Hz), 5.08-5.21 (1H, m), 6.40 (1H, d, J=16 Hz), 6.79 (1H, d, J=8 Hz), 7.22-7.33 (2H, m), 7.54-7.64 (2H, m), 7.77-7.82 (1H, m), 8.39-8.42 (1H, m)

MS (ES+) m/z 466 (M+1)

Preparation 147

(2E)-3-{6-[[(3R)-1-(1-Benzofuran-2-ylmethyl)-3-pyrrolidinyl](tert-butoxycarbonyl)amino]-3-pyridyl}acrylic acid dihydrochloride NMR (DMSO-d$_6$, δ): 1.41 (9H, s), 2.25-2.71 (2H, m), 3.44-4.00 (4H, m), 4.50-4.56 (2H, m), 5.16-5.30 (1H, m), 6.36 (1H, d, J=16 Hz), 7.16 (1H, s), 7.29-70.40 (3H, m), 7.47-7.65 (3H, m), 7.77 (1H, dd, J 2, 8 Hz), 8.14-8.35 (1H, m)

MS (ES+) m/z 464 (M+1).

Preparation 148

(2E)-3-{6-[[(3R)-1-(1-Benzofuran-5-ylmethyl)-3-pyrrolidinyl](tert-butoxycarbonyl)amino]-3-pyridyl}acrylic acid dihydrochloride NMR (DMSO-d$_6$, δ): 1.45 (9H, s), 2.33-2.76 (2H, m), 3.39-3.99 (4H, m), 4.37-4.50 (2H, m), 5.09-5.23 (1H, m), 6.39 (1H, d, J=16 Hz), 6.82 (1H, d, J=2 Hz), 7.30 (1H, d, J=8 Hz), 7.50-7.62 (3H, m), 7.68 (1H, d, J=2 Hz), 7.78 (1H, dd, J=2, 8 Hz), 7.95 (1H, s), 8.30-8.44 (1H, m)

MS (ES+) m/z 464 (M+1)

Preparation 149

To a mixture of (2E)-3-{6-[[(3R)-1-(4-benzoylbenzyl)-3-pyrrolidinyl](tert-butoxycarbonyl)amino]-3-pyridyl}acrylic acid dihydrochloride (93 mg), O-tetrahydro-2H-pyran-2-yl-hydroxylamine (27 mg.), and 1-hydroxybenzotriazole (31 mg) in N,N-dimethylformamide (1.6 mL) was added 1-(3-dimethylaminopropyl)-3-ethylcarbodiimide (36 mg) at 4° C. The mixture was warmed to ambient temperature and stirred for 8 hours. The reaction mixture was added saturated NaHCO$_3$ (2 mL) and water (8 mL), and extracted with ethyl acetate. The organic layer was washed with water and brine, dried over MgSO$_4$, filtered, and evaporated in vacuo. The residue was purified by column chromatography on silica gel to give tert-butyl [(3R)-1-(4-benzoylbenzyl)-3-pyrrolidinyl](5-{(1E)-3-oxo-3-[(tetrahydro-2H-pyran-2-yloxy)amino]-1-propen-1-yl}-2-pyridyl)carbamate (35 mg)

NMR (DMSO-d$_6$, δ): 1.36 (9H, s), 1.49-1.72 (6H, m), 1.88-2.20 (2H, m), 2.50-2.86 (4H, m), 3.50-3.70 (3H, m), 3.89-4.02 (1H, m), 4.70-4.83 (1H, m), 4.90-4.94 (1H, m), 6.59 (1H, d, J=16 Hz), 7.33-8.05 (12H, m), 8.62-8.65 (1H, m).

MS (ES+) m/z 627 (M+1).

The following compounds were obtained according to a similar manner to that of Preparation 149.

Preparation 150 tert-Butyl (5-{(1E)-3-oxo-3-[(tetrahydro-2H-pyran-2-yloxy)amino]-1-propen-1-yl}-2-pyridyl){(3R)-1-[(2-phenyl-1,3-thiazol-4-yl)methyl]-3-pyrrolidinyl}carbamate NMR (DMSO-d$_6$, δ): 1.35 (9H, s), 1.49-1.75 (6H, m), 1.88-2.18 (2H, m), 2.52-2.99 (4H, m), 3.50-3.59 (1H, m), 3.65-3.79 (2H, m), 3.91-4.03 (1H, m), 4.68-4.81 (1H, m), 4.90-4.96 (1H, m), 6.56 (1H, d, J=16 Hz), 7.33-7.55 (6H, m), 7.87-8.02 (3H, m), 8.58-8.62 (1H, m).

MS (ES+) m/z 606 (M+1).

Preparation 151 tert-Butyl [(3R)-1-(2,3-dihydro-1-benzofuran-5-ylmethyl)-3-pyrrolidinyl](5-{(1E)-3-oxo-3-[(tetrahydro-2H-pyran-2-yloxy)amino]-1-propen-1-yl}-2-pyridyl)carbamate NMR (DMSO-d$_6$, δ): 1.35 (9H, s), 1.49-1.75 (6H, m), 1.93-2.1.2 (2H, m), 3.11 (2H, t, J=9 Hz), 3.28-3.58 (7H, m), 3.92-4.02 (1H, m), 4.48 (2H, t, J=9 Hz), 4.67-4.79 (1H, m), 4.90-4.94 (1H, m), 6.55-7.02 (4H, m), 7.32-7.60 (2H, m), 7.99-8.05 (1H, m), 8.61-8.63 (1H, m)

MS (ES+) m/z 565 (M+1)

Preparation 152 tert-Butyl [(3R)-1-(1-benzofuran-2-ylmethyl)-3-pyrrolidinyl](5-{(1E)-3-oxo-3-[(tetrahydro-2H-pyran-2-yloxy)amino]-1-propen-1-yl}-2-pyridyl)carbamate NMR (DMSO-d$_6$, δ): 1.34 (9H, s), 1.49-1.76 (6H, m), 1.87-2.19 (2H, m), 2.52-2.99 (4H, m), 3.49-3.59 (1H, m), 3.65-3.78 (2H, m), 3.90-4.03 (1H, m), 4.67-4.80 (1H, m), 4.89-4.96 (1H, m), 6.56 (1H, d, J=16 Hz), 6.66 (1H, s), 7.17-7.29 (2H, m), 7.34 (1H, d, J=8 Hz), 7.47-7.59 (3H, m), 7.95-8.01 (1H, m), 8.55-8.59 (1H, m)

MS (ES+) m/z 563 (M+1)

Preparation 153 tert-Butyl [(3R)-1-(1-benzofuran-5-ylmethyl)-3-pyrrolidinyl](5-{(1E)-3-oxo-3-[(tetrahydro-2H-pyran-2-yloxy)amino]-1-propen-1-yl}-2-pyridyl)carbamate NMR (DMSO-d$_6$, δ): 1.35 (9H, s), 1.49-1.76 (6H, m), 1.89-2.19 (2H, m), 2.43-2.81 (4H, m), 3.41-3.66 (3H, m), 3.90-4.04 (1H, m), 4.67-4.80 (1H, m), 4.91-4.97 (1H, m), 6.60 (1H, d, J=16 Hz), 6.88 (1H, d, J=2 Hz), 7.10 (1H, d, J=8 Hz), 7.33 (1H, d, J=8 Hz), 7.42 (1H, s), 7.46 (1H, d, J=8 Hz), 7.55 (1H, d, J=16 Hz), 7.95 (1H, d, J=2 Hz), 8.01 (1H, d, J=8 Hz), 8.62 (1H, s)

MS (ES+) m/z 563 (M+1)

Preparation 154

To a solution of tert-butyl 4-({5-[(1E)-3-ethoxy-3-oxo-1-propen-1-yl]-2-pyridyl}amino)-1-piperidinecarboxylate (2.8 g) in EtOH (20 ml) was added 4N HCl in dioxane (18.6 ml), the mixture was stirred at 23° C. for 30 minutes. The precipitate was collected, washed with IPE, dried under reduced pressure to give ethyl (2E)-3-[6-(4-piperidylamino)-3-pyridyl]acrylate dihydrochloride.

NMR (DMSO-d$_6$, δ): 1.25(3H, t, J=7.0 Hz), 1.6-2.0(2H, m), 2.0-2.3 (2H, m), 2.8-3.1(2H, m), 3.33-3.40(2H, m), 4.18(2H, q, J=7.0 Hz), 6.58(1H, d, J=16.0 Hz), 7.11(1H, d, J=9.7 Hz), 7.65(1H, d, J=16.0 Hz), 8.24-8.28(2H, m), 9.11(2H, brs)

MASS (APCI): 276(M+H)+

The following compounds were obtained according to a similar manner to that of Preparation 154.

Preparation 155

Ethyl (2E)-3-[5-chloro-6-(4-piperidylamino)-3-pyridyl]acrylate dihydrochloride

NMR (DMSO-d$_6$, δ): 1.24(3H, t, J=7.4 Hz), 1.8-2.8(4H, m), 2.8-3.1(2H, m), 3.2-3.4(2H, m), 4.16(2H, q, J=7.4 Hz), 6.44 (1H, d, J=16.0 Hz), 7.53(1H, d, J=16.0 Hz), 8.17(1H, d, J=2.0 Hz), 8.30(1H, d, J=2.0 Hz)

MASS (APCI): 310(M+H)+

Preparation 156

Ethyl (2E)-3-{6-[methyl(4-piperidyl)amino]-3-pyridyl}acrylate dihydrochloride

NMR (DMSO-d$_6$, δ): 1.25(3H, t, J=7.4 Hz), 1.80-1.86(2H, m), 2.10-2.26(2H, m), 2.95-3.20(2H, m), 3.04(3H, s), 3.27-

3.39(2H, m), 4.18(2H, q, J=7.4 Hz), 4.60-4.85(1H, m), 6.64(1H, d, J=16.0 Hz), 7.27(1H, d, J=8.0 Hz), 7.67(1H, d, J=16.0 Hz), 8.31-8.36(2H, m), 9.10-6.40(2H, m)

MASS (APCI): 290(M+H)+

Preparation 157

To an ice-cooled solution of ethyl (2E)-3-[6-(4-piperidylamino)-3-pyridyl]acrylate dihydrochloride (309 mg) and Et$_3$N (0.448 ml) in DMF (8 ml) was added benzoyl chloride (124 mg), the mixture was stirred at 23° C. for 1 hour. The mixed solution was poured into water (20 ml). The precipitate was collected, washed with water, dried under reduced pressure to give ethyl (2E)-3-{6-[(1-benzoyl-4-piperidyl)amino]-3-pyridyl}acrylate.

NMR (DMSO-d$_6$, δ): 1.33(3H, t, J=7.0 Hz), 1.22-1.46(2H, m), 2.04-2.30(2H, m), 3.00-3.30(2H, m), 3.50-4.20(2H, m), 4.20(2H, q, J=7.0 Hz), 4.50-4.80(2H, m), 6.22(1H, d, J=15.8 Hz), 6.39(1H, d, J=8.8 Hz), 7.32-7.46(5H, m), 7.46-7.63(2H, m), 8.19(1H, d, J=2.1 Hz)

MASS (APCI): 380(M+H)+

The following compounds were obtained according to a similar manner to that of Preparation 157.

Preparation 158

Ethyl (2E)-3-(6-{[1-(4-fluorobenzoyl)-4-piperidyl]amino}-3-pyridyl)acrylate

NMR (DMSO-d$_6$, δ): 1.32(3H, t, J=7.1 Hz), 1.30-1.60(2H, m), 2.10-2.30(2H, m), 3.00-3.30(2H, m), 3.99-4.14(2H, m), 4.25(2H, q, J=7.1 Hz), 4.68(1H, d, J=7.8 Hz), 6.22(1H, d, J=16.0 Hz), 6.39(1H, d, J=8.8 Hz), 7.07-7.13(2H, m), 7.39-7.64(4H, m), 8.19(1H, d, J=2.2 Hz)

MASS (APCI): 398(M+H)+

Preparation 159

Ethyl (2E)-3-(6-{[1-(4-methylbenzoyl)-4-piperidyl]amino}-3-pyridyl)acrylate

NMR (DMSO-d$_6$, δ): 1.32(3H, t, J=7.1 Hz), 1.30-1.60(2H, m), 2.10-2.30(2H, m), 2.37(3H, s), 3.00-3.30(2H, m), 3.99-4.14(2H, m), 4.25(2H, q, J=7.1 Hz), 4.68(1H, d, J=7.8 Hz), 6.21(1H, d, J=16.0 Hz), 6.38(1H, d, J=8.8 Hz), 7.18-7.34(4H, m), 8.18-7.56-7.63(2H, m), 8.18(1H, d, J=2.0 Hz)

MASS (APCI): 394(M+H)+

Preparation 160

Ethyl (2E)-3-(6-{[1-(4-methoxybenzoyl)-4-piperidyl]amino}-3-pyridyl)acrylate

NMR (DMSO-d$_6$, δ): 1.32(3H, t, J=7.1 Hz), 1.30-1.60(2H, m), 2.10-2.30(2H, m), 3.00-3.30(2H, m), 3.80(3H, s), 3.99-4.14(2H, m), 4.25(2H, q, J=7.1 Hz), 4.68(1H, d, J=7.8 Hz), 6.21(1H, d, J=16.0 Hz), 6.28(1H, d, J=8.8 Hz), 7.92(2H, d, J=8.8 Hz), 7.39(2H, d, J=8.8 Hz), 7.53-7.64(2H, m), 8.18(1H, d, J=2.0 Hz)

MASS (APCI): 410(M+H)+

Preparation 161

Ethyl (2E)-3-{6-[(1-benzoyl-4-piperidyl)amino]-5-chloro-3-pyridyl}acrylate

NMR (DMSO-d$_6$, δ): 1.24(3H, t, J=7.2 Hz), 1.5-2.1(4H, m), 2.70-3.25(2H, m), 3.50-3.70(1H, m), 4.15(2H, q, J=7.2 Hz), 4.20-4.60(2H, m), 6.48(1H, d, J=16.0 Hz), 6.74(1H, d, J=8.0 Hz), 7.3-7.55(6H, m), 8.12(1H, d, J=2.0 Hz), 8.29(1H, d, J=2.0 Hz)

MASS (APCI): 436(M+Na)+

Preparation 162

Ethyl (2E)-3-(5-chloro-6-{[1-(4-chlorobenzoyl)-4-piperidyl]amino}-3-pyridyl)acrylate NMR (DMSO-d$_6$, δ): 1.24(3H, t, J=7.2 Hz), 1.5-2.1(4H, m), 2.70-3.25(2H, m), 3.50-3.70(1H, m), 4.15(2H, q, J=7.2 Hz), 4.20-4.60(2H, m), 6.49(1H, d, J=16.0 Hz), 6.72(1H, d, J=8.0 Hz), 7.30-7.60(5H, m), 8.12(1H, d, J=2.0 Hz), 8.29(1H, d, J=2.0 Hz)

MASS (APCI): 470(M+Na)+

Preparation 163

Ethyl (2E)-3-(5-chloro-6-{[1-(3-chlorobenzoyl)-4-piperidyl]amino}-3-pyridyl)acrylate NMR (DMSO-d$_6$, δ): 1.24(3H, t, J=7.4 Hz), 1.53-1.94(4H, m), 2.75-3.30(2H, m), 3.45-3.70(1H, m), 4.60(2H, q, J=7.4 Hz), 4.20-4.60(2H, m), 6.49(1H, d, J=16.0 Hz), 6.72(1H, d, J=7.0 Hz), 7.33-7.56(5H, m), 8.13(1H, d, J=2.0 Hz), 8.30(1H, d, J=2.0 Hz)

Preparation 164

Ethyl (2E)-3-(5-chloro-6-{[1-(2-chlorobenzoyl)-4-piperidyl]amino}-3-pyridyl)acrylate

MASS (ESI): 448(M+H)+

Preparation 165

Ethyl (2E)-3-(6-[[1-(4-chlorobenzoyl)-4-piperidyl](methyl)amino]-3-pyridyl)acrylate NMR (DMSO-d$_6$, δ): 1.24(3H, t, J=7.4 Hz), 1.55-1.99(4H, m), 2.80-3.87(3H, m), 3.08(3H, s), 4.15(2H, q, J=7.4 Hz), 4.50-5.00(2H, m), 6.40(1H, d, J=16.0 Hz), 6.73(1H, d, J=8.8 Hz), 7.45-7.58(4H, m), 7.93(1H, dd, J=2.0, 8.8 Hz), 8.34(1H, d, J=2.0 Hz)

MASS (APCI): 428(M+H)+

Preparation 166

To a suspension of (2E)-3-{6-[(1-benzoyl-4-piperidyl)amino]-3-pyridyl}acrylic acid (170 mg) in DMF (3 ml) was added O-(tetrahydro-2H-pyran-2-yl)hydroxylamine (62.3 mg), EDCI HCl (102 mg), HOBt (71.9 mg), Et$_3$N (0.201 ml), the mixture was stirred at 23° C. for 8 hours. The mixed solution was poured into a mixture of water (20 ml) and AcOEt (20 ml). The organic layer was separated, washed with water twice and brine, dried over sodium sulfate and concentrated in vacuo. The residue was purified by silica gel column chromatography eluted with 8% MeOH in dichloromethane to give (2E)-3-{6-[(1-benzoyl-4-piperidyl)amino]-3-pyridyl}-N-(tetrahydro-2H-pyran-2-yloxy)acrylamide (50 mg).

NMR (DMSO-d$_6$, δ): 1.20-1.70(8H, m), 1.80-2.10(4H, m), 3.00-3.30(2H, m), 3.40-3.80(2H, m), 3.80-4.20(2H, m), 4.20-4.50(1H, m), 4.87(1H, s), 6.19(1H, d, J=16.0 Hz), 6.52(1H, d, J=8.8 Hz), 7.07(1H, d, J=7.4 Hz), 7.30-7.47(6H, m), 7.60(1H, d, J=8.8 Hz), 8.13(1H, d, J=2.0 Hz), 11.03(1H, brs).

MASS (APCI): 451(M+H)+

The following compounds were obtained according to a similar manner to that of Preparation 166.

Preparation 167

(2E)-3-(6-{[1-(4-Fluorobenzoyl)-4-piperidyl]amino}-3-pyridyl)-N-(tetrahydro-2H-pyran-2-yloxy)acrylamide NMR (DMSO-$d_6$, δ): 1.20-1.80(6H, m), 1.80-2.10(2H, m), 3.01-3.25(2H, m), 3.50-3.60(2H, m), 4.90-4.18(2H, m), 4.33 (1H, brs), 4.87(1H, s), 6.20(1H, m), 6.52(1H, d, J=8.8 Hz), 6.96(1H, d, J=4.0 Hz), 7.26-7.36(2H, m), 7.44-7.48(2H, m), 7.60(1H, d), 8.14(1H, s), 11.04(1H, s)

MASS (APCI): 491(M+Na)+

Preparation 168

(2E)-3-(6-{[1-(4-Methylbenzoyl)-4-piperidyl]amino}-3-pyridyl)-N-(tetrahydro-2H-pyran-2-yloxy)acrylamide NMR (DMSO-$d_6$, δ): 1.24-1.80(6H, m), 1.80-2.10(2H, m), 2.33(3H, s), 3.10-3.29(2H, m), 3.43-3.70(2H, m), 3.90-4.15(2H, m), 4.33(1H, brs), 4.87(1H, s), 6.20(1H, d, J=15.4 Hz), 6.52(1H, d, J=8.8 Hz), 7.07(1H, d, J=7.3 Hz), 7.23-7.29(3H, m), 7.34(1H, d, J=15.4 Hz), 7.60(1H, d, J=8.8 Hz), 8.14(1H, s)

MASS (APCI): 465(M+H)+

Preparation 169

(2E)-3-(6-{[1-(4-Methoxybenzoyl)-4-piperidyl]amino}-3-pyridyl)-N-(tetrahydro-2H-pyran-2-yloxy)acrylamide NMR (DMSO-$d_6$, δ): 1.20-1.45(4H, m), 1.50-1.60(3H, m), 1.30-1.75(3H, m), 1.80-2.0(2H, m), 2.90-3.20(2H, m), 3.50-3.55(1H, m), 3.95-4.20(2H, m), 4.87(1H, s), 6.20(1H, d, J=15.4 Hz), 6.53(1H, d, J=8.8 Hz), 6.98(2H, d, J=8.8 Hz), 7.07(1H, d, J=7.4 Hz), 7.33-7.37(3H, m), 7.60(1H, d, J=8.8 Hz), 8.1(1H, s), 11.04(1H, s)

MASS (APCI): 503(M+Na)+

Preparation 170

(2E)-3-[6-({1-[4-(1H-Pyrrol-1-yl)benzoyl]-4-piperidyl}amino)-3-pyridyl]-N-(tetrahydro-2H-pyran-2-yloxy)acrylamide NMR (DMSO-$d_6$, δ): 1.30-1.80(9H, m), 1.85-2.10(2H, m), 3.10-3.20(2H, m), 3.45-3.60(1H, m), 3.80-4.20(2H, m), 4.88 (1H, s), 6.25-6.35(2H, m), 6.53(1H, d, J=8.8 Hz), 7.10(1H, d, J=7.3 Hz), 7.35(1H, d, J=16.0 Hz), 7.43-7.84(7H, m), 8.15 (1H, d, J=2.0 Hz), 11.04(1H, s)

Preparation 171

N-(4-Chlorophenyl)-4-[(5-{(1E)-3-oxo-3-[(tetrahydro-2H-pyran-2-yloxy)amino]-1-propen-1-yl}-2-pyridyl)amino]-1-piperidinecarboxamide NMR (DMSO-$d_6$, δ): 1.20-1.80(8H, m), 1.80-2.10(2H, m), 2.85-3.13(2H, m), 3.40-3.46(1H, m), 3.84-4.12(4H, m), 4.88 (1H, s), 6.23(1H, d, J=16.0 Hz), 6.53(1H, d, J=8.8 Hz), 7.13-7.70(7H, m), 8.15(1H, d, J=2.0 Hz), 8.66(1H, s), 11.04(1H, brs)

MASS (APCI): 522(M+Na)+

Preparation 172

N-(4-Methylphenyl)-4-[(5-{(1E)-3-oxo-3-[(tetrahydro-2H-pyran-2-yloxy)amino]-1-propen-1-yl}-2-pyridyl)amino]-1-piperidinecarboxamide NMR (DMSO-$d_6$, δ): 1.20-1.45(3H, m), 1.50-1.60(3H, m), 1.30-1.75(3H, m), 1.80-2.0(2H, m), 2.22(3H, s), 2.90-3.20 (2H, m), 3.50-3.55(1H, m), 3.95-4.07(4H, m), 4.89(1H, s), 6.20(1H, d, J=15.4 Hz), 6.51(1H, d, J=8.8 Hz), 7.02(2H, d, J=8.8 Hz), 7.07(1H, d, J=7.4 Hz), 7.33(2H, d, J=8.8 Hz), 7.36(1H, d, J=15.4 Hz), 7.60(1H, d, J=8.8 Hz), 8.15(1H, s), 8.42(1H, s), 11.05(1H, s)

MASS (APCI): 502(M+Na)+

Preparation 173

N-(4-Methoxyphenyl)-4-[(5-{(1E)-3-oxo-3-[(tetrahydro-2H-pyran-2-yloxy)amino]-1-propen-1-yl}-2-pyridyl)amino]-1-piperidinecarboxamide NMR (DMSO-$d_6$, δ): 1.20-1.45(3H, m), 1.50-1.60(3H, m), 1.30-1.75(3H, m), 1.80-2.0(2H, m), 2.90-3.20(2H, m), 3.50-3.55(2H, m), 3.70(3H, s), 3.95-4.07(4H, m), 4.87(1H, s), 6.20(1H, d, J=15.4 Hz), 6.51(1H, d, J=8.8 Hz), 6.81(2H, d, J=8.8 Hz), 7.07(1H, d, J=7.4 Hz), 7.32-7.37(3H, m), 7.60(1H, d, J=8.8 Hz), 8.15(1H, s), 8.37(1H, s), 11.05(1H, s)

MASS (APCI): 518(M+Na)+

Preparation 174

(2E)-3-(6-[(1-Benzoyl-4-piperidyl)amino]-5-chloro-3-pyridyl)-N-(tetrahydro-2H-pyran-2-yloxy)acrylamide NMR (DMSO-$d_6$, δ): 1.56-2.00(11H, m), 2.60-3.30(2H, m), 3.40-3.70(2H, m), 3.89-4.10(1H, m), 4.20-4.60(2H, m), 4.88 (1H, s), 6.33(1H, d, J=15.7 Hz), 6.64(1H, d, J=8.0 Hz), 7.33-7.48(6H, m), 7.86(1H, s), 8.21(1H, s), 11.08(1H, s)

MASS (APCI): 507(M+Na)+

Preparation 175

(2E)-3-(5-Chloro-6-{[1-(4-chlorobenzoyl)-4-piperidyl]amino}-3-pyridyl)-N-(tetrahydro-2H-pyran-2-yloxy)acrylamide NMR (DMSO-$d_6$, δ): 1.56-2.00(11H, m), 2.60-3.30(2H, m), 3.40-3.70(2H, m), 3.89-4.10(1H, m), 4.20-4.60(2H, m), 4.88 (1H, s), 6.31(1H, d, J=15.7 Hz), 6.62(1H, d, J=8.0 Hz), 7.33-7.55(5H, m), 7.86(1H, s), 8.21(1H, s), 11.08(1H, s)

MASS (APCI): 541(M+Na)+

Preparation 176

To a suspension of ethyl (2E)-3-[6-(4-piperidylamino)-3-pyridyl]acrylate dihydrochloride (500 mg) in DMF (5 ml) was added 4-(1H-pyrrol-1-yl)benzoic acid (309 mg), EDCI HCl (317 mg), HOBt (223 mg), Et$_3$N (0.63 ml), the mixture was stirred at 23° C. for 8 hours. The mixed solution was poured into a mixture of water (20 ml) and AcOEt (20 ml).

The organic layer was separated, washed with water twice and brine, dried over sodium sulfate and concentrated in vacuo. The residue was purified by silica gel column chromatography eluted with 5% MeOH in dichloromethane to give ethyl (2E)-3-[6-({1-[4-(1H-pyrrol-1-yl)benzoyl]-4-piperidyl}amino)-3-pyridyl]acrylate (686 mg).

NMR (DMSO-$d_6$, δ): 1.24(3H, t, J=7.4 Hz), 1.40-1.55(2H, m), 1.80-2.10(2H, m), 3.10-3.30(2H, m), 3.55-3.80(1H, m), 4.14(2H, q, J=7.4 Hz), 4.20-4.40(1H, m), 6.28-6.36(3H, m), 6.52(1H, d, J=8.8 Hz), 7.20(1H, d, J=7.4 Hz), 7.44-7.51(5H, m), 7.66(2H, d, J=8.6 Hz), 7.46-7.83(1H, m), 8.23(1H, d, J=2.0 Hz)

MASS (APCI): 445(M+H)+

The following compounds were obtained according to a similar manner to that of Preparation 176.

Preparation 177

Ethyl (2E)-3-(5-chloro-6-{[1-(4-phenoxybenzoyl)-4-piperidyl]amino}-3-pyridyl)acrylate NMR (DMSO-$d_6$, δ): 1.24(3H, t, J=7.4 Hz), 1.45-3.00(4H, m), 4.15(2H, q, J=7.4 Hz), 4.25-4.60(2H, m), 6.49(1H, d, J=16.0 Hz), 6.75(1H, d, J=8.4 Hz), 7.01-7.24(5H, m), 7.39-7.47(4H, m), 7.41(1H, d, J=16.0 Hz), 7.12 (1H, d, J=2.0 Hz), 8.29(1H, d, J=2.0 Hz)

MASS (APCI): 528(M+Na)+

Preparation 178

To an ice-cooled solution of ethyl (2E)-3-[6-(4-piperidylamino)-3-pyridyl]acrylate dihydrochloride (309 mg) and Et$_3$N (0.448 ml) in DMF (3 ml) was added 1-chloro-4-isocyanatobenzene (136 mg), the mixture was stirred at 23° C. for 1 hour. The mixed solution was poured into water (20 ml). The precipitate was collected, washed with hexane and water, dried under reduced pressure to give ethyl (2E)-3-{6-[(1-{[(4-chlorophenyl)amino]carbonyl}-4-piperidyl)amino]-3-pyridyl}acrylate (341 mg).

NMR (DMSO-$d_6$, δ): 1.20-1.63(7H, m), 2.10-2.19(2H, m), 3.04-3.19(3H, m), 3.94-4.03(3H, m), 4.23(2H, q, J=7.0 Hz), 4.67(1H, d, J=7.8 Hz), 6.20(1H, d, J=16.0 Hz), 6.36-6.45(2H, m), 7.21-7.34(5H, m), 7.53-7.64(2H, m), 8.20(1H, d, J=2.0 Hz)

MASS (APCI): 429(M+H)+

The following compounds were obtained according to a similar manner to that of Preparation 178.

Preparation 179

Ethyl (2E)-3-{6-[(1-{[(4-methylphenyl)amino]carbonyl}-4-piperidyl)amino]-3-pyridyl}acrylate NMR (DMSO-$d_6$, δ): 1.32(3H, t, J=7.1 Hz), 1.40-1.60(2H, m), 2.10-2.18(2H, m), 2.29(3H, s), 3.90-4.14(2H, m), 4.25 (2H, q, J=7.1 Hz), 7.42(1H, d, J=7.8 Hz), 6.22(1H, d, J=16.0 Hz), 6.36-6.40(2H, m), 7.08(2H, d, J=8.8 Hz), 7.22(2H, d, J=8.8 Hz), 7.54(1H, d, J=16.0 Hz), 7.62(1H, dd, J=2.0, 8.8 Hz), 8.19(1H, d, J=2.0 Hz)

MASS (APCI): 431(M+Na)+

Preparation 180

Ethyl (2E)-3-{6-[(1-{[(4-methoxyphenyl)amino]carbonyl}-4-piperidyl)amino]-3-pyridyl}acrylate

MASS (APCI): 425(M+H)+

Preparation 181

Ethyl (2E)-3-{5-chloro-6-[(1-{[(4-chlorophenyl)amino]carbonyl}-4-piperidyl)amino]-3-pyridyl}acrylate NMR (DMSO-$d_6$, δ): 1.24(3H, t, J=7.4 Hz), 1.50-1.67(2H, m), 1.82-1.88(2H, m), 2.84-2.96(2H, m), 4.10-4.26(3H, m), 4.15(2H, q, J=7.4 Hz), 6.49(1H, d, J=16.0 Hz), 6.78(1H, d, J=8.0 Hz), 7.26(2H, d, J=8.8 Hz), 7.49(2H, d, J=8.8 Hz), 7.50(1H, d, J=16.0 Hz), 8.12(1H, d, J=2.0 Hz), 8.30(1H, d, J=2.0 Hz), 8.68(1H, s)

Preparation 182

To a solution of ethyl (2E)-3-{5-chloro-6-[(1-{[(4-chlorophenyl)amino]carbonyl}-4-piperidyl)amino]-3-pyridyl}acrylate (363 mg) in THF (3 ml) and MeOH (3 ml) was added 1N NaOH aq (2.35 ml), the mixture was stirred at 80° C. for 1 hour. The pH of the mixture was adjusted to ca.4.5 with 1N HCl aq. The solution was evaporated under reduced pressure to give crude 3-{5-Chloro-6-[1-(4-chlorophenylcarbamoyl)-piperidin-4-ylamino]-pyridin-3-yl}-acrylic acid.

To a suspension of crude 3-{5-Chloro-6-[1-(4-chlorophenylcarbamoyl)-piperidin-4-ylamino]-pyridin-3-yl}-acrylic acid (247 mg) in DMF (3 ml) was added O-(tetrahydro-2H-pyran-2-yl)hydroxylamine (73.1 mg), EDCI (96.9 mg), HOBt (84.3 mg,), the mixture was stirred at 23° C. for 8 hours. The mixed solution was poured into a mixture of water (20 ml) and AcOEt (20 ml). The organic layer was separated, washed with water twice and brine, dried over sodium sulfate and concentrated in vacuo. The residue was purified by silica gel column chromatography eluted with 5% MeOH in dichloromethane to give 4-[(3-chloro-5-{(1E)-3-oxo-3-[(tetrahydro-2H-pyran-2-yloxy)amino]-1-propen-1-yl}-2-pyridyl)amino]-N-(4-chlorophenyl)-1-piperidinecarboxamide (246 mg).

NMR (DMSO-$d_6$, δ): 1.45-1.95(10H, m), 2.75-3.00(2H, m), 3.45-3.50(1H, m), 3.80-4.30(3H, m), 4.89(1H, s), 6.31(1H, d, J=16.0 Hz), 6.68(1H, d, J=8.4 Hz), 7.27(2H, d, J=8.8 Hz), 7.36(1H, d, J=16.0 Hz), 7.51(2H, d, J=8.8 Hz), 7.85(1H, s), 8.22(1H, s), 8.68(1H, s)

MASS (APCI): 556(M+Na)+

The following compounds were obtained according to a similar manner to that of Preparation 182.

Preparation 183

(2E)-3-(5-Chloro-6-{[1-(3-chlorobenzoyl)-4-piperidyl]amino}-3-pyridyl)-N-(tetrahydro-2H-pyran-2-yloxy)acrylamide

MASS (ESI): 519(M+H)+

Preparation 184

(2E)-3-(5-Chloro-6-{[1-(2-chlorobenzoyl)-4-piperidyl]amino}-3-pyridyl)-N-(tetrahydro-2H-pyran-2-yloxy)acrylamide

MASS (ESI): 519(M+H)+

Preparation 185

(2E)-3-{6-[(1-Benzyl-4-piperidyl]amino}-5-chloro-3-pyridyl)-N-(tetrahydro-2H-pyran-2-yloxy)acrylamide NMR (DMSO-$d_6$, δ): 1.40-2.35(11H, m), 2.80-3.10(2H, m), 3.40-3.75(3H, m), 3.82-4.15(2H, m), 4.88(1H, s), 6.32(1H, d, J=16.0 Hz), 9.59(1H, m), 7.20-7.40(6H, m), 7.84(1H, s), 8.20(1H, s), 11.10(1H, s)

Preparation 186

(2E)-3-(5-Chloro-6-{[1-(4-methylbenzyl)-4-piperidyl]amino}-3-pyridyl)-N-(tetrahydro-2H-pyran-2-yloxy)acrylamide NMR (DMSO-d$_6$, δ): 1.45-1.85(9H, m), 1.90-2.10(2H, m), 2.28(3H, s), 2.75-2.85(2H, m), 3.41(2H, s), 3.49-3.55(1H, m), 3.85-4.10(2H, m), 4.89(1H, s), 6.31(1H, d, J=16.0 Hz), 6.50(1H, d, J=7.0 Hz), 7.11(2H, d, J=8.8 Hz), 7.18(2H, d, J=8.8 Hz), 7.36(1H, d, J=16.0 Hz), 7.83(1H, s), 8.20(1H, s), 11.08(1H, brs)

Preparation 187

(2E)-3-(5-Chloro-6-{[1-(4-methoxybenzyl)-4-piperidyl]amino}-3-pyridyl)-N-(tetrahydro-2H-pyran-2-yloxy)acrylamide NMR (DMSO-d$_6$, δ): 1.45-1.90(11H, m), 1.90-2.15(2H, m), 2.78-2.84(2H, m), 3.40(2H, s), 3.48-3.55(1H, m), 3.74(3H, s), 3.80-4.05(2H, m), 4.89(1H, s), 6.30(1H, d, J=16.0 Hz), 6.50(1H, d, J=7.0 Hz), 6.88(1H, d, J=8.8 Hz), 7.20(1H, d, J=8.8 Hz), 7.35(1H, d, J=16.0 Hz), 7.83(1H, s), 8.20(1H, s), 11.08(1H, s)

Preparation 188

(2E)-3-(5-Chloro-6-[(1-isobutyl-4-piperidyl)amino]-3-pyridyl)-N-(tetrahydro-2H-pyran-2-yloxy)acrylamide NMR (DMSO-d$_6$, δ): 0.86(6H, d, J=6.5 Hz), 1.40-2.10(15H, m), 2.70-2.90(2H, m), 3.45-3.70(1H, m), 3.80-4.00(2H, m), 4.88(1H, brs), 6.30(1H, d, J=16.0 Hz), 6.50(1H, d, J=8.0 Hz), 7.35(1H, d, J=16.0 Hz), 7.83(1H, s), 8.20(1H, s), 11.06(1H, brs)

Preparation 189

(2E)-3-(5-Chloro-6-{[1-(cyclopropylmethyl)-4-piperidyl]amino}-3-pyridyl)-N-(tetrahydro-2H-pyran-2-yloxy)acrylamide NMR (DMSO-d$_6$, δ): 0.05-0.15(2H, m), 0.42-0.51(2H, m), 0.75-0.95(1H, m), 1.40-2.30(14H, m), 2.90-3.15(2H, m), 3.40-3.60(1H, m), 3.80-4.10(2H, m), 4.89(1H, s), 6.31(1H, d, J=16.0 Hz), 6.53(1H, d, J=8.0 Hz), 7.35(1H, d, J=16.0 Hz), 7.85(1H, s), 8.21(1H, s), 11.07(1H, brs)

Preparation 190

(2E)-3-{6-[[1-(4-Chlorobenzoyl)-4-piperidyl](methyl)amino]-3-pyridyl}-N-(tetrahydro-2H-pyran-2-yloxy)acrylamide NMR (DMSO-d$_6$, δ): 1.40-1.90(11H, m), 2.75-3.30(2H, m), 2.90(3H, s), 3.45-3.60(2H, m), 3.85-4.10(1H, m), 4.45-4.90(3H, m), 6.27(1H, d, J=16.0 Hz), 6.74(1H, d, J=8.8 Hz), 7.39(1H, d, J=16.0 Hz), 7.45-7.55(4H, m), 7.74(1H, dd, J=2.0, 8.8 Hz), 8.27(1H, d, J=2.0 Hz), 11.08(1H, brs)

Preparation 191

(2E)-3-(5-Chloro-6-{[(3R)-1-(4-fluorobenzyl)-3-pyrrolidinyl]amino}-3-pyridyl)-N-(tetrahydro-2H-pyran-2-yloxy)acrylamide NMR (DMSO-d$_6$, δ): 1.50-19.0(7H, m), 2.08-2.29(1H, m), 2.37-2.65(2H, m), 2.78-2.87(1H, m), 3.40-3.65(1H, m), 3.57(2H, s), 3.86-4.12(1H, m), 4.45-4.55(1H, m), 4.89(1H, s, J=16.0 Hz), 6.32(1H, d, J=7.0 Hz), 6.62(1H, d), 7.09-7.17(2H, m), 7.85-7.30-7.40(3H, m), 8.20-7.85(1H, s), 8.20(1H, s), 11.08(1H, brs)

Preparation 192

(2E)-3-(5-Chloro-6-{[(3R)-1-(4-methylbenzyl)-3-pyrrolidinyl]amino}-3-pyridyl)-N-(tetrahydro-2H-pyran-2-yloxy)acrylamide NMR (DMSO-d$_6$, δ): 1.45-1.90(7H, m), 2.10-2.30(1H, m), 2.27(3H, s), 2.36-2.84(3H, m), 3.45-3.53(1H, m), 3.60(2H, s), 3.94-4.05(1H, m), 4.40-4.60(1H, m), 4.89(1H, s), 6.32(1H, d, J=16.0 Hz), 6.60(1H, d, J=7.0 Hz), 7.10(2H, d, J=8.8 Hz), 7.28(2H, d, J=8.8 Hz), 7.36(1H, d, J=16.0 Hz), 7.84(1H, s), 8.20(1H, s), 11.08(1H, brs)

Preparation 193

(2E)-3-(5-Chloro-6-{[(3R)-1-(4-methoxybenzyl)-3-pyrrolidinyl]amino}-3-pyridyl)-N-(tetrahydro-2H-pyran-2-yloxy)acrylamide NMR (DMSO-d$_6$, δ): 1.76-1.92(7H, m), 2.12-2.30(1H, m), 2.32-2.86(3H, m), 3.40-3.60(1H, m), 3.51(2H, s), 3.72(3H, s), 3.86-4.05(1H, m), 4.35-4.60(1H, m), 4.89(1H, s), 6.31(1H, d, J=16.0 Hz), 6.61(1H, d, J=7.0 Hz), 6.86(2H, d, J=8.8 Hz), 7.21(2H, d, J=8.8 Hz), 7.35(1H, d, J=16.0 Hz), 7.84(1H, s), 8.19(1H, s), 11.07(1H, brs)

Preparation 194

To a solution of ethyl (2E)-3-[6-(4-piperidylamino)-3-pyridyl]acrylate dihydrochloride (309 mg) in EtOH (5 ml) was added Et$_3$N (0.921 ml), then benzaldehyde (0.117 ml) and titanium(IV) isopropoxide (0.463 ml), the mixture was stirred at 23° C. for 12 hours. To the mixture was added sodium borohydride, the mixture was stirred at 23° C. for 24 hours. The reaction mixture was poured into sat.NaHCO$_3$aq. (20 ml)-AcOEt (20 ml), the insoluble material was removed by filtration, then the filtrate was extracted with ethyl acetate. The extracts were washed with water, dried over magnesium sulfate and concentrated. The residue was purified by silica gel column chromatography eluted with 5% MeOH in dichloromethane to give ethyl (2E)-3-{6-[(1-benzyl-4-piperidyl)amino]-5-chloro-3-pyridyl}acrylate (328 mg).

NMR (DMSO-d$_6$, δ): 1.24(3H, t, J=7.4 Hz), 1.55-1.68(4H, m), 1.95-2.07(2H, m), 2.75-2.87(2H, m), 3.46(2H, s), 3.90-4.10(1H, m), 4.15(2H, q, J=7.4 Hz), 6.47(1H, d, J=16.0 Hz), 6.63(1H, d, J=8.0 Hz), 7.21-7.37(5H, m), 7.50(1H, d, J=16.0 Hz), 8.10(1H, d, J=2.0 Hz), 8.27(1H, d, J=2.0 Hz).

MASS (APCI): 400(M+H)+

The following compounds were obtained according to a similar manner to that of Preparation 194.

Preparation 195

Ethyl (2E)-3-(5-chloro-6-{[1-(4-chlorobenzyl)-4-piperidyl]amino}-3-pyridyl)acrylate NMR (DMSO-d$_6$, δ): 1.24(3H, t, J=7.2 Hz), 1.50-2.10(6H, m), 2.67-2.89(2H, m), 3.46(2H, s), 3.89-4.10(1H, m), 4.15(2H, q, J=7.2 Hz), 6.47(1H, d, J=16.0 Hz), 6.63(1H, d, J=8.0 Hz), 7.30-7.41(4H, m), 7.50(1H, d, J=16.0 Hz), 8.10(1H, d, J=2.0 Hz), 8.27(1H, d, J=2.0 Hz)

MASS (APCI): 434(M+H)+

Preparation 196

Ethyl (2E)-3-(5-chloro-6-{[1-(4-fluorobenzyl)-4-piperidyl]amino}-3-pyridyl)acrylate NMR (DMSO-$d_6$, δ): 1.24(3H, t, J=7.4 Hz), 1.55-1.68(4H, m), 1.95-2.07(2H, m), 2.75-2.87(2H, m), 3.46(2H, s), 3.90-4.10(1H, m), 4.15(2H, q, J=7.4 Hz), 6.47(1H, d, J=16.0 Hz), 6.63(1H, d, J=8.0 Hz), 7.09-7.38(4H, m), 7.50(1H, d, J=16.0 Hz), 8.10(1H, d, J=2.0 Hz), 8.27(1H, d, J=2.0 Hz).

MASS (APCI): 418(M+H)+

Preparation 197 tert-Butyl 4-(methylamino)-1-piperidinecarboxylate

NMR (DMSO-$d_6$, δ): 0.95-1.12(2H, m), 1.38(9H, s), 1.68-1.76(2H, m), 2.25(3H, s), 2.30-2.40(1H, m), 2.65-2.95(2H, m), 3.32(1H, brs), 3.70-3.85(2H, m).

Preparation 198

To a solution of ethyl (2E)-3-[5-chloro-6-(4-piperidylamino)-3-pyridyl]acrylate dihydrochloride (710 mg) in CH$_2$Cl$_2$ (14 ml) was added Et$_3$N (0.517 ml), the mixture was stirred at 23° C. for 30 minutes. To the mixture was added 4-Methyl-benzaldehyde (0.241 ml) and SODIUM triacetoxyborohydride (590 mg), the mixture was stirred at 23° C. for 24 hours. The reaction mixture was poured into sat.NaHCO$_3$aq. (20 ml)-AcOEt (20 ml). The organic layer was washed with water, dried over magnesium sulfate and concentrated. The residue was purified by silica gel column chromatography eluted with 5% MeOH in dichloromethane to give ethyl (2E)-3-(5-chloro-6-{[1-(4-methylbenzyl)-4-piperidyl]amino}-3-pyridyl)acrylate (671 mg).

NMR (DMSO-$d_6$, δ): 1.24(3H, t, J=7.4 Hz), 1.50-1.87(4H, m), 1.94-2.05(2H, m), 2.28(3H, s), 2.77-2.83(2H, m), 3.41 (2H, s), 3.85-4.07(1H, m), 4.15(2H, q, J=7.4 Hz), 6.47(1H, d, J=16.0 Hz), 6.62(1H, d, J=7.0 Hz), 7.11(2H, d, J=8.8 Hz), 7.18(2H, d, J=8.8 Hz), 7.50(1H, d, J=16.0 Hz), 8.10(1H, d, J=2.0 Hz), 8.27(1H, d, J=2.0 Hz),

The following compounds were obtained according to a similar manner to that of Preparation 198.

Preparation 199

Ethyl (2E)-3-(5-chloro-6-{[1-(4-methoxybenzyl)-4-piperidyl]amino}-3-pyridyl)acrylate NMR (DMSO-$d_6$, δ): 1.21(3H, t, J=7.4 Hz), 1.56-1.89(4H, m), 1.90-2.15(2H, m), 2.78-2.84(2H, m), 3.40(2H, s), 3.74 (3H, s), 3.85-4.10(1H, m), 4.16(2H, q, J=7.4 Hz), 6.47(1H, d, J=16.0 Hz), 6.61(2H, d, J=8.8 Hz), 7.20(2H, d, J=8.8 Hz), 7.50(1H, d, J=16.0 Hz), 8.09(1H, d, J=2.0 Hz), 8.27(1H, d, J=2.0 Hz)

Preparation 200

Ethyl (2E)-3-{5-chloro-6-[(1-isobutyl-4-piperidyl)amino]-3-pyridyl}acrylate

MASS (ESI): 366(M+H)+

Preparation 201

Ethyl (2E)-3-(5-chloro-6-{[1-(cyclopropylmethyl)-4-piperidyl]amino}-3-pyridyl)acrylate

MASS (ESI): 364(M+H)+

Preparation 202

To a solution of (3R)-(+)-3-(tert-butoxycarbonylamino)pyrrolidine (5.0 g) in DMF (50 ml) was added 4-fuluorobenzylchloride (3.38 ml) and N,N-diisopropylethylamine (9.35 ml), the mixture was stirred at 70° C. for 2 hours. The mixed solution was poured into a mixture of water (300 ml) and AcOEt (30 0 ml). The organic layer was separated, washed with water twice and brine, dried over sodium sulfate and concentrated in vacuo. The residue was purified by silica gel column chromatography eluted with 5% MeOH in dichloromethane to give [1-(4-fluoro-benzyl)-pyrrolidin-3-yl]-carbamic acid tert-butyl ester (6.8 g). To a solution of [1-(4-fluoro-benzyl)-pyrrolidin-3-yl]-carbamic acid tert-butyl ester (6.8 g) in MeOH (34 ml) was treated with 4N HCl in AcOEt (29 ml) and was stirred at 25° C. for 12 hours.

The solvent was removed under reduced pressure. Recrystallization (acetonitrile-MeOH) provided (3R)-1-(4-fluorobenzyl)-3-pyrrolidinamine dihydrochloride as white solid (3.77 g).

NMR (DMSO-$d_6$, δ): 1.96-2.55(2H, m), 3.10-3.78(4H, m), 3.80-4.22(1H, m), 4.47-4.52(2H, m), 7.26-7.36(2H, m), 7.61-7.72(2H, m), 8.60-8.90(2H, m), 11.50-11.99(1H, m)

MASS (APCI): 195(M+H)+

The following compounds were obtained according to a similar manner to that of Preparation 202.

Preparation 203

(3R)-1-(4-Methylbenzyl)-3-pyrrolidinamine dihydrochloride

NMR (DMSO-$d_6$, δ): 1.96-2.55(2H, m), 2.33(3H, s), 3.10-3.78(4H, m), 3.80-4.22(1H, m), 4.47-4.52(2H, m), 7.25(2H, d, J=8.8 Hz), 7.50(2H, brs), 8.73-8.23(2H, m), 11.39-11.87 (1H, m).

MASS (APCI): 191(M+H)+

Preparation 204

(3R)-1-(4-Methoxybenzyl)-3-pyrrolidinamine dihydrochloride

NMR (DMSO-$d_6$, δ): 1.90-2.30(2H, m), 3.10-3.75(4H, m), 3.78(3H, s), 3.80-4.15(1H, m), 7.37(2H, brs), 7.00(2H, d, J=8.8 Hz), 7.54(2H, brs), 8.67-8.76(2H, m)

MASS (APCI): 206(M+H)+

Preparation 205

To a solution of (3R)-1-(4-fluorobenzyl)-3-pyrrolidinamine dihydrochloride (3.5 g) in DMF (35 ml) was added 5,6-dichloronicotinic acid ethyl ester (3.38 ml) and K$_2$CO$_3$ (6.34 g), the mixture was stirred at 100° C. for 4 hours under N$_2$ atmosphere. The mixed solution was poured into a mixture of water (250 ml) and AcOEt (250 ml). The organic layer was separated, washed with water twice and brine, dried over sodium sulfate and concentrated in vacuo. The residue was purified by silica gel column chromatography eluted with AcOEt:hexane=1:2 to give ethyl 5-chloro-6-{[(3R)-1-(4-fluorobenzyl)-3-pyrrolidinyl]amino}nicotinate (3.75 g).

NMR (DMSO-$d_6$, δ): 1.28(3H, t, J=7.4 Hz), 1.73-1.98(1H, m), 2.10-2.30(1H, m), 2.40-2.70(3H, m), 2.82-2.87(1H, m), 3.57(2H, s), 4.25(2H, q, J=7.4 Hz), 4.51-4.61(1H, m), 4.02-7.18(3H, m), 7.31-7.38(2H, m), 7.93(1H, d, J=2.0 Hz), 8.54 (1H, d, J=2.0 Hz)

MASS (APCI): 378(M+H)+

The following compounds were obtained according to a similar manner to that of Preparation 205.

Preparation 206

Ethyl 5-chloro-6-{[(3R)-1-(4-methylbenzyl)-3-pyrrolidinyl]amino}nicotinate

NMR (DMSO-d$_6$, δ): 1.24(3H, t, J=7.4 Hz), 1.76-1.95(1H, m), 2.12-2.34(1H, m), 2.27(3H, s), 2.45-2.70(3H, m), 2.71-2.85(1H, m), 3.54(2H, s), 4.24(2H, q, J=7.4 Hz), 4.46-4.60 (1H, m), 7.00-7.21(5H, m), 7.93(1H, d, J=2.0 Hz), 8.53(1H, d, J=2.0 Hz)

MASS (APCI): 374(M+H)+

Preparation 207

Ethyl 5-chloro-6-{[(3R)-1-(4-methoxybenzyl)-3-pyrrolidinyl]amino}nicotinate

MASS (ESI): 390(M+H)+

Preparation 208

To a solution of 2-chloro-5-iodopyridine (37.7 g) in DMF (300 mL) was added palladium(II) acetate (1.77 g), tri-o-tolylphosphine (7.19 g), diisopropylethylamine (82 mL), and ethyl acrylate (17.9 mL), and the mixture was heated at 100° C. for 10 hours. Resulting mixture was poured into water and extracted with AcOEt. The organic layer was washed with water and brine and dried over Na$_2$SO$_4$, and the solvent was removed in vacuo. Obtained brown solid was suspended in a mixture of hexane and AcOEt (4:1), and the precipitate was filtered off. The filtrate was concentrated in vacuo, and residual brown oil was purified by silica gel column chromatography eluted with AcOEt and hexane (1:4-1:2). Resulting solid was triturated with IPE to give ethyl (2E)-3-(6-chloro-3-pyridyl)acrylate as pale yellow powder (20.58 g).

NMR (DMSO-d$_6$, δ): 1.35 (3H, t, J=7.0 Hz), 4.28 (2H, q, J=7.0 Hz), 6.49 (1H, d, J=16.1 Hz), 7.37 (1H, d, J=8.1 Hz), 7.63 (1H, d, J=16.1 Hz), 7.80 (1H, dd, J=8.2, 2.6 Hz), 8.52 (1H, d, J=2.6 Hz)

MS (ES+) m/z 212 (M+1)

Preparation 209

To a solution of ethyl (2E)-3-(6-chloro-3-pyridyl)acrylate (14.3 g) in dioxane (140 mL) was added palladium(II) acetate (1.52 g), 2'-(dicyclohexylphosphino)-N,N-dimethyl-2-biphenylamine (3.99 g), cesium carbonate (30.2 g), and (3R)-(−)-1-benzyl-3-aminopyrrolidine (13.1 g), and the mixture was heated at 95° C. for 2.5 days. The resulting mixture was poured into sat.NH$_4$Cl aqueous solution and extracted with AcOEt. The organic layer was washed with sat. NH$_4$Cl aq solution, water, and brine, and dried over Na$_2$SO$_4$. The solvent was removed in vacuo and residual brown oil was purified by silica gel column chromatography eluted with AcOEt to give ethyl (2E)-3-(6-{[(3R)-1-benzyl-3-pyrrolidinyl]amino}-3-pyridyl)acrylate as pale yellow oil (10.7 g)

NMR (DMSO-d$_6$, δ): 1.32 (3H, t, J=7.0 Hz), 1.70 (1H, m), 2.39 (2H, m), 2.61 (1H, m), 2.75 (1H, m), 2.84 (1H, m), 3.64 (2H, d, J=2.2 Hz), 4.24 (2H, q, J=7.0 Hz), 4.35 (1H, m), 5.09 (1H, d, J=8.0 Hz), 6.20 (1H, d, J=16.1 Hz), 6.36 (1H, d, J=8.8 Hz), 7.27 (2H, m), 7.32 (3H, m), 7.56 (1H, d, J=15.8 Hz), 7.60 (1H, d, J=8.8, 2.2 Hz), 8.19 (1H, d, J=2.2 Hz)

MS (ES+) m/z 352 (M+1)

Preparation 210

To a solution of ethyl (2E)-3-(6-{[(3R)-1-benzyl-3-pyrrolidinyl]amino}-3-pyridyl)acrylate (11 g) in THF (105 mL) was added di-tert-butyl bicarbonate (13.7 g) and 4-dimethylaminopyridine (95.6 mg), and the mixture was heated at 60° C. for 13 hours. The solvent was removed in vacuo and residual oil was purified by silica gel column chromatography eluted with AcOEt to give ethyl (2E)-3-{6-[[(3R)-1-benzyl-3-pyrrolidinyl](tert-butoxycarbonyl)amino]-3-pyridyl}acrylate as pale yellow oil (13.0 g).

NMR (DMSO-d$_6$, δ): 1.35 (3H, t, J=7.0 Hz), 1.44 (9H, s), 2.08 (1H, m), 2.23 (1H, m), 2.57-2.73 (3H, m), 2.93 (1H, t, J=8.8 Hz), 3.53 (1H, d, J=12.6 Hz), 3.63 (1H, d, J=12.8 Hz), 4.29 (2H, q, J=7.0 Hz), 4.91 (1H, m), 6.46 (1H, d, J=16.1 Hz), 7.20-7.27 (5H, m), 7.29 (1H, d, J=8.8 Hz), 7.66 (1H, d, J=16.1 Hz), 7.80 (1H, dd, J=8.4, 2.2 Hz), 8.53 (1H, d, J=2.2 Hz)

MS (ES+) m/z 452 (M+1)

Preparation 211

To a solution of ethyl (2E)-3-{6-[[(3R)-1-benzyl-3-pyrrolidinyl](tert-butoxycarbonyl)amino]-3-pyridyl}acrylate as pale yellow oil (16.6 g) in toluene (80 mL) was added diisopropylethylamine (2.17 mL) and 1-chloroethyl chloridecarbonate (5.76 mL) at 5° C. The mixture was warmed to ambient temperature and stirred for 1 hour, and diluted with IPE (150 mL). The precipitate was removed by filtration and the solvent was removed in vacuo. Residual colorless oil was purified by silica gel column chromatography eluted with AcOEt and hexane (1:2-1:1). Obtained oil was dissolved in EtOH (70 mL) and heated at 70° C. for 1 hour. The solvent was removed in vacuo to give ethyl (2E)-3-(6-{(tert-butoxycarbonyl)[(3R)-3-pyrrolidinyl]amino}-3-pyridyl)acrylate dihydrochloride (8.9 g) as pale yellow oil.

NMR (DMSO-d$_6$, δ): 1.27 (3H, t, J=7.0 Hz), 1.42 (9H, s), 1.98 (1H, m), 2.23 (1H, m), 3.15 (1H, m), 3.34 (3H, br), 4.21 (2H, q, J=7.0 Hz), 4.96 (1H, m), 6.78 (1H, d, J=16.1 Hz), 7.45 (1H, d, J=8.4 Hz), 7.70 (1H, d, J=16.1 Hz), 8.25 (1H, dd, J=8.6, 2.2 Hz), 8.75 (1H, d, J=2.2 Hz),

MS (ES+) m/z 362 (M+1)

Preparation 212

To a solution of ethyl (2E)-3-(6-{(tert-butoxycarbonyl)[(3R)-3-pyrrolidinyl]amino}-3-pyridyl)acrylate dihydrochloride (3.0 g) in 1,2-dichloroethane (30 mL) was added diisopropylethylamine (2.41 mL) and 3-fluorobenzaldehyde (857 mg), and the mixture was stirred at room temperature for 5 minutes. To the mixture was added sodium triacetoxyborohydride (3.1 g) and stirred for 3 hours, and resulting mixture was poured into sat NH$_4$Cl aq solution, and extracted with AcOEt. The organic layer was washed with sat NH$_4$Cl aq solution, water, and brine, and dried over Na$_2$SO$_4$. The solvent was removed in vacuo and the residual oil was purified by silica gel column chromatography eluted with AcOEt and hexane (1:1) to give ethyl (2E)-3-(6-{(tert-butoxycarbonyl)[(3R)-1-(2-fluorobenzyl)-3-pyrrolidinyl]amino}-3-pyridyl)acrylate (2.40 g) as colorless oil.

NMR (DMSO-d$_6$, δ): 1.35 (3H, t, J=7.0 Hz), 1.44 (9H, s), 2.09 (1H, m), 2.24 (1H, m), 2.64 (2H, t, J=7.4 Hz), 2.74 (1H, dd, J=9.2, 7.0 Hz), 2.89 (1H, t, J=8.1 Hz), 3.51 (1H, d, J=13.3 Hz), 3.62 (1H, d, J=13.3 Hz), 4.28 (2H, q, J=7.0 Hz), 4.91 (1H, m), 6.47 (1H, d, J=16.1 Hz), 6.91 (2H, m), 6.99 (1H, d, J=8.0 Hz), 7.21 (1H, m), 7.28 (1H, d, J=8.4 Hz), 7.66 (1H, d, J=16.1 Hz), 7.81 (1H, dd, J=8.4, 2.6 Hz), 8.54 (1H, d, J=2.2 Hz)

MS (ES+) m/z 470 (M+1)

The following compounds were obtained according to a similar manner to that of Preparation 212.

Preparation 213

Ethyl (2E)-3-(6-{(tert-butoxycarbonyl)[(3R)-1-(4-tert-butylbenzyl)-3-pyrrolidinyl]amino}-3-pyridyl)acrylate NMR (DMSO-$d_6$, δ): 1.31 (9H, s), 1.36 (3H, t, J=7.0 Hz), 1.44 (9H, s), 1.97-2.32 (2H, m), 2.53-2.77 (3H, m), 2.89-3.01 (1H, m), 3.54 (1H, d, J=12.1 Hz), 3.60 (1H, d, J=12.1 Hz), 4.83-4.98 (1H, m), 6.47 (1H, d, J=16.1 Hz), 7.16 (2H, d, J=8.1 Hz), 7.23-7.34 (1H, m), 7.30 (2H, d, J=8.1 Hz), 7.67 (1H, d, J=16.1 Hz), 7.81 (1H, dd, J=8.4, 2.6 Hz), 8.54 (1H, d, J=2.6 Hz)

MS (ES+) m/z 508.36

Preparation 214

Ethyl (2E)-3-[6-((tert-butoxycarbonyl){(3R)-1-[4-(trifluoromethyl)benzyl]-3-pyrrolidinyl}amino)-3-pyridyl]acrylate NMR (DMSO-$d_6$, δ): 1.35 (3H, t, J=7.0 Hz), 1.44 (9H, s), 1.97-2.14 (1H, m), 2.16-2.31 (1H, m), 2.56-2.79 (3H, m), 2.88-2.97 (1H, m), 3.59 (1H, d, J=13.2 Hz), 3.67 (1H, d, J=13.2 Hz), 4.29 (2H, q, J=7.0 Hz), 4.83-4.99 (1H, m), 6.47 (1H, d, J=16.1 Hz), 7.29 (1H, d, J=8.4 Hz), 7.35 (2H, d, J=8.1 Hz), 7.53 (2H, d, J=8.1 Hz), 7.66 (1H, d, J=16.1 Hz), 7.80 (1H, dd, J=8.4, 2.6 Hz), 8.53 (1H, d, J=2.6 Hz)

MS (ES+) m/z 520.32(M+1)

Preparation 215

Ethyl (2E)-3-[6-((tert-butoxycarbonyl){(3R)-1-[4-(trifluoromethoxy)benzyl]-3-pyrrolidinyl}amino)-3-pyridyl]acrylate NMR (DMSO-$d_6$, δ): 1.35 (3H, t, J=7.3 Hz), 1.43 (9H, s), 1.97-2.32 (2H, m), 2.53-2.77 (3H, m), 2.87-2.98 (1H, m), 3.54 (1H, d, J=13.2 Hz), 3.62 (1H, d, J=13.2 Hz), 4.29 (2H, q, J=7.3 Hz), 4.83-4.97 (1H, m), 6.47 (1H, d, J=16.1 Hz), 7.12 (2H, d, J=8.1 Hz), 7.25 (2H, d, J=8.1 Hz), 7.29 (1H, d, J=8.4 Hz), 7.66 (1H, d, J=16.1 Hz), 7.80 (1H, dd, J=8.4, 2.6 Hz), 8.53 (1H, d, J=2.6 Hz)

MS (ES+) m/z 536.24(M+1)

Preparation 216

Ethyl (2E)-3-(6-{(tert-butoxycarbonyl)[(3R)-1-(cyclohexylmethyl)-3-pyrrolidinyl]amino}-3-pyridyl)acrylate NMR (CDCl$_3$, δ): 0.69-0.95 (2H, m), 1.02-1.48 (3H, m), 1.35 (3H, t, J=7.0 Hz), 1.45 (9H, s), 1.52-1.80 (6H, m), 1.92-2.34 (4H, m), 2.41-2.74 (3H, m), 2.80-3.02 (1H, m), 4.29 (2H, q, J=7.0 Hz), 4.82-4.98 (1H, m), 6.46 (1H, d, J=16.1 Hz), 7.31 (1H, d, J=8.4 Hz), 7.66 (1H, d, J=16.1 Hz), 7.81 (1H, dd, J=8.4, 2.6 Hz), 8.86 (1H, d, J=2.6 Hz)

MS (ES+) m/z 458.37(M+1)

Preparation 217

Ethyl (2E)-3-(6-{(tert-butoxycarbonyl)[(3R)-1-(1-cyclohexen-1-ylmethyl)-3-pyrrolidinyl]amino}-3-pyridyl)acrylate NMR (DMSO-$d_6$, δ): 1.35 (3H, q, J=7.0 Hz), 1.45 (9H, s), 1.48-1.73 (4H, m), 1.83-2.09 (5H, m), 2.14-2.32 (1H, m), 2.45-2.67 (3H, m), 2.77-2.99 (3H, m), 4.28 (2H, q, J=7.0 Hz), 4.80-4.95 (1H, m), 5.52 (1H, brs), 6.46 (1H, d, J=16.1 Hz), 7.31 (1H, d, J=8.4 Hz), 7.66 (1H, d, J=16.1 Hz), 7.81 (1H, dd, J=8.4, 2.6 Hz), 8.56 (1H, d, J=2.6 Hz)

MS (ES+) m/z 456.54(M+1)

Preparation 218

Ethyl (2E)-3-{6-[[(3R)-1-(1-benzofuran-2-ylmethyl)-3-pyrrolidinyl](tert-butoxycarbonyl)amino]-3-pyridyl}acrylate NMR (CDCl$_3$, δ): 1.35 (3H, t, J=7 Hz), 1.43 (9H, s), 2.01-2.35 (2H, m), 2.70-3.23 (4H, m), 3.76-3.90 (2H, m), 4.28 (2H, q, J=7 Hz), 4.90-5.02 (1H, m), 6.42 (1H, d, J=16 Hz), 6.57 (1H, s), 7.17-7.27 (2H; m), 7.29 (1H, d, J=8 Hz), 7.42-7.54 (2H, m), 7.61 (1H, d, J=16 Hz), 7.76 (1H, dd, J=2, 8 Hz), 8.45 (1H, d, J=2 Hz)

MS (ES+) m/z 492 (M+1)

Preparation 219

Ethyl (2E)-3-(6-{[(3R)-1-(1-benzofuran-5-ylmethyl)-3-pyrrolidinyl](tert-butoxycarbonyl)amino]-3-pyridyl}acrylate NMR (CDCl$_3$, δ): 1.35 (3H, t, J=7 Hz), 1.43 (9H, s), 2.06-2.42 (2H, m), 2.79-3.27 (4H, m), 3.80-3.96 (2H, m), 4.29 (2H, q, J=7 Hz), 4.91-5.04 (1H, m), 6.45 (1H, d, J=16 Hz), 6.73-6.75 (1H, m), 7.28 (2H, d, J=8 Hz), 7.44 (1H, d, J=8 Hz), 7.57-7.67 (3H, m), 7.78 (1H, dd, J=2, 8 Hz), 8.49 (1H, d, J=2 Hz)

MS (ES+) m/z 492 (M+1)

Preparation 220

Ethyl (2E)-3-(6-{(tert-butoxycarbonyl)[(3R)-1-(3-methoxybenzyl)-3-pyrrolidinyl]amino}-3-pyridyl)acrylate NMR (CDCl$_3$, δ): 1.35 (3H, t, J=7.0 Hz), 1.44 (9H, s), 2.07 (1H, m), 2.24 (1H, m), 2.58-2.76 (3H, m), 2.94 (1H, m), 3.53 (1H, d, J=12.8 Hz), 3.61 (1H, d, J=12.8 Hz), 4.29 (2H, q, J=7.0 Hz), 4.91 (1H, m), 6.47 (1H, d, J=16.1 Hz), 6.76-6.83 (3H, m), 7.19 (1H, t, J=8.1 Hz), 7.29 (1H, d, J=8.4 Hz), 7.66 (1H, d, J=16.1 Hz), 7.80 (1H, dd, J=8.4, 2.6 Hz), 8.54 (1H, d, J=2.2 Hz)

MS (ES+) m/z 482 (M+1)

Preparation 221

Ethyl (2E)-3-(6-{(tert-butoxycarbonyl)[(3R)-1-(3-phenylpropyl)-3-pyrrolidinyl]amino}-3-pyridyl)acrylate NMR (CDCl$_3$, δ): 1.35 (3H, t, J=7.0 Hz), 1.45 (9H, s), 1.78 (2H, m), 2.01 (1H, m), 2.19 (1H, m), 2.36-2.77 (7H, m), 3.02 (1H, t, J=8.4 Hz), 4.28 (2H, q, J=7.0 Hz), 4.89 (1H, m), 6.44 (1H, d, J=16.1 Hz), 7.14-7.19 (3H, m), 7.23-7.28 (2H, m), 7.31 (1H, d, J=8.4 Hz), 7.65 (1H, d, J=16.1 Hz), 7.80 (1H, dd, J=8.4, 2.6 Hz), 8.54 (1H, d, J=2.6 Hz)

MS (ES+) m/z 480 (M+1)

Preparation 222

Ethyl (2E)-3-[6-((tert-butoxycarbonyl){(3R)-1-[4-(dimethylamino)benzyl]-3-pyrrolidinyl}amino)-3-pyridyl]acrylate NMR (CDCl$_3$, δ): 1.36 (3H, t, J=7.1 Hz), 1.45 (9H, s), 2.19 (1H, br), 2.46 (1H, br), 2.96 (6H, s), 3.14 (2H, br), 3.42 (1H, br), 3.92 (1H, br), 4.29 (2H, q, J=7.1 Hz), 5.04 (1H, br), 6.45

(1H, d, J=16.1 Hz), 6.69 (2H, d, J=8.8 Hz), 7.29 (3H, m), 7.63 (1H, d, J=16.1 Hz), 7.79 (1H, dd, J=8.4, 2.5 Hz), 8.46 (1H, br)

MS (ES+) m/z 495 (M+1)

Preparation 223

Ethyl (2E)-3-(6-{(tert-butoxycarbonyl)[(3R)-1-(2-methoxybenzyl)-3-pyrrolidinyl]amino}-3-pyridyl)acrylate NMR (CDCl$_3$, δ): 1.35 (3H, t, J=7.0 Hz), 1.44 (9H, s), 2.20 (1H, m), 2.52 (1H, m), 3.29 (3H, m), 3.60 (1H, m), 3.86 (3H, s), 4.18 (2H, br), 4.28 (2H, q, J=7.0 Hz), 5.10 (1H, m), 6.44 (1H, d, J=16.1 Hz), 6.91 (1H, d, J=7.4 Hz), 6.98 (1H, dd, J=7.5, 1.1 Hz), 7.32 (1H, d, J=84 Hz), 7.35 (1H, td, J=7.8, 1.8 Hz), 7.50 (1H, dd, J=7.7, 1.1 Hz), 7.63 (1H, d, J=16.1 Hz), 7.79 (1H, dd, J=8.4, 2.2 Hz), 8.44 (1H, d, J=2.2 Hz)

MS (ES+) m/z 482 (M+1)

Preparation 224

Ethyl (2E)-3-(6-{(tert-butoxycarbonyl)[(3R)-1-(2-fluorobenzyl)-3-pyrrolidinyl]amino}-3-pyridyl)acrylate NMR (CDCl$_3$, δ): 1.35 (3H, t, J=7.0 Hz), 1.44 (9H, s), 2.11 (1H, br), 2.33 (1H, br), 2.89 (3H, br), 3.13 (1H, br), 3.82 (1H, br), 4.29 (2H, q, J=7.0 Hz), 4.97 (1H, br), 6.45 (1H, d, J=16.1 Hz), 7.02 (1H, t, J=8.0 Hz), 7.11 (1H, t, J=7.3 Hz), 7.25 (1H, br), 7.31 (1H, d, J=8.8 Hz), 7.40 (1H, br), 7.65 (1H, d, J=16.1 Hz), 7.79 (1H, dd, J=8.4, 2.6 Hz), 8.49 (1H, d)

MS (ES+) m/z 470 (M+1)

Preparation 225

Ethyl (2E)-3-(6-{(tert-butoxycarbonyl)[(3R)-1-(2-quinolinylmethyl)-3-pyrrolidinyl]amino}-3-pyridyl)acrylate NMR (DMSO-d, 6): 1.36 (3H, t, J=7.0 Hz), 1.45 (9H, s), 2.20 (1H, m), 2.43 (1H, m), 3.17 (3H, br), 3.44 (1H, br), 4.29 (2+2H, q, J=7.0 Hz), 5.09 (1H, m), 6.45 (1H, d, J=16.1 Hz), 7.32 (1H, d, J=8.4 Hz), 7.55 (1H, tm, J=7.0 Hz), 7.63 (1H, d, J=16.1 Hz), 7.70 (1H, dd, J=7.0, 1.5 Hz), 7.73 (1H, dd, J=7.0, 1.7 Hz), 7.79 (1H, dd, J=8.8, 2.2 Hz), 7.82 (1H, d, J=8.4 Hz), 7.06 (1H, d, J=8.4 Hz), 7.26 (1H, d, J=8.4 Hz), 8.50 (1H, d, J=2.2 Hz)

MS (ES+) m/z 503 (M+1)

Preparation 226

Ethyl (2E)-3-(6-{(tert-butoxycarbonyl)[(3R)-1-(3-isoquinolinylmethyl)-3-pyrrolidinyl]amino}-3-pyridyl)acrylate NMR (CDCl$_3$, δ): 1.37 (3H, t, J=7.0 Hz), 1.45 (9H, s), 2.12 (1H, m), 2.25 (1H, m), 2.72 (2H, m), 2.81 (1H, m), 2.89 (1H, m), 3.72 (1H, m), 3.75 (1H, d, J=12.8 Hz), 3.84 (1H, d, J=12.8 Hz), 4.30 (2H, q, J=7.0 Hz), 4.93 (1H, m), 6.46 (1H, d, J=16.1 Hz), 7.28 (1H, d, J=8.0 Hz), 7.54 (1H, m), 7.65 (1H, d, J=16.1 Hz), 7.70 (1H, m), 7.79 (2H, m$^{-1}$), 8.00 (1H, br), 8.10 (1H, d, J=8.4 Hz), 8.51 (1H, d, J=2.2 Hz), 8.83 (1H, d, J=2.2 Hz)

MS (ES+) m/z 503 (M+1)

Preparation 227

Ethyl (2E)-3-[6-((tert-butoxycarbonyl){(3R)-1-[(5-methyl-2-thienyl)methyl]-3-pyrrolidinyl}amino)-3-pyridyl]acrylate NMR (CDCl$_3$, δ): 1.35 (3H, t, J=7.0 Hz), 1.45 (9H, s), 2.06 (1H, br), 2.22 (1H, br), 2.44 (3H, s), 2.64 (1H, br), 2.74 (2H, br), 3.01 (1H, br), 3.72 (2H, br), 4.27 (2H, q, J=7.0 Hz), 4.91 (1H, m) 6.46 (1H, d, J=16.1 Hz), 6.54 (1H, br), 6.64 (1H, br), 7.31 (1H, d, J=8.4 Hz), 7.66 (1H, d, J=16.1 Hz), 7.81 (1H, dd, J=8.4, 2.6 Hz), 8.54 (1H, d, J=2.2 Hz)

MS (ES+) m/z 472 (M+1)

Preparation 228

Ethyl (2E)-3-[6-((tert-butoxycarbonyl){(3R)-1-[(5-methyl-2-furyl)methyl]-3-pyrrolidinyl}amino)-3-pyridyl]acrylate NMR (CDCl$_3$, δ): 1.36 (3H, t, J=7.0 Hz), 1.46 (9H, s), 2.14 (1H, m), 2.29 (3H, s), 2.39 (1H, m), 3.10 (3H, br), 3.42 (1H, br), 3.89 (2H, br), 4.29 (2H, q, J=7.0 Hz), 5.03 (1H, m), 5.95 (1H, br), 6.28 (1H, br), 6.46 (1H, d, J=16.1 Hz), 7.33 (1H, d, J=8.4 Hz), 7.65 (1H, d, J=16.1 Hz), 7.81 (1H, dd, J=8.4, 2.2 Hz), 8.50 (1H, d)

MS (ES+) m/z 456 (M+1)

Preparation 229

Ethyl (2E)-3-{6-[(tert-butoxycarbonyl)((3R)-1-{(2E)-3-[4-(dimethylamino)phenyl]-2-propen-1-yl}-3-pyrrolidinyl)amino]-3-pyridyl}acrylate NMR (CDCl$_3$, δ): 1.35 (3H, t, J=7.0 Hz), 1.47 (9H, s), 2.33 (2H, br), 2.61 (2H, br), 2.99 (6H, s), 3.45 (2H, br), 3.82 (2H, br), 4.28 (2H, q, J=7.0 Hz), 5.12 (1H, m), 6.19 (1H, dt, J=15.4, 7.0 Hz), 6.44 (1H, d, J=16.1 Hz), 6.63 (1H, d, J=15.4 Hz), 6.66 (2H, d, J=9.2 Hz), 7.31 (2H, d, J=8.8 Hz), 7.31 (1H, d, J=8.8 Hz), 7.63 (1H, d, J=16.1 Hz), 7.80 (1H, dd, J=8.4, 2.6 Hz), 8.47 (1H, br)

MS (ES+) m/z 521 (M+1)

Preparation 230

Ethyl (2E)-3-(6-{(tert-butoxycarbonyl)[(3R)-1-(2,2-dimethylpropyl)-3-pyrrolidinyl]amino}-3-pyridyl)acrylate NMR (CDCl$_3$, δ): 0.81 (9H, s), 1.35 (3H, t, J=7.0 Hz), 1.44 (9H, s), 2.01 (1H, m), 2.17 (2H, br.), 2.66 (2H, br.), 2.88 (2H, br.), 4.28 (2H, q, J=7.0 Hz), 4.86 (1H, br.), 6.46 (1H, d, J=16.1 Hz), 7.31 (1H, d, J=8.4 Hz), 7.66 (1H, d, J=16.1 Hz), 7.81 (1H, dd, J=8.1, 2.2 Hz), 8.56 (1H, d, J=2.2 Hz)

MS (ES+) m/z 432 (M+1)

Preparation 231

To a solution of ethyl (2E)-3-(6-{(tert-butoxycarbonyl)[(3R)-1-(2-fluorobenzyl)-3-pyrrolidinyl]amino}-3-pyridyl)acrylate (2.40 g) in MeOH (10 mL) and dioxane (10 mL) was added 1N NaOH aq solution (10.2 mL), and the mixture was stirred for 3 hours at ambient temperature. The pH value of the mixture was adjusted to 7 with 1N HCl, and the solvent was removed in vacuo. Obtained solid was suspended in toluene and the residual water was geotropically removed to give (2E)-3-(6-{(tert-butoxycarbonyl)[(3R)-1-(3-fluorobenzyl)-3-pyrrolidinyl]amino}-3-pyridyl)acrylic acid and the crude product was used in next reaction without further purification.

NMR (DMSO-d$_6$, δ): 1.36 (9H, s), 1.99 (1H, m), 2.12 (1H, m), 2.62 (1H, dd, J=8.9, 7.0 Hz), 2.74 (1H, t, J=8.2 Hz), 3.46 (1H, d, J=13.6 Hz), 3.58 (1H, d, J=13.6 Hz), 4.76 (1H, m), 6.66 (1H, d, J=16.1 Hz), 6.95 (1H, m), 7.03 (1H, m), 7.29 (1H, m), 1.32 (1H, m), 7.33 (1H, d, J=8.4 Hz), 7.62 (1H, d, J=16.1 Hz), 8.16 (1H, dd, J=8.4, 2.6 Hz), 8.69 (1H, d, J=2.2 Hz)

MS (ES+) m/z 442 (M+1)

The following compounds were obtained according to a similar manner to that of Preparation 231.

Preparation 232

(2E)-3-(6-{(tert-Butoxycarbonyl)[(3R)-1-(3-methoxybenzyl)-3-pyrrolidinyl]amino}-3-pyridyl)acrylic acid NMR (DMSO-$d_6$, δ): 1.36 (9H, s), 1.96 (1H, m), 2.12 (1H, m), 2.62 (1H, m), 2.77 (1H, m), 3.45 (1H, d, J=17.5 Hz), 3.53 (1H, d, J=17.5 Hz), 3.71 (3H, s), 4.75 (1H, m), 6.66 (1H, d, J=16.1 Hz), 6.76 (3H, m), 7.16 (1H, t, J=8.1 Hz), 7.33 (1H, d, J=8.4 Hz), 7.63 (1H, d, J=15.8 Hz), 8.16 (1H, dd, J=8.4, 2.2 Hz), 8.69 (1H, d, J=2.2 Hz)

MS (ES+) m/z 454 (M+1)

Preparation 233

(2E)-3-(6-{(tert-Butoxycarbonyl)[(3R)-(3-phenylpropyl)-3-pyrrolidinyl]amino}-3-pyridyl)acrylic acid NMR (DMSO-$d_6$, δ): 1.37 (9H, s), 1.62 (2H, m), 1.93 (1H, m), 2.06 (1H, m), 2.27 (1H, m), 2.29 (2H, m), 2.55 (1H, m), 2.79 (2H, m), 4.73 (1H, m), 6.61 (1H, d, J=16.1 Hz), 7.15 (3H, m), 7.24 (2H, m), 7.32 (1H, d, J=8.4 Hz), 7.52 (1H, d, J=16.1 Hz), 8.12 (1H, d, J=8.4, 2.2 Hz), 8.66 (1H, d, J=2.2 Hz)

MS (ES+) m/z 452 (M+1)

Preparation 234

(2E)-3-[6-((tert-Butoxycarbonyl){(3R)-1-[4-(dimethylamino)benzyl]-3-pyrrolidinyl}amino)-3-pyridyl]acrylic acid NMR (DMSO-$d_6$, δ): 1.37 (9H, s), 2.03 (1H, m), 2.24 (1H, m), 2.89 (6H, s), 4.00 (2H, br), 4.90 (1H, m), 6.66 (1H, d, J=16.1 Hz), 6.69 (2H, d, J=8.4 Hz), 7.25 (2H, d, J=8.4 Hz), 7.38 (1H, d, J=8.1 Hz), 7.63 (1H, d, J=16.1 Hz), 8.19 (1H, dd, J=8.1, 2.2 Hz), 8.66 (1H, d, J=2.2 Hz)

MS (ES+) m/z 467 (M+1)

Preparation 235

(2E)-3-(6-{(tert-Butoxycarbonyl)[(3R)-1-(2-methoxybenzyl)-3-pyrrolidinyl]amino}-3-pyridyl)acrylic acid NMR (DMSO-$d_6$, δ): 1.34 (9H, s), 1.93 (1H, m), 2.09 (1H, m), 2.61 (1H, m), 2.72 (1H, m), 3.43 (1H, d, J=14.3 Hz), 3.52 (1H, d, J=14.3 Hz), 3.72 (3H, s), 4.69 (1H, m), 6.48 (1H, d, J=16.1 Hz), 6.82 (1H, t, J=8.1 Hz), 6.91 (1H, d, J=8.1 Hz), 7.01 (1H, d, J=8.1 Hz), 7.09 (1H, d, J=16.1 Hz), 7.19 (2H, m), 7.93 (1H, dd, J=8.4, 2.2 Hz), 8.49 (1H, d, J=2.2 Hz)

MS (ES+) m/z 454 (M+1)

Preparation 236

(2E)-3-(6-{(tert-Butoxycarbonyl)[(3R)-1-(2-fluorobenzyl)-3-pyrrolidinyl]amino}-3-pyridyl)acrylic acid NMR (DMSO-$d_6$, δ): 1.35 (9H, s), 1.96 (1H, br), 2.10 (1H, br), 2.61 (1H, br), 2.81 (1H, br), 3.46 (1H, m), 3.58 (1H, m), 4.73 (1H, br), 6.66 (1H, d, J=16.1 Hz), 7.13 (2H, m), 7.25 (2H, m), 7.33 (1H, d, J=8.4 Hz), 7.62 (1H, d, J=16.1 Hz), 8.15 (1H, dd, J=8.4, 2.2 Hz), 8.67 (1H, d, J=2.2 Hz)

MS (ES+) m/z 442 (M+1)

Preparation 237

(2E)-3-(6-{(tert-Butoxycarbonyl)[(3R)-1-(2-quinolinylmethyl)-3-pyrrolidinyl]amino}-3-pyridyl)acrylic acid NMR (DMSO-$d_6$, δ): 1.40 (9H, s), 2.09 (1H, m), 2.35 (1H, m), 3.16 (2H, br), 4.50 (2H, br), 5.04 (1H, br), 6.67 (1H, d, J=16.1 Hz), 7.44 (1H, d, J=8.4 Hz), 7.64 (1H, d, J=16.1 Hz), 7.64 (2H, m), 7.79 (1H, t, J=7.7 Hz), 8.00 (3H, m), 8.21 (1H, dd, J=8.4, 2.2 Hz), 8.43 (1H, d, J=8.1 Hz), 8.71 (1H, s)

MS (ES+) m/z 475 (M+1)

Preparation 238

(2E)-3-(6-{(tert-Butoxycarbonyl)[(3R)-1-(3-isoquinolinylmethyl)-3-pyrrolidinyl]amino}-3-pyridyl)acrylic acid NMR (DMSO-$d_6$, δ): 1.35 (9H, s), 2.00 (1H, m), 2.14 (1H, m), 2.58 (2H, m), 2.67 (1H, m), 2.84 (1H, m), 3.68 (1H, d, J=13.9 Hz), 3.78 (1H, d, J=13.9 Hz), 4.77 (1H, m), 6.65 (1H, d, J=16.1 Hz), 7.33 (1H, d, J=8.4 Hz), 7.58 (1H, t, J=7.7 Hz), 7.61 (1H, d, J=16.1 Hz), 7.72 (1H, t, J=8.1 Hz), 7.93 (1H, d, J=8.4 Hz), 7.99 (1H, d, J=8.4 Hz), 8.10 (1H, s), 8.15 (1H, dd, J=8.4, 2.2 Hz), 8.66 (1H, d, J=2.2 Hz), 8.74 (1H, d, J=2.2 Hz)

MS (ES+) m/z 475 (M+1)

Preparation 239

(2E)-3-[6-((tert-Butoxycarbonyl){(3R)-1-[(5-methyl-2-thienyl)methyl]-3-pyrrolidinyl}amino)-3-pyridyl]acrylic acid NMR (DMSO-$d_6$, δ): 1.36 (9H, s), 1.94 (1H, m), 2.08 (1H, m), 2.37 (3H, s), 2.58 (1H, m), 2.82 (1H, m), 3.57 (1H, d, J=13.5 Hz), 3.65 (1H, d, J=13.5 Hz), 4.72 (1H, m), 6.58 (1H, m), 6.65 (1H, d, J=2.9 Hz), 6.66 (1H, d, J=16.1 Hz), 7.32 (1H, d, J=8.4 Hz), 7.61 (1H, d, J=16.1 Hz), 8.15 (1H, d, J=8.4, 2.2 Hz), 8.68 (1H, d, J=2.2 Hz)

MS (ES+) m/z 444 (M+1)

Preparation 240

(2E)-3-[6-((tert-Butoxycarbonyl){(3R)-1-[(5-methyl-2-furyl)methyl]-3-pyrrolidinyl}amino)-3-pyridyl]acrylic acid NMR (DMSO-$d_6$, δ): 1.37 (9H, s), 1.97 (4H, m), 2.15 (4H, m), 2.23 (3H, m), 2.90 (2H, br), 3.85 (2H, br), 4.82 (1H, m), 6.04 (1H, br), 6.28 (1H, br), 6.67 (1H, d, J=16.1 Hz), 7.37 (1H, d, J=8.4 Hz), 7.62 (1H, d, J=16.1 Hz), 8.18 (1H, dd, J=8.4, 2.2 Hz), 8.67 (1H, d, J=2.2 Hz), MS (ES+) m/z 428 (M+1)

Preparation 241

(2E)-3-{6-[(tert-Butoxycarbonyl)((3R)-1-{(2E)-3-[4-(dimethylamino)phenyl]-2-propen-1-yl}-3-pyrrolidinyl)amino]-3-pyridyl}acrylic acid NMR (DMSO-$d_6$, δ): 1.40 (9H, s), 2.07 (1H, m), 2.28 (1H, m), 2.92 (6H, s), 3.17 (2H, d), 3.81 (2H, br), 5.00 (1H, br), 6.04 (1H, m), 6.65 (1H, d, J=16.1 Hz), 6.69 (1H, d, J=8.1 Hz), 6.69 (2H, d, J=8.1 Hz), 7.30 (2H, d, J=8.1 Hz), 7.43 (1H, d, J=8.4 Hz), 7.61 (1H, d, J=16.1 Hz), 8.20 (1H, br.d, J=8.4 Hz), 8.68 (1H, br)

MS (ES+) m/z 493 (M+1)

Preparation 242

(2E)-3-(6-{(tert-Butoxycarbonyl)[(3R)-1-(2,2-dimethylpropyl)-3-pyrrolidinyl]amino}-3-pyridyl)acrylic acid NMR (DMSO-$d_6$, δ): 0.75 (9H, s), 1.37 (9H, s), 1.94 (1H, m), 2.05 (1H, m), 2.07 (1H, d, J=13.1 Hz), 2.15 (1H, d, J=13.1 Hz), 2.58 (2H, m), 2.77 (2H, m), 4.73 (1H, m), 6.64 (1H, d, J=16.1 Hz), 7.33 (1H, d, J=8.4 Hz), 7.60 (1H, d, J=16.1 Hz), 8.15 (1H, dd, J=8.4, 2.2 Hz), 8.70 (1H, d, J=2.2 Hz)

MS (ES+) m/z 404 (M+1)

Preparation 243

To a solution of (2E)-3-(6-{(tert-butoxycarbonyl)[(3R)-1-(3-fluorobenzyl)-3-pyrrolidinyl]amino}-3-pyridyl)acrylic acid (2.25 g, crude) in DMF (23 mL) was added was added O-(tetrahydro-2H-pyran-2-yl)hydroxylamine (776 mg), HOBt (1.03 g), and EDCI (1.19 g) and the resulting mixture was stirred at ambient temperature for 3 hours. The reaction mixture was diluted with water and extracted with AcOEt. The organic phase was washed with sat NH$_4$Cl aq solution, sat NaHCO$_3$ aq solution, and brine, and dried over Na$_2$SO$_4$. The solvent was removed in vacuo and the residue was purified by silica gel column chromatography eluted with AcOEt to give tert-butyl [(3R)-1-(3-fluorobenzyl)-3-pyrrolidinyl](5-{(1E)-3-oxo-3-[(tetrahydro-2H-pyran-2-yloxy)amino]-1-propen-1-yl}-2-pyridyl)carbamate (2.51 mg) as pale yellow form.

NMR (CDCl$_3$, δ): 1.44 (9H, s), 1.63 (3H, br), 1.87 (3H, br), 2.08 (1H, m), 2.23 (1H, m), 2.63 (2H, t, J=7.3 Hz), 2.73 (1H, dd, J=9.2, 7.3 Hz), 2.88 (1H, t, J=8.0 Hz), 3.51 (1H, d, J=13.2 Hz), 3.62 (1H, d, J=13.2 Hz), 3.67 (1H, m), 3.99 (1H, m), 4.90 (1H, m), 5.05 (1H, br), 6.41 (1H, br), 6.91 (2H, m), 6.98 (1H, m), 7.21 (1H, m), 7.27 (1H, m), 7.70 (1H, d, J=16.1 Hz), 7.78 (1H, dd, J=8.8, 2.2 Hz), 8.56 (1H, d, J=2.2 Hz)

MS (ES+) m/z 541 (M+1)

The following compounds were obtained according to a similar manner to that of Preparation 243.

Preparation 244 tert-Butyl [(3R)-1-(3-methoxybenzyl)-3-pyrrolidinyl](5-{(1E)-3-oxo-3-[(tetrahydro-2H-pyran-2-yloxy)amino]-1-propen-1-yl}-2-pyridyl)carbamate NMR (CDCl$_3$, δ): 1.44 (9H, s), 1.64 (3H, br), 1.87 (3H, br), 2.08 (1H, m), 2.25 (1H, m), 2.70 (3H, br), 2.97 (1H, br), 3.63 (2H, m), 3.70 (1H, m), 3.98 (1H, m), 4.91 (1H, m), 5.03 (1H, br), 6.40 (1H, br), 6.78 (1H, br.d, J=8.4 Hz), 6.83 (2H, br.d, J=7.0 Hz), 7.19 (1H, t, J=7.7 Hz), 7.28 (1H, d, J=7.7 Hz), 7.69 (1H, d, J=16.1 Hz), 7.77 (1H, dd, J=8.4 and 2.2 Hz), 8.55 (1H, d, J=2.0 Hz)

MS (ES+) m/z 553 (M+1)

Preparation 245 tert-Butyl (5-{(1E)-3-oxo-3-[(tetrahydro-2H-pyran-2-yloxy)amino]-1-propen-1-yl}-2-pyridyl)[(3R)-1-(3-phenylpropyl)-3-pyrrolidinyl]carbamate NMR (CDCl$_3$, δ): 1.45 (9H, s), 1.63 (3H, br), 1.82 (2H, br), 1.86 (3H, br), 2.03 (1H, br), 2.23 (1H, br), 2.51 (2H, br), 2.60 (1H, m), 2.73 (2H, br), 3.05 (1H, br), 3.69 (1H, m), 3.97 (1H, m), 4.91 (1H, m), 5.02 (1H, br), 6.31 (1H, br), 7.17 (3H, m), 7.27 (2H, m), 7.29 (1H, d, J=8.4 Hz), 7.68 (1H, d, J=16.1 Hz), 7.77 (1H, dd, J=8.4 and 2.2 Hz), 8.55 (1H, br)

MS (ES+) m/z 551 (M+1)

Preparation 246 tert-Butyl {(3R)-1-[4-(dimethylamino)benzyl]-3-pyrrolidinyl}(5-{(1E)-3-oxo-3-[(tetrahydro-2H-pyran-2-yloxy)amino]-1-propen-1-yl}-2-pyridyl)carbamate NMR (CDCl$_3$, δ): 1.44 (9H, s), 1.63 (3H, br), 1.87 (3H, br), 2.08 (1H, br), 2.28 (1H, br), 2.78 (3H, br), 2.93 (3H, s), 3.07 (1H, br), 3.63 (2H, br), 3.68 (1H, m), 3.99 (1H, m), 4.94 (1H, br), 5.04 (1H, br), 6.44 (1H, br), 6.67 (1H, d, J=8.1 Hz), 7.16 (2H, br.d, J=7.0 Hz), 7.28 (1H, d, J=8.4 Hz), 7.68 (1H, d, J=16.1 Hz), 7.75 (1H, d, J=8.4 Hz), 8.52 (1H, s)

MS (ES+) m/z 566 (M+1)

Preparation 247 tert-Butyl [(3R)-1-(2-methoxybenzyl)-3-pyrrolidinyl](5-{(1E)-3-oxo-3-[(tetrahydro-2H-pyran-2-yloxy)amino]-1-propen-1-yl}-2-pyridyl)carbamate NMR (CDCl$_3$, δ): 1.44 (9H, s), 1.63 (3H, br), 1.86 (3H, br), 2.05 (1H, br), 2.26 (1H, br), 2.68 (1H, br), 2.77 (2H, br), 3.03 (1H, br), 3.68 (2H, br), 3.80 (2H, s), 3.97 (1H, m), 4.92 (1H, m), 5.03 (1H, br), 6.43 (1H, br), 6.84 (1H, d, J=8.1 Hz), 6.88 (1H, t, J=7.4 Hz), 7.22 (2H, m), 7.29 (1H, d, J=8.8 Hz), 7.69 (1H, d, J=16.1 Hz), 7.75 (1H, d, J=8.1 Hz), 8.53 (1H, s)

MS (ES+) m/z 553 (M+1)

Preparation 248 tert-Butyl [(3R)-1-(2-fluorobenzyl)-3-pyrrolidinyl](5-{(1E)-3-oxo-3-[(tetrahydro-2H-pyran-2-yloxy)amino]-1-propen-1-yl}-2-pyridyl)carbamate NMR (CDCl$_3$, δ): 1.43 (9H, s), 1.63 (3H, br), 1.86 (3H, br), 2.05 (1H, m), 2.23 (1H, m), 2.72 (3H, m), 2.99 (1H, m), 3.64 (1H, d, J=12.8 Hz), 3.69 (1H, d, J=12.8 Hz), 3.71 (1H, m), 4.91 (1H, m), 5.04 (1H, s), 6.43 (1H, br), 7.00 (1H, t, J=8.4 Hz), 7.07 (1H, d, J=7.7 Hz), 7.24 (2H, m), 7.28 (1H, d, J=8.4 Hz), 7.68 (1H, d, J=16.1 Hz), 7.75 (1H, dd, J=8.4, 2.2 Hz), 8.52 (1H, d, J=2.2 Hz)

MS (ES+) m/z 541 (M+1)

Preparation 249 tert-Butyl (5-{(1E)-3-oxo-3-[(tetrahydro-2H-pyran-2-yloxy)amino]-1-propen-1-yl}-2-pyridyl)[(3R)-1-(2-quinolinylmethyl)-3-pyrrolidinyl]carbamate NMR (CDCl$_3$, δ): 1.45 (9H, s), 1.63 (3H, br), 1.87 (3H, br), 2.12 (1H, br), 2.29 (1H, br), 2.74 (1H, br), 2.80 (1H, br), 3.04 (1H, br), 3.68 (1H, m), 3.94 (2H, d), 3.98 (1H, m), 4.96 (1H, br), 5.03 (1H, br), 6.36 (1H, br), 7.29 (1H, d, J=8.4 Hz), 7.46 (1H, m), 7.53 (1H, d, J=8.1 Hz), 7.69 (2H, m), 7.78 (2H, m), 8.07 (2H, m), 8.55 (1H, br)

MS (ES+) m/z 574 (M+1)

Preparation 250 tert-Butyl [(3R)-1-(3-isoquinolinylmethyl)-3-pyrrolidinyl](5-{(1E)-3-oxo-3-[(tetrahydro-2H-pyran-2-yloxy)amino]-1-propen-1-yl}-2-pyridyl)carbamate NMR (CDCl$_3$, δ): 1.43 (9H, s), 1.64 (3H, br), 1.86 (3H, br), 2.09 (1H, m), 2.25 (1H, m), 2.70 (2H, m), 2.82 (1H, m), 2.94 (1H, m), 3.67 (1H, m), 3.73 (1H, d, J=13.6 Hz), 3.82 (1H, d, J=13.6 Hz), 3.99 (1H, m), 4.92 (1H, m), 5.05 (1H, br), 6.48 (1H, br), 7.25 (1H, d, J=7.5 Hz), 7.54 (1H, t, J=7.5 Hz), 7.69 (2H, m), 7.76 (2H, m), 8.00 (1H, br), 8.10 (1H, d, J=8.8 Hz), 8.51 (1H, br), 8.80 (1H, dd, J=1.8 Hz)

MS (ES+) m/z 574 (M+1)

Preparation 251 tert-Butyl {(3R)-1-[(5-methyl-2-thienyl)methyl]-3-pyrrolidinyl}(5-{(1E)-3-oxo-3-[(tetrahydro-2H-pyran-2-yloxy)amino]-1-propen-1-yl}-2-pyridyl)carbamate NMR (CDCl$_3$, δ): 1.44 (9H, s), 1.64 (3H, br), 1.87 (3H, br), 2.05 (1H, m), 2.22 (1H, m), 2.64 (1H, m), 2.74 (2H, m), 3.01 (1H, t), 3.66 (1H, m), 3.69 (1H, d, J=13.6 Hz), 3.75 (1H, d, J=13.2 Hz), 3.98 (1H, m), 4.90 (1H, m), 5.03 (1H, br), 6.43 (1H, br), 6.54 (1H, d, J=2.9 Hz), 6.64 (1H, d, J=3.3 Hz), 7.30 (1H, d, J=8.4 Hz), 7.69 (1H, d, J=16.1 Hz), 7.77 (1H, d, J=8.4, 2.6 Hz), 8.55 (1H, br),
MS (ES+) m/z 543 (M+1)

Preparation 252 tert-Butyl {(3R)-1-[(5-methyl-2-furyl)methyl]-3-pyrrolidinyl}(5-{(1E)-3-oxo-3-[(tetrahydro-2H-pyran-2-yloxy)amino]-1-propen-1-yl}-2-pyridyl)carbamate NMR (CDCl$_3$, δ): 1.45 (9H, s), 1.63 (3H, br), 1.86 (3H, br), 2.03 (1H, m), 2.22 (1H, m), 2.26 (3H, s), 2.59 (1H, q, J=8.4 Hz), 2.69 (1H, t, J=8.6 Hz), 2.82 (1H, m), 3.11 (1H, t, J=8.4 Hz), 3.55 (1H, d, J=13.9 Hz), 3.62 (1H, d, J=13.6 Hz), 3.66 (1H, m), 3.98 (1H, m), 4.92 (1H, m), 5.03 (1H, br), 5.86 (1H, dd, J=2.9, 1.0 Hz), 6.03 (1H, d, J=2.9 Hz), 6.40 (1H, br), 7.30 (1H, d, J=8.4 Hz), 7.68 (1H, d, J=15.4 Hz), 7.76 (1H, dd, J=8.4 and 2.2 Hz), 8.53 (1H, d, J=2.2 Hz)
MS (ES+) m/z 527 (M+1)

Preparation 253 tert-Butyl ((3R)-1-{(2E)-3-[4-(dimethylamino)phenyl]-2-propen-1-yl}-3-pyrrolidinyl)(5-{(1E)-3-oxo-3-[(tetrahydro-2H-pyran-2-yloxy)amino]-1-propen-1-yl}-2-pyridyl)carbamate NMR (CDCl$_3$, δ): 1.45 (9H, s), 1.62 (3H, br), 1.85 (3H, br), 2.05 (1H, br), 2.26 (1H, br), 2.69 (1H, br), 2.86 (2H, br), 3.18 (1H, br), 3.28 (2H, br), 3.66 (1H, m), 3.98 (1H, m), 4.93 (1H, m), 5.02 (1H, br), 6.06 (1H, dt, J=15.8 and 6.6 Hz), 6.43 (1H, d, J=15.4 Hz), 6.54 (1H, br), 6.67 (2H, d, J=8.8 Hz), 7.25 (2H, d, J=8.1 Hz), 7.29 (1H, d, J=8.4 Hz)" 7.67 (1H, d, J=16.1 Hz), 7.76 (1H, d, J=8.4 Hz), 8.53 (1H, s)
MS (ES+) m/z 592 (M+1)

Preparation 254 tert-Butyl [(3R)-1-(2,2-dimethylpropyl)-3-pyrrolidinyl](5-{(1E)-3-oxo-3-[(tetrahydro-2H-pyran-2-yloxy)amino]-1-propen-1-yl}-2-pyridyl)carbamate NMR (CDCl$_3$, δ): 0.81 (9H, s), 1.44 (9H, s), 1.62 (3H, br), 1.86 (3H, br), 2.01 (1H, m), 2.17 (3H, m), 2.67 (2H, m), 2.88 (2H, m), 3.67 (1H, m), 3.97 (1H, m), 4.86 (1H, m), 5.03 (1H, br), 6.41 (1H, br), 7.30 (1H, d, J=8.4 Hz), 7.71 (1H, br.d, J=15.8 Hz), 7.78 (1H, d, J=8.1 Hz), 8.58 (1H, s),
MS (ES+) m/z 503 (M+1)

Preparation 255

To a solution of ethyl (2E)-3-(4-bromophenyl)acrylate (300 mg) in toluene (3 mL) was added palladium(II) acetate (26.4 mg), (R)-(+)-2,2'-bis(diphenylphosphino)-1,1'-binaphthyl (110 mg), cesium carbonate (583 mg), and (3R)-1-(4-chlorobenzoyl)-3-pyrrolidinamine (291 mg). The mixture was heated at 90° C. for 2 days. The resulting mixture was poured into sat.NH$_4$Cl aq solution and extracted with AcOEt. The organic layer was washed with sat. NH$_4$Cl aq solution, water, and brine, and dried over Na$_2$SO$_4$. The solvent was removed in vacuo and residual brown oil was purified by preparative thin layer chromatography (chloroform:methanol 95:5) to give ethyl (2E)-3-(4-{[(3R)-1-(4-chlorobenzoyl)-3-pyrrolidinyl]amino}phenyl)acrylate (297 mg) as pale yellow form.
NMR (CDCl$_3$, δ): 1.33 (3H, t, J=7.1 Hz), 2.00 (1H, m), 2.23 (0.5H, m), 2.36 (0.5H, m), 3.35 (0.5H, m), 3.60 (1.5H, m), 3.81 (1H, m), 4.03 (1H, m), 4.10 (1H, m), 4.24 (2H, q, J=7.1 Hz), 6.22 (0.5H, d, J=15.8 Hz), 6.24 (0.5H, d, J=15.8 Hz), 6.51 (1H, d, J=8.4 Hz), 6.62 (1H, d, J=8.1 Hz), 7.33-7.62 (7H, m)
MS (ES+) m/z 399 (M+1)

Preparation 256

To a solution of ethyl (2E)-3-(4-{[(3R)-1-(4-chlorobenzoyl)-3-pyrrolidinyl]amino}phenyl)acrylate (297 mg) in dioxane (3 mL) was added 1N NaOH aq solution (2.23 mL), and the mixture was heated at 70° C. for 18 hours. Resulting mixture was diluted with water and washed with ether. The pH value of aqueous phase was adjusted to 5, and the precipitate was collected by filtration and dried in vacuo to give (2E)-3-(4-{[(3R)-1-(4-chlorobenzoyl)-3-pyrrolidinyl]amino}phenyl)acrylic acid (103 mg) as pale yellow powder.
NMR (DMSO-d$_6$, δ): 1.88 (1H, m), 2.19 (1H, m), 3.25 (1H, m), 3.43 (1H, m), 3.59 (1H, m), 3.79 (1H, m), 4.07 (1H, m), 6.14 (0.5H, d, J=16.1 Hz), 6.18 (0.5H, d, J=16.1 Hz), 6.57 (1H, d, J=8.8 Hz), 6.64 (1H, d, J=8.8 Hz), 7.36-7.47 (2H, m), 7.50 (1H, s), 7.53 (2H, d, J=8.1 Hz), 7.57 (2H, d, J=8.1 Hz), 7.93 (1H, d, J=8.4 Hz)
MS (ES+) m/z 371 (M+1)

Preparation 257

To a solution of (2E)-3-(4-{[(3R)-1-(4-chlorobenzoyl)-3-pyrrolidinyl]amino}phenyl)acrylic acid (103 mg) in DMF (2 mL) was added O-(tetrahydro-2H-pyran-2-yl)hydroxylamine (35.8 mg), HOBt (48.8 mg), and EDCI (56.1 mg) and the resulting mixture was stirred at ambient temperature for 3 hours. The reaction mixture was diluted with water and extracted with AcOEt. The organic phase was washed with sat NH$_4$Cl aq solution, sat NaHCO$_3$ aq solution, and brine, and dried over Na$_2$SO$_4$. The solvent was removed in vacuo and the residue was purified by preparative thin layer chromatography (chloroform:methanol 10:1) to give (2E)-3-(4-{[(3R)-1-(4-chlorobenzoyl)-3-pyrrolidinyl]amino}phenyl)-N-(tetrahydro-2H-pyran-2-yloxy)acrylamide (76 mg) as pale yellow form.
NMR (DMSO-d$_6$, δ): 1.54 (3H, br), 1.68 (3H, br), 1.89 (1H, br), 2.19 (1H, br), 3.24 (1H, br), 3.53 (3H, br), 3.79 (1H, m), 3.95 (1H, br), 4.07 (1H, br), 4.87 (1H, br), 6.17 (1H, br), 6.44 (0.5H, d, J=16.1 Hz), 6.46 (0.5H, d, J=16.1 Hz), 6.57 (1H, d, J=8.8 Hz), 6.65 (1H, d, J=8.4 Hz), 7.26-7.37 (3H, m), 7.47-7.58 (4H, m)
MS (ES+) m/z 470 (M+1)

Preparation 258

To a solution of ethyl (2E)-3-(6-chloro-3-pyridyl)acrylate (3.5 g) in dioxane (70 mL) was added palladium(II) acetate (371 mg) and 2'-(dicyclohexylphosphino)-N,N-dimethyl-2-biphenylamine (110 mg) and cesium carbonate (583 mg), and (3R)-1-(4-chlorobenzoyl)-3-pyrrolidinamine (4.09 g). The mixture was heated at 90° C. for 3 hours. The resulting mixture was diluted with AcOEt, and the precipitate was removed by filtration. The filtrate was concentrated and residual brown oil was purified by purified by silica gel column chromatography eluted with AcOEt and hexane (1:4)-AcOEt to give ethyl (2E)-3-(6-{[(3R)-1-(4-chlorobenzoyl)-3-pyrrolidinyl]amino}-3-pyridyl)acrylate (2.16 g) as dark yellow form.
NMR (CDCl$_3$, δ): 1.33 (3H, t, J=7.0 Hz), 2.01 (1H, m), 2.35 (1H, m), 3.37 (0.5H, dd, J=11.0, 5.5 Hz), 3.60 (1.5H, m), 3.78 (0.5H, m), 3.88 (1H, m), 4.04 (0.5H, m), 4.25 (2H, q, J=7.0 Hz), 4.53 (1H, m), 4.77 (0.5H, d, J=6.9 Hz), 4.89 (0.5H, d, J=6.6 Hz), 6.22 (0.5H, d, J=16.1 Hz), 6.26 (0.5H, d, J=16.1 Hz), 6.38 (0.5H, d, J=8.4 Hz), 6.46 (0.5H, d, J=8.8 Hz), 7.38 (2H, m), 7.48 (2H, m), 7.62 (2H, m), 8.16 (0.5H, s), 8.23 (0.5H, s)
MS (ES+) m/z 400 (M+1)

The following compounds were obtained according to a similar manner to that of Preparation 258.

Preparation 259

Ethyl (2E)-3-(6-{[(3S)-1-(4-chlorobenzoyl)-3-pyrrolidinyl]amino}-3-pyridyl)acrylate NMR (CDCl$_3$, δ): 1.33 (3H, t, J=7.0 Hz), 2.01 (1H, m), 2.35 (1H, m), 3.37 (0.5H, dd, J=11.0, 5.5 Hz), 3.60 (1.5H, m), 3.78 (0.5H, m), 3.88 (1H, m), 4.04 (0.5H, m), 4.25 (2H, q, J=7.0 Hz), 4.53 (1H, m), 4.77 (0.5H, d, J=6.9 Hz), 4.89 (0.5H, d, J=6.6 Hz), 6.22 (0.5H, d, J=16.1 Hz), 6.26 (0.5H, d, J=16.1 Hz), 6.38 (0.5H, d, J=8.4 Hz), 6.46 (0.5H, d, J=8.8 Hz), 7.38 (2H, m), 7.48 (2H, m), 7.62 (2H, m), 8.16 (0.5H, s), 8.23 (0.5H, s)

MS (ES+) m/z 400 (M+1)

Preparation 260

To a solution of ethyl (2E)-3-(6-{[(3R)-1-(4-chlorobenzoyl)-3-pyrrolidinyl]amino}-3-pyridyl)acrylate (2.16 g) in MeOH (30 mL) and dioxane (30 mL) was added 1N NaOH aq solution (27.1 mL). The mixture was heated at 70° C. for 1.5 hour and diluted with water (120 mL) and washed with ether. The pH value of aqueous phase was adjusted to 5.5, and the precipitate was collected by filtration and dried in vacuo to give (2E)-3-(6-{[(3R)-1-(4-chlorobenzoyl)-3-pyrrolidinyl]amino}-3-pyridyl)acrylic acid (1.58 g) as pale yellow powder.

NMR (DMSO-d$_6$, δ): 1.93 (1H, m), 2.20 (1H, m), 3.25-3.72 (4H, m), 3.80 (1H, m), 4.37 (0.5H, m), 4.50 (0.5H, m), 6.24 (0.5H, d, J=16.1 Hz), 6.27 (0.5H, d, J=15.8 Hz), 6.52 (0.5H, d, J=8.9 Hz), 6.57 (0.5H, d, J=9.1 Hz), 7.39-7.60 (5H, m), 7.77 (0.5H, dd, J=9.1, 2.2 Hz), 7.82 (0.5H, dd, J=9.1, 2.2 Hz), 8.15 (0.5H, d, J=2.2 Hz), 8.25 (0.5H, d, J=1.8 Hz)

MS (ES+) m/z 372 (M+1)

The following compounds were obtained according to a similar manner to that of Preparation 260.

Preparation 261

(2E)-3-(6-{[(3S)-1-(4-Chlorobenzoyl)-3-pyrrolidinyl]amino}-3-pyridyl)acrylic acid NMR (DMSO-d$_6$, δ): 1.93 (1H, m), 2.20 (1H, m), 3.25-3.72 (4H, m), 3.80 (1H, m), 4.37 (0.5H, m), 4.50 (0.5H, m), 6.24 (0.5H, d, J=16.1 Hz), 6.27 (0.5H, d, J=15.8 Hz), 6.52 (0.5H, d, J=8.9 Hz), 6.57 (0.5H, d, J=9.1 Hz), 7.39-7.60 (5H, m), 7.77 (0.5H, dd, J=9.1, 2.2 Hz), 7.82 (0.5H, dd, J=9.1, 2.2 Hz), 8.15 (0.5H, d, J=2.2 Hz), 8.25 (0.5H, d, J=1.8 Hz)

MS (ES+) m/z 372 (M+1)

Preparation 262

To a solution of (2E)-3-(6-{[(3R)-1-(4-chlorobenzoyl)-3-pyrrolidinyl]amino}-3-pyridyl)acrylic acid (1.58 g) in DMF (16 mL) was added O-(tetrahydro-2H-pyran-2-yl)hydroxylamine (546 mg), HOBt (744 mg), and EDCI.HCl (1.06 mg) and the resulting mixture was stirred at ambient temperature for 4 hours. The reaction mixture was diluted with water and extracted with AcOEt. The organic phase was washed with sat NH$_4$Cl aq solution and sat NaHCO$_3$ aq solution, and brine, and dried over Na$_2$SO$_4$. The solvent was removed in vacuo and the residue was purified by silica gel column chromatography eluted with chloroform:methanol=97.5:2.5 to give (2E)-3-(6-{[(3R)-1-(4-chlorobenzoyl)-3-pyrrolidinyl]amino}-3-pyridyl)-N-(tetrahydro-2H-pyran-2-yloxy)acrylamide (1.89 g) as colorless oil.

NMR (DMSO-d$_6$, δ): 1.53 (brH, ), 1.69 (brH, ), 1.92 (mH,), 2.19 (mH, ), 3.23-3.70 (mH, ), 3.80 (mH, ), 3.95 (mH, ), 4.36 (mH, ), 4.49 (mH, ), 4.87 (brH, ), 6.22 (dH, 16.1), 6.25 (dH, 16.1), 6.52 (dH, 8.8), 6.56 (dH, 9.1), 7.36 (mH, ), 7.47-7.66 (mH, ), 8.11 (sH, ), 8.20 (sH, )

MS (ES+) m/z 471 (M+1)

The following compounds were obtained according to a similar manner to that of Preparation 262.

Preparation 263

(2E)-3-(6-{[(3S)-1-(4-Chlorobenzoyl)-3-pyrrolidinyl]amino}-3-pyridyl)-N-(tetrahydro-2H-pyran-2-yloxy)acrylamide NMR (DMSO-d$_6$, δ): 1.53 (3H, br), 1.69 (3H, br), 1.92 (1H, m), 2.19 (1H, m), 3.23-3.70 (4H, m), 3.80 (1H, m), 3.95 (1H, m), 4.36 (0.5H, m), 4.49 (0.5H, m), 4.87 (1H, br), 6.22 (0.5H, d, J=16.1 Hz), 6.25 (0.5H, d, J=16.1 Hz), 6.52 (0.5H, d, J=8.8 Hz), 6.56 (0.5H, d, J=9.1 Hz), 7.36 (2H, m), 7.47-7.66 (4H, m), 8.11 (1H, s), 8.20 (1H, s)

MS (ES+) m/z 471 (M+1)

Preparation 264

To a solution of ethyl (2E)-3-(4-bromophenyl)acrylate (1.0 g) in dioxane (70 mL) was added palladium(II) acetate (88 mg), 2'-(dicyclohexylphosphino)-N,N-dimethyl-2-biphenylamine (231 mg), cesium carbonate (1.79 g), and (3R)-1-benzyl-3-pyrrolidinamine (760 mg). The mixture was heated at 90 for 24 hours. The resulting mixture was poured into sat NH4Cl aq solution and extracted with AcOEt. The organic layer was washed with sat. NH$_4$Cl aq solution, water, and brine, and dried over Na$_2$SO$_4$. The solvent was removed in vacuo and residual brown oil was purified by silica gel column chromatography eluted with chloroform:methanol=9:1 to give ethyl (2E)-3-(4-{[(3R)-1-benzyl-3-pyrrolidinyl]amino}phenyl)acrylate (1.017 g) as pale yellow oil.

NMR (CDCl$_3$, δ): 1.32 (3H, t, J=7.0 Hz), 2.33 (1H, m), 2.44 (1H, m), 2.56 (1H, m), 2.78 (2H, m), 3.63 (2H, s), 4.03 (1H, m), 4.23 (2H, q, J=7.0 Hz), 4.26 (1H, m), 6.20 (1H, d, J=15.8 Hz), 6.52 (2H, d, J=8.8 Hz), 7.32 (7H, m), 7.58 (1H, d, J=15.8 Hz)

MS (ES+) m/z 351 (M+1)

Preparation 265

To a solution of ethyl (2E)-3-(4-{[(3R)-1-benzyl-3-pyrrolidinyl]amino}phenyl)acrylate (1.017 g) in MeOH (3 mL) and dioxane (3 mL) was added 1N NaOH aq solution (5.8 mL), and the mixture was stirred at ambient temperature for 2 hours. To the mixture was added 1N NaOH aq solution (5.8 mL) and heated at 50° C. for 2 hours. The pH value of the mixture was adjusted to 7 with 1N HCl, and the solvent was removed in vacuo. Obtained solid was suspended in toluene and the residual water was geotropically removed to give (2E)-3-(4-{[(3R)-1-benzyl-3-pyrrolidinyl]amino}phenyl)acrylic acid and the crude product was used in next reaction without further purification.

NMR (DMSO-d$_6$, δ): 1.65 (1H, br), 2.26 (1H, br), 2.74 (1H, br), 2.89 (1H, br), 3.43 (1H, br), 3.69 (1H, br), 3.97 (1H, br), 4.10 (0.5H, br), 4.37 (0.5H, br), 6.14 (1H, d, J=15.8 Hz), 6.46 (1H, d, J=5.9 Hz), 6.55 (2H, d, J=8.4 Hz), 7.28 (1H, br), 7.37 (4H, m), 7.42 (1H, d, J=15.8 Hz), 7.04 (1H, m)

MS (ES+) m/z 323 (M+1)

Preparation 266

To a solution of (2E)-3-(4-{[(3R)-1-benzyl-3-pyrrolidinyl]amino}phenyl)acrylic acid (936 mg, crude) in DMF (10 mL) was added was added O-(tetrahydro-2H-pyran-2-yl)hydroxylamine (442 mg), HOBt (588 mg), and EDCI (676 mg) and the resulting mixture was stirred at ambient temperature for 3 hours. The reaction mixture was diluted with water and extracted with AcOEt. The organic phase was washed with sat NH$_4$Cl aq solution, sat NaHCO$_3$ aq solution, and brine, and dried over Na$_2$SO$_4$. The solvent was removed in vacuo and the residue was purified by preparative thin layer chromatography (chloroform:methanol=10:1) to give (2E)-3-(4-{[(3R)-1-benzyl-3-pyrrolidinyl]amino}phenyl)-N-(tetrahydro-2H-pyran-2-yloxy)acrylamide (945 mg) as pale yellow form.

NMR (CDCl$_3$, δ): 1.63 (3H, br), 1.85 (3H, br), 2.33 (1H, m), 2.45 (1H, m), 2.59 (1H, dd, J=9.9, 3.3 Hz), 2.80 (1H, m), 3.64 (2H, s), 2.64 (1H, m), 4.00 (1H, m), 4.00 (1H, m), 4.29 (1H, d, J=7.7 Hz), 4.99 (1H, s), 6.26 (1H, br), 6.51 (1H, d, J=8.4 Hz), 7.27 (1H, m), 7.32 (6H, m), 7.62 (1H, d, J=15.8 Hz),

MS (ES+) m/z 422 (M+1)

Preparation 267

To a solution of 3-methyl-2-pyridinamine (10 g) in a mixed solution of AcOH (60 mL), water (12 mL), and sulfuric acid (4.2 mL) was added periodic acid dihydrate (4.22 g) and iodine (9.39 g), and the mixture was heated at 80° C. for 2 hours. The reaction mixture was poured into 5% Na$_2$S$_2$O$_3$ aq solution and extracted with ether. The organic layer was washed with 1N NaOH aq solution and brine, and dried over Na$_2$SO$_4$. The solvent was removed in vacuo and obtained residual solid was recrystallized with EtOH to give 5-iodo-3-methyl-2-pyridinamine (9.00 g) as pale yellow powder.

NMR (CDCl$_3$, δ): 2.09 (3H, s), 4.95 (2H, br), 7.54 (1H, m), 8.03 (1H, m)

Preparation 268

To a suspension of 5-iodo-3-methyl-2-pyridinamine (7.0 g) in 47% hydrobromic acid was successively added bromine (2.31 mL) and aq solution of NaNO$_2$ (5.16 g), the temperature being kept below 0° C. during addition. The reaction mixture was stirred for 1 hour at 5° C. and warmed to ambient temperature. The reaction was continued for 4 hours at ambient temperature and the mixture was diluted with NaOH (18 g in water 150 mL) and extracted with AcOEt. The organic phase was washed with 5% Na$_2$S$_2$O$_3$ aq solution, water, and brine, and dried over Na$_2$SO$_4$. The solvent was removed in vacuo, and the residue was purified by silica gel column chromatography eluted with chloroform to give 2-bromo-5-iodo-3-methylpyridine (2.95 g) as pale yellow powder.

NMR (CDCl$_3$, δ): 2.36 (3H, s), 7.83 (1H, s), 8.41 (1H, s),

Preparation 269

To a solution of 2-bromo-5-iodo-3-methylpyridine (1.5 g) in DMF (15 mL) was added palladium(II) acetate (56.5 mg) and tri-o-tolylphosphine (230 mg) and diisopropylethylamine (3.5 mL), and ethyl acrylate (1.09 mL). The mixture was heated at 90° C. for 1 hour. Resulting mixture was poured into water and extracted with AcOEt. The organic layer was washed with water and brine, and dried over Na$_2$SO$_4$, and the solvent was removed in vacuo. Residual brown oil was purified by silica gel column chromatography eluted with AcOEt and hexane (1:4-1:2) to give ethyl (2E)-3-(6-bromo-5-methyl-3-pyridyl)acrylate (1.00 g) as pale yellow powder.

NMR (CDCl$_3$, δ): 1.35 (3H, t, J=7.0 Hz), 2.43 (3H, s), 4.29 (2H, q, J=7.0 Hz), 6.50 (1H, d, J=16.1 Hz), 7.60 (1H, d, J=16.1 Hz), 7.66 (1H, m), 8.33 (1H, m)

MS (ES+) m/z 270 (M+1)

Preparation 270

To a solution of ethyl (2E)-3-(6-bromo-5-methyl-3-pyridyl)acrylate (500 mg) in dioxane (5 mL) was added palladium(II) acetate (41.6 mg) and 2'-(dicyclohexylphosphino)-N,N-dimethyl-2-biphenylamine (109 mg) and cesium carbonate (843 mg), and (3R)-(−)-1-benzyl-3-aminopyrrolidine (359 mg). The mixture was heated at 100° C. for 18 hours. The resulting mixture was poured into sat.NH$_4$Cl aqueous solution and extracted with AcOEt. The organic layer was washed with sat. NH$_4$Cl aq solution, water, and brine, and dried over Na$_2$SO$_4$. The solvent was removed in vacuo and residual brown oil was purified by preparative thin layer chromatography (chloroform:methanol=90:10) to give ethyl (2E)-3-(6-{[(3R)-1-benzyl-3-pyrrolidinyl]amino}-5-methyl-3-pyridyl)acrylate (366 mg) as pale yellow oil.

NMR (CDCl$_3$, δ): 1.32 (3H, t, J=7.0 Hz), 1.72 (1H, m), 2.10 (3H, s), 2.38 (2H, m), 2.72 (2H, m), 2.95 (1H, m), 6.67 (2H, s), 4.24 (2H, q, J=7.0 Hz), 4.72 (1H, m), 4.89 (1H, m), 6.20 (1H, d, J=16.1 Hz), 7.33 (5H, m), 7.42 (1H, s), 7.56 (1H, d, J=16.1 Hz), 8.09 (1H, s)

MS (ES+) m/z 366 (M+1)

Preparation 271

To a solution of ethyl (2E)-3-(6-{[(3R)-1-benzyl-3-pyrrolidinyl]amino}-5-methyl-3-pyridyl)acrylate (366 mg) in MeOH (2 mL) and dioxane (2 mL) was added 1N NaOH aq solution (2.0 mL), and the mixture was stirred at ambient temperature for 3 hours. The pH value of the mixture was adjusted to 7 with 1N HCl, and the solvent was removed in vacuo. Obtained solid was suspended in toluene and the residual water was geotropically removed to give (2E)-3-(6-{[(3R)-1-benzyl-3-pyrrolidinyl]amino}-5-methyl-3-pyridyl)acrylic acid and the crude product was used in next reaction without further purification.

NMR (DMSO-d$_6$, δ): 1.92 (1H, br), 2.11 (3H, s), 2.26 (1H, br), 2.60-2.89 (2H, br), 2.97-3.23 (2H, br), 3.85 (2H, br), 4.59 (1H, br), 6.25 (1H, d, J=16.1 Hz), 7.34 (5H, m), 7.43 (1H, d, J=16.1 Hz), 7.67 (1H, s), 8.08 (1H, s)

MS (ES+) m/z 338 (M+1)

Preparation 272

To a solution of (2E)-3-(6-{[(3R)-1-benzyl-3-pyrrolidinyl]amino}-5-methyl-3-pyridyl)acrylic acid (338 mg, crude) in DMF (4 mL) was added O-(tetrahydro-2H-pyran-2-yl)hydroxylamine (153 mg), HOBt (203 mg), and EDCI (233 mg) and the resulting mixture was stirred at ambient temperature for 3 hours. The reaction mixture was diluted with water and extracted with AcOEt. The organic phase was washed with sat NH$_4$Cl aq solution, sat NaHCO$_3$ aq solution, and brine, and dried over Na$_2$SO$_4$. The solvent was removed in vacuo and the residue was purified by preparative thin layer chromatography (chloroform:methanol=90:10) to give (2E)-3-(6-{[(3R)-1-benzyl-3-pyrrolidinyl]amino}-5-methyl-3-pyridyl)-N-(tetrahydro-2H-pyran-2-yloxy)acrylamide (306 mg) as pale yellow form.

NMR (CDCl$_3$, δ): 1.67 (3H, br), 1.85 (3H, br), 2.10 (3H, s), 2.39 (2H, m), 2.72 (2H, m), 2.95 (1H, m), 3.65 (1H, m), 3.67 (2H, s), 4.72 (1H, m), 4.87 (1H, m), 5.00 (1H, br), 6.25 (1H, br), 7.33 (5H, m), 7.38 (1H, s), 7.61 (1H, d, J=16.1 Hz), 8.11 (1H, s)

MS (ES+){m/z 437 (M+1)

The following compound was obtained in a similar manner to that of Preparation 274.

Preparation 273 tert-Butyl (3R)-3-({5-[(1E)-3-ethoxy-3-oxo-1-propen-1-yl]-2-pyrazinyl}amino)-1-piperidinecarboxylate $^1$H-NMR (300 MHz, CDCl$_3$) δ 1.33 (3H, t, J=7 Hz), 1.43 (9H, s), 1.59-1.81 (3H, m), 1.87-2.03 (1H, m), 3.30-3.47 (3H, m), 3.71 (1H, d, J=10 Hz), 3.96 (1H, br peak), 4.25 (2H, q, J=7 Hz), 4.96 (1H, br peak), 6.70 (1H, d, J=15 Hz), 7.57 (1H, d, J=15 Hz), 7.91 (1H, d, J=2 Hz), 8.07 (1H, d, J=2 Hz)

MS (ES+) m/z 377

Preparation 274

Ethyl (2E)-3-(5-chloro-2-pyrazinyl)acrylate (4.70 g) and (3R)-1-(cyclohexylmethyl)-3-piperidinamine (4.77 g) were combined in 1,4-dioxane (80 mL) at ambient temperature. To this solution were added palladium(II) acetate (248 mg) and 2-dicyclohexylphosphino-2'-(N,N-dimethylamino)biphenyl (652 mg) at the same temperature and the mixture was stirred for 5 minutes. To the resulting mixture was added cesium carbonate (10.1 g) and the mixture was heated at 95° C. for twenty-four hours. The reaction mixture was allowed to cool to ambient temperature and the insoluble solid was filtered off. The filtrate was concentrated in vacuo and the residue was extracted with chloroform (300 mL). The chloroform phase was washed with saturated sodium bicarbonate (100 mL) and brine (100 mL). The aqueous layer was reextracted with chloroform (100 mL). The organic phase were combined, dried over anhydrous sodium sulfate and concentrated in vacuo. The residue was purified by a flash column chromatography eluting with a gradient solvent system from EtOAc-Hexane (1:1 v/v) to EtOAc to afford ethyl (2E)-3-(5-{[(3R)-1-(cyclohexylmethyl)-3-piperidinyl]amino}-2-pyrazinyl)acrylate (4.80 g) as a yellow amorphous solid.

$^1$H-NMR (300 MHz, CDCl$_3$) δ 0.78-0.96 (mH, 2), 1.08-1.29 (3H, m), 1.33 (3H, t, J=7.3 Hz), 1.41-1.85 (10H, m), 2.04-2.19 (3H, m), 2.35-2.46 (1H, m), 2.51-2.69 (2H, m), 4.04-4.15 (1H, m), 4.25 (2H, q, J=7.3 Hz), 5.63 (1H, br.s), 6.67 (1H, d, J=15.4 Hz), 7.58 (1H, d, J=15.4 Hz), 7.89 (1H, d, J=1.1 Hz), 8.05 (1H, d, J=1.1 Hz)

MS (ES+) m/z 373(M+1)

Preparation 275

To a solution of ethyl (2E)-3-{5-[(3R)-3-piperidinylamino]-2-pyrazinyl)acrylate dihydrochloride (300 mg) in 1,2-dichloroethane (5 mL) were added diisopropylethylamine (222 mg) and cyclohexanone (93 mg), and the mixture was stirred at ambient temperature for 5 min. To the mixture was added sodium triacetoxybrohydryde (364 mg) and stirred for 4 hrs, and resulting mixture was poured into saturated sodium bicarbonate solution, and extracted with chloroform. The organic layer was washed with water, and brine, and dried over magnesium sulfate. The solvent was removed in vacuo and the residue was purified by preparative thin layer chromatography (chloroform-MeOH=10-1) to give ethyl (2E)-3-(5-{[(3R)-1-cyclohexyl-3-piperidinyl]amino}-2-pyrazinyl)acrylate (235 mg) as an amorphous powder.

$^1$H-NMR (300 MHz, CDCl$_3$) δ 0.96-1.36 (9H, m), 1.49-1.88 (8H, m), 2.24-2.38 (1H, m), 2.38-2.51 (1H, m), 2.57-2.75 (3H, m), 4.06 (1H, br peak), 4.25 (2H, q, J=7 Hz), 5.69 (1H, br peak), 6.66 (1H, d, J=15 Hz), 7.56 (1H, d, J=15 Hz), 7.90 (1H, d, J=2 Hz), 8.05 (1H, d, 3=2 Hz)

MS (ES+) m/z 359

The following compounds were obtained in a similar manner to that of Preparation 275.

Preparation 276 tert-Butyl [(3R)-1-(cyclohexylmethyl)-3-piperidinyl]carbamate $^1$H-NMR (300 MHz, CDCl$_3$) δ 0.73-0.92 (2H, m), 1.08-1.31 (3H, m), 1.35-1.82 (10H, m), 1.45 (9H, s), 1.98-2.51 (6H, m), 3.65-3.80 (1H, m), 4.91-5.11 (1H, m)

MS (ES+) m/z 297(M+1)

Preparation 277

Ethyl (2E)-3-(5-{[(3R)-1-(4-methylbenzyl)-3-piperidinyl]amino}-2-pyrazinyl)acrylate $^1$H-NMR (300 MHz, CDCl$_3$) δ 1.32 (3H, t, J=7 Hz), 1.50-1.84 (4H, m), 2.10-2.30 (1H, m), 2.34 (3H, s), 2.40-2.74 (3H, m), 3.44 (1H, d, J=12 Hz), 3.53 (1H, d, J=12 Hz), 4.10 (1H, br peak), 4.25 (2H, q, J=7 Hz), 5.57 (1H, br peak), 6.67 (1H, d, J=15 Hz), 7.14 (2H, d, J=8 Hz), 7.20 (2H, d, J=8 Hz), 7.56 (1H, d, J=15 Hz), 7.89 (1H, d, J=2 Hz), 8.04 (1H, d, J=2 Hz)

MS (ES+) m/z 381

Preparation 278

Ethyl (2E)-3-(5-{[(3R)-1-(4-chlorobenzyl)-3-piperidinyl]amino}-2-pyrazinyl)acrylate $^1$H-NMR (300 MHz, CDCl$_3$) δ 1.32 (3H, t, J=7 Hz), 1.40-1.85 (4H, m), 2.15-2.32 (1H, m), 2.45-2.65 (3H, m), 3.44 (1H, d, J=12 Hz), 3.51 (1H, d, J=12 Hz), 4.10 (1H, br peak), 4.25 (2H, q, J=7 Hz), 5.45 (1H, br peak), 6.65 (1H, d, J=15 Hz), 7.16-7.32 (4H, m), 7.56 (1H, d, J=15 Hz), 7.89 (1H, s), 8.04 (1H, s)

MS (ES+) m/z 401

Preparation 279

Ethyl (2E)-3-(5-{[(3R)-1-cyclopentyl-3-piperidinyl]amino}-2-pyrazinyl)acrylate $^1$H-NMR (300 MHz, CDCl$_3$) δ 1.21-1.93 (14H, m), 2.20-2.39 (1H, m), 2.47-2.76 (4H, m), 4.09 (1H, br peak), 4.25 (2H, q, J=7 Hz), 5.58 (1H, br peak), 6.68 (1H, d, J=15 Hz), 7.58 (1H, d, J=15 Hz), 7.93 (1H, s), 8.06 (1H, s)

MS (ES+) m/z 345

Preparation 280

Ethyl (2E)-3-(5-{[(3R)-1-(cyclopentylmethyl)-3-piperidinyl]amino}-2-pyrazinyl)acrylate $^1$H-NMR (300 MHz, CDCl$_3$) δ 1.11-1.29 (2H, m), 1.22 (3H, t, J=7 Hz), 1.45-1.65 (6H, m), 1.65-1.85 (4H, m), 1.97-2.30 (4H, m), 2.36-2.50 (1H, m), 2.58-2.77 (2H, m), 4.10 (1H, br peak), 4.25 (2H, q, J=7 Hz), 5.66 (1H, br peak), 6.66 (1H, d, J=15 Hz), 7.58 (1H, d, J=15 Hz), 7.90 (1H, s), 8.05 (1H, s)

MS (ES+) m/z 359

Preparation 281

To a solution of mixture of ethyl (2E)-3-(5-{[(3R)-1-cyclohexyl-3-piperidinyl]amino}-2-pyrazinyl)acrylate (227 mg) in EtOH (2 mL) was added 1N sodium hydroxide solution (1.3 mL) at ambient temperature and the mixture was allowed to stand for 18 hrs. The reaction mixture was adjusted to pH 6.0 with 1 mol/L hydrochloric acid and evaporated in vacuo. The residue was dissolved in a mixture of chloroform and MeOH (5-1) and the precipitate was filtered off. The filtrate was concentrated in vacuo to give (2E)-3-(5-{[(3R)-1-cyclohexyl-3-piperidinyl]amino}-2-pyrazinyl)acrylic acid (209 mg) as a solid.

$^1$H-NMR (300 MHz, DMSO-$d_6$) δ 0.96-1.49 (6H, m), 1.49-1.64 (2H, m), 1.64-2.00 (6H, m), 2.50-3.60 (5H, m), 4.04 (1H, br peak), 6.46 (1H, d, J=15 Hz), 7.49 (1H, d, J=15 Hz), 7.48 (1H, br peak), 8.01 (1H, s), 8.21 (1H, s)

The following compounds were obtained in a similar manner to that of Preparation 281.

Preparation 282

(2E)-3-(5-{[(3R)-1-Benzyl-3-piperidinyl]amino}-2-pyrazinyl)acrylic acid $^1$H-NMR (300 MHz, DMSO-$d_6$) δ 1.15-1.45 (1H, m), 1.45-2.20 (3H, m), 2.55-3.07 (2H, m), 3.40-3.50 (2H, m), 4.25-4.42 (3H, m), 6.46 (1H, d, J=15 Hz), 7.16-7.54 (6H, m), 8.00 (1H, s), 8.16 (1H, s)

MS (ES+) m/z 339

Preparation 283

(2E)-3-(5-{[(3R)-1-(Cyclohexylmethyl)-3-pyrrolidinyl]amino}-2-pyrazinyl)acrylic acid $^1$H-NMR (300 MHz, DMSO-$d_6$) δ 0.74-0.94 (2H, m), 1.04-1.30 (3H, m), 1.41 (1H, m), 1.52-1.82 (6H, m), 2.11-2.31 (3H, m), 2.34-2.47 (2H, m), 2.52-2.80 (2H, m), 4.30 (1H, m), 6.45 (1H, d, J=15.5 Hz), 7.47 (1H, d, J=15.5 Hz), 7.85 (1H, d, J=6.6 Hz), 8.00 (1H, s), 8.19 (1H, s)

MS (ES+) m/z 331

Preparation 284

(2E)-3-(5-{[(3R)-1-(4-Methylbenzyl)-3-piperidinyl]amino}-2-pyrazinyl)acrylic acid $^1$H-NMR (300 MHz, DMSO-$d_6$) δ 1.30-1.54 (1H, m), 1.69-2.15 (3H, m), 2.33 (3H, s), 2.44-3.05 (2H, m), 3.21-3.56 (2H, m), 4.20-4.40 (3H, m), 6.50 (1H, d, J=15 Hz), 7.28 (2H, d, J=8 Hz), 7.44 (2H, d, J=8 Hz), 7.51 (1H, d, J=15 Hz), 7.86 (1H, d, J=8 Hz), 8.01 (1H, s), 8.21 (1H, s)

MS (ES+) m/z 353

Preparation 285

(2E)-3-(5-{[(3R)-1-(4-Chlorobenzyl)-3-piperidinyl]amino}-2-pyrazinyl)acrylic acid $^1$H-NMR (300 MHz, DMSO-$d_6$) δ 1.35-1.65 (1H, m), 1.65-2.14 (3H, m), 2.56-2.75 (1H, m), 2.75-2.95 (1H, m), 3.25-3.59 (2H, m), 4.16-4.49 (3H, m), 6.50 (1H, d, J=15 Hz), 7.45-7.70 (5H, m), 7.85 (1H, d, J=8 Hz), 8.01 (1H, s), 8.22 (1H, s)

MS (ES+){m/z 373

Preparation 286

A mixture of (2E)-3-(5-{[(3R)-1-cyclohexyl-3-piperidinyl]amino}-2-pyrazinyl)acrylic acid (209 mg), O-(tetrahydro-2H-pyran-2-yl)-hydroxylamine (89 mg), HOBt (111 μg) and EDCI (158 mg) in DMF (4.5 mL) was stirred at 0° C. for 1 hr and the mixture was stirred at ambient temperature for 18 hrs. The reaction mixture was evaporated in vacuo and the residue was partitioned between saturated sodium bicarbonate solution and EtOAc. The organic layer was separated, washed water and brine, dried over magnesium sulfate, and evaporated in vacuo. The residue was purified by silica gel column chromatography (chloroform-MeOH=95-5) to give (2E)-3-(5-{[(3R)-1-cyclohexyl-3-piperidinyl]amino}-2-pyrazinyl)-N-(tetrahydro-2H-pyran-2-yloxy)acrylamide (198 mg) as an amorphous powder.

$^1$H-NMR (300 MHz, CDCl$_3$) δ 0.91-1.35 (6H, m), 1.35-1.95 (13H, m), 2.20-2.38 (1H, m), 2.38-2.53 (1H, m), 2.53-2.74 (3H, m), 3.59-3.70 (1H, m), 3.90-4.02 (1H, m), 4.02-4.14 (1H, m), 5.01 (1H, br s), 5.60-5.75 (1H, m), 6.65 (1H, br peak), 7.63 (1H, d, J=15 Hz), 7.88 (1H, s), 8.04 (1H, s), 8.31 (1H, br peak)

MS (ES+) m/z 430

The following compounds were obtained in a similar manner to that of Preparation 286.

Preparation 287

(2E)-3-(5-{[(3R)-1-Benzyl-3-piperidinyl]amino}-2-pyrazinyl)-N-(tetrahydro-2H-pyran-2-yloxy)acrylamide $^1$H-NMR (300 MHz, CDCl$_3$) δ 1.35-1.96 (9H, m), 2.14-2.35 (1H, m), 2.40-2.70 (3H, m), 3.49 (1H, d, J=13 Hz), 3.55 (1H, d, J=13 Hz), 3.60-3.78 (1H, m), 3.86-4.03 (1H, m), 4.03-4.15 (1H, m), 4.94-5.05 (1H, m), 5.45-5.60 (1H, m), 6.65 (1H, br peak), 7.15-7.35 (5H, m), 7.62 (1H, d, J=15 Hz), 7.86 (1H, s), 8.01 (1H, s), 8.19-8.35 (1H, m)

Preparation 288

(2E)-3-(5-{[(3R)-1-(4-Methylbenzyl)-3-piperidinyl]amino}-2-pyrazinyl)-N-(tetrahydro-2H-pyran-2-yloxy)acrylamide $^1$H-NMR (300 MHz, CDCl$_3$) δ 1.45-1.96 (9H, m), 2.11-2.29 (1H, m), 2.34 (3H, s), 2.43-2.72 (3H, m), 3.43 (1H, d, J=12 Hz), 3.52 (1H, d, J=12 Hz), 3.59-3.71 (1H, m), 3.90-4.04 (1H, m), 4.04 (1H, br peak), 5.01 (1H, br s), 5.58 (1H, br peak), 6.66 (1H, br peak), 7.14 (2H, d, J=8 Hz), 7.19 (2H, d, J=8 Hz), 7.61 (1H, d, j=15 Hz), 7.87 (1H, s), 8.00 (1H, s), 8.35 (1H, br peak)

MS (ES+) m/z 452

Preparation 289

(2E)-3-(5-{[(3R)-1-(4-Chlorobenzyl)-3-piperidinyl]amino}-2-pyrazinyl)-N-(tetrahydro-2H-pyran-2-yloxy)acrylamide $^1$H-NMR (300 MHz, CDCl$_3$) δ 1.56-1.95 (9H, m), 2.15-2.33 (1H, m), 2.43-2.66 (3H, m), 3.44 (1H, d, J=12 Hz), 3.50 (1H, d, J=12 Hz), 3.59-3.71 (1H, m), 3.86-4.04 (1H, m), 4.10 (1H, br peak), 5.00 (1H, br s), 5.48 (1H, br peak), 6.70 (1H, br peak), 7.19-7.35 (4H, m), 7.53 (1H, d, J=15 Hz), 7.86 (1H, s), 8.01 (1H, s), 8.35 (1H, br peak)

MS (ES+) m/z 472

Preparation 290

(2E)-3-(5-{[(3R)-1-(Cyclohexylmethyl)-3-pyrrolidinyl]amino}-2-pyrazinyl)-N-(tetrahydro-2H-pyran-2-yloxy)acrylamide $^1$H-NMR (300 MHz, DMSO-$d_6$) δ 0.73-0.93 (2H, m), 1.06-1.28 (3H, m), 1.30-1.83 (13H, m), 2.10-2.30 (3H, m), 2.31-2.44 (2H, m), 2.61 (1H, m), 2.72 (1H, m), 3.52 (1H, m), 3.95

(1H, m), 4.29 (1H, m), 4.89 (1H, m), 6.60 (1H, d, J=15.2 Hz), 7.38 (1H, d, J=15.2 Hz), 7.73 (1H, d, J=6.6 Hz), 7.98 (1H, s), 8.11 (1H, s), 11.18 (1H, s)

MS (ES+) m/z 430

Preparation 291

To a mixture of tert-butyl (3R)-3-pyrrolidinylcarbamate (4.0 g) and 1-(chloromethyl)-4-methylbenzene (3.17 g) in DMF (40 mL) was added N-ethyl-N-isopropyl-2-propanamine (5.55 g) at ambient temperature and the resulting mixture was heated at 70 for four hours. The mixture was allowed to cool to ambient temperature and extracted with ethyl acetate (100 mL). The organic phase was washed with water (50 mL) and brine (50 mL). The organic layer was dried over anhydrous sodium sulfate and concentrated in vacuo. The residue was purified by a flash chromatography etluting with gradient solvent system (ethyl acetate-hexane from 1:4 v/v to 1:1 v/v) to give tert-butyl [(3R)-1-(4-methylbenzyl)-3-pyrrolidinyl]carbamate (4.69 g) as a pale yellow syrup.

$^1$H-NMR (300 MHz, CDCl$_3$) δ 1.43 (9H, s), 1.49-1.64 (1H, m), 2.12-2.37 (2H, m), 2.34 (3H, s), 2.43-2.64 (2H, m), 2.68-2.84 (1H, m), 3.55 (2H, s), 4.07-4.23 (1H, m), 4.76-4.92 (1H, m), 7.12 (2H, d, J=8.1 Hz), 7.19 (2H, d, J=8.1 Hz)

MS (ES+) m/z 291(M+1)

The following compounds were obtained in a similar manner to that of Preparation 291.

Preparation 292 tert-Butyl [(3R)-1-(cyclohexylmethyl)-3-pyrrolidinyl]carbamate $^1$H-NMR (300 MHz, CDCl$_3$) δ 0.75-0.95 (2H, m), 1.06-1.31 (3H, m), 1.44 (3×3H, s), 1.50-1.83 (7H, m), 2.11-2.30 (4H, m), 2.39-2.58 (2H, m), 2.73 (1H, m), 4.13 (1H, m), 4.82 (1H, m)

MS (ES+) m/z 283

Preparation 293

To a stirred solution of tert-butyl [(3R)-1-(4-methylbenzyl)-3-pyrrolidinyl]carbamate (4.6 g) in ethyl acetate (10 mL) was added 4N hydrogen chloride in ethyl acetate (60 mL) at ambient temperature and the resulting mixture was stirred at the same temperature for three hours. The mixture was concentrated in vacuo and the residual syrup was dissolved in chloroform (100 mL). To this solution was added saturated sodium bicarbonate (50 mL) and the resulting biphasic mixture was vigorously stirred at ambient temperature for half an hour. The organic layer was separated and the aqueous layer was reextracted with chloroform (50 mL) two times. The combined organic layer was dried over anhydrous sodium sulfate and evaporated in vacuo to afford (3R)-1-(4-methylbenzyl)-3-pyrrolidinamine (2.1 g) as a pale brown viscous oil, which was used in the next step without further purification.

$^1$H-NMR (300 MHz, CDCl$_3$) δ 1.43-1.57 (1H, m), 1.81 (2H, br.s), 2.12-2.37 (1H, m), 2.28-2.37 (1H, m), 2.34 (3H, s), 2.43-2.55 (1H, m), 2.67-2.79 (2H, m), 3.46-3.55 (1H, m), 3.56 (1H, d, J=12.8 Hz), 3.62 (1H, d, J=12.8 Hz), 7.12 (2H, d, J=7.7 Hz), 7.22 (2H, d, J=7.7 Hz)

MS (ES+) m/z 191(M+1)

The following compound was obtained in a similar manner to that of Preparation 293.

Preparation 294

(3R)-1-(Cyclohexylmethyl)-3-pyrrolidinamine dihydrochloride $^1$H-NMR (300 MHz, DMSO-d$_6$) δ 0.83-1.03 (2H, m), 1.04-1.34 (3H, m), 1.52-1.77 (4H, m), 1.77-1.97 (2H, m), 2.12 (1H, m), 2.39 (1H, m), 2.95-3.26 (3H, m), 3.28-4.09 (4H, m), 8.65 (2H, br)

MS (ES+) m/z 183

Preparation 295

To a solution of ethyl (2E)-3-(5-chloro-2-pyrazinyl)acrylate (300 mg) and potassium carbonate (4.94 mg) in DMF (15 mL) was added (3R)-1-benzyl-3-piperidinamine dihydrochloride (668 mg) under nitrogen at ambient temperature and the mixture was stirred at 85° C. for 18 hrs. The reaction mixture was evaporated in vacuo and the residue was partitioned between water and ethyl acetate. The organic layer was washed with water and brine, dried over magnesium sulfate, and evaporated in vacuo. The residue was purified by silica gel column chromatography (chloroform-MeOH=97-3) to give ethyl (2E)-3-(5-{[(3R)-1-benzyl-3-piperidinyl]amino}-2-pyrazinyl)acrylate (125 mg) as an oil.

$^1$H-NMR (300 MHz, CDCl$_3$) δ 1.32 (3H, t, J=7.1 Hz), 1.47-1.83 (3H, m), 2.16-2.33 (1H, m), 2.42-2.73 (3H, m), 3.49 (1H, d, J=13.0 Hz), 3.56 (1H, d, J=13.0 Hz), 4.06-4.17 (1H, m), 4.25 (2H, q, J=7.1 Hz), 5.55 (1H, br peak), 6.67 (1H, d, J=15.5 Hz), 7.23-7.38 (5H, m), 7.57 (1H, d, J=15.5 Hz), 7.89 (1H, d, J=1.3 Hz), 8.04 (1H, d, J=1.3 Hz)

MS (ES+) m/z 367

The following compound was obtained in a similar manner to that of Preparation 295.

Preparation 296

Ethyl (2E)-3-(5-{[(3R)-1-(cyclohexylmethyl)-3-pyrrolidinyl]amino}-2-pyrazinyl)acrylate $^1$H-NMR (300 MHz, CDCl$_3$) δ 0.80-0.98 (2H, m), 1.08-1.31 (3H, m), 1.33 (3H, t, J=7 Hz), 1.44 (1H, m), 1.57-1.85 (6H, m), 2.18-2.42 (4H, m), 2.54-2.69 (2H, m), 2.88 (1H, m), 4.25 (2H, q, J=7 Hz), 4.43 (1H, m), 5.23 (1H, d, J=8 Hz), 6.68 (1H, d, J=15.5 Hz), 7.57 (1H, d, J=15.5 Hz), 7.89 (1H, s), 8.06 (1H, s)

MS (ES+) m/z 359

Preparation 297

To a solution of tert-butyl (3R)-3-({5-[(1E)-3-ethoxy-3-oxo-1-propen-1-yl]-2-pyrazinyl}amino)-1-piperidinecarboxylate (6.26 g) in a mixture of 1,4-dioxane (25 mL) and MeOH (5 mL) was added 4N hydrogen chloride solution in ethyl acetate (30 mL) in water bath.

The mixture was stirred at same temperature for 3 hrs. After evaporation of solvent, the residue was triturated with isopropylether to give ethyl (2E)-3-{5-[(3R)-3-piperidinylamino]-2-pyrazinyl}acrylate dihydrochloride (5.8 g) as an amorphous powder.

$^1$H-NMR (300 MHz, DMSO-d$_6$) δ 1.25 (3H, t, J=7 Hz), 1.46-1.65 (1H, m), 1.65-1.85 (1H, m), 1.85-2.06 (3H, m), 2.66-3.00 (2H, m), 3.05-3.25 (1H, m), 3.25-3.41 (1H, m), 4.18 (2H, q, J=7 Hz), 6.54 (1H, d, J=15 Hz), 7.57 (1H, d, J=15 Hz), 7.95-8.19 (2H, m), 8.28 (1H, s), 9.14 (2H, br peak)

MS (ES+) m/z 277

The following compound was obtained in a similar manner to that of Preparation 297.

Preparation 298

(3R)-1-(Cyclohexylmethyl)-3-piperidinamine

¹H-NMR (300 MHz, CDCl₃) δ 0.75-0.92 (2H, m), 1.02-1.31 (4H, m), 1.31-1.61 (4H, m), 1.60-1.87 (8H, m), 1.92-2.07 (1H, m), 2.08 (2H, d, J=7.2 Hz), 2.46-2.58 (1H, m), 2.62-2.73 (1H, m), 2.80-2.92 (1H, m)

MS (ES+) m/z 197(M+1)

Preparation 299

To a solution of (5-chloro-2-pyrazinyl)methanol (11.0 g) in dioxane (carbethoxymethylene)triphenylphosphorane (29.2 g). After stirring for 2 hours at room temperature, a resulting precipitate was filtered and the filtrate was evaporated in vacuo. The residue was purified by column chromatography on silica gel to give ethyl (2E)-3-(5-chloro-2-pyrazinyl)acrylate (11.0 g).

¹H-NMR (300 MHz, CDCl₃) δ 1.35 (3H, t, J=7 Hz), 4.30 (2H, q, J=7 Hz), 7.01 (1H, d, J=15 Hz), 7.66 (1H, d, J=15 Hz), 8.43 (1H, s), 8.60 (1H, s)

Preparation 300

To a solution of ethyl (2E)-3-(5-chloro-2-pyrazinyl)acrylate (1.50 g) in DMF (21 mL) was added (3R)-1-benzyl-3-pyrrolidinamine (2.24 g) and Et₃N (3.44 mL). After stirring for 3 hours at 100° C., the reaction mixture was partitioned between ethyl acetate and H₂O. The organic layer was washed with brine, dried over MgSO₄, filtered, and evaporated in vacuo. The residue was purified by column chromatography on silica gel to give ethyl (2E)-3-(5-{[(3R)-1-benzyl-3-pyrrolidinyl]amino}-2-pyrazinyl)acrylate (1.15 g)

¹H-NMR (300 MHz, CDCl₃) δ 1.32 (3H, t, J=7 Hz), 1.65-1.76 (1H, m), 2.32-2.43 (2H, m), 2.66-2.70 (2H, m), 2.87-2.95 (1H, m), 3.62-3.66 (2H, m), 4.25 (2H, q, J=7 Hz), 4.40-4.52 (1H, m), 5.21 (1H, d, J=8 Hz), 6.67 (1H, d, J=15 Hz), 7.24-7.35 (5H, m), 7.57 (1H, d, J=15 Hz), 7.87 (1H, s), 8.05 (1H, s)

MS (ES+) m/z 353 (M+1)

Preparation 301

To a solution of ethyl (2E)-3-(5-chloro-2-pyrazinyl)acrylate (1.78 g) and (3R)-1-(4-chlorobenzyl)-3-pyrrolidinamine (2.65 g) in DMF (25 mL) was added K₂CO₃ (5.79 g). After stirring for 3 hours at 100° C., the reaction mixture was partitioned between ethyl acetate and H₂O. The organic layer was washed with H₂O, dried over MgSO₄, filtered, and evaporated in vacuo. The residue was purified by column chromatography on silica gel to give ethyl (2E)-3-(5-{[(3R)-1-(4-chlorobenzyl)-3-pyrrolidinyl]amino}-2-pyrazinyl)acrylate (1.58 g).

¹H-NMR (300 MHz, CDCl₃) δ 1.32 (3H, t, J=7 Hz), 1.66-1.74 (1H, m), 2.31-2.43 (2H, m), 2.62-2.71 (2H, m), 2.85-2.92 (1H, m), 3.59-3.62 (2H, m), 4.25 (2H, q, J=7 Hz), 4.41-4.52 (1H, m), 5.19 (1H, d, J=8 Hz), 6.68 (1H, d, J=0.15 Hz), 7.23-7.32 (4H, m), 7.57 (1H, d, J=15 Hz), 7.88 (1H, s), 8.05 (1H, s)

MS (ES+) m/z 387 (M+1)

The following compound was obtained in a similar manner to that of Preparation 301.

Preparation 302

Ethyl (2E)-3-(5-{[(3R)-1-(4-methylbenzyl)-3-pyrrolidinyl]amino}-2-pyrazinyl)acrylate ¹H-NMR (300 MHz, CDCl₃) δ 1.32 (3H, t, J=7 Hz), 1.67-1.73 (1H, m), 2.32-2.42 (2H, m), 2.34 (3H, s), 2.66-2.69 (2H, m), 2.88-2.95 (1H, m), 3.60-3.63 (2H, m), 4.25 (2H, q, J=7 Hz), 4.41-4.51 (1H, m), 5.24-5.31 (1H, m), 6.67 (1H, d, J=15 Hz), 7.13 (2H, d, J=8 Hz), 7.21 (2H, d, J=8 Hz), 7.57 (1H, d, J=15 Hz), 7.87 (1H, s), 8.05 (1H, s)

MS (ES+) m/z 367 (M+1)

Preparation 303

1) To a solution of ethyl (2E)-3-(5-{[(3R)-1-(4-chlorobenzyl)-3-pyrrolidinyl]amino}-2-pyrazinyl)acrylate (1.57 g) in dioxane (20 mL) was added 1N sodium hydroxide (12.2 mL). After stirring at 60° C. for 2 hours, the reaction mixture was added H₂O (100 mL) and acidified with 1N hydrochloric acid (to pH 4). A resulting mixture was evaporated in vacuo 2) To a mixture of above product, O-tetrahydro-2H-pyran-2-ylhydroxylamine (713 mg), and 1-hydroxybenzotriazole (823 mg) in N,N-dimethylformamide (20 mL) was added 1-(3-dimethylaminopropyl)-3-ethylcarbodiimide (945 mg) at 4° C. The mixture was warmed to ambient temperature and stirred for 8 hours. The reaction mixture was added saturated NaHCO₃ (20 mL) and water (80 mL), and extracted with ethyl acetate. The organic layer was dried over MgSO₄, filtered, and evaporated in vacuo. The residue was purified by column chromatography on silica gel to give (2E)-3-(5-{[(3R)-1-(4-chlorobenzyl)-3-pyrrolidinyl]amino}-2-pyrazinyl)-N-(tetrahydro-2H-pyran-2-yloxy)acrylamide (1.44 g).

¹H-NMR (300 MHz, DMSO-d₆) δ 1.47-1.74 (7H, m), 2.16-2.30 (1H, m), 2.37-2.45 (2H, m), 2.61-2.80 (2H, m), 3.48-3.60 (3H, m), 3.89-4.00 (1H, m), 4.25-4.35 (1H, m), 4.89 (1H, brs), 6.59 (1H, d, J=15 Hz), 7.32-7.42 (5H, m), 7.77 (1H, d, J=6 Hz), 7.97 (1H, s), 8.09 (1H, s), 11.2 (1H, brs)

MS (ES+) m/z 458 (M+1)

The following compounds were obtained in a similar manner to that of Preparation 303.

Preparation 304

(2E)-3-(5-{[(3R)-1-Cyclopentyl-3-piperidinyl]amino}-2-pyrazinyl)-N-(tetrahydro-2H-pyran-2-yloxy)acrylamide ¹H-NMR (300 MHz, CDCl₃) δ 1.20-1.96 (20H, m), 2.20-2.37 (1H, m), 2.47-2.80 (4H, m), 3.59-3.71 (1H, m), 3.88-4.02 (1H, m), 4.02-4.15 (1H, m), 5.02 (1H, br s), 5.56 (1H, br peak), 6.68 (1H, br peak), 7.63 (1H, d, J=15 Hz), 7.90 (1H, s), 8.02 (1H, s), 8.30 (1H, br peak)

MS (ES+) m/z 416

Preparation 305

(2E)-3-(5-{[(3R)-1-(Cyclopentylmethyl)-3-piperidinyl]amino}-2-pyrazinyl)-N-(tetrahydro-2H-pyran-2-yloxy)acrylamide ¹H-NMR (300 MHz, CDCl₃) δ 1.11-1.30 (2H, m), 1.45-1.98 (16H, m), 1.96-2.29 (4H, m), 2.35-2.51 (1H, m), 2.56-2.76 (2H, m), 3.59-3.70 (1H, m), 3.90-4.03 (1H, m), 4.10 (1H, br peak), 5.01 (1H, br s), 5.65 (1H, br peak), 6.67 (1H, br peak), 7.62 (1H, d, J=15 Hz), 7.87 (1H, s), 8.03 (1H, s), 8.34 (1H, br peak)

MS (ES+) m/z 430

Preparation 306

(2E)-3-(5-{[(3R)-1-Benzyl-3-pyrrolidinyl]amino}-2-pyrazinyl)-N-(tetrahydro-2H-pyran-2-yloxy)acrylamide $^1$H-NMR (300 MHz, DMSO-$d_6$) δ 1.47-1.74 (7H, m), 2.16-2.30 (1H, m), 2.36-2.46 (2H, m), 2.60-2.80 (2H, m), 3.47-3.60 (3H, m), 3.88-4.00 (1H, m), 4.25-4.35 (1H, m), 4.89 (1H, brs), 6.59 (1H, d, J=15 Hz), 7.21-7.34 (5H, m), 7.37 (1H, d, J=15 Hz), 7.77 (1H, d, J=6 Hz), 7.97 (1H, s), 8.09 (1H, s), 11.2 (1H, brs)

MS (ES+) m/z 424 (M+1)

Preparation 307

(2E)-3-(5-{[(3R)-1-(4-Methylbenzyl)-3-pyrrolidinyl]amino}-2-pyrazinyl)-N-(tetrahydro-2H-pyran-2-yloxy)acrylamide $^1$H-NMR (300 MHz, DMSO-$d_6$) δ 1.47-1.74 (7H, m), 2.15-2.30 (1H, m), 2.27 (3H, s), 2.34-2.45 (2H, m), 2.60-2.77 (2H, m), 3.47-3.57 (3H, m), 3.89-4.01 (1H, m), 4.24-4.36 (1H, m), 4.89 (1H, brs), 6.59 (1H, d, J=15 Hz), 7.11 (2H, d, J=8 Hz), 7.19 (2H, d, J=8 Hz), 7.37 (1H, d, J=15 Hz), 7.76 (1H, d, J=6 Hz), 7.97 (1H, s), 8.09 (1H, s), 11.2 (1H, brs)

MS (ES+) m/z 438 (M+1)

The following compound was obtained in similar manners to those of Preparations 281 and 286.

Preparation 308

(2E)-3-(5-{[(3R)-1-(Cyclohexylmethyl)-3-piperidinyl]amino}-2-pyrazinyl)-N-(tetrahydro-2H-pyran-2-yloxy)acrylamide $^1$H-NMR (300 MHz, DMSO-$d_6$) δ 0.70-0.91 (2H, m), 1.02-1.32 (3H, m), 1.36-2.00 (16H, m), 2.02-2.11 (2H, m), 2.44-2.5.5 (2H, m), 2.56-2.67 (1H, m), 2.75-2.86 (1H, m), 3.46-3.58 (1H, m), 3.82-4.03 (2H, m), 4.89 (1H, br.s), 6.59 (1H, d, J=15.4 Hz), 7.38 (1H, d, J=15.4 Hz), 7.43 (1H, br.s), 7.97 (1H, s), 8.11 (1H, s)

MS (ES+) m/z 444(M+1)

Preparation 309

To a solution of 5,6-dichloronicotinic acid (7.0 g, 35 mmol) in DMF were added iodoethane (6.0 g, 38.5 mmol) and $K_2CO_3$ (5.8 g, 42 mmol) at ambient temperature and the mixture was stirred at 45° C. for 5 hrs. To the reaction mixture were added (3R)-1-benzyl-3-piperidinamine dihydrochloride (10.1 g, 38.5 mmol) and $K_2CO_3$ (16.9 g, 122 mmol) and the reaction mixture was stirred at 90° C. for 18 hrs. The reaction mixture was evaporated in vacuo and the residue was partitioned between water and EtOAc. The organic layer was separated, washed water and brine, dried over magnesium sulfate, and evaporated in vacuo. The residue was purified by silica gel column chromatography (EtOAc-hexane/1-4~1-3) to give ethyl 6-{[(3R)-1-benzyl-3-piperidinyl]amino}-5-chloronicotinate (6.75 g, 52%) as a powder.

$^1$H-NMR (300 MHz, CDCl$_3$) δ 1.36 (3H, t, J=7.1 Hz), 1.51-1.69 (2H, m), 1.69-1.88 (2H, m), 2.18-2.33 (1H, m), 2.41-2.54 (1H, m), 2.54-2.67 (1H, m), 2.67-2.79 (1H, m), 3.45 (1H, d, J=13 Hz), 3.61 (1H, d, J=13 Hz), 4.32 (2H, q, J=7.1 Hz), 6.24 (1H, br peak), 7.21-7.41 (5H, m), 8.00 (1H, d, J=2 Hz), 8.65 (1H, d, J=2 Hz);

MS (ES+) m/z 374.

Preparation 310

A mixture of ethyl (2E)-3-(5-bromo-2-pyridinyl)acrylate (480 mg), (3R)-1-benzyl-3-pyrrolidinamine (363 mg), cesium carbonate (855 mg, 1.4 eq.), CyDMABP (2-Dicyclohexylphosphino-2'-(N,N-dimethylamino)biphenyl, 63 mg, 0.15 eq.), and palladium acetate (250 mg, 0.6 eq.) in dioxane (25 ml) was stirred at 100° C. for 2 days.

Water and ethyl acetate was added and aqueous layer was separated.

Aqueous layer was extracted with ethyl acetate (twice).

Combined organic layer was washed with water and brine, dried over MgSO$_4$, filtered and evaporated.

The residue was column chromatographed on silica gel to give 37 mg (6%) of ethyl (2E)-3-(5-{[(3R)-1-benzyl-3-pyrrolidinyl]amino}-2-pyridinyl)acrylate as an oil.

MASS (ESI+): m/z=352.3 (M+1).

$^1$HNMR (400 MHz, CDCl$_3$): δ 1.31 (3H, t, J=7.1 Hz), 1.68-1.78 (1H, m), 2.31-2.95 (5H, m), 3.69 (2H, s), 4.01-4.09 (1H, m), 4.24 (2H, q, J=7.1 Hz), 4.44-4.51 (1H, m), 6.62 (1H, d, J=15.5 Hz), 6.79 (1H, dd, J=8.5 and 2.9 Hz), 7.23-7.36 (6H, m), 7.18 (1H, d, J=8.4 Hz), 7.24 (1H, d, J=8.5 Hz), 7.32-7.40 (5H, m), 7.60 (1H, d, J=15.5 Hz), 8.01 (1H, d, J=2.9 Hz).

Preparation 311

To a solution of ethyl (2E)-3-(6-{(tert-butoxycarbonyl)[(3R)-3-pyrrolidinyl]amino}-3-pyridinyl)acrylate dihydrochloride (220 mg, 0.51 mmol) in 1,2-dichloroethane (4 mL) were added diisopropylethylamine (131 mg, 1.01 mmol) and cyclopentanecarboxaldehyde (52 mg, 0.53 mmol), and the mixture was stirred at ambient temperature for 5 min. To the mixture was added sodium triacetoxyborohydride (215 mg, 1.01 mmol) and stirred for 2 hrs, and resulting mixture was poured into saturated sodium bicarbonate solution, and extracted with ethyl acetate. The organic layer was washed with water, and brine, and dried over magnesium sulfate. The solvent was removed in vacuo and the residue was purified by preparative thin layer chromatography (chloroform-MeOH=10-1) to give ethyl (2E)-3-(6-{(tert-butoxycarbonyl)[(3R)-1-(cyclopentylmethyl)-3-pyrrolidinyl]amino}-3-pyridinyl)acrylate (225 mg, 100%) as an amorphous powder.

$^1$H-NMR (300 MHz, CDCl$_3$) δ 1.00-1.21 (2H, m), 1.36 (3H, t, J=7.5 Hz), 1.46 (9H, s), 1.48-1.80 (8H, m), 1.80-2.10 (2H, m), 2.10-2.44 (2H, m), 2.44-2.80 (2H, m), 2.90-3.06 (1H, m), 4.29 (2H, q, J=7.5 Hz), 4.80-4.96 (1H, m), 6.46 (1H, d, J=15 Hz), 7.32 (1H, d, J=8 Hz), 7.66 (1H, d, J=15 Hz), 7.80 (1H, dd, J=8, 2 Hz), 8.55 (1H, d, J=2 Hz);

MS (ES+) m/z 444.

The following compounds were obtained in a similar manner to that of Preparation 311.

Preparation 312 ethyl 6-{[(3R)-1-benzyl-3-piperidinyl]amino}nicotinate $^1$H-NMR (300 MHz, CDCl$_3$) δ 1.36 (3H, t, J=7.1 Hz), 1.46-1.84 (5H, m), 2.20-2.40 (1H, m), 2.40-2.67 (2H, m), 3.45-

3.58 (2H, m), 3.97 (1H, br peak), 4.32 (2H, q, J=7.1 Hz), 5.54 (1H, br peak), 6.33 (1H, d, J=8.7 Hz), 7.23-7.40 (5H, m), 7.96 (1H, dd, J=8.8, 2.2 Hz), 8.73 (1H, d, J=2.2 Hz);

MS (ES+) m/z 340.

Preparation 313 ethyl 6-{[(3R)-1-(cyclohexylmethyl)-3-piperidinyl]amino}nicotinate $^1$H-NMR (300 MHz, CDCl3) δ 0.77-0.97 (2H, m), 1.05-1.30 (3H, m), 1.36 (3H, t, J=7.1 Hz), 1.40-1.86 (10H, m), 1.97-2.25 (3H, m), 2.37-2.64 (3H, m), 3.84-4.08 (1H, m), 4.30 (2H, q, J=7.1 Hz), 5.59 (1H, br peak), 6.35 (1H, d, J=8.4 Hz), 7.97 (1H, dd, J=8.6, 2.0 Hz), 8.74 (1H, d, J=2.0 Hz).

Preparation 314 ethyl (2E)-3-(6-{[(3R)-1-(4-chlorobenzyl)-3-piperidinyl]amino}-3-pyridinyl)acrylate $^1$H-NMR (300 MHz, CDCl$_3$) δ 1.33 (3H, t, J=7.1 Hz), 1.46-1.84 (3H, m), 2.18-2.36 (1H, m), 2.36-2.66 (3H, m), 3.43 (1H, d, J=13.5 Hz), 3.50 (1H, d, J=13.5 Hz), 3.88-4.04 (1H, m), 4.24 (2H, q, J=7.1 Hz), 5.21-5.41 (1H, m), 6.20 (1H, d, J=15.9 Hz), 6.38 (1H, d, J=8.8 Hz), 7.18-7.38 (4H, m), 7.56 (1H, d, J=16.1 Hz), 7.60 (1H, dd, J=9.4, 2.3 Hz), 8.18 (1H, d, J=2.3 Hz); MS (ES+) m/z 400.

Preparation 315 ethyl (2E)-3-(6-{[(3R)-1-cyclopentyl-3-piperidinyl]amino}-3-pyridinyl}acrylate $^1$H-NMR (300 MHz, CDCl$_3$) δ 1.16-1.90 (15H, m), 2.20-2.77 (5H, m), 3.92 (1H, br peak), 4.24 (2H, q, J=7.1 Hz), 5.40 (1H, br peak), 6.20 (1H, d, J=15.9 Hz), 6.40 (1H, d, J=8.8 Hz), 7.56 (1H, d, J=15.9 Hz), 7.61 (1H, dd, J=8.7, 2.3 Hz), 8.18 (1H, d, J=2.1 Hz);

MS (ES+) m/z 344.

Preparation 316 ethyl (2Z)-3-(6-{[(3R)-1-cyclohexyl-3-pyrrolidinyl]amino}-3-pyridinyl)-2-fluoroacrylate $^1$H-NMR (300 MHz, CDCl$_3$) δ 1.06-1.33 (6H, m), 1.38 (3H, t, J=7.1 Hz), 1.44-1.84 (3H, m), 1.84-2.00 (2H, m), 2.00-2.15 (1H, m), 2.25-2.56 (2H, m), 2.68-2.89 (2H, m), 2.89-3.05 (1H, m), 4.23-4.45 (3H, m), 5.24 (1H, br peak), 6.40 (1H, d, J=8.8 Hz), 6.81 (1H, d, J=36.3 Hz), 7.82 (1H, dd, J=8.8, 1.9 Hz), 8.24 (1H, s);

MS (ES+) m/z 362.

Preparation 317 ethyl (2E)-3-{6-[[(3R)-1-(1-adamantylmethyl)-3-pyrrolidinyl](tert-butoxycarbonyl)amino]-3-pyridinyl}acrylate $^1$H-NMR (300 MHz, CDCl$_3$) δ 1.35 (3H, t, J=7.1 Hz), 1.44 (9H, s), 1.50-2.30 (20H, m), 2.65-3.20 (1H, m), 4.29 (2H, q, J=7.2 Hz), 6.46 (1H, d, J=16.1 Hz), 8.31 (1H, d, J=8.2 Hz), 7.66 (1H, d, J=16.5 Hz), 7.81 (1H, dd, J=8.3, 2.7 Hz), 8.56 (1H, d, J=2.7 Hz);

MS (ES+) m/z 510.

Preparation 318 ethyl (2E)-3-(6-{[(3R)-1-(4-methylbenzyl)-3-piperidinyl]amino}-3-pyridinyl)acrylate $^1$H-NMR (300 MHz, CDCl$_3$) δ 1.32 (3H, t, J=7.1 Hz), 1.47-1.84 (4H, m), 2.18-2.37 (4H, m), 2.40-2.70 (3H, m), 3.44 (1H, d, J=13.1 Hz), 3.50 (1H, d, J=13.1 Hz), 3.95 (1H, br peak), 4.24 (2H, q, J=7.1 Hz), 5.40 (1H, br peak), 6.20 (1H, d, J=15.9 Hz), 6.38 (1H, d, J=8.8 Hz), 7.12 (2H, d, J=7.9 Hz), 7.20 (2H, d, J=7.9 Hz), 7.55 (1H, d, J=15.5 Hz), 7.60 (1H, dd, J=8.8, 2.2 Hz), 8.17 (1H, d, J=2.1 Hz).

Preparation 319 ethyl (2Z)-2-fluoro-3-(6-{[(3R)-1-(4-methylbenzyl)-3-pyrrolidinyl]amino}-3-pyridinyl)acrylate $^1$H-NMR (300 MHz, CDCl$_3$) δ 1.37 (3H, t, J=7.1 Hz), 1.59-1.78 (1H, m), 2.26-2.47 (5H, m), 2.60 (1H, dd, J=9.6, 3.2 Hz), 2.74 (1H, dd, J=9.7, 6.4 Hz), 2.78-2.90 (1H, m), 3.56 (1H, d, J=12.8 Hz), 3.64 (1H, d, J=12.8 Hz), 4.25-4.41 (3H, m), 5.12 (1H, br d, J=7.8 Hz), 6.38 (1H, d, J=8.9 Hz), 6.79 (1H, d, J=36.2 Hz), 7.12 (2H, d, J=7.9 Hz), 7.21 (2H, d, J=7.9 Hz), 7.81 (1H, dd, J=8.9, 2.2 Hz), 8.23 (1H, d, J=1.8 Hz);

MS (ES+) m/z 384.

Preparation 320 ethyl (2Z)-3-(6-{[(3R)-1-(4-chlorobenzyl)-3-pyrrolidinyl]amino}-3-pyridinyl)-2-fluoroacrylate $^1$H-NMR (300 MHz, CDCl$_3$) δ 1.37 (3H, t, J=7.1 Hz), 1.56-1.78 (1H, m), 2.28-2.46 (2H, m), 2.60 (1H, dd, J=9.7, 3.2 Hz), 2.73 (1H, dd, J=9.7, 6.3 Hz), 2.77-2.88 (1H, m), 3.56 (1H, d, J=13.6 Hz), 3.61 (1H, d, J=13.6 Hz), 4.26-4.42 (3H, m), 5.08 (1H, br d, J=7.9 Hz), 6.38 (1H, d, J=8.8 Hz), 6.80 (1H, d, J=36.2 Hz), 7.25 (2H, d, J=8.7 Hz), 7.30 (2H, d, J=8.7 Hz), 7.82 (1H, dd, J=8.9, 2.2 Hz), 8.24 (1H, d, J=2.0 Hz).

Preparation 321 ethyl (2E)-3-(5-{[(3R)-1-(3-chlorobenzyl)-3-piperidinyl]amino}-2-pyrazinyl)acrylate $^1$H-NMR (300 MHz, CDCl$_3$) δ 1.32 (3H, t, J=7.1 Hz), 1.5-1.85 (4H, m), 2.20-2.35 (1H, m), 2.49-2.71 (3H, m), 3.46 (1H, d, J=13.5 Hz), 3.53 (1H, d, J=13.5 Hz), 4.12 (1H, br peak), 4.25 (2H, q, J=7.1 Hz), 5.50 (1H, br peak), 6.67 (1H, d, J=15.5 Hz), 7.15-7.40 (4H, m), 7.58 (1H, d, J=15.5 Hz), 7.91 (1H, s), 8.05 (1H, s);

MS (ES+) m/z 401.

Preparation 322 ethyl (2E)-3-(5-{[(3R)-1-(2-chlorobenzyl)-3-piperidinyl]amino}-2-pyrazinyl)acrylate $^1$H-NMR (300 MHz, CDCl$_3$) δ 1.32 (3H, t, J=7.1 Hz), 1.48-1.88 (4H, m), 2.20-2.36 (1H, m), 2.54-2.80 (3H, m), 3.56 (1H, d, J=13.6 Hz), 3.64 (1H, d, J=13.6 Hz), 4.14 (1H, br peak), 4.25 (2H, q, J=7.1 Hz), 5.72 (1H, br peak), 6.66 (1H, d, J=1-5.5 Hz), 7.16-7.25 (2H, m), 7.34-7.42 (2H, m), 7.56 (1H, d, J=15.5 Hz), 7.89 (1H, s), 8.03 (1H, s);

MS (ES+) m/z 401.

Preparation 323 ethyl (2E)-3-(5-{[(3R)-1-(4-fluorobenzyl)-3-piperidinyl]amino}-2-pyrazinyl)acrylate $^1$H-NMR (300 MHz, CDCl$_3$) δ 1.32 (3H, t, J=7.1 Hz), 1.50-1.82 (4H, m), 2.18-2.31 (1H, m), 2.44-2.66 (3H, m), 3.45 (1H, d, J=13.2 Hz), 3.51 (1H, d, J=13.1 Hz), 4.10 (1H, br peak), 4.25 (2H, q, J=7.1 Hz), 5.46 (1H, br peak), 6.67 (1H, d, J=15.6 Hz), 7.01 (2H, t, J=8.7 Hz), 7.21-7.33 (2H, m), 7.56 (1H, d, J=15.6 Hz), 7.90 (1H, s), 8.03 (1H, s);

MS (ES+) m/z 385.

Preparation 324 ethyl (2E)-3-(5-{[(3R)-1-(2-thienylmethyl)-3-piperidinyl]amino}-2-pyrazinyl)acrylate $^1$H-NMR (300 MHz, CDCl$_3$) δ 1.33 (3H, t, J=7.1 Hz), 1.50-1.69 (2H, m), 1.69-1.89 (2H, m), 2.24-2.37 (1H, m), 2.43-2.55 (1H, m), 2.60-2.84 (2H, m), 3.70 (1H, d, J=13.9 Hz), 3.80 (1H, d, J=13.9 Hz), 4.14 (1H, br peak), 4.25 (2H, q, J=7.1 Hz), 5.64 (1H, br peak), 6.68 (1H, d, J=15.5 Hz), 6.88-6.93 (1H, m), 6.93-6.99 (1H, m), 7.20-7.30 (1H, m), 7.58 (1H, d, J=15.5 Hz), 7.92 (1H, s), 8.05 (1H, s);

MS (ES+) m/z 373.

Preparation 325 ethyl (2E)-3-(5-{[(3R)-1-(3-thienylmethyl)-3-piperidinyl]amino}-2-pyrazinyl)acrylate $^1$H-NMR (300 MHz, CDCl$_3$) δ 1.32 (3H, t, J=7.1 Hz), 1.40-1.82 (4H, m), 2.17-2.32 (1H, m), 2.43-2.72 (3H, m), 3.51 (1H, d, J=13.4 Hz), 3.60 (1H, d, J=13.4 Hz), 4.10 (1H, br peak), 4.25 (2H, q, J=7.1 Hz), 5.52 (1H, br peak), 6.67 (1H, d, J=15.5 Hz), 7.06 (1H, d, J=4.9 Hz), 7.10 (1H, d, J=2.3 Hz), 7.29 (1H, dd, J=7.7, 3.0 Hz), 7.56 (1H, d, J=15.6 Hz), 7.9 (1H, s), 8.05 (1H, s);

MS (ES+) m/z 373.

Preparation 326 ethyl (2E)-3-(5-{[(3R)-1-(2-pyridinylmethyl)-3-piperidinyl]amino}-2-pyrazinyl)acrylate $^1$H-NMR (300 MHz, CDCl$_3$) δ 1.32 (3H, t, J=7.1 Hz), 1.53-1.91 (4H, m), 2.26-2.45 (1H, m), 2.50-2.75 (3H, m), 3.63 (1H, d, J=13.8 Hz), 3.71 (1H, d, J=13.8 Hz), 4.05-4.18 (1H, m), 4.25 (2H, q, J=7.1 Hz), 5.68 (1H, br peak), 6.65 (1H, d, J=15.5 Hz), 7.19 (1H, dd, J=7.5, 5.5 Hz), 7.38 (1H, d, J=7.7 Hz), 7.56 (1H, d, J=15.5 Hz), 7.66 (~1H, t, J=7.5 Hz), 7.91 (1H, s), 8.01 (1H, s), 8.55 (1H, d, J=4.4 Hz);

MS (ES+) m/z 368.

Preparation 327 ethyl (2E)-3-(5-{[(3R)-1-(3-pyridinylmethyl)-3-piperidinyl]amino}-2-pyrazinyl)acrylate $^1$H-NMR (300 MHz, CDCl$_3$) δ 1.32 (3H, t, J=7.1 Hz), 1.50-1.84 (4H, m), 2.20-2.35 (1H, m), 2.45-2.68 (3H, m), 3.50 (1H, d, J=14.7 Hz), 3.66 (1H, d, J=14.7 Hz), 4.14 (1H, br peak), 4.25 (2H, q, J=7.1 Hz), 5.45 (1H, br peak), 6.66 (1H, d, J=15.5 Hz), 7.23-7.32 (1H, m), 7.56 (1H, d, J=15.5 Hz), 7.66 (1H, d, J=7.8 Hz), 7.90 (1H, s), 8.04 (1H, s), 8.51 (1H, d, J=4.7 Hz), 8.54 (1H, s);

MS (ES+) m/z 368.

Preparation 328 ethyl (2E)-3-(5-{[(3R)-1-(cycloheptylmethyl)-3-piperidinyl]amino}-2-pyrazinyl)acrylate $^1$H-NMR (300 MHz, CDCl$_3$) δ 1.04-1.23 (2H, m), 1.23-1.84 (18H, m), 2.01-2.19 (3H, m), 2.33-2.48 (1H, m), 2.48-2.70 (2H, m), 4.10 (1H, br peak), 4.25 (2H, q, J=7.0 Hz), 5.64 (1H, br peak), 6.66 (1H, d, J=15.8 Hz), 7.57 (1H, d, J=15.4 Hz), 7.89 (1H, d, J=1.1 Hz), 8.05 (1H, d, J=1.5 Hz);

MS (ES+) m/z 387.

Preparation 329 ethyl (2E)-3-(5-{[(3R)-1-(2-phenylethyl)-3-piperidinyl]amino}-2-pyrazinyl)acrylate $^1$H-NMR (300 MHz, CDCl$_3$) δ 1.32 (3H, t, J=7.1 Hz), 1.50-1.85 (4H, m), 2.20-2.35 (1H, m), 2.46-2.86 (7H, m), 4.11 (1H, br peak), 4.25 (2H, q, J=7.1 Hz), 5.46 (1H, br peak), 6.67 (1H, d, J=15.5 Hz), 7.16-7.37 (5H, m), 7.56 (1H, d, J=15.5 Hz), 7.77 (1H, s), 8.04 (1H, s);

MS (ES+) m/z 381.

Preparation 330 ethyl (2E)-3-(5-{[(3R)-1-cycloheptyl-3-piperidinyl]amino}-2-pyrazinyl)acrylate $^1$H-NMR (300 MHz, CDCl$_3$) δ 1.22-1.90 (19H, m), 2.35-2.72 (5H, m), 4.06 (1H, br peak), 4.25 (2H, q, J=7.1 Hz), 5.68 (1H, br d, J=7.0 Hz), 6.66 (1H, d, J=15.5 Hz), 7.58 (1H, d, J=15.5 Hz), 7.91 (1H, s), 8.05 (1H, s);

MS (ES+) m/z 373.

Preparation 331 ethyl (2E)-3-(5-{[(3R)-1-(4-pyridinylmethyl)-3-piperidinyl]amino}-2-pyrazinyl)acrylate $^1$H-NMR (300 MHz, CDCl$_3$) δ 1.33 (3H, t, J=7.1 Hz), 1.50-1.86 (4H, m), 2.24-2.36 (1H, m), 2.44-2.71 (3H, m), 3.48 (1H, d, J=14.8 Hz), 3.55 (1H, d, J=14.8 Hz), 4.06-4.20 (1H, m), 4.25 (2H, q, J=7.1 Hz), 5.42 (1H, br peak), 6.68 (1H, d, J=15.5 Hz), 7.21-7.29 (2H, m), 7.57 (1H, d, J=15.5 Hz), 7.92 (1H, s), 8.05 (1H, s), 8.55 (2H, d, J=5.8 Hz);

MS (ES+) m/z 368.

Preparation 332 ethyl (2E)-3-(6-{[(3R)-1-cyclohexyl-3-piperidinyl]amino}-3-pyridinyl)acrylate $^1$H-NMR (300 MHz, CDCl$_3$) δ 0.96-1.36 (10H, m), 1.46-1.86 (7H, m), 2.20-2.40 (1H, m), 2.40-2.65 (3H, m), 4.74 (1H, br d, J=11 Hz), 3.81-3.98 (1H, m), 4.24 (2H, q, J=7.1 Hz), 5.36-5.55 (1H, m), 6.20 (1H, d, J=15.9 Hz), 6.40 (1H, d, J=8.8 Hz), 7.57 (1H, d, J=15.8 Hz), 7.60 (1H, dd, J=8.7, 2.3 Hz), 8.18 (1H, d, J=2.2 Hz);

MS (ES+) m/z 358.

Preparation 333 ethyl (2E)-3-(6-{(tert-butoxycarbonyl)[(3R)-1-(cycloheptylmethyl)-3-pyrrolidinyl]amino}-3-pyridinyl)acrylate ¹H-NMR (300 MHz, CDCl₃) δ 0.98-1.15 (2H, m), 1.21-1.91 (24H, m), 1.93-2.30 (4H, m), 2.50-2.76 (2H, m), 2.91 (1H, br peak), 4.28 (2H, q, J=7.2 Hz), 4.90 (1H, br peak), 6.46 (1H, d, J=16 Hz), 7.31 (1H, d, J=8 Hz), 7.65 (1H, d, J=16 Hz), 7.80 (1H, dd, J=8, 2 Hz), 8.55 (1H, d, J=2 Hz);

MS (ES+) m/z 472.

Preparation 334 ethyl (2E)-3-(5-{[(3R)-1-(2,3-dihydro-1H-inden-2-yl)-3-piperidinyl]amino}-2-pyrazinyl)acrylate ¹H-NMR (300 MHz, CDCl₃) δ 1.19-1.38 (4H, m), 1.57-1.86 (3H, m), 2.28-2.43 (1H, m), 2.55-2.80 (3H, m), 2.80-2.98 (2H, m), 2.98-3.16 (2H, m), 3.16-3.35 (1H, m), 4.14 (1H, br peak), 4.26 (2H, q, J=7.3 Hz), 5.57 (1H, br peak), 6.68 (1H, d, J=15.8 Hz), 7.10-7.22 (4H, m), 7.59 (1H, d, MS (ES+) m/z 392.

Preparation 335

A mixture of ethyl (2E)-3-(2-chloro-5-pyrimidinyl)acrylate (200 mg), (3R)-1-benzyl-3-pyrrolidinamine (0.244 mL), and N,N-dimethylformamide (5 mL) was stirred for 3 hours at 60° C. The reaction mixture was partitioned between ethyl acetate and H₂O. The organic layer was washed with saturated NaHCO₃ and brine, dried over MgSO₄, filtered, and evaporated in vacuo to give ethyl (2E)-3-(2-{[(3R)-1-benzyl-3-pyrrolidinyl]amino}-5-pyrimidinyl)acrylate (330 mg).

¹H-NMR (300 MHz, CDCl₃) δ 1.33 (3H, t, J=7 Hz), 1.64-1.78 (1H, m), 2.30-2.43 (2H, m), 2.61-2.75 (2H, m), 2.82-2.92 (1H, m), 3.59-3.70 (2H, m), 4.25 (2H, q, J=7 Hz), 4.50-4.62 (1H, m), 5.74 (1H, d, J=8 Hz), 6.28 (1H, d, J=16 Hz), 7.22-7.34 (5H, m), 7.47 (1H, d, J=16 Hz), 8.43 (2H, s).

MS (ES+) m/z 353 (M+1).

Preparation 336

To a solution of ethyl (2E)-3-(6-{(tert-butoxycarbonyl)[(3R)-1-(cyclopentylmethyl)-3-pyrrolidinyl]amino}-3-pyridinyl)acrylate (225 mg, 0.51 mmol) in EtOH (2.5 mL) was added 1N sodium hydroxide solution (1.0 mL) at ambient temperature and the mixture was allowed to stand for 18 hrs. The reaction mixture was adjusted to PH 5.0 with 1 mol/L hydrochloric acid and evaporated in vacuo to give (2E)-3-(6-{(tert-butoxycarbonyl)[(3R)-1-(cyclopentylmethyl)-3-pyrrolidinyl]amino}-3-pyridinyl)acrylic acid.

A mixture of (2E)-3-(6-{(tert-butoxycarbonyl)[(3R)-1-(cyclopentylmethyl)-3-pyrrolidinyl]amino}-3-pyridinyl) acrylic acid, O-(tetrahydro-2H-pyran-2-yl)hydroxylamine (77 mg, 0.66 mmol), HOBt (89 mg, 0.66 mmol) and EDCI (126 mg, 0.66 mmol) in DMF (4.5 mL) was stirred at 0° C. for 1 hr and the mixture was stirred at ambient temperature for 18 hrs. The reaction mixture was evaporated in vacuo and the residue was partitioned between saturated sodium bicarbonate solution and EtOAc. The organic layer was separated, evaporated in vacuo. The residue was purified by preparative thin layer chromatography (chloroform-MeOH=10-1) to give tert-butyl [(3R)-1-(cyclopentylmethyl)-3-pyrrolidinyl](5-{(1E)-3-oxo-3-[(tetrahydro-2H-pyran-2-yloxy)amino]-1-propen-1-yl}-2-pyridinyl)carbamate (181 mg, 69%) as an amorphous powder.

¹H-NMR (300 MHz, CDCl₃) δ 1.05-1.21 (2H, m), 1.46 (9H, s), 1.46-2.10 (16H, m), 2.10-2.48 (2H, m), 2.48-2.85 (2H, m), 2.90-3.09 (1H, m), 3.60-3.76 (1H, m), 3.90-4.05 (1H, m), 4.80-4.96 (1H, m), 4.96-5.11 (1H, m), 6.41 (1H, br peak), 7.30 (1H, d, J=8 Hz), 7.69 (1H, d, J=15 Hz), 7.78 (1H, d, J=8 Hz), 8.56 (1H, s).

The following compounds were obtained in a similar manner to that of Preparation 336.

Preparation 337

(2E)-3-(6-{[(3R)-1-(cyclohexylmethyl)-3-pyrrolidinyl]amino}-3-pyridinyl)-2-methyl-N-(tetrahydro-2H-pyran-2-yloxy)acrylamide ¹H-NMR (300 MHz, CDCl₃) 0.80-0.97 (2H, m), 1.11-1.34 (4H, m), 1.34-1.53 (1H, m), 1.53-1.97 (10H, m), 2.11 (3H, d, J=1.3 Hz), 2.19-2.41 (4H, m), 2.56 (1H, dd, J=9.4, 3.2 Hz), 2.69 (1H, dd, J=9.6, 6.3 Hz), 2.77-2.86 (1H, m), 3.62-3.73 (1H, m), 3.95-4.07 (1H, m), 4.23-4.37 (1H, m), 4.99-5.08 (2H, m), 6.38 (1H, d, J=8.7 Hz), 7.11 (1H, s), 7.47 (1H, dd, J=8.9, 2.4 Hz), 8.14 (1H, d, J=2.3 Hz), 8.58 (1H, br peak);

MS (ES+) m/z 443.

Preparation 338

(2E)-3-(6-{[(3R)-1-benzyl-3-piperidinyl]amino}-3-pyridinyl)-N-(tetrahydro-2H-pyran-2-yloxy)acrylamide ¹H-NMR (300 MHz, CDCl₃) δ 1.30-1.71 (8H, m), 1.75-1.91 (2H, m), 2.15-2.65 (3H, m), 3.40-3.55 (2H, m), 3.55-3.72 (1H, m), 3.85-4.05 (2H, m), 4.90-5.10 (2H, m), 6.36 (1H, d, J=8 Hz), 6.64 (1H, br peak), 7.19-7.40 (5H, m), 7.53-7.68 (2H, m), 8.20 (1H, d, J=2 Hz);

MS (ES+) m/z 437.

Preparation 339

(2E)-3-(6-{[(3R)-1-(4-chlorobenzyl)-3-piperidinyl]amino}-3-pyridinyl)-N-(tetrahydro-2H-pyran-2yloxy)acrylamide ¹H-NMR (300 MHz, CDCl₃) δ 1.46-1.95 (10H, m), 2.19-2.36 (1H, m), 2.36-2.66 (3H, m), 3.43 (1H, d, J=13.5 Hz), 3.50 (1H, d, J=13.5 Hz), 3.56-3.70 (1H, m), 3.85-4.01 (2H, m), 5.00 (1H, br s), 5.32 (1H, br peak), 6.24 (1H, br peak), 6.36 (1H, d, J=8.8 Hz), 7.20-8.34 (4H, m), 7.57 (1H, d, J=9.3 Hz), 7.63 (1H, d, J=15.9 Hz), 8.21 (1H, s), 8.26 (1H, br peak);

MS (ES+) m/z 471.

Preparation 340

(2E)-3-(6-{[(3R)-1-cyclopentyl-3-piperidinyl]amino}-3-pyridinyl)-N-(tetrahydro-2H-pyran-2-yloxy)acrylamide ¹H-NMR (300 MHz, CDCl₃) δ 1.00-1.97 (18H, m), 2.23-2.84 (5H, m), 3.56-3.80 (1H, m), 3.80-4.07 (2H, m), 5.00 (1H, br s), 5.88 (1H, br peak), 6.27 (1H, br peak), 6.41 (1H, d, J=8.8 Hz), 7.50-7.72 (2H, m), 8.14-8.42 (2H, m); MS (ES+) m/z 415.

Preparation 341

(2Z)-3-(6-{[(3R)-1-(4-chlorobenzyl)-3-pyrrolidinyl]amino}-3-pyridinyl)-2-fluoro-N-(tetrahydro-2H-pyran-2-yloxy)acrylamide ¹H-NMR (300 MHz, CDCl₃) δ 1.50-1.77 (6H, m), 1.77-1.98 (3H, m), 2.26-2.46 (2H, m), 2.60 (1H, dd, J=9.6, 3.0 Hz), 2.74 (1H, dd, J=9.6, 6.3 Hz), 2.80-2.90 (1H, m), 3.60 (2H, s), 3.61-3.75 (1H, m), 3.91-4.07 (1H, m), 4.35 (1H, br peak), 4.96-5.13 (2H, m), 6.36 (1H, d, J=8.8 Hz), 6.82 (1H, d, J=40.4 Hz), 7.14-7.34 (4H, m), 7.72 (1H, dd, J=8.8, 2.1 Hz), 8.25 (1H, d, J=1.8 Hz), 8.93 (1H, br peak).

Preparation 342

(2E)-3-(5-{[(3R)-1-(2-pyrimidinyl)-3-piperidinyl]amino}-2-pyrazinyl)-N-(tetrahydro-2H-pyran-2-yloxy)acrylamide ¹H-NMR (300 MHz, CDCl₃) δ 1.50-1.75 (2H, m), 1.75-1.95 (6H, m), 1.95-2.11 (1H, m), 3.58-3.83 (4H, m), 3.83-4.13 (4H, m), 4.13-4.25 (1H, m), 5.00 (1H, br s), 5.12 (1H, br d, J=7.3 Hz), 6.51 (1H, t, J=4.7 Hz), 6.70 (1H, br peak), 7.65 (1H, d, J=15.2 Hz), 7.90 (1H, s), 8.05 (1H, s), 8.30 (2H, d, J=4.7 Hz), 8.35 (1H, br peak);

MS (ES+) m/z 426.

Preparation 343

(2E)-3-(5-{[(3R)-1-(4-fluorobenzyl)-3-piperidinyl]amino}-2-pyrazinyl)-N-(tetrahydro-2H-pyran-2-yloxy)acrylamide ¹H-NMR (300 MHz, CDCl₃) δ 1.50-1.96 (9H, m), 2.12-2.34 (1H, m), 2.44-2.70 (3H, m), 3.45 (1H, d, J=13.3 Hz), 3.51 (1H, d, J=13.3 Hz), 3.90-4.04 (1H, m), 4.04-4.16 (1H, m), 5.00 (1H, br s), 5.48 (1H, br peak), 6.68 (1H, br peak), 7.03 (2H, t, J=8.6 Hz), 7.22-7.35 (2H, m), 7.64 (1H, d, J=15.2 Hz), 7.88 (1H, s), 8.04 (1H, s), 8.32 (1H, br peak);

MS (ES+) m/z 456.

Preparation 344

(2E)-3-(5-{[(3R)-1-(2-pyridinylmethyl)-3-piperidinyl]amino}-2-pyrazinyl)-N-(tetrahydro-2H-pyran-2-yloxy)acrylamide ¹H-NMR (300 MHz, CDCl₃) δ 1.54-1.96 (10H, m), 2.29-2.49 (1H, m), 2.54-2.78 (3H, m), 3.60-3.76 (3H, m), 3.90-4.03 (1H, m), 4.06-4.19 (1H, m), 5.01 (1H, br s), 5.72 (1H, br peak), 7.68 (1H, br peak), 7.19 (1H, dd, J=7.0, 4.9 Hz), 7.38 (1H, d, J=7.7 Hz), 7.56-7.73 (2H, m), 7.90 (1H, s), 8.00 (1H, s), 8.36 (1H, br peak), 8.56 (1H, d, J=4.7 Hz);

MS (ES+) m/z 439.

Preparation 345

(2E)-3-(5-{[(3R)-1-(3-pyridinylmethyl)-3-piperidinyl]amino}-2-pyrazinyl)-N-(tetrahydro-2H-pyran-2-yloxy)acrylamide ¹H-NMR (300 MHz, CDCl₃) δ 1.50-1.96 (10H, m), 2.20-2.40 (1H, m), 2.40-2.70 (3H, m), 3.55 (2H, s), 3.60-3.73 (1H, m), 3.90-4.05 (1H, m), 4.05-4.20 (1H, m), 5.02 (1H, br s), 5.36-5.51 (1H, m), 6.68 (1H, br peak), 7.23-7.36 (1H, m), 7.58-7.74 (2H, m), 7.90 (1H, s), 8.04 (1H, s), 8.39 (1H, br peak), 8.50-8.63 (2H, m);

MS (ES+) m/z 439.

Preparation 346

(2E)-3-(5-{[(3R)-1-(2-phenylethyl)-3-pyrrolidinyl]amino}-2-pyrazinyl)-N-(tetrahydro-2H-pyran-2-yloxy)acrylamide ¹H-NMR (300 MHz, CDCl₃) δ 1.50-1.98 (8H, m), 2.30-2.48 (2H, m), 2.61-2.88 (6H, m), 2.96-3.11 (1H, m), 3.57-3.72 (1H, m), 3.90-4.04 (1H, m), 4.41-4.55 (1H, m), 5.01 (1H, br s), 5.30 (1H, d, J=7.7 Hz), 6.70 (1H, br peak), 7.15-7.35 (5H, m), 7.64 (1H, d, J=15.0 Hz), 7.85 (1H, s), 8.05 (1H, s);

MS (ES+) m/z 438.

Preparation 347

(2E)-3-(5-{[(3R)-1-(cycloheptylmethyl)-3-piperidinyl]amino}-2-pyrazinyl)-N-(tetrahydro-2H-pyran-2-yloxy)acrylamide ¹H-NMR (300 MHz, CDCl₃) δ 1.04-1.23 (2H, m), 1.30-1.96 (20H, m), 1.96-2.20 (3H, m), 2.33-2.48 (1H, m), 2.48-2.69 (2H, m), 3.58-3.72 (1H, m), 3.89-4.03 (1H, m), 4.03-4.15 (1H, m), 5.01 (1H, br s), 5.61 (1H, br peak), 6.71 (1H, br peak), 7.64 (1H, d, J=15 Hz), 7.86 (1H, s), 8.03 (1H, s), 8.28 (1H, br peak);

MS (ES+) m/z 458.

Preparation 348

(2E)-3-(5-{[(3R)-1-(2-phenylethyl)-3-piperidinyl]amino}-2-pyrazinyl)-N-(tetrahydro-2H-pyran-2-yloxy)acrylamide ¹H-NMR (300 MHz, CDCl₃) δ 1.35-1.96 (16H, m), 2.17-2.35 (1H, m), 2.43-2.88 (7H, m), 3.60-3.72 (1H, m), 3.90-4.04 (1H, m), 4.11 (1H, br. peak), 5.01 (1H, br s), 5.38-5.55 (1H, m), 6.70 (1H, br peak), 7.15-7.38 (5H, m), 7.51 (1H, d, J=15 Hz), 7.75 (1H, s), 8.01 (1H, s), 8.34 (1H, br peak);

MS (ES+) m/z 452.

Preparation 349

(2E)-3-(5-{[(3R)-1-cycloheptyl-3-piperidinyl]amino}-2-pyrazinyl)-N-(tetrahydro-2H-pyran-2-yloxy)acrylamide ¹H-NMR (300 MHz, CDCl₃) δ 1.30-1.96 (21H, m), 2.35-2.46 (1H, m), 2.46-2.70 (4H, m), 3.59-3.70 (1H, m), 3.86-4.01 (1H, m), 4.05 (1H, br peak), 5.02 (1H, br s), 5.61-5.74 (1H, m), 6.65 (1H, br peak), 7.63 (1H, d, J=15 Hz), 7.88 (1H, s), 8.02 (1H, s), 8.34 (1H, br peak);

MS (ES+) m/z 444.

Preparation 350 tert-butyl [(3R)-1-(1-adamantylmethyl)-3-pyrrolidinyl](5-{(1E)-3-oxo-3-[(tetrahydro-2H-pyran-2-yloxy)amino]-1-propen-1-yl}-2-pyridinyl)carbamate ¹H-NMR (300 MHz, CDCl₃) δ 1.18-2.40 (36H, m), 2.64 (1H, br peak), 2.87 (1H, br peak), 3.63-3.76 (1H, m), 3.91-4.10 (1H, m), 4.86 (1H, br peak), 4.95-5.10 (1H, m), 6.41 (1H, br peak), 7.30 (1H, d, J=9 Hz), 7.59-7.90 (2H, m), 8.59 (1H, s);

MS (ES+) m/z 581.

Preparation 351

(2Z)-3-(6-{[(3R)-1-cyclohexyl-3-pyrrolidinyl]amino}-3-pyridinyl)-2-fluoro-N-(tetrahydro-2H-pyran-2-yloxy)acrylamide $^1$H-NMR (300 MHz, CDCl$_3$) δ 1.08-1.35 (6H, m), 1.45-1.99 (10H, m), 1.99-2.12 (1H, m), 2.25-2.41 (1H, m), 2.41-2.54 (1H, m), 2.71 (1H, dd, J=9.3, 2.5 Hz), 2.82 (1H, dd, J=9.8, 6.7 Hz), 2.89-3.01 (1H, m), 3.61-3.75 (1H, m), 3.94-4.06 (1H, m), 4.27-4.43 (1H, m), 4.99-5.06 (1H, m), 5.06-5.21 (1H, m), 6.37 (1H, d, J=8.8 Hz), 6.82 (1H, d, J=40.4 Hz), 7.72 (1H, dd, J=8.8, 2.1 Hz), 8.26 (1H, s);

MS (ES+) m/z 433.

Preparation 352

(2E)-3-(6-{[(3R)-1-(4-methylbenzyl)-3-piperidinyl]amino}-3-pyridinyl)-N-(tetrahydro-2H-pyran-2-yloxy)acrylamide $^1$H-NMR (300 MHz, CDCl$_3$) δ 1.40-1.95 (10H, m), 2.10-2.35 (4H, m), 2.35-2.66 (3H, m), 3.43 (1H, d, J=12.9 Hz), 3.50 (1H, d, J=12.9 Hz), 3.60-3.71 (1H, m), 3.86-4.03 (2H, m), 4.99 (1H, br peak), 5.40 (1H, br peak), 6.25 (1H, br peak), 6.36 (1H, d, J=8.7 Hz), 7.13 (1H, d, J=7.9 Hz), 7.20 (1H, d, J=7.9 Hz), 7.52-7.69 (2H, m), 8.14-8.35 (2H, m);

MS (ES+) m/z 451.

Preparation 353

(2E)-N-(tetrahydro-2H-pyran-2-yloxy)-3-(5-{[(3R)-1-(2-thienylmethyl)-3-piperidinyl]amino}-2-pyrazinyl)acrylamide $^1$H-NMR (300 MHz, CDCl$_3$) δ 1.50-1.96 (9H, m), 2.21-2.39 (1H, m), 2.39-2.55 (1H, m), 2.55-2.85 (2H, m), 3.59-3.70 (1H, m), 3.70 (1H, d, J=13.9 Hz), 3.80 (1H, d, J=13.9 Hz), 3.90-4.04 (1H, m), 4.06-4.20 (1H, m), 5.00 (1H, br s), 5.64 (1H, br peak), 6.68 (1H, br peak), 6.85-6.91 (1H, m), 6.95 (1H, dd, J=4.8, 3.5 Hz), 7.21-7.30 (1H, m), 7.63 (1H, d, J=15.1 Hz), 7.90 (1H, s), 8.02 (1H, s), 8.34 (1H, br peak);

MS (ES+) m/z 444.

Preparation 354

(2E)-3-(5-{[(3R)-1-(4-fluorobenzyl)-3-pyrrolidinyl]amino}-2-pyrazinyl)-N-(tetrahydro-2H-pyran-2-yloxy)acrylamide $^1$H-NMR (300 MHz, CDCl$_3$) δ 1.50-1.78 (4H, m), 1.78-1.95 (3H, m), 2.28-2.48 (2H, m), 2.60-2.72 (2H, m), 2.82-2.95 (1H, m), 3.60 (2H, s), 3.61-3.71 (1H, m), 3.90-4.04 (1H, m), 4.46 (1H, br peak), 5.01 (1H, br s), 5.21 (1H, d, J=7 Hz), 6.67 (1H, br peak), 7.00 (1H, dd, J=8.7, 8.7 Hz), 7.27 (1H, dd, J=8.4, 5.6 Hz), 7.61 (1H, d, J=15.1 Hz), 7.85 (1H, s), 8.03 (1H, s), 8.34 (1H, br peak);

MS (ES+) m/z 442.

Preparation 355

(2E)-3-(6-{[(3R)-1-cyclohexyl-3-piperidinyl]amino}-3-pyridinyl)-N-(tetrahydro-2H-pyran-2-yloxy)acrylamide $^1$H-NMR (300 MHz, CDCl$_3$) δ 0.96-1.35 (7H, m), 1.35-1.95 (13H, m), 2.20-2.40 (1H, m), 2.40-2.67 (3H, m), 2.67-2.83 (1H, m), 3.60-3.72 (1H, m), 3.80-4.06 (2H, m), 4.99 (1H, br s), 5.30-5.51 (1H, m), 6.26 (1H, br peak), 6.39 (1H, d, J=8.7 Hz), 7.57 (1H, d, J=8.2 Hz), 7.62 (1H, d, J=15.0 Hz), 8.13-8.35 (1H, m);

MS (ES+) m/z 429.

Preparation 356 tert-butyl [(3R) 1-(cycloheptylmethyl)-3-pyrrolidinyl](5-{(1E)-3-oxo-3-[(tetrahydro-2H-pyran-2-yloxy)amino]-1-propen-1-yl}-2-pyridinyl)carbamate $^1$H-NMR (300 MHz, CDCl$_3$) δ 0.95-1.18 (2H, m), 1.18-1.93 (28H, m), 1.93-2.09 (1H, m), 2.09-2.38 (2H, m), 2.38-2.75 (2H, m), 2.75-2.95 (1H, m), 3.61-3.75 (1H, m), 3.89-4.06 (1H, m), 4.82-4.96 (1H, m), 4.96-5.09 (1H, m), 6.20-6.50 (1H, m), 7.29 (1H, d, J=8.4 Hz), 7.70 (1H, d, J=16.5 Hz), 7.78 (1H, dd, J=8.3, 2.6 Hz), 8.57 (1H, s);

MS (ES+) m/z 543.

Preparation 357

(2E)-3-(5-{[(3R)-1-(4-pyridinylmethyl)-3-piperidinyl]amino}-2-pyrazinyl)-N-(tetrahydro-2H-pyran-2-yloxy)acrylamide $^1$H-NMR (300 MHz, CDCl$_3$) δ 1.45-1.97 (10H, m), 2.20-2.36 (1H, m), 2.44-2.71 (3H, m), 3.52 (2H, s), 3.60-3.71 (1H, m), 3.88-4.04 (1H, m), 4.15 (1H, br peak), 5.02 (1H, br s), 5.43 (1H, br peak), 6.65 (1H, br peak), 7.20-7.31 (2H, m), 7.63 (1H, d, J=15.0 Hz), 7.90 (1H, s), 8.03 (1H, s), 8.39 (1H, br peak), 8.56 (2H, d, J=5.8 Hz);

MS (ES+) m/z 439.

Preparation 358

(2E)-N-(tetrahydro-2H-pyran-2-yloxy)-3-(5-{[(3R)-1-(3-thienylmethyl)-3-piperidinyl]amino}-2-pyrazinyl)acrylamide $^1$H-NMR (300 MHz, CDCl$_3$) δ 1.48-1.95 (10H, m), 2.18-2.34 (1H, m), 2.45-2.74 (3H, m), 3.51 (1H, d, J=13.5 Hz), 3.59 (1H, d, J=13.5 Hz), 3.61-3.71 (1H, m), 3.90-4.05 (1H, m), 4.05-4.15 (1H, m), 5.01 (1H, br s), 5.53 (1H, br peak), 6.66 (1H, br peak), 7.05 (1H, d, J=5.0 Hz), 7.10 (1H, d, J=2.3 Hz), 7.23-7.32 (1H, m), 7.62 (1H, d, J=15.0 Hz), 7.88 (1H, s), 8.02 (1H, s), 8.31 (1H, br peak);

MS (ES+) m/z 444.

Preparation 359

(2E)-3-(5-{[(3R)-1-(2,3-dihydro-1H-inden-2-yl)-3-piperidinyl]amino}-2-pyrazinyl)-N-(tetrahydro-2H-pyran-2-yloxy)acrylamide $^1$H-NMR (300 MHz, CDCl$_3$) δ 1.50-1.96 (10H, m), 2.25-2.45 (1H, m), 2.54-2.80 (3H, m), 2.80-2.98 (2H, m), 2.98-3.15 (2H, m), 3.20-3.35 (1H, m), 3.59-3.71 (1H, m), 3.90-4.04 (1H, m), 4.09-4.20 (1H, m), 5.02 (1H, br s), 5.59 (1H, br peak), 6.68 (1H, br peak), 7.10-7.30 (5H, m), 7.65 (1H, d, J=15.4 Hz), 7.91 (1H, s), 8.05 (1H, s), 8.34 (1H, br peak);

MS (ES+) m/z 464.

Preparation 360

(2Z)-2-fluoro-3-(6-{[(3R)-1-(4-methylbenzyl)-3-pyrrolidinyl]amino}-3-pyridinyl)-N-(tetrahydro-2H-pyran-2-yloxy)acrylamide $^1$H-NMR (300 MHz, CDCl$_3$) δ 1.52-1.98 (9H, m), 2.25-2.49 (5H, m), 2.60 (1H, dd, J=9.7, 3.1 Hz), 2.75 (1H, dd, J=9.7, 6.4 Hz), 2.78-2.90 (1H, m), 3.57 (1H, d, J=12.9 Hz), 3.64 (1H, d, J=12.9 Hz), 3.64-3.74 (1H, m), 3.93-4.08 (1H, m), 4.26-4.42 (1H, m), 5.00-5.07 (1H, m), 5.11 (1H, d, J=7.7 Hz), 6.35 (1H, d, J=8.8 Hz), 6.82 (1H, d, J=40.5% Hz), 7.13 (2H, d, J=7.9 Hz), 7.21 (2H, d, J=7.9 Hz), 7.71 (1H, dd, J=8.8, 2.2 Hz), 8.25 (1H, d, J=1.9 Hz); MS (ES+) m/z 455, 909.

Preparation 361

To a suspension of lithium aluminum hydride (70 mg, 1.8 mmol) in tetrahydrofuran (2 mL) was added a solution of ethyl 6-{[(3R)-1-benzyl-3-piperidinyl]amino}nicotinate (250 mg, 0.74 mmol) in tetrahydrofuran (5 mL) dropwise at 0° C. under nitrogen and the mixture was stirred at same temperature for 3 hrs. To the reaction mixture was added methanol and water dropwise at 0' and the mixture was stirred for 1 h. The precipitate was removed by vacuum filtration and the filtrate was evaporated in vacuo. The residue was partitioned between water and ethyl acetate. The organic layer was separated, washed with brine, dried over magnesium sulfate, and evaporated in vacuo to give (6-{[(3R)-1-benzyl-3-piperidinyl]amino}-3-pyridinyl)methanol (219 mg, 100%) as an oil.

MS (ES+) m/z 298.

The following compound was obtained in a similar manner to that of Preparation 361.

Preparation 362

(6-{[(3S)-1-(cyclohexylmethyl)-3-piperidinyl]amino}-3-pyridinyl)methanol $^1$H-NMR (300 MHz, CDCl$_3$) δ 0.75-0.95 (2H, m), 1.06-1.31 (3H, m), 1.38-1.85 (10H, m), 2.00-2.14 (2H, m), 2.14-2.30 (1H, m), 2.30-2.59 (3H, m), 3.80-3.93 (1H, m), 4.52 (2H, s), 5.11 (1H, br peak), 6.40 (1H, d, J=8.6 Hz), 7.46 (1H, dd, J=8.5, 2.3 Hz), 8.04 (1H, d, J=2.3 Hz).

Preparation 363

To a solution of 6-{[(3R)-1-benzyl-3-piperidinyl]amino}nicotinaldehyde (110 mg, 0.37 mmol) in tetrahydrofuran (4 mL) was added (carbethoxymethylene)triphenylphosphorane (260 mg, 0.75 mmol) and the mixture was stirred at ambient temperature for 18 hrs. The reaction mixture was evaporated in vacuo and the residue was partitioned between water and EtOAc. The organic layer was separated, washed water and brine, dried over magnesium sulfate, and evaporated in vacuo. The residue was purified by preparative thin layer chromatography (chloroform-MeOH=15-1) to give ethyl (2E)-3-(6-{[(3R)-1-benzyl-3-piperidinyl]amino}-3-pyridinyl)acrylate (77 mg, 57%) as an oil.

$^1$H-NMR (300 MHz, CDCl$_3$) δ 1.19-1.40 (3H, m), 1.49-1.82 (4H, m), 2.19-2.36 (1H, m), 2.36-2.68 (3H, m), 3.40-3.5.9 (2H, m), 4.06-4.40 (3H, m), 5.40 (1H, br peak), 6.19 (1H, d, J=15.8 Hz), 6.38 (1H, d, J=8.1 Hz), 7.19-7.40 (5H, m), 7.40-7.75 (2H, m), 8.16 (1H, s);

MS (ES+) m/z 366.

The following compounds were obtained in a similar manner to that of Preparation 363.

Preparation 364 ethyl (2E)-3-(6-{[(3R)-1-(cyclohexylmethyl)-3-pyrrolidinyl]amino}-3-pyridinyl)-2-methylacrylate $^1$H-NMR (300 MHz, CDCl$_3$) δ 0.80-0.97 (2H, m), 1.11-1.28 (4H, m), 1.34 (3H, t, J=7.1 Hz), 1.37-1.52 (1H, m), 1.60-1.85 (5H, m), 2.13 (3H, d, J=1.4 Hz), 2.19-2.41 (4H, m), 2.57 (1H, dd, J=10, 3 Hz), 2.69 (1H, dd, J=10, 6 Hz), 2.81 (1H, dt, J=8, 4 Hz), 4.20-4.38 (3H, m), 5.04 (1H, d, J=7.7 Hz), 6.39 (1H, d, J=8.7 Hz), 7.53 (1H, s), 7.56 (1H, dd, J=8.7, 2.3 Hz), 8.21 (1H, d, J=2.3 Hz);

MS (ES+) m/z 372.

Preparation 365 ethyl (2E)-3-(6-{[(3S)-1-(cyclohexylmethyl)-3-piperidinyl]amino}-3-pyridinyl)acrylate $^1$H-NMR (300 MHz, CDCl$_3$) δ 0.78-0.96 (2H, m), 1.06-1.40 (5H, m), 1.40-1.84 (11H, m), 2.00-2.25 (3H, m), 2.38-2.64 (3H, m), 3.96 (1H, br peak), 4.25 (2H, q, J=7.1 Hz), 5.49 (1H, br peak), 6.21 (1H, d, J=15.9 Hz), 6.39 (1H, d, J=8.8 Hz), 7.57 (1H, d, J=15.9 Hz), 7.61 (1H, dd, J=8.7, 2.4 Hz), 8.19 (1H, d, J=2.2 Hz).

Preparation 366

To a solution of tert-butyl (3R)-3-({3-chloro-5-[(1Z)-3-ethoxy-2-fluoro-3-oxo-1-propen-1-yl]-2-pyridinyl}amino)-1-piperidinecarboxylate (3.3 g) in EtOH (19.3 ml) was added solution of 4N HCl in dioxane (19.3 ml) at ambient temperature and the mixture was stirred at same temperature for 1.5 hr. Diisopropylether was added to the mixture and precipitate was collected by filtration to give ethyl (2Z)-3-{5-chloro-6-[(3R)-3-piperidinylamino]-3-pyridinyl)-2-fluoroacrylate dihydrochloride (2.98 g).

$^1$H-NMR(DMSO-d$_6$): δ 1.29(3H, t, J=7.2 Hz), 1.61-1.97(4H, m), 2.70-2.81(1H, m), 2.88-2.99(1H, m), 3.13-3.22(1H, m), 3.23-3.31(1H, m), 4.28(2H, q, J=7.2 Hz), 4.42-4.51(1H, m), 7.03(1H, d, J=37.6 Hz), 7.96(1H, d, J=1.9 Hz), 8.37(1H, d, J=1.9 Hz), (+)ESI-MS: 328(M+H)+.

The following compounds were obtained in a similar manner to that of Preparation 366.

Preparation 367 ethyl (2E)-3-{6-[(3R)-3-piperidinylamino]-3-pyridinyl}acrylate dihydrochloride $^1$H-NMR (300 MHz, DMSO-d$_6$) δ 1.25 (3H, t, J=7.1 Hz), 1.54-1.68 (1H, m), 1.68-1.86 (1H, m), 1.86-2.11 (2H, m), 2.84-3.02 (2H, m), 3.10-3.23 (1H, m), 3.23-3.44 (1H, m), 4.10-4.30 (3H, m), 6.55 (1H, d, J=16.0 Hz), 7.00 (1H, d, J=8.9 Hz), 7.63 (1H, d, J=16.1 Hz), 8.21 (1H, d, J=8.9 Hz), 8.31 (1H, d, J=1.7 Hz), 8.80-9.15 (2H, m), 9.26-9.43 (1H, m).

Preparation 368 ethyl (2Z)-2-fluoro-3-{6-[(3R)-3-pyrrolidinylamino]-3-pyridinyl}acrylate dihydrochloride $^1$H-NMR (300 MHz, DMSO-d$_6$) δ 1.29 (3H, t, J=7.1 Hz), 1.93-2.09 (1H, m), 2.20-2.40 (1H, m), 3.12-3.60 (4H, m), 4.28 (2H, q, J=7.1 Hz), 4.60 (1H, br peak), 6.99 (1H, d, J=9.2

Hz), 7.10 (1H, d, J=37.3 Hz), 8.05 (1H, d, J=9.2 Hz), 8.34 (1H, s), 9.10 (1H, br peak), 9.45 (2H, br peak);

MS (ES+) m/z 280.

Preparation 369 ethyl (2Z)-2-fluoro-3-{6-[(3R)-3-piperidinylamino]-3-pyridinyl}acrylate dihydrochloride $^1$H-NMR(DMSO-d$_6$): δ 1.30(3H, t, J=7.0 Hz), 1.59-1.69(1H, m), 1.74-1.84(1H, m), 1.89-1.99(1H, m), 2.00-2.08(1H, m), 2.89-3.04(2H, m), 3.11-3.20(1H, m), 3.34-3.44(1H, m), 4.24-4.36(3H, m), 7.16(1H, d, J=36.8 Hz), 7.18(1H, d, J=9.2 Hz), 8.14(1H, d, J=9.2 Hz), 8.34(1H, s), 9.13-9.73(3H, m), (+)ESI-MS: 294(M+H)+.

Preparation 370

To a solution of ethyl 6-{[(3R)-1-benzyl-3-piperidinyl]amino}-5-chloronicotinate (6.75 g, 18.1 mmol) in ethanol (200 mL) were added ammonium formate (6.83 g, 108 mmol) and 10% Pd/C (20% w/w, 1.2 g) at ambient temperature and the mixture was heated to reflux with stirring for 8 hrs. After cooling, the catalyst in the reaction mixture was removed by filtration. The solvent was evaporated in vacuo. The residue was purified by silica gel column chromatography (NH, CHCl$_3$ only-CHCl$_3$:MeOH/50:1~25:1) to give ethyl 6-[(3R)-3-piperidinylamino]nicotinate (4.5 g, 100%) as an oil.

$^1$H-NMR (300 MHz, CDCl$_3$) δ 1.36 (3H, t, J=7.1 Hz), 1.40-1.67 (3H, m), 1.67-1.83 (1H, m), 1.83-1.99 (1H, m), 2.65 (1H, dd, J=11.6, 7.0 Hz), 2.70-2.81 (1H, m), 2.81-2.93 (1H, m), 3.16 (1H, dd, J=11.4, 3.3 Hz), 3.77-3.92 (1H, m), 4.33 (2H, q, J=7.1 Hz), 5.29 (1H, br d, J=7.1 Hz), 6.37 (1H, d, J=8.9 Hz), 7.97 (1H, dd, J=8.8, 2.3 Hz), 8.74 (1H, d, J=2.3 Hz);

MS (ES+) m/z 250.

The following compound was obtained in a similar manner to that of Preparation 370.

Preparation 371 ethyl 6-{[(3S)-1-(cyclohexylmethyl)-3-piperidinyl]amino}nicotinate $^1$H-NMR (300 MHz, CDCl$_3$) δ 0.77-0.97 (2H, m), 1.05-1.30 (3H, m), 1.36 (3H, t, J=7.1 Hz), 1.40-1.86 (10H, m), 1.97-2.25 (3H, m), 2.37-2.64 (3H, m), 3.84-4.08 (1H, m), 4.30 (2H, q, J=7.1 Hz), 5.59 (1H, br peak), 6.35 (1H, d, J=8.4 Hz), 7.97 (1H, dd, J=8.6, 2.0 Hz), 8.74 (1H, d, J=2.0 Hz).

Preparation 372

1) To a mixture of tert-butyl (3R)-3-pyrrolidinylcarbamate (1.00 g), 2,3-dimethylbenzaldehyde (720 mg), N,N-diisopropylethylamine (1.87 mL), and ethanol (10 mL) was added sodium triacetoxyborohydride (2.28 g). After stirring for 3 hours at room temperature, the reaction mixture was partitioned between ethyl acetate and saturated NH$_4$Cl. The organic layer was washed with H$_2$O, dried over MgSO$_4$, filtered, and evaporated in vacuo.

2) To a mixture of above product and ethyl acetate (10 mL) was added 4N hydrogen chloride in ethyl acetate (8.40 mL) at 4° C. After stirring at room temperature for 5 hours, the reaction mixture was neutrized with saturated NaHCO$_3$. The resulting mixture was evaporated in vacuo. The residue was added chloroform, dried over Na$_2$SO$_4$, filtered, and evaporated in vacuo to give (3R)-1-(2,3-dimethylbenzyl)-3-pyrrolidinamine (193 mg).

$^1$H-NMR (300 MHz, CDCl$_3$) δ 1.41-1.53 (1H, m), 2.12-2.46 (3H, m), 2.27 (3H, s), 2.29 (3H, s), 2.64-2.77 (2H, m), 3.42-3.51 (1H, m), 3.58 (2H, s), 7.00-7.14 (3H, m),

MS (ES+) m/z 205 (M+1).

Preparation 373

To a suspension of sodium hydride (60%, 208 mg, 5.2 mmol) in tetrahydrofuran (2 mL) was added a solution of ethyl (diethoxyphosphoryl)(fluoro)acetate (1.26 g, 5.2 mmol) in tetrahydrofuran (5 mL) dropwise at 0° C. and the mixture was stirred at same temperature for 1 hr. To the mixture was added a solution of 6-{[(3R)-1-(cyclohexylmethyl)-3-pyrrolidinyl]amino}nicotinaldehyde (1.0 g, 3.5 mmol) in tetrahydrofuran (10 mL) dropwise at 0° C. and the mixture was stirred at same temperature for 4 hrs. The reaction mixture was evaporated in vacuo and the residue was partitioned between water and EtOAc. The organic layer was separated, washed water and brine, dried over magnesium sulfate, and evaporated in vacuo to a mixture of ethyl (2Z)-3-(6-{[(3R)-1-(cyclohexylmethyl)-3-pyrrolidinyl]amino}-3-pyridinyl)-2-fluoroacrylate and ethyl (2E)-3-(6-{[(3R)-1-(cyclohexylmethyl)-3-pyrrolidinyl]amino}-3-pyridinyl)-2-fluoroacrylate (1:1) as an oil.

$^1$H-NMR (300 MHz, CDCl$_3$) δ 0.80-1.00 (2H, m), 1.10-1.51 (9H, m), 1.51-1.85 (4H, m), 2.15-2.40 (4H, m), 2.51-2.61 (1H, m), 2.61-2.72 (1H, m), 2.72-2.86 (1H, m), 4.20-4.40 (3H, m), 5.11 (1H, br d, J=8.4 Hz), 6.39 (1H, d, J=8.8 Hz), 6.80 (1H, d, J=36.3 Hz), 8.03 (1H, dd, J=9.2, 2.6 Hz), 8.25 (1H, d, J=2.6 Hz).

Preparation 374

To a solution of ethyl 6-[(3R)-3-piperidinylamino]nicotinate (3.9 g, 15.6 mmol) in ethanol (40 mL) was added di-tert-butyl dicarbonate (3.76 g, 17.2 mmol) at ambient temperature and the mixture was stirred at same temperature for 18 hrs. The reaction mixture was evaporated in vacuo and the residue was partitioned between water and EtOAc. The organic layer was separated, washed water and brine, dried over magnesium sulfate, and evaporated in vacuo. The residue was purified by silica gel column chromatography (hexane:EtOAc/1:1) to give ethyl 6-{[(3R)-1-(tert-butoxycarbonyl)-3-piperidinyl]amino}nicotinate (5.4 g, 99%) as an oil.

$^1$H-NMR (300 MHz, CDCl$_3$) δ 1.37 (3H, t, J=7.1 Hz), 1.44 (9H, s), 1.51-1.82 (2H, m), 1.90-2.06 (1H, m), 3.09-3.36 (2H, m), 3.48-3.60 (1H, m), 3.70-3.91 (2H, m), 4.33 (2H, q, J=7.1 Hz), 4.39-5.03 (1H, m), 6.40 (1H, d, J=8.8 Hz), 8.01 (1H, dd, J=8.7, 2.3 Hz), 8.75 (1H, d, J=2.2 Hz);

MS (ES+) m/z 350.

Preparation 375

To a solution of ethyl (2E)-3-{6-[(3R)-3-piperidinylamino]-3-pyridinyl}acrylate dihydrochloride (300 mg, 0.86 mmol) in DMF (4 mL) were added triethylamine (349 mg, 3.45 mmol) and 4-chlorobenzoyl chloride (181 mg, 1.03 mmol) at 0° C. under nitrogen and the mixture was stirred at same temperature for 1 hr and at ambient temperature for 2 hrs. The reaction mixture was poured into water and extracted with EtOAc. The organic layer was separated, washed water and brine, dried over magnesium sulfate, and evaporated in vacuo. The residue was purified by preparative thin layer chromatography (hexane-EtOAc=1-1) to give ethyl (2E)-3-(6-{[(3R)-1-(4-chlorobenzoyl)-3-piperidinyl]amino}-3-pyridinyl)acrylate (270 mg, 76%) as an amorphous powder.

$^1$H-NMR (300 MHz, DMSO-d$_6$) δ 1.24 (3H, t, J=7.1 Hz), 1.41-1.76 (2H, m), 1.76-2.07 (2H, m), 2.78-3.49 (3H, m), 3.49-4.46 (4H, m), 6.33 (1H, d, J=15.9 Hz), 6.44-6.60 (1H, m), 7.08-7.28 (1H, m), 7.28-7.59 (5H, m), 7.70-7.87 (1H, m), 8.00-8.32 (1H, m);

MS (ES+) m/z 414.

Preparation 376

The mixture of ethyl (2E)-5-chloro-4-oxo-2-pentenoate (0.8 g) and 1-[(3R)-1-(cyclohexylmethyl)-3-pyrrolidinyl]thiourea (1.09 g) in CH$_3$CN (16 mL) was stirred at 70° C. for 2 hrs. To the reaction mixture was added an AcOEt (32 mL) and isolated precipitate was collected by filtration to give ethyl (2E)-3-(2-{[(3R)-1-(cyclohexylmethyl)-3-pyrrolidinyl]amino}thiazol-4-yl)acrylate hydrochloride (1.10 g).

$^1$H-NMR(DMSO-d$_6$): δ 0.80-1.36(6H, m), 1.24(3H, t, J=7.1 Hz), 1.52-2.56(8H, m), 2.92-4.06(5H, m), 4.16(2H, q, J=7.1 Hz), 4.31-4.61(1H, m), 6.38 and 6.40(total 1H, each d, J=each 15.3 Hz), 7.24(1H, s), 7.36(1H, d, J=15.3 Hz), 8.26-8.45(1H, m), 10.51(1H, s)

(+)ESI-MS: 364(M+H)+.

Preparation 377

A mixture of 5-bromo-2-pyrazinecarboxylic acid (650 mg) in thionyl chloride (2.35 ml) was stirred under reflux condition.

After 3 hrs, the reaction mixture was evaporated.

To this residue in tetrahydrofuran (10 ml) was added sodium borohydride (465 mg) under ice cooling.

The mixture was quenched with water and extracted with ethyl acetate (three times).

The combined organic layer was washed with water, dried over Na$_2$SO$_4$, filtered and evaporated to give 230 mg (39%) of (5-bromo-2-pyridinyl)methanol as an oil.

MASS (ESI+,): 210.1, 211.0 (M+Na).

$^1$H-NMR (400 MHz, CDCl$_3$): δ 4.73 (2H, s), 7.20 (1H, d, J=8.2 Hz), 7.82 (1H, dd, J=8.2 and 1.8 Hz), 8.63 (1H, d, J=1.8 Hz).

Preparation 378

A mixture of (5-bromo-2-pyridinyl)methanol (200 mg), ethyl (triphenylphosphoranylidene)acetate (408 mg) and manganese oxide (370 mg) in dioxane (5 ml) was stirred at 60° C. for 5 hrs.

After cooling, the reaction mixture was filtered.

Filtrate was evaporated.

The residue was column chromatographed on silica gel to give 150 mg (55%) of ethyl (2E)-3-(5-bromo-2-pyridinyl}acrylate as a solid.

MASS (ESI+): m/z 258.1(M+1), 259.0 (M+2).

$^1$HNMR (400 MHz, CDCl$_3$): δ 1.34 (3H, t, J=7.1 Hz), 4.28 (2H, q, J=7.1 Hz), 6.91 (1H, d, J=15.5 Hz), 7.31 (1H, d, J=8.3 Hz), 7.62 (1H, d, J=15.5 Hz), 7.84 (1H, dd, J=8.3 and 2.2 Hz), 8.69 (1H, d, J=2.2 Hz).

Preparation 379

To a solution of ethyl 5,6-dichloronicotinate (10.0 g) and N,N-diisopropylethylamine (17.4 mL) in 1,3-dimethyl-2-imidazolidinone (100 mL) was added tert-butyl (3R)-3-amino-1-piperidinecarboxylate (10.9) at ambient temperature and the mixture was stirred at 100° C. for 9 hr. The reaction mixture was poured into a mixture of AcOEt and water. The separated organic layer was added ice-water and the mixture was adjusted to pH 3.5 with 1N-HCl. The separated organic layer was washed with water, dried over magnesium sulfate and evaporated in vacuo to give ethyl 6-{[(3R)-1-(tert-butoxycarbonyl)-3-piperidinyl]amino}-5-chloronicotinate (16.74 g).

$^1$H-NMR(DMSO-d$_6$): δ 1.26-1.51(10H, m), 1.30(3H, t, J=7.1 Hz), 1.60-1.71(2H, m), 1.83-1.95(1H, m), 2.78-3.25(2H, m), 3.56-4.12(3H, m), 4.27(2H, q, J=7.1 Hz), 6.82(1H, s), 7.96 (1H, d, J=1.9 Hz), 8.56(1H, d, J=1.9 Hz), (+)ESI-MS: 384(M+H)+, 406(M+Na)+.

Preparation 380

0.94 M solution of diisobutylaluminium hydride in hexane (139 ml) was added to dropwise a solution of ethyl 6-{[(3R)-1-(tert-butoxycarbonyl)-3-piperidinyl]amino}-5-chloronicotinate (16.7 g) in THF (250 ml) with stirred at −5 to 0° C. under atmospheric pressure of nitrogen, and the reaction mixture was stirred at 0° C. for 1.5 hr. To the reaction mixture was added MeOH (26.4 ml) was stirred at 0 to 10 for 20 minutes. The potassium sodium tartarate tetrahydrate (36.8 g) was added to a above solution and the resultant mixture was stirred at ambient temperature for 3 hours. The reaction mixture was filtrated and the filtrate was evaporated in vacuo. The residue was chromatographed on silicagel eluting with solution of CHCl$_3$ and AcOEt (3:2). The eluted fractions containing the desired product were collected and evaporated in vacuo to give tert-butyl tert-butyl (3R)-3-{[3-chloro-5-(hydroxymethyl)-2-pyridinyl]amino}-1-piperidinecarboxylate (10.29 g).

(+)ESI-MS: 342(M+H)+, 364(M+Na)+

$^1$H-NMR(DMSO-d$_6$): δ 1.24-1.48(10H, m), 1.59-1.71(2H, m), 1.82-1.92(1H, m), 2.75-3.14(2H, m), 3.53-3.96(3H, m), 4.33(2H, d, J=5.6 Hz), 5.08(1H, t, J=5.6 Hz), 5.82(1H, s), 7.56(1H, d, J=2.0 Hz), 7.93(1H, d, J=2.0 Hz).

The following compound was obtained in a similar manner to that of Preparation 380.

Preparation 381 tert-butyl (3R)-3-{[5-(hydroxymethyl)-2-pyridinyl]amino}-1-piperidinecarboxylate $^1$H-NMR (300 MHz, CDCl$_3$) δ 1.44 (9H, s), 1.50-1.66 (3H, m), 1.66-1.81 (1H, m), 1.89-2.07 (1H, m), 2.90-3.30 (2H, m), 3.52-3.66 (1H, m), 3.66-3.78 (1H, m), 3.78-4.03 (1H, m), 4.44-4.61 (3H, m), 6.44 (1H, d, J=9.1 Hz), 7.49 (1H, dd, J=8.5, 2.4 Hz), 8.06 (1H, d, J=2.1 Hz);

MS (ES+) m/z 308.

Preparation 382

A mixture of tert-butyl (3R)-3-{[3-chloro-5-(hydroxymethyl)-2-pyridinyl]amino}-1-piperidinecarboxylate (10.0 g) and MnO$_2$ (25.4 g) in CHCl$_3$ (200 ml) was stirred at 60° C. for 3.5 hours. After removal of the insoluble material, and the solvent was evaporated in vacuo to give tert-butyl (3R)-3-[(3-chloro-5-formyl-2-pyridinyl)amino]-1-piperidinecarboxylate (9.08 g).

$^1$H-NMR(DMSO-d$_6$): δ 1.24-1.52 (10H, m), 1.63-1.81(2H, m), 1.85-1.95(1H, m), 2.79-3.21(2H, m), 3.59-4.00(2H, m), 4.04-4.16(1H, m), 7.08(1H, s), 7.96(1H, d, J=1.9 Hz), 8.56 (1H, d, J=1.9 Hz), 9.76(1H, s), (+)ESI-MS: 340(M+H)+.

The following compounds were obtained in a similar manner to that of Preparation 382.

Preparation 383

6-{[(3R)-1-benzyl-3-piperidinyl]amino}nicotinaldehyde

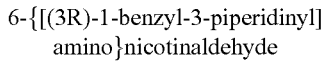

¹H-NMR (300 MHz, CDCl₃) δ 1.44-2.38 (5H, m), 2.38-2.71 (3H, m), 3.41-3.60 (2H, m), 4.00-4.40 (1H, m), 6.41 (1H, d, J=8.8 Hz), 7.13-7.41 (5H, m), 7.86 (1H, d, J=8.8 Hz), 8.46 (1H, s), 9.74 (1H, s);

MS (ES+) m/z 296.

Preparation 384

6-{[(3R)-1-(cyclohexylmethyl)-3-piperidinyl]amino}nicotinaldehyde

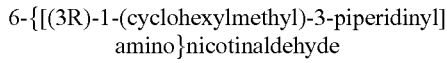

¹H-NMR (300 MHz, CDCl₃) δ 0.76-0.95 (2H, m), 1.06-1.331 (3H, m), 1.39-1.85 (10H, m), 2.00-2.20 (3H, m), 2.31-2.49 (1H, m), 2.49-2.70 (2H, m), 3.92-4.20 (1H, m), 5.88 (1H, br peak), 6.42 (1H, d, J=8.8 Hz), 7.88 (1H, dd, J=8.5, 1.7 Hz), 8.50 (1H, d, J=2.2 Hz), 9.75 (1H, s);

MS (ES+) m/z 302.

Preparation 385

6-{[(3S)-1-(cyclohexylmethyl)-3-piperidinyl]amino}nicotinaldehyde

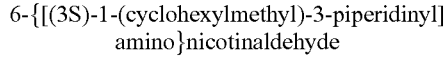

¹H-NMR (300 MHz, CDCl₃) δ 0.77-0.97 (2H, m), 1.07-1.32 (3H, m), 1.40-1.84 (10H, m), 2.00-2.23 (3H, m), 2.34-2.68 (3H, m), 4.02 (1H, br peak), 5.87 (1H, br peak), 6.42 (1H, d, J=8.8 Hz), 7.87 (1H, d, J=8.8 Hz), 8.49 (1H, d, J=1.9 Hz), 9.75 (1H, s);

MS (ES+) m/z 302.

Preparation 386

The mixture of ethyl (diethoxyphosphoryl)(fluoro)acetate (2.51 mL), MgBr₂ (2.73 g), Et₃N (1.89 mL) in THF (45 mL) was stirred at 3-5° C. for 1 hr and to the mixture was dropwise added a solution of tert-butyl (3R)-3-[(3-chloro-5-formyl-2-pyridinyl)amino]-1-piperidinecarboxylate (3.0 g) in THF (21 mL) at 3-5° C. The reaction mixture was stirred at same temperature for 2.5 hrs. The reaction mixture was poured into a mixture of AcOEt and ice-water and the mixture was adjusted to pH 3.5 with 1N-HCl. The separated organic layer was washed with water, dried over magnesium sulfate and evaporated in vacuo. The residue was purified by column chromatography on silica gel using a mixture of AcOEt and hexane (1:2 v/v) as an eluant. The eluted fractions containing the desired product were collected and evaporated in vacuo to give tert-butyl (3R)-3-({3-chloro-5-[(1Z)-3-ethoxy-2-fluoro-3-oxo-1-propen-1-yl]-2-pyridinyl}amino)-1-piperidinecarboxylate (3.38 g).

¹H-NMR(DMSO-d₆): δ 1.25-1.48(10H, m), 1.29(3H, t, J=7.1 Hz), 1.64-1.75(2H, m), 1.84-1.93(1H, m), 2.77-3.20(2H, m), 3.57-4.07(3H, m), 4.27(2H, q, J=7.1 Hz), 6.60(1H, s), 7.01 (1H, d, J=37.5 Hz), 7.94(1H, d, J=1.8 Hz), 8.36(1H, d, J=1.8 Hz), (+)ESI-MS: 428(M+H)+.

The following compounds were obtained in a similar manner to that of Preparation 386.

Preparation 387

(3R)-3-({5-[(1Z)-3-ethoxy-2-fluoro-3-oxo-1-propen-1-yl]-2-pyridinyl}amino)-1-pyrrolidinecarboxylate

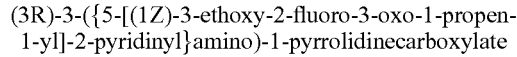

¹H-NMR (300 MHz, CDCl₃) δ 1.38 (3H, t, J=7.1 Hz), 1.47 (9H, s), 1.93 (1H, br peak), 2.16-2.33 (1H, m), 3.15-3.39 (1H, m), 3.39-3.59 (2H, m), 3.74 (1H, dd, J=11.3, 6.0 Hz), 4.35 (2H, q, J=7.1 Hz), 4.43 (1H, br peak), 7.77-4.90 (1H, m), 6.43 (1H, d, J=8.8 Hz), 6.80 (1H, d, J=36.1 Hz), 7.83 (1H, dd, J=8.8, 2.1 Hz), 8.26 (1H, s);

MS (ES+) m/z 380.

Preparation 388 tert-butyl (3R)-3-({5-[(1Z)-3-ethoxy-2-fluoro-3-oxo-1-propen-1-yl]-2-pyridinyl}amino)-1-piperidinecarboxylate

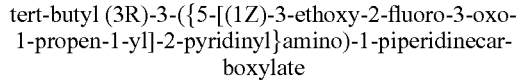

(+)ESI-MS: 394(M+H)+

Preparation 389

To a solution of ethyl (2E)-3-(5-chloro-2-pyrazinyl)acrylate (416 mg) in DMF (10 mL) was added (3R)-1-cyclohexyl-3-pyrrolidinamine dihydrochloride (849 mg) and K₂CO₃ (1.35 g). After stirring for 2 hours at 120° C., the reaction mixture was partitioned between ethyl acetate and H₂O. The organic layer was washed with H₂O, dried over MgSO₄, filtered, and evaporated in vacuo. The residue was purified by column chromatography on silica gel to give ethyl (2E)-3-(5-{[(3R)-1-cyclohexyl-3-pyrrolidinyl]amino}-2-pyrazinyl)acrylate (318 mg).

¹H-NMR (300 MHz, CDCl₃) δ 1.11-1.34 (6H, m), 1.32 (3H, t, J=7 Hz), 1.57-2.09 (6H, m), 2.30-2.44 (2H, m), 2.67-2.74 (1H, m), 2.78-2.84 (1H, m), 2.98-3.06 (1H, m), 4.25 (2H, q, J=7 Hz), 4.39-4.50 (1H, m), 5.32 (1H, d, J=8 Hz), 6.68 (1H, d, J=16 Hz), 7.57 (1H, d, J=16 Hz), 7.88 (1H, d, J=1 Hz), 8.06 (1H, d, J=1 Hz).

MS (ES+) m/z 345 (M+1).

Preparation 390

The mixture of ethyl (2E)-3-(5-{[(3R)-1-(3-chlorobenzyl)-3-piperidinyl]amino}-2-pyrazinyl)acrylate (235 mg, 0.59 mmol) and 1N-NaOH (1.2 mL) in EtOH (2 mL) was stirred at ambient temperature for 1 hr and the mixture was allowed to stand for 18 hrs. The reaction mixture was adjusted to PH 5.0 with 1 mol/L hydrochloric acid and evaporated in vacuo to give (2E)-3-(5-{[(3R)-1-(3-chlorobenzyl)-3-piperidinyl]amino}-2-pyrazinyl)acrylic acid (218 mg, 100%).

¹H-NMR (300. MHz, DMSO-d₆) δ 1.21-1.40 (1H, m), 1.40-1.60 (1H, m), 1.60-1.77 (1H, m), 1.77-1.90 (1H, m), 1.90-2.15 (2H, m), 2.53-2.90 (2H, m), 3.35-3.60 (2H, m), 3.90-4.03 (1H, m), 6.45 (1H, d, J=15.5 Hz), 7.24-7.40 (4H, m), 7.46 (1H, d, J=7.9 Hz), 7.98 (1H, s), 8.10 (1H, s);

MS (ES+) m/z 373, 375.

The following compounds were obtained in a similar manner to that of Preparation 390.

Preparation 391

(2E)-3-(6-{[(3R)-1-(cyclohexylmethyl)-3-piperidinyl]amino}-3-pyridinyl)acrylic acid

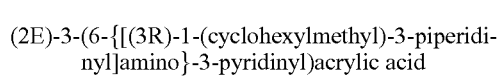

¹H-NMR (300 MHz, DMSO-d₆) 0.74-1.01 (2H, m), 1.01-1.34 (3H, m), 1.34-2.10 (10H, m), 2.59-3.65 (6H, m), 4.04-

4.45 (1H, m), 6.26 (1H, d, J=16.9 Hz), 6.55 (1H, d, J=8.7 Hz), 7.28 (1H, br peak), 7.47 (1H, d, J=15.8 Hz), 7.81 (1H, d, J=8.1 Hz), 8.21 (1H, s);

MS (ES+) m/z 344.

Preparation 392

(2E)-3-(6-{[(3S)-1-(cyclohexylmethyl)-3-piperidinyl]amino}-3-pyridinyl)acrylic acid $^1$H-NMR (300 MHz, DMSO-d$_6$) δ 0.78-1.05 (2H, m), 1.05-1.34 (3H, m), 1.34-2.11 (10H, m), 2.53-3.66 (6H, m), 3.94-4.41 (1H, m), 6.28 (1H, d, J=16.1 Hz), 6.55 (1H, d, J=8.8 Hz), 7.31 (1H, br peak), 7.48 (1H, d, J=15.4 Hz), 7.83 (1H, d, J=9.5 Hz), 8.24 (1H, s), 9.25 (1H, br peak).

Preparation 393

(2Z)-3-(6-{(tert-butoxycarbonyl)[(3R)-1-(cyclohexylmethyl)-3-pyrrolidinyl]amino}-3-pyridinyl)-2-fluoroacrylic acid $^1$H-NMR (300 MHz, DMSO-d$_6$) δ 0.81-1.03 (2H, m), 1.03-1.31 (3H, m), 1.39 (9H, s), 1.53-1.82 (6H, m), 1.90-2.08 (1H, m), 2.19-2.40 (1H, m), 2.79-3.00 (2H, m), 3.00-3.81 (4H, m), 5.10 (1H, br peak), 6.87 (1H, d, J=34.1 Hz), 7.41 (1H, d, J=8.4 Hz), 8.09 (1H, dd, J=8.1, 1.8 Hz), 8.15 (1H, s).

Preparation 394

(2E)-3-(6-{[(3R)-1-(cyclohexylcarbonyl)-3-piperidinyl]amino}-3-pyridinyl)acrylic acid $^1$H-NMR (300 MHz, DMSO-d$_6$) δ 0.83-2.04 (13H, m), 2.22-2.64 (2H, m), 2.94-3.20 (2H, m), 3.51-4.41 (3H, m), 6.24 (1H, d, J=15.9 Hz), 6.45-6.64 (1H, m), 7.03-7.28 (1H, m), 7.41-7.54 (1H, m), 7.74-7.85 (1H, m), 8.20 (1H, br s);

MS (ES+) m/z 358.

Preparation 395

(2E)-3-(5-{[(3R)-1-(2-chlorobenzyl)-3-piperidinyl]amino}-2-pyrazinyl)acrylic acid $^1$H-NMR (300 MHz, DMSO-d$_6$) δ 1.24-1.41 (1H, m), 1.45-1.65 (1H, m), 1.65-1.80 (1H, m), 1.80-1.95 (1H, m), 1.95-2.25 (2H, m), 2.56-2.76 (1H, m), 2.83-2.98 (1H, m), 3.59 (2H, s), 3.90-4.05 (1H, m), 6.45 (1H, d, J=15.5 Hz), 7.22-7.45 (3H, m), 7.50-7.60 (1H, m), 8.00 (1H, s), 8.11 (1H, s);

MS (ES+) m/z 373, 375.

Preparation 396

(2E)-3-(6-{[(3R)-1-(4-chlorobenzoyl)-3-piperidinyl]amino}-3-pyridinyl)acrylic acid $^1$H-NMR (300 MHz, DMSO-d$_6$) δ 1.43-2.09 (2H, m), 2.65-3.21 (1H, m), 3.54-3.95 (2H, m), 4.03-4.20 (1H, m), 4.39-4.44 (2H, m), 6.24 (1H, d, J=15.9 Hz), 6.45-6.60 (1H, m), 7.07-7.21 (1H, m), 7.29-7.60 (5H, m), 7.67-7.84 (1H, m), 7.94-8.27 (1H, m);

MS (ES+) m/z 386.

Preparation 397

A mixture of (2E)-3-(5-{[(3R)-1-(3-chlorobenzyl)-3-piperidinyl]amino}-2-pyrazinyl)acrylic acid (218 mg, 0.59 mmol), O-(tetrahydro-2H-pyran-2-yl)hydroxylamine (82 mg, 0.70 mmol), HOBt (103 mg, 0.76 mmol) and EDCI (146 mg, 0.76 mmol) in DMF (6 mL) was stirred at 0° C. for 1 hr and the mixture was stirred at ambient temperature for 18 hrs. The reaction mixture was evaporated in vacuo and the residue was partitioned between saturated sodium bicarbonate solution and EtOAc. The organic layer was separated, washed water and brine, dried over magnesium sulfate, and evaporated in vacuo. The residue was purified by silica gel column chromatography (chloroform-MeOH=95-5) to give (2E)-3-(5-{[(3R)-1-(3-chlorobenzyl)-3-piperidinyl]amino}-2-pyrazinyl)-N-(tetrahydro-2H-pyran-2-yloxy)acrylamide (251 mg, 91%) as an amorphous powder.

$^1$H-NMR (300 MHz, CDCl$_3$) δ 1.50-1.99 (10H, m), 2.19-2.36 (1H, m), 2.44-2.70 (3H, m), 3.45 (1H, d, J=13.4 Hz), 3.53 (1H, d, J=13.4 Hz), 3.58-3.74 (1H, m), 3.90-4.04 (1H, m), 4.04-4.20 (1H, m), 5.01 (1H, br s), 5.49 (1H, br peak), 6.70 (1H, br peak), 7.15-7.36 (4H, m), 7.64 (1H, d, J=15.2 Hz), 7.90 (1H, s), 8.03 (1H, s), 8.36 (1H, br peak);

MS (ES+) m/z 472.

The following compounds were obtained in a similar manner to that of Preparation 397.

Preparation 398

(2E)-3-(6-{[(3R)-1-(cyclohexylmethyl)-3-piperidinyl]amino}-3-pyridinyl)-N-(tetrahydro-2H-pyran-2-yloxy)acrylamide $^1$H-NMR (300 MHz, CDCl$_3$) δ 0.76-0.96 (3H, m), 1.08-1.32 (3H, m), 1.39-1.94 (15H, m), 1.98-2.25 (3H, m), 2.35-2.61 (3H, m), 3.59-3.62 (1H, m), 3.86-4.03 (2H, m), 5.00 (1H, br s), 5.46 (1H, br peak), 6.25 (1H, br peak), 6.37 (1H, d, J=8.7 Hz), 7.53-7.70 (2H, m), 8.22 (1H, d, J=2.0 Hz), 8.25 (1H, br peak);

MS (ES+) m/z 443.

Preparation 399

(2E)-3-(6-{[(3S)-1-(cyclohexylmethyl)-3-piperidinyl]amino}-3-pyridinyl)-N-(tetrahydro-2H-pyran-2-yloxy)acrylamide $^1$H-NMR (300 MHz, CDCl$_3$) δ 0.76-0.96 (3H, m), 1.08-1.32 (3H, m), 1.39-1.94 (15H, m), 1.98-2.25 (3H, m), 2.35-2.61 (3H, m), 3.59-3.62 (1H, m), 3.86-4.03 (2H, m), 5.00 (1H, br s), 5.46 (1H, br peak), 6.25 (1H, br peak), 6.37 (1H, d, J=8.7 Hz), 7.53-7.70 (2H, m), 8.22 (1H, d, J=2.0 Hz), 8.25 (1H, br peak);

MS (ES+) m/z 443.

Preparation 400 tert-butyl [(3R)-1-(cyclohexylmethyl)-3-pyrrolidinyl] (5-{(1Z)-2-fluoro-3-oxo-3-[(tetrahydro-2H-pyran-2-yloxy)amino]-1-propen-1-yl}-2-pyridinyl)carbamate $^1$H-NMR (300 MHz, CDCl$_3$) δ 0.66-0.93 (2H, m), 1.04-1.46 (18H, m), 1.48-2.06 (8H, m), 2.06-2.29 (3H, m), 2.36-2.71 (3H, m), 2.81-2.96 (1H, m), 3.60-3.75 (1H, m), 3.93-4.06 (1H, m), 4.78-4.95 (1H, m), 5.06 (1H, s), 6.96 (1H, d, J=39.2 Hz), 7.31 (1H, d, J=8.5 Hz), 7.92 (1H, dd, J=8.4, 2.3 Hz), 8.61 (1H, d, J=2.2 Hz);

MS (ES+) m/z 547.

Preparation 401

(2E)-3-(5-{[(3R)-1-(2-chlorobenzyl)-3-piperidinyl]amino}-2-pyrazinyl)-N-(tetrahydro-2H-pyran-2-yloxy)acrylamide $^1$H-NMR (300 MHz, CDCl$_3$) 1.48-1.95 (10H, m), 2.20-2.35 (1H, m), 2.54-2.80 (3H, m), 3.50-3.72 (3H, m), 3.89-4.04 (1H, m), 4.06-4.20 (1H, m), 5.00 (1H, br s), 5.71 (1H, br peak), 6.66 (1H, br peak), 7.16-7.28 (2H, m), 7.30-7.43 (2H, m), 7.62 (1H, d, J=15.1 Hz), 7.86 (1H, s), 8.00 (1H, s), 8.35 (1H, br peak);

MS (ES+) m/z 472.

Preparation 402

(2E)-3-(6-{[(3R)-1-(cyclohexylcarbonyl)-3-piperidinyl]amino}-3-pyridinyl)-N-(tetrahydro-2H-pyran-2-yloxy)acrylamide $^1$H-NMR (300 MHz, DMSO-d$_6$) δ 0.93-1.97 (18H, m), 1.97-2.15 (1H, m), 2.32-2.59 (1H, m), 2.98-3.42 (2H, m), 3.53-3.81 (2H, m), 3.81-4.28 (4H, m), 4.50-4.95 (1H, m), 5.00 (1H, br s), 6.10-6.76 (2H, m), 7.54-7.75 (2H, m), 8.10-8.40 (2H, m);

MS (ES+) m/z 457.

Preparation 403

(2E)-3-(6-{[(3R)-1-(4-chlorobenzoyl)-3-piperidinyl]amino}-3-pyridinyl)-N-(tetrahydro-2H-pyran-2-yloxy)acrylamide $^1$H-NMR (300 MHz, CDCl$_3$) δ 1.35-1.96 (8H, m), 1.96-2.17 (1H, m), 3.08-3.71 (4H, m), 3.71-4.06 (4H, m), 4.04-4.75 (1H, m), 5.00 (1H, br s), 6.10-6.63 (2H, m), 7.14-7.46 (4H, m), 7.46-7.70 (2H, m), 7.94-8.43 (2H, m);

MS (ES+) m/z 485.

Preparation 404

To a solution of ethyl (2E)-3-{5-[(3R)-3-piperidinylamino]-2-pyrazinyl)acrylate dihydrochloride (300 mg, 0.86 mmol) in DMF (6 mL) were added diiopropylethylamine (366 mg, 2.84 mmol) and 6-chloropyrimidine (128 mg, 1.11 mmol) at ambient temperature and the mixture was stirred at ambient temperature for 18 hrs. The reaction mixture was evaporated in vacuo and the residue was partitioned between water and EtOAc. The organic layer was separated, washed water and brine, dried over magnesium sulfate, and evaporated in vacuo. The residue was purified by silica gel column chromatography (chloroform-MeOH=95-5/hexane-EtOAc=1/4) to give ethyl (2E)-3-(5-{[(3R)-1-(2-pyrimidinyl)-3-piperidinyl]amino}-2-pyrazinyl)acrylate (141 mg, 46%) as an amorphous powder.

$^1$H-NMR (300 MHz, CDCl$_3$) δ 1.33 (3H, t, J=7.1 Hz), 1.61-1.75 (1H, m), 1.75-1.91 (2H, m), 1.96-2.12 (1H, m), 3.66-3.84 (2H, m), 3.84-3.98 (1H, m), 4.00-4.14 (1H, m), 4.20 (1H, dd, J=13.6, 3.2 Hz), 4.25 (2H, q, J=7.1 Hz), 5.13 (1H, br d, J=7.4 Hz), 6.52 (1H, t, J=4.7 Hz), 6.69 (1H, d, J=15.6 Hz), 7.58 (1H, d, J=15.6 Hz), 7.94 (1H, s), 8.09 (1H, s), 8.32 (2H, d, J=4.7 Hz);

MS (ES+) m/z 355.

Preparation 405

The mixture of ethyl (2Z)-3-(5-chloro-6-{[(3R)-1-(cyclohexylmethyl)-3-piperidinyl]amino}-3-pyridinyl)-2-fluoroacrylate (0.73 g) and 1N-NaOH (3.44 mL) in MeOH (20 mL) was stirred at 60° C. for 3 hr. To the reaction mixture was added 1N-NaCl 3.44 mL and the mixture was evaporated in vacuo to give (2Z)-3-(5-chloro-6-{[(3R)-1-(cyclohexylmethyl)-3-piperidinyl]amino}-3-pyridinyl)-2-fluoroacrylic acid (0.68 g).

$^1$H-NMR(DMSO-d$_6$): δ 0.83-0.96(2H, m), 1.08-1.28(3H, m), 1.56-1.86(10H, m), 2.42-2.75(4H, m), 2.75-3.10(2H, m), 4.33-4.45(1H, m), 6.73(1H, s), 7.77(1H, d, J=37.5 Hz), 7.88 (1H, d, J=1.7 Hz), 8.26(1H, d, J=1.7 Hz), (−)ESI-MS: 394(M−H)−.

The following compounds were obtained in a similar manner to that of Preparation 405.

Preparation 406

(2E)-3-(2-{[(3R)-1-(cyclohexylmethyl)-3-pyrrolidinyl]amino}-1,3-thiazol-4-yl)acrylic acid (−)ESI-MS: 334(M−H)−.

Preparation 407

(2Z)-3-(6-{[(3R)-1-benzyl-3-piperidinyl]amino}-5-chloro-3-pyridinyl)-2-fluoroacrylic acid (−)ESI-MS: 388(M−H)−.

Preparation 408

(2Z)-3-(5-chloro-6-{[(3R)-1-cyclopentyl-3-piperidinyl]amino}-3-pyridinyl)-2-fluoroacrylic acid (−)ESI-MS: 366(M−H)−.

Preparation 409

(2Z)-3-(5-chloro-6-{[(3R)-1-cyclohexyl-3-piperidinyl]amino}-3-pyridinyl)-2-fluoroacrylic acid $^1$H-NMR(DMSO-d$_6$): δ 1.00-1.15(1H, m), 1.16-1.31(2H, m), 1.31-1.45(2H, m), 1.50-2.07(9H, m), 2.66-3.29(5H, m), 4.40-4.56(1H, m), 6.54-6.73(1H, m), 6.66(1H, d, J=37.6 Hz), 7.86(1H, d, J=1.7 Hz), 8.22(1H, d, J=1.7 Hz), (−)ESI-MS: 380(M−H)−.

Preparation 410

(2Z)-3-(6-{[(3R)-1-benzyl-3-piperidinyl]amino}-3-pyridinyl)-2-fluoroacrylic acid $^1$H-NMR(DMSO-d$_6$): δ 1.29-1.43(1H, m), 1.64-1.93(3H, m), 2.25-2.54(2H, m), 2.85-2.98(1H, m), 3.07-3.18(1H, m), 3.91(2H, s), 4.12-4.24(1H, m), 6.58(1H, d, J=8.9 Hz), 6.78 (1H, d, J=38.1 Hz), 7.21-7.41(4H, m), 7.44-7.52(2H, m), 7.71(1H, dd, J=2.2 Hz, 8.9 Hz), 8.20(1H, d, J=2.2 Hz), (−)ESI-MS: 354(M−H)−.

Preparation 411

(2Z)-3-(6-{[(3R)-1-(cyclohexylmethyl)-3-piperidinyl]amino}-3-pyridinyl)-2-fluoroacrylic acid (−)ESI-MS: 360(M−H)−.

Preparation 412

(2Z)-3-(6-{[(3R)-1-cyclohexyl-3-piperidinyl]amino}-3-pyridinyl)-2-fluoroacrylic acid (−)ESI-MS: 346(M−H)−.

Preparation 413

(2Z)-3-(6-{[(3R)-1-cyclopentyl-3-piperidinyl]amino}-3-pyridinyl)-2-fluoroacrylic acid (−)ESI-MS: 332(M−H)−.

Preparation 414

EDCI (0.32 g) was added to the solution of (2Z)-3-(5-chloro-6-{[(3R)-1-(cyclohexylmethyl)-3-piperidinyl]amino}-3-pyridinyl)-2-fluoroacrylic acid (0.68 g), O-(tetrahydro-2H-pyran-2-yl)hydroxylamine (0.24 g), and HOBT (0.28 g) in DMF (13.6 ml) and the mixture was stirred at ambient temperature for 20 hr. The reaction mixture was poured into a mixture of AcOEt and aq NaHCO₃. The separated organic layer was washed with water, dried over magnesium sulfate and evaporated in vacuo. The residue was crystallization with solution of iPE and hexane to give (2Z)-3-(5-chloro-6-{[(3R)-1-(cyclohexylmethyl)-3-piperidinyl]amino}-3-pyridinyl)-2-fluoro-N-(tetrahydro-2H-pyran-2-yloxy)acrylamide (0.57 g).

¹H-NMR(DMSO-d₆): δ 0.77-0.92(2H, m), 1.06-1.27(3H, m), 1.40-1.81(16H, m), 2.08(2H, d, J=7.1 Hz), 2.16-2.44(3H, m), 2.48-2.61(1H, m), 3.47-3.56(1H, m), 4.01-4.11(1H, m), 4.12-4.22(1H, m), 4.97(1H, s), 6.43(1H, d, J=8.2 Hz), 6.79(1H, d, J=39.7 Hz), 7.87(1H, s, J=1.8 Hz), 8.29(1H, d, J=1.8 Hz), 11.76(1H, s), (+)ESI-MS: 495(M+H)+.

The following compounds were obtained in a similar manner to that of Preparation 414.

Preparation 415

(2Z)-3-(6-{[(3R)-1-benzyl-3-piperidinyl]amino}-5-chloro-3-pyridinyl)-2-fluoro-N-(tetrahydro-2H-pyran-2-yloxy)acrylamide ¹H-NMR(DMSO-d₆):d 1.45-1.76(10H, m), 2.12-2.28(2H, m), 2.44-2.55(1H, m), 2.62-2.73(1H, m), 3.42-3.58(3H, m), 4.01-4.11(1H, m), 4.14-4.25(1H, m), 4.97(1H, s), 6.47(1H, d, J=8.2 Hz), 6.77(1H, d, J=39.8 Hz), 7.21-7.27(1H, m), 7.29-7.34(4H, m), 7.86(1H, d, J=1.9 Hz), 8.27(1H, d, J=1.9 Hz), 11.76(1H, s), (+)ESI-MS: 489(M+H)+.

Preparation 416

(2E)-3-(2-{[(3R)-1-(cyclohexylmethyl)-3-pyrrolidinyl]amino}-1,3-thiazol-4-yl)-N-(tetrahydro-2H-pyran-2-yloxy)acrylamide ¹H-NMR(DMSO-d₆): δ 0.74-0.91(2H, m), 1.07-1.27(3H, m), 1.32-1.83(13H, m), 2.11-2.79(7H, m), 3.48-3.56(1H, m), 3.88-3.98(1H, m), 4.10-4.21(1H, m), 4.89(1H, s), 6.44(1H, d, J=15.2 Hz), 6.97(1H, s), 7.17(1H, d, J=15.2 Hz), 7.86(1H, d, J=6.6 Hz), 11.19(1H, s), (+)ESI-MS: 435(M+H)+.

Preparation 417

(2Z)-3-(5-chloro-6-{[(3R)-1-cyclopentyl-3-piperidinyl]amino}-3-pyridinyl)-2-fluoro-N-(tetrahydro-2H-pyran-2-yloxy)acrylamide (+)ESI-MS: 467(M+H)+.

Preparation 418

(2Z)-3-(5-chloro-6-{[(3R)-1-cyclohexyl-3-piperidinyl]amino}-3-pyridinyl)-2-fluoro-N-(tetrahydro-2H-pyran-2-yloxy)acrylamide ¹H-NMR(DMSO-d₆): δ 0.98-1.10(1H, m), 1.11-1.29(4H, m), 1.39-1.78(15H, m), 2.24-2.34(1H, m), 2.36-2.46(2H, m), 2.49-2.60(1H, m), 2.68-2.76(1H, m), 3.47-3.55(1H, m), 4.00-4.18(2H, m), 4.97(1H, s), 6.43(1H, d, J=8.2 Hz), 6.78(1H, d, J=39.7 Hz), 7.87(1H, d, J=1.9 Hz), 8.29(1H, d, J=1.9 Hz), 11.76(1H, s), (+)ESI-MS: 481(M+H)+.

Preparation 419

(2Z)-3-(6-{[(3R)-1-benzyl-3-piperidinyl]amino}-3-pyridinyl)-2-fluoro-N-(tetrahydro-2H-pyran-2-yloxy)acrylamide ¹H-NMR(DMSO-d₆): δ 1.17-1.30(1H, m), 1.44-1.75(8H, m), 1.77-2.04(3H, m), 2.57-2.67(1H, m), 2.82-2.92(1H, m), 3.43-3.54(3H, m), 3.90-4.12(2H, m), 4.96(1H, s), 6.52(1H, d, J=8.8 Hz), 6.69(1H, d, J=40.4 Hz), 6.95(1H, d, J=8.0 Hz), 7.20-7.27(1H, m), 7.28-7.34(4H, m), 7.65 and 7.67(total 1H, each d, J=each 2.2 Hz), 8.19(1H, d, J=2.2 Hz), 11.66(1H, s), (+)ESI-MS: 455(M+H)+.

Preparation 420

(2Z)-3-(6-{[(3R)-1-(cyclohexylmethyl)-3-piperidinyl]amino}-3-pyridinyl)-2-fluoro-N-(tetrahydro-2H-pyran-2-yloxy)acrylamide ¹H-NMR(DMSO-d₆): δ 0.73-0.88(2H, m), 1.05-1.29(4H, m), 1.37-1.94(17H, m), 2.05(2H, d, J=7.2 Hz), 2.57-2.67(1H, m), 2.79-2.88(1H, m), 3.47-3.54(1H, m), 3.93(1H, s), 4.02-4.11(1H, m), 4.96(1H, s), 6.53(1H, d, J=8.9 Hz), 6.70(1H, d, J=38.9 Hz), 6.89(1H, d, J=7.8 Hz), 6.67(1H, dd, J=2.2 Hz, 8.9 Hz), 8.21(1H, d, J=2.2 Hz), 11.66(1H, s), (+)ESI-MS: 461(M+H)+.

Preparation 421

(2Z)-3-(6-{[(3R)-1-cyclohexyl-3-piperidinyl]amino}-3-pyridinyl)-2-fluoro-N-(tetrahydro-2H-pyran-2-yloxy)acrylamide ¹H-NMR(DMSO-d₆): δ 0.96-1.29(6H, m), 1.39-1.85(14H, m), 2.01-2.11(1H, m), 2.16-2.32(2H, m), 2.61-2.71(1H, m), 2.86-2.96(1H, m), 3.47-3.55(1H, m), 3.87(1H, s), 4.02-4.11 (1H, m), 4.96(1H, s), 6.53(1H, d, J=8.9 Hz), 6.70(1H, d, J=40.0 Hz), 6.90(1H, d, J=7.8 Hz), 7.67(1H, dd, J=2.2 Hz, 8.9 Hz), 8.21(1H, d, J=2.2 Hz), 11.66(1H, (+)ESI-MS: 447(M+H)+.

Preparation 422

(2Z)-3-(6-{[(3R)-1-cyclopentyl-3-piperidinyl]amino}-3-pyridinyl)-2-fluoro-N-(tetrahydro-2H-pyran-2-yloxy)acrylamide ¹H-NMR(DMSO-d₆): δ 1.14-2.06(19H, m), 2.44-2.56(2H, m), 2.64-2.75(1H, m), 2.88-2.98(1H, m), 3.46-3.54(1H, m), 3.84-3.97(1H, m), 4.00-4.11(1H, m), 4.94-4.98(1H, m), 6.54

(1H, d, J=9.0 Hz), 6.70(1H, d, J=40.0 Hz), 6.94(1H, d, J=7.9 Hz), 7.67(1H, dd, J=2.2 Hz, 9.0 Hz), 8.21(1H, d, J=2.2 Hz), 11.66(1H, s), (+)ESI-MS: 433(M+H)+.

Preparation 423

A mixture of ethyl (2E)-3-(5-chloro-2-pyrazinyl)acrylate (300 mg, 1.41 mmol), (3R)-1-(4-fluorobenzyl)-3-pyrrolidinamine dihydrochloride (565 mg, 2.11 mmol) and triethylamine (928 mg, 9.17 mmol) was stirred at 100° C. for 6 hrs. The reaction mixture was evaporated in vacuo and the residue was partitioned between water and EtOAc. The organic layer was separated, washed water and brine, dried over magnesium sulfate, and evaporated in vacuo. The residue was purified by silica gel column chromatography (35% EtOAc/hexane-50% EtOAc/hexane) to give ethyl (2E)-3-(5-{[(3R)-1-(4-fluorobenzyl)-3-pyrrolidinyl]amino}-2-pyrazinyl)acrylate (245 mg, 47%) as an oil.

$^1$H-NMR (300 MHz, CDCl$_3$) δ 1.32 (3H, t, J=7.1 Hz), 1.65-1.80 (1H, m), 2.30-2.46 (2H, m), 2.60-2.73 (2H, m), 2.82-2.95 (1H, m), 3.60 (2H, s), 4.25 (2H, q, J=7.1 Hz), 4.46 (1H, br peak), 5.20 (1H, d, J=7.7 Hz), 6.68 (1H, d, J=15.5 Hz), 7.01 (1H, dd, J=8.6, 8.6 Hz), 7.28 (1H, dd, J=8.4, 5.6 Hz), 7.56 (1H, d, J=15.5 Hz), 7.88 (1H, s), 8.05 (1H, s);

MS (ES+) m/z 371.

The following compound was obtained in a similar manner to that of Preparation 423.

Preparation 424 ethyl (2E)-3-(5-{[(3R)-1-(2-phenylethyl)-3-pyrrolidinyl]amino}-2-pyrazinyl)acrylate $^1$H-NMR (300 MHz, CDCl$_3$) δ 1.33 (3H, t, J=7.1 Hz), 1.56-1.79 (1H, m), 2.30-2.47 (2H, m), 2.61-2.87 (6H, m), 2.96-3.09 (1H, m), 4.26 (2H, q, J=7.1 Hz), 4.41-4.55 (1H, m), 5.25 (1H, d, J=7.8 Hz), 6.68 (1H, d, J=15.5 Hz), 7.16-7.35 (5H, m), 7.58 (1H, d, J=15.5 Hz), 7.87 (1H, s), 8.06 (1H, s);

MS (ES+) m/z 367.

Preparation 425

To a mixture of 2-chloro-5-iodopyrimidine (7.62 g), palladium(II) acetate (356 mg), tri(o-tolyl)phosphine (965 mg), and DMF (32 mL) was added ethyl acrylate (17.2 mL) and N,N-diisopropylethylamine (13.8 mL). After stirring for 3 hours at 100° C., the reaction mixture was partitioned between ethyl acetate and H$_2$O. The organic layer was dried over MgSO$_4$, filtered, and evaporated in vacuo. The residue was purified by column chromatography on silica gel to give ethyl (2E)-3-(2-chloro-5-pyrimidinyl)acrylate (2.32 g).

$^1$H-NMR (300 MHz, CDCl$_3$) δ 1.35 (3H, t, J=7 Hz), 4.30 (2H, q, J=7 Hz), 6.58 (1H, d, J=16 Hz), 7.58 (1H, d, J=16 Hz), 8.76 (2H, s).

Preparation 426

Sodium triacetoxyborohydride (0.56 g) was added a mixture of ethyl (2Z)-3-{5-chloro-6-[(3R)-3-piperidinylamino]-3-pyridinyl}-2-fluoroacrylate dihydrochloride (0.7 g), Et$_3$N (0.49 mL) and cyclohexanecarboxaldehyde (0.23 mL) in CH$_2$Cl$_2$ (14 mL) and the mixture was stirred at ambient temperature for 20 hr. The reaction mixture was poured into a mixture of CHCl$_3$ and aq NaHCO$_3$. The separated organic layer was washed with water, dried over magnesium sulfate and evaporated in vacuo to give ethyl (2Z)-3-(5-chloro-6-{[(3R)-1-(cyclohexylmethyl)-3-piperidinyl]amino}-3-pyridinyl)-2-fluoroacrylate (0.74 g).

$^1$H-NMR(DMSO-d$_6$): δ 0.77-0.89(2H, m), 1.09-1.24(3H, m), 1.29(3H, t, J=7.1 Hz), 1.41-1.54(2H, m), 1.55-1.79(8H, m), 2.08(2H, d, J=7.1 Hz), 2.20-2.40(3H, m), 2.90-2.59(1H, m), 4.14-4.22(1H, m), 4.27(2H, q, J=7.1 Hz), 6.51(1H, d, J=8.2 Hz), 6.99(1H, d, J=37.6 Hz), 7.92(1H, d, J=1.9 Hz), 8.34(1H, d, J=1.9 Hz), (+)ESI-MS: 424(M+H)+.

The following compounds were obtained in a similar manner to that of Preparation 426.

Preparation 427 ethyl (2Z)-3-(6-{[(3R)-1-benzyl-3-piperidinyl]amino}-5-chloro-3-pyridinyl)-2-fluoroacrylate $^1$H-NMR(DMSO-d$_6$): δ 1.29(3H, t, J=7.1 Hz), 1.46-1.73(4H, m), 2.15-2.27(2H, m), 2.46-2.55(1H, m), 2.62-2.73(1H, m), 3.43-3.58(2H, m), 4.15-4.30(1H, m), 4.27(2H, q, J=7.1 Hz), 6.57(1H, d, J=8.2 Hz), 6.98(1H, d, J=37.5 Hz), 7.20-7.27(1H, m), 7.29-7.34(4H, m), 7.91(1H, d, J=1.9 Hz), 8.32(1H, d, J=1.9 Hz), (+)ESI-MS: 418(M+H)+.

Preparation 428 ethyl (2Z)-3-(5-chloro-6-{[(3R)-1-cyclopentyl-3-piperidinyl]amino}-3-pyridinyl)-2-fluoroacrylate $^1$H-NMR(DMSO-d$_6$): δ 1.25-1.37(2H, m), 1.29(3H, t, J=7.1 Hz), 1.41-1.80(10H, m), 2.13-2.25(2H, m), 2.49-2.62(2H, m), 2.72-2.80(1H, m), 4.12-4.21(1H, m), 4.27(2H, q, J=7.1 Hz), 6.55(1H, d, J=8.2 Hz), 6.99(1H, d, J=37.6 Hz), 7.91(1H, d, J=1.9 Hz), 8.34(1H, d, J=1.9 Hz), (+)ESI-MS: 396(M+H)+.

Preparation 429 ethyl (2Z)-3-(5-chloro-6-{[(3R)-1-cyclohexyl-3-piperidinyl]amino}-3-pyridinyl)-2-fluoroacrylate $^1$H-NMR(DMSO-d$_6$): δ 0.98-1.10(1H, m), 1.00-1.26(4H, m), 1.29(3H, t, J=7.1 Hz), 1.40-1.51(1H, m), 1.51-1.79(8H, m), 2.24-2.33(1H, m), 2.35-2.46(2H, m), 2.49-2.59(1H, m), 2.68-2.75(1H, m), 4.09-4.19(1H, m), 4.27(2H, q, J=7.1 Hz), 6.52(1H, d, J=8.1 Hz), 6.99(1H, d, J=37.6 Hz), 7.91(1H, d, J=1.9 Hz), 8.33(1H, d, J=1.9 Hz), (+)ESI-MS: 410(M+H)+.

Preparation 430 ethyl (2Z)-3-(6-{[(3R)-1-cyclopentyl-3-piperidinyl]amino}-3-pyridinyl)-2-fluoroacrylate $^1$H-NMR(DMSO-d$_6$): δ 1.18-1.40(3H, m), 1.28(3H, t, J=7.1 Hz), 1.40-1.94(10H, m), 1.94-2.05(1H, m), 2.45-2.56(1H, m), 2.64-2.75(1H, m), 2.87-2.99(1H, m), 3.87-3.99(1H, m), 4.26(2H, q, J=7.1 Hz), 6.56(1H, d, J=8.9 Hz), 6.91(1H, d, J=38.2 Hz), 7.06(1H, d, J=8.0 Hz), 7.73(1H, dd, J=2.0 Hz, 8.9 Hz), 8.27(1H, d, J=2.0 Hz), (+)ESI-MS: 362(M+H)+.

Preparation 431 ethyl (2Z)-3-(6-{[(3R)-1-cyclohexyl-3-piperidinyl]amino}-3-pyridinyl)-2-fluoroacrylate $^1$H-NMR(DMSO-d$_6$): δ 0.98-1.33(5H, m), 1.28(3H, t, J=7.1 Hz), 1.39-1.84(9H, m), 2.03-2.11(1H, m), 2.17-2.30(2H, m), 2.62-2.69(1H, m), 2.87-2.93(1H, m), 3.89(1H, s), 4.26(2H, q, J=7.1 Hz), 6.55(1H, d, J=9.0 Hz), 6.91(1H, d, J=38.2 Hz), 7.01(1H, d, J=7.8 Hz), 7.72(1H, dd, J=2.3 Hz, 9.0 Hz), 8.26(1H, d, J=2.3 Hz), (+)ESI-MS: 376(M+H)+.

Preparation 432 ethyl (2Z)-3-(6-{[(3R)-1-(cyclohexylmethyl)-3-piperidinyl]amino}-3-pyridinyl)-2-fluoroacrylate $^1$H-NMR(DMSO-d$_6$): 0.74-0.87(2H, m), 1.08-1.31(4H, m), 1.28(3H, t, J=7.0 Hz), 1.37-1.94(11H, m), 2.03-2.07(2H, m), 2.57-2.65(1H, m), 2.79-2.86(1H, m), 3.89-3.99(1H, m), 4.26 (2H, q, J=7.0 Hz), 6.54(1H, d, J=8.9 Hz), 6.91(1H, d, J=38.2 Hz), 7.02(1H, d, J=7.8 Hz), 7.73(1H, dd, J=2.3 Hz, 8.9 Hz), 8.26(1H, d, J=2.3 Hz), (+)ESI-MS: 390(M+H)+.

Preparation 433 ethyl (2Z)-3-(6-{[(3R)-1-benzyl-3-piperidinyl]amino}-3-pyridinyl)-2-fluoroacrylate $^1$H-NMR(DMSO-d$_6$): 1.21-1.31(1H, m), 1.28(3H, t, J=7.1 Hz), 1.47-1.56(1H, m), 1.64-1.72(1H, m), 1.80-1.94(2H, m), 1.94-2.03(1H, m), 2.57-2.66(1H, m), 2.83-2.90(1H, m), 3.48 (2H, dd, J=13.4 Hz, 17.6 Hz), 3.93-4.05(1H, m), 4.25(2H, q, J=7.1 Hz), 6.54(1H, d, J=8.9 Hz), 6.91(1H, d, J=38.2 Hz), 7.08(1H, d, J=8.0 Hz), 7.20-7.27(1H, m), 7.28-7.34(4H, m), 7.72(1H, dd, J=2.2 Hz, 8.9 Hz), 8.25(1H, d, J=2.2 Hz), (+)ESI-MS: 384(M+H)+.

Preparation 434

A mixture of cyclohexanecarboxylic acid (133 mg, 1.03 mmol), ethyl (2E)-3-{6-[(3R)-3-piperidinylamino]-3-pyridinyl}acrylate dihydrochloride (300 mg, 0.86 mmol), HOBt (163 mg, 1.21 mmol) and EDCI (174 mg, 1.12 mmol) in DMF (6 mL) was stirred at 0° C. for 1 hr and the mixture was stirred at ambient temperature for 18 hrs. The reaction mixture was evaporated in vacuo and the residue was partitioned between saturated sodium bicarbonate solution and EtOAc. The organic layer was separated, washed water and brine, dried over magnesium sulfate, and evaporated in vacuo. The residue was purified by preparative thin layer chromatography (hexane-EtOAc=1-1) to give ethyl (2E)-3-(6-{[(3R)-1-(cyclohexylcarbonyl)-3-piperidinyl]amino}-3-pyridinyl)acrylate (313 mg, 94%) as an amorphous powder.

$^1$H-NMR (300 MHz, CDCl$_3$) δ 0.95-2.14 (17H, m), 2.34-2.61 (1H, m), 3.05-3.43 (2H, m), 3.43-4.31 (4H, m), 4.56-4.94 (1H, m), 6.16-6.29 (1H, m), 6.36-6.54 (1H, m), 7.51-7.66 (2H, m), 8.15-8.25 (1H, m);

MS (ES+) m/z 386.

Preparation 435

To a solution of ethyl (2E)-3-(5-{[(3R)-1-benzyl-3-pyrrolidinyl]amino}-2-pyridinyl}acrylate (360 mg) in methanol (10 ml) was added 1NNaOH (5 ml) at room temperature and stirred for 2 hrs.

After then, the reaction mixture was neutralized with 1N HCl (5 ml).

The mixture was evaporated under reduced pressure and co-evaporated with toluene (twice).

To the residue in DMF (10 ml) was added O-(tetrahydro-2H-pyran-2-yl)hydroxylamine (180 mg), HOBt (138 mg) and WSCD (318 mg) and the mixture was stirred overnight.

After 12 hours, water was added and extracted with ethyl acetate (Three times).

Combined organic layer was washed with water, dried over Na$_2$SO$_4$, filtered and evaporated.

The reside was column chromatographed on silica gel (CHCl$_3$ MeOH) to give crude product.

Crude product was purified by HPLC (Yamazene packed column, 26 mm×100 mm) to give 190 mg (44%) of (2E)-3-(5-{[(3R)-1-benzyl-3-pyrrolidinyl]amino}-2-pyridinyl)-N-(tetrahydro-2H-pyran-2-yloxy)acrylamide as an oil.

MASS (ESI+): m/z=423.3(M+1).

$^1$HNMR (400 MHz, CDCl$_3$): δ 1.50-2.20 (7H, m), 2.30-3.00 (5H, m), 3.69 (2H, s), 3.90-4.10 (2H, m), 4.48 (1H, br.s), 5.01 (1H, br.s), 6.77 (1H, dd, J=8.4 and 2.8 Hz), 7.18 (1H, d, J=8.4 Hz), 7.25-7.40 (6H, m), 7.61 (1H, d, J=15.2 Hz), 7.98 (1H, s).

Preparation 436

A mixture of ethyl (2Z)-3-(6-{[(3R)-1-(cyclohexylmethyl)-3-pyrrolidinyl]amino}-3-pyridinyl)-2-fluoroacrylate and ethyl (2E)-3-(6-{[(3R)-1-(cyclohexylmethyl)-3-pyrrolidinyl]amino}-3-pyridinyl)-2-fluoroacrylate (1:1, 1.15 g), di-tert-butyl dicarbonate (1.34 g, 6.1 mmol) and 4-dimethylaminopyridine (11 mg) in tetrahydrofuran (20 mL) was stirred at 60° C. for 48 hrs. The reaction mixture was evaporated in vacuo and the residue was partitioned between water and EtOAc. The organic layer was separated, washed water and brine, dried over magnesium sulfate, and evaporated in vacuo. The residue was purified by silica gel column chromatography (CHCl$_3$/methanol=95/5) and preparative thin layer chromatography (CHCl$_3$/methanol=15/1) to give ethyl (2Z)-3-(6-{(tert-butoxycarbonyl)[(3R)-1-(cyclohexylmethyl)-3-pyrrolidinyl]amino}-3-pyridinyl)-2-fluoroacrylate (575 mg) as an oil.

$^1$H-NMR (300 MHz, CDCl$_3$) δ 0.70-0.90 (2H, m), 1.04-1.30 (3H, m), 1.30-1.49 (12H, m), 1.49-1.78 (7H, m), 1.89-2.10 (1H, m), 2.10-2.30 (3H, m), 2.40-2.74 (3H, m), 2.84-2.99 (1H, m), 4.36 (2H, q, J=7.1 Hz), 4.89 (1H, br peak), 6.90 (1H, d, J=35.0 Hz), 7.32 (1H, d, J=9.0 Hz), 8.0 (1H, d, J=9.0 Hz), 8.60 (1H, d, J=2.2 Hz);

MS (ES+) m/z 476.

Preparation 437

Ethyl (2E)-3-(5-chloro-2-Pyrazinyl)acrylate (250 mg, 1.18 mmol) and (5R)-5-amino-1-(benzyloxy)-2-piperidinone (388 mg, 1.86 mmol) were combined in 1,4-dioxane (4 mL) at ambient temperature. To this solution were added palladium(II) acetate (18 mg, 0.8 mmol) and 2-dicyclohexylphosphino-2'-(N,N-dimethylamino)biphenyl (46 mg, 0.1 mmol) at the same temperature and the mixture was stirred for 5 minutes. To the resulting mixture was added cesium carbonate (536 mg, 1.86 mmol) and the mixture was heated at 95° C. for 24 hrs. The reaction mixture was evaporated in vacuo and the residue was partitioned between water and EtOAc. The organic layer was separated, washed water and brine, dried over magnesium sulfate, and evaporated in vacuo. The residue was purified by silica gel column chromatography (CHCl₃/methanol=95/1) to give ethyl (2E)-3-(5-{[(3R)-1-(benzyloxy)-6-oxo-3-piperidinyl]amino}-2-pyrazinyl)acrylate (202 mg, 43%) as an amorphous solid.

$^1$H-NMR (300 MHz, CDCl₃) δ 1.54-1.75 (3H, m), 1.75-1.94 (3H, m), 1.94-2.07 (2H, m), 2.50-2.60 (2H, m), 3.20 (1H, dd, J=11.7, 5.1 Hz), 3.61-3.79 (2H, m), 3.90-4.05 (1H, m), 4.23-4.36 (1H, m), 4.61 (1H, br d, J=6.6 Hz), 4.98 (1H, d, J=11.0 Hz), 5.03 (1H, br peak), 5.08 (1H, d, J=11.0 Hz), 6.70 (1H, br peak), 7.31-7.41 (3H, m), 7.41-7.50 (2H, m), 7.64 (1H, d, J=15.8 Hz), 7.80 (1H, s), 8.00 (1H, s), 8.36 (1H, br peak);

MS (ES+) m/z 468, 935.

Preparation 438

To a solution of tert-butyl (3R)-3-{[5-(hydroxymethyl)-2-pyridinyl]amino}-1-piperidinecarboxylate (3.65 g, 11.9 mmol) in dioxane (50 mL) was added manganese(IV) oxide (7.7 g, 89 mmol) and, (carbethoxymethylene)triphenylphosphorane (6.2 g, 17.8 mmol). After stirring for 18 hrs at 60, a resulting precipitate was filtered and the filtrate was evaporated in vacuo and the residue was partitioned between water and EtOAc. The organic layer was separated, washed water and brine, dried over magnesium sulfate, and evaporated in vacuo. The residue was purified by silica gel column chromatography (CHCl₃/methanol=95/5) to give tert-butyl (3R)-3-({5-[(1E)-3-ethoxy-3-oxo-1-propen-1-yl]-2-pyridinyl}amino)-1-piperidinecarboxylate (3.99 g, 89%).

$^1$H-NMR (300 MHz, CDCl₃) δ 1.33 (3H, t, J=7.1 Hz), 1.43 (9H, s), 1.50-1.82 (2H, m), 1.90-2.06 (1H, m), 3.09-3.36 (2H, m), 3.48-3.62 (1H, m), 3.71-3.90 (2H, m), 4.25 (2H, q, J=7.1 Hz), 4.76-4.90 (1H, m), 6.23 (1H, d, J=15.9 Hz), 6.43 (1H, d, J=8.8 Hz), 7.58 (1H, d, J=16.0 Hz), 7.64 (1H, dd, J=8.8, 2.3 Hz), 8.21 (1H, d, J=2.2 Hz);

MS (ES+) m/z 376.

Preparation 439

To a solution of ethyl (2E)-3-(5-chloro-2-pyrazinyl)acrylate (500 mg) in DMF (5 mL) was added (3R)-1-(4-chlorobenzoyl)-3-pyrrolidinamine (951 mg) and Et₃N (1.15 mL). After stirring for 3 hours at 120° C., the reaction mixture was partitioned between ethyl acetate and H₂O. The organic layer was washed with H₂O, dried over MgSO₄, filtered, and evaporated in vacuo. The residue was purified by column chromatography on silica gel to give ethyl (2E)-3-(5-{[(3R)-1-(4-chlorobenzoyl)-3-pyrrolidinyl]amino}-2-pyrazinyl)acrylate (601 mg).

$^1$H-NMR (300 MHz, DMSO-d₆) δ 1.21-1.28 (3H, m), 1.84-2.29 (2H, m), 3.25-3.85 (4H, m), 4.10-4.21 (2H, m), 4.33-4.53 (1H, m), 6.47-6.58 (1H, m), 7.46-7.61 (6H, m), 7.96-8.31 (3H, m).

MS (ES+) m/z 401 (M+1).

The following compounds were obtained in a similar manner to that of Preparation 439.

Preparation 440 ethyl (2E)-3-(5-{[(3R)-1-(2,3-dimethylbenzyl)-3-pyrrolidinyl]amino}-2-pyrazinyl)acrylate $^1$H-NMR (300 MHz, CDCl₃) δ 1.32 (3H, t, J=7 Hz), 1.58-1.75 (1H, m), 2.28 (3H, s), 2.30 (3H, s), 2.33-2.43 (2H, m), 2.62-2.73 (2H, m), 2.86-2.94 (1H, m), 3.58-3.68 (2H, m), 4.25 (2H, q, J=7 Hz), 4.39-4.50 (1H, m), 5.20 (1H, d, J=7 Hz), 6.67 (1H, d, J=16 Hz), 7.01-7.12 (3H, m), 7.57 (1H, d, J=16 Hz), 7.87 (1H, d, J=1 Hz), 8.05 (1H, d, J=1 Hz).

MS (ES+) m/z 381 (M+1).

Preparation 441 ethyl (2E)-3-(5-{[(3R)-1-(2-chlorobenzyl)-3-pyrrolidinyl]amino}-2-pyrazinyl)acrylate $^1$H-NMR (300 MHz, CDCl₃) δ 1.32 (3H, t, J=7 Hz), 1.67-1.76 (1H, m), 2.33-2.51 (2H, m), 2.69-2.82 (2H, m), 2.63-3.01 (1H, m), 3.78 (2H, s), 4.25 (2H, q, J=7 Hz), 4.42-4.53 (1H, m), 5.25 (1H, d, J=8 Hz), 6.68 (1H, d, J=16 Hz), 7.16-7.28 (2H, m), 7.34-7.45 (2H, m), 7.57 (1H, d, J=16 Hz), 7.88 (1H, d, J=1 Hz), 8.05 (1H, d, J=1 Hz).

MS (ES+) m/z 385 (M−1).

Preparation 442 ethyl (2E)-3-(6-{(tert-butoxycarbonyl)[(3R)-1-(2-ethylbutyl)-3-pyrrolidinyl]amino}-3-pyridinyl)acrylate $^1$H-NMR (300 MHz, CDCl₃) δ 0.80 (6H, t, J=7 Hz), 1.16-1.66 (5H, m), 1.35 (3H, t, J=7 Hz), 1.44 (9H, s), 1.94-2.09 (1H, m), 2.14-2.28 (3H, m), 2.50-2.70 (3H, m), 2.80-2.89 (1H, m), 4.28 (2H, q, J=7 Hz), 4.83-4.94 (1H, m), 6.46 (1H, d, J=16 Hz), 7.26-7.34 (1H, m), 7.66 (1H, d, J=16 Hz), 7.81 (1H, dd, J=2, 8 Hz), 8.56 (1H, d, J=2 Hz).

MS (ES+) m/z 446 (M+1).

Preparation 443 ethyl (2E)-3-(6-{(tert-butoxycarbonyl)[(3R)-1-isobutyl-3-pyrrolidinyl]amino}-3-pyridinyl)acrylate $^1$H-NMR (300 MHz, CDCl₃) δ 0.84 (6H, d, J=7 Hz), 1.35 (3H, t, J=7 Hz), 1.45 (9H, s), 1.58-1.72 (1H, m), 1.94-2.06 (1H, m), 2.10-2.27 (3H, m), 2.47-2.68 (3H, m), 2.86-2.94 (1H, m), 4.28 (2H, q, J=7 Hz), 4.86-4.94 (1H, m), 6.46 (1H, d, J=16 Hz), 7.32 (1H, d, J=8 Hz), 7.66 (1H, d, J=16 Hz), 7.81 (1H, dd, J=2, 8 Hz), 8.55 (1H, d, J=2 Hz).

MS (ES+) m/z 418 (M+1).

Preparation 444 ethyl (2E)-3-(5-{[(3R)-1-benzyl-3-pyrrolidinyl]amino}-6-methyl-2-pyrazinyl)acrylate $^1$H-NMR (300 MHz, CDCl₃) δ 1.32 (3H, t, J=7 Hz), 1.60-1.77 (1H, m), 2.22-2.97 (8H, m), 3.64-3.67 (2H, m), 4.24 (2H, q, J=7 Hz), 4.56-4.66 (1H, m), 5.00-5.06 (1H, m), 6.71 (1H, d, J=16 Hz), 7.25-7.35 (5H, m), 7.56 (1H, d, J=16 Hz), 7.95 (1H, s).

MS (ES+) m/z 367 (M+1).

Preparation 445 ethyl (2E)-3-(5-{[(3R)-1-(3-chlorobenzyl)-3-pyrrolidinyl]amino}-2-pyrazinyl)acrylate $^1$H-NMR (300 MHz, CDCl₃) δ 1.32 (3H, t, J=7 Hz), 1.64-1.77 (1H, m), 2.32-2.47 (2H, m), 2.63-2.75 (2H, m), 2.85-2.93 (1H, m), 3.61 (2H, s), 4.25 (2H, q, J=7 Hz), 4.43-4.52 (1H, m), 5.20 (1H, d, J=8 Hz), 6.68 (1H, d, J=16 Hz), 7.18-

7.28 (3H, m), 7.33 (1H, s), 7.57 (1H, d, J=16 Hz), 7.89 (1H, d, J=1 Hz), 8.05 (1H, d, J=1 Hz).

MS (ES+) m/z 387 (M+1).

Preparation 446

1) To a solution of ethyl (2E)-3-(5-{[(3R)-1-(4-chlorobenzoyl)-3-pyrrolidinyl]amino}-2-pyrazinyl)acrylate (591 mg) in dioxane (15 mL) was added 1N sodium hydroxide (4.40 mL). After stirring at 60° C. for 2 hours, the reaction mixture was added H₂O (15 mL) and neutrized with 1N hydrochloric acid (to pH 7). A resulting mixture was evaporated in vacuo.

2) To a mixture of above product, O-tetrahydro-2H-pyran-2-ylhydroxylamine (259 mg), and 1-hydroxybenzotriazole (299 mg) in N,N-dimethylformamide (7.4 mL) was added 1-(3-dimethylaminopropyl)-3-ethylcarbodiimide hydrochloride (424 mg). The mixture was stirred for 6 hours at room temperature. The reaction mixture was added saturated NaHCO₃ (8 mL) and water (30 mL), and extracted with ethyl acetate. The organic layer was dried over MgSO₄, filtered, and evaporated in vacuo. The residue was purified by column chromatography on silica gel to give (2E)-3-(5-{[(3R)-1-(4-chlorobenzoyl)-3-pyrrolidinyl]amino}-2-pyrazinyl)-N-(tetrahydro-2H-pyran-2-yloxy)acrylamide ¹H-NMR (300 MHz, DMSO-d6) δ 1.48-1.74 (6H, m), 1.82-2.31 (2H, m), 3.25-4.02 (6H, m), 4.31-4.50 (1H, m), 4.90 (1H, brs), 6.57-6.69 (1H, m), 7.33-8.19 (7H, m), 11.2 (1H, brs).

MS (ES+) m/z 472 (M+1).

The following compounds were obtained in a similar manner to that of Preparation 446.

Preparation 447

(2E)-3-(5-{[(3R)-1-(2,3-dimethylbenzyl)-3-pyrrolidinyl]amino}-2-pyrazinyl)-N-(tetrahydro-2H-pyran-2-yloxy)acrylamide ¹H-NMR (300 MHz, DMSO-d6) δ 1.46-1.74 (7H, m), 2.11-2.28 (1H, m), 2.22 (3H, s), 2.23 (3H, s), 2.34-2.53 (2H, m), 2.59-2.83 (2H, m), 3.30-3.60 (3H, m), 3.90-4.01 (1H, m), 4.23-4.35 (1H, m), 4.89 (1H, brs), 6.59 (1H, d, 3=16 Hz), 6.97-7.11 (3H, m), 7.37 (1H, d, J=16 Hz), 7.75 (1H, d, J=6 Hz), 7.97 (1H, s), 8.09 (1H, s).

MS (ES+) m/z 452 (M+1).

Preparation 448

(2E)-3-(5-{[(3R)-1-(2-chlorobenzyl)-3-pyrrolidinyl]amino}-2-pyrazinyl)-N-(tetrahydro-2H-pyran-2-yloxy)acrylamide ¹H-NMR (300 MHz, DMSO-d6) δ 1.47-1.74 (7H, m), 2.18-2.31 (1H, m), 2.44-2.56 (2H, m), 2.69-2.89 (2H, m), 3.48-3.57 (1H, m), 3.65-3.77 (2H, m), 3.90-4.01 (1H, m), 4.27-4.39 (1H, m), 4.89 (1H, brs), 6.60 (1H, d, J=16 Hz), 7.24-7.54 (5H, m), 7.80 (1H, d, J=6 Hz), 7.98 (1H, s), 8.10 (1H, s), 11.2 (1H, brs).

MS (ES+) m/z 458 (M+1).

Preparation 449

(2E)-3-(5-{[(3R)-1-(3-chlorobenzyl)-3-pyrrolidinyl]amino}-2-pyrazinyl)-N-(tetrahydro-2H-pyran-2-yloxy)acrylamide ¹H-NMR (300 MHz, DMSO-d6) δ 1.46-1.74 (7H, m), 2.17-2.30 (1H, m), 2.38-2.48 (2H, m), 2.63-2.81 (2H, m), 3.48-3.57 (1H, m), 3.60 (2H, s), 3.89-4.01 (1H, m), 4.25-4.37 (1H, m), 4.89 (1H, brs), 6.60 (1H, d, J=16 Hz), 7.26-7.42 (5H, m), 7.79 (1H, d, J=6Hz), 7.98 (1H, s), 8.10 (1H, s), 11.2 (1H, brs).

MS (ES+) m/z 458 (M+1).

Preparation 450

To a mixture of tert-butyl (3R)-3-pyrrolidinylcarbamate (450 mg) and 3-methoxybenzaldehyde (352 uL) in CH₂Cl₂ (4.5 mL) was added sodium triacetoxyborohydride (922 mg), which was stirred at room temperature for 2 hours. To the resultant was added sat. NaHCO₃ aq., which was stirred for 20 min. The mixture was extracted with CH₂Cl₂. The organic phase was washed with brine and dried over Na₂SO₄, filtered, and evaporated in vacuo. The residue was purified by column chromatography on silica gel to give tert-butyl [(3R)-1-(3-methoxybenzyl)-3-pyrrolidinyl]carbamate (744 mg) as a off-white solid.

¹H NMR (200 MHz, CDCl₃) d 1.43 (9H, s), 1.49-1.72 (1H, m), 2.16-2.46 (2H, m), 2.58-2.72 (2H, m), 2.80-2.98 (1H, m), 3.63 (2H, br. s), 3.82 (3H, s), 4.08-4.31 (1H, br), 4.90-5.14 (1H, br), 6.76-6.95 (3H, m), 7.24 (1H, t, J=8.1 Hz);

MS (ES+) m/z 307 (M+1).

The following compound was obtained in a similar manner to that of Preparation 450.

Preparation 451 tert-butyl [(3R)-1-(3-cyanobenzyl)-3-pyrrolidinyl]carbamate

¹H NMR (CDCl₃, 200 MHz) d 1.44 (9H, s), 1.50-1.82 (1H, m), 2.12-2.42 (2H, m), 2.48-2.72 (2H, m), 2.72-2.89 (1H, m), 3.63 (2H, s), 4.08-4.31 (1H, br), 4.70-4.99 (1H, br), 7.36-7.68 (4H, m);

MS (ES+) 302 (M+1).

Preparation 452

To a solution of tert-butyl [(3R)-1-(3-methoxybenzyl)-3-pyrrolidinyl]carbamate (739 mg) in ethyl acetate (3.7 mL) was added 4N HCl-ethyl acetate (6.0 mL), which was stirred at room temperature for 1.5 hours. The mixture was concentrated to give (3R)-1-(3-methoxybenzyl)-3-pyrrolidinamine dihydrochloride (702 mg) as a off-white amorphous.

¹H NMR (DMSO-d6, 200 MHz) δ 1.90-2.42 (2H, m), 3.06-4.16 (5H, m), 3.79 (3H, s), 4.34-4.58 (2H, br), 6.95-7.42 (4H, m), 8.47-8.58 (2H, br); MS (ES+) m/z 207 (M+1).

The following compounds were obtained in a similar manner to that of Preparation 452.

Preparation 453

3-{[(3R)-3-amino-1-pyrrolidinyl]methyl}benzonitrile dihydrochloride

¹H NMR(DMSO-d6, 200 MHz) δ 1.89-2.34 (2H, m), 3.05-4.22 (5H, m), 4.41-4.71 (2H, m), 7.69 (1H, t, J=7.8 Hz), 7.89-8.23 (3H, m), 8.25-8.82 (2H, m);

MS (ES+) m/z 202 (M+1).

Preparation 454

N-(3-{[(3R)-3-amino-1-pyrrolidinyl]methyl}phenyl)acetamide dihydrochloride

¹H NMR (DMSO-d6, 200 MHz) δ 2.06 (3H, s), 1.91-2.35 (2H, m), 3.03-4.19 (5H, m), 4.42 (2H, m), 7.23-7.46 (2H, m), 7.49-7.65 (2H, m), 7.82 (1H, s), 8.39-8.85 (3H, m), 10.21 (1H, s), 11.10-11.67 (1H, m); MS (ES+) m/z 234 (M+1).

Preparation 455

(3R)-1-[3-(dimethylamino)benzyl]-3-pyrrolidinamine trihydrochloride $^1$H NMR (DMSO-d6, 200 MHz) δ 1.94-2.41 (2H, m), 3.03 (6H, s), 3.03-4.18 (5H, m), 4.31-4.63 (2H, m), 7.02-7.74 (4H, m), 8.51-9.05 (3H, m), 11.29-12.15 (1H, m);

MS (ES+) m/z 220 (M+1).

Preparation 456

N-(3-{[(3R)-3-amino-1-pyrrolidinyl]methyl}phenyl)methanesulfonamide dihydrochloride $^1$H NMR (DMSO-d6, 200 MHz) δ 1.95-2.37 (2H, m), 3.10 (3H, s), 3.11-4.17 (5H, m), 4.32-4.58 (2H, br), 6.93-7.51 (4H, m, J=q Hz), 8.34-8.94 (3H, m), 10.00 (1H, s), 11.16-11.98 (1H, m);

MS (ES+) m/z 270 (M+1).

Preparation 457

To a mixture of ethyl (2E)-3-(5-chloro-2-pyrazinyl)acrylate (278 mg) in 1,3-dimethyl-2-imidazolidinone (2.78 mL) was added (3R)-1-(3-methoxybenzyl)-3-pyrrolidinamine dihydrochloride (547.5 mg) and K$_2$CO$_3$ (1.08 g), which was stirred at 106° C. for 3 hours. To the resultant was added H$_2$O, which was extracted with ethyl acetate. The organic phase was washed with brine, dried over Na$_2$SO$_4$, filtered, and evaporated in vacuo. The residue was purified by column chromatography on silica gel to give ethyl (2E)-3-(5-{[(3R)-1-(3-methoxybenzyl)-3-pyrrolidinyl]amino}-2-pyrazinyl)acrylate (367.5 mg) as a brown solid.

$^1$H NMR(CDCl$_3$, 200 MHz) δ 1.32 (3H, t, J=7.1 Hz), 1.62-1.86 (1H, m), 2.28-2.50 (2H, m), 2.72 (2H, d, J=4.6 Hz), 2.89-3.04 (1H, m), 3.6.6 (2H, s), 3.81 (3H, s), 4.25 (2H, q, J=7.1 Hz), 4.39-4.58 (1H, m), 5.29-5.44 (1H, m), 6.68 (1H, d, J=15.5 Hz), 6.74-6.96 (3H, m), 7.25 (1H, t, J=7.9 Hz), 7.57 (1H, d, J=15.5 Hz), 7.89 (1H, d, J=1.2 Hz), 8.22 (1H, d, J=1.2 Hz);

MS (ES+) m/z 383 (M+1).

The following compounds were obtained in a similar manner to that of Preparation 457.

Preparation 458 ethyl (2E)-3-(5-{[(3R)-1-(3-cyanobenzyl)-3-pyrrolidinyl]amino}-2-pyrazinyl)acrylate $^1$H NMR δ (DMSO-d6, 400 MHz) d 1.24 (3H, t, J=7.0 Hz), 1.62-1.72 (1H, m), 2.18-2.30 (1H, m), 2.39-2.48(2H, m), 2.64-2.73 (1H, m), 2.75-2.83 (1H, m), 3.66 (2H, s), 4.17 (2H, q, J=7.12 Hz), 4.34 (1H, br), 6.50 (1H, d, J=15.6 Hz), 7.50-7.58 (2H, m), 7.65-7.79 (3H, m), 7.92-7.79 (1H, m), 8.00 (1H, s), 8.21 (1H, s);

MS (ES+) m/z 378 (M+1).

Preparation 459 ethyl (2E)-3-[5-({(3R)-1-[3-(acetylamino)benzyl]-3-pyrrolidinyl}amino)-2-pyrazinyl]acrylate $^1$H NMR (DMSO-d6, 400 MHz) δ 1.24 (3H, t, J=7.2 Hz), 1.60-1.71 (1H, m), 2.02 (3H, s), 2.16-2.29 (1H, m), 2.31-2.53 (2H, m), 2.59-2.68 (1H, m), 2.75-2.83 (1H, m), 3.54 (2H, s), 4.16 (2H, q, J=7.1 Hz), 4.26-4.37 (1H, m), 6.49 (1H, d, J=15.5 Hz), 6.97 (1H, d, J=7.5 Hz), 7.21 (1H, t, J=7.8 Hz), 7.45 (1H, d, J=8.2 Hz), 7.49-7.57 (2H, m), 7.92 (1H, d, J=6.6 Hz), 7.99 (1H, s), 8.20 (1H, s), 9.89 (1H, s);

MS (ES+) m/z 410 (M+1).

Preparation 460 ethyl (2E)-3-[5-({(3R)-1-[3-(dimethylamino)benzyl]-3-pyrrolidinyl}amino)-2-pyrazinyl]acrylate $^1$H NMR (DMSO-d6, 400 MHz) δ 1.24 (3H, t, J=7.2 Hz), 1.60-1.71 (1H, m), 2.17-2.28 (1H, m), 2.38-2.57 (2H, m), 2.63-2.78 (2H, m), 2.86 (6H, s), 3.49 (1H, d, J=12.9 Hz), 3.54 (1H, d, J=12.9 Hz), 4.16 (2H, q, J=7.12 Hz), 4.26-4.39 (1H, m), 6.49 (1H, d, J=15.6 Hz), 6.56-6.68 (3H, m), 7.10 (1H, t, J=7.8 Hz), 7.52 (1H, d, J=15.6 Hz), 7.90-7.97 (1H, m), 7.99 (1H, d, J=1.0 Hz), 8.20 (1H, d, J=1.1 Hz);

MS (ES+) m/z 396 (M+1).

Preparation 461 ethyl (2E)-3-(5-{[(3R)-1-{3-[(methylsulfonyl)amino]benzyl}-3-pyrrolidinyl]amino}-2-pyrazinyl)acrylate $^1$H NMR (DMSO-d6, 400 MHz) δ 1.24 (3H, t, J=7.0 Hz), 1.59-1.72 (1H, m), 2.16-2.29 (1H, m), 2.37-2.53 (2H, m), 2.61-2.70 (1H, m), 2.74-2.82 (1H, m), 2.94 (3H, s), 3.50-3.61 (2H, m), 4.16 (2H, q, J=7.1 Hz), 4.25-4.37 (1H, m), 6.49 (1H, d, J=15.4 Hz), 7.00-7.11 (2H, m), 7.16 (1H, s), 7.26 (1H, t, J=7.7 Hz), 7.53 (1H, d, J=15.6 Hz), 7.93 (1H, d, J=6.5 Hz), 7.99 (1H, d, J=1.0 Hz), 8.20 (1H, d, J=1.1 Hz), 9.20-9.70 (1H, br);

MS (ES+) 446 (M+1).

Preparation 462

To a solution of ethyl (2E)-3-(5-{[(3R)-1-(3-methoxybenzyl)-3-pyrrolidinyl]amino}-2-pyrazinyl)acrylate (362 mg) in methanol (2.9 mL) was added 1N NaOH aq. (947 uL), which was stirred at 55° C. for 45 minutes. The reaction mixture was added 1N HCl aq. (947 uL), and evaporated in vacuo to give (2E)-3-(5-{[(3R)-1-(3-methoxybenzyl)-3-pyrrolidinyl]amino}-2-pyrazinyl)acrylic acid, which was used in the next step without further purification.

The following compounds were obtained in a similar manner to that of Preparation 462.

Preparation 463

(2E)-3-(5-{[(3R)-1-(3-cyanobenzyl)-3-pyrrolidinyl]amino}-2-pyrazinyl)acrylic acid Preparation 464

(2E)-3-[5-({(3R)-1-[3-(acetylamino)benzyl]-3-pyrrolidinyl}amino)-2-pyrazinyl]acrylic acid Preparation 465

(2E)-3-[5-({(3R)-1-[3-(dimethylamino)benzyl]-3-pyrrolidinyl}amino)-2-pyrazinyl]acrylic acid Preparation 466

(2E)-3-(5-{[(3R)-1-(3-[(methylsulfonyl)amino]benzyl}-3-pyrrolidinyl]amino}-2-pyrazinyl)acrylic acid Preparation 467

(2E)-3-(5-{[(3R)-1-(2-hydroxybenzyl)-3-pyrrolidinyl]amino}-2-pyrazinyl)acrylic acid Preparation 468

(2E)-3-(5-{[(3R)-1-(2-methoxybenzyl)-3-pyrrolidinyl]amino}-2-pyrazinyl)acrylic acid Preparation 469

(2E)-3-(5-{[(3R)-1-(3-hydroxybenzyl)-3-pyrrolidinyl]amino}-2-pyrazinyl)acrylic acid Preparation 470

(2E)-3-(5-{[(3R)-1-(3-isopropoxybenzyl)-3-pyrrolidinyl]amino}-2-pyrazinyl)acrylic acid Preparation 471

To a mixture of (2E)-3-(5-{[(3R)-1-(3-methoxybenzyl)-3-pyrrolidinyl]amino}-2-pyrazinyl)acrylic acid (crude of reaction), O-(tetrahydro-2H-pyran-2-yl)hydroxylamine (166.4 mg), and 1-hydroxybenzotriazole (191.9 mg) in DMF (3.4 mL) was added N-(3-dimethylaminopropyl)-N'-ethylcarbodiimide (251 uL), which was stirred at room temperature for 16.5 hours. To the resultant was added sat. NaHCO$_3$ aq. The mixture was extracted with CH$_2$Cl$_2$. The organic phase was washed with brine, dried over Na$_2$SO$_4$, filtered, and evaporated in vacuo. The residue was purified by column chromatography on silica gel to give (2E)-3-(5-{[(3R)-1-(3-methoxybenzyl)-3-pyrrolidinyl]amino}-2-pyrazinyl)-N-(tetrahydro-2H-pyran-2-yloxy)acrylamide (312 mg) as a yellow amorphous.

$^1$H NMR (200 MHz, DMSO-d6) δ 1.42-1.83 (7H, m), 2.12-2.34 (1H, m), 2.37-2.57 (2H, m), 2.58-2.88 (2H, m), 3.44-3.63 (3H, m), 3.73 (3H, s), 3.84-4.08 (1H, m), 4.12-4.42 (1H, m), 4.89 (1H, br), 6.59 (1H, d, J=15.0 Hz), 6.73-6.96 (3H, m), 7.22 (1H, t, J=7.9 Hz), 7.37 (1H, d, J=15.3 Hz), 7.77 (1H, d, J=6.8 Hz), 7.97 (1H, s), 8.09 (1H, s), 11.17 (1H, br); MS (ES+) m/z 454 (M+1))

The following compounds were obtained in a similar manner to that of Preparation 471.

Preparation 472

(2E)-3-(5-{[(3R)-1-(3-cyanobenzyl)-3-pyrrolidinyl]amino}-2-pyrazinyl)-N-(tetrahydro-2H-pyran-2-yloxy)acrylamide $^1$H NMR (DMSO-d6, 400 MHz) δ 1.45-1.60 (3H, m), 1.60-1.80 (4H, m), 2.17-2.30 (1H, m), 2.39-2.48 (2H, m), 2.64-2.73 (1H, m), 2.74-2.83 (1H, m), 3.46-3.57 (1H, m), 3.66 (2H, s), 3.89-4.01 (1H, br), 4.23-4.39 (1H, br), 4.90 (sH, s), 6.69 (1H, d, J=15.1 Hz), 7.38 (1H, d, J=15.4 Hz), 7.54 (1H, t, J=7.7 Hz), 7.68 (1H, d, J=7.8 Hz), 7.73 (1H, d, J=7.7 Hz), 7.74-7.83 (2H, m), 7.98 (1H, s), 8.10 (1H, s), 11.18 (1H, s);

MS (ES+) m/z 449 (M+1).

Preparation 473

(2E)-3-[5-({(3R)-1-[3-(acetylamino)benzyl]-3-pyrrolidinyl}amino)-2-pyrazinyl]-N-(tetrahydro-2H-pyran-2-yloxy)acrylamide $^1$H NMR (DMSO-d6, 400 MHz) δ 1.45-1.77 (7H, m), 1.02 (3H, s), 2.16-2.29 (1H, m), 2.33-2.40 (1H, m), 2.41-2.53 (1H, m), 2.58-2.69 (1H, m), 2.75-2.84 (1H, m), 3.47-3.60 (3H, m), 3.88-4.02 (1H, m), 4.21-4.38 (1H, m), 4.89 (1H, s), 6.60 (1H, d, J=15.1 Hz), 6.97 (1H, d, J=7.6 Hz), 7.21 (1H, t, J=7.8 Hz), 7.37 (1H, d, J=15.2 Hz), 7.45 (1H, d, J=8.1 Hz), 7.54 (1H, s), 7.77 (1H, d, J=6.3 Hz), 7.96 (1H, s), 8.09 (1H, s), 9.90 (1H, s), 11.18 (1H, s);

MS (ES+) m/z 481 (M+1).

Preparation 474

(2E)-3-(5-{[(3R)-1-{3-[(methylsulfonyl)amino]benzyl}-3-pyrrolidinyl]amino}-2-pyrazinyl)-N-(tetrahydro-2H-pyran-2-yloxy)acrylamide $^1$H NMR (DMSO-d6, 400 MHz) δ 1.44-1.78 (7H, m), 2.15-2.28 (1H, m), 2.31-2.57 (2H, m), 2.61-2.71 (1H, m), 2.73-2.83 (1H, m), 2.94 (3H, s), 3.48-3.61 (3H, m), 3.88-4.00 (1H, m), 4.24-4.36 (1H, m), 4.89 (1H, s), 6.59 (1H, d, J=15.2 Hz), 7.01-7.11 (2H, m), 7.16 (1H, s), 7.26 (1H, t, J=7.8 Hz), 7.37 (1H, d, J=15.2 Hz), 7.77 (1H, d, J=6.3 Hz), 7.97 (1H, s), 8.09 (1H, s), 9.55-9.85 (1H, br), 11.07-11.29 (1H, br); MS (ES+) m/z 517 (M+1).

Preparation 475

(2E)-3-[5-({(3R)-1-[3-(dimethylamino)benzyl]-3-pyrrolidinyl}amino)-2-pyrazinyl]-N-(tetrahydro-2H-pyran-2-yloxy)acrylamide $^1$H NMR (DMSO-d6, 400 MHz) δ 1.42-1.77 (7H, m), 2.13-2.28 (1H, m), 2.34-2.57 (2H, m), 2.62-2.78 (2H, m), 2.86 (6H, s), 3.43-3.58 (3H, m), 3.89-4.01 (1H, m), 4.24-4.34 (1H, m), 4.89 (1H, s), 6.54-6.67 (4H, m), 7.10 (1H, t, J=8.0 Hz), 7.36 (1H, d, J=15.2 Hz), 7.77 (1H, d, J=6.5 Hz), 7.97 (1H, s), 8.09 (1H, s), 11.18 (1H, s);

MS (ES+) m/z 467 (M+1).

Preparation 476

(2E)-3-(5-{[(3R)-1-(2-methoxybenzyl)-3-pyrrolidinyl]amino}-2-pyrazinyl)-N-(tetrahydro-2H-pyran-2-yloxy)acrylamide $^1$H NMR (DMSO-d6, 400 MHz) δ 1.44-1.77 (7H, m), 2.13-2.28 (1H, m), 2.40-2.55 (2H, m), 2.65-2.74 (1H, m), 2.74-2.81 (1H, m), 3.48-3.65 (3H, m), 3.77 (3H, s), 3.89-4.00 (1H, m), 4.25-4.36 (1H, m), 4.89 (1H, s), 6.59 (1H, d, J=15.1 Hz), 6.91 (1H, t, J=7.5 Hz), 6.96 (1H, d, J=8.2 Hz), 7.24 (1H, t, J=7.3 Hz), 7.31 (1H, d, J=7.4 Hz), 7.37 (1H, d, J=15.4 Hz), 7.77 (1H, d, J=6.3 Hz), 7.97 (1H, s), 8.09 (1H, s), 11.17 (1H, s);

MS (ES+) m/z 454 (M+1).

Preparation 477

(2E)-3-(5-{[(3R)-1-(3-hydroxybenzyl)-3-pyrrolidinyl]amino}-2-pyrazinyl)-N-(tetrahydro-2H-pyran-2-yloxy)acrylamide $^1$H NMR (DMSO-d6, 400 MHz) δ 1.41-1.79 (7H, m), 2.15-2.29 (1H, m), 2.33-2.48 (2H, m), 2.59-2.69 (1H, m), 2.73-2.81 (1H, m), 3.40-3.56 (3H, m), 3.87-4.00 (1H, m), 4.24-4.35 (1H, m), 4.83-4.93 (1H, m), 6.54-6.66 (2H, m), 6.66-6.77 (2H, m), 7.08 (1H, t, J=8.1 Hz), 7.37 (1H, d, J=15.2 Hz), 7.76 (1H, d, J=6.4 Hz), 7.97 (1H, s), 8.09 (1H, s), 9.29 (1H, s), 11.17 (1H, br);

MS (ES+) m/z 440 (M+1).

Preparation 478

(2E)-3-(5-{[(3R)-1-(3-isopropoxybenzyl)-3-pyrrolidinyl]amino}-2-pyrazinyl)-N-(tetrahydro-2H-pyran-2-yloxy)acrylamide $^1$H NMR (DMSO-d6, 400 MHz) δ 1.20-1.27 (6H, m), 1.47-1.76 (7H, m), 2.14-2.28 (1H, m), 2.37-2.47 (2H, m), 2.63-2.77 (2H, m), 3.47-3.61 (3H, m), 3.89-4.00 (1H, m), 4.25-4.35 (1H, m), 4.56 (1H, septet, J=6.0 Hz), 4.89 (1H, s), 6.59 (1H, d, J=15.2 Hz), 6.77 (1H, d, J=7.8 Hz), 6.82-6.87 (2H, m), 7.19 (1H, t, J=8.0 Hz), 7.37 (1H, d, J=15.2 Hz), 7.77 (1H, d, J=6.2 Hz), 7.97 (1H, s), 8.09 (1H, s), 11.17 (1H, s); MS (ES+) m/z 482.

Preparation 479

(2E)-3-(5-{[(3R)-1-(2-hydroxybenzyl)-3-pyrrolidinyl]amino}-2-pyrazinyl)-N-(tetrahydro-2H-pyran-2-yloxy)acrylamide $^1$H NMR (DMSO-d6, 400 MHz) δ 1.44-1.79 (7H, m), 2.19-2.35 (1H, m), 2.44-2.56 (2H, m), 2.71-2.86 (2H, m), 3.12-3.60 (3H, m), 3.87-4.01 (1H, m), 4.27-4.39 (1H, m), 4.82-4.92 (1H, m), 6.62 (1H, d, J=15.2 Hz), 6.69-6.80 (3H, m), 7.00-7.14 (2H, m), 7.38 (1H, d, J=15.3 Hz), 7.77-7.87 (1H, m), 7.98 (1H, s), 8.10 (1H, s), 11.17 (1H, br);

MS (ES+) m/z 440 (M+1).

Preparation 480

To a mixture of tert-butyl (3R)-3-pyrrolidinylcarbamate (450 mg), 1-(chloromethyl)-3-nitrobenzene (435 mg) in DMF (4.5 mL) was added N,N-diisopropylamine (463 uL), which was stirred at 75° C. for 4 hours. To the resultant was added H$_2$O. The mixture was extracted with ethyl acetate. The organic phase was washed brine, dried over Na$_2$SO$_4$, filtered, and evaporated in vacuo. The residue was purified by column chromatography on silica gel to give tert-butyl [(3R)-1-(3-nitrobenzyl)-3-pyrrolidinyl]carbamate (, 757 mg) as a orange oil.

$^1$H NMR (200 MHz, CDCl$_3$) δ 1.44 (9H, s), 1.50-1.77 (1H, m), 2.17-2.96 (5H, m), 3.60-3.80 (2H, m), 4.19 (1H, br), 4.84 (1H, br), 7.49 (1H, t, J=7.9 Hz), 7.68 (1H, d, J=7.4 Hz), 7.99-8.24 (2H, m);

MS (ES+) 322 (M+1).

Preparation 481 tert-butyl [(3R)-1-(3-aminobenzyl)-3-pyrrolidinyl]carbamate

To a solution of tert-butyl [(3R)-1-(3-nitrobenzyl)-3-pyrrolidinyl]carbamate (750 mg) in ethanol (5.6 mL) and H$_2$O (1.9 mL) was added NH$_4$Cl (62.4 mg) and Fe (391 mg), which was stirred under reflux for 1 hour. The resultant was filtered and evaporated in vacuo. The residue was washed water and brine. The organic layer was dried over Na$_2$SO$_4$, filtered, and evaporated in vacuo to give tert-butyl [(3R)-1-(3-aminobenzyl)-3-pyrrolidinyl]carbamate (645 mg) as a brown oil.

$^1$H NMR(CDCl$_3$, 200 MHz) δ 1.43 (9H, s), 1.48-1.71 (1H, m), 2.12-2.43 (2H, m), 2.44-3.00 (3H, m), 3.51 (2H, s), 3.65 (2H, br), 4.17 (1H, br), 4.88 (1H, br), 6.53-6.73 (3H, m), 7.09 (1H, t, J=7.9 Hz);

API-ES(posi) 292 (M+1).

Preparation 482

To a solution of tert-butyl [(3R)-1-(3-aminobenzyl)-3-pyrrolidinyl]carbamate (640 mg) in CH$_2$Cl$_2$ (6.4 mL) was added 35% HCHO ag. (1.42 mL) and sodium triacetoxyborohydride (1.4 g), which was stirred at room temp temperature at 24 hours. To the resultant was added sat. NaHCO$_3$ aq., which was stirred for 20 min. The mixture was extracted with ethyl acetate. The organic phase was washed by brine, dried over Na$_2$SO$_4$, filtered, and evaporated in vacuo. The residue was purified by column chromatography on silica gel to give tert-butyl {(3R)-1-[3-(dimethylamino)benzyl]-3-pyrrolidinyl}carbamate (365 mg) as a white solid.

$^1$H NMR(CDCl$_3$, 200 MHz) δ 1.43 (9H, s), 1.50-1.76 (1H, m), 2.12-2.44 (2H, m), 2.47-2.70 (2H, m), 2.72-2.93 (1H, m), 2.95 (6H, s), 3.57 (2H, s), 4.17 (1H, br), 4.90 (1H, br), 6.58-6.74 (3H, m), 7.18 (1H, t, J=7.7 Hz);

MS (ES+) m/z 320 (M+1).

Preparation 483

To a solution of tert-butyl [(3R)-1-(3-aminobenzyl)-3-pyrrolidinyl]carbamate (681 mg) in CH$_2$Cl$_2$ (6.8 mL) was added pyridine (28:4 uL), acetic anhydride (265 uL), and N,N-dimethylaminopyridine (14 mg), which was stirred at room temperature for 1.5 hours. To the resultant was added H$_2$O. The mixture was extracted with CH$_2$Cl$_2$. The organic phase was washed by brine, dried over Na$_2$SO$_4$, filtered, and evaporated in vacuo to give tert-butyl {(3R)-1-[3-(acetylamino)benzyl]-3-pyrrolidinyl}carbamate (944 mg) as a off-white amorphous.

$^1$H NMR(CDCl$_3$, 200 MHz) δ 1.42 (9H, s), 1.71-2.00 (1H, m), 2.18 (3H, s), 36-2.47 (1H, m), 2.58-2.75 (1H, m), 2.78-3.07 (2H, m), 3.07-3.36 (1H, m), 3.86 (2H, s), 4.34 (1H, br), 5.06 (1H, br), 7.10 (1H, d, J=7.5 Hz), 7.30 (1H, t, J=7.6 Hz), 7.56-7.69 (2H, m), 7.81 (1H, br);

MS (ES+) m/z 334 (M+1).

Preparation 484

To tert-butyl [(3R)-1-(3-fluorobenzyl)-3-pyrrolidinyl]carbamate (3.0 g) was added 4NHCl/Dioxane (38 ml) at room temperature.

The mixture was stirred for 2 hrs at the same temperature.

Evaporated and decantated with diisopropyl ether (three times).

Evaporated to give 2.85 g of (3R)-1-(3-fluorobenzyl)-3-pyrrolidinamine dihydrochloride as an amorphous.

MASS (ESI+): m/z=195.2 (M+1).

$^1$HNMR (400 MHz, CDCl$_3$): δ 2.00-2.42 (2H, m), 3.00-4.20 (6H, m), 4.40-4.64 (2H, br.s), 7.20-7.40 (1H, m), 7.40-7.70 (3H, m), 8.67 and 8.84 (3H, br.s).

Preparation 485

To a solution of tert-butyl [(3R)-1-(3-aminobenzyl)-3-pyrrolidinyl]carbamate (659 mg) in CH$_2$Cl$_2$ (6.6 mL) was added pyridine (274 uL) and methanesulfonyl chloride (193 uL), which was stirred at room temperature for 20 hours. To the resultant was added H$_2$O. The mixture was extracted with 1-butanol. The organic phase was washed brine, dried Na$_2$SO$_4$, filtered, and evaporated in vacuo. The residue was purified by column chromatography on silica gel to give tert-butyl [(3R)-1-{3-[(methylsulfonyl)amino]benzyl}-3-pyrrolidinyl]carbamate (845 mg) as pale yellow amorphous.

$^1$H NMR (CDCl$_3$. 200 MHz) δ 1.43 (9H, s), 1.44-1.78 (1H, m), 2.16-2.46 (2H, m), 2.50-2.76 (2H, m), 2.78-2.95 (1H, m), 3.02 (3H, s), 3.62 (2H, s), 4.20 (1H, br), 4.93 (1H, br), 7.08-7.36 (4H, m);

MS(ES+) m/z 370.3 (M+1).

Preparation 486

To a mixture of tert-butyl (3R)-3-pyrrolidinylcarbamate (2.0 g) and 2-fluorobenzaldehyde (1.4 g) was added NaBH(OAc)$_3$ 2.73 g (1.2 eq) under ice-cooling.

After 30 min, the mixture was allowed to warm to room temperature and stirred for 8 hrs.

Dichloromethane and water was added. Separated organic layer. Extracted with dichloromethane. sat. aq. NaHCO$_3$ was added to combined organic layer.

Separated organic layer. Dried with Na$_2$SO$_4$.

Evaporated to give 3.21 g of tert-butyl [(3R)-1-(2-fluorobenzyl)-3-pyrrolidinyl]carbamate.

MASS (ESI+): m/z 295.3 (M+1).

$^1$HNMR (400 MHz, CDCl$_3$): δ 1.43 (9H, s), 1.5-1.7 (1H, m), 2.2-2.9 (5H, m), 3.67 (2H, s), 4.17 (1H, br.s), 4.87 (1H, br.s), 7.00-7.05 (1H, m), 7.08-7.12 (1H, m), 7.21-7.24 (1H, m), 7.33-7.37 (1H, m).

Preparation 487

To tert-butyl [(3R)-1-(2-fluorobenzyl)-3-pyrrolidinyl]carbamate (3.0 g) was added 4NHCl/Dioxane (38 ml) at room temperature.

The mixture was stirred for 2 hrs at the same temperature.

Evaporated and decantated with diisopropyl ether (three times).

Evaporated to give 3.74 g of (3R)-1-(2-fluorobenzyl)-3-pyrrolidinamine dihydrochloride.

MASS (ESI+): m/z=195.2 (M+1).

$^1$HNMR (400 MHz, CDCl$_3$): δ 2.0-2.6 (2H, m), 3.18-4.15 (4H, m), 3.57 (s, 2H), 4.52 (2H, br.s), 7.29-7.36 (2H, m), 7.50-7.56 (1H, m), 7.70-7.80 (1H, m), 8.63 and 8.76 (3H, br.s).

Preparation 488

A mixture of (3R)-1-(3-fluorobenzyl)-3-pyrrolidinamine dihydrochloride (1.0 g), methyl (2E)-3-(5-chloro-2-pyrazinyl)acrylate (1.74 g) and Na$_2$CO$_3$ (4.18 g) was stirred under heating condition (oil bath temperature: 206° C.).

After 8 hours, the reaction mixture was added to ice water and extracted with CHCl$_3$.

Aqueous layer was extracted with CHCl$_3$ (twice).

Combined organic layer was washed with water (three times), dried over MgSO$_4$, filtered and evaporated.

Residue was column chromatographed on silica gel (Hex: EtOAc to CHCl$_3$:MeOH=8:1) to give 1.68 g (94%) of methyl (2E)-3-(5-{[(3R)-1-(3-fluorobenzyl)-3-pyrrolidinyl]amino}-2-pyrazinyl)acrylate as an oil.

MASS (ESI+): m/z=357.2 (M+1).

$^1$HNMR (400 MHz, CDCl$_3$): δ 1.70-1.80 (1H, m), 2.35-2.50 (2H, m), 2.65-2.75 (2H, m), 2.79 (3H, s), 2.90-3.00 (1H, m), 3.65 (2H, s), 4.50 (1H, br.s), 5.45 (1H, d, J=6.6 Hz), 6.68 (1H, d, J=15.6 Hz), 6.95-7.35 (4H, m), 7.58 (1H, d, J=15.6 Hz), 7.90 (1H, d, J=1.28 Hz), 8.03 (1H, d, J=1.28 Hz).

Preparation 489

To a solution of methyl (2E)-3-(5-{[(3R)-1-(3-fluorobenzyl)-3-pyrrolidinyl]amino}-2-pyrazinyl)acrylate (1.98 g) in methanol (42 ml) was added 1NNaOH (21 ml) at room temperature. After stirring for 2 hrs, 1N HCl (21 ml) was added. The mixture was evaporated under reduced pressure. To a residue was added DMF (40 ml), O-(tetrahydro-2H-pyran-2-yl)hydroxylamine (815 mg), HOBt (940 mg) and WSCD (1.25 g) at room temperature. After stirring for 12 hrs, water was added, the mixture was extracted with CHCl$_3$ (3 times), and organic layer was washed with water (twice), dried over Na$_2$SO$_4$, filtered and evaporated.

The residue was column chromatographed on silica gel (Hex EtOAc to CHCl$_3$:MeOH) to give crude product.

The crude product was purified with HPLC (Yamazene packed column 26×100 mm) to give 730 mg (30%) of (2E)-3-(5-{[(3R)-1-(3-fluorobenzyl)-3-pyrrolidinyl]amino}-2-pyrazinyl)-N-(tetrahydro-2H-pyran-2-yloxy)acrylamide as an oil.

MASS (ESI+): m/z=442.3 (M+1).

MASS (ESI−): m/z=440.4 (M+1).

$^1$HNMR (400 MHz, CDCl$_3$): δ 1.51-2.03 (7H, m), 2.33-2.46 (2H, m), 2.71 (2H, d, J=4.8 Hz), 2.90-2.97 (1H, m), 3.65 (2H, s), 3.96 (1H, t, J=9.8 Hz), 4.44-4.53 (1H, m), 5.01 (1H, br.s), 5.38 (1H, d, J=8.0 Hz), 6.96 (1H, dt, J=2.5 and 8.4 Hz), 7.04-7.12 (2H, m), 7.27 (1H, s), 7.25-7.31 (1H, m), 7.61 (1H, d, J=15.1 Hz), 7.87 (1H, s), 8.02 (1H, s).

Preparation 490

A mixture of (3R)-1-(2-fluorobenzyl)-3-pyrrolidinamine dihydrochloride (1.0 g), methyl (2E)-3-(5-chloro-2-pyrazinyl)acrylate (1.74 g) and Na$_2$CO$_3$ (4.18 g) was stirred under heating condition (oil bath temperature: 206° C.).

After 8 hours, the reaction mixture Was added to ice water and extracted with CHCl$_3$.

Aqueous layer was extracted with CHCl$_3$ (twice).

Combined organic layer was washed with water (three times), dried over MgSO$_4$, filtered and evaporated.

Residue was column chromatographed on silica gel (Hex: EtOAc to CHCl$_3$:MeOH=8:1) to give 1.22 g (68%) of methyl (2E)-3-(5-{[(3R)-1-(2-fluorobenzyl)-3-pyrrolidinyl]amino}-2-pyrazinyl)acrylate as an oil.

MASS (ESI+): m/z=357.2 (M+1).

$^1$HNMR (400 MHz, CDCl$_3$): δ 1.61-1.84 (1H, m), 2.25-3.00 (m, 5H), 3.79 (2H, s), 4.45-4.53 (1H, m), 5.45 (1H, d, J=6.6 Hz), 6.68 (1H, d, J=15.6 Hz), 7.00-7.45 (4H, m), 7.27 (2H, s), 7.57 (1H, d, J=15.6 Hz), 7.88 (1H, d, J=1.28 Hz), 8.03 (1H, d, J=1.28 Hz).

Preparation 491

To a solution of methyl (2E)-3-(5-{[(3R)-1-(2-fluorobenzyl)-3-pyrrolidinyl]amino}-2-pyrazinyl)acrylate (1.20 g) in methanol (34 ml) was added 1NNaOH (16.9 ml) at room temperature and stirred for 2 hrs. After then, the reaction mixture was neutralized with 1N HCl (16.9 ml).

The mixture was evaporated under reduced pressure and co-evaporated with toluene (twice).

To the residue in DMF (30 ml) was added O-(tetrahydro-2H-pyran-2-yl)hydroxylamine (513 mg), HOBt (591 mg) and WSCD (784 mg) and the mixture was stirred overnight.

After 12 hours, water was added and extracted with CHCl$_3$ (Three times).

Combined organic layer was washed with water, dried over Na$_2$SO$_4$, filtered and evaporated.

The reside was column chromatographed on silica gel (Hex:EtOAc to CHCl$_3$ MeOH) to give crude (2E)-3-(5-{[(3R)-1-(2-fluorobenzyl)-3-pyrrolidinyl]amino}-2-pyrazinyl)-N-(tetrahydro-2H-pyran-2-yloxy)acrylamide.

Crude product was purified with HPLC (Yamazene packed column, 26 mm×100 mm) to give 540 mg (36%) of (2E)-3-(5-{[(3R)-1-(2-fluorobenzyl)-3-pyrrolidinyl]amino}-2-pyrazinyl)-N-(tetrahydro-2H-pyran-2-yloxy)acrylamide as an oil.

MASS (ESI+): m/z=442.3 (M+1).

$^1$HNMR (400 MHz): δ 1.56-2.13 (7H, m), 2.26-2.53 (2H, m), 2.63-3.06 (3H, m), 3.57-3.83 (3H, m), 3.97 (1H, m), 4.49 (1H, m), 5.01 (1H, br.s), 5.46 (1H, m), 7.05 (1H, ddd, J=1.0, 8.2 and 9.8 Hz), 7.12 (1H, dt, J=1.2 and 7.5 Hz), 7.22-7.30 (1H, m), 7.26 (2H, s), 7.38 (1H, dt, J=1.6 and 7.5 Hz), 7.61 (1H, d, J=14.1 Hz), 7.85 (1H, s), 8.02 (1H, s).

Preparation 492

To a suspension of methyl (2E)-3-{5-[(3R)-3-pyrrolidinylamino]-2-pyrazinyl)acrylate dihydrochloride (260 mg) in CH₂Cl₂ (2.6 mL) was added N,N-diisopropylethylamine (282 uL), 2-methoxybenzaldehyde (121.2 mg), and sodium triacetoxyborohydride (343 mg), which was stirred at room temperature for 1 hour. To the resultant was added sat. NaHCO₃ aq., which was stirred for 20 min. The mixture was extracted with CH₂Cl₂. The organic phase was washed with brine and dried over Na₂SO₄, filtered, and evaporated in vacuo. The residue was purified by column chromatography on silica gel to give methyl (2E)-3-(5-{[(3R)-1-(2-methoxybenzyl)-3-pyrrolidinyl]amino}-2-pyrazinyl)acrylate (193 mg) as a yellow amorphous.

¹H NMR (DMSO-d6, 400 MHz) δ 1.59-1.70 (1H, m), 2.16-2.28 (1H, m), 2.40-2.53 (2H, m), 2.65-2.74 (1H, m), 2.74-2.81 (1H, m), 3.53-3.64 (2H, m), 3.69 (3H, s), 3.77 (3H, s), 4.26-4.38 (1H, m), 6.51 (1H, d, J=15.4 Hz), 6.91 (1H, t, J=7.4 Hz), 6.96 (1H, d, J=8.2 Hz), 7.22 (1H, t, J=8.2 Hz), 7.31 (1H, d, J=7.2 Hz), 7.55 (1H, d, J=15.6 Hz), 7.95 (1H, d, J=6.6 Hz), 8.00 (1H, s), 8.21 (1H, s);

MS (ES+) m/z 369 (M+1).

The following compounds were obtained in a similar manner to that of Preparation 492.

Preparation 493 methyl (2E)-3-(5-{[(3R)-1-(3-hydroxybenzyl)-3-pyrrolidinyl]amino}-2-pyrazinyl)acrylate ¹H NMR (DMSO-d6, 400 MHz) δ 1.60-1.71 (1H, m), 2.16-2.28 (1H, m), 2.32-2.47 (2H, m), 2.59-2.69 (1H, m), 2.73-2.81 (1H, m), 3.49 (2H, s), 3.69 (3H, s), 4.25-4.37 (1H, m), 6.51 (1H, d, J=15.4 Hz), 6.62 (1H, d, J=7.0 Hz), 6.67-6.79 (2H, m), 7.08 (1H, t, J=8.0 Hz), 7.55 (1H, d, J=15.4 Hz), 7.94 (1H, d, J=6.5 Hz), 8.00 (1H, s), 8.20 (1H, s), 9.28 (1H, s);

MS (ES+) m/z 355 (M+1).

Preparation 494 methyl (2E)-3-(5-{[(3R)-1-(3-isopropoxybenzyl)-3-pyrrolidinyl]amino}-2-pyrazinyl)acrylate ¹H NMR (DMSO-d6, 400 MHz) δ 1.18-1.31 (6H, m), 1.61-1.73 (1H, m), 2.16-2.29 (1H, m), 2.37-2.47 (2H, m), 2.61-2.79 (2H, m), 3.52 (1H, d, J=13.1 Hz), 3.57 (1H, d, J=13.2 Hz), 3.69 (3H, s), 4.23-4.38 (1H, m), 4.56 (1H, septet, J=6.0 Hz), 6.51 (1H, d, J=15.5 Hz), 6.77 (1H, dd, J=2.0, 8.0 Hz), 6.80-6.90 (2H, m), 7.19 (1H, t, J=8.0 Hz), 7.55 (1H, d, J=15.5 Hz), 7.94 (1H, d, J=6.7 Hz), 8.00 (1H, d, J=2.4 Hz), 8.20 (1H, s);

MS (ES+) m/z 397 (M+1).

Preparation 495 methyl (2E)-3-(5-{[(3R)-1-(2-hydroxybenzyl)-3-pyrrolidinyl]amino}-2-pyrazinyl)acrylate ¹H NMR (DMSO-d6, 400 MHz) δ 1.66-1.79 (1H, m), 2.19-2.35 (1H, m), 2.43-2.58 (2H, m), 2.72-2.88 (2H, m), 3.70 (3H, s), 3.71 (2H, s), 4.27-4.42 (1H, m), 6.52 (1H, d, J=15.5 Hz), 6.67-6.79 (2H, m), 7.02-7.15 (2H, m), 7.56 (1H, d, J=15.5 Hz), 7.95-8.04 (2H, m), 8.21 (1H, d, J=1.1 Hz);

MS (ES+) m/z 355 (M+1).

Preparation 496

To a solution of methyl (2E)-3-(5-chloro-2-pyrazinyl)acrylate (680 mg) in DMI (1.4 mL) was added tert-butyl (3R)-3-amino-1-pyrrolidinecarboxylate (957 mg) and K₂CO₃ (1.42 g), which was stirred at 120° C. for 2 hours. The reaction mixture was filtered and evaporated in vacuo. To the residue was added H₂O, which was extracted with ethyl acetate. The organic layer was washed with brine, dried over Na₂SO₄, filtered, and evaporated in vacuo. The residue was purified by column chromatography on silica gel to give tert-butyl (3R)-3-({5-[(1E)-3-methoxy-3-oxo-1-propen-1-yl]-2-pyrazinyl}amino)-1-pyrrolidinecarboxylate (834 mg) as a off-white powder.

¹H NMR (400 MHz, CDCl₃) δ 1.47 (9H, s), 1.88-2.03 (1H, br), 2.20-2.33 (1H, m), 3.19-3.40 (1H, m), 3.41-3.58 (2H, m), 3.69-3.77 (1H, m), 3.80 (3H, s), 4.51 (1H, br), 5.08 (1H, br), 6.72 (1H, d, J=15.5 Hz), 7.60 (1H, d, J=15.6 Hz), 7.95 (1H, d, J=1.3 Hz), 8.08 (1H, s);

MS (ES+) m/z 371 (M+23).

Preparation 497

To a solution of tert-butyl (3R)-3-({5-[(1E)-3-methoxy-3-oxo-1-propen-1-yl]-2-pyrazinyl}amino)-1-pyrrolidinecarboxylate (830 mg) in dioxane (8.3 mL) was added 4N HCl/dioxane (6.0 mL), which was stirred at room temperature for 1 hour. To the reaction mixture was added diisopropylether, and the precipitate was filtered to give methyl (2E)-3-{5-[(3R)-3-pyrrolidinylamino]-2-pyrazinyl}acrylate dihydrochloride (742 mg) as a yellow powder.

¹H NMR (DMSO-d6, 400 MHz) δ 1.92-2.02 (1H, m), 2.16-2.28 (1H, m), 3.05-3.15 (1H, m), 3.21-3.49 (3H, m), 3.71 (3H, s), 4.43-4.52 (1H, br), 6.57 (1H, d, J=15.7 Hz), 7.60 (1H, d, J=15.6 Hz), 8.07 (1H, d, J=1.1 Hz), 8.23-8.39 (2H, m), 9.43 (2H, br);

MS (ES+) m/z 249 (M+1).

Preparation 498

To a solution of ethyl (2E)-3-(6-{[(3R)-1-phenyl-3-pyrrolidinyl]amino}-3-pyridinyl)acrylate (47 mg) in dioxane (1.4 mL) was added 1N sodium hydroxide (0.42 mL). After stirring at 60° C. for 2 hours, the reaction mixture was added H₂O (7 mL) and acidified with 1N hydrochloric acid (to pH 4). A resulting precipitate was collected by filtration, and washed with water to give (2E)-3-(6-{[(3R)-1-phenyl-3-pyrrolidinyl]amino}-3-pyridinyl)acrylic acid hydrochloride (39 mg).

¹H-NMR (300 MHz, DMSO-d6) δ 1.93-2.05 (1H, m), 2.23-2.36 (1H, m), 3.09-3.64 (4H, m), 4.54-4.62 (1H, m), 6.25 (1H, d, J=16 Hz), 6.51-6.63 (4H, m), 7.12-7.21 (2H, m), 7.44-7.51 (2H, m), 7.79 (1H, d, J=9 Hz), 8.24 (1H, brs), 12.1 (1H, brs).

MS (ES+) m/z 310 (M+1).

Preparation 499

To a solution of ethyl (2E)-3-(6-{(tert-butoxycarbonyl)[(3R)-1-(4-nitrophenyl)-3-pyrrolidinyl]amino}-3-pyridinyl)acrylate (297 mg) in ethanol (3 mL) was added tin(II) chloride (583 mg), and the mixture was heated at reflux for 6 hours. After cooling, the reaction mixture was basified with 2N sodium hydroxide and extracted with ethyl acetate. The organic layer was dried over Na₂SO₄, filtered, and evaporated in vacuo. The residue was purified by column chromatography on silica gel to give ethyl (2E)-3-(6-{[(3R)-1-(4-aminophenyl)-3-pyrrolidinyl]amino}-3-pyridinyl)acrylate (186 mg).

$^1$H-NMR (300 MHz, CDCl$_3$) δ 1.33 (3H, t, J=7 Hz), 1.97-2.08 (1H, m), 2.32-2.45 (1H, m), 3.19-3.61 (4H, m), 4.25 (2H, q, J=7 Hz), 4.53-4.64 (1H, m), 4.96-5.00 (1H, m), 6.23 (1H, d, J=16 Hz), 6.41 (1H, d, J=9 Hz), 6.49 (2H, d, J=9 Hz), 6.68 (2H, d, J=9 Hz), 7.58 (1H, d, J=16 Hz), 7.63 (1H, dd, J=2, 9 Hz), 8.22 (1H, d, J=2 Hz),

MS (ES+) m/z 353 (M+1).

Preparation 500

To a mixture of ethyl (2E)-3-(6-{[(3R)-1-(4-aminophenyl)-3-pyrrolidinyl]amino}-3-pyridinyl)acrylate (178 mg) and 50% phosphinic acid (5 mL) was added sodium nitrite (62.7 mg) in H$_2$O at 4° C. The reaction mixture was stirred for 2 hours at 4° C. The resulting mixture was neutrized with saturated NaHCO$_3$ and extracted with chloroform. The organic layer was dried over MgSO$_4$, filtered, and evaporated in vacuo. The residue was purified by column chromatography on silica gel to give ethyl (2E)-3-(6-{[(3R)-1-phenyl-3-pyrrolidinyl]amino}-3-pyridinyl)acrylate (49.0 mg).

$^1$H-NMR (300 MHz, CDCl$_3$) δ 1.33 (3H, t, J=7 Hz), 2.01-2.13 (1H, m), 2.34-2.47 (1H, m), 3.25-3.74 (4H, m), 4.25 (2H, q, J=7 Hz), 4.57-4.67 (1H, m), 4.91-4.97 (1H, m), 6.24 (1H, d, J=16 Hz), 6.42 (1H, d, J=9 Hz), 6.59 (2H, d, J=9 Hz), 6.69-6.76 (1H, m), 7.22-7.30 (2H, m), 7.58 (1H, d, J=16 Hz), 7.63 (1H, dd, J=2, 9 Hz), 8.23 (1H, d, J=2 Hz).

MS (ES+) m/z 338 (M+1).

Preparation 501

To a solution of ethyl (2E)-3-(6-{(tert-butoxycarbonyl)[(3R)-3-pyrrolidinyl]amino}-3-pyridinyl)acrylate dihydrochloride (268 mg) in DMF (3 mL) was added 1-fluoro-4-nitrobenzene (91.4 mg) and N,N-diisopropylethylamine (0.376 mL). After stirring for 3 hours at 120° C., the reaction mixture was partitioned between ethyl acetate and H$_2$O. The organic layer was washed with H$_2$O and brine, dried over MgSO$_4$, filtered, and evaporated in vacuo to give ethyl (2E)-3-(6-{(tert-butoxycarbonyl)[(3R)-1-(4-nitrophenyl)-3-pyrrolidinyl]amino}-3-pyridinyl)acrylate (299 mg).

$^1$H-NMR (300 MHz, CDCl$_3$) δ 1.34 (3H, t, J=7 Hz), 1.45 (9H, s), 2.27-2.48 (2H, m), 3.33-3.52 (2H, m), 3.67-3.82 (2H, m), 4.28 (2H, q, J=7 Hz), 5.06-5.18 (1H, m), 6.44 (2H, d, J=9 Hz), 6.45 (1H, d, J=16 Hz), 7.32 (1H, d, J=8 Hz), 7.63 (1H, d, J=16 Hz), 7.83 (1H, dd, J=2, 8 Hz), 8.11 (2H, d, J=9 Hz), 8.50 (1H, d, J=2 Hz),

MS (ES+) m/z 483 (M+1).

Preparation 502

1) To a mixture of 6-chloro-3-pyridazinecarbaldehyde (500 mg) and THF (10 mL) was added (carbethoxymethylene)triphenylphosphorane (1.35 g). The reaction mixture was stirred for 2 hours at room temperature, and evaporated in vacuo.

2) To a mixture of above product and DMF (11 mL) was added (3R)-1-(cyclohexylmethyl)-3-pyrrolidinamine dihydrochloride (1.34 g) and K$_2$CO$_3$ (2.42 g). After stirring for 5 hours at 120° C., the reaction mixture was partitioned between ethyl acetate and H$_2$O. The organic layer was washed with H$_2$O, dried over MgSO$_4$, filtered, and evaporated in vacuo. The residue was purified by column chromatography on silica gel to give ethyl (2E)-3-(6-{[(3R)-1-(cyclohexylmethyl)-3-pyrrolidinyl]amino}-3-pyridazinyl)acrylate (499 mg).

$^1$H-NMR (300 MHz, CDCl$_3$) δ 0.81-0.96 (2H, m), 1.22-1.28 (4H, m), 1.34 (3H, t, J=7 Hz), 1.37-1.49 (1H, m), 1.62-1.83 (5H, m), 2.19-2.45 (4H, m), 2.59-2.72 (2H, m), 2.82-2.93 (1H, m), 4.27 (2H, q, J=7 Hz), 4.46-4.59 (1H, m), 5.29-5.35 (1H, m), 6.61 (1H, d, J=16 Hz), 6.62 (1H, d, J=9 Hz); 7.37 (1H, d, J=9 Hz), 7.79 (1H, d, J=16 Hz).

MS (ES+) m/z 359 (M+1).

Preparation 503

To a mixture of ethyl (2E)-3-(6-{(tert-butoxycarbonyl)[(3R)-3-pyrrolidinyl]amino}-3-pyridinyl)acrylate dihydrochloride (250 mg), 4-(chloromethyl)-1,2-dimethylbenzene (89.0 mg), and DMF (5.8 mL) was added K$_2$CO$_3$ (278 mg). After stirring for 2 hours at room temperature, the reaction mixture was partitioned between ethyl acetate and H$_2$O. The organic layer was washed with brine, dried over MgSO$_4$, filtered, and evaporated in vacuo. The residue was purified by column chromatography on silica gel to give ethyl (2E)-3-(6-{(tert-butoxycarbonyl)[(3R)-1-(3,4-dimethylbenzyl)-3-pyrrolidinyl]amino}-3-pyridinyl)acrylate (263 mg).

$^1$H-NMR (300 MHz, CDCl$_3$) δ 1.35 (3H, t, J=7 Hz), 1.44 (9H, s), 1.98-2.27 (8H, m), 2.53-3.00 (4H, m), 3.46-3.60 (2H, m), 4.28 (2H, q, J=7 Hz), 4.84-4.96 (1H, m), 6.46 (1H, d, J=16 Hz), 6.93-7.06 (3H, m), 7.25-7.31 (1H, m), 7.66 (1H, d, J=16 Hz), 7.75-7.82 (1H, m), 8.53 (1H, d, J=2 Hz).

MS (ES+) m/z 480 (M+1).

Preparation 504

To a solution of (2E)-3-(6-{[(3R)-1-phenyl-3-pyrrolidinyl]amino}-3-pyridinyl)acrylic acid hydrochloride (37 mg), O-tetrahydro-2H-pyran-2-ylhydroxylamine (19 mg), and 1-hydroxybenzotriazole (22 mg) in N,N-dimethylformamide (1 mL) was added 1-(3-dimethylaminopropyl)-3-ethylcarbodiimide (25 mg) at 4° C. The mixture was warmed to ambient temperature and stirred for 8 hours. The reaction mixture was added saturated NaHCO$_3$ (1 mL) and water (4 mL). A resulting precipitate was collected by filtration, and washed with water to give (2E)-3-(6-{([(3R)-1-phenyl-3-pyrrolidinyl]amino}-3-pyridinyl)-N-(tetrahydro-2H-pyran-2-yloxy)acrylamide (43 mg).

$^1$H-NMR (300 MHz, DMSO-d6) δ 1.48-1.74 (6H, m), 1.92-2.04 (1H, m), 2.23-2.36 (1H, m), 3.09-3.64(5H, m), 3.89-4.00 (1H, m), 4.52-4.63 (1H, m), 4.88 (1H, brs), 6.23 (1H, d, J=16 Hz), 6.51-6.62 (4H, m), 7.12-7.19 (2H, m), 7.32-7.41 (2H, m), 7.59-7.66 (1H, m), 8.20(1H, brs), 11.1 (1H, brs).

MS (ES+) m/z 409 (M+1).

Preparation 505 i) A mixture of 5-chloro-6-methyl-2-pyrazinecarboxylic acid (3.83 g) and thionyl chloride (8.09 mL) was stirred for 3 hours at reflux. After cooling, the reaction mixture was evaporated in vacuo.

ii) To a suspension of sodium borohydride (2.52 g) in H$_2$O (110 mL) was added above product in dioxane (10 mL) at 10° C. After stirring for 1 hours at 10° C., the reaction mixture was extracted with ethyl acetate. The organic layer was dried over MgSO$_4$, filtered, and evaporated in vacuo to give (5-chloro-6-methyl-2-pyrazinyl)methanol (2.36 g).

$^1$H-NMR (300 MHz, CDCl$_3$) δ 2.67 (3H, s), 2.86-2.95 (1H, m), 4.79 (2H, d, J=3 Hz), 8.25 (1H, s).

MS (ES+) m/z 159 (M+1).

Preparation 506

1) To a mixture of (5-chloro-6-methyl-2-pyrazinyl)methanol (2.35 g), ethyl acetate (50 mL), and dioxane (25 mL) was added manganese(IV) oxide (12.9 g). After stirring for 2 hours at reflux, a resulting precipitate was filtered and the filtrate was evaporated in vacuo.

2) To a mixture of above product and THF (50 mL) was added (carbethoxymethylene)triphenylphosphorane (6.19 g). The reaction mixture was stirred for 6 hours at room temperature, and evaporated in vacuo. The residue was purified by column chromatography on silica gel to give ethyl (2E)-3-(5-chloro-6-methyl-2-pyrazinyl)acrylate (863 mg).

$^1$H-NMR (300 MHz, CDCl$_3$) δ 1.35 (3H, t, J=7 Hz), 2.68 (3H, s), 4.29 (2H, q, J=7 Hz), 7.01 (1H, d, J=16 Hz), 7.63 (1H, d, J=16 Hz), 8.26 (1H, s).

MS (ES+) m/z 227 (M+1).

Preparation 507

1) To a mixture of 6-chloro-3-pyridazinecarbaldehyde (300 mg) and THF (6 mL) was added (carbethoxymethylene)triphenylphosphorane (805 mg). The reaction mixture was stirred for 2 hours at room temperature, and evaporated in vacuo.

2) To a mixture of above product and DMF (10 mL) was added (3R)-1-benzyl-3-pyrrolidinamine (556 mg) and Et$_3$N (0.880 mL). After stirring for 5-hours at 100° C., the reaction mixture was partitioned between ethyl acetate and H$_2$O. The organic layer was washed with brine, dried over MgSO$_4$, filtered, and evaporated in vacuo. The residue was purified by column chromatography on silica gel to give ethyl (2E)-3-(6-{[(3R)-1-benzyl-3-pyrrolidinyl]amino}-3-pyridazinyl)acrylate (237 mg).

$^1$H-NMR (300 MHz, CDCl$_3$) δ 1.33 (3H, t, J=7 Hz), 1.60-1.79 (1H, m), 2.25-2.94 (5H, m), 3.63-3.66 (2H, m), 4.27 (2H, q, J=7 Hz), 4.48-4.60 (1H, m), 5.17-5.23 (1H, m), 6.59 (1H, d, J=9 Hz), 6.61 (1H, d, J=16 Hz), 7.25-7.38 (6H, m), 7.78 (1H, d, J=16 Hz).

MS (ES+) m/z 353 (M+1).

Preparation 508

To a mixture of ethyl (2E)-3-(6-{(tert-butoxycarbonyl)[(3R)-3-pyrrolidinyl]amino}-3-pyridinyl)acrylate dihydrochloride (500 mg), (2-bromoethoxy)benzene (347 mg), and DMF (5 mL) was added Na$_2$CO$_3$ (488 mg). After stirring for 3 hours at 100° C., the reaction mixture was partitioned between ethyl acetate and H$_2$O. The organic layer was washed with H$_2$O, dried over MgSO$_4$, filtered, and evaporated in vacuo. The residue was purified by column chromatography on silica gel to give ethyl (2E)-3-(6-{(tert-butoxycarbonyl)[(3R)-1-(2-phenoxyethyl)-3-pyrrolidinyl]amino}-3-pyridinyl)acrylate (516 mg).

$^1$H-NMR (300 MHz, CDCl$_3$) δ 1.35 (3H, t, J=7 Hz), 1.46 (9H, s), 1.98-2.10 (1H, m), 2.16-2.30 (1H, m), 2.63-2.73 (1H, m), 2.78-2.98 (4H, m), 3.08-3.16 (1H, m), 4.00-4.16 (2H, m), 4.28 (2H, q, J=7 Hz), 4.87-4.98 (1H, m), 6.44 (1H, d, J=16 Hz), 6.86-6.97 (3H, m), 7.24-7.34 (3H, m), 7.63 (1H, d, J=16 Hz), 7.78 (1H, dd, J=2, 8 Hz), 8.51 (1H, d, J=2 Hz).

MS (ES+) m/z 482 (M+1).

The following compound was obtained in a similar manner to that of Preparation 508.

Preparation 509 ethyl (2E)-3-(6-{(tert-butoxycarbonyl)[(3R)-1-butyl-3-pyrrolidinyl]amino}-3-pyridinyl)acrylate $^1$H-NMR (300 MHz, CDCl$_3$) δ 0.93 (3H, t, J=7 Hz), 1.23-1.51 (2H, m), 1.35 (3H, t, J=7 Hz), 1.46 (9H, s), 1.57-1.71 (2H, m), 2.08-2.20 (1H, m), 2.33-2.48 (1H, m), 2.60-3.50 (6H, m), 4.28 (2H, q, J=7 Hz), 4.95-5.08 (1H, m), 6.47 (1H, d, J=16 Hz), 7.33 (1H, d, J=0.8 Hz), 7.65 (1H, d, J=16 Hz), 7.81 (1H, dd, J=2, 8 Hz), 8.57 (1H, brs).

MS (ES+) m/z 418 (M+1).

Preparation 510

1) To a solution of ethyl (2E)-3-(6-{(tert-butoxycarbonyl)[(3R)-1-isobutyl-3-pyrrolidinyl]amino}-3-pyridinyl)acrylate (464 mg) in dioxane (11 mL) was added 1N sodium hydroxide (3.30 mL). After stirring at 60° C. for 2 hours, the reaction mixture was added H$_2$O (55 mL) and acidified with 1N hydrochloric acid (to pH 4). A resulting mixture was evaporated in vacuo 2) To a mixture of above product, O-tetrahydro-2H-pyran-2-ylhydroxylamine (195 mg), and 1-hydroxybenzotriazole (225 mg) in N,N-dimethylformamide (6 mL) was added 1-(3-dimethylaminopropyl)-3-ethylcarbodiimide (259 mg) at 4° C. The mixture was warmed to ambient temperature and stirred for 8 hours. The reaction mixture was added saturated NaHCO$_3$ (6 mL) and water (24 mL), and extracted with ethyl acetate. The organic layer was dried over MgSO$_4$, filtered, and evaporated in vacuo. The residue was purified by column chromatography on silica gel to give (2E)-3-(5-{(tert-butoxycarbonyl){(3R)-1-isobutyl-3-pyrrolidinyl}amino}-2-pyridinyl)-N-(tetrahydro-2H-pyran-2-yloxy)acrylamide $^1$H-NMR (300 MHz, DMSO-d6) δ 0.71-0.79 (6H, m), 1.36 (9H, s), 1.48-1.76 (7H, m), 1.86-2.14 (4H, m), 2.35-2.59 (3H, m), 2.69-2.76 (1H, m), 3.49-3.58 (1H, m), 3.90-4.03 (1H, m), 4.67-4.78 (1H, m), 4.92 (1H, brs), 6.58 (1H, d, J=16 Hz), 7.34 (1H, d, J=8 Hz), 7.52 (1H, d, J=16 Hz), 8.00 (1H, d, J=8 Hz), 8.62 (1H, brs), 11.3 (1H, brs).

MS (ES+) m/z 489 (M+1).

The following compounds were obtained in a similar manner to that of Preparation 510.

Preparation 511

(2E)-3-(5-{[(3R)-1-cyclohexyl-3-pyrrolidinyl]amino}-2-pyrazinyl)-N-(tetrahydro-2H-pyran-2-yloxy)acrylamide $^1$H-NMR (300 MHz, DMSO-d6) δ 1.08-1.29 (6H, m), 1.47-2.25 (13H, m), 2.39-2.53 (2H, m), 2.68-2.84 (2H, m), 3.49-3.57 (1H, m), 3.90-4.01 (1H, m), 4.22-4.33 (1H, m), 4.89 (1H, brs), 6.60 (1H, d, J=16 Hz), 7.38 (1H, d, J=16 Hz), 7.71-7.76 (1H, m), 7.97 (1H, brs), 8.11 (1H, brs), 11.2 (1H, brs).

MS (ES+) m/z 416 (M+1).

Preparation 512

(2E)-3-(2-{[(3R)-1-benzyl-3-pyrrolidinyl]amino}-5-pyrimidinyl)-N-(tetrahydro-2H-pyran-2-yloxy)acrylamide $^1$H-NMR (300 MHz, DMSO-d6) δ 1.47-1.79 (7H, m), 2.08-2.21 (1H, m), 2.30-2.37 (1H, m), 2.44-2.63 (2H, m), 2.78-

2.84 (1H, m), 3.47-3.61 (3H, m), 3.88-3.99 (1H, m), 4.27-4.37 (1H, m), 4.88 (1H, brs), 6.34 (1H, d, J=16 Hz), 7.20-7.34 (5H, m), 7.74-7.82 (1H, m), 8.51 (2H, s), 11.1 (1H, brs).

MS (ES+) m/z 424 (M+1').

Preparation 513

(2E)-3-(6-{[(3R)-1-benzyl-3-pyrrolidinyl]amino}-3-pyridazinyl)-N-(tetrahydro-2H-pyran-2-yloxy)acrylamide $^1$H-NMR (300 MHz, CDCl$_3$) δ 1.52-1.96 (7H, m), 2.34-2.52 (2H, m), 2.62-2.93 (3H, m), 3.58-3.68 (3H, m), 3.95-4.07 (1H, m), 4.34-4.50 (1H, m), 4.97-5.03 (1H, m), 6.60 (1H, d, J=9 Hz), 7.23-7.35 (7H, m), 7.67 (1H, d, J=16 Hz).

MS (ES+) m/z 424 (M+1).

Preparation 514

(2E)-3-(5-{[(3R)-1-benzyl-3-pyrrolidinyl]amino}-6-methyl-2-pyrazinyl)-N-(tetrahydro-2H-pyran-2-yloxy)acrylamide $^1$H-NMR (300 MHz, DMSO-d6) δ 1.48-1.71 (6H, m), 1.79-1.92 (1H, m), 2.06-2.68 (7H, m), 2.81-2.93 (1H, m), 3.48-3.63 (3H, m), 3.88-3.99 (1H, m), 4.36-4.48 (1H, m), 4.90 (1H, brs), 6.63 (1H, d, J=16 Hz), 6.81 (1H, d, J=7 Hz), 7.20-7.39 (6H, m), 8.00 (1H, s), 11.2 (1H, brs).

MS (ES+) m/z 438 (M+1).

Preparation 515

(2E)-3-(6-{[(3R)-1-(cyclohexylmethyl)-3-pyrrolidinyl]amino}-3-pyridazinyl)-N-(tetrahydro-2H-pyran-2-yloxy)acrylamide $^1$H-NMR (300 MHz, DMSO-d6) δ 0.76-0.92 (2H, m), 1.08-1.27 (4H, m), 1.32-1.81 (12H, m), 2.15-2.29 (3H, m), 2.34-2.45 (2H, m), 2.56-2.66 (1H, m), 2.73-2.81 (1H, m), 3.49-3.58 (1H, m), 3.91-4.03 (1H, m), 4.35-4.48 (1H, m), 4.92 (1H, brs), 6.62 (1H, d, J=16 Hz), 6.83 (1H, d, J=9 Hz), 7.33-7.55 (3H, m), 11.3 (1H, brs).

MS (ES+) m/z 430 (M+1).

Preparation 516

To a solution of ethyl (2E)-3-(6-{(tert-butoxycarbonyl)[(3R)-1-butyl-3-pyrrolidinyl]amino}-3-pyridinyl)acrylate (308 mg) in dioxane (7.4 mL) was added 1N sodium hydroxide (2.21 mL). After stirring at 60° C. for 2 hours, the reaction mixture was added H$_2$O (37 mL) and acidified with 1N hydrochloric acid (to pH 1). A resulting mixture was extracted with CHCl$_3$, and the organic layer was dried over MgSO$_4$, filtered, and evaporated in vacuo to give (2E)-3-(6-{(tert-butoxycarbonyl)[(3R)-1-butyl-3-pyrrolidinyl]amino}-3-pyridinyl)acrylic acid dihydrochloride (214 mg).

$^1$H-NMR (300 MHz, DMSO-d6) δ 0.88 (3H, t, J=7 Hz), 1.23-1.37 (2H, m), 1.40 (9H, s), 1.52-1.65 (2H, m), 1.91-3.85 (9H, m), 6.65 (1H, d, J=16 Hz), 7.42 (1H, d, J=8 Hz), 7.62 (1H, d, J=16 Hz), 8.20 (1H, dd, J=2, 8 Hz), 8.70 (1H, d, J=2 Hz).

MS (ES+) m/z 390 (M+1).

The following compounds were obtained in a similar manner to that of Preparation 516.

Preparation 517

(2E)-3-(6-{(tert-butoxycarbonyl)[(3R)-1-(3,4-dimethylbenzyl)-3-pyrrolidinyl]amino}-3-pyridinyl)acrylic acid dihydrochloride $^1$H-NMR (300 MHz, CDCl$_3$) δ 1.45 (9H, s), 2.23-2.89 (8H, m), 3.37-4.46 (6H, m), 5.10-5.24 (1H, m), 6.39 (1H, dd, J=2, 16 Hz), 7.16-7.40 (4H, m), 7.55 (1H, dd, J=2, 16 Hz), 7.78 (1H, dd, J=2, 8 Hz), 8.35-8.43 (1H, m).

MS (ES+) m/z 452 (M+1).

Preparation 518

(2E)-3-(6-{(tert-butoxycarbonyl)[(3R)-1-(2-ethylbutyl)-3-pyrrolidinyl]amino}-3-pyridinyl)acrylic acid dihydrochloride $^1$H-NMR (300 MHz, DMSO-d6) δ 0.8.0-0.92 (6H, m), 1.15-5.22 (14H, m), 1.42 (9H; s), 6.68 (1H, d, J=16 Hz), 7.42-7.51 (1H, m), 7.61-7.70 (1H, m), 8.20-8.28 (1H, m), 8.67-8.75 (1H, m).

MS (ES+) m/z 418 (M+1).

Preparation 519

(2E)-3-(6-{(tert-butoxycarbonyl)[(3R)-1-(2-phenoxyethyl)-3-pyrrolidinyl]amino}-3-pyridinyl)acrylic acid dihydrochloride $^1$H-NMR (300 MHz, DMSO-d6) δ 1.40 (9H, s), 1.87-5.20 (11H, m), 6.63 (1H, d, J=16 Hz), 6.94-7.02 (3H, m), 7.28-7.35 (2H, m), 7.40-7.48 (1H, m), 7.60 (1H, d, J=16 Hz), 8.20 (1H, dd, J=2, 8 Hz), 8.67 (1H, d, J=2 Hz).

MS (ES+) m/z 454 (M+1).

Preparation 520

To a mixture of (2E)-3-(6-{(tert-butoxycarbonyl)[(3R)-1-(2-ethylbutyl)-3-pyrrolidinyl]amino}-3-pyridinyl)acrylic acid dihydrochloride (303 mg), O-tetrahydro-2H-pyran-2-ylhydroxylamine (109 mg.), and 1-hydroxybenzotriazole (125 mg) in N,N-dimethylformamide (3.1 mL) was added 1-(3-dimethylaminopropyl)-3-ethylcarbodiimide (144 mg) at 4° C. The mixture was warmed to ambient temperature and stirred for 8 hours. The reaction mixture was added saturated NaHCO$_3$ (3 mL) and water (12 mL), and extracted with ethyl acetate. The organic layer was washed with H$_2$O and brine, dried over MgSO$_4$, filtered, and evaporated in vacuo. The residue was purified by column chromatography on silica gel to give (2E)-3-(5-{(tert-butoxycarbonyl){(3R)-1-(2-ethylbutyl)-3-pyrrolidinyl}amino}-2-pyridinyl)-N-(tetrahydro-2H-pyran-2-yloxy)acrylamide (135 mg).

$^1$H-NMR (300 MHz, DMSO-d6) δ 0.74 (6H, t, J=7 Hz), 1.09-1.25 (5H, m), 1.36 (9H, s), 1.49-1.75 (6H, m), 1.88-2.19 (4H, m), 2.36-2.71 (4H, m), 3.49-3.58 (1H, m), 3.90-4.02 (1H, m), 4.67-4.78 (1H, m), 4.92 (1H, brs), 6.58 (1H, d, J=16 Hz), 7.33 (1H, d, J=8 Hz), 7.53 (1H, d, J=16 Hz), 8.00 (1H, d, J=8 Hz), 8.63 (1H, brs).

MS (ES+) m/z 517 (M+1).

The following compounds were obtained in a similar manner to that of Preparation 520.

Preparation 521

(2E)-3-(5-{(tert-butoxycarbonyl){(3R)-1-(3,4-dimethylbenzyl)-3-pyrrolidinyl}amino}-2-pyridinyl)-N-(tetrahydro-2H-pyran-2-yloxy)acrylamide $^1$H-NMR (300 MHz, DMSO-d6) δ 1.35 (9H, s), 1.50-1.77 (6H, m), 1.88-2.23 (8H, m), 2.42-3.59 (7H, m), 3.91-4.03 (1H, m), 4.68-4.77 (1H, m), 4.91-4.95 (1H, m), 6.59 (1H, d, J=16 Hz), 6.85 (1H, d, J=8 Hz), 6.93 (1H, s), 7.00 (1H, d, J=8 Hz), 7.33 (1H, d, J=8 Hz), 7.54 (1H, d, J=16 Hz), 7.97-8.03 (1H, m), 8.61 (1H, brs), 11.3 (1H, brs).

MS (ES+) m/z 551 (M+1).

Preparation 522

(2E)-3-(5-{(tert-butoxycarbonyl){(3R)-1-butyl-3-pyrrolidinyl}amino}-2-pyridinyl)-N-(tetrahydro-2H-pyran-2-yloxy)acrylamide $^1$H-NMR (300 MHz, CDCl$_3$) δ 0.91 (3H, t, J=7 Hz), 1.23-3.45 (12H, m), 1.46 (9H, s), 3.64-3.72 (1H, m), 3.93-4.04 (1H, m), 4.89-5.06 (2H, m), 6.30-7.34 (2H, m), 7.68 (1H, d, J=16 Hz), 7.78 (1H, dd, J=2, 8 Hz), 8.56 (1H, brs).

MS (ES+) m/z 489 (M+1).

Preparation 523

(2E)-3-(5-[(tert-butoxycarbonyl) ]{(3R)-1-(2-phenoxyethyl)-3-pyrrolidinyl{amino}-2-pyridinyl)-N-(tetrahydro-2H-pyran-2-yloxy)acrylamide $^1$H-NMR (300 MHz, CDCl$_3$) δ 1.45 (9H, s), 1.54-1.90 (6H, m), 1.98-2.10 (1H, m), 2.16-2.31 (1H, m), 2.65-2.98 (5H, m), 3.07-3.19 (1H, m), 3.63-3.74 (1H, m), 3.93-4.07 (3H, m), 4.86-5.07 (2H, m), 6.86-6.98 (3H, m), 7.24-7.34 (4H, m), 7.62-7.79 (2H, m), 8.53 (1H, brs).

MS (ES+) m/z 553 (M+1).

The following compound was obtained in a similar manner to that of Preparation 309.

Preparation 524 ethyl 5-chloro-6-{[(3S)-1-(cyclohexylmethyl)-3-piperidinyl]amino}nicotinate $^1$H-NMR (300 MHz, CDCl$_3$) δ 0.79-0.98 (2H, m), 1.07-1.31 (4H, m), 1.36 (3H, t, J=7.1 Hz), 1.40-1.88 (9H, m), 2.01-2.24 (3H, m), 2.30-2.43 (1H, m), 2.58-2.76 (2H, m), 4.24-4.39 (3H, m), 6.37 (1H, br peak), 8.00 (1H, d, J=2.0 Hz), 8.66 (1H, d, J=2.0 Hz);

MS (ES+) m/z 380.

The following compound was obtained in a similar manner to that of Preparation 3.

Preparation 525 ethyl (2E)-3-[5-chloro-6-(cyclopentylamino)-3-pyridinyl]acrylate $^1$H-NMR (DMSO-d6): δ 1.25 (3H, t J=7.08 Hz), 1.51-1.71 (6H, m), 1.92-1.99 (2H, m), 4.16 (2H, q J=7.08 Hz), 4.32-4.43 (1H, m), 6.47 (1H, d J=15.84 Hz), 6.65 (1H, d J=7.24 Hz), 7.51 (1H, d J=15.84 Hz), 8.08 (1H, d J=1.96 Hz), 8.28 (1H, d J=1.96 Hz).

The following compound was obtained in a similar manner to that of Preparation 426.

Preparation 526 ethyl (2E)-3-{6-[(tert-butoxycarbonyl){(3R)-1-[(2,6,6-trimethyl-1-cyclohexen-1-yl)methyl]-3-pyrrolidinyl}amino]-3-pyridinyl}acrylate $^1$H-NMR (300 MHz, CDCl$_3$) δ 0.91-1.02, (6H, m), 1.35 (3H, t, J=7.3 Hz), 1.44 (9H, s), 1.50-1.72 (13H, m), 1.85-2.01 (3H, m), 2.07-2.33 (1H, m), 2.44-2.59 (2H, m), 2.61-2.74 (1H, m), 2.76-2.89 (1H, m), 2.96-3.10 (2H, m), 4.28 (2H, q, J=7.3 Hz), 4.76-4.91 (1H, m), 6.46 (1H, d, J=16.1 Hz), 7.28 (1H, d, J=8.8 Hz), 7.66 (1H, d, J=16.1 Hz), 7.80 (1H, dd, J=8.8, 2.6 Hz), 8.56 (1H, d, J=2.6 Hz);

MS (ES+) m/z 498(M+1).

The following compounds were obtained in a similar manner to that of Preparation 405, Preparation 414.

Preparation 527 tert-butyl (5-{(1E)-3-oxo-3-[(tetrahydro-2H-pyran-2-yloxy)amino]-1-propen-1-yl}-2-pyridinyl){(3R)-1-[(2,6,6-trimethyl-1-cyclohexen-1-yl)methyl]-3-pyrrolidinyl}carbamate $^1$H-NMR (300 MHz, DMSO-d6) δ 0.90 (3H, s), 0.92 (3H, s), 1.21-2.20 (7H, m), 1.36 (9H, s), 2.35-2.78 (4H, m), 2.95 (2H, br.s), 3.48-3.61 (1H, m), 3.89-4.04 (1H, m), 4.62-4.80 (1H, m), 4.92 (1H, br.s), 6.58 (1H, d, J=16.5 Hz), 7.33 (1H, d, J=8.4 Hz), 7.53 (1H, d, J=16.5 Hz), 7.99 (1H, br.d, J=8.4 Hz), 8.62 (1H, br.s);

MS (ES+) m/z 569(M+1).

Preparation 528

(2E)-3-(5-{[(3R)-1-(phenylacetyl)-3-piperidinyl]amino}-2-pyrazinyl)-N-(tetrahydro-2H-pyran-2-yloxy)acrylamide $^1$H-NMR (300 MHz, DMSO-d6) δ 1.21-2.01 (10H, m), 2.66-2.78 (0.6H, m), 3.01-4.03 (8H, m), 4.24-4.34 (0.4H, m), 4.90 (1H, br.s), 6.56-6.69 (1H, m), 7.11-7.68 (6H, m), 8.13 (0.4H, s), 8.18 (0.6H, s).

The following compound was obtained in a similar manner to that of Preparation 439.

Preparation 529 ethyl (2E)-3-(5-{[(3R)-1-(3-methylbenzyl)-3-pyrrolidinyl]amino}-2-pyrazinyl)acrylate $^1$H-NMR (300 MHz, CDCl$_3$) δ 1.32 (3H, t, J=7.0 Hz), 1.63-1.77 (1H, m), 2.31-2.46 (2H, m), 2.35 (3H, s), 2.62-2.75 (2H, m), 2.85-2.95 (1H, m), 3.60 (2H, br.s), 4.25 (2H, q, J=7.0 Hz), 4.39-4.54 (1H, m), 5.23 (1H, br.d, J=8.1 Hz), 6.67 (1H, d, J=15.8 Hz), 7.04-7.15 (3H, m), 7.18-7.25 (1H, m), 7.57 (1H, d, J=15.8 Hz), 7.87 (1H, br.s), 8.05 (1H, br.s);

MS (ES+) m/z 367(M+1).

The following compound was obtained in a similar manner to that of Preparation 405, Preparation 414.

Preparation 530

(2E)-3-(5-{[(3R)-1-(3-methylbenzyl)-3-pyrrolidinyl]amino}-2-pyrazinyl)-N-(tetrahydro-2H-pyran-2-yloxy)acrylamide ¹H-NMR (300 MHz, DMSO-d6) δ 1.44-1.77 (7H, m), 2.14-2.33 (1H, m), 2.28 (3H, s), 2.34-2.50 (2H, m), 2.58-2.70 (1H, m), 2.71-2.80 (1H, m), 3.47-3.57 (1H, m), 3.54 (2H, s), 3.87-4.03 (1H, m), 4.23-4.37 (1H, m), 4.89 (1H, br.s), 6.59 (1H, d, J=15.0 Hz), 7.01-7.14 (3H, m), 7.15-7.23 (1H, m), 7.37 (1H, d, J=15.0 Hz), 7.77 (1H, br.d), 7.97 (1H, br.s), 8.09 (1H, br.s); MS (ES+) m/z 438(M+1).

The following compound was obtained in a similar manner to that of Preparation 506.

Preparation 531 ethyl (2E)-3-(5-chloro-6-{[(3R)-1-(cyclohexylmethyl)-3-piperidinyl]amino}-3-pyridinyl)acrylate ¹H-NMR (300 MHz, CDCl₃) 0.79-0.99 (2H, m), 1.09-1.39 (4H, m), 1.33 (3H, t, J=7.0 Hz), 1.39-1.90 (9H, m), 2.03-2.20 (3H, m), 2.32-2.43 (1H, m), 2.55-2.76 (2H, m), 4.22-4.33 (1H, m), 4.24 (2H, q, J=7.0 Hz), 6.19 (1H, d, J=15.8 Hz), 7.53 (1H, d, J=15.8 Hz), 7.66 (1H, d, J=1.8 Hz), 8.10 (1H, d, J=1.8 Hz); MS (ES+) m/z 406(M+1).

The following compound was obtained in a similar manner to that of Preparation 426.

Preparation 532 ethyl (2E)-3-(6-{(tert-butoxycarbonyl)[(3R)-1-(3,3,5,5-tetramethylcyclohexyl)-3-pyrrolidinyl]amino}-3-pyridinyl)acrylate ¹H-NMR (300 MHz, CDCl₃) δ 0.90 (6H, br.s), 1.01 (6H, br.s), 1.36 (3H, t, J=7.0 Hz), 1.47 (9H, s), 1.57-1.75 (6H, m), 1.90-2.26 (2H, m), 2.32-2.97 (4H, m), 3.17-3.30 (1H, m), 4.29 (2H, q, J=7.0 Hz), 4.77-4.94 (1H, m), 6.47 (1H, d, J=16.1 Hz), 7.32 (1H, d, J=8.4 Hz), 7.67 (1H, d, J=16.1 Hz), 7.82 (1H, dd, J=8.4, 2.6 Hz), 8.56 (1H, d, J=2.6 Hz);

MS (ES+) m/z 550(M+1).

The following compound was obtained in a similar manner to that of Preparation 405, Preparation 414.

Preparation 533 tert-butyl (5-{(1E)-3-oxo-3-[(tetrahydro-2H-pyran-2-yloxy)amino]-1-propen-1-yl}-2-pyridinyl)[(3R)-1-(3,3,5,5-tetramethylcyclohexyl)-3-pyrrolidinyl]carbamate ¹H-NMR (300 MHz, DMSO-d6) δ 0.86 (6H, s), 0.95 (6H, s), 1.12-1.77 (12H, m), 1.37 (9H, s), 1.78-2.08 (2H, m), 2.23-2.54 (2H, m), 2.54-2.77 (2H, m), 2.88-3.01 (1H, m), 3.49-3.60 (1H, m), 3.87-4.06 (1H, m), 4.57-4.72 (1H, m), 4.89-4.96 (1H, m), 6.58 (1H, d, J=15.8 Hz), 7.34 (1H, d, J=8.4 Hz), 7.52 (1H, d, J=15.8 Hz), 7.97-8.05 (1H, m), 8.60-8.66 (1H, m).

The following compounds were obtained in a similar manner to that of Preparation 426.

Preparation 534 ethyl (2E)-3-(6-{(tert-butoxycarbonyl)[(3R)-1-(2,2,6,6-tetramethyl-4-piperidinyl)-3-pyrrolidinyl]amino}-3-pyridinyl)acrylate ¹H-NMR (300 MHz, CDCl₃) δ 0.74-0.90 (2H, m), 0.98 (6H, s), 1.08 (6H, s), 1.27 (3H, t, J=7.3 Hz), 1.37 (9H, s), 1.54-1.68 (4H, m), 1.78-1.93 (1H, m), 1.93-2.09 (1H, m), 2.34-2.69 (4H, m), 2.87-2.98 (1H, m), 4.21 (2H, q, J=7.3 Hz), 4.58-4.73 (1H, m), 6.76 (1H, d, J=16.1 Hz), 7.35 (1H, d, J=8.8 Hz), 7.69 (1H, d, J=16.1 Hz), 8.19 (1H, dd, J=8.8, 2.6 Hz), 8.73 (1H, d, J=2.6 Hz);

MS (ES+) m/z 501(M+1).

Preparation 535 ethyl (2E)-3-(6-{(tert-butoxycarbonyl)[(3R)-1-(tetrahydro-2H-pyran-4-yl)-3-pyrrolidinyl]amino}-3-pyridinyl)acrylate ¹H-NMR (300 MHz, CDCl₃) δ 1.35 (3H, t, J=7.3 Hz), 1.40-1.59 (2H, m), 1.46 (9H, s), 1.72-1.82 (2H, m), 1.96-2.09 (1H, m), 2.11-2.35 (2H, m), 2.50-2.63 (1H, m), 2.69 (1H, t, J=8.4 Hz), 2.76-2.88 (1H, m), 3.15 (1H, t, J=8.4 Hz), 3.32-3.44 (2H, m), 3.90-4.00 (2H, m), 4.28 (2H, q, J=7.3 Hz), 4.81-4.97 (1H, m), 6.46 (1H, d, J=16.1 Hz), 7.32 (1H, d, J=8.4 Hz), 7.66 (1H, d, J=16.1 Hz), 7.81 (1H, dd, J=8.4, 2.6 Hz), 8.54 (1H, di J=2.6 Hz);

MS (ES+) m/z 446(M+1).

The following compound was obtained in a similar manner to that of Example 129.

Preparation 536

(3R) 1-(cyclohexylmethyl)-3-piperidinamine dihydrochloride

¹H-NMR (300 MHz, DMSO-d6) δ 0.83-2.13 (15H, m), 2.69-3.95 (7H, m), 8.42-8.66 (2H, m).

The following compound was obtained in a similar manner to that of Preparation 405, Preparation 414.

Preparation 537

(2E)-3-(5-chloro-6-{[(3R)-1-(cyclohexylmethyl)-3-piperidinyl]amino}-3-pyridinyl)-N-(tetrahydro-2H-pyran-2-yloxy)acrylamide ¹H-NMR (300 MHz, DMSO-d6) δ 0.72-0.94 (2H, m), 1.01-1.31 (4H, m), 1.37-1.82 (15H, m), 2.03-2.61 (6H, m), 3.46-3.59 (1H, m), 4.11-4.25 (1H, m), 4.89 (1H, br.s), 6.26-6.46 (2H, m), 7.36 (1H, d, J=15.8 Hz), 7.87 (1H, br.s), 8.18-8.26 (1H, m); MS (ES+) m/z 477(M+1).

Preparation 538

A mixture of tert-butyl (3R)-3-({3-chloro-5-[(1E)-3-ethoxy-3-oxo-1-propen-1-yl]-2-pyridinyl}amino)-1-pyrrolidinecarboxylate (0.98 g) and 4N hydrogen chloride in dioxane solution (5 ml) in EtOH (10 ml) was stirred at ambient temperature for 4 hours. The reaction mixture was evaporated in vacuo and the residue was triturated with hexane was collected by filtration to give ethyl (2E)-3-{5-chloro-6-[(3R)-3-]pyrrolidinylamino)]-3-{pyridinyl}acrylate dihydrochloride (0.9 g).ethyl (2E)-3-{5-chloro-6-[(3R)-3-pyrrolidinylamino]-3-pyridinyl}acrylate dihydrochloride ¹H-NMR (DMSO-d6): δ 1.25 (3H, t J=7.08 Hz), 1.99-2.12 (2H, m), 3.19-3.45 (3H, m), 3.56-3.65 (1H, m), 4.16 (2H, q J=7.08 Hz), 4.52-4.57 (1H, m), 6.52 (1H, d J=15.94 Hz), 6.95 (1H, d J=6.52 Hz), 7.53 (1H, d J=15.94 Hz), 8.13 (1H, d J=1.90 Hz), 8.31 (1H, d J=1.90 Hz).

The following compound was obtained in a similar manner to that of Preparation 538.

Preparation 539 ethyl (2E)-3-{6-[(3R)-3-pyrrolidinylamino]-3-pyridinyl}acrylate dihydrochloride

¹H-NMR (DMSO-d6): δ 1.25 (3H, t J=7.06 Hz), 2.04-2.05 (1H, m), 2.29-2.34 (1H, m), 3.24-3.29 (2H, m), 3.40-3.43 (1H, m), 3.45-3.52 (1H, m), 4.18 (2H, q J=7.06 Hz), 4.66 (1H, br.s), 6.59 (1H, d J=16.00 Hz), 7.11 (1H, d J=9.12 Hz), 7.65 (1H, d J=16.00 Hz), 8.27-8.32 (2H, m), 9.56 (1H, br.s), 9.69 (1H, br, s).

Preparation 540

A solution of benzyl 4-methyl-2-(methylthio)-5-pyrimidinecarboxylate (6.0 g) and 1-benzyl-3-aminopyrrolidine (5.78 g) in dioxane (10 ml) was stirred at 130° C. for 15 hours under atmospheric pressure of nitrogen. The reaction mixture was poured into a mixture of AcOEt and H₂O and the organic layer was washed with brine and dried over MgSO₄. The solvent was evaporated in vacuo and the residue was chromatographed on allunima eluting with AcOEt-n-hexane (6:4). The eluted fractions containing the desired product were collected and evaporated in vacuo to give benzyl 2-[(1-benzyl-3-pyrrolidinyl)amino]-4-methyl-5-pyrimidinecarboxylate (3.06 g).

¹H-NMR (DMSO-d6): δ 1.71-1.81 (1H, m), 2.09-2.17 (1H, m), 2.47 (3H, s), 2.35-2.60 (3H, m), 2.79-2.81 (1H, m), 3.56 (2H, s), 4.39 (1H, m), 5.27 (2H, s), 7.22-7.47 (10H, m), 8.11-8.16 (H, m), 8.70 & 8.75 (total 1H, each s).

Preparation 541

A solution of benzyl 4-methyl-2-(methylsulfinyl)-5-pyrimidinecarboxylate (3.27 g), 1-benzyl-3-aminopyrrolidine (2.98 g) and N,N-diisopropylethylamine (1.75 g) in dioxane (15 ml) was stirred at 130° C. for 11 hours under atmospheric pressure of nitrogen. The reaction mixture was poured into a mixture of AcOEt and H₂O and the organic layer was washed with brine and dried over MgSO₄. The solvent was evaporated in vacuo and the residue was chromatographed on allumina eluting with AcOEt-n-hexane (5:5). The eluted fractions containing the desired product were collected and evaporated in vacuo to give benzyl 2-[(1-benzyl-3-pyrrolidinyl)amino]-4-methyl-5-pyrimidinecarboxylate (3.9 g).

¹H-NMR (DMSO-d6): δ 1.71-1.81 (1H, m), 2.09-2.17 (1H, m), 2.47 (3H, s), 2.35-2.60 (3H, m), 2.79-2.81 (1H, m), 3.56 (2H, s), 4.39 (1H, m), 5.27 (2H, s), 7.22-7.47 (10H, m), 8.11-8.16 (1H, m), 8.70 & 8.75 (total 1H, each s).

The following compounds were obtained in a similar manner to that of Preparation 541.

Preparation 542 benzyl 2-[(1-benzyl-4-piperidinyl)amino]-4-methyl-5-pyrimidinecarboxylate

¹H-NMR (DMSO-d6): δ 1.45-1.62 (2H, m), 1.78-1.83 (2H, m), 1.94-2.06 (2H, s), 2.52 (3H, s), 2.76-2.82 (2H, m), 3.36 (2H, s)$_{m\ 3.78}$-3.81 (1H, m), 5.27 (2H, s), 7.23-7.44 (10H, m), 7.91-8.00 (1H, m), 8.68 & 8.77 (total 1H, each s).

Preparation 543 benzyl 4-methyl-2-{[(3R)-1-(4-methylbenzyl)-3-pyrrolidinyl]amino}-5-pyrimidinecarboxylate ¹H-NMR (DMSO-d6): δ 1.73-1.76 (1H, m), 2.13-2.60 (4H m), 2.27 (3H, s), 2.45 (3H, s), 2.74-2.89 (1H, m), 3.51 (2H, s), 4.37 (1H, m), 5.26 (2H, s), 7.08-7.20 (5H, m), 7.30-7.48 (4H, m), 8.10-8.15 (1H, m), 8.69 & 8.75 (total 1H, each s).

Preparation 544 benzyl 2-{[(3R)-1-(cyclohexylmethyl)-3-pyrrolidinyl]amino}-4-methyl-5-pyrimidinecarboxylate ¹H-NMR (DMSO-d6): δ 0.77-0.86 (2H, m), 1.12-1.32 (5H, m), 1.61-1.76 (5H, m), 2.00-2.56 (6H, m), 2.43 (3H, s), 2.74-2.78 (1H, m), 4.37-4.51 (1H, m), 5.27 (2H, s), 7.22-7.70 (5H, m), 8.65-8.69 (1H, m), 8.69 & 8.77 (total 1H, each s).

Preparation 545

A solution of benzyl 4-methyl-2-(methylthio)-5-pyrimidinecarboxylate (3.6 g) and m-chloroperbenzoic acid (P=75%) (2.72 g) in AcOEt (30 ml) was stirred at ambient temperature for 2 hours. The reaction mixture was poured into a mixture of AcOEt and H₂O and the organic layer was washed with saturated NaHCO₃ solution, brine and dried over MgSO₄. The solvent was evaporated in vacuo to give benzyl 4-methyl-2-(methylsulfinyl)-5-pyrimidinecarboxylate (3.2 g)

¹H-NMR (DMSO-d6): δ 2.81 (3H, s), 2.90 (3H, s), 5.42 (2H, s) 7.23-7.55 (5H, m), 9.27 (1H, s).

Preparation 546

A mixture of {2-[(1-benzyl-3-pyrrolidinyl)amino]-4-methyl-5-pyrimidinyl}methanol (1.75 g) and MnO₂ (5.1 g) in AcOEt (30 ml) was refluxed under stirring for 1.5 hours. After removal of the insoluble material, and the solvent was evaporated in vacuo to give 2-[(1-benzyl-3-pyrrolidinyl)amino]-4-methyl-5-pyrimidinecarbaldehyde (1.58 g).

¹H-NMR (DMSO-d6): δ 1.72-1.78 (1H, m), 2.15-2.19 (1H, m), 2.36-2.61 (3H, m), 2.48 (3H, s), 2.80-2.88 (1H, m), 3.35 (2H, s), 4.39-4.47 (1H, m), 7.18-7.32 (5H, m), 8.34-8.43 (1H, m), 8.58 & 8.62 (total 1H, each s), 9.81 & 9.84 (total 1H, each s).

The following compounds were obtained in a similar manner to that of Preparation 546.

Preparation 547

2-[(1-benzyl-4-piperidinyl)amino]-4-methyl-5-pyrimidinecarbaldehyde

¹H-NMR (DMSO-d6): δ 1.44-1.63 (2H, m), 1.78-1.84 (2H, m), 1.96-2.07 (2H, m), 2.49 (3H, s), 2.77-2.83 (2H, m), 3.45 (2H, s), 3.81-3.87 (1H, m), 7.19-7.37 (5H, m), 8.14-8.26 (1H, m), 8.18 & 8.26 (total 1H, each s), 9.81 & 9.84 (total 1H, each s).

Preparation 548

4-methyl-2-{[(3R)-1-(4-methylbenzyl)-3-pyrrolidinyl]amino}-5-pyrimidinecarbaldehyde ¹H-NMR (DMSO-d6): δ 1.74-1.77 (1H, m), 2.14-2.60 (4H, m), 2.27 (3H, s), 2.46 (3H, s), 2.77-2.86 (1H, m), 3.52 (2H, s), 4.41-4.48 (1H, m), 7.10 (2H, d J=8.02 Hz), 7.19 (2H, d J=8.02 Hz), 8.32-8.42 (1H, m), 8.58 & 8.61 (total 1H, each s), 9.81 & 8.93 (total 1H, each s).

Preparation 549

2-{[(3R)-1-(cyclohexylmethyl)-3-pyrrolidinyl]amino}-4-methyl-5-pyrimidinecarbaldehyde ¹H-NMR (DMSO-d6): 0.78-0.84 (2H, m), 1.13-1.73 (10H, m), 2.00-2.57 (6H, m), 2.47 (3H, s), 2.79-2.82 (1H, m), 4.41-

4.51 (1H, m), 8.28-8.34 (1H, m), 8.64 & 8.73 (total 1H, each s), 9.86 & 9.90 (total 1H, each s).

Preparation 550

A solution of diethylphosphonoacetcacid ethyl ester (1.79 g) in THF (5 ml) was added dropwise to a mixture of 60% sodium hydride in oil (341 mg) in THF (60 mL) with stirring at 10-20° C. under atmospheric pressure of nitrogen, and the reaction mixture was stirred at ambient temperature for 30 minutes. A solution of 2-[(1-benzyl-3-pyrrolidinyl)amino]-4-methyl-5-pyrimidinecarbaldehyde (1.58 g) in THF (10 ml) solution was added the above mixture and resultant mixture was stirred at ambient temperature for 1.5 hours. The reaction mixture was poured into a mixture of AcOEt-H$_2$O and the organic layer was washed with brine and dried over MgSO$_4$. The solvent was evaporated in vacuo and the residue was chromatographed on silicagel eluting with AcOEt-MeOH (9:1). The eluted fractions containing the desired product were collected and evaporated in vacuo to give ethyl (2E)-3-{2-[(1-benzyl-3-pyrrolidinyl)amino]-4-methyl-5-pyrimidinyl}acrylate (1.7 g).

$^1$H-NMR (DMSO-d6): δ 1.24 (3H, t J=7.06 Hz), 1.63-1.82 (1H, m), 2.04-2.30 (1H, m), 2.34 (3H, s), 2.38-2.57 (3H, m), 2.79-2.84 (1H, m), 3.56 (2H, s), 4.18 (2H, q J=7.06 Hz), 4.35 (1H, m), 6.40 (1H, d J=15.94 Hz), 7.18-7.32 (5H, m), 7.63 (1H, d J=15.94 Hz), 7.78-7.80 (1H, m), 8.63 (1H, s).

The following compounds were obtained in a similar manner to that of Preparation 550.

Preparation 551 ethyl (2E)-3-{2-[(1-benzyl-4-piperidinyl)amino]-4-methyl-5-pyrimidinyl}acrylate $^1$H-NMR (DMSO-d6): 1.24 (3H, t J=7.06 Hz), 1.47-1.54 (2H, m), 1.78-1.83 (2H, m), 1.95-2.06 (2H, m), 2.37 (3H, s), 2.76-2.82 (2H, m), 3.45 (2H, s), 3.80 (1H, m), 4.18 (2H, q J=7.06 Hz), 6.39 (1H, d J=15.94 Hz), 7.19-7.36 (6H, m), 7.63 (1H, d J=15.94 Hz), 8.64 (1H, s).

Preparation 552 ethyl (2E)-3-(4-methyl-2-{[(3R)-1-(4-methylbenzyl)-3-pyrrolidinyl]amino}-5-pyrimidinyl)acrylate $^1$H-NMR (DMSO-d6): δ 1.24 (3H, t J=7.06 Hz), 1.67-1.80 (1H, m), 2.02-2.49 (2H, m), 2.27 (3H, s), 2.45 (3H, s), 2.49-2.55 (2H, m), 2.77-2.81 (1H, m), 3.51 (2H, s), 4.17 (2H, q J=7.06 Hz), 4.35 (1H, m), 6.39 (1H, d J=15.96 Hz), 7.10 (2H, d J=8.02 Hz), 7.18 (2H, d J=8.02 Hz), 7.63 (1H, d J=15.96 Hz), 7.76-7.79 (1H, m), 8.63 (1H, s).

Preparation 553 ethyl (2E)-3-(2-{[(3R)-1-(cyclohexylmethyl)-3-pyrrolidinyl]amino}-4-methyl-5-pyrimidinyl)acrylate $^1$H-NMR (DMSO-d6): δ 0.77-0.83 (2H, m), 1.25 (3H, t J=7.08 Hz), 1.15-1.17 (4H, m), 1.23-1.26 (1H, m), 1.63-1.74 (6H, m), 2.15-2.19 (3H, m), 2.37 (3H, s), 2.19-2.52 (2H, m), 2.76-2.78 (1H, m), 4.17 (2H, q J=7.08 Hz), 4.33-4.34 (1H, m), 6.40 (1H, d J=15.96 Hz), 7.63 (1H, d J=15.96 Hz), 7.74 (1H, m), 8.65 (1H, s).

Preparation 554

Lithium aluminium hydride (646 mg) was portionwise added to a solution of benzyl 2-[(1-benzyl-3-pyrrolidinyl) amino]-4-methyl-5-pyrimidinecarboxylate (4.56 g) in THF (60 ml) with stirring at 5-15° C. under atmospheric pressure of nitrogen, and the reaction mixture was stirred at 5-20° C. for 2 hours. The reaction mixture was cooled at 5° C. and H$_2$O (0.7 ml), 15% NaOH solution (0.7 ml) and H$_2$O (2.1 ml) was added and the resultant mixture was stirred at ambient temperature for 30 minutes. The reaction mixture was filtrated and the filtrate was dried over MgSO$_4$. The solvent was evaporated in vacuo and the residue was chromatographed on silicagel eluting with AcOEt-MeOH (9:1). The eluted fractions containing the desired product were collected and evaporated in vacuo to give (2-[(1-benzyl-3-pyrrolidinyl) amino]-4-methyl-5-pyrimidinyl)methanol (1.1 g).

$^1$H-NMR (DMSO-d6): δ 1.69-1.72 (1H, m), 2.12-2.36 (2H, m), 2.29 (3H, s), 2.47-2.59 (2H, m), 2.79-2.87 (1H, m), 3.52 (1H, d J=13.02 Hz), 3.59 (1H, d J=13.02 Hz), 4.29-4.32 (3H, m), 4.90 (1H, br.s), 7.07 (1H, d J=6.94 Hz), 7.12-7.32 (5H, m), 8.04 (1H, s).

The following compounds were obtained in a similar manner to that of Preparation 554.

Preparation 555

{2-[(1-benzyl-4-piperidinyl)amino]-4-methyl-5-pyrimidinyl}methanol $^1$H-NMR (DMSO-d6): δ 1.37-1.56 (2H, m), 1.77-1.82 (2H, m), 1.96-2.06 (2H, m), 2.27 (3H, s), 2.74-2.80 (2H, m), 3.44 (2H, s), 3.66-3.71 (1H, m), 4.30 (2H, d J=5.16 Hz), 4.85 (1H, t J=5.16 Hz), 6.85 (1H, d J=7.96 Hz), 7.19-7.36 (5H, m), 8.02 (1H, s).

Preparation 556

(4-methyl-2-{[(3R)-1-(4-methylbenzyl)-3-pyrrolidinyl]amino}-5-pyrimidinyl)methanol $^1$H-NMR (DMSO-d6): δ 1.68-1.70 (1H, m), 1.91-2.33 (2H, m), 2.27 (3H, s), 2.45 (3H, s), 2.45-2.58 (2H, m), 2.76-2.84 (1H, m), 3.47 (1H, d J=12.90 Hz), 3.55 (1H, d J=12.90 Hz), 4.31 (2H, s), 3.98-7.04 (1H, m), 7.02-7.20 (6H, m), 8.02 (1H, s).

Preparation 557

(2-{[(3R)-1-(cyclohexylmethyl)-3-pyrrolidinyl]amino}-4-methyl-5-pyrimidinyl)methanol $^1$H-NMR (DMSO-d6): δ 0.78-0.89 (2H, m), 1.13-1.62 (5H, m), 1.69-1.99 (5H, m), 2.28 (3H, s), 2.00-2.28 (4H, m), 2.42-2.52 (2H, m), 2.73-2.81 (1H, m), 4.41-4.49 (1H, m), 4.49 (2H, s), 5.27 (1H, m), 6.91 (1H, d J=6.98 Hz), 8.03 (1H, s).

Preparation 558

A solution of ethyl (2E)-3-{2-[(1-benzyl-3-pyrrolidinyl) amino]-4-methyl-5-pyrimidinyl}acrylate (750 mg) and 1N NaOH solution (4.1 ml) in MeOH (10 ml) and THF (10 ml) was stirred at 80-85° C. for 2 hours. The reaction mixture was evaporated in vacuo and the residue was dissolved in a mixture was AcOEt and H$_2$O. The aqueous solution was adjusted to PH 5.4 with 5% HCl solution and resultant solution was evaporated in vacuo and the residue was dissolved in a MeOH and THF. The solvent was evaporated in vacuo and dried to give (2E)-3-{2-[(1-benzyl-3-pyrrolidinyl)amino]-4-methyl-5-pyrimidinyl}acrylic acid (693 mg).

¹H-NMR (DMSO-d6): δ 1.72-1.84 (1H, m), 2.13-2.30 (1H, m), 2.34 (3H, s), 2.34-2.87 (4H, m), 3.57 (2H, s), 4.27-4.33 (1H, m), 6.29 (1H, d J=15.90 Hz), 7.11-7.32 (6H, m), 7.41-7.62 (2H, m), 8.47 (1H, s).

The following compounds were obtained in a similar manner to that of Preparation 558.

Preparation 559

(2E)-3-{2-[(1-benzyl-4-piperidinyl)amino]-4-methyl-5-pyrimidinyl}acrylic acid

¹H-NMR (DMSO-d6): δ 1.74-2.09 (4H, m), 2.38 (3H, s), 2.69 (2H, m), 3.04-3.09 (2H, m), 3.95-4.11 (3H, m), 6.34 (1H, d J=15.96 Hz), 7.38-7.54 (5H, m), 7.58 (1H, d J=15.96 Hz), 7.72 (1H, d J=7.20 Hz), 8.61 (1H, s).

Preparation 560

(2E)-3-(4-methyl-2-{[(3R)-1-(4-methylbenzyl)-3-pyrrolidinyl]amino}-5-pyrimidinyl)acrylic acid ¹H-NMR (DMSO-d6): δ 1.73-1.82 (1H, m), 2.00-2.33 (2H, m), 2.27 (3H, s), 2.45 (3H, s), 2.45-2.68 (2H, m), 2.77-2.85 (1H, m), 3.51-3.52 (2H, m), 4.31-4.34 (1H, m), 6.26 (1H, d J=15.68 Hz), 7.08-7.36 (5H, m), 7.47 (1H, d J=6.90 Hz), 8.45 (1H, s).

Preparation 561

(2E)-3-(2-{[(3R)-1-(cyclohexylmethyl)-3-pyrrolidinyl]amino}-4-methyl-5-pyrimidinyl)acrylic acid ¹H-NMR (DMSO-d6): δ 0.78-0.90 (2H, m), 1.13-1.63 (5H, m), 1.50-1.84 (6H, m), 2.00-2.53 (5H, m), 2.35 (3H, s), 2.75-2.80 (1H, m), 4.20 (1H, m), 6.29 (1H, d J=15.86 Hz), 7.32 (1H, d J=15.86 Hz), 7.42-7.49 (1H, m), 8.49 (1H, s).

Preparation 562

A mixture of A mixture of (2E)-3-{2-[(1-benzyl-3-pyrrolidinyl)amino]-4-methyl-5-pyrimidinyl}acrylic acid (693 mg), O-(tetrahydro-2H-pyran-2-yl)hydroxylamine (264 mg), HOBt (290 mg) and EDCI (334 mg) in DMF (20 ml) was stirred at ambient temperature for 15 hours. The reaction mixture was poured into a mixture of AcOEt-H₂O and the organic layer was washed with brine and dried over MgSO₄. The solvent was evaporated in vacuo and the residue was chromatographed on silicagel eluting with AcOEt-MeOH (9:1). The eluted fractions containing the desired product were collected and evaporated in vacuo to give (2E)-3-{2-[(1-benzyl-3-pyrrolidinyl)amino]-4-methyl-5-pyrimidinyl}-N-(tetrahydro-2H-pyran-2-yloxy)acrylamide (200 mg).

¹H-NMR (DMSO-d6): δ 1.59-1.74 (7H, m), 1.99-2.59 (4H, m), 2.37 (3H, s), 2.79-2.87 (1H, m), 3.56 (2H, s), 3.98-4.05 (1H, m), 4.34 (1H, m), 4.89 (1H, s), 6.26 (1H, d J=15.98 Hz), 7.18-7.36 (5H, m), 7.46 (1H, d J=15.98 Hz), 7.64-7.69 (1H, m), 8.42 (1H, s), 11.13 (1H, s).

The following compounds were obtained in a similar manner to that of Preparation 562.

Preparation 563

(2E)-3-{2-[(1-benzyl-4-piperidinyl)amino]-4-methyl-5-pyrimidinyl}-N-(tetrahydro-2H-pyran-2-yloxy)acrylamide ¹H-NMR (DMSO-d6): δ 1.42-1.83 (10H, m), 1.95-2.12 (2H, m), 2.36 (3H, s), 2.73-2.82 (2H, m), 3.33 (2H, s), 3.27-3.45 (1H, m), 3.78-3.80 (1H, m), 3.95 (1H, m), 4.88 (1H, s), 6.25 (1H, d J=15.50 Hz), 7.23-7.72 (6H, m), 7.46 (1H, d J=15.50 Hz), 8.42 (1H, s), 11.13 (1H, s).

Preparation 564

(2E)-3-(4-methyl-2-{[(3R)-1-(4-methylbenzyl)-3-pyrrolidinyl]amino}-5-pyrimidinyl)-N-(tetrahydro-2H-pyran-2-yloxy)acrylamide ¹H-NMR (DMSO-d6): δ 1.65-1.99 (7H, m), 2.09-2.36 (4H, m), 2.27 (3H, s), 2.45 (3H, s), 2.76-2.84 (1H, m), 3.51-3.55 (3H, m), 3.98-7.02 (1H, m), 7.32 (1H, m), 4.88 (1H, s), 6.26 (1H, d J=15.62 Hz), 7.10 (2H, d J=8.04 Hz), 7.18 (2H, d J=8.04 Hz), 7.46 (1H, d J=15.62 Hz), 7.63 (1H, d J=6.52 Hz), 8.41 (1H, s), 11.12 (1H, s).

Preparation 565

(2E)-3-(2-{[(3R)-1-(cyclohexylmethyl)-3-pyrrolidinyl]amino}-4-methyl-5-pyrimidinyl)-N-(tetrahydro-2H-pyran-2-yloxy)acrylamide ¹H-NMR (DMSO-d6): 0.79-0.84 (2H, m), 1.06-1.77 (15H, m), 2.09-2.52 (7H, m), 2.35 (3H, s), 3.54-3.56 (1H, m), 3.93-3.99 (1H, m), 4.32 (1H, m), 4.89 (1H, s), 6.27 (1H, d J=15.52 Hz), 7.48 (1H, d J=15.52 Hz), 7.59 (1H, d J=6.72 Hz), 8.43 (1H, s), 11.13 (1H, br.s).

Preparation 566

A mixture of ethyl 5,6-dichloronicotinate (5.0 g), tert-butyl (3R)-3-amino-1-pyrrolidinecarboxylate (5.08 g) and K₂CO₃ (4.71 g) in DMF (40 ml) was stirred at 100° C. for 12 hours under atmospheric pressure of nitrogen. The reaction mixture was poured into a mixture of AcOEt and H₂O and the organic layer was washed with brine and dried over MgSO₄. The solvent was evaporated in vacuo and the residue was chromatographed on silicagel eluting with n-Hexane-AcOEt (9:1). The eluted fractions containing the desired product were collected and evaporated in vacuo to give ethyl 6-{[(3R)-1-(tert-butoxycarbonyl)-3-pyrrolidinyl]amino}-5-chloronicotinate (6.6 g).

¹H-NMR (DMSO-d6): δ 1.26 (3H, t J=7.06 Hz), 1.40 (9H, s), 1.96-2.13 (2H, m), 3.18-3.45 (3H, m), 3.58-3.66 (1H, m), 4.27 (2H, q J=7.06 Hz), 4.58-4.62 (1H, m), 7.24 (1H, d J=6.64 Hz), 7.95 (1H, d J=1.96 Hz), 8.57 (1H, d J=1.96 Hz).

The following compounds were obtained in a similar manner to that of Preparation 566.

Preparation 567 ethyl 6-[(4-tert-butylcyclohexyl)amino]-5-chloronicotinate

¹H-NMR (DMSO-d6): δ 0.85(9H, s), 0.94-2.05(9H, m), 1.29 (3H, t, J=7.0 Hz), 3.85-4.05 and 4.16-4.33(total 1H, each m), 1.18-4.33(2H, m), 6.03 and 6.83(total 1H, each d, J=6.4 Hz), 7.90 and 7.97(total 1H, each d, J=2.0 Hz), 8.53 and 8.57(total 1H, each d, J=2.0 Hz).

Preparation 568 ethyl 5-chloro-6-(cyclopentylamino)nicotinate

¹H-NMR (DMSO-d6): δ 1.26 (3H, t J=7.06 Hz), 1.56-1.73 (6H, m), 1.93-2.00 (2H, m), 4.26 (2H, q J=7.06 Hz), 4.37-4.48 (1H, m), 6.93 (1H, d J=7.34 Hz), 7.91 (1H, d J=1.98 Hz), 8.54 (1H, d J=1.98 Hz).

Preparation 569 methyl 6-{[(3R)-1-(tert-butoxycarbonyl)-3-pyrrolidinyl]amino}nicotinate

¹H-NMR (DMSO-d6): δ 1.40 (9H, s), 1.80-1.89 (1H, m), 2.10-2.16 (1H, m), 3.11-3.16 (1H, m), 3.32-3.38 (2H, m), 3.42-3.56 (1H, m), 3.77 (3H, s), 4.43 (1H, m), 6.54 (1H, d J=8.86 Hz), 7.65 (1H, d J=6.34 Hz), 7.83 (1H, dd J=2.24 Hz, 8.86 Hz), 8.59 (1H, d J=2.24 Hz).

Preparation 570

A solution of diisobutylaluminium hydride in hexane solution (0.93M) (138 ml) was added to dropwise a solution of ethyl 6-{[(3R)-1-(tert-butoxycarbonyl)-3-pyrrolidinyl]amino}-5-chloronicotinate (15.9 g) in THF (200 ml) with stirring at 0-15° C. under atmospheric pressure of nitrogen, and the reaction mixture was stirred at 5-20° C. for 4 hours. The reaction mixture was cooled at 5° C. and MeOH (10 ml) was added and the reaction mixture was stirred at ambient temperature for 20 minutes. The potassium sodium tatarate tetrahydrate (36.4 g) was added to a above solution and the resultant mixture was stirred at ambient temperature for 2 hours. The reaction mixture was filtrated and the filtrate was dried over MgSO₄. The solvent was evaporated in vacuo and the residue was chromatographed on silicagel eluting with AcOEt-n-hexane (9:1). The eluted fractions containing the desired product were collected and evaporated in vacuo to give tert-butyl (3R)-3-{[3-chloro-5-(hydroxymethyl)-2-pyridinyl]amino}-1-pyrrolidinecarboxylate (5.85 g).

¹H-NMR (DMSO-d6): δ 1.39 (9H, s), 1.90-2.14 (2H, m), 3.11-3.46 (3H, m), 3.56-3.65 (1H, m), 4.35 (2H, d J=5.56 Hz), 4.38-4.48 (1H, m), 5.09 (1H, t J=5.56 Hz), 6.38 (1H, d J=6.20 Hz), 7.56 (1H, d J=1.90 Hz), 7.95 (1H, d J=1.90 Hz).

Preparation 571

A mixture of tert-butyl (3R)-3-{[3-chloro-5-(hydroxymethyl)-2-pyridinyl]amino}-1-pyrrolidinecarboxylate (0.95 g) and MnO₂ (3.02 g) in AcOEt (30 ml) was refluxed under stirring for 1.5 hours. After removal of the insoluble material, and the solvent was evaporated in vacuo to give tert-butyl (3R)-3-[(3-chloro-5-formyl-2-pyridinyl)amino]-1-pyrrolidinecarboxylate (0.95 g).

¹H-NMR (DMSO-d6): δ 1.40 (9H, s), 1.99-2.15 (2H, m), 3.20-3.46 (3H, m); 3.56-3.67 (1H, m), 4.64-4.72 (1H, m), 7.49 (1H, d J=6.70 Hz), 7.95 (1H, d J=1.90 Hz), 8.57 (1H, d J=1.90 Hz), 9.76 (1H, s).

The following compounds were obtained in a similar manner to that of Preparation 571.

Preparation 572

5-chloro-6-(cyclopentylamino)nicotinaldehyde

¹H-NMR (DMSO-d6): δ 1.53-1.73 (6H, m), 1.80-1.97 (2H, m), 4.40-4.57 (1H, m), 7.24 (1H, d J=7.32 Hz), 7.90 (1H, d J=1.88 Hz), 8.53 (1H, d J=1.88 Hz), 9.72 (1H, s).

Preparation 573

6-[(4-tert-butylcyclohexyl)amino]-5-chloronicotinaldehyde

¹H-NMR (DMSO-d6): δ 0.98 (9H, s), 0.98-1.65 (6H, m), 1.61-1.93 (3H, m), 4.39-4.10 & 4.29-4.30 (total 1H, m), 6.25 & 7.14 (total 1H, each d J=6.40 Hz), 7.89 & 7.96 (total 1H, each d J=1.82 Hz), 8.52 & 8.57 (total 1H, each d J=1.82 Hz), 9.71 & 9.75 (total 1H, each s).

Preparation 574 tert-butyl (3R)-3-[(5-formyl-2-pyridinyl)amino]-1-pyrrolidinecarboxylate

¹H-NMR (DMSO-d6): δ 1.40 (9H, s), 1.82-1.88 (1H, m), 2.12-2.14 (1H, m), 3.13-3.18 (1H, m), 3.33-3.44 (2H, m), 3.56-3.63 (1H, m), 4.48 (1H, m), 6.61 (1H, d J=8.78 Hz), 7.56 (1H, dd J=2.18 Hz, 8.78 Hz), 8.53 (1H, d J=2.18 Hz), 9.70 (1H, s).

Preparation 575

A solution of diethylphosphonoacetcacid ethyl ester (980 mg), in THF (5 ml) was added dropwise to admixture of 60% sodium hydride in oil (187 mg) in THF (30 mL) with stirring at 10-20° C. under atmospheric pressure of nitrogen, and the reaction mixture was stirred at ambient temperature for 30 minutes. A solution of tert-butyl (3R)-3-[(3-chloro-5-formyl-2-pyridinyl)amino]-1-pyrrolidinecarboxylate (0.95 g) in THF (10 ml) solution was added the above mixture and resultant mixture was stirred at ambient temperature for 1.5 hours. The reaction mixture was poured into a mixture of AcOEt-H₂O and the organic layer was washed with brine and dried over MgSO₄. The solvent was evaporated in vacuo and the residue was chromatographed on silicagel eluting with AcOEt-n-hexane (6:4). The eluted fractions containing the desired product were collected and evaporated in vacuo to give tert-butyl (3R)-3-({3-chloro-5-[(1E)-3-ethoxy-3-oxo-1-propen-1-yl]-2-pyridinyl}amino)-1-pyrrolidinecarboxylate (0.98 g)

¹H-NMR (DMSO-d6): δ 1.25 (3H, t J=7.10 Hz), 1.40 (9H, s), 1.90-2.12 (2H, m), 3.19-3.45 (3H, m), 3.56-3.65 (1H, m), 4.16 (2H, q J=7.10 Hz), 4.57-4.60 (1H, m), 6.52 (1H, d J=15.96 Hz), 6.96 (1H, d J=6.50 Hz), 7.53 (1H, d J=15.96 Hz), 8.13 (1H, d J=1.82 Hz), 8.31 (1H, d J=1.82 Hz).

The following compounds were obtained in a similar manner to that of Preparation 575.

Preparation 576 ethyl (2E)-3-{6-[(4-tert-butylcyclohexyl)amino]-5-chloro-3-pyridinyl}acrylate

¹H-NMR (DMSO-d6): δ 0.97 (9H, s), 1.01-2.00 (9H, m), 1.24 (3H, t J=7.06 Hz), 3.96-4.02 (1H, m), 4.16 (2H, q J=7.06 Hz), 5.78 & 6.53 (total 1H, each d J=6.58 Hz), 6.46 & 6.50 (total 1H, each d J=15.98 Hz), 7.50 & 7.52 (total 1H, each d J=15.98 Hz), 8.08 & 8.14 (total 1H, each d J=1.94 Hz), 8.25 & 8.30 (total 1H, each d J=1.94 Hz), APCI-MS (m/z): 395 (M+H)+.

Preparation 577 tert-butyl (3R)-3-({5-[(1E)-3-ethoxy-3-oxo-1-propen-1-yl]-2-pyridinyl}amino)-1-pyrrolidinecarboxylate ¹H-NMR (DMSO-d6): δ 1.24 (3H, t J=7.06 Hz), 1.40 (9H, s), 1.80-1.86 (1H, m), 2.10-2.13 (1H, m), 3.05-3.16 (1H, m), 3.31-3.40 (2H, m), 3.53-3.58 (1H, m), 4.13 (2H, q, J=7.06 Hz), 4.39 (1H, m), 6.35 (1H, d J=15.86 Hz), 6.55 (1H, d J=8.84 Hz), 7.46 (1H, d J=6.78 Hz), 7.52 (1H, d J=15.86 Hz), 7.83 (1H, dd J=2.02 Hz, 8.84 Hz), 8.25 (1H, d J=2.02 Hz).

Preparation 578

Lithium aluminium hydride (1.02 g) was added to a solution of methyl 6-{[(3R)-1-(tert-butoxycarbonyl)-3-pyrrolidinyl]amino}nicotinate (5.76 g) in THF (80 ml) with stirring at 5-15° C. under atmospheric pressure of nitrogen, and the reaction mixture was stirred at 5-20° C. for 3 hours. The reaction mixture was cooled at 5° C. and H$_2$O (1 ml), 15% NaOH solution (1 ml) and H$_2$O (3 ml) was added and the resultant mixture was stirred at ambient temperature for 30 minutes. The reaction mixture was filtrated and the filtrate was dried over MgSO$_4$. The solvent was evaporated in vacuo and the residue was chromatographed on silicagel eluting with AcOEt-MeOH (9:1). The eluted fractions containing the desired product were collected and evaporated in vacuo to give tert-butyl (3R)-3-{[5-(hydroxymethyl)-2-pyridinyl]amino}-1-pyrrolidinecarboxylate (1.82 g).

$^1$H-NMR (DMSO-d6): δ 1.39 (9H, s), 1.76-1.99 (1H, m), 2.07-2.12 (1H, m), 3.06-3.13 (1H, m), 3.29-3.41 (2H, m), 3.42-3.57 (1H, m), 4.29 (2H, d J=5.52 Hz), 4.28-4.38 (1H, m), 4.91 (1H, t J=5.52 Hz), 6.47 (1H, d J=8.50 Hz), 6.66 (1H, d J=5.80 Hz), 7.35 (1H, dd J=2.02 Hz, 8.50 Hz), 7.90 (1H, d J=2.02 Hz).

The following compounds were obtained in a similar manner to that of Preparation 578.

Preparation 579

[5-chloro-6-(cyclopentylamino)-3-pyridinyl]methanol $^1$H-NMR (DMSO-d6): δ 1.44-1.68 (6H, m), 1.87-1.99 (2H, m), 4.20-4.37 (1H, m), 4.32 (2H, d J=5.72 Hz), 5.04 (1H, t J=5.72 Hz), 5.90 (1H, d J=7.12 Hz), 7.51 (1H, d J=1.94 Hz), 7.92 (1H, d J=1.94 Hz).

Preparation 580

{6-[(4-tert-butylcyclohexyl)amino]-5-chloro-3-pyridinyl}methanol $^1$H-NMR (DMSO-d6): 0.97 (9H, s), 0.97-1.56 (6H, m), 1.73-1.99 (3H, m), 3.78-3.82 (1H, m), 4.16-4.35 (2H, m), 5.01-5.10 (1H, m), 5.27 & 5.74 (total 1H, each d J=5.88 Hz), 7.50 & 7.56 (total 1H, each d J=1.92 Hz), 7.89 & 7.94 (total 1H, each d J=1.92 Hz).

Preparation 581

A solution of ethyl (2E)-3-{5-chloro-6-[(3R)-3-pyrrolidinylamino]-3-pyridinyl}acrylate dihydrochloride (2.0 g) in H$_2$O (10 ml) was adjusted to pH 8.5 With 20% K$_2$CO$_3$ solution and extracted with CHCl$_3$. The extract was dried over MgSO$_4$, the solvent was evaporated in vacuo to give ethyl (2E)-3-{5-chloro-6-[(3R)-3-pyrrolidinylamino]-3-pyridinyl}acrylate (1.47 g).

$^1$H-NMR (DMSO-d6): δ 1.25 (3H, t J=7.08 Hz), 1.99-2.09 (2H, m), 2.64-2.75 (2H, m), 2.87-3.01 (2H, m), 4.16 (2H, q J=7.08 Hz), 4.44-4.47 (1H, m), 6.49 (1H, d J=15.94 Hz), 6.72 (1H, d J=7.14 Hz), 7.52 (1H, d J=15.94 Hz), 8.09 (1H, d J=1.96 Hz), 8.28 (1H, d J=1.96 Hz).

Preparation 582

A mixture of tert-butyl (3R)-3-({5-[(1E)-3-ethoxy-3-oxo-1-propen-1-yl]-2-pyridinyl}amino)-1-pyrrolidinecarboxylate (600 mg) and 1N NaOH solution (3.3 ml) in MeOH (10 ml) and THF (10 ml) was stirred at 70-75° C. for 2 hours. The reaction mixture was evaporated in vacuo and the residue was dissolved in a mixture of AcOEt and H$_2$O. The aqueous solution was adjusted to PH4.5 and extracted with AcOEt and THF. The organic layer was washed with brine and dried over MgSO$_4$. The solvent was concentrated in vacuo and the precipitate was collected by filtration to give (2E)-3-(6-{[(3R)-1-(tert-butoxycarbonyl)-3-pyrrolidinyl]amino}-3-pyridinyl)acrylic acid (0.45 g).

$^1$H-NMR (DMSO-d6): δ 1.41 (9H, s), 1.84-1.87 (1H, m), 2.11-2.14 (1H, m), 3.10-3.19 (1H, m), 3.34-3.42 (2H, m), 3.55-3.58 (1H, m), 4.36-4.42 (1H, m), 6.29 (1H, d J=15.88 Hz), 6.62 (1H, d J=8.76 Hz), 7.48 (1H, d J=15.88 Hz), 7.64 (1H, m), 7.85 (1H, dd J=2.16 Hz, 8.76 Hz), 8.23 (1H, d J=2.16 Hz), 11.14 (1H, s).

Preparation 583

A mixture of (2E)-3-(6-{[(3R)-1-(tert-butoxycarbonyl)-3-pyrrolidinyl]amino}-3-pyridinyl)acrylic acid (450 mg), 0-(tetrahydro-2H-pyran-2-yl)hydroxylamine (174 mg), HOBt (191 mg) and EDCI (220 mg) in DMF (20 ml) was stirred at ambient temperature for 15 hours. The reaction mixture was poured into a mixture of AcOEt-H$_2$O and the organic layer was washed with brine and dried over MgSO$_4$. The solvent was evaporated in vacuo and the residue was chromatographed on silicagel eluting with AcOEt-MeOH (95:5). The eluted fractions containing the desired product were collected and evaporated in vacuo to give tert-butyl (3R)-3-[(5-[(1E)-3-oxo-3-[(tetrahydro-2H-pyran-2-yloxy)amino]-1-propen-1-yl)-2-pyridinyl)amino]-1-pyrrolidinecarboxylate (450 mg).

$^1$H-NMR (DMSO-d6): δ 1.39 (9H, s), 1.69-2.00 (7H, m), 2.00-2.12 (1H, m), 3.09-3.15 (1H, m), 3.34-3.43 (3H, m), 3.50-3.55 (2H, m), 3.93-3.95 (1H, m), 4.37 (1H, m), 4.88 (1H, s), 6.24 (1H, d J=15.74 Hz), 6.55 (1H, d J=8.76 Hz), 7.30 (1H, d J=8.12 Hz), 7.37 (1H, d J=15.74 Hz), 7.63 (1H, d J=8.76 Hz), 8.17 (1H, s), 11.06 (1H, s).

Preparation 584

A solution of ethyl (2E)-3-(5-chloro-6-{[(3R)-1-(cyclohexylmethyl)-3-pyrrolidinyl]amino}-3-pyridinyl)acrylate (330 mg) and 1N NaOH solution (1.5 ml) in MeOH (30 ml) was stirred at 80-85° C. for 2 hours. The reaction mixture was evaporated in vacuo and the residue was dissolved in a mixture was AcOEt and H$_2$O. The aquous solution was adjusted to PH 5.4 with 5% HCl solution and resultant solution was evaporated in vacuo and the residue was dissolved in a MeOH and THF. The solvent was evaporated in vacuo and dried to give (2E)-3-(5-chloro-6-{[(3R)-1-(cyclohexylmethyl)-3-pyrrolidinyl]amino}-3-pyridinyl)acrylic acid (306 mg).

$^1$H-NMR (DMSO-d6): δ 0.80-0.91 (2H, m), 1.14-1.62 (4H, m), 1.71-1.84 (7H, m), 2.13-2.62 (4H, m), 2.73-2.81 (1H, m), 4.39-4.45 (1H, m), 6.36 (1H, d J=15.88 Hz), 6.45 (1H, d J=7.08 Hz), 7.26 (1H, d J=15.88 Hz), 7.94 $_1$(1H, d J=1.76 Hz), 8.17 (1H, d J=1.76 Hz).

The following compounds were obtained in a similar manner to that of Preparation 584.

Preparation 585

(2E)-3-(5-chloro-6-{[(3R)-1-(cyclobutylmethyl)-3-pyrrolidinyl]amino}-3-pyridinyl)acrylic acid $^1$H-NMR (DMSO-d6): δ 1.62-1.81 (9H, m), 2.30-2.52 (5H, m), 2.75-2.79 (1H, m), 4.38-4.45 (1H, m), 6.29 (1H, d J=15.84 Hz), 6.30 (1H, d J=7.20 Hz), 7.07 (1H, d J=15.84 Hz), 7.84 (1H, d J=1.84 Hz), 8.10 (1H, d J=1.84 Hz).

Preparation 586

(2E)-3-(5-chloro-6-{[(3R)-1-(3-methyl-2-buten-1-yl)-3-pyrrolidinyl]amino}-3-pyridinyl)acrylic acid $^1$H-NMR (DMSO-d6): δ 1.61 (3H, s), 1.68 (3H, s), 1.68-1.79 (1H, m), 2.00-2.30 (1H, m), 2.42-2.82 (4H, m), 3.00 (2H, m), 4.44-4.49 (1H, m), 5.20-5.27 (1H, m), 6.37 (1H, d J=15.88 Hz), 6.50 (1H, d J=6.98 Hz), 7.27 (1H, d J=15.68 Hz), 7.96 (1H, d J=1.86 Hz), 8.18 (1H, d J=1.86 Hz).

Preparation 587

(2E)-3-(5-chloro-6-{[(3R)-1-(2-pyridinylmethyl)-3-pyrrolidinyl]amino}-3-pyridinyl)acrylic acid $^1$H-NMR (DMSO-d6): 1.80-1.87 (1H, m), 2.18-2.47 (1H, m), 2.47-2.57 (2H, m), 2.66-2.73 (1H, m), 2.85-2.90 (1H, m), 3.72 (2H, s), 4.48-4.51 (1H, m), 6.34 (1H, d J=15.90 Hz), 6.46 (1H, d J=6.94 Hz), 7.13-7.28 (2H, m), 7.42-7.46 (1H, m), 7.72-7.76 (1H, m), 7.88 (1H, d J=1.80 Hz), 8.12 (1H, d J=1.80 Hz), 8.47-8.50 (1H, m).

Preparation 588

(2E)-3-(5-chloro-6-{[(3R)-1-(cyclopropylmethyl)-3-pyrrolidinyl]amino}-3-pyridinyl)acrylic acid $^1$H-NMR (DMSO-d6): δ 0.08-0.13 (2H, m), 0.40-0.49 (2H, m), 0.78-0.95 (1H, m), 1.70-1.90 (1H, m), 2.08-2.25 (1H, m), 2.31 (2H, d J=6.60 Hz), 2.50-2.60 (2H, m), 2.73-2.90 (2H, m), 4.49-4.56 (1H, m), 6.38 (1H, d J=15.90 Hz), 6.56 (1H, d J=7.06 Hz), 7.26 (1H, d J=15.90 Hz), 7.94 (1H, d J=1.84 Hz), 8.18 (1H, d J=1.84 Hz).

Preparation 589

(2E)-3-(5-chloro-6-{[(3R)-1-(cyclopentylmethyl)-3-pyrrolidinyl]amino}-3-pyridinyl)acrylic acid $^1$H-NMR (DMSO-d6): δ 1.16-1.22 (2H, m), 1.45-2.30 (14H, m), 2.52-2.67 (1H, m), 2.79-2.84 (1H, m), 4.44-4.51 (1H, m), 6.39 (1H, d J=15.86 Hz), 6.55 (1H, d J=7.08 Hz), 7.34 (1H, d J=15.86 Hz), 7.99 (1H, d J=1.82 Hz), 8.20 (1H, d J=1.82 Hz).

Preparation 590

A solution of ethyl (2E)-3-{5-chloro-6-[(3R)-3-pyrrolidinylamino]-3-pyridinyl}acrylate dihydrochloride (1.0 g), bromomethylcyclobutane (456 mg) and N,N-diisopropylethylamine (1.26 g) in DMF (30 ml) was stirred at 80-85° C. for 12 hours under atmospheric pressure of nitrogen. The reaction mixture was poured into a mixture of AcOEt and H$_2$O and the organic layer was washed with brine and dried over MgSO$_4$. The solvent was evaporated in vacuo and the residue was chromatographed on silicagel eluting with AcOEt-MeOH (95:5). The eluted fractions containing the desired product were collected and evaporated in vacuo to give ethyl (2E)-3-(5-chloro-6-{[(3R)-1-(cyclobutylmethyl)-3-pyrrolidinyl]amino}-3-pyridinyl)acrylate (356 mg).

$^1$H-NMR (DMSO-d6): δ 1.24 (3H, t J=7.08 Hz), 1.70-2.09 (9H, m), 2.46-2.52 (6H, m), 2.73-2.77 (1H, m), 4.16 (2H, q J=7.08 Hz), 4.43-4.50 (1H, m), 6.49 (1H, d J=15.96 Hz), 6.67 (1H, d J=7.00 Hz), 7.52 (1H, d J=15.96 Hz), 8.10 (1H, d J=1.92 Hz), 8.28 (1H, d J=1.92 Hz).

The following compound was obtained in a similar manner to that of Preparation 590.

Preparation 591 ethyl (2E)-3-(5-chloro-6-{[(3R)-1-(3-methyl-2-buten-1-yl)-3-pyrrolidinyl]amino}-3-pyridinyl)acrylate $^1$H-NMR (DMSO-d6): δ 1.24 (3H, t J=7.08 Hz), 1.61 (3H, s), 1.68 (3H, s), 1.78-1.81 (1H, m), 2.14-2.19 (1H, m), 2.43-2.52 (2H, m), 2.60-2.89 (2H, m), 3.02 (2H, d J=6.76 Hz), 3.39 (1H, m), 4.16 (2H, q J=7.08 Hz), 4.44-4.51 (1H, m), 5.20-5.26 (1H, m), 6.49 (1H, d J=15.94 Hz), 6.69 (1H, d J=6.94 Hz), 7.52 (1H, d J=15.94 Hz), 8.10 (1H, d J=1.94 Hz), 8.28 (1H, d J=1.94 Hz).

Preparation 592

A mixture of ethyl (2E)-3-{5-chloro-6-[(3R)-3-pyrrolidinylamino]-3-pyridinyl}acrylate (0.73 g), m-tolualdehyde (356 mg) and sodium triacetoxyborohydride (1.57 g) in CH$_2$Cl$_2$ (30 ml) was stirred at 25-30° C. for 15 hours. The 10% K$_2$CO$_3$ solution (20 ml) was added to a reaction mixture and resultant mixture was stirred at ambient temperature for 30 minutes and extracted with CH$_2$Cl$_2$ and washed with brine and dried over MgSO$_4$. The solvent was evaporated in vacuo and the residue was chromatographed on silicagel eluting with AcOEt-MeOH (97:3). The eluted fractions containing the desired product were collected and evaporated in vacuo to give ethyl (2E)-3-(5-chloro-6-{[(3R)-1-(3-methylbenzyl)-3-pyrrolidinyl]amino}-3-pyridinyl)acrylate (820 mg).

$^1$H-NMR (DMSO-d6): δ 1.24 (3H, t J=7.06 Hz), 1.86-1.99 (1H, m), 2.16-2.40 (1H, m), 2.40 (3H, s), 2.42-2.53 (2H, m), 2.62-2.66 (1H, m), 2.77-2.85 (1H, m), 3.54 (2H, s), 4.16 (2H, q J=7.06 Hz), 4.45-4.53 (1H, m), 6.49 (1H, d J=15.96 Hz), 6.72 (1H, d J=6.92 Hz), 7.02-7.24)$_4$H, m), 7.51 (1H, d J=15.96 Hz), 8.10 (1H, d J=1.90 Hz), 8.20 (1H, d J=1.90 Hz).

The following compounds were obtained in a similar manner to that of Preparation 592.

Preparation 593 ethyl (2E)-3-(5-chloro-6-{[(3R)-1-(cyclohexylmethyl)-3-pyrrolidinyl]amino}-3-pyridinyl)acrylate $^1$H-NMR (DMSO-d6): δ 0.80-0.92 (2H, m), 1.12-1.34 (4H, m), 1.24 (3H, t J=7.08 Hz), 1.63-1.78 (5H, m), 2.18-2.22 (2H, m), 2.37-2.52 (3H, m), 2.76-2.80 (1H, m), 3.16-3.22 (2H, m), 4.16 (2H, q J=7.08 Hz), 4.48-4.51 (1H, m), 6.49 (1H, d J=15.96 Hz), 6.95 (1H, d J=7.02 Hz), 7.52 (1H, d J=15.96 Hz), 8.10 (1H, d J=1.90 Hz), 8.28 (1H, d J=1.90 Hz).

Preparation 594 ethyl (2E)-3-(5-chloro-6-{[(3R)-1-(3-fluorobenzyl)-3-pyrrolidinyl]amino}-3-pyridinyl)acrylate $^1$H-NMR (DMSO-d6): δ 1.25 (3H, t J=7.08 Hz), 1.85-1.92 (1H, m), 2.18-2.22 (1H, m), 2.42-2.49 (2H, m), 2.61-2.68 (1H, m), 2.80-2.89 (1H, m), 3.62 (2H, s), 4.16 (2H, q J=7.08 Hz), 5.31-5.36 (1H, m), 6.49 (1H, d J=15.92 Hz), 6.74 (1H, d J=6.92 Hz), 7.01-7.17 (3H, m), 7.30-7.41 (1H, m), 7.52 (1H, d J=15.92 Hz), 8.10 (1H, d J=1.84 Hz), 8.27 (1H, d J=1.84 Hz).

Preparation 595 ethyl (2E)-3-(5-chloro-6-{[(3R)-1-(2-pyridinylmethyl)-3-pyrrolidinyl]amino}-3-pyridinyl)acrylate $^1$H-NMR (DMSO-d6): δ 1.24 (3H, t J=7.06 Hz), 1.84-1.91 (1H, m), 2.10-2.23 (1H, m), 2.49-2.58 (2H, m), 2.70-2.74

(1H, m), 2.86-2.95 (1H, m), 3.73 (2H, s), 4.16 (2H, q J=7.06 Hz), 4.52-4.59 (1H, m), 6.49 (1H, d J=15.90 Hz), 6.75 (1H, d J=6.92 Hz), 7.22-7.28 (1H, m), 7.42-7.48 (1H, m), 7.52 (1H, d J=15.90 Hz), 7.72-7.76 (1H, m), 8.10 (1H, d J=1.92 Hz), 8.27 (1H, d J=1.92 Hz), 8.47-8.50 (1H, m).

Preparation 596 ethyl (2E)-3-(5-chloro-6-{[(3R)-1-(cyclopropylmethyl)-3-pyrrolidinyl]amino}-3-pyridinyl)acrylate $^1$H-NMR (DMSO-d6): δ 0.34-0.11 (2H, m), 0.39-0.48 (2H, m), 0.70-0.92 (1H, m), 1.24 (3H, t J=7.06 Hz), 1.70-1.90 (1H, m), 2.05-2.26 (1H, m), 2.26 (2H, d J=6.64 Hz), 2.46-2.67 (2H, m), 2.67-2.71 (1H, m), 2.80-2.88 (1H, m), 4.16 (1H, d J=7.06 Hz), 6.49 (1H, d J=15.90 Hz), 6.70 (1H, d J=6.98 Hz), 7.52 (1H, d J=15.90 Hz), 8.10 (1H, d J=1.90 Hz), 8.28 (1H, d J=1.90 Hz).

Preparation 597 ethyl (2E)-3-(5-chloro-6-{[(3R)-1-(cyclopentylmethyl)-3-pyrrolidinyl]amino}-3-pyridinyl)acrylate $^1$H-NMR (DMSO-d6): δ 1.06-1.28 (2H, m), 1.24 (3H, t J=7.06 Hz), 1.47-2.50 (14H, m), 2.55-2.69 (1H, m), 2.70-2.82 (1H, m), 4.16 (2H, q J=7.06 Hz), 6.49 (1H, d J=15.92 Hz), 6.66 (1H, d J=7.02 Hz), 7.52 (1H, d J=15.92 Hz), 8.10 (1H, d J=1.92 Hz), 8.28 (1H, d J=1.92 Hz).

Preparation 598

A solution of ethyl (2E)-3-(5-chloro-6-{[(3R)-1-(3-methylbenzyl)-3-pyrrolidinyl]amino}-3-pyridinyl)acrylate (820 mg) and 1N NaOH solution (4.1 ml) in MeOH (20 ml) was stirred at 80-85° C. for 2 hours. The reaction mixture was evaporated in vacuo and the residue was dissolved in a mixture of AcOEt and brine. The aquous solution was adjusted to PH 5.4 with 5% HCl solution and extracted with THF and AcOEt. The solvent was evaporated in vacuo and The precipitate was washed with n-hexane to give (2E)-3-(5-chloro-6-{[(3R)-1-(3-methylbenzyl)-3-pyrrolidinyl]amino}-3-pyridinyl)acrylic acid (410 mg).

$^1$H-NMR (DMSO-d6): δ 1.76-1.90 (1H, m), 2.17-2.29 (1H, m), 2.49 (3H, s), 2.49-2.61 (2H, m), 2.74-2.77 (1H, m), 2.87-2.95 (1H, m), 3.60 (2H, s), 4.46-4.58 (1H, m), 6.39 (1H, d J=15.92 Hz), 6.75 (1H, d J=6.88 Hz), 7.05-7.25 (4H, m), 7.45 (1H, d J=15.92 Hz), 8.07 (1H, d J=1.82 Hz), 8.24 (1H, d J=1.82 Hz).

The following compounds were obtained in a similar manner to that of Preparation 598.

Preparation 599

(2E)-3-[5-chloro-6-(cyclopentylamino)-3-pyridinyl]acrylic acid $^1$H-NMR (DMSO-d6): δ 1.54-1.71 (6H, m), 1.90-2.00 (2H, m), 4.32-4.46 (1H, m), 6.38 (1H, d J=15.84 Hz), 6.60 (1H, d J=7.26 Hz), 7.47 (1H; d J=15.84 Hz), 8.04 (1H, d J=1.96 Hz), 8.25 (1H, d J=1.96 Hz).

Preparation 600

(2E)-3-{6-[(4-tert-butylcyclohexyl)amino]-5-chloro-3-pyridinyl}acrylic acid $^1$H-NMR (DMSO-d6): δ 0.97 (9H, s), 1.02-1.99 (9H, m), 3.85-3.98 & 4.20 (total 1H, each m), 5.78 & 6.50 (total 1H, each d J=6.58 Hz), 6.36 & 6.58 (total 1H, each J=15.96 Hz), 7.45 & 7.47 (total 1H, each d J=15.96 Hz), 8.03 & 8.11 (total 1H, each d J=1.90 Hz), 8.23 & 8.28 (total 1H, each d J=1.90 Hz).

Preparation 601

(2E)-3-(5-chloro-6-{[(3R)-1-(3-fluorobenzyl)-3-pyrrolidinyl]amino}-3-pyridinyl)acrylic acid $^1$H-NMR (DMSO-d6): δ 1.76-1.93 (1H, m), 2.19-2.26 (1H, m), 2.50-2.63 (2H, m), 2.77-2.80 (1H, m), 2.91-2.99 (1H, m), 3.73 (2H, s), 4.53-4.61 (1H, m), 6.41 (1H, d J=15.94 Hz), 6.78 (1H, d J=6.90 Hz), 6.88-7.22 (3H, m), 7.33-7.40 (1H, m), 7.47 (1H, d J=15.94 Hz), 8.07 (1H, d J=1.84 Hz), 8.25 (1H, d J=1.84 Hz).

Preparation 602

(2E)-3-(5-chloro-6-{[(3R)-1-(cyclohexylcarbonyl)-3-pyrrolidinyl]amino}-3-pyridinyl)acrylic acid $^1$H-NMR (DMSO-d6): δ 1.14-1.36 (6H, m), 1.66-1.69 (4H, m), 1.91-2.18 (3H, m), 3.27-3.71 (4H, m), 4.52-4.72 (1H, m), 6.42 (1H, d J=15.90 Hz), 6.87-6.98 (1H, m), 7.48 (1H, d J=15.90 Hz), 8.10 (1H, d J=1.92 Hz), 8.28 (1H, d J=1.92 Hz), 12.21 (1H, br.s).

Preparation 603

(2E)-3-[5-chloro-6-({(3R)-1-[(4-methylphenyl)sulfonyl]-3-pyrrolidinyl}amino)-3-pyridinyl]acrylic acid $^1$H-NMR (DMSO-d6): δ 1.90-2.06 (2H, m), 2.39 (3H, s), 3.09-3.52 (4H, m), 4.28-4.37 (1H, m), 6.42 (1H, d J=15.90 Hz), 6.61 (1H, d J=5.92 Hz), 7.36 (2H, d J=8.14 Hz), 7.47 (1H, d J=15.90 Hz), 7.64 (2H, d J=8.14 Hz), 8.06 (1H, d J=1.90 Hz), 8.24 (1H, d J=1.90 Hz), 12.23 (1H, br.s).

Preparation 604

(2E)-3-[6-({(3R)-1-[(4-methylphenyl)sulfonyl]-3-pyrrolidinyl}amino)-3-pyridinyl]acrylic acid $^1$H-NMR (DMSO-d6): δ 1.72-1.74° (1H, m), 1.91-2.02 (1H, m), 2.39 (3H, s), 3.03-3.10 (1H, m), 3.19-3.45 (3H, m), 4.18-4.26 (1H, m), 6.26 (1H, d J=15.82 Hz), 6.41 (1H, d J=8.82 Hz), 7.28 (1H, m), 7.38 (2H, d J=8.06 Hz), 7.46 (1H, d J=15.82 Hz), 7.65 (2H, d J=8.06 Hz), 7.78 (1H, dd J=2.04 Hz, 8.82 Hz), 8.18 (1H, d J=2.04 Hz).

Preparation 605

(2E)-3-(6-{[(3R)-1-(1-piperidinylcarbonyl)-3-pyrrolidinyl]amino}-3-pyridinyl)acrylic acid $^1$H-NMR (DMSO-d6): δ 1.36-1.49 (6H, m), 1.71-1.91 (1H, m), 1.99-2.13 (1H, m), 3.12-3.17 (4H, m), 3.34-3.47 (3H, m), 3.57-3.66 (1H, m), 4.30-4.36 (1H, m), 6.25 (1H, d J=15.92 Hz), 6.55 (1H, d J=8.86 Hz), 7.38 (1H, d J=6.16 Hz), 7.46 (1H, d J=15.92 Hz), 7.79 (1H, dd J=2.08 Hz, 8.86 Hz), 8.21 (1H, d J=2.08 Hz), 12.06 (1H, s).

Preparation 606

(2E)-3-(5-chloro-6-{[(3R)-1-(1-piperidinylcarbonyl)-3-pyrrolidinyl]amino}-3-pyridinyl)acrylic acid $^1$H-NMR (DMSO-d6): δ 1.76 (6H, br.s), 1.91-2.12 (2H, m), 3.12 (4H, br.s), 3.25-3.43 (3H, m), 3.53-3.62 (1H, m), 4.46-

4.56 (1H, m), 6.41 (1H, d J=15.98 Hz), 6.69 (1H, d J=6.40 Hz), 7.47 (1H, d J=15.98 Hz), 8.09 (1H, d J=1.84 Hz), 8.28 (1H, d J=1.84 Hz).

Preparation 607

(2E)-3-(5-chloro-6-{[(3R)-1-(cyclopentylcarbonyl)-3-pyrrolidinyl]amino}-3-pyridinyl)acrylic acid ¹H-NMR (DMSO-d6): δ 1.49-1.77 (8H, m), 1.90-2.30 (2H, m), 2.70-2.86 (1H, m), 3.28-3.67 (3H, m), 3.68-3.84 (1H, m), 4.49-4.68 (1H, m), 6.42 (1H, d J=15.96 Hz), 6.87-6.98 (1H, m), 7.48 (1H, d J=15.96 Hz), 8.10 (1H, d J=1.76 Hz), 8.29 (1H, d J=1.78 Hz), 12.15 (1H, br.s).

Preparation 608

(2E)-3-(5-chloro-6-{[(3R)-1-(cyclobutylcarbonyl)-3-pyrrolidinyl]amino}-3-pyridinyl)acrylic acid ¹H-NMR (DMSO-d6): δ 1.72-2.18 (9H, m), 3.21-3.71 (4H, m), 4.48-4.64 (1H, m), 6.41 (1H, d J=15.94 Hz), 6.85-6.97 (1H, m), 7.44 (1H, d J=15.94 Hz), 8.11 (1H, s), 8.29 (1H, s), 12.21 (1H, br.s).

Preparation-609

(2E)-3-(5-chloro-6-{[(3R)-1-(4-chlorobenzoyl)-3-pyrrolidinyl]amino}-3-pyridinyl)acrylic acid ¹H-NMR (DMSO-d6): δ 2.12-2.18 (2H, m), 3.38-3.66 (4H, m), 4.54-4.69 (1H, m), 6.36-6.47 (1H, m), 6.88-7.07 (1H, m), 7.40-7.59 (5H, m), 8.09 & 8.12 (total 1H, each s), 8.22- & 8.31 (total 1H, each s).

Preparation 610

(2E)-3-(5-chloro-6-{[(3R)-1-(2-pyrimidinyl)-3-pyrrolidinyl]amino}-3-{pyridinyl}acrylic acid ¹H-NMR (DMSO-d6): δ 2.06-2.31 (2H, m), 3.55-3.70 (3H, m), 3.84-3.93 (1H, m), 4.67-4.77 (1H, m), 6.42 (1H, d J=15.90 Hz), 6.49-6.59 (1H, m), 7.00 (1H, d J=6.42 Hz), 7.49 (1H, d J=15.90 Hz), 8.10 (1H, d J=1.90 Hz), 8.31-8.46 (3H, m), 12.17 (1H, br, s).

Preparation 611

(2E)-3-(5-chloro-6-{[(3R)-1-(4-fluorobenzoyl)-3-pyrrolidinyl]amino}-3-pyridinyl)acrylic acid ¹H-NMR (DMSO-d6): δ 2.09-2.21 (2H, m), 3.34-3.76 (4H, m), 4.54-4.68 (1H, m), 6.39 & 6.43 (total 1H, each d J=15.96 Hz), 6.98 & 7.04 (total 1H, each d J=6.32 Hz), 7.21 (2H, m), 7.44 & 7.49 (total 1H, each d J=15.96 Hz), 7.56-7.65 (2H, m), 8.08 & 8.11 (total 1H, each s), 8.22 & 8.31 (total 1H, each s), 12.26 (1H, br.s).

Preparation 612

(2E)-3-(5-chloro-6-{[(3R)-1-(3-methylbenzoyl)-3-pyrrolidinyl]amino}-3-pyridinyl)acrylic acid ¹H-NMR (DMSO-d6): δ 2.09-2.21 (2H, m), 2.32 & 2.35 (total 1H, each s), 3.36-3.74 (4H, m), 4.52-4.69 (1H, m), 6.39 & 6.43 (total 1H, each d J=15.92 Hz), 6.97 & 7.03 (total 1H, each d J=6.52 Hz), 7.29-7.36 (4H, m), 7.43 & 7.49 (total 1H, d each d J=15.92 Hz), 8.08 & 8.12 (total 1H, each d J=1.40 Hz), 8.23 & 8.31 (total 1H, each d J=1.40 Hz), 12.20 (1H, br.s).

Preparation 613

(2E)-3-(5-chloro-6-{[(3R)-1-(3-chlorobenzoyl)-3-pyrrolidinyl]amino}-3-pyridinyl)acrylic acid ¹H-NMR (DMSO-d6): δ 2.09-2.19 (2H, m), 3.35-3.73 (4H, m), 4.55-4.70 (1H, m), 6.40 & 6.43 (total 1H, each d J=15.96 Hz), 6.93 & 7.00 (total 1H, each d J=6.26 Hz), 7.36-7.57 (5H, m), 8.08 & 8.12 (total 1H, each d J=1.70 Hz), 8.23 & 8.31 (total 1H, each d J=1.70 Hz), 12.19 (1H, br.s).

Preparation 614

(2E)-3-(5-chloro-6-{[(3R)-1-(2-chlorobenzoyl)-3-pyrrolidinyl]amino}-3-pyridinyl)acrylic acid ¹H-NMR (DMSO-d6): 2.07-2.18 (2H, m), 3.09-3.56 (3H, m), 3.83-3.86 (1H, m), 4.57-4.67 (1H, m), 6.40 & 6.43 (total 1H, each d J=15.96 Hz), 6.93 & 7.00 (total 1H, each d J=6.40 Hz), 7.36-7.57 (5H, m), 8.08 & 8.11 (total 1H, each d J=1.86 Hz), 8.22 & 8.31 (total 1H, each d J=1.86 Hz), 12.19 (1H, br.s).

Preparation 615

A mixture of A mixture of (2E)-3-(5-chloro-6-{[(3R)-1-(3-methylbenzyl)-3-pyrrolidinyl]amino}-3-pyridinyl)acrylic acid (410 mg), O-(tetrahydro-2H-pyran-2-yl)hydroxylamine (142 mg), HOBt (156 mg) and EDCI (180 mg) in DMF (15 ml) was stirred at ambient temperature for 15 hours. The reaction mixture was poured into a mixture of AcOEt-H₂O and the organic layer was washed with brine and dried over MgSO₄. The solvent was evaporated in vacuo and the residue was chromatographed on silicagel eluting with AcOEt-MeOH (9:1). The eluted fractions containing the desired product were collected and evaporated in vacuo to give (2E)-3-(5-chloro-6-{[(3R)-1-(3-methylbenzyl)-3-pyrrolidinyl]amino}-3-pyridinyl)-N-(tetrahydro-2H-pyran-2-yloxy)acrylamide (400 mg).

¹H-NMR (DMSO-d6): δ 1.23-1.84 (7H, m), 2.09-2.29 (1H, m), 2.29 (3H, s), 2.37-2.53 (2H, m), 2.63-2.65 (1H, m), 2.74-2.89 (1H, m), 3.55 (2H, s), 3.30-3.57 (2H, m), 3.94-4.01 (1H, m), 4.44-4.55 (1H, m), 4.89 (1H, s), 6.32 (1H, d J=15.64 Hz), 6.61 (1H, d J=6.88 Hz), 7.02-7.23 (4H, m), 7.36 (1H, d J=15.64 Hz), 7.84 (1H, s), 7.20 (1H, s), 11.07 (1H, s).

The following compounds were obtained in a similar manner to that of Preparation 615.

Preparation 616

(2E)-3-[5-chloro-6-(cyclopentylamino)-3-pyridinyl]-N-(tetrahydro-2H-pyran-2-yloxy)acrylamide ¹H-NMR (DMSO-d6): δ 1.53-1.84 (12H, m), 1.89-1.99 (2H, m), 3.49-3.55 (1H, m), 3.93-4.05 (1H, m), 4.30-4.41 (1H, m), 4.89 (1H, s), 6.31 (1H, d J=15.76 Hz), 6.54 (1H, d J=7.26 Hz), 7.36 (1H, d J=15.76 Hz), 7.82 (1H, s), 8.21 (1H, s), 11.07 (1H, s).

Preparation 617

(2E)-3-{6-[(4-tert-butylcyclohexyl)amino]-5-chloro-3-pyridinyl}-N-(tetrahydro-2H-pyran-2-yloxy)acrylamide ¹H-NMR (DMSO-d6): δ 0.85 (9H, s), 1.00-2.00 (15H, m), 3.49-3.55 (1H, m), 3.86-4.20 (2H, m), 4.89 (1H, s), 5.70 &

6.43 (total 1H, each d J=6.58 Hz), 6.34-6.41 (1H, m), 7.32-7.40 (1H, m), 7.82 & 7.87 (total 1H, each s), 8.19 & 8.23 (total 1H, each s), 11.07 (1H, s).

Preparation 618

A mixture of (2E)-3-(5-chloro-6-{[(3R)-1-(cyclohexylmethyl)-3-pyrrolidinyl]amino}-3-pyridinyl)acrylic acid (306 mg), O-(tetrahydro-2H-pyran-2-yl)hydroxylamine (108 mg) HOBt (119 mg) and EDCI (137 mg) in DMF (15 ml) was stirred at ambient temperature for 15 hours. The reaction mixture was poured into a mixture of AcOEt-$H_2O$ and the organic layer was washed with brine and dried over $MgSO_4$. The solvent was evaporated in vacuo and the residue was chromatographed on silicagel eluting with AcOEt-MeOH (9:1). The eluted fractions containing the desired product were collected and evaporated in vacuo to give (2E)-3-(5-chloro-6-{[(3R)-1-(cyclohexylmethyl)-3-pyrrolidinyl]amino}-3-pyridinyl)-N-(tetrahydro-2H-pyran-2-yloxy)acrylamide (100 mg).

$^1$H-NMR (DMSO-d6): δ 0.64-0.92 (2H, m), 1.02-1.23 (4H, m), 1.23-1.91 (12H, m), 2.09-3.06 (7H, m), 3.49-3.55 (1H, m), 3.95-4.02 (1H, m), 4.48-4.56 (1H, m), 4.89 (1H, s), 6.32 (1H, d J=15.76 Hz), 6.59 (1H, d J=5.04 Hz), 7.36 (1H, d J=15.76 Hz), 7.85 (1H, s), 8.21 (1H, s), 11.08 (1H, s).

The following compounds were obtained in a similar manner to that of Preparation 618.

Preparation 619

(2E)-3-(5-chloro-6-{[(3R)-1-(cyclobutylmethyl)-3-pyrrolidinyl]amino}-3-pyridinyl)-N-(tetrahydro-2H-pyran-2-yloxy)acrylamide $^1$H-NMR (DMSO-d6): δ 1.53-2.09 (15H, m), 2.39-2.52 (6H, m), 2.78-2.79 (1H, m), 3.36-3.55 (3H, m), 3.93-3.49 (1H, m), 4.39-4.46 (1H, m), 4.89 (1H, s), 6.32 (1H, d J=15.80 Hz), 6.58 (1H, d J=7.00 Hz), 7.36 (1H, d J=15.80 Hz), 7.84 (1H, d J=1.60 Hz), 8.21 (1H, d J=1.60 Hz), 11.07 (1H, br.s).

Preparation 620

(2E)-3-(5-chloro-6-{[(3R)-1-(3-methyl-2-buten-1-yl)-3-pyrrolidinyl]amino}-3-pyridinyl)-N-(tetrahydro-2H-pyran-2-yloxy)acrylamide $^1$H-NMR (DMSO-d6): δ 1.14-1.91 (7H, m), 1.63 (3H, s), 1.69 (3H, s), 2.09-2.16 (1H, m), 2.49-2.57 (2H, m), 2.73-2.92 (2H, m), 2.92-3.10 (2H, m), 3.49-3.51 (1H, m), 3.95 (1H, m), 4.48-4.52 (1H, m), 4.89 (1H, s), 5.24-5.27 (1H, m), 6.33 (1H, d J=15.74 Hz), 6.65 (1H, d J=6.90 Hz), 7.36 (1H, d J=15.74 Hz), 7.86 (1H, s), 8.21 (1H, s), 11.08 (1H, s).

The following compounds were obtained in a similar manner to that of Preparation 615.

Preparation 621

(2E)-3-(5-chloro-6-{[(3R)-1-(3-fluorobenzyl)-3-pyrrolidinyl]amino}-3-pyridinyl)-N-(tetrahydro-2H-pyran-2-yloxy)acrylamide $^1$H-NMR (DMSO-d6): δ 1.22-2.00 (7H, m), 2.18-2.20 (1H, m), 2.41-2.52 (2H, m), 2.61-2.68 (1H, m), 2.81-2.90 (1H, m), 3.50-3.55 (2H, m), 3.55 (2H, m), 3.94-4.05 (1H, m), 4.47-4.57 (1H, m), 4.90 (1H, s), 6.33 (1H, d J=15.66 Hz), 6.65 (1H, d J=6.88 Hz), 7.01-7.18 (3H, m), 7.30-7.41 (2H, m), 7.85 (1H, s), 8.20 (1H, s), 10.96 (1H, s).

Preparation 622

(2E)-3-[5-chloro-6-({(3R)-1-[(4-methylphenyl)sulfonyl]-3-pyrrolidinyl}amino)-3-pyridinyl]-N-(tetrahydro-2H-pyran-2-yloxy)acrylamide $^1$H-NMR (DMSO-d6): δ 1.53-1.69 (6H, m), 1.95-2.05 (2H, m), 2.39 (3H, s), 3.11-3.28 (3H, m), 3.34-3.55 (2H, m), 3.96-3.98 (1H, m), 4.30-4.33 (1H, m), 4.89 (1H, s), 6.35 (1H, d J=15.92 Hz), 6.56 (1H, d J=5.78 Hz), 7.36 (2H, d J=8.14 Hz), 7.48 (1H d J=15.92 Hz), 7.64 (2H, d J=8.14 Hz), 7.84 (1H, s), 8.20 (1H, s), 11.10 (1H, br.s).

Preparation 623

(2E)-3-(5-chloro-6-{[(3R)-1-(cyclohexylcarbonyl)-3-pyrrolidinyl]amino}-3-pyridinyl)-N-(tetrahydro-2H-pyran-2-yloxy)acrylamide $^1$H-NMR (DMSO-d6): δ 1.14-1.29 (6H, m), 1.53-1.69 (10H, m), 1.96-2.14 (3H, m), 3.23-3.96 (6H, m), 4.51-4.68 (1H, m), 4.89 (1H, s), 6.35 (1H, d J=15.90 Hz), 6.84-6.92 (1H, m), 7.38 (1H, d J=15.90 Hz), 7.88 (1H, s), 8.25 (1H, s), 11.10 (1H, s).

Preparation 624

(2E)-3-[6-({(3R)-1-[(4-methylphenyl)sulfonyl]-3-pyrrolidinyl}amino)-3-pyridinyl]-N-(tetrahydro-2H-pyran-2-yloxy)acrylamide $^1$H-NMR (DMSO-d6): δ 1.52-1.77 (7H, m), 1.99-2.02 (1H, m), 2.39 (3H, s), 3.02-3.09 (1H, m), 3.20-3.55 (4H, m), 3.98-4.01 (1H, m), 4.20-4.23 (1H, m), 4.88 (1H, s), 6.24 (1H, d J=15.48 Hz), 6.40 (1H, d J=8.76 Hz), 7.13 (1H, d J=5.74 Hz), 7.36 (1H, d J=15.48 Hz), 7.38 (2H, d J=8.18 Hz), 7.61 (1H, d J=8.76 Hz), 7.65 (2H, d J=8.18 Hz), 8.18 (1H, s), 11.07 (1H, s).

Preparation 625

(2E)-3-(6-{[(3R)-1-(1-piperidinylcarbonyl)-3-pyrrolidinyl]amino}-3-pyridinyl)-N-(tetrahydro-2H-pyran-2-yloxy)acrylamide $^1$H-NMR (DMSO-d6): δ 1.23-1.84 (13H, m), 2.07-2.09 (1H, m), 3.11 (4H, m), 3.35-3.66 (4H, m), 3.93-3.95 (1H, m), 4.30-4.35 (1H, m), 4.88 (1H, s), 6.24 (1H, d J=15.44 Hz), 6.55 (1H, d J=8.80 Hz), 7.28 (1H, d J=6.24 Hz), 7.37 (1H, d J=15.44 Hz), 7.63 (1H, d J=8.80 Hz), 8.17 (1H, s), 11.06 (1H, s).

Preparation 626

(2E)-3-(5-chloro-6-{[(3R)-1-(1-piperidinylcarbonyl)-3-pyrrolidinyl]amino}-3-pyridinyl)-N-(tetrahydro-2H-pyran-2-yloxy)acrylamide $^1$H-NMR (DMSO-d6): δ 1.14-1.70 (12H, m), 1.85-2.12 (2H, m), 3.08 (4H, br.s), 3.25-3.62 (4H, m), 3.98-4.01 (1H, m), 4.44-4.48 (1H, m), 4.90 (1H, s), 6.35 (1H, d J=15.78 Hz), 6.81 (1H, d J=6.58 Hz), 7.38 (1H, d J=15.78 Hz), 7.96 (1H, s), 8.24 (1H, s), 11.08 (1H, br.s).

Preparation 627

(2E)-3-(5-chloro-6-{[(3R)-1-(cyclopentylcarbonyl)-3-pyrrolidinyl]amino}-3-pyridinyl)-N-(tetrahydro-2H-pyran-2-yloxy)acrylamide $^1$H-NMR (DMSO-d6): δ 1.53-1.69 (14H, m), 1.99-2.12 (2H, m), 2.73-2.89 (1H, m), 3.28-4.00 (6H, m), 4.51-4.70 (1H, m), 4.89 (1H, s), 6.35 (1H, d J=15.84 Hz), 6.85-6.92 (1H, m), 7.38 (1H, d J=15.84 Hz), 7.88 (1H, s), 8.25 (1H, s), 11.09 (1H, br.s).

Preparation 628

(2E)-3-(5-chloro-6-{[(3R)-1-(cyclobutylcarbonyl)-3-pyrrolidinyl]amino}-3-pyridinyl)-N-(tetrahydro-2H-pyran-2-yloxy)acrylamide $^1$H-NMR (DMSO-d6): 1.53-2.18 (15H, m), 3.25-3.71 (4H, m), 3.93-3.95 (1H, m), 4.50-4.60 (1H, m), 4.89 (1H, s), 6.35 (1H, d J=15.98 Hz), 6.84-6.91 (1H, m), 7.38 (1H, d J=15.98 Hz), 7.95 (1H, s), 8.24 (1H, s), 11.08 (1H, br.s).

The following compounds were obtained in a similar manner to that of Preparation 618.

Preparation 629

(2E)-3-(5-chloro-6-{[(3R)-1-(2-pyridinylmethyl)-3-pyrrolidinyl]amino}-3-pyridinyl)-N-(tetrahydro-2H-pyran-2-yloxy)acrylamide $^1$H-NMR (DMSO-d6): δ 1.53-1.99 (8H, m), 2.00-2.18 (1H, m), 2.47-2.58 (2H, m), 2.69-2.73 (1H, m), 2.86-2.94 (1H, m), 3.34 (2H, s), 3.49-3.50 (1H, m), 3.98-4.05 (1H, m), 4.50-4.56 (1H, m), 4.89 (1H, s), 6.36 (1H, d J=15.90 Hz), 6.96, (1H, d J=6.90 Hz), 7.22-7.28 (1H, m), 7.41-7.45 (1H, m), 7.72-7.85 (2H, m), 7.96 (1H, s), 8.26 (1H, s), 8.46-8.50 (1H, m), 11.07 (1H, br.s).

The following compound was obtained in a similar manner to that of Preparation 615.

Preparation 630

(2E)-3-(5-chloro-6-{[(3R)-1-(4-chlorobenzoyl)-3-pyrrolidinyl]amino}-3-pyridinyl)-N-(tetrahydro-2H-pyran-2-yloxy)acrylamide $^1$H-NMR (DMSO-d6): δ 1.69-1.74 (6H, m), 1.99-2.21 (2H, m), 3.34-3.91 (5H, m), 4.54-4.72 (2H, m), 4.89 (1H, s), 6.28-6.36 (1H, m), 6.91-6.97 (1H, m), 7.31-7.60 (5H, m), 7.86-7.96 (1H, m), 8.11-8.27 (1H, m), 11.09 (1H, s).

The following compounds were obtained in a similar manner to that of Preparation 618.

Preparation 631

(2E)-3-(5-chloro-6-{[(3R)-1-(cyclopropylmethyl)-3-pyrrolidinyl]amino}-3-pyridinyl)-N-(tetrahydro-2H-pyran-2-yloxy)acrylamide $^1$H-NMR (DMSO-d6): δ 0.04-0.11 (2H, m), 0.39-0.48 (2H, m), 0.70-0.90 (1H, m), 1.53-1.90 (7H, m), 2.09-2.24 (1H, m), 2.26 (2H, d J=6.62 Hz), 2.46-2.52 (2H, m), 2.68-2.71 (1H, m), 2.80-2.88 (1H, m), 3.34-3.49 (1H, m), 3.93-3.96 (1H, m), 4.47-4.58 (1H, m), 4.89 (1H, s), 6.33 (1H, d J=15.78 Hz), 6.59 (1H, d J=6.98 Hz), 7.37 (1H, d J=15.78 Hz), 7.85 (1H, s), 8.22 (1H, s), 11.07 (1H, br.s).

Preparation 632

(2E)-3-(5-chloro-6-{[(3R)-1-(cyclopentylmethyl)-3-pyrrolidinyl]amino}-3-pyridinyl)-N-(tetrahydro-2H-pyran-2-yloxy)acrylamide $^1$H-NMR (DMSO-d6) δ 1.16-1.21 (2H, m), 1.49-2.52 (20H, m), 2.52-2.69 (1H, m), 2.70-2.90 (1H, m), 3.49-3.55 (1H, m), 3.94-3.99 (1H, m), 4.41-4.47 (1H, m), 4.89 (1H, s), 6.34 (1H, d J=15.78 Hz), 6.55 (1H, d J=7.04 Hz), 7.33 (1H, d J=15.78 Hz), 7.85 (1H, s), 8.21 (1H, s), 11.07 (1H, br.s).

The following compounds were obtained in a similar manner to that of Preparation 615.

Preparation 633

(2E)-3-(5-chloro-6-{[(3R)-1-(2-pyrimidinyl)-3-pyrrolidinyl]amino}-3-pyridinyl)-N-(tetrahydro-2H-pyran-2-yloxy)acrylamide $^1$H-NMR (DMSO-d6): δ 1.54 (3H, br.s), 1.69 (1H, br.s), 1.74-2.09 (1H, m), 2.15-2.17 (1H, m), 3.35-3.55 (3H, m), 3.67-3.69 (1H, m), 3.86-3.96 (2H, m), 4.66-4.71 (1H, m), 4.89 (1H, s), 6.35 (1H, d J=15.78 Hz), 6.58-6.60 (1H, m), 6.95 (1H, d J=6.40 Hz), 7.88 (1H, s), 8.27 (1H, s), 8.32-8.33 (2H, m), 11.11 (1H, s).

Preparation 634

(2E)-3-(5-chloro-6-{[(3R)-1-(4-fluorobenzoyl)-3-pyrrolidinyl]amino}-3-pyridinyl)-N-(tetrahydro-2H-pyran-2-yloxy)acrylamide $^1$H-NMR (DMSO-d6): δ 1.53 (3H, s), 1.69 (3H, s), 2.09-2.15 (2H, m), 3.35-3.59 (4H, m), 3.59-3.95 (2H, m), 4.53-4.68 (1H, m), 4.90 (1H, s), 6.30-6.34 (1H, m), 6.93 & 6.99 (total 1H, each d J=6.06 Hz), 7.27-7.41 (3H, m), 7.58-7.64 (2H, m), 7.86 & 7.89 (total 1H, each s), 8.18 & 8.27 (total 1H, each s), 11.10 (1H, s).

Preparation 635

(2E)-3-(5-chloro-6-{[(3R)-1-(3-methylbenzoyl)-3-pyrrolidinyl]amino}-3-pyridinyl)-N-(tetrahydro-2H-pyran-2-yloxy)acrylamide $^1$H-NMR (DMSO-d6): δ 1.53 (3H, s), 1.69 (3H, s), 1.99-2.11 (2H, m), 2.32 & 2.35 (total 3H, each s), 3.30-3.55 (4H, m), 3.71-4.02 (2H, m), 4.52-4.54 (1H, m), 4.89 (1H, s), 6.30-6.37 (1H, m), 6.91 & 6.98 (total 1H, each d J=6.12 Hz), 7.24-7.47 (5H, m), 7.85 & 7.89 (total 1H, each s), 8.17 & 8.27 (total 1H, each s), 11.10 (1H, s).

Preparation 636

(2E)-3-(5-chloro-6-{[(3R)-1-(3-chlorobenzoyl)-3-pyrrolidinyl]amino}-3-pyridinyl)-N-(tetrahydro-2H-pyran-2-yloxy)acrylamide $^1$H-NMR (DMSO-d6): δ 1.53 (3H, s), 1.69 (3H, s), 1.99-2.22 (2H, m), 3.35-3.58 (4H, m), 3.72-4.04 (2H, m), 4.55-4.68 (1H, m), 4.89 (1H, s), 6.30-6.34 (1H, m), 6.93 & 7.02 (total 1H, each d J=6.10 Hz), 7.33-7.58 (5H, m), 7.85 & 7.89 (total 1H, each s), 8.19 & 8.27 (total 1H, each s), 11.10 (1H, s).

Preparation 637

(2E)-3-(5-chloro-6-{[(3R)-1-(2-chlorobenzoyl)-3-pyrrolidinyl]amino}-3-pyridinyl)-N-(tetrahydro-2H-pyran-2-yloxy)acrylamide $^1$H-NMR (DMSO-d6): δ 1.53 (3H, s), 1.69 (3H, s), 2.09-2.17 (2H, m), 3.16-3.55 (4H, m), 3.87-4.04 (2H, m), 4.58-4.66 (1H, m), 4.90 (1H, s), 6.34 (1H, m), 6.87-6.94 (1H, m), 7.37-7.53 (5H, m), 7.86 & 7.90 (total 1H, each s), 8.17 & 8.27 (total 1H, each s), 11.11 (1H, s).

Preparation 638

A solution of ethyl (2E)-3-{5-chloro-6-[(3R)-3-pyrrolidinylamino]-3-pyridinyl}acrylate dihydrochloride (560 mg), p-toluenesulfonyl chloride (318 mg) and $Et_3N$ (0.7 ml) in DMF (15 ml) was stirred at ambient temperature for 10 hours. The reaction mixture was poured into a mixture of AcOEt and $H_2O$ and the organic layer was washed with brine and dried over $MgSO_4$. The solvent was evaporated in vacuo and the residue was crystallized from AcOEt-n-hexane to give ethyl (2E)-3-[5-chloro-6-({(3R)-1-[(4-methylphenyl)sulfonyl]-3-pyrrolidinyl}amino)-3-pyridinyl]acrylate (490 mg).

$^1$H-NMR (DMSO-d6): δ 1.25 (3H, t J=7.12 Hz), 1.98-2.05 (2H, m), 2.38 (3H, s), 3.14-3.17 (1H, m), 3.23-3.34 (2H, m), 3.45-3.49 (1H, m), 4.16 (2H, q J=7.12 Hz), 4.32-4.33 (1H, m), 6.53 (1H, d J=15.96 Hz), 6.65 (1H, d J=5.92 Hz), 7.36 (2H, d J=8.12 Hz), 7.54 (1H, d J=15.96 Hz), 7.62 (2H, d J=8.12 Hz), 8.11 (1H, d J=1.96 Hz), 8.27 (1H, d J=1.96 Hz).

The following compound was obtained in a similar manner to that of Preparation 638.

Preparation 639 ethyl (2E)-3-[6-({(3R)-1-[(4-methylphenyl)sulfonyl]-3-pyrrolidinyl}amino)-3-pyridinyl]acrylate $^1$H-NMR (DMSO-d6): δ 1.24 (3H, t=7.06 Hz), 1.68-1.82 (1H, m), 1.92-2.22 (1H, m), 2.39 (3H, s), 3.04-3.11 (1H, m), 3.21-3.45 (3H, m), 4.18 (2H, q J=7.06 Hz), 6.34 (1H, d J=15.90 Hz), 6.39 (1H, d J=8.76 Hz), 7.23 (1H, d J=5.86 Hz), 7.38 (2H, d J=8.08 Hz), 7.52 (1H, d J=15.90 Hz), 7.65 (2H, d J=8.08 Hz), 7.79 (1H, dd J=2.08 Hz, 8.78 Hz), 8.21 (1H, d J=2.08 Hz).

Preparation 640

A solution of ethyl (2E)-3-{5-chloro-6-[(3R)-3-pyrrolidinylamino]-3-pyridinyl}acrylate dihydrochloride (610 mg), cyclohexanecarbonyl chloride (267 mg) and $Et_3N$ (0.76 ml) in DMF (15 ml) was stirred at ambient temperature for 8 hours. The reaction mixture was poured into a mixture of AcOEt and $H_2O$ and the organic layer was washed with brine and dried over $MgSO_4$ The solvent was evaporated in vacuo and the residue was chromatographed on silicagel eluting with AcOEt-MeOH (95:5). The eluted fractions containing the desired product were collected and evaporated in vacuo to give ethyl (2E)-3-(5-chloro-6-{[(3R)-1-(cyclohexylcarbonyl)-3-pyrrolidinyl]amino}-3-pyridinyl)acrylate (630 mg).

$^1$H-NMR (DMSO-d6): δ 1.21-1.31 (6H, m), 1.25 (3H, t J=7.08 Hz), 1.63-1.69 (5H, m), 1.93-2.10 (2H, m), 3.28-3.84 (4H, m), 4.15 (2H, q J=7.08 Hz), 4.67-4.68 (1H, m), 6.52 (1H, d J=15.98 Hz), 6.95-7.19 (1H, m), 7.53 (1H, d J=15.98 Hz), 8.14 (1H, d J=1.86 Hz), 8.32 (1H, d J=1.86 Hz).

The following compounds were obtained in a similar manner to that of Preparation 640.

Preparation 641 ethyl (2E)-3-(6-{[(3R)-1-(1-piperidinylcarbonyl)-3-pyrrolidinyl]amino}-3-pyridinyl)acrylate $^1$H-NMR (DMSO-d6): δ 1.24 (3H, t J=7.06 Hz), 1.49 (6H, br.s), 1.70-1.89 (1H, m), 2.00-2.16 (1H, m), 3.15 (4H, br, s), 3.15-3.46 (3H, m), 3.58-3.66 (1H, m), 4.18 (2H, q J=7.06 Hz), 4.34-4.40 (1H, m), 6.34 (1H, d J=15.82 Hz), 6.55 (1H, d J=8.84 Hz), 7.39 (1H, d J=6.28 Hz), 7.52 (1H, d J=15.82 Hz), 7.81 (1H, dd J=2.14 Hz, 8.84 Hz), 8.24 (1H, d J=2.14 Hz).

Preparation 642 ethyl (2E)-3-(5-chloro-6-{[(3R)-1-(1-piperidinylcarbonyl)-3-pyrrolidinyl]amino}-3-pyridinyl)acrylate $^1$H-NMR (DMSO-d6): δ 1.24 (3H, t J=7.08 Hz), 1.49 (6H, br.s), 1.90-2.12 (2H, m), 3.12 (4H, br.s), 3.25-3.43 (3H, m), 3.53-3.62 (1H, m), 4.16 (2H, q J=7.08 Hz), 4.46-4.56 (1H, m), 6.51 (1H, d J=15.90 Hz), 6.91 (1H, d J=6.62 Hz), 7.53 (1H, d J=15.90 Hz), 8.13 (1H, d J=1.90 Hz), 8.31 (1H, d J=1.90 Hz).

Preparation 643 ethyl (2E)-3-(5-chloro-6-{[(3R)-1-(cyclobutylcarbonyl)-3-pyrrolidinyl]amino}-3-pyridinyl)acrylate $^1$H-NMR (DMSO-d6): δ 1.25 (3H, t J=7.06 Hz), 1.97-2.18 (9H, m), 3.21-3.60 (3H, m), 3.60-3.72 (1H, m), 4.16 (2H, q J=7.06 Hz), 4.52-4.62 (1H, m), 6.52 (1H, d J=15.86 Hz), 6.89-7.01 (1H, m), 7.53 (1H, d J=15.86 Hz), 8.13 (1H, s), 8.32(1H, s).

Preparation 644 ethyl (2E)-3-(5-chloro-6-{[(3R)-1-(cyclopentylcarbonyl)-3-pyrrolidinyl]amino}-3-pyridinyl)acrylate $^1$H-NMR (DMSO-d6): δ 1.25 (3H, t J=7.06 Hz), 1.49-1.77 (8H, m), 1.90-2.20 (2H, m), 2.70-2.86 (1H, m), 3.30-3.51 (3H, m), 3.98-4.02 (1H, m), 4.16 (2H, q J=7.06 Hz), 4.53-4.69 (1H, m), 6.52 (1H, d J=15.96 Hz), 6.94-7.02 (1H, m), 7.54 (1H, d J=15.96 Hz), 8.13-8.15 (1H, m), 8.31-8.33 (1H, m).

Preparation 645

A solution of ethyl (2E)-3-{5-chloro-6-[(3R)-3-pyrrolidinylamino]-3-pyridinyl}acrylate dihydrochloride (500 mg), 4-chlorobenzoyl chloride (249 mg) and $Et_3N$ (0.624 ml) in DMF (20 ml) was stirred at ambient temperature for 10 hours. The reaction mixture was poured into a mixture of AcOEt and $H_2O$ and the organic layer was washed with brine and dried over $MgSO_4$. The solvent was evaporated in vacuo and the residue was washed with IPE and n-hexane to give ethyl (2E)-3-(5-chloro-6-{[(3R)-1-(4-chlorobenzoyl)-3-pyrrolidinyl]amino}-3-pyridinyl)acrylate (570 mg).

$^1$H-NMR (DMSO-d6): δ 1.20-1.28 (3H, m), 2.11-2.18 (2H, m), 3.34-3.63 (4H, m), 4.10-4.18 (2H, m), 4.43-4.71 (1H, m), 6.46-6.57 (1H, m), 7.00-7.07 (1H, m), 7.46-7.60 (5H, m), 8.11-8.18 (1H, m), 8.25 & 8.34 (total 1H, each s).

The following compounds were obtained in a similar manner to that of Preparation 645.

Preparation 646 ethyl (2E)-3-(5-chloro-6-{[(3R)-1-(4-fluorobenzoyl)-3-pyrrolidinyl]amino}-3-pyridinyl)acrylate $^1$H-NMR (DMSO-d6): δ 1.24 (3H, t J=7.08 Hz), 2.00-2.16 (2H, m), 3.35-3.78 (4H, m), 4.15 (2H, q J=7.08 Hz), 4.56-4.70 (1H, m), 6.50 & 6.54 (total 1H, each d J=15.88 Hz), 7.03 & 7.04 (total 1H, each d J=6.32 Hz), 7.23-7.28 (2H, m), 7.48-7.63 (3H, m), 8.12 & 8.16 (total 1H, each d J=1.72 Hz), 8.26.& 8.34 (total 1H, each d J=1.72 Hz).

Preparation 647 ethyl (2E)-3-(5-chloro-6-{[(3R)-1-(3-methylbenzoyl)-3-pyrrolidinyl]amino}-3-pyridinyl)acrylate $^1$H-NMR (DMSO-d6): 1.24 (3H, t J=7.08 Hz), 2.03-2.14 (2H, m), 2.31 & 2.35 (total 3H, each s), 3.43-3.73 (4H, m), 4.15 (2H, q J=7.08 Hz), 4.53-4.70 (1H, m), 6.50 & 6.54 (total 1H, each d J=15.86 Hz), 7.01 & 7.08 (total 1H, each d J=6.56 Hz), 7.24-7.33 (4H, m), 7.49 & 7.54 (total 1H, each d J=15.86 Hz), 8.12 & 8.16 (total 1H, each d J=1.76 Hz), 8.25 & 8.34 (total 1H, each d J=1.76 Hz).

Preparation 648 ethyl (2E)-3-(5-chloro-6-{[(3R)-1-(3-chlorobenzoyl)-3-pyrrolidinyl]amino}-3-pyridinyl)acrylate $^1$H-NMR (DMSO-d6): δ 1.24 (3H, t J=7.06 Hz), 1.99-2.30 (2H, m), 3.34-3.58 (3H, m), 3.58-3.74 (1H, m), 4.15 (2H, q J=7.06 Hz), 4.56-4.70 (1H, m), 6.50 & 6.53 (total 1H, each d J=15.92 Hz), 7.03 & 7.04 (total 1H, each d J=6.32 Hz), 7.47-7.58 (5H, m), 8.12 & 8.16 (total 1H, each d J=1.92 Hz), 8.26 & 8.34 (total 1H, each d J=1.92 Hz).

Preparation 649 ethyl (2E)-3-(5-chloro-6-{[(3R)-1-(2-chlorobenzoyl)-3-pyrrolidinyl]amino}-3-pyridinyl)acrylate $^1$H-NMR (DMSO-d6): 1.24 (3H, t J=7.06 Hz), 2.09-2.17 (2H, m), 3.13-3.43 (2H, m), 3.40-3.55 (1H, m), 3.70-3.76 (1H, m), 4.15 (2H, q J=7.06 Hz), 4.56-4.70 (1H, m), 6.50 & 6.54 (total 1H, each d J=16.00 Hz), 6.97 & 6.99 (total 1H, each d, J=6.52 Hz), 7.38-7.52 (5H, m), 8.12 & 8.16 (total 1H, each d J=2.00 Hz), 8.25 & 8.34 (total 1H, each d J=2.00 Hz).

Preparation 650

A solution of ethyl (2E)-3-{5-chloro-6-[(3R)-3-pyrrolidinylamino]-3-pyridinyl}acrylate dihydrochloride (700 mg), 2-chloropyrimidine (283 mg) and N,N-diisopropylethylamine (1.09 ml) in DMF (20 ml) was stirred at 80-85° C. for 12 hours under atmospheric pressure of nitrogen. The reaction mixture was poured into a mixture of AcOEt and H$_2$O and the organic layer was washed with brine and dried over MgSO$_4$. The solvent was evaporated in vacuo and the residue was chromatographed on silicagel eluting with AcOEt. The eluted fractions containing the desired product were collected and evaporated in vacuo to give ethyl (2E)-3-(5-chloro-6-{[(3R)-1-(2-pyrimidinyl)-3-pyrrolidinyl]amino}-3-pyridinyl) acrylate (0.560 mg).

$^1$H-NMR (DMSO-d6): δ 1.25 (3H, t J=7.12 Hz), 2.16-2.27 (2H, m), 3.35-3.56 (2H, m), 3.67-3.70 (1H, m), 3.84-3.93 (1H, m), 4.17 (2H, q J=7.12 Hz), 4.65-4.71 (1H, m), 6.52 (1H, d J=16.12 Hz), 6.60 (1H, d J=4.48 Hz), 7.04 (1H, d J=6.42 Hz), 7.54 (1H, d J=16.14 Hz), 8.32-8.35 (3H, m).

Preparation 651

To a mixture of ethyl (diethoxyphosphoryl)(fluoro)acetate (2.08 g) and magnesium bromide (1.9 g) in THF (20 ml) was added dropwise to a Et$_3$N (1.32 ml) with stirring at 0-15° C. under atmospheric pressure of nitrogen, and the reaction mixture was stirred at same condition for an hour. A solution of tert-butyl (3R)-3-[(3-chloro-5-formyl-2-pyridinyl)amino]-1-pyrrolidinecarboxylate (2.0 g) in THF (10 ml) solution was added the above mixture and resultant mixture was stirred at 0-15° C. for 4 hours. The reaction mixture was poured into a mixture of AcOEt-H$_2$O and the organic layer was washed with brine and dried over MgSO$_4$. The solvent was evaporated in vacuo and the residue was chromatographed on sili- cagel eluting with AcOEt-n-hexane (3:7). The eluted fractions containing the desired product were collected and evaporated in vacuo to give tert-butyl (3R)-3-({3-chloro-5-[(1Z)-3-ethoxy-2-fluoro-3-oxo-1-propen-1-yl]-2-pyridinyl}amino)-1-pyrrolidinecarboxylate (2.34 g)

$^1$H-NMR (CDCl$_3$): δ 1.37 (3H, t J=7.08 Hz), 1.40 (9H, s), 1.96 (1H, m), 2.24-2.33 (1H, m), 3.21-3.35 (1H, m), 3.48-3.55 (2H, m), 3.76-3.81 (1H, m), 4.34 (2H, q J=7.08 Hz), 4.66-4.67 (1H, m), 5.30-5.32 (1H, m), 6.78 (1H, d J=35.36 Hz), 7.90 (1H, d J=1.64 Hz), 8.15 (1H, d J=1.64 Hz).

Preparation 652

A mixture of tert-butyl (3R)-3-({3-chloro-5-[(1Z)-3-ethoxy-2-fluoro-3-oxo-1-propen-1-yl]-2-pyridinyl}amino)-1-pyrrolidinecarboxylate (2.34 g) and 4N hydrogen chloride in dioxane solution (11 ml) in EtOH (10 ml) was stirred at ambient temperature for 4 hours. IPE (100 ml) was added to a reaction mixture and the precipitate was collected by filtration to give ethyl (2Z)-3-{5-chloro-6-[(3R)-3-pyrrolidinylamino]-3-pyridinyl}-2-fluoroacrylate dihydrochloride (1.95 g).

$^1$H-NMR (DMSO-d6): δ 1.29 (3H, t J=70.10 Hz), 2.03-2.04 (1H, m), 2.22-2.26 (1H, m), 3.19-3.25 (2H, m), 3.35-3.57 (2H, m), 4.28 (2H, q J=7.10 Hz), 4.73-4.86 (1H, m), 7.03 (1H, d J=37.48 Hz), 7.97 (1H, d J=1.82 Hz), 8.38 (1H, d J=1.82 Hz), 9.65 (2H, br.s).

Preparation 653

A mixture of ethyl (2Z)-3-{5-chloro-6-[(3R)-3-pyrrolidinylamino]-3-pyridinyl}-2-fluoroacrylate dihydrochloride (720 mg), cyclopentanone (188 mg), sodium triacetoxyborohydride (1.18 g) and Et$_3$N (0.52 ml) in CHCl$_3$ (20 ml) was stirred at 25-30° C. for 15 hours. The 10% K$_2$CO$_3$ solution (20 ml) was added to a reaction mixture and stirred at ambient temperature for 30 minutes and extracted with CH$_2$Cl$_2$ and washed with brine and dried over MgSO$_4$. The solvent was evaporated in vacuo and the residue was chromatographed on silicagel eluting with CHCl$_3$-MeOH (96:4). The eluted fractions containing the desired product were collected and evaporated in vacuo to give ethyl (2Z)-3-(5-chloro-6-{[(3R)-1-cyclopentyl-3-pyrrolidinyl]amino}-3-pyridinyl)-2-fluoroacrylate (710 mg).

$^1$H-NMR (CDCl$_3$): δ 1.37 (3H, t J=7.16 Hz), 1.53-1.57 (3H, m), 1.71-1.74 (5H, m), 2.39-2.42 (3H, m), 2.73-2.81 (2H, m), 2.95 (1H, m), 4.33 (2H, q J=7.16 Hz), 4.64-4.68 (1H, m), 5.61-5.63 (1H, m), 6.76 (1H, d J=35.52 Hz), 7.87 (1H, d J=1.84 Hz), 8.15 (1H, d J=1.84 Hz).

The following compounds were obtained in a similar manner to that of Preparation 653.

Preparation 654 ethyl (2Z)-3-(5-chloro-6-{[(3R)-1-cyclohexyl-3-pyrrolidinyl]amino}-3-pyridinyl)-2-fluoroacrylate $^1$H-NMR (CDCl$_3$): δ 1.21-1.28 (4H, m), 1.37 (3H, t J=7.16 Hz), 1.73-1.77 (4H, m), 1.93 (2H, m), 2.17 (1H, m), 2.42-2.45 (2H, m), 2.78-2.85 (2H, m), 3.00 (1H, m), 4.33 (2H, q J=7.16 Hz), 4.62-4.66 (1H, m), 5.61-5.63 (1H, m), 6.76 (1H, d J=35.52 Hz), 7.87 (1H, d J=1.84 Hz), 8.15 (1H, d J=1.84 Hz).

Preparation 655 ethyl (2Z)-3-(5-chloro-6-{[(3R)-1-(cyclohexylmethyl)-3-pyrrolidinyl]amino}-3-pyridinyl)-2-fluoroacrylate $^1$H-NMR (CDCl$_3$): δ 0.88-0.91 (2H, m), 1.19-1.21 (3H, m), 1.37 (3H, t J=7.16 Hz), 1.40-1.60 (1H, m), 1.68-1.73 (6H, m), 2.27-2.34 (4H, m), 2.65-2.66 (2H, m), 2.89 (1H, m), 4.33 (2H, q J=7.16 Hz), 4.62-4.67 (1H, m), 5.63-5.65 (1H, m), 6.77 (1H, d J=35.52 Hz), 7.87 (1H, d J=1.76 Hz), 8.17 (1H, d J=1.76 Hz).

Preparation 656

A mixture of ethyl (2Z)-3-(5-chloro-6-{[(3R)-1-cyclopentyl-3-pyrrolidinyl]amino}-3-pyridinyl)-2-fluoroacrylate (710 mg) and 1N NaOH solution (3.8 ml) in MeOH (20 ml) was stirred at 75-80° C. for 2 hours. To the reaction mixture was added 1N HCl solution (3.8 ml) and the resultant solution was evaporated in vacuo and the residue was dissolved in a mixture of MeOH and toluene and evaporated in vacuo and the residue was dried to give (2Z)-3-(5-chloro-6-{[(3R)-1-cyclopentyl-3-pyrrolidinyl]amino}-3-pyridinyl)-2-fluoroacrylic acid (658 mg).

$^1$H-NMR (DMSO-d6): δ 1.75-2.12 (9H, m), 2.35-2.52 (2H, m), 2.99-3.81 (4H, m), 4.78-4.91 (1H, m), 6.67 (1H, d J=37.52 Hz), 7.09 (1H, d J=7.34 Hz), 7.86 (1H, d J=1.64 Hz), 8.24 (1H, d J=1.64 Hz).

The following compounds were obtained in a similar manner to that of Preparation 656.

Preparation 657

(2Z)-3-(5-chloro-6-{([(3R)-1-cyclohexyl-3-pyrrolidinyl}amino]-3-pyridinyl)-2-fluoroacrylic acid $^1$H-NMR (DMSO-d6): δ 1.06-1.62 (7H, m), 1.76-1.81 (2H, m), 1.97-2.06 (2H, m), 2.30-2.50 (2H, m), 3.04-3.52 (4H, m), 4.77-4.80 (1H, m), 6.66 (1H, d J=37.56 Hz), 7.09 (1H, d. J=7.33 Hz), 7.86 (1H, d J=1.28 Hz), 8.23 (1H, d J=1.28 Hz).

Preparation 658

(2Z)-3-(5-chloro-6-{[(3R)-1-(cyclohexylmethyl)-3-pyrrolidinyl]amino}-3-pyridinyl)-2-fluoroacrylic acid $^1$H-NMR (DMSO-d6): δ 0.89-1.26 (6H, m), 1.64-2.06 (7H, m), 2.30-2.44 (2H, m), 2.84-2.88 (2H, m), 3.17-3.20 (1H, m), 3.40 (1H, m), 4.76-4.79 (1H, m), 6.69 (1H, d J=37.54 Hz), 7.06 (1H, d J=7.21 Hz), 7.87 (1H, d J=1.68 Hz), 8.24 (1H, d J=1.68 Hz).

Preparation 659

(2Z)-3-(6-{[(3R)-1-benzyl-3-pyrrolidinyl]amino}-5-chloro-3-pyridinyl)-2-fluoroacrylic acid $^1$H-NMR (DMSO-d6): δ 1.99-2.11 (1H, m), 2.30-2.41 (1H, m), 3.11-3.52 (4H, m), 4.30 (2H, s), 4.71-4.81 (1H, m), 6.82 (1H, d J=37.42 Hz), 7.11-7.29 (3H, m), 7.40-7.47 (2H, m), 7.60-7.62 (1H, m), 7.90 (1H, s), 8.28 (1H, s).

Preparation 660

(2Z)-3-(6-{[(3R)-1-benzyl-3-pyrrolidinyl]amino}-3-pyridinyl)-2-fluoroacrylic acid $^1$H-NMR (DMSO-d6): δ 1.83-1.89 (1H, m), 2.26-2.36 (1H, m), 2.75-3.28 (4H, m), 3.96-4.09 (2H, m), 4.46-4.49 (1H, m), 6.57 (1H, d J=8.88 Hz), 6.75 (1H, d J=37.98 Hz), 7.14-7.51 (6H, m), 7.74 (1H, dd J=1.92 Hz, 8.88 Hz), 8.23 (1H, d J=1.92 Hz).

Preparation 661

A mixture of (2Z)-3-(5-chloro-6-{[(3R)-1-cyclopentyl-3-pyrrolidinyl]amino}-3-pyridinyl)-2-fluoroacrylic acid (658 mg), O-(tetrahydro-2H-pyran-2-yl)hydroxylamine (229 mg), HOBt (264 mg) and EDCI (303 mg) in DMF (15 ml) was stirred at ambient temperature for 15 hours. The reaction mixture was poured into a mixture of AcOEt-H$_2$O and the organic layer was washed with brine and dried over MgSO$_4$ The solvent was evaporated in vacuo and the residue was chromatographed on silicagel eluting with AcOEt-MeOH (95:5). The eluted fractions containing the desired product were collected and evaporated in vacuo to give (2Z)-3-(5-chloro-6-{[(3R)-1-cyclopentyl-3-pyrrolidinyl]amino}-3-pyridinyl)-2-fluoro-N-(tetrahydro-2H-pyran-2-yloxy)acrylamide (620 mg).

$^1$H-NMR (DMSO-d6): δ 1.37-1.72 (12H, m), 2.09-2.20 (1H, m), 2.73 (1H, m), 2.89 (1H, m), 3.36 (6H, m), 3.50-3.52 (1H, m), 4.05-4.07 (1H, m), 4.48-4.50 (1H, m), 4.97 (1H, s), 6.66 (1H, d J=7.00 Hz), 7.85 (1H, d J=1.88 Hz), 8.28-8.32 (1H, m).

The following compounds were obtained in a similar manner to that of Preparation 661.

Preparation 662

(2Z)-3-(5-chloro-6-{[(3R)-1-cyclohexyl-3-pyrrolidinyl]amino}-3-pyridinyl)-2-fluoro-N-(tetrahydro-2H-pyran-2-yloxy)acrylamide $^1$H-NMR (DMSO-d6): δ 1.09-1.23 (4H, m), 1.54-1.84 (9H, m), 2.09-2.13 (2H, m), 2.50-2.52 (2H, m), 2.74-2.75 (1H, m), 2.88-2.92 (1H, m), 3.36 (4H, m), 3.36 (4H, m), 3.50-3.53 (1H, m), 4.03-4.08 (1H, m), 4.46-4.50 (1H, m), 4.97 (1H, s), 6.50 (1H, d J=6.96 Hz), 6.78 (1H, d J=39.72 Hz), 7.85 (1H, d J=1.88 Hz), 8.29-8.32 (1H, m).

Preparation 663

(2Z)-3-(5-chloro-6-{[(3R)-1-(cyclohexylmethyl)-3-pyrrolidinyl]amino}-3-pyridinyl)-2-fluoro-N-(tetrahydro-2H-pyran-2-yloxy)acrylamide $^1$H-NMR (DMSO-d6): δ 0.81-0.84 (2H, m), 1.15-1.17 (3H, m), 1.53-1.57 (1H, m), 1.63-1.84 (14H, m), 2.17-2.23 (3H, m), 2.41-2.43 (2H, m), 2.51-2.52 (2H, m), 2.74-2.78 (1H, m), 3.50-3.53 (1H, m), 4.07-4.08 (1H, m), 4.4974.51 (1H, m), 4.98 (1H, s), 6.62 (1H, d J=7.04 Hz), 6.79 (1H, d J=69.72 Hz), 7.85 (1H, d J=1.88 Hz), 8.29 (1H, d J=1.88 Hz).

Preparation 664

(2Z)-3-(6-{[(3R)-1-benzyl-3-pyrrolidinyl]amino}-5-chloro-3-pyridinyl)-2-fluoro-N-(tetrahydro-2H-pyran-2-yloxy)acrylamide $^1$H-NMR (DMSO-d6): δ 1.54 (3H, m), 1.70 (3H, s), 1.81-1.84 (1H, m), 2.10-2.22 (1H, m), 2.37-2.40 (2H, m), 2.64-2.65 (1H, m), 2.81-2.85 (1H, m), 3.50-3.52 (1H, m), 3.59 (2H, s), 4.02-4.07 (1H, m), 4.49-4.52 (1H, m), 4.98 (1H, s), 6.68 (1H, d J=6.96 Hz), 6.78 (1H, d J=39.68 Hz), 7.21-7.26 (1H, m), 7.28-7.34 (1H, m), 7.85 (1H, d J=1.88 Hz), 8.31 (1H, d J=1.88 Hz).

Preparation 665

(2Z)-3-(6-{[(3R)-1-benzyl-3-pyrrolidinyl]amino}-3-pyridinyl)-2-fluoro-N-(tetrahydro-2H-pyran-2-yloxy)acrylamide $^1$H-NMR (DMSO-d6): δ 1.63 (3H, s), 1.64-1.69 (4H, m), 2.20 (1H, m), 2.35-2.45 (2H, m), 2.63-2.64 (1H, m), 2.75-2.79 (1H, m), 3.49-3.51 (1H, m), 3.57 (2H, d J=4.76 Hz), 4.03-4.06 (1H, m), 4.32 (1H, m), 4.96 (1H, s), 6.53 (1H, d J=8.90 Hz), 6.69 (1H, d J=40.40 Hz), 7.21-7.26 (2H, m), 7.28-7.33 (4H, m), 7.67 (1H, dd J=2.20 Hz, 8.90 Hz), 8.19 (1H, d J=2.20 Hz), 11.66 (1H, s).

Preparation 666

To a mixture of ethyl (diethoxyphosphoryl)(fluoro)acetate (1.46 g) and magnesium bromide (1.33 g) in THF (20 ml) was added dropwise to a Et$_3$N (0.92 ml) with stirring at 0-15° C. under atmospheric pressure of nitrogen, and the reaction mixture was stirred at same condition for an hour. A solution of 6-{[(3R)-1-benzyl-3-pyrrolidinyl]amino}-5-chloronicotinaldehyde (1.36 g) in THF (10 ml) solution was added the above mixture and resultant mixture was stirred at 0-15° C. for 4 hours. The reaction mixture was poured into a mixture of AcOEt-H$_2$O and the organic layer was washed with brine and dried over MgSO$_4$. The solvent was evaporated in vacuo and the residue was chromatographed on silicagel eluting with AcOEt-n-hexane (3:7). The eluted fractions containing the desired product were collected and evaporated in vacuo to give ethyl (2Z)-3-(6-{[(3R)-1-benzyl-3-pyrrolidinyl]amino}-5-chloro-3-pyridinyl)-2-fluoroacrylate (1.42 g).

$^1$H-NMR (CDCl$_3$): δ 1.36 (3H, t J=7.16 Hz), 1.33-1.39 (1H, m), 1.68-1.73 (1H, m), 2.38-2.40 (1H, m), 2.66-2.67 (1H, m), 1.73-2.74 (1H, m), 2.89 (1H, m), 3.65 (2H, s), 4.33 (2H, q J=7.16 Hz), 5.69 (1H, d J=7.70 Hz), 6.75 (1H, d J=35.52 Hz), 7.23-7.34 (5H, m), 7.86 (1H, d J=1.84 Hz), 8.15 (1H, d J=1.84 Hz).

The following compound was obtained in a similar manner to that of Preparation 666.

Preparation 667 ethyl (2Z)-3-(6-{[(3R)-1-benzyl-3-pyrrolidinyl]amino}-3-pyridinyl)-2-fluoroacrylate $^1$H-NMR (CDCl$_3$): δ 1.36 (3H, t J=7.14 Hz), 1.71-1.72 (1H, m), 2.33-2.45 (2H, m), 2.57-2.88 (3H, m), 3.64 (2H, s), 4.29 (2H, q J=7.14 Hz), 5.19 (1H, d J=7.84 Hz), 6.37 (1H, d J=8.80 Hz), 6.79 (1H, d J=36.28 Hz), 7.2-7.33 (5H, m), 7.81 (1H, dd J=20.10 Hz, 8.80 Hz), 8.22 (1H, d J=20.10 Hz).

Preparation 668

To a stirred suspension of ethyl (2E)-3-{5-[(3R)-3-piperidinylamino]-2-pyrazinyl}acrylate dihydrochloride (300 mg) in dichloromethane (6 mL) was added N,N-diisopropylethylamine (348 mg) and phenylacetyl chloride (139 mg) in dichloromethane (1 mL) in an ice bath and the resulting mixture was stirred at the same temperature for three hours. The mixture was extracted with chloroform and washed with saturated sodium bicarbonate and brine. The organic phase was dried over anhydrous sodium sulfate, filtered and concentrated in vacuo. The residue was purified by flash chromatography with ethyl acetate to afford ethyl (2E)-3-(5-{[(3R)-1-(phenylacetyl)-3-piperidinyl]amino}-2-pyrazinyl)acrylate (225 mg) as a pale brown viscous oil.

$^1$H-NMR (300 MHz, CDCl$_3$) δ 1.33 (3H, t, J=7.3 Hz), 1.35-1.50 (1H, m), 1.57-2.03 (3H, m), 3.19-3.57 (2H, m), 3.67-4.67 (4H, m), 4.26 (2H, q, J=7.3 Hz), 4.65 (0.6H, br.d, J=7.0 Hz), 4.98 (0.4H, br.d, J=6.2 Hz), 6.69 (0.4H, d, J=15.4 Hz), 6.71 (0.6H, d, J=15.4 Hz), 7.19-7.41 (5H, m), 7.57 (0.4H, d, J=15.4 Hz), 7.58 (0.6H, d, J=15.4 Hz), 7.67 (0.6H, br.s), 7.87 (0.4H, br.s), 8.03-8.06 (1H, m); MS (ES+) m/z 395.

Preparation 669

A mixture of 5,6-dichloronicotinic acid (356 mg), iodoethane (318 mg) and potassium carbonate (308 mg) in N,N-dimethylformamide (3 mL) was heated at eighty degree for fourteen hours. The mixture was allowed to cool to ambient temperature and to this was added (3R)-1-(cyclohexylmethyl)-3-piperidinamine dihydrochloride (549 mg) and potassium carbonate (898 mg) and heated at eighty degree for thirtyeight hours. The mixture was allowed to cool to ambient temperature and was added water. The mixture was extracted with ethyl acetate (100 mL) and aqueous phase was separated. The organic layer was washed with brine and dried over anhydrous sodium sulfate. The solvent was filtered and evaporated in vacuo to give an amorphous solid. The crude solid was purified by a flash chromatography eluting with 3% methanol-chloroform (v/v) to give ethyl 5-chloro-6-{[(3R)-1-(cyclohexylmethyl)-3-piperidinyl]amino}nicotinate (154 mg) as a pale yellow amorphous solid.

$^1$H-NMR (300 MHz, CDCl$_3$) δ 0.79-0.98 (2H, m), 1.12-1.32 (4H, m), 1.37 (3H, t, J=7.3 Hz), 1.43-1.88 (9H, m), 2.03-2.21 (3H, m), 2.33-2.43 (1H, m), 2.59-2.75 (2H, m), 4.33 (2H, q, J=7.3 Hz), 4.36-4.48 (1H, m), 6.36 (1H, br.s), 8.00 (1H, d, J=1.8 Hz), 8.66 (1H, d, J=1.8 Hz).

Preparation 670

To a stirred solution of ethyl 5-chloro-6-{[(3R)-1-(cyclohexylmethyl)-3-piperidinyl]amino}nicotinate (321 mg) in tetrahydrofuran (6 mL) was added lithium aluminumhydride (80.2 mg) portionwise in an ice bath and the resulting suspension was stirred at the same temperature for three hours. To this was added saturated aqueous potassium sodium (+)-tartrate tetrahydrate solution portionwise at the same temperature and the mixture was stirred at ambient temperature for one hour. The mixture was extracted with ethyl acetate and the aqueous phase was removed. The organic layer was washed with brine, dried over anhydrous sodium sulfate, filtered and concentrated in vacuo. The residue was purified by flash chromatography eluting with ethylacetate-hexane 1:1 (v/v) to afford (5-chloro-6-{[(3R)-1-(cyclohexylmethyl)-3-piperidinyl]amino}-3-pyridinyl)methanol (210 mg) as a colorless oil.

$^1$H-NMR (300 MHz, CDCl$_3$) δ 0.77-0.98 (2H, m), 1.08-1.34 (4H, m), 1.39-1.89 (9H, m), 2.03-2.21 (3H, m), 2.34-2.48 (1H, m), 2.52-2.71 (2H, m), 4.17-4.29 (1H, m), 4.52 (2H, s), 5.87 (1H, br.s), 7.51 (1H, d, J=2.2 Hz), 7.96 (1H, d, J=2.2 Hz); MS (ES+) m/z 338(M+1).

Preparation 671

To a stirred solution of ethyl (2E)-3-(6-{(tert-butoxycarbonyl)[(3R)-1-(2,2,6,6-tetramethyl-4-piperidinyl)-3-pyrrolidinyl]amino}-3-pyridinyl)acrylate (265 mg, 0.529 mmol) in methanol (5 mL) was added hydroxylamine hydrochloride (184 mg, 2.65 mmol) at ambient temperature. To this mixture was added 1N potassium methoxide in methanol (5.29 mL, 5.29 mmol) dropwise in an ice bath and the resulting mixture was stirred at ambient temperature for three hours. To the mixture was added 1N hydrogen chloride to neutralize the solution. The solvent was removed in vacuo and the residue was desalted using ion-exchange resin. The crude product was purified by preparative high-pressure liquid chromatography to afford tert-butyl (5-[(1E)-3-(hydroxyamino)-3-oxo-1-propen-1-yl]-2-pyridinyl)[(3R)-1-(2,2,6,6-tetramethyl-4-piperidinyl)-3-pyrrolidinyl]carbamate (103 mg) as a colorless wax.

$^1$H-NMR (300 MHz, DMSO-d6) δ 0.74-0.90 (2H, m), 0.99 (6H, s), 1.09 (6H, s), 1.36 (9H, s), 1.54-1.69 (2H, m), 1.74-2.11 (2H, m), 2.34-2.53 (2H, m), 2.53-2.67 (2H, m), 2.87-2.98 (1H, m), 4.57-4.72 (1H, m), 6.54 (1H, d, J=16.1 Hz), 7.32 (1H, d, J=8.4 Hz), 7.48 (1H, d, J=16.1 Hz), 7.99 (1H, dd, 3=8.4, 2.2 Hz), 8.60 (1H, d, J=2.2 Hz); MS (ES+) m/z 488 (M+1).

The following compound was obtained in a similar manner to that of Preparation 671.

Preparation 672 tert-butyl {5}-[(1E)-3-(hydroxyamino)-3-oxo-1-propen-1-yl]-2-pyridinyl)][(3R)-1-(tetrahydro-2H-pyran-4-yl)-3-pyrrolidinyl]carbamate $^1$H-NMR (300 MHz, DMSO-d6) 1.13-1.36 (2H, m), 1.37 (9H, s), 1.60-1.74 (2H, m), 1.80-2.21 (3H, m), 2.35-2.67 (3H, m), 2.86-2.97 (1H, m), 3.19-3.33 (2H, m), 3.70-3.83 (2H, m), 4.61-4.78 (1H, m), 6.54 (1H, d, J=15.8 Hz), 7.34 (1H, d, J=8.4 Hz), 7.49 (1H, d, J=15.8 Hz), 7.99 (1H, br.d, J=8.8 Hz), 8.61 (1H, br.s); MS (ES+) m/z 433(M+1).

The following compound was obtained in a similar manner to that of Preparation 871.

Preparation 673 ethyl 6-[(2-benzylphenyl)amino]-5-chloronicotinate $^1$H-NMR (300 MHz, CDCl$_3$) δ 1.37 (3H, t, J=7 Hz), 4.03 (2H, s), 4.34 (2H, q, J=7 Hz), 6.93 (1H, s), 7.14-7.38 (8H, m), 7.88 (1H, d, J=8 Hz), 8.08 (1H, d, J=2 Hz), 8.69 (1H, d, J=2 Hz); MS (ES+) m/z 367.

Preparation 674

To a mixture of ethyl 5-chloro-6-(2,3-dihydro-1H-inden-2-ylamino)nicotinate (395 mg) and ammonium formate (472 mg) in ethanol (10 mL) was added 10% palladium on carbon (40 mg), and the mixture was stirred at 100° C. for 10 hours. The catalyst in the reaction mixture was removed by filtration. The solvent was evaporated in vacuo. The residual solid was collected with hexane and ethyl acetate (2/1 v/v) to give ethyl 6-(2,3-dihydro-1H-inden-2-ylamino)nicotinate (104 mg). The mother liquid was concentrated in vacuo, and the residue was purified by preparative thin layer column chromatography (hexane/ethyl acetate=2/1) to give ethyl 6-(2,3-dihydro-1H-inden-2-ylamino)nicotinate (209 mg) as a pale yellow solid.

$^1$H-NMR (300 MHz, DMSO-d6) δ 1.28 (3H, t, J=7 Hz), 2.84 (2H, dd, J=16, 6 Hz), 3.29 (2H, dd, J=16, 7 Hz), 4.24 (2H, q, J=7 Hz), 4.67 (1H, m), 6.52 (1H, d, J=9 Hz), 7.11-7.19 (2H, m), 7.20-7.29 (2H, m), 7.72 (1H, d, J=6.5 Hz), 7.81 (1H, dd, J=9, 2.5 Hz), 8.60 (1H, d, J=2.5 Hz); MS (ES+) m/z 283.

Preparation 675 tert-Butyl [(1R)-1-{[(cyclohexylmethyl)amino]}carbonyl)-3-(methylthio)propyl]carbamate (5.12 g) was dissolved in methyl iodide (23 mL) and stirred at room temperature for 18 hours. The excess methyl iodide was evaporated in vacuo. The residue was dissolved in tetrahydrofuran (50 mL), added lithium bis(trimethylsilyl)amide 1.0M solution in hexane (16.3 mL) at 0° C., and then allowed to warm to room temperature and stirred for 5 hours. The resulting mixture was poured into aqueous ammonium chloride and extracted with ethyl acetate. The organic phase was washed with brine, dried over MgSO$_4$, concentrated in vacuo. The residue was purified by silica gel column chromatography (hexane/ethyl acetate=from 80/20 (v/v) to 60/40 (v/v)) to give tert-butyl [(3R)-1-(cyclohexylmethyl)-2-oxo-3-pyrrolidinyl]carbamate (2.0 g) as a pale yellow solid.

$^1$H-NMR (300 MHz, CDCl$_3$) δ 0.86-1.04 (2H, m), 1.10-1.29 (3H, m), 1.45 (3×3H, s), 1.51-1.91 (7H, m), 2.65 (1H, m), 3.03-3.41 (4H, m), 4.17 (1H, m), 5.14 (1H, m); MS (ES+) m/z 297.

Preparation 676 ethyl (2E)-3-(5-{[(3R)-1-benzyl-3-pyrrolidinyl]amino}-2-pyrazinyl)acrylate

To an ice-cooled solution of ethyl (2E)-3-(5-{[(3R)-1-benzyl-3-pyrrolidinyl](tert-butoxycarbonyl)amino}-2-pyrazinyl)acrylate (4.63 g) in dichloromethane (7.8 ml) were added anisole (4.7 ml) and trifluoroacetic acid (15.6 ml), the mixture was stirred at 25° C. for 3.5 hours. The mixed solution was poured into a mixture of water and AcOEt. The pH of the aqueous layer was adjusted to ca.8 with NaHCO$_3$. The organic layer was separated, washed with brine, dried over sodium sulfate and evaporated under reduced pressure to give crude powder. The resulting residue was purified by column chromatography on silica gel (50 g) using a mixed solvent of CH$_2$Cl$_2$ and MeOH (100:1 to 20:1). The fractions containing the objective compound were collected and evaporated under reduced pressure. Title compound (3.05 g, 85%) was obtained as slightly yellowish powder.

MASS(API-ES); 353 (M+H), $^1$H-NMR (200 MHz), (DMSO-d6, δ): 1.24 (3H, t, J=7.1 Hz), 1.50-1.80 (1H, m), 2.10-2.35 (1H, m), 2.36-2.55 (2H, m), 2.60-2.85 (2H, m), 3.50-3.66 (2H, m), 4.16 (2H, a, J=7.1 Hz), 4.25-4.45 (1H, m), 6.49 (1H, d, J=15 Hz), 7.15-7.40 (5H, m), 7.53 (1H, d, J=15 Hz), 7.93 (1H, d, J=6.6 Hz), 8.00 (1H, s), 8.20 (1H, s).

The following compound was obtained in a similar manner to that of Preparation 676.

Preparation 677 ethyl 3-(5-{[(3R)-1-benzyl-3-pyrrolidinyl]amino}-2-pyrazinyl)-2-fluoroacrylate(E,Z-Mixture)

MASS(API-ES); 371 (M+H)+, $^1$H-NMR (200 MHz), (CDCl$_3$, δ): 1.20-1.50 (3H, m), 1.60-1.90 (1H, m), 2.25-2.50 (2H, m), 2.60-2.80 (2H, m), 2.85-3.03 (1H, m), 3.67 (2H, s), 4.33 (2H, q, J=7.2 Hz), 4.37-4.65 (1H, m), 5.24 (0.5H, d, J=7.6 Hz), 5.37 (0.5H, d, J=7.6 Hz), 6.78 (0.5H, d, J=22 Hz), 6.98 (0.5H, d, J=37 Hz), 7.20-7.40 (5H, m), 7.83 (0.5H, d, J=1.1 Hz), 7.89 (0.5H, d, J=1.1 Hz), 8.47 (0.5H, d, J=1.1 Hz), 8.56 (0.5H, d, J=1.1 Hz).

Preparation 678

To a mixture of ethyl (2E)-3-(6-{(tert-butoxycarbonyl)[(3R)-3-pyrrolidinyl]amino}-3-pyridinyl)acrylate dihydrochloride (256 mg) and cyclohexanone (64 mg) in 1,2-dichloroethane (5 mL) was added sodium triacetoxyborohydride (253 mg) and N,N-diisopropylethylamine (0.21 mL), and the mixture was stirred at room temperature for 2 hours. To the resultant was added saturated aqueous ammonium chloride and ethyl acetate, and the mixture was stirred for 20 min. The organic phase was separated, washed with brine and dried over Na$_2$SO$_4$, filtered, and concentrated in vacuo. The residue was purified by silica gel column chromatography (chloroform/methanol=95/5 v/v) to give ethyl (2E)-3-(6-{(tert-butoxycarbonyl)[(3R)-1-cyclohexyl-3-pyrrolidinyl]amino}-3-pyridinyl)acrylate (338 mg) as a pale yellow foam.

$^1$H-NMR (300 MHz, CDCl$_3$) δ 1.18-1.38 (4H, m), 1.35 (3H, t, J=7 Hz), 1.46 (9H, s), 1.58-1.86 (5H, m), 2.06-2.35 (3H, m), 2.68 (1H, m), 2.95 (1H, m), 3.41 (1H, m), 3.65 (1H, m), 3.96 (1H, m), 4.28 (2H, q, J=7 Hz), 5.09 (1H, m), 6.46 (1H, d, J=16 Hz), 7.30 (1H, d, J=9 Hz), 7.64 (1H, d, J=16 Hz), 7.81 (1H, d, J=9 Hz), 8.48 (1H, s); MS (ES+) m/z 444.

The following compounds were obtained in a similar manner to that of Preparation 678.

Preparation 679 ethyl (2E)-3-(6-{(tert-butoxycarbonyl)[(3R)-1-cycloheptyl-3-pyrrolidinyl]amino}-3-pyridinyl)acrylate $^1$H-NMR (300 MHz, CDCl$_3$) δ 1.21-1.72 (11H, m), 1.35 (3H, t, J=7 Hz), 1.45 (9H, s), 1.73-1.88 (2H, m), 1.99 (1H, m), 2.18 (1H, m), 2.35 (1H, m), 2.60 (1H, m), 2.75 (1H, m), 3.10 (1H, m), 4.28 (2H, q, J=7 Hz), 4.86 (1H, m), 6.46 (1H, d, J=16 Hz), 7.31 (1H, d, J=8.5 Hz), 7.65 (1H, d, J=16 Hz), 7.81 (1H, d, J=8.5, 2.5 Hz), 8.54 (1H, d, J=2.5 Hz); MS (ES+) m/z 458.

Preparation 680 ethyl (2E)-3-(6-{(tert-butoxycarbonyl)[(3R)-1-cyclopentyl-3-pyrrolidinyl]amino}-3-pyridinyl)acrylate $^1$H-NMR (300 MHz, CDCl$_3$) δ 1.20-1.86 (8H, m), 1.35 (3H, t, J=7 Hz), 1.46 (9H, s), 2.01 (1H, m), 2.21 (1H, m), 2.42-2.57 (2H, m), 2.63 (1H, m), 2.83 (1H, m), 3.14 (1H, m), 4.28 (2H, q, J=7 Hz), 4.90 (1H, m), 6.46 (1H, d, J=16 Hz), 7.32 (1H, d, J=8.5 Hz), 7.65 (1H, d, J=16 Hz), 7.81 (1H, dd, J=8.5, 2 Hz), 8.54 (1H, d, J=2 Hz); MS (ES+) m/z 430.

Preparation 681

0.94 M solution of diisobutylaluminium hydride in hexane (2.73 ml) was added dropwise to a solution of ethyl 6-{[(3R)-1-benzyl-3-pyrrolidinyl]amino}-5-fluoronicotinate (294 mg) in THF (10 ml) with stirred below 5° C. under atmospheric pressure of nitrogen, and the reaction mixture was stirred at the same temperature for 1.5 hrs. To the reaction mixture was added saturated aqueous ammonium chloride (0.727 ml) below 5° C., then the mixture was stirred at 25° C. for 30 minutes. Na$_2$SO$_4$ (2.87 g) was added to the solution, and the mixture was stirred at 25° C. for 15 minutes. The reaction mixture was filtrated, the filtrate was evaporated in vacuo. Toluene (15 ml) was added to the residue, and the mixture was evaporated in vacuo. The resulting residue and activated MnO$_2$ (744 mg) in ethyl, acetate (20 ml) were stirred at 75° C. for 1 hour. After removal of the insoluble material by filtration, the filtrate was evaporated in vacuo to give 6-{[(3R)-1-benzyl-3-pyrrolidinyl]amino}-5-fluoronicotinaldehyde (250 mg, 98%) as syrup. The compound was used in the next step reaction without purification.

Preparation 682

To an ice-cooled solution of ethyl (2E)-3-(6-{(tert-butoxycarbonyl)[(3R)-1-(cyclohexylcarbonyl)-3-pyrrolidinyl]amino}-3-{pyridinyl}acrylate (355 mg) in dichloromethane (2 ml) was added anisole (1.0 ml) and trifluoroacetic acid (2.0 ml), the mixture was stirred at 25° C. for 1 hour. The mixed solution was poured into a mixture of water and AcOEt. The pH of the aqueous layer was adjusted to ca.9 with NaHCO$_3$. The organic layer was separated, washed with brine, dried over sodium sulfate and evaporated under reduced pressure to give syrup. The residue was dissolved in a mixed solvent of tetrahydrofuran (6 ml) and methanol (2.5 ml), and 1 mol/L-NaOH (1.5 mL) was added to the solution at 25° C. The mixture was stirred at 50° C. for 1.5 hours. The reaction mixture was evaporated in vacuo, the resulting residue was poured into a mixture of water and AcOEt. The pH of the aqueous layer was adjusted to ca.5 with 1 mol/L hydrochloric acid. The organic layer was separated, dried over sodium sulfate and evaporated under reduced pressure to give (2E)-3-(6-{[(3R)-1-(cyclohexylcarbonyl)-3-pyrrolidinyl]amino}-3-pyridinyl)acrylic acid (250 mg, 97%) as powder.

MASS(API-ES); 344 (M+H)+Free $^1$H-NMR (200 MHz), (DMSO-d6, δ): 1.05-1.77 (10H, m), 1.78-2.47 (3H, m), 3.10-3.90 (4H, m), 4.24-4.57 (1H, m), 6.25 (1H, d, J=16 Hz), 6.54 (1H, dd, J=2.2 Hz, J=8.8 Hz), 7.30-7.45 (1H, m), 7.46 (1H, d, J=16 Hz), 7.79 (1H, d, J=8.8 Hz), 8.22 (1H, d, J=2.2 Hz).

Preparation 683

To a stirred solution of 6-(2,3-dihydro-1H-inden-2-ylamino)nicotinaldehyde (160 mg) and malonic acid (84 mg) in pyridine (6 mL) was added piperidine (0.01 mL), and the mixture was stirred at 100° C. for 2 hours. The solvent was evaporated in vacuo and the resulting powder was collected by filtration to give (2E)-3-[6-(2,3-dihydro-1H-inden-2-ylamino)-3-pyridinyl]acrylic acid (190 mg) as a pale yellow powder.

$^1$H-NMR (300 MHz, DMSO-d6) δ 2.83 (2H, dd, J=16, 6 Hz), 3.29 (2H, dd, J=16, 7 Hz), 4.64 (1H, m), 6.24 (1H, d, J=16 Hz), 6.52 (1H, d, J=9 Hz), 7.10-7.29 (4H, m), 7.4-7.52 (2H, m), 7.77 (1H, dd, J=9, 2.2 Hz), 8.23 (1H, d, J=2.2 Hz), 12.06 (1H, br); MS (ES+) m/z 281.

The following compounds were obtained in a similar manner to that of Preparation 683.

Preparation 684

(2E)-3-(6-{[(1R,2R)-2-(benzyloxy)cyclopentyl]amino}-5-chloro-3-{pyridinyl}acrylic acid $^1$H-NMR (300 MHz, CDCl$_3$) δ 1.50 (1H, m), 1.68-2.06 (4H, m), 2.33 (1H, m), 3.87 (1H, m), 4.49 (1H, m), 4.67 (2H, s), 5.21 (1H, d, J=7 Hz), 6.23 (1H, d, J=16 Hz), 7.23-7.38 (5H, m), 7.65 (1H, d, J=16 Hz), 7.68 (1H, d, J=1.8 Hz), 8.18 (1H, d, J=1.8 Hz); MS (ES+) m/z 373.

Preparation 685

(2E)-3-(5-chloro-6-{[(1S,2R)-2-phenylcyclopropyl]amino}-3-pyridinyl)acrylic acid $^1$H-NMR (300 MHz, CDCl$_3$) δ 1.26 (1H, m), 1.40 (1H, m), 2.14 (1H, ddd, J=9, 6, 3 Hz), 3.09 (1H, m), 5.65 (1H, d, J=3 Hz), 6.25 (1H, d, J=15.7 Hz), 7.17-7.36 (5H, m), 7.64 (1H, d, J=15.7 Hz), 7.70 (1H, d, J=2 Hz), 8.24 (1H, d, J=2 Hz); MS (ES+) m/z 315.

Preparation 686

(2E)-3-{6-[(2-benzylphenyl)amino]-5-chloro-3-pyridinyl}acrylic acid $^1$H-NMR (300 MHz, DMSO-d6) δ 3.92 (2H, s), 6.44 (1H, br), 7.07-7.30 (8H, m), 7.39 (1H, br), 7.45 (1H, d, J=8 Hz), 8.08-8.25 (3H, m); MS (ES+) m/z 365.

Preparation 687

(2E)-3-[5-chloro-6-({2-[(cyclohexylcarbonyl)amino]phenyl}amino)-3-pyridinyl]acrylic acid $^1$H-NMR (300 MHz, DMSO-d6) δ 1.10-1.86 (10H, m), 2.41 (1H, m), 6.49 (1H, d, J=16 Hz), 7.11-7.30 (3H, m), 7.48 (1H, d, J=16 Hz), 7.77 (1H, d, J=7.5 Hz), 8.24 (1H, d, J=1 Hz), 8.26 (1H, d, J=1 Hz), 8.36 (1H, s), 9.93 (1H, s), 12.28 (1H, br-s); MS (ES+) m/z 400.

Preparation 688

(2E)-3-[5-chloro-6-({3-[(cyclohexylcarbonyl)amino]phenyl}amino)-3-pyridinyl]acrylic acid $^1$H-NMR (300 MHz, DMSO-d6) δ 1.13-1.48 (5H, m), 1.58-1.84 (5H, m), 2.33 (1H, m), 6.51 (1H, d, J=16 Hz), 7.16-7.34 (3H, m), 7.52 (1H, d, J=16 Hz), 7.95 (1H, s), 8.25 (1H, d, J=2 Hz), 8.33 (1H, d, J=2 Hz), 8.70 (1H, s), 9.80 (1H, s); MS (ES+) m/z 400.

Preparation 689

A mixture of ethyl (2E)-3-{5-chloro-6-[(3R)-3-pyrrolidinylamino]-3-pyridinyl}acrylate dihydrochloride (2.0 g), trans-4-{[(tert-butoxycarbonyl)amino]methyl}cyclohexanecarboxylate (1.68 g), HOBt (880 mg) and WSCD (1.26 g) in dichloromethane (40 ml) and Et$_3$N (1.51 ml) (2.0 eq) was stirred at room temperature for 8 hours.

After then, water was added and the reaction mixture was extracted with dichloromethane (twice).

Combined organic layer was washed with water (twice) and brine, dried over MgSO$_4$, filtered and evaporated.

Residue was column chromatographed on silica gel to give 2.85 g (98%) of ethyl (2E)-3-[6-({(3R)-1-[(trans-4-{[(tert-butoxycarbonyl)amino]methyl}cyclohexyl)carbonyl]-3-pyrrolidinyl}amino)-5-chloro-3-pyridinyl]acrylate.

MASS (ESI+): m/z=557.2 (M+Na).

$^1$HNMR (400 MHz, CDCl$_3$): δ 0.8-2.4 (12H, m), 1.43 and 1.44 (9H, s), 1.33 (3H, t, J=7.1 Hz), 2.8-4 (6H, m), 4.24 (1H, t, J=7.1 Hz), 4.25 (1H, t, J=7.1 Hz), 4.53-4.8 (2H, m), 5.26 (1H, dd, J=6.4, 20 Hz), 6.25 (1H, dd, J=6.6, 16 Hz), 7.54 (1H, dd, J 4.6, 16 Hz), 7.69 (1H, dd, J=2, 7.9 Hz), 8.15 (1H, dd, J=2, 7.6 Hz).

Preparation 690

4NHCl/Dioxane (14 ml) was added to ethyl (2E)-3-[6-({(3R)-1-[(trans-4-{[(tert-butoxycarbonyl)amino]methyl}cyclohexyl)carbonyl]-3-pyrrolidinyl}amino)-5-chloro-3-pyridinyl]acrylate (3.0 g) under ice cooling.

After 2 hours, IPE was added to this reaction mixture.

The mixture was decantated and dioxane and IPE was separated.

Residue was evaporated under reduced pressure to give 2.80 g (98%) of ethyl (2E)-3-{6-[((3R)-1-{[trans-4-(aminomethyl)cyclohexyl]carbonyl}-3-pyrrolidinyl)amino]-5-chloro-3-pyridinyl}acrylate dihydrochloride as an amorphous.

MASS (ESI+): m/z=435.2 (M+1).

$^1$HNMR (400 MHz, CDCl$_3$): δ 0.90-2.80 (12H, m), 1.24 (3H, t, J=7.1 Hz), 2.94-3.88 (6H, m), 4.16 (2H, q, J=7.1 Hz), 4.54 and 4.68 (1H, br.s), 6.53 (1H, dd, J=3.2, 15.9 Hz), 7.54 (1H, dd, J=2.6, 15.9 Hz), 7.9-8.02 (2H, m), 8.17 (1H, dd, J=1.9, 5.8 Hz), 8.33 (1H, dd, J=1.9, 4.8 Hz).

Preparation 691

A mixture of ethyl (2E)-3-{6-[((3R)-1-{[trans-4-(aminomethyl)cyclohexyl]carbonyl}-3-pyrrolidinyl)amino]-5-chloro-3-pyridinyl}acrylate dihydrochloride (1.0 g), Formaldehyde (1.0 ml), NaBH(OAc)$_3$ (1.25 g) and triethylamine (2.0 eq. 398 mg, 0.55 ml) in dichloromethane (20 ml) was stirred at room temperature for 8 hours.

After then, water was added and the reaction mixture was extracted with dichloromethane (twice).

Combined organic layer was washed with sat. sodium bicarbonate and water, and dried over MgSO$_4$, filtered and evaporated.

Residue was column chromatographed on silica gel to give 660 mg (72%) of ethyl (2E)-3-(5-chloro-6-{[(3R)-1-({trans-4-[(dimethylamino)methyl]cyclohexyl)carbonyl)-3-pyrrolidinyl]amino}-3-pyridinyl)acrylate.

MASS (ESI+): m/z=463.3 (M+1).

$^1$HNMR (400 MHz): δ 0.80-2.45 (14H, m), 1.33 (3H, t, J=7.2 Hz), 1.33 (3H, t, J=7.1 Hz), 2.23 and 2.24 (6H, s), 3.36-4.01 (4H, m), 4.25 (1H, q, J=7.2 Hz), 4.26 (1H, q, J=7.1 Hz), 4.6-4.75 (1H, m), 5.26 (1H, dd, J=6.5, 21.2 Hz), 6.25 (1H, dd, J=6, 15.9 Hz), 7.54 (1H, dd, J=4, 15.9 Hz), 7.69 (1H, dd, J=2, 7.7 Hz), 8.15 (1H, dd, J=2, 6.3 Hz).

Preparation 692

A mixture of I (610 mg) and 1NNaOH (5 ml) in THF (20 ml) and MeOH (20 ml) was stirred at 60° C. for 3 hrs.

1N HCl (5 ml) was added.

The mixture was evaporated under reduced pressure.

Toluene was added and evaporated again to give 600 mg (quant.) of (2E)-3-(5-chloro-6-{[(3R)-1-({trans-4-[(dimethylamino)methyl]cyclohexyl)carbonyl)-3-pyrrolidinyl]amino}-3-pyridinyl)acrylic acid.

This product was used for next transformation.

MASS (ESI−): m/z=433.3 (M−1).

Preparation 693

A mixture of (2E)-3-(5-chloro-6-{[(3R)-1-({trans-4-[(dimethylamino)methyl]cyclohexyl)carbonyl)-3-pyrrolidinyl]amino}-3-pyridinyl)acrylic acid (600 mg), O-(tetrahydro-2H-pyran-2-yl)hydroxylamine (194 mg), HOBt (242 mg) and WSCD (321 mg) in DMF (40 ml) was stirred at room temperature for 8 hours.

After then, water was added and the reaction mixture was extracted with dichloromethane (twice).

Combined organic layer was washed with water (twice) and brine, dried over MgSO$_4$, filtered and evaporated.

Residue was column chromatographed on silica gel to give 530 mg (72%) of (2E)-3-(5-chloro-6-{[(3R)}-1-({trans-4-[(dimethylamino)methyl]cyclohexyl)carbonyl)-3-pyrrolidinyl]amino}-3-pyridinyl)-N-(tetrahydro-2H-pyran-2-yloxy)acrylamide.

MASS (ESI+): m/z=534.2 (M+1).

$^1$HNMR (400 MHz, CDCl$_3$): δ 0.82-2.44 (20H, m), 2.23 and 2.24 (6H, s), 3.32-4.05 (6H, m), 4.60-4.75 (1H, m), 5.01 (1H, br.s), 5.23 (1H, dd, J=6.5, 20.6 Hz), 7.56 (1H, d, J=5.2 Hz), 7.6 (1H, d, J=5.2 Hz), 7.66 (1H, d, J=8.8 Hz), 8.16 (H, d, J=8.8 Hz).

Preparation 694

A diisobutylaluminium hydride in toluene solution (4.6 mL) was dropwise added to a solution of ethyl 5-chloro-6-{[(1S,2R)-2-phenylcyclopropyl]amino}nicotinate (488 mg) in tetrahydrofuran (15 mL) with stirring at 0° C. under atmospheric pressure of nitrogen, and the reaction mixture was stirred at 0° C. for 1 hour. A methanol (1 mL) was added to a reaction mixture at 0° C. and allowed to warm to room temperature. Tetrahydrofuran (20 mL) and saturated sodium potassium tartarate aqueous solution (5 mL) was added and the resultant mixture was stirred at ambient temperature for 1 hour. The reaction mixture was filtrated and the filtrate was dried over MgSO$_4$. The solvent was evaporated in vacuo and the residue was purified by silica gel column chromatography (hexane/ethyl acetate=2:1 v/v) to give (5-chloro-6-{[(1S,2R)-2-phenylcyclopropyl]amino}-3-pyridinyl)methanol (398 mg).

¹H-NMR (300 MHz, CDCl₃) δ 1.24 (1H, m), 1.37 (1H, m), 1.62 (1H, t, J=5 Hz), 2.10 (1H, m), 3.03 (1H, m), 4.56 (1H, d, J=5 Hz), 5.37 (1H, s), 7.16-7.34 (6H, m), 7.54 (1H, d, 3=2 Hz), 8.07 (1H, d, J=2 Hz); MS (ES+) m/z 275.

The following compounds were obtained in a similar manner to that of Preparation 694.

Preparation 695

N-(2-{[3-chloro-5-(hydroxymethyl)-2-pyridinyl]amino}phenyl)cyclohexanecarboxamide ¹H-NMR (300 MHz, CDCl₃) δ 1.18-1.38 (3H, m), 1.42-1.59 (2H, m), 1.68 (1H, m), 1.74-1.97 (4H, m), 2.28 (1H, m), 3.68 (1H, t, J=5.5 Hz), 4.54 (2H, d, J=5.5 Hz), 7.13 (1H, ddd, J=7.7, 7.7, 1.5 Hz), 7.21 (1H, ddd, J=7.7, 7.7, 1.5 Hz), 7.44 (1H, dd, J=7.7, 1.5 Hz), 7.48 (1H, s), 7.65-7.72 (2H, m), 7.99 (1H, d, J=1.8 Hz), 8.37 (1H, s); MS (ES+) m/z 360.

Preparation 696

{6}-[(2-benzylphenyl)amino]-5-chloro-3-pyridinyl)methanol

¹H-NMR (300 MHz, CDCl₃) δ 1.60 (1H, t, J=5.5 Hz), 4.03 (2H, s), 4.56 (2H, d, J=5.5 Hz), 6.65 (1H, s), 7.08-7.36 (8H, m), 7.59 (1H, d, J=2 Hz), 7.92 (1H, d, J=8 Hz), 8.02 (1H, d, J=2 Hz); MS (ES+) m/z 325.

Preparation 697

A mixture of ethyl (2E)-3-{5-chloro-6-[(3R)-3-pyrrolidinylamino]-3-pyridinyl}acrylate dihydrochloride (600 mg), cyclohexylacetic acid (255 mg), HOBt (264 mg) and WSCD (379 mg) in dichlroromethane (20 ml) was stirred at room temperature for 8 hours.

After then, water was added and the reaction mixture was extracted with dichloromethane (twice).

Combined organic layer was washed with water (twice) and brine, dried over MgSO₄, filtered and evaporated.

Residue was column chromatographed on silica gel to give 630 mg (92%) of ethyl (2E)-3-(5-chloro-6-{[(3R)-1-(cyclohexylacetyl)-3-pyrrolidinyl]amino}-3-pyridinyl)acrylate.

MASS (ESI+): m/z=442.3 (M+Na).

¹HNMR (400 MHz, CDCl₃): δ 0.85-1.38 (3H, m), 1.33 (3H, t, J=7.1 Hz), 1.6-2.4 (12H, m), 3.35-3.95 (4H, m), 4.25 (1H, q, J=7.1 Hz), 4.26 (1H, q, J=7.1 Hz), 4.61-4.75 (1H, m), 5.26 (1H, dd, J=6.4, 15.5 Hz), 6.25 (1H, dd, J=5.2, 16 Hz), 7.54 (1H, dd, J=3.3, 15.9 Hz), 7.69 (1H, dd, J=2.1, 6.4 Hz), 8.15 (1H, dd, J=2, 4.7 Hz).

Preparation 698

A mixture of ethyl (2E)-3-(5-chloro-6-{[(3R)-1-(cyclohexylacetyl)-3-pyrrolidinyl]amino}-3-pyridinyl)acrylate (600 mg) and 1N NaOH (6 ml) in THF (20 ml) and MeOH (20 ml) was stirred at 50° C. for 2 hrs. 1N HCl (6 ml) was added.

Evaporated under reduced pressure.

Added toluene and evaporated to give 550 mg of crude (2E)-3-(5-chloro-6-{[(3R)-1-(cyclohexylacetyl)-3-pyrrolidinyl]amino}-3-pyridinyl)acrylic acid.

This product was used for next transformation.

MASS (ESI-): m/z=390.2 (M-1).

Preparation 699 ethyl 6-{[(3R)-1-benzyl-3-pyrrolidinyl]amino}-5-fluoronicotinate

To a solution of ethyl 6-{[(3R)-1-benzyl-3-pyrrolidinyl]amino}-2-chloro-5-fluoronicotinate (500 mg) in ethanol (20 mL) were added ammonium formate (584 mg) and 10% Pd/C (300 mg) at 25° C. and the mixture was heated to reflux with stirring for 1 hour. After cooling, the catalyst in the reaction mixture was removed by filtration. The filtrate was evaporated in vacuo. To the residue were added CH₂Cl₂ (30 ml), ethanol (7 mL), and benzaldehyde (140 mg) at 25° C. After stirring for 5 minutes, sodium triacetoxyborohydride (280 mg) was added to the mixture. The reaction mixture was stirred at 25° C. for 3 hours, and then poured into a mixture of CH₂Cl₂ and aqueous NaHCO₃. The organic layer was separated, dried over sodium sulfate, and concentrated in vacuo. The residue was purified by column chromatography on silica gel (11 g) using a mixed solvent of dichloromethane and MeOH (100:1 to 40:1). The fractions containing the objective compound were collected and evaporated under reduced pressure. Title compound (302 mg, 66%) was obtained as colorless syrup.

MASS(API-ES); 344 (M+H)+

¹H-NMR (200 MHz, (DMSO-d6, δ): 1.28 (3H, t, J=7.1 Hz), 1.70-1.95 (1H, m), 2.05-2.30 (1H, m), 2.35-2.70 (3H, m), 2.80-2.90 (1H, m), 3.58 (2H, s), 4.24 (2H, q, J=7.1 Hz), 4.40-4.60 (1H, m), 7.15-7.35 (5H, m), 7.54 (1H, d, J=6.3 Hz), 7.64 (1H, dd, J=1.9 Hz, J=12 Hz), 8.41 (1H, d, J=1.9 Hz).

Preparation 700

A mixture of m-phenylenediamine (2.00 g), cyclohexanecarboxylic acid (2.37 g), HOBt (2.75 g) and EDCI (3.9 g) in DMF (20 mL) was stirred at ambient temperature for 2 hours. The reaction mixture was diluted with water and the resulting solid was collected by filtration. The solid was purified by silica gel column chromatography (hexane/ethyl acetate=4/1 to 1/2 v/v) to give N-(3-aminophenyl)cyclohexanecarboxamide (2.2 g) as a white powder.

¹H-NMR (300 MHz, CDCl₃) δ 1.20-1.39 (3H, m), 1.44-1.62 (2H, m), 1.70 (1H, m), 1.77-2.00 (4H, m), 2.20 (1H, m), 3.68 (2H, s), 6.42 (1H, dd, J=8, 2 Hz), 6.64 (1H, dd, J=8, 2 Hz), 7.06 (1H, dd, J=8, 8 Hz), 7.07 (1H, br), 7.23 (1H, s); MS (ES+) m/z 219.

The following compound was obtained in a similar manner to that of Preparation 700.

Preparation 701

N-(2-aminophenyl)cyclohexanecarboxamide

¹H-NMR (300 MHz, CDCl₃) δ 1.20-2.06 (10H, m), 2.31 (1H, m), 3.83 (2H, br-s), 6.74-6.86 (2H, m), 7.05 (1H, m), 7.10-7.23 (2H, m); MS (ES+) m/z 219.

Preparation 702 ethyl (2E)-3-(5-{[(3R)-1-benzyl-3-pyrrolidinyl](tert-butoxycarbonyl)amino}-2-pyrazinyl)acrylate 0.94 M solution of diisobutylaluminium hydride in hexane (4.82 ml) was added dropwise to a solution of methyl 5-{[(3R)-1-benzyl-3-pyrrolidinyl](tert-butoxycarbonyl)amino}-2-pyrazinecarboxylate (1.01 g) in THF (20 ml) with stirred below −60° C. under atmospheric pressure of nitrogen, and the reaction mixture was stirred at −55 to −50° C. for 1 hr. To the reaction mixture was added saturated aqueous ammonium chloride (1.28 ml) at the same temperature, then the mixture was stirred at 25° C. for 40 minutes. THF (14 ml) and MgSO$_4$ (4.36 G) were added to the solution, and the mixture was stirred at 25° C. for 15 minutes. The reaction mixture was filtered, and then to the filtrate was added ETHYL (triphenylphosphoranylidene)acetate (1.07 g), and the mixture was stirred at 25° C. for 16 hr. The reaction mixture was poured into a mixture of AcOEt and 5% aqueous NaCl. The separated organic layer was washed with brine, dried over sodium sulfate and evaporated in vacuo. The resulting residue was purified by column chromatography on silica gel (51 g) using a mixed solvent of hexane and ethyl acetate (7:2 to 2:1). The fractions containing the objective compound were collected and evaporated under reduced pressure. Title compound (584 mg, 53%) was obtained as slightly yellowish oil.

MASS(API-ES); 453 (M+H)+

$^1$H-NMR (200 MHz), (DMSO-d6, δ): 1.21-1.42 (13H, m), 1.88-2.30 (2H, m), 2.35-2.77 (3H, m), 3.42, 3.51 (2H, ABq, J=13 Hz), 4.24 (2H, q, J=7.1 Hz), 4.66-4.88 (1H, m), 6.94 (1H, d, J=16 Hz), 7.03-7.33 (5H, m), 7.76 (1H, d, J=16 Hz), 8.67 (1H, d, J=1.0 Hz), 8.80 (1H, d, J=1.0 Hz).

Preparation 703

Palladium(II) acetate (75 mg) and 2,2'-bis(diphenylphosphino)-1,1'-binaphthalene (313 mg) in dioxane (5 mL) was stirred at ambient temperature for 15 minutes. To this suspension was added 2,6-dichloropyrazine (1.00 g), (3R)-(−)-1-benzyl-3-aminopyrrolidine (1.42 g), and cesium carbonate (3.28 g), and the mixture was heated at 80 C for 8 hours. The resulting mixture was allowed to cool to ambient temperature, poured into water, and extracted with ethyl acetate. The organic phase was washed with brine, dried over anhydrous sodium sulfate and concentrated in vacuo. The residue was purified by silica gel column chromatography (chloroform/methanol=96/4 v/v) to give N-[(3R)-1-benzyl-3-pyrrolidinyl]-6-chloro-2-pyrazinamine (1.00 g) as a yellow solid.

$^1$H-NMR (300 MHz, CDCl$_3$) δ 1.67 (1H, m), 2.30-2.44 (2H, m), 2.64 (1H, dd, J=10, 4 Hz), 2.68 (1H, dd, J=10, 5.5 Hz), 2.89 (1H, m), 3.62 (1H, d, J=13 Hz), 3.66 (1H, d, J=13 Hz), 4.38 (1H, m), 5.09 (1H, d, J=8 Hz), 7.22-7.38 (5H, m), 7.71 (1H, s), 7.77 (1H, s); MS (ES+) m/z 289.

The following compounds were obtained in a similar manner to that of Preparation 703.

Preparation 704 ethyl (2E)-3-(5-{[2-(1-piperidinyl)phenyl]amino}-2-pyrazinyl)acrylate $^1$H-NMR (300 MHz, CDCl$_3$) δ 1.34 (3H, t, J=7 Hz), 1.63 (2H, m), 1.69-1.80 (4H, m), 2.79-2.88 (4H, m), 4.27 (2H, q, J=7 Hz), 6.78 (1H, d, J=15.5 Hz), 7.04 (1H, ddd, J=7.5, 7.5, 1.5 Hz), 7.11-7.20 (2H, m), 7.63 (1H, d, J=15.5 Hz), 8.19-8.24 (3H, m), 8.28 (1H, dd, J=7.5, 1.5 Hz); MS (ES+) m/z 353.

Preparation 705 ethyl (2E)-3-[4-({2-[(cyclohexylcarbonyl)amino]phenyl}amino)phenyl]acrylate $^1$H-NMR (300 MHz, CDCl$_3$) δ 1.18-1.38 (5H, m), 1.33 (3H, t, J=7 Hz), 1.42 (1H, m), 1.65 (1H, m), 1.72-1.91 (4H, m), 2.20 (1H, m), 4.24 (2H, q, J=7 Hz), 6.08 (1H, s), 6.27 (1H, d, J=15.7. Hz), 6.75 (2H, d, J=8.5 Hz), 7.12-7.22 (2H, m), 7.31 (1H, m), 7.38 (2H, d, J=8.5 Hz), 7.53 (1H, s), 7.61 (1H, d, J=15.7 Hz), 7.82 (1H, m); MS (ES+) m/z 393.

Preparation 706 ethyl 3-(5-{[(3R)-1-benzyl-3-pyrrolidinyl](tert-butoxycarbonyl)amino}-2-pyrazinyl)-2-fluoroacrylate (E,Z-Mixture)

0.94 M solution of diisobutylaluminium hydride in hexane (5.79 ml) was added dropwise to a solution of methyl 5-{[(3R)-1-benzyl-3-pyrrolidinyl](tert-butoxycarbonyl)amino}-2-pyrazinecarboxylate (1.18 g) in THF (25 ml) with stirred below −60° C. under atmospheric pressure of nitrogen, and the reaction mixture was stirred at −55 to −50° C. for 1 hr. To the reaction mixture was added saturated aqueous ammonium chloride (1.54 ml) at the same temperature, then the mixture was stirred at 25° C. for 40 minutes. THF (15 ml), MgSO$_4$ (7 G) and Na$_2$SO$_4$ (15 g) were added to the solution, and the mixture was stirred at 25° C. for 15 minutes. The reaction mixture was filtered, the filtrate was Filtrate (A). On the other hand, to an ice-cooled solution of ethyl (diethoxyphosphoryl)(fluoro)acetate (970 mg) in THF (21 ml) was added MgBr$_2$ (885 mg), and triethylamine (0.614 ml), then the mixture was stirred at 50° C. for 2 hours. The reaction mixture was poured into a mixture of AcOEt and 5% aqueous NaCl. The separated organic layer was washed with brine, dried over sodium sulfate and evaporated in vacuo. The resulting residue was purified by column chromatography on silica gel (20 g) using a mixed solvent of hexane and ethyl acetate (2:1 to 1:1). The fractions containing the objective compound were collected and evaporated under reduced pressure. Title compound (674 mg, 50%) was obtained as oil.

MASS(API-ES); 471 (M+H)+

Preparation 707

A mixture of N-[(3R)-1-benzyl-3-pyrrolidinyl]-6-chloro-2-pyrazinamine (980 mg), di-tert-butyl dicarbonate (1.48 g) and 4-dimethylaminopyridine (83 mg) in acetonitrile (20 mL) was stirred at 100° C. for 3 days. The reaction mixture was poured into brine and extracted with ethyl acetate. The organic phase was washed with aqueous ammonium chloride, aqueous sodium hydrogen carbonate, and brine, dried over magnesium sulfate, and concentrated in vacuo. The residue was purified by silica gel column chromatography (hexane/ethyl acetate=75/25) to give tert-butyl [(3R)-1-benzyl-3-pyrrolidinyl](6-chloro-2-pyrazinyl)carbamate (925 mg) as a pale yellow oil.

$^1$H-NMR (300 MHz, CDCl$_3$) δ 1.44 (9H, s), 1.90-2.11 (2H, m), 2.26 (1H, m), 2.58-2.78 (3H, m), 2.88 (1H, m), 3.53 (1H, d, J=13 Hz), 3.62 (1H, d, J=13 Hz), 4.92 (1H, m), 7.17-7.36 (5H, m), 8.35 (1H, s), 8.51 (1H, s);

MS (ES+) m/z 389.

The following compound was obtained in a similar manner to that of Preparation 336.

Preparation 708 tert-butyl [(3R)-1-cyclopentyl-3-pyrrolidinyl](5-{(1E)-3-oxo-3-[(tetrahydro-2H-pyran-2-yloxy)amino]-1-propen-1-yl}-2-pyridinyl)carbamate $^1$H-NMR (300 MHz, DMSO-d6) δ 1.20-1.78 (14H, m), 1.38 (9H, s), 1.82-2.15 (2H, m), 2.20-2.53 (4H, m), 3.54 (1H, m), 3.96 (1H, m), 4.72 (1H, m), 4.92 (1H, m), 6.58 (1H, d, 3=16

Hz), 7.36 (1H, d, J=7 Hz), 7.53 (1H, d, J=16 Hz), 8.01 (1H, dd, J=7, 2 Hz), 8.63 (1H, d, J=2 Hz), 11.32 (1H, br-s); MS (ES+) m/z 501.

Preparation 709

To a stirred solution of 1-(bromomethyl)-2-nitrobenzene (2.10 g) in DMF (20 mL) was added pyrrolidine (0.95 mL) and N,N-diisopropylethylamine (2.54 mL), and the mixture was stirred at 60° C. for 24 hours. The resulting mixture was poured into ethyl acetate and brine. The organic phase was separated and washed with brine, dried over sodium sulfate. The solvent was evaporated in vacuo and the residue was purified by silica gel column chromatography to give 1-(2-nitrobenzyl)pyrrolidine (1.92 g) as a pale yellow oil.

$^1$H-NMR (300 MHz, CDCl$_3$) δ 1.71-1.83 (4H, m), 2.46-2.57 (4H, m), 3.93 (2H, s), 7.37 (1H, ddd, J=8, 7.5, 1.5 Hz), 7.55 (1H, ddd, J=8, 7.5, 1.5 Hz), 7.69 (1H, br-d, J=8 Hz), 7.85 (1H, dd, J=8, 1.5 Hz); MS (ES−) m/z 205.

Preparation 710

A mixture of (2E)-3-(5-chloro-6-{[(3R)-1-(cyclohexylacetyl)-3-pyrrolidinyl]amino}-3-pyridinyl)acrylic acid (550 mg), O-(tetrahydro-2H-pyran-2-yl)hydroxyamine (198 mg), HOBt (247 mg) and WSCD (218 mg) in DMF (40 ml) was stirred at room temperature for 8 hours.

After then, water was added and the reaction mixture was extracted with dichloromethane (twice).

Combined organic layer was washed with water (twice) and brine, dried over MgSO$_4$, filtered and evaporated.

Residue was column chromatographed on silica gel to give 680 mg (99%) of (2E)-3-(5-chloro-6-{[(3R)-1-(cyclohexylacetyl)-3-pyrrolidinyl]amino}-3-pyridinyl)-N-(tetrahydro-2H-pyran-2-yloxy)acrylamide.

MASS (ESI+): m/z=513.3 (M+Na).

$^1$HNMR (400 MHz, CDCl$_3$): δ 0.85-1.35 (5H, m), 1.55-2.41 (15H, m), 3.35-4.05 (6H, m), 4.60-4.73 (1H, m), 4.99 (1H, br.s), 5.19-5.28 (1H, m), 4.61-4.75 (1H, m), 7.56-7.70 (2H, m), 8.02 (1H, s), 8.16 (1H, s), 8.48-8.52 (1H, m).

Preparation 711 ethyl (2E)-3-(6-{[(3R)-1-benzyl-3-pyrrolidinyl]amino}-5-fluoro-3-{pyridinyl}acrylate To an ice-cooled suspension of sodium hydride (38.5 mg) in THF (10 ml) was added ethyl (diethoxyphosphoryl)acetate (206 mg), and the mixture was stirred at 24° C. for 40 minutes. To the mixture was added 6-{[(3R)-1-benzyl-3-pyrrolidinyl]amino}-5-fluoronicotinaldehyde (250 mg) at 24° C., the reaction mixture was stirred at same temperature for 30 minutes. The reaction mixture was poured into a mixture of AcOEt and 5% aqueous NaCl. The separated organic layer was washed with brine, dried over sodium sulfate and evaporated in vacuo. The resulting residue was purified by column chromatography on silica gel (8.2 g) using a mixed solvent of CH$_2$Cl$_2$ and MeOH (100:1 to 35:1). The fractions containing the objective compound were collected and evaporated under reduced pressure. Title compound (111 mg, 36%) was obtained as oil.

MASS(API-ES); 370 (M+H)+

$^1$H-NMR (200 MHz), (DMSO-d6, δ): 1.23 (3H, t, J=7.0 Hz), 1.45-2.70 (5H, m), 2.80-2.90 (1H, m), 3.57 (2H, s), 4.15 (2H, q, 0.3=7.0 Hz), 4.35-4.60 (1H; m); 6.41 (1H, d, J=16 Hz), 7.15-7.40 (6H, m), 7.53 (1H, d, J=16 Hz), 7.84 (1H, dd, J=1.1 Hz, J=13 Hz), 8.08 (1H, d, J=1.1 Hz).

Preparation 712 ethyl (2E)-3-(5-{[(3R)-1-benzyl-3-pyrrolidinyl](tert-butoxycarbonyl)amino}-2-pyrazinyl)acrylate 0.94 M solution of diisobutylaluminium hydride in hexane (38.3 ml) was added dropwise to a solution of methyl 5-{[(3R)-1-benzyl-3-pyrrolidinyl](tert-butoxycarbonyl)amino}-2-pyrazinecarboxylate (8.42 g) in THF (170 ml) with stirred below −60° C. under atmospheric pressure of nitrogen, and the reaction mixture was stirred at −55 to −50° C. for 1 hr. To the reaction mixture was added saturated aqueous ammonium chloride (10.2 ml) at the same temperature, then the mixture was stirred at 25° C. for 40 minutes. THF (60 ml) and MgSO$_4$ (34.1 G) were added to the solution, and the mixture was stirred at 25° C. for 15 minutes. The reaction mixture was filtrated, the filtrate was Filtrate (A). On the other hand, to an ice-cooled suspension of sodium hydride (938 mg) in THF (90 ml) was added ethyl (diethoxyphosphoryl)acetate (5.26 g), and the mixture was stirred at 25° C. for 1 hr. To the mixture was added Filtrate (A) at 25° C., the reaction mixture was stirred at same temperature for 30 minutes. The reaction mixture was poured into a mixture of AcOEt and 5% aqueous NaCl. The separated organic layer was washed with brine, dried over sodium sulfate and evaporated in vacuo. The resulting residue was purified by column chromatography on silica gel (116 g) using a mixed solvent of hexane and ethyl acetate (5:1 to 1:1). The fractions containing the objective compound were collected and evaporated under reduced pressure. Title compound (6.74 g, 73%), was obtained as slightly yellowish oil.

MASS(API-ES); 453 (M+H)+, $^1$H-NMR (200 MHz), (DMSO-d6, δ): 1.24-1.45 (13H, m), 1.90-2.30 (2H, m), 2.35-2.80 (3H, m), 3.42, 3.51 (2H, ABq, J=13 Hz), 4.24 (2H, q, J=7.1 Hz), 4.65-4.90 (1H, m), 6.94 (1H, d, J=16 Hz), 7.00-7.30 (5H, m), 7.76 (1H, d, J=16 Hz), 8.67 (1H, d, J=1.0 Hz), 8.80 (1H, d, J=1.0 Hz).

Preparation 713 ethyl 6-{[(3R)-1-(tert-butoxycarbonyl)-3-pyrrolidinyl]amino}-5-fluoronicotinate

To a solution of ethyl 6-{[(3R)-1-benzyl-3-pyrrolidinyl]amino}-2-chloro-5-fluoronicotinate (1.43 g) in ethanol (30 mL) were added ammonium formate (1.67 g) and 10% Pd/C (600 mg) at 25° C. and the mixture was heated to reflux with stirring for 30 minutes. After cooling, the catalyst in the reaction mixture was removed by filtration. The filtrate was evaporated in vacuo. To the residue were added CH$_2$Cl$_2$ (15 ml), ethanol (3 mL), di-tert-butyl dicarbonate (830 mg), and N,N-diisopropylethylamine (0.66 ml) at 25° C. After stirring for 5 minutes, sodium triacetoxyborohydride (280 mg) was added to the mixture. The reaction mixture was stirred at 25° C. for 2 hours, and then evaporated under reduced pressure. The residue was poured into a mixture of ethyl acetate, THF and water. The organic layer was separated, washed with brine, dried over sodium sulfate, and concentrated in vacuo. The residue was purified by column chromatography on silica gel (34 g) using a mixed solvent of hexane and ethyl acetate (4:1 to 3:1). The fractions containing the objective compound were collected and evaporated under reduced pressure. Title compound (1.088 g, 81%) was obtained as colorless syrup.

MASS(API-ES); 354 (M+H)+, $^1$H-NMR (200 MHz), (DMSO-d6, δ): 1.29 (3H, t, J=7.1 Hz), 1.39 (9H, s), 1.80-2.30 (2H, m), 3.10-3.70 (4H, m), 4.26 (2H, q, J=7.1 Hz), 4.45-4.65 (1H, m), 7.67 (1H, d, J=6.8 Hz), 7.69 (1H, dd, J=1.7 Hz, J=12 Hz), 8.46 (1H, d, J=1.7 Hz).

Preparation 714 tert-butyl (3R)-3-({5-[(1E)-3-ethoxy-3-oxo-1-propen-1-yl]-3-fluoro-2-pyridinyl}amino)-1-pyrrolidinecarboxylate Tert-butyl (3R)-3-{[3-fluoro-5-(hydroxymethyl)-2-pyridinyl]amino}-1-pyrrolidinecarboxylate (990 mg) and activated $MnO_2$ (2.76 g) in ethyl acetate (20 ml) were stirred at 75° C. for 1 hour. After removal of the insoluble material by filtration, the filtrate was evaporated in vacuo to give syrup (A). On the other hand, to an ice-cooled suspension of sodium hydride (159 mg) in THF (20 ml) was added ethyl (diethoxyphosphoryl)acetate (855 mg), and the mixture was stirred at 24° C. for 60 minutes. To the mixture was added syrup (A) at 24° C., the reaction mixture was stirred at same temperature for 30 minutes. The reaction mixture was poured into a mixture of AcOEt and 5% aqueous NaCl. The separated organic layer was washed with brine, dried over sodium sulfate and evaporated in vacuo. The resulting residue was purified by column chromatography on silica gel (19 g) using a mixed solvent of hexane and ethyl acetate (5:1 to 3:2). The fractions containing the objective compound were collected and evaporated under reduced pressure. Title compound (1.09 g, 90%) was obtained as colorless oil.

MASS(API-ES); 380 (M+H)+, $^1$H-NMR (200 MHz), (DMSO-d6, δ): 1.24 (3H, t, J=7.1 Hz), 1.39 (9H, s), 1.80-2.30 (2H, m), 3.10-3.70 (4H, m), 4.16 (2H, q, J=7.1 Hz), 4.35-4.65 (1H, m), 6.46 (1H, d, J=16 Hz), 7.42 (1H, d, J=5.9 Hz), 7.56 (1H, dd, J=1.8 Hz, J=16 Hz), 7.89 (1H, dd, J=1.5 Hz, J=13 Hz), 8.14 (1H, d, J=1.5 Hz).

Preparation 715

To a stirred solution of tert-butyl [(3R)-1-benzyl-3-pyrrolidinyl](6-chloro-2-pyrazinyl)carbamate (910 mg) in DMF (15 mL) was added ethyl acrylate (1.27 mL), palladium(II) acetate (26 mg), tris(2-methylphenyl)phosphine (107 mg), and N,N-diisopropylethylamine (1.22 mL). The mixture was stirred in the sealed tube at 150° C. for 3 days. The resulting mixture was allowed to cool to ambient temperature, poured into water, and extracted with ethyl acetate. The organic phase was washed with brine, dried over $Na_2SO_4$, and concentrated in vacuo. The residue was purified by silica gel column chromatography eluting with a mixture of chloroform and methanol (96:4 v/v) to give ethyl (2E)-3-(6-{[(3R)-1-benzyl-3-pyrrolidinyl](tert-butoxycarbonyl)amino}-2-pyrazinyl)acrylate (755 mg) as a pale yellow foam.

$^1$H-NMR (300 MHz, CDCl$_3$) δ 1.36 (3H, t, J=7 Hz), 1.45 (9H, s), 2.12 (1H, m), 2.27 (1H, m), 2.58-2.70 (2H, m), 2.77 (1H, dd, J=9, 7 Hz), 2.94 (1H, dd, J=9, 8 Hz), 3.54 (1H, d, J=13 Hz), 3.63 (1H, d, J=13 Hz), 4.30 (2H, q, J=7 Hz), 4.95 (1H, m), 6.96 (1H, d, J=15.5 Hz), 7.04-7.49 (5H, m), 7.64 (1H, d, J=15.5 Hz), 8.38 (1H, s), 8.54 (1H, s); MS (ES+) m/z 453.

Preparation 716

A mixture of (2R)-2-[(tert-butoxycarbonyl)amino]-4-(methylthio)butanoic acid (4.57 g), cyclohexanemethylamine (2.28 g), HOBt (2.72 g), and EDCI (3.87 g) in DMF (50 mL) was stirred at ambient temperature for 15 hours. The reaction mixture was poured into a mixture of AcOEt-H$_2$O and the organic layer was washed with aqueous ammonium chloride, aqueous sodium hydrogen carbonate, and brine and dried over MgSO$_4$. The solvent was evaporated in vacuo and the residue was crystallized from ethyl acetate and hexane to give tert-butyl [(1R)-1-{[(cyclohexylmethyl)amino]carbonyl}-3-(methylthio)propyl]carbamate (5.65 g).

$^1$H-NMR (300 MHz, CDCl$_3$) δ 0.84-1.00 (2H, m), 1.08-1.32 (3H, m), 1.45 (3×3H, s), 1.45 (1H, m), 1.60-1.77 (5H, m), 1.92 (1H, m), 2.09 (1H, m), 2.11 (3H, s), 2.45-2.65 (2H, m), 3.02-3.18 (2H, m), 4.21 (1H, m), 5.14 (1H, m), 6.22 (1H, br-t, J=6 Hz); MS (ES+) m/z 345.

Preparation 717

1) A solution of methyl 5-chloro-2-pyrazinecarboxylate (10 g) in THF (100 ml) was cooled under −5° C. by NaCl-ice bath.
To this solution was added dropwise DIBAL (60 ml) for 15 min under −8–0° C.
After stirring for 30 min under 0° C., the reaction mixture was quenched with EtOH (17 ml).

2) To a solution of ethyl (diethoxyphosphoryl)acetate (14.2 g) in THF (100 ml) was added portionwise NaH under ice-cooling.
The reaction mixture was allowed stirred at 30° C. for 1 hr.
To a solution of 1) was added dropwise 2) under 0° C.
After stirring for 1 hr, the reaction mixture was added to water and EtOAc, adjusted pH at 3.0.
Aqueous layer was separated and extracted twice with EtOAc, washed with water, dried over MgSO$_4$, filtered and evaporated.
The residue was column chromatographed on silica gel (Yamazen HPLC).
Desired Fraction was evaporated and hexane was added.
Crystal was filtered and dried to give 3.15 g of ethyl (2E)-3-(5-chloro-2-pyrazinyl)acrylate.
Combined unpure fractions was chromatographed to give additional 1.6 g of ethyl (2E)-3-(5-chloro-2-pyrazinyl)acrylate.

$^1$HNMR (400 MHz, CDCl$_3$): δ 1.35 (3H, t, J=7.1 Hz), 4.30 (2H, q, J=7.1 Hz), 7.00 (1H, d, J=15.7 Hz), 7.66 (1H, d, J=15.7 Hz), 8.43 (1H, d, J=1.3 Hz), 8.60 (1H, d, J=1.3 Hz).

Preparation 718

To an ice-cooled solution of tert-butyl (3R)-3-({5-[(1E)-3-ethoxy-3-oxo-1-propen-1-yl]-3-fluoro-2-pyridinyl}amino)-1-pyrrolidinecarboxylate (11.6 g) in EtOH (70 ml) was added solution of 4N HCl in dioxane (76.4 ml). The mixture was stirred at 24° C. for 3.5 hr, and evaporated under reduced pressure. The residue was poured into a mixture of water and CH$_2$Cl$_2$. The pH of the aqueous layer was adjusted to ca.9 with NaHCO$_3$. The organic layer was separated, dried over sodium sulfate and evaporated under reduced pressure to give ethyl (2E)-3-{5-fluoro-6-[(3R)-3-pyrrolidinylamino]-3-pyridinyl}acrylate (7.1 g, 83%) as colorless powder.

MASS(API-ES); 280 (M+H)+, $^1$H-NMR (200 MHz), (DMSO-d6, δ): 1.23 (3H, t, J=7.1 Hz), 1.50-2.20 (2H, m), 2.60-3.03 (4H, m), 3.18 (1H, br), 4.16 (2H, q, J=7.1 Hz), 4.30-4.50 (1H, m), 6.42 (1H, d, J=16 Hz), 7.19 (1H, d, J=6.4 Hz), 7.55 (1H, dd, J=2.0 Hz, J=16 Hz), 7.84 (1H, dd, J=1.8 Hz, J=13 Hz), 8.11 (1H, d, J=1.8 Hz).

Preparation 719 ethyl (2E)-3-[5]-fluoro-6-({(3R)}-1-[2-(1H-pyrazol-1-yl)ethyl]-3-{pyrrolidinyl}amino)-3-pyridinyl}acrylate To a mixed solution of 1-(2,2-dimethoxyethyl)-1H-pyrazole (705 mg) in dioxane (3 mL) and water (3 ml) were added 4N-HCl in 1,4-dioxane solution (3.01 ml) at 25° C. and the mixture was heated at 60° C. with stirring for 40 minutes. After cooling, to the reaction mixture was added ethyl acetate, THF, and water. The pH of the aqueous layer was adjusted to ca.3 with NaHCO$_3$. The organic layer was separated, dried over sodium sulfate and evaporated under reduced pressure. To the resulting residue were added CH$_2$Cl$_2$ (6 ml), ethyl (2E)-3-{5-fluoro-6-[(3R)-3-pyrrolidinylamino]-3-pyridinyl}acrylate (420 mg) at 25° C. After stirring for 5 minutes, sodium triacetoxyborohydride (637 mg) was added to the mixture. The reaction mixture was stirred at 25° C. for 5 hours, and then poured into a mixture of CH$_2$Cl$_2$ and aqueous NaHCO$_3$. The organic layer was separated, dried over sodium sulfate, and concentrated in vacuo. The residue was purified by column chromatography on silica gel using a mixed solvent of dichloromethane and MeOH (60:1 to 20:1). The fractions containing the objective compound were collected and evaporated under reduced pressure. Title compound (165 mg, 29%) was obtained as colorless oil.

MASS(API-ES); 374 (M+H)+

$^1$H-NMR (200 MHz), (DMSO-d6, δ): 1.23 (3H, t, J=7.0 Hz), 1.67-1.92 (1H, m), 2.00-2.25 (1H, m), 2.40-2.95 (6H, m), 3.95-4.28 (4H, m), 4.34-4.58 (1H, m), 6.20 (1H, t, J=2.0 Hz), 6.43 (1H, d, J=16 Hz), 7.23 (1H, d, J=6.4 Hz), 7.40 (1H, d, J=2.0 Hz), 7.55 (1H, dd, J=1.8 Hz, J=16 Hz), 7.74 (1H, d, J=2.0 Hz), 7.85 (1H, dd, J=1.6 Hz, J=13 Hz), 8.10 (1H, d, J=1.6 Hz).

The following compound was obtained in a similar manner to that of Preparation 336.

Preparation 720

N-{2-[(4-{(1E)-3-oxo-3-[(tetrahydro-2H-pyran-2-yloxy)amino]-1-propen-1-yl}phenyl)amino]phenyl}cyclohexanecarboxamide $^1$H-NMR (300 MHz, DMSO-d6) δ 1.08-1.42 (5H, m), 1.46-1.78 (11H, m), 2.33 (1H, m), 3.52 (1H, m), 3.95 (1H, m), 4.88 (1H, m), 6.26 (1H, d, J=16 Hz), 6.80 (2H, d, J=8.5 Hz), 7.02-7.19 (2H, m), 7.28 (1H, dd, J=7.5, 1 Hz), 7.33-7.44 (3H, m), 7.59 (1H, dd, J=7.5, 1 Hz), 7.71 (1H, s), 9.23 (1H, s), 11.07 (1H, s); MS (ES−) m/z 462.

The following compound was obtained in a similar manner to that of Preparation 382.

Preparation 721

6-[(2-benzylphenyl)amino]-5-chloronicotinaldehyde $^1$H-NMR (300 MHz, CDCl$_3$) δ 4.04 (2H, s), 7.09 (1H, s), 7.12-7.41 (8H, m), 7.85 (1H, d, J=8 Hz), 7.99 (1H, d, J=2 Hz), 8.45 (1H, d, J=2 Hz), 9.80 (1H, s); MS (ES+) m/z 323.

The following compound was obtained in a similar manner to that of Preparation 379.

Preparation 722 ethyl 6-{[(3R)-1-benzyl-3-pyrrolidinyl]amino}-2-chloro-5-fluoronicotinate

MASS(API-ES); 378 (M+H)+, $^1$H-NMR (200 MHz), (DMSO-d6, δ): 1.28 (3H, t, J=7.1 Hz), 1.70-1.95 (1H, m), 2.05-2.30 (1H, m), 2.35-2.75 (3H, m), 2.80-2.90 (1H, m), 3.50-3.70 (2H, m), 4.23 (2H, q, J=7.1 Hz), 4.30-4.55 (1H, m), 7.15-7.40 (5H, m), 7.77 (1H, d, J=11 Hz), 7.89 (1H, d, J=6.4 Hz).

The following compound was obtained in a similar manner to that of Preparation 336.

Preparation 723 tert-butyl (5-{(1E)-3-oxo-3-[(tetrahydro-2H-pyran-2-yloxy)amino]-1-propen-1-yl}-2-pyrimidinyl)[(3R)-1-(2-phenylethyl)-3-pyrrolidinyl]carbamate $^1$H-NMR (300 MHz, CDCl$_3$) δ 1.47 (3×3H, s), 1.56-1.95 (6H, m), 2.06-2.32 (2H, m), 2.56-2.84 (7H, m), 3.08 (1H, dd, J=8, 8 Hz), 3.68 (1H, m), 3.97 (1H, m), 4.92-5.10 (2H, m), 6.46 (1H, br), 7.13-7.33 (5H, m), 7.63 (1H, d, J=15.5 Hz), 8.78 (2×1H, s); MS (ES+) m/z 538.

The following compounds were obtained in a similar manner to that of Preparation 414.

Preparation 724

(2E)-3-(5-{[2-(1-piperidinyl)phenyl]amino}-2-pyrazinyl)-N-(tetrahydro-2H-pyran-2-yloxy)acrylamide $^1$H-NMR (300 MHz, DMSO-d6) δ 1.42-1.76 (12H, m), 2.71-2.83 (4H, m), 3.52 (1H, m), 3.96 (1H, m), 4.91 (1H, m), 6.74 (1H, d, J=15.5 Hz), 7.03-7.10 (2H, m), 7.14 (1H, m), 7.48 (1H, d, J=15.5 Hz), 7.92 (1H, dd, J=6, 3.5 Hz), 8.27 (1H, s), 8.32 (1H, s), 8.78 (1H, s), 11.26 (1H, s); MS (ES+) m/z 424.

The following compound was obtained in a similar manner to that of Preparation 375.

Preparation 725 ethyl (2E)-3-(6-{[(3R)-1-(cyclohexylcarbonyl)-3-pyrrolidinyl]amino}-5-fluoro-3-pyridinyl)acrylate

MASS(API-ES); 39.0 (M+H)+

$^1$H-NMR (200 MHz), (DMSO-d6, δ): 1.05-1.79 (10H, m), 1.24 (3H, t, J=7.1 Hz), 1.80-2.55 (3H, m), 3.15-3.90 (4H, m), 4.16 (2H, q, J=7.1 Hz), 4.35-4.75 (1H, m), 6.46 (1H, d, J=16 Hz), 7.38-7.50 (1H, m), 7.56 (1H, d, J=16 Hz), 7.90 (1H, d, J=13 Hz), 8.15 (1H, s).

The following compound was obtained in a similar manner to that of Preparation 450.

Preparation 726 tert-butyl [(3R)-1-(2,3-dihydro-1H-inden-2-yl)-3-pyrrolidinyl]carbamate $^1$H-NMR (300 MHz, CDCl$_3$) δ 1.46 (9H, s), 1.63 (1H, m), 2.20-2.47 (2H, m), 2.56-2.76 (2H, m), 2.79-2.96 (3H, m), 2.97-3.11 (3H, m), 4.20 (1H, m), 4.86 (1H, m), 7.10-7.22 (4H, m); MS (ES+) m/z 303.

The following compound was obtained in a similar manner to that of Preparation 452.

Preparation 727

(3R)-1-(2,3-dihydro-1H-inden-2-yl)-3-pyrrolidinamine dihydrochloride $^1$H-NMR (300 MHz, DMSO-d6) δ 2.00-2.40 (1H, m), 3.05-4.32 (11H, m), 7.17-7.30 (4H, m), 8.59 (2H, br); MS (ES+) m/z 203.

The following compound was obtained in a similar manner to that of Preparation 439.

Preparation 728 ethyl (2E)-3-(5-{[(3R)-1-(2,3-dihydro-1H-inden-2-yl)-3-pyrrolidinyl]amino}-2-pyrazinyl)acrylate $^1$H-NMR (300 MHz, CDCl$_3$) δ 1.33 (3H, t, J=7 Hz), 1.75 (1H, m), 2.35-2.50 (2H, m), 2.75 (1H, dd, J=10, 6 Hz), 2.79 (1H, dd, J=10, 3 Hz), 2.83-3.19 (6H, m), 4.25 (2H, q, J=7 Hz), 4.51 (1H, m), 5.25 (1H, d, J=8 Hz), 6.69 (1H, d, J=15.5 Hz), 7.10-7.23 (4H, m), 7.58 (1H, d, J=15.5 Hz), 7.90 (1H, d, J=1 Hz), 8.07 (1H, d, J=1 Hz); MS (ES+) m/z 379.

The following compound was obtained in a similar manner to that of Preparation 397.

Preparation 729

(2E)-3-(6-{[(3R)-1-(cyclohexylcarbonyl)-3-pyrrolidinyl]amino}-5-fluoro-3-pyridinyl)-N-(tetrahydro-2H-pyran-2-yloxy)acrylamide

MASS(API-ES); 461 (M+H)+, $^1$H-NMR (200 MHz), (DMSO-d6, δ): 1.05-1.80 (16H, m); 1.82-2.55 (3H, m), 3.15-4.10 (6H, m), 4.35-4.70 (1H, m), 4.89 (1H, s), 6.29 (1H, d, J=16 Hz), 7.25-7.38 (1H, m), 7.41 (1H, d, J=16 Hz), 7.62 (1H, d, J=12 Hz), 8.09 (1H, s).

The following compound was obtained in a similar manner to that of Preparation 311.

Preparation 730 ethyl (2E)-3-(6-{[(3R)-1-(2,6-difluorobenzyl)-3-pyrrolidinyl]amino}-5-fluoro-3-pyridinyl)acrylate

MASS(API-ES); 406 (M+H)+, $^1$H-NMR (200 MHz), (DMSO-d6, δ): 1.24 (3H, t, J=7.1 Hz), 1.65-1.90 (1H, m), 2.00-2.30 (1H, m), 2.35-2.73 (3H, m), 2.80-2.95 (1H, m), 3.69 (2H, s), 4.15 (2H, q, J=7.1 Hz), 4.30°-4.55 (1H, m), 6.42 (1H, d, J=16 Hz), 7.00-7.20 (2H, m), 7.25-7.50 (2H, m), 7.53 (1H, dd, J=1.9 Hz, J=16 Hz), 7.84 (1H, dd, J=1.7 Hz, J=13 Hz), 8.09 (1H, d, J=1.7 Hz).

The following compound was obtained in a similar manner to that of Preparation 414.

Preparation 731

(2E)-3-(5-{[(3R)-1-(2,3-dihydro-1H-inden-2-yl)-3-pyrrolidinyl]amino}-2-pyrazinyl)-N-(tetrahydro-2H-pyran-2-yloxy)acrylamide $^1$H-NMR (300 MHz, CDCl$_3$) δ 1.52-1.94 (7H, m), 2.36-2.50 (2H, m), 2.74 (1H, dd, J=10, 6 Hz), 2.78-3.17 (7H, m), 3.65 (1H, m), 3.96 (1H, m), 4.51 (1H, m), 5.02 (1H, m), 5.33 (1H, d, J=7 Hz), 6.70 (1H, br), 7.12-7.22 (4H, m), 7.63 (1H, d, J=15.5 Hz), 7.88 (1H, s), 8.05 (1H, s); MS (ES+) m/z 450.

The following compound was obtained in a similar manner to that of Preparation 405.

Preparation 732

(2E)-3-(5-{[(3R)-1-(2,3-dihydro-1H-inden-2-yl)-3-pyrrolidinyl]amino}-2-pyrazinyl)acrylic acid $^1$H-NMR (300 MHz, DMSO-d6) δ 1.68 (1H, m), 2.25 (1H, m), 2.44-2.56 (1H, m), 2.71-2.90 (4H, m), 2.94-3.60 (4H, m), 4.35 (1H, m), 6.46 (1H, d, J=15.3 Hz), 7.07-7.22 (4H, m), 7.48 (1H, d, J=15.3 Hz), 7.92 (1H, d, J=6.5 Hz), 8.00 (1H, d, J=1 Hz), 8.20 (1H, d, J=1 Hz); MS (ES+) m/z 351.

The following compound was obtained in a similar manner to that of Preparation 414.

Preparation 733 tert-butyl [(3R)-1-cyclohexyl-3-pyrrolidinyl](5-{(1E)-3-oxo-3-[(tetrahydro-2H-pyran-2-yloxy)amino]-1-propen-1-yl}-2-pyridinyl)carbamate $^1$H-NMR (300 MHz, DMSO-d6) δ 1.00-2.15 (18H, m), 2.30-3.20 (5H, m), 3.54 (1H, m), 3.96 (1H, m), 4.72 (1H, m), 4.92 (1H, m), 6.59 (1H, d, J=16 Hz), 7.36 (1H, d, J=8 Hz), 7.53 (1H, d, J=16 Hz), 8.01 (1H, d, J=8 Hz), 8.63 (1H, s), 11.31 (1H, br-s); MS (ES+) m/z 515.

The following compound was obtained in a similar manner to that of Preparation 397.

Preparation 734

(2E)-3-(6-{[(3R)-1-(2,6-difluorobenzyl)-3-pyrrolidinyl]amino}-5-fluoro-3-pyridinyl)-N-(tetrahydro-2H-pyran-2-yloxy)acrylamide

MASS(API-ES); 477 (M+H)+, $^1$H-NMR (200 MHz), (DMSO-d6, δ): 1.40-1.90 (7H, m), 2.00-2.28 (1H, m), 2.30-2.75 (3H, m), 2.80-3.00 (1H, m), 3.40-3.60 (1H, m), 3.69 (2H, s), 3.80-4.05 (1H, m), 4.25-4.60 (1H, m), 4.88 (1H, s), 6.25 (1H, d, J=0.15 Hz), 7.00-7.25 (3H, m), 7.30-7.75 (3H, m), 8.03 (1H, s).

The following compounds were obtained in a similar manner to that of Preparation 336.

Preparation 735

(2E)-3-(6-{[(3R)-1-benzyl-3-pyrrolidinyl]amino}-5-fluoro-3-pyridinyl)-N-(tetrahydro-2H-pyran-2-yloxy)acrylamide

MASS(API-ES); 441 (M+H)+, $^1$H-NMR (200 MHz), (DMSO-d6, δ): 1.40-1.95 (7H, m), 2.05-2.30 (1H, m), 2.32-2.70 (3H, m), 2.80-2.90 (1H, m), 3.40-3.65 (3H, m), 3.80-4.10 (1H, m), 4.30-4.60 (1H, m), 4.88 (1H, s), 6.25 (1H, d, J=15 Hz), 7.15 (1H, d, J=6.5 Hz), 7.18-7.45 (6H, m), 7.56 (1H, d, J=12 Hz), 8.02 (1H, s).

Preparation 736 tert-butyl [(3R)-1-(cyclohexylmethyl)-3-pyrrolidinyl](5-{(1E)-3-oxo-3-[(tetrahydro-2H-pyran-2-yloxy)amino]-1-propen-1-yl}-2-pyrimidinyl)carbamate $^1$H-NMR (300 MHz, DMSO-d6) δ 0.54-0.72 (2H, m), 1.00-1.78 (15H, m), 1.33 (3×3H, s), 1.94-2.14 (4H, m), 2.25 (1H, m), 2.37-2.58 (2H, m), 2.68 (1H, m), 3.54 (1H, m), 3.96 (1H, m), 4.76 (1H, m), 4.93 (1H, m), 6.70 (1H, d, J=16 Hz), 7.51 (1H, d, J=16 Hz), 9.01 (2×1H, s), 11.41 (1H, s); MS (ES+) m/z 530.

The following compound was obtained in a similar manner to that of Preparation 810.

Preparation 737 ethyl (2E)-3-(6-{[1-(4-fluorobenzyl)-4-piperidinyl]amino}-3-pyridinyl)acrylate $^1$H NMR (DMSO-d6, δ): 1.23 (3H, t, J=7.4 Hz), 1.26-1.50 (2H, m), 1.85-1.90 (2H, m), 1.99-2.11 (2H, m), 2.74-2.80 (2H, m), 3.45 (2H, s), 3.77-3.90 (1H, m), 4.14 (2H, q, J=7.4 Hz), 6.29 (1H, d, J=15.9 Hz), 6.48 (1H, d, J=7.8 Hz), 7.09-7.18 (3H, m), 7.30-7.37 (2H, m), 7.48 (1H, d, J=15.9 Hz), 7.76 (1H, dd, J=1.9, 8.0 Hz), 8.20 (1H, d, J=1.9 Hz), Mass (ESI): 384(M+H)+.

The following compound was obtained in a similar manner to that of Preparation 198.

Preparation 738 ethyl (2E)-3-(6-{[1-(cyclohexylmethyl)-4-piperidinyl]amino}-3-pyridinyl)acrylate ¹H NMR (DMSO-d6, δ): 0.79-0.91 (2H, m), 1.02-2.15 (17H, m), 1.23 (3H, t, J=7.4 Hz), 2.80 (2H, brs), 3.65-3.85 (1H, m), 4.14 (2H, q, J=7.4 Hz), 6.30 (1H, d, J=15.9 Hz), 6.49 (1H, d, J=8.8 Hz), 7.12 (1H, d, J=7.2 Hz), 7.49 (1H, d, J=15.9 Hz), 7.76 (1H, dd, J=2.2, 8.8 Hz), 8.20 (1H, d, J=2.2 Hz), Mass (ESI): 372(M+H)+.

The following compounds were obtained in a similar manner to that of Preparation 862.

Preparation 739

(2E)-3-(6-{[1-(4-fluorobenzyl)-4-piperidinyl]amino}-3-pyridinyl)acrylic acid

Mass (ESI): 356(M+H)+.

Preparation 740

(2E)-3-(6-{[1-(cyclohexylmethyl)-4-piperidinyl]amino}-3-pyridinyl)acrylic acid

Mass (ESI): 344(M+H)+.

The following compounds were obtained in a similar manner to that of Preparation 62.

Preparation 741

(2E)-3-(6-{[1-(4-fluorobenzyl)-4-piperidinyl]amino}-3-pyridinyl)-N-(tetrahydro-2H-pyran-2-yloxy)acrylamide

MASS(API-ES); 455 (M+H)+.

Preparation 742

(2E)-3-(6-{[1-(cyclohexylmethyl)-4-piperidinyl]amino}-3-pyridinyl)-N-(tetrahydro-2H-pyran-2-yloxy)acrylamide

MASS(API-ES); 443 (M+H)+.

The following compound was obtained in a similar manner to that of Preparation 375.

Preparation 743 ethyl (2E)-3-(6-{(tert-butoxycarbonyl)[(3R)-1-(cyclohexylcarbonyl)-3-pyrrolidinyl]amino}-3-pyridinyl)acrylate MASS(API-ES); 472 (M+H)+Free ¹H-NMR (200 MHz), (DMSO-d6, δ): 1.10-1.80 (22H, m), 1.85-2.40 (3H, m), 3.00-3.90 (4H, m), 4.21 (2H, q, J=7.1 Hz), 4.61-4.97 (1H, m), 6.78 (1H, d, J=16 Hz), 7.38 (1H, dd, J=3.4 Hz, J=8.6 Hz), 7.69 (1H, d, J=16 Hz), 8.22 (1H, d, J=8.6 Hz), 8.73 (1H, d, J=3.4 Hz).

The following compound was obtained in a similar manner to that of Preparation 397.

Preparation 744

(2E)-3-(6-{[(3R)-1-(cyclohexylcarbonyl)-3-pyrrolidinyl]amino}-3-pyridinyl)-N-(tetrahydro-2H-pyran-2-yloxy)acrylamide MASS(API-ES); 443 (M+H)+Free ¹H-NMR (200 MHz), (DMSO-d6, δ): 1.03-2.57 (19H, m), 3.10-4.08 (~6H, m), 4.20-4.60 (1H, m), 4.88 (1H, s), 6.23 (1H, d, J=15 Hz), 6.55 (1H, dd, J=3.2 Hz, J=8.8 Hz), 7.28 (1H, d, J=6.7 Hz), 7.37 (1H, d, J=15 Hz), 7.63 (1H, d, J=8.8 Hz), 8.18 (1H, s).

The following compounds were obtained in a similar manner to that of Preparation 871.

Preparation 745 ethyl 6-{[(1R,2R)-2-(benzyloxy)cyclopentyl]amino}-5-chloronicotinate

¹H-NMR (300 MHz, CDCl₃) δ 1.37 (3H, t, J=7 Hz), 1.51 (1H, m), 1.67-2.03 (4H, m), 2.33 (1H, m), 3.87 (1H, m), 4.34 (2H, q, J=7 Hz), 4.52 (1H, m), 4.67 (1H, d, J=12.7 Hz), 4.69 (1H, d, J=12.7 Hz), 5.27 (1H, d, J=7 Hz), 7.22-7.38 (5H, m), 8.01 (1H, d, J=2.2 Hz), 8.71 (1H, d, J=2.2 Hz); MS (ES+) m/z 375.

The following compound was obtained in a similar manner to that of Preparation 361.

Preparation 746

[6-(2,3-dihydro-1H-inden-2-ylamino)-3-pyridinyl]methanol

¹H-NMR (300 MHz, CDCl₃) δ 2.88 (2H, dd, J=16, 4.5 Hz), 3.39 (2H, dd, J=16, 7 Hz), 4.54 (2H, s), 4.60 (1H, m), 4.82 (1H, br-d, J=6 Hz), 6.43 (1H, d, J=9 Hz), 7.114-7.30 (4H, m), 7.49 (1H, dd, J=8.5, 2.5 Hz), 8.06 (1H, d, J=2.5 Hz); MS (ES+) m/z 241.

The following compound was obtained in a similar manner to that of Preparation 382.

Preparation 747

6-(2,3-dihydro-1H-inden-2-ylamino)nicotinaldehyde

¹H-NMR (300 MHz, CDCl₃) δ 2.93 (2H, dd, J=16, 4.5 Hz), 3.43 (2H, dd, J=16, 7 Hz), 4.75 (1H, br), 5.42 (1H, br.), 6.45 (1H, d, J=8.8 Hz), 7.16-7.30 (4H, m), 7.90 (1H, dd, J=8.8, 2.2 Hz), 8.52 (1H, d, J=2.2 Hz), 9.78 (1H, s); MS (ES+) m/z 239.

The following compound was obtained in a similar manner to that of Preparation 414.

Preparation 748

(2E)-3-[6-(2,3-dihydro-1H-inden-2-ylamino)-3-pyridinyl]-N-(tetrahydro-2H-pyran-2-yloxy)acrylamide ¹H-NMR (300 MHz, DMSO-d6) δ 1.45-1.78 (6H, m), 2.83 (2H, dd, J=16, 5.5 Hz), 3.29 (1H, dd, J=16, 7 Hz), 3.53 (1H, m), 3.95 (1H, m), 4.64 (1H, m), 4.88 (1H, m), 6.22 (1H, br-d, J=16 Hz), 6.54 (1H, d, J=8.5 Hz), 7.11-7.28 (4H, m), 7.31-7.45 (2H, m), 7.61 (1H, br-d, J=8.5 Hz), 8.19 (1H, s), 11.16 (1H, br); MS (ES+) m/z 380.

The following compound was obtained in a similar manner to that of Preparation 405.

Preparation 749

(2E)-3-{4-[(6-methyl-2-pyridinyl)amino]phenyl}acrylic acid

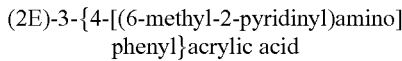

¹H-NMR (300 MHz, DMSO-d6) δ 2.40 (3H, s), 6.33 (1H, d, J=16 Hz), 6.67 (1H, d, J=7.5 Hz), 6.69 (1H, d, J=7.5 Hz), 7.49 (1H, dd, J=7.5, 7.5 Hz), 7.51 (1H, d, J=16 Hz), 7.57 (2H, d, J=8.5 Hz), 7.77 (2H, d, J=8.5 Hz), 9.29 (1H, s), 12.13 (1H, br); MS (ES+) m/z 255.

The following compound was obtained in a similar manner to that of Preparation 414.

Preparation 750

(2E)-3-{4-[(6-methyl-2-pyridinyl)amino]phenyl}-N-(tetrahydro-2H-pyran-2-yloxy)acrylamide

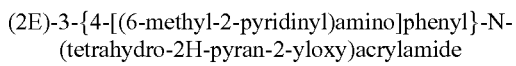

¹H-NMR (300 MHz, DMSO-d6) δ 1.46-1.76 (6H, m), 2.39 (3H, s), 3.53 (1H, m), 3.96 (1H, m), 4.90 (1H, m), 6.33 (1H, br-d, J=16 Hz), 6.66 (1H, d, J=7 Hz), 6.68 (1H, d, J=7 Hz), 7.37-7.54 (4H, m), 7.77 (2×1H, d, J=8.5 Hz), 9.25 (1H, s), 11.12 (1H, s); MS (ES+) m/z 354.

The following compound was obtained in a similar manner to that of Preparation 361.

Preparation 751

(6-{[(1R,2R)-2-(benzyloxy)cyclopentyl]amino}-5-chloro-3-pyridinyl)methanol

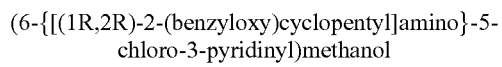

¹H-NMR (300 MHz, CDCl₃) δ 1.49 (1H, m), 1.68-2.02 (4H, m), 2.31 (1H, m), 3.87 (1H, m), 4.44 (1H, m), 4.54 (2H, s), 4.66 (1H, d, J=12 Hz), 4.69 (1H, d, J=12 Hz), 4.89 (1H, d, J=7.5 Hz), 7.23-7.42 (4H, m), 7.51 (1H, d, J=2 Hz), 8.01 (1H, d, J=2 Hz); MS (ES+) m/z 333.

The following compound was obtained in a similar manner to that of Preparation 382.

Preparation 752

6-{[(1R,2R)-2-(benzyloxy)cyclopentyl]amino}-5-chloronicotinaldehyde

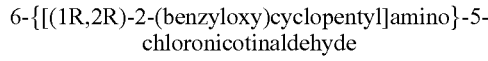

¹H-NMR (300 MHz, CDCl₃) δ 1.53 (1H, m), 1.68-2.06 (4H, m), 2.34 (1H, m), 3.89 (1H, m), 4.56 (1H, m), 4.67 (2H, s), 5.50 (1H, d, J=7 Hz), 7.22-7.38 (5H, m), 7.93 (1H, d, J=2 Hz), 8.47 (1H, d, J=2 Hz), 9.78 (1H, s); MS (ES+) m/z 331.

The following compound was obtained in a similar manner to that of Preparation 414.

Preparation 753

(2E)-3-(6-{[(1R,2R)-2-(benzyloxy)cyclopentyl]amino}-5-chloro-3-pyridinyl)-N-(tetrahydro-2H-pyran-2-yloxy)acrylamide

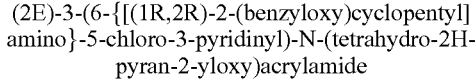

¹H-NMR (300 MHz, DMSO-d6) δ 1.45-1.78 (10H, m), 1.87-2.12 (2H, m), 3.53 (1H, m), 3.90-4.02 (2H, m), 4.45 (1H, m), 4.54 (2H, s), 4.89 (1H, m), 6.33 (1H, br-d, J=16 Hz), 6.74 (1H, d, J=7.7 Hz), 7.22-7.37 (5H, m), 7.37 (1H, d, J=16 Hz), 7.84 (1H, s), 8.24 (1H, s), 11.08 (1H, s); MS (ES+) m/z 472.

The following compound was obtained in a similar manner to that of Preparation 336.

Preparation 754 tert-butyl [(3R)-1-cycloheptyl-3-pyrrolidinyl](5-{(1E)-3-oxo-3-[(tetrahydro-2H-pyran-2-yloxy)amino]-1-propen-1-yl}-2-pyridinyl)carbamate

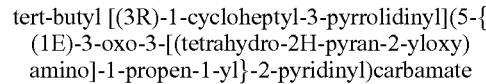

¹H-NMR (300 MHz, DMSO-d6) δ 1.13-1.78 (20H, m), 1.89 (1H, m), 2.03 (1H, m), 2.25 (1H, m), 2.62 (1H, m), 2.81 (1H, m), 3.54 (1H, m), 3.95 (1H, m), 4.68 (1H, m), 4.92 (1H, m), 6.58 (1H, d, J=15 Hz), 7.34 (1H, d, J=8 Hz), 7.52 (1H, d, J=15 Hz), 8.00 (1H, d, J=8, 2 Hz), 8.62 (1H, d, J=2 Hz), 11.32 (1H, br-s); MS (ES+) m/z 529.

The following compound was obtained in a similar manner to that of Preparation 486.

Preparation 755 tert-butyl, [(3R)-1-(3-fluorobenzyl)-3-pyrrolidinyl]carbamate

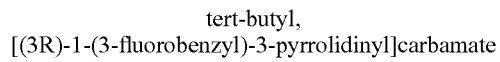

¹HNMR (400 MHz, CDCl₃): δ 1.44 (9H, s), 1.54-1.66 (1H, m), 2.20-2.35 (2H, m), 2.51-2.64 (2H, m), 2.74-2.84 (1H, m), 3.56, 3.61 (2H, q, Jab=13.2 Hz), 4.18 (1H, br.s), 4.92 (1H, br.s), 7.11 (1H, dt, J=2.7, 8.3 Hz), 7.02-7.09 (2H, m), 7.23-7.29 (1H, m),

MASS (ESI): m/z=295.3 (M+1).

The following compound was obtained in a similar manner to that of Preparation 871.

Preparation 756 ethyl 5-chloro-6-{[(1S,2R)-2-phenylcyclopropyl]amino}nicotinate

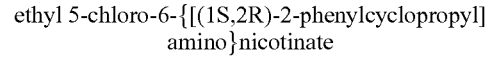

¹H-NMR (300 MHz, CDCl₃) δ 1.26 (1H, m), 1.37 (3H, t, J=7 Hz), 1.39 (1H, m), 2.13 (1H, m), 3.10 (1H, m), 4.34 (2H, q, J=7 Hz), 5.70 (1H, br), 7.17-7.35 (5H, m), 8.04 (1H, d, J=2 Hz), 8.77 (1H, d, J=2 Hz); MS (ES+) m/z 317.

The following compound was obtained in a similar manner to that of Preparation 382.

Preparation 757

5-chloro-6-{[(1S,2R)-2-phenylcyclopropyl]amino}nicotinaldehyde

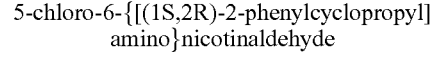

¹H-NMR (300 MHz, CDCl₃) δ 1.29 (1H, m), 1.44 (1H, m), 2.17 (1H, ddd, J=9, 6, 3 Hz), 3.15 (1H, m), 5.91 (1H, br-s), 7.19-7.36 (5H, m), 7.96 (1H, d, J=1.8 Hz), 8.53 (1H, d, J=1.8 Hz), 9.81 (1H, s); MS (ES+) m/z 273.

The following compound was obtained in a similar manner to that of Preparation 414.

Preparation 758

(2E)-3-(5-chloro-6-{[(1S,2R)-2-phenylcyclopropyl]amino}-3-pyridinyl)-N-(tetrahydro-2H-pyran-2-yloxy)acrylamide

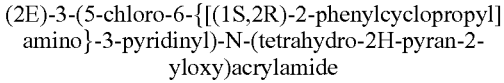

¹H-NMR (300 MHz, DMSO-d6) δ 1.24 (1H, m), 1.42 (1H, m), 1.46-1.77 (6H, m), 2.06 (1H, m), 3.03 (1H, m), 3.52 (1H, m), 3.95 (1H, m), 4.88 (1H, m), 6.33 (1H, d, J=16 Hz), 7.13-7.22 (3H, m), 7.24-7.32 (3H, m), 7.36 (1H, d, J=16 Hz), 7.85 (1H, br-s), 8.22 (1H, br-s), 11.09 (1H, br-s);

MS (ES+) m/z 414.

The following compound was obtained in a similar manner to that of Preparation 871.

Preparation 759 ethyl 5-chloro-6-({3-[(cyclohexylcarbonyl)amino]phenyl}amino)nicotinate $^1$H-NMR (300 MHz, CDCl$_3$) δ 1.20-1.42 (3H, m), 1.39 (3H, t, J=7 Hz), 1.48-1.64 (2H, m), 1.72 (1H, m), 1.80-1.90 (2H, m), 1.92-2.02 (2H, m), 2.24 (1H, m), 4.36 (2H, q, J=7 Hz), 7.15-7.36 (4H, m), 7.46 (1H, m), 8.09 (1H, s), 8.16 (1H, d, J=2 Hz), 8.79 (1H, d, J=2 Hz); MS (ES+) m/z 402.

The following compound was obtained in a similar manner to that of Preparation 414.

Preparation 760

(2E)-3-{6-[(2-benzylphenyl)amino]-5-chloro-3-pyridinyl}-N-(tetrahydro-2H-pyran-2-yloxy)acrylamide $^1$H-NMR (300 MHz, DMSO-d6) δ 1.46-1.78 (6H, m), 3.53 (1H, m), 3.92 (2H, s), 3.95 (1H, m), 4.89 (1H, m), 6.36 (1H, d, J=16 Hz), 7.07-7.30 (8H, m), 7.37 (1H, d, J=16 Hz), 7.44 (1H; d, J=8 Hz), 7.95 (1H, s), 8.13 (1H, s), 8.23 (1H, s), 11.13 (1H, s); MS (ES+) m/z 464.

The following compound was obtained in a similar manner to that of Preparation 361.

Preparation 761

N-(3-{[3-chloro-5-(hydroxymethyl)-2-pyridinyl]amino}phenyl)cyclohexanecarboxamide $^1$H-NMR (300 MHz, CDCl$_3$) δ 1.20-1.40 (3H, m), 1.45-1.75 (3H, m), 1.76-2.01 (4H, m), 2.22 (1H, m), 4.59 (2H, s), 7.03 (1H, s), 7.13 (1H, d, J=8 Hz), 7.22-7.32 (2H, m), 7.39 (1H, d, J=8 Hz), 7.65 (1H, d, J=2 Hz), 8.04 (1H, s), 8.09 (1H, d, J=2 Hz); MS (ES+) m/z 360.

The following compound was obtained in a similar manner to that of Preparation 414.

Preparation 762

N-{2-[(3-chloro-5-{(1E)-3-oxo-3-[(tetrahydro-2H-pyran-2-yloxy)amino]-1-propen-1-yl}-2-pyridinyl)amino]phenyl}cyclohexanecarboxamide $^1$H-NMR (300 MHz, DMSO-d6) δ 1.12-1.34 (3H, m), 1.36-1.86 (13H, m), 2.41 (1H, m), 3.53 (1H, m), 3.96 (1H, m), 4.89 (1H, m), 6.40 (1H, d, J=16 Hz), 7.14 (1H, dd, J=7.5, 7.5 Hz), 7.21-7.29 (2H, m), 7.40 (1H, d, J=16 Hz), 7.78 (1H, d, J=7.5 Hz), 8.02 (1H, s), 8.22 (1H, s), 8.32 (1H, s), 9.92 (1H, s), 11.16 (1H, s); MS (ES+) m/z 499.

The following compound was obtained in a similar manner to that of Preparation 871.

Preparation 763 ethyl 5-chloro-6-({2-[(cyclohexylcarbonyl)amino]phenyl}amino)nicotinate $^1$H-NMR (300 MHz, CDCl$_3$) δ 1.20-1.40 (3H, m), 1.37 (3H, t, J=7 Hz), 1.43-1.59 (2H, m), 1.69 (1H, m), 1.75-1.99 (4H, m), 2.27 (1H, m), 4.35 (2H, q, J=7 Hz), 7.19 (1H, ddd, J=7.7, 7.7, 1.5 Hz), 7.24-7.37 (2H, m), 7.58 (1H, s), 7.70 (1H, dd, J=7.7, 1.5 Hz), 7.95 (1H, s), 8.15 (1H, d, J=1.7 Hz), 8.67 (1H, d, J=1.7 Hz); MS (ES+) m/z 402.

The following compounds were obtained in a similar manner to that of Preparation 382.

Preparation 764

N-{2-[(3-chloro-5-formyl-2-pyridinyl)amino]phenyl}cyclohexanecarboxamide $^1$H-NMR (300 MHz, CDCl$_3$) δ 1.18-1.38 (3H, m), 1.42-1.64 (2H, m), 1.70 (1H, m), 1.76-1.88 (2H, m), 1.90-2.00 (2H, m), 2.30 (1H, m), 7.17-7.36 (5H, m), 7.50 (1H, s), 7.77 (1H, d, J=7.5 Hz), 8.05 (1H, d, J=1.5 Hz), 8.34 (1H, s), 8.44 (1H, d, J=1.5 Hz), 9.81 (1H, s); MS (ES+) m/z 358.

Preparation 765

N-{3-[(3-chloro-5-formyl-2-pyridinyl)amino]phenyl}cyclohexanecarboxamide $^1$H-NMR (300 MHz, CDCl$_3$) δ 1.22-1.41 (3H, m), 1.48-1.64 (2H, m), 1.72 (1H, m), 1.79-1.91 (2H, m), 1.92-2.02 (2H, m), 2.25 (1H, m), 7.17 (1H, d, J=8 Hz), 7.23 (1H, s), 7.33 (1H, dd, J=8, 8 Hz), 7.44-7.54 (2H, m), 8.07 (1H, d, J=2 Hz), 8.14 (1H, s), 8.56 (1H, d, J=2 Hz), 9.85 (1H, s); MS (ES+) m/z 358.

The following compound was obtained in a similar manner to that of Preparation 414.

Preparation 766

N-(3-[(3-chloro-5-{(1E)-3-oxo-3-[(tetrahydro-2H-pyran-2-yloxy)amino]-1-propen-1-yl}-2-pyridinyl)amino]phenyl)cyclohexanecarboxamide $^1$H-NMR (300 MHz, DMSO-d6) δ 1.13-1.85 (16H, m), 2.33 (1H, m), 3.53 (1H, m), 3.96 (1H, m), 4.90 (1H, m), 6.43 (1H, d, J=16 Hz), 7.16-7.34 (4H, m), 7.43 (1H, d, J=16 Hz), 7.95 (1H, s), 8.03 (1H, s), 8.29 (1H, s), 8.66 (1H, s), 9.79 (1H, s), 11.19 (1H, s); MS (ES+) m/z 499.

The following compound was obtained in a similar manner to that of Preparation 405.

Preparation 767

(2E)-3-(5-{[2-(1-piperidinyl)phenyl]amino}-2-pyrazinyl)acrylic acid $^1$H-NMR (300 MHz, DMSO-d6) δ 1.50 (2H, m), 1.56-1.68 (4H, m), 2.76-2.88 (4H, m), 6.58 (1H, d, J=15.5 Hz), 7.04-7.14 (2H, m), 7.17 (1H, m), 7.56 (1H, d, J=15.5 Hz), 7.90 (1H, m), 8.33-8.38 (2H, m), 8.92 (1H, br-s);

MS (ES+) m/z 325.

The following compound was obtained in a similar manner to that of Preparation 366.

Preparation 768 ethyl (2E)-3-{5-fluoro-6-[(3R)-3-pyrrolidinylamino]-3-pyridinyl}acrylate dihydrochloride MASS(API-ES); 280 (M+H)+Free $^1$H-NMR (200 MHz), (DMSO-d6, δ): 1.24 (3H, t, J=7.1 Hz), 1.90-2.35 (2H, m), 3.05-3.60 (4H, m), 4.17 (2H, q, J=7.1 Hz), 4.55-4.75 (1H, m), 6.50 (1H, d, J=16 Hz), 7.58 (1H, dd, J=1.8 Hz, J=16 Hz), 7.65 (1H, br), 7.97 (1H, dd, J=1.6 Hz, J=13 Hz), 8.17 (1H, d, J=1.6 Hz), 9.47 (2H, br).

The following compound was obtained in a similar manner to that of Preparation 452.

Preparation 769

(3R)-1-(2-quinolinylmethyl)-3-pyrrolidinamine trihydrochloride $^1$H-NMR (300 MHz, DMSO-d6) δ 2.21 (1H, m), 2.44 (1H, m), 3.55 (1H, m), 3.66 (1H, m), 3.76-3.9.4 (2H, m), 4.04 (1H, m), 4.91 (2H, s), 7.69 (1H, m), 7.73 (1H, d, J=8.5 Hz), 7.86 (1H, ddd, J=7, 7, 1.5 Hz), 8.03-8.13 (2H, m), 8.52 (1H, d, J=8.5 Hz), 8.77 (2H, br-s); MS (ES+) m/z 228.

The following compound was obtained in a similar manner to that of Preparation 439.

Preparation 770 ethyl (2E)-3-(5-{[(3R)-1-(2-quinolinylmethyl)-3-pyrrolidinyl]amino}-2-pyrazinyl)acrylate $^1$H-NMR (300 MHz, CDCl$_3$) δ 1.32 (3H, t, J=7 Hz), 1.76 (1H, m), 2.42 (1H, m), 2.54 (1H, m), 2.75-2.88 (2H, m), 3.03 (1H, m), 3.98 (1H, d, J=13.5 Hz), 4.02 (1H, d, J=13.5 Hz), 4.25 (2H, q, J=7 Hz), 4.51 (1H, m), 5.39 (1H, d, J=8 Hz), 6.68 (1H, d, J=15.5 Hz), 7.49-7.62 (3H, m), 7.71 (1H, ddd, J=7, 7, 1.5 Hz), 7.81 (1H, dd, J=8, 1.5 Hz), 7.89 (1H, d, J=1 Hz), 8.04 (1H, d, J=1 Hz), 8.08 (1H, d, J=8 Hz), 8.15 (1H, d, J=8 Hz); MS (ES+) m/z 404.

The following compound was obtained in a similar manner to that of Preparation 390.

Preparation 771

(2E)-3-(5-fluoro-6-{[(3R)-1-(2-phenylethyl)-3-pyrrolidinyl]amino}-3-pyridinyl)acrylic acid

MASS(API-ES); 356 (M+H)+

The following compound was obtained in a similar manner to that of Preparation 452.

Preparation 772

(3R)-1-(2-methylbenzyl)-3-pyrrolidinamine dihydrochloride $^1$H-NMR (300 MHz, DMSO-d6) δ 2.00-2.65 (2H, m), 2.46 (3H, s), 3.16-4.16 (5H, m), 4.37-4.62 (2H, m), 7.22-7.38 (3H, m), 7.60 (1H, m), 8.44-8.75 (2H, m); MS (ES+) m/z 191.

The following compounds were obtained in a similar manner to that of Preparation 450.

Preparation 773 tert-butyl [(3R)-1-(2-phenylethyl)-3-pyrrolidinyl]carbamate $^1$H-NMR (300 MHz, CDCl$_3$) δ 1.44 (9H, s), 2.25 (1H, m), 2.51 (1H, m), 2.77 (1H, m), 3.02 (1H, m), 3.14-3.40 (4H, m), 3.64 (1H, m), 3.90 (1H, m), 4.63 (1H, m), 6.45 (1H, d, J=8.5 Hz), 7.20-7.38 (5H, m); MS (ES+) m/z 291.

The following compound was obtained in a similar manner to that of Preparation 439.

Preparation 774 ethyl (2E)-3-(5-{[(3R)-1-(2-methylbenzyl)-3-pyrrolidinyl]amino}-2-pyrazinyl)acrylate $^1$H-NMR (300 MHz, CDCl$_3$) δ 1.32 (3H, t, J=7 Hz), 1.69 (1H, m), 2.29-2.45 (2H, m), 2.38 (3H, s), 2.66 (1H, dd, J=10, 3 Hz), 2.70 (1H, dd, J=10, 6 Hz), 2.91 (1H, m), 3.62 (2H, s), 4.25 (2H, q, J=7 Hz), 4.45 (1H, m), 5.19 (1H, d, J=8 Hz), 6.68 (1H, d, J=15.5 Hz), 7.11-7.20 (3H, m), 7.26 (1H, m), 7.56 (1H, d, J=15.5 Hz), 7.87 (1H, d, J=1 Hz), 8.05 (1H, d, J=1 Hz); MS (ES+) m/z 367.

The following compound was obtained in a similar manner to that of Preparation 397.

Preparation 775

(2E)-3-(5-fluoro-6-{[(3R)-1-(2-phenylethyl)-3-pyrrolidinyl]amino}-3-pyridinyl)-N-(tetrahydro-2H-pyran-2-yloxy)acrylamide

MASS(API-ES); 455 (M+H)+.

$^1$H-NMR (200 MHz), (DMSO-d6, δ): 1.40-1.95 (7H, m), 2.00-2.30 (1H, m), 2.45-2.80 (7H, m), 2.85-3.00 (1H, m), 3.40-3.65 (1H, m), 3.80-4.10 (1H, m), 4.35-4.60 (1H, m), 4.89 (1H, s), 6.27 (1H, d, J=16 Hz), 7.05-7.35 (6H, m), 7.39 (1H, d, J=16 Hz), 7.58 (1H, d, J=12 Hz), 8.05 (1H, s).

The following compound was obtained in a similar manner to that of Preparation 439.

Preparation 776 ethyl (2E)-3-(2-{[(3R)-1-(cyclohexylmethyl)-3-pyrrolidinyl]amino}-5-pyrimidinyl)acrylate $^1$H-NMR (300 MHz, CDCl$_3$) δ 0.78-0.96 (2H, m), 1.10-1.29 (4H, m), 1.33 (3H, t, J=7 Hz), 1.43 (1H, m), 1.58-1.84 (5H, m), 2.18-2.38 (4H, m), 2.61 (2H, d, J=5 Hz), 2.83 (1H, m), 4.25 (2H, q, J=7 Hz), 4.53 (1H, m), 5.75 (1H, d, J=8 Hz), 6.30 (1H, d, J=16 Hz), 7.48 (1H, d, J=16 Hz), 8.44 (2×1H, s); MS (ES+) m/z 359.

The following compound was obtained in a similar manner to that of Preparation 480.

Preparation 777 tert-butyl [(3R)-1-(1-phenylethyl)-3-pyrrolidinyl]carbamate $^1$H-NMR (300 MHz, CDCl$_3$) δ 1.35 (1.5H, d, J=6.6 Hz), 1.37 (1.5H, d, J=6.6 Hz), 1.42 (4.5H, s), 1.44 (4.5H, s), 1.47-1.68 (1H, m), 2.10-2.36 (2.5H, m), 2.49-2.68 (2H, m), 2.88 (0.5H, m), 3.19 (1H, q, J=6.6 Hz), 4.12 (1H, m), 4.82 (1H, m), 7.19-7.36 (5H, m); MS (ES+) m/z 291.

The following compound was obtained in a similar manner to that of Preparation 336.

Preparation 778

(2E)-3-(5-{[(3R)-1-(1-phenylethyl)-3-pyrrolidinyl]amino}-2-pyrazinyl)-N-(tetrahydro-2H-pyran-2-yloxy)acrylamide $^1$H-NMR (300 MHz, DMSO-d6) δ 1.29 (1.5H, d, J=6.5 Hz), 1.30 (1.5H, d, J=6.5 Hz), 1.46-1.76 (7H, m), 2.11-2.34 (2H, m), 2.37-2.56 (1H, m), 2.65-2.83 (2H, m), 3.20-3.42 (1H, m), 3.52 (1H, m), 3.95 (1H, m), 4.27 (1H, m), 4.89 (2H, m), 6.60 (1H, d, J=15 Hz), 7.19-7.37 (5H, m), 7.36 (1H, d, J=15 Hz), 7.73 (0.5H, d, J=6 Hz), 7.76 (0.5H, d, J=6 Hz), 7.97 (1H, s), 8.08 (0.5H, s), 8.09 (0.5H, s), 11.18 (1H, br-s); MS (ES+) m/z 438.

The following compounds were obtained in a similar manner to that of Preparation 452.

Preparation 779

(3R)-1-(1-phenylethyl)-3-pyrrolidinamine $^1$H-NMR (300 MHz, CDCl$_3$) δ 1.37 (1.5H, d, J=6.6 Hz), 1.38 (1.5H, d, J=6.6 Hz), 1.39-1.70 (3H, m), 2.08-2.23 (1.5H, m), 2.32 (1H, m), 2.54 (1H, dd, J=7, 7 Hz), 2.62 (0.5H, dd, J=9.5, 6.5 Hz), 2.67-2.82 (1H, m), 3.20 (1H, q, J=6.6 Hz), 3.46 (1H, m), 7.18-7.36 (5H, m); MS (ES+) m/z 191.

Preparation 780

(3R)-1-(2-phenylethyl)-3-pyrrolidinamine $^1$H-NMR (300 MHz, CDCl$_3$) δ 1.42-1.66 (3H, m), 2.21 (1H, dddd, J=13, 8.5, 8.5, 5.5 Hz), 2.37 (1H, dd, J=9.5, 4.5 Hz), 2.53 (1H, ddd, J=8.5, 8.5, 6.5 Hz), 2.60-2.86 (4H, m), 3.53 (1H, m), 7.15-7.33 (5H, m); MS (ES+) m/z 191.

Preparation 781

(3R)-1-(2,3-dihydro-1H-inden-2-yl)-3-pyrrolidinamine $^1$H-NMR (300 MHz, CDCl$_3$) δ 1.35 (2H, br), 1.52 (1H, m), 2.24 (1H, dddd, J=13, 8.5, 8.5, 5 Hz), 2.36 (1H, dd, J=9.5, 5 Hz), 2.59 (1H, ddd, J=8.5, 8.5, 6 Hz), 2.77 (1H, ddd, J=8.5, 8.5, 6 Hz), 2.82-2.97 (3H, m), 2.98-3.14 (3H, m), 3.57 (1H, m), 7.08-7.22 (4H, m); MS (ES+) m/z 203.

The following compound was obtained in a similar manner to that of Preparation 405.

Preparation 782

(2E)-3-(6-{(tert-butoxycarbonyl)[(3R)-1-cyclohexyl-3-pyrrolidinyl]amino}-3-pyridinyl)acrylic acid $^1$H-NMR (300 MHz, DMSO-d6) δ 1.00-2.38 (12H, m), 1.39 (3H, s), 1.42 (6H, s), 3.00-4.00 (5H, m), 4.97 (1H, m), 6.68 (0.7H, d, J=16 Hz), 6.70 (0.3H, d, J=16 Hz), 7.43 (1H, d, J=8.5 Hz), 7.63 (0.7H, d, J=16 Hz), 7.64 (0.3H, d, J=16 Hz), 8.23 (1H, m), 8.73 (1H, m), 11.48 (1H, br); MS (ES+) m/z 416.

The following compound was obtained in a similar manner to that of Preparation 452.

Preparation 783

(3R)-3-amino-1-(cyclohexylmethyl)-2-pyrrolidinone $^1$H-NMR (300 MHz, CDCl$_3$) δ 0.86-1.06 (2H, m), 1.10-1.30 (3H, m), 1.52-1.80 (9H, m), 2.42 (1H, m), 3.08 (1H, dd, J=14, 7 Hz), 3.15 (1H, dd, J=14, 7 Hz), 3.23-3.35 (2H, m), 3.53 (1H, dd, J=10, 8.5 Hz); MS (ES+) m/z 197.

The following compound was obtained in a similar manner to that of Preparation 414.

Preparation 784

(2E)-3-(5-{[(3R)-1-(cyclohexylmethyl)-3-pyrrolidinyl]amino}-2-pyrazinyl)-N-(tetrahydro-2H-pyran-2-yloxy)acrylamide $^1$H-NMR (300 MHz, DMSO-d6) δ 0.73-0.93 (2H, m), 1.06-1.28 (3H, m), 1.30-1.83 (13H, m), 2.10-2.30 (3H, m), 2.31-2.44 (2H, m), 2.61 (1H, m), 2.72 (1H, m), 3.52 (1H, m), 3.95 (1H, m), 4.29 (1H, m), 4.89 (1H, m), 6.60 (1H, d, J=15.2 Hz), 7.38 (1H, d, J=15.2 Hz), 7.73 (1H, d, J=6.6 Hz), 7.98 (1H, s), 8.11 (1H, s), 11.18 (1H, s); MS (ES+) m/z 430.

The following compound was obtained in a similar manner to that of Preparation 480.

Preparation 785 tert-butyl [(3R)-1-(2-methylbenzyl)-3-pyrrolidinyl]carbamate $^1$H-NMR (300 MHz, CDCl$_3$) δ 1.43 (9H, s), 1.67 (1H, m), 2.16-2.33 (2H, m), 2.52 (1H, m), 2.59 (1H, dd, J=9.5, 6 Hz), 2.79 (1H, m), 3.56 (2H, s), 4.16 (1H, m), 4.80 (1H, m), 7.10-7.20 (3H, m), 7.25 (1H, m); MS (ES+) m/z 291.

The following compound was obtained in a similar manner to that of Preparation 336.

Preparation 786

(2E)-3-(5-{[(3R)-1-(cyclohexylmethyl)-2-oxo-3-pyrrolidinyl]amino}-2-pyrazinyl)-N-(tetrahydro-2H-pyran-2-yloxy)acrylamide $^1$H-NMR (300 MHz, DMSO-d6) δ 0.80-0.96 (2H, m), 1.10-1.30 (3H, m), 1.45-1.76 (12H, m), 1.84 (1H, m), 2.44 (1H, m), 2.97-3.12 (2H, m), 3.27-3.39 (2H, m), 3.52 (1H, m), 3.95 (1H, m), 4.64 (1H, m), 4.90 (1H, m), 6.64 (1H, d, J=15.5 Hz), 7.41 (1H, d, J=15.5 Hz), 7.88 (1H, d, J=7.5 Hz), 8.06 (1H, s), 8.10 (1H, s), 11.21 (1H, s); MS (ES+) m/z 444.

The following compound was obtained in a similar manner to that of Preparation 390.

Preparation 787

(2E)-3-(6-{[(3R)-1-(cyclohexylcarbonyl)-3-pyrrolidinyl]amino}-5-fluoro-3-pyridinyl)acrylic acid

MASS(API-ES); 362 (M+H)+.

$^1$H-NMR (200 MHz), (DMSO-d6, δ): 1.05-1.79 (10H, m), 1.80-2.55 (3H, m), 3.15-3.90 (4H, m), 4.40-4.70 (1H, m), 6.36 (1H, d, J=16 Hz), 7.35-7.45 (1H, m), 7.51 (1H, d, J=16 Hz), 7.86 (1H, dd, J=1.8 Hz, J=12 Hz), 8.12 (1H, d, J=1.8 Hz).

The following compound was obtained in a similar manner to that of Preparation 336.

Preparation 788

(2E)-3-(5-{[(3R)-1-(2-quinolinylmethyl)-3-pyrrolidinyl]amino}-2-pyrazinyl)-N-(tetrahydro-2H-pyran-2-yloxy)acrylamide $^1$H-NMR (300 MHz, DMSO-d6) δ 1.46-1.77 (7H, m), 2.26 (1H, m), 2.46-2.60 (2H, m), 2.77 (1H, m), 2.89 (1H, dd, J=9.5, 7 Hz), 3.52 (1H, m), 3.90 (2H, s), 3.95 (1H, m), 4.35 (1H; m), 4.89 (1H, m), 6.59 (1H, d, J=15 Hz), 7.37 (1H, d, J=15 Hz), 7.57 (1H, m), 7.65 (1H, d, J=8.5 Hz), 7.73 (1H, m), 7.81 (1H, d, J=7 Hz), 7.93-8.02 (3H, m), 8.09 (1H, s), 8.33 (1H, d, J=8.5 Hz), 11.18 (1H, s); MS (ES+) m/z 475.

The following compound was obtained in a similar manner to that of Preparation 859.

Preparation 789 ethyl (2E)-3-(2-{(tert-butoxycarbonyl)[(3R)-1-(2-phenylethyl)-3-pyrrolidinyl]amino}-5-pyrimidinyl)acrylate $^1$H-NMR (300 MHz, CDCl$_3$) δ 1.35 (3H, t, J=7 Hz), 1.47 (3×3H, s), 2.07-2.33 (2H, m), 2.56-2.83 (7H, m), 3.08 (1H, dd, J=8, 8 Hz), 4.29 (2H, q, J=7 Hz), 5.00 (1H, m), 6.54 (1H, d, J=16 Hz), 7.14-7.33 (5H, m), 7.59 (1H, d, J=16 Hz), 8.79 (2×1H, s); MS (ES+) m/z 467.

The following compound was obtained in a similar manner to that of Preparation 436.

Preparation 790 methyl 5-{[(3R)-1-benzyl-3-pyrrolidinyl](tert-butoxycarbonyl)amino]-2-pyrazinecarboxylate

MASS(API-ES); 413 (M+H)+

$^1$H-NMR (200 MHz), (DMSO-d6, δ): 1.39 (10H, s), 1.95-2.30 (2H, m), 2.40-2.85 (3H, m), 3.45, 3.53 (2H, ABq, J=13

Hz), 3.93 (3H, s), 4.70-4.95 (1H, m), 7.05-7.30 (5H, m), 8.79 (1H, d, J=1.3 Hz), 9.00 (1H, d, J=1.3 Hz).

The following compound was obtained in a similar manner to that of Preparation 379.

Preparation 791 methyl 5-{[(3R)-1-benzyl-3-pyrrolidinyl]amino}-2-pyrazinecarboxylate

MASS(API-ES); 313 (M+H)+

$^1$H-NMR (200 MHz), (DMSO-d6, δ): 1.55-1.80 (1H, m), 2.10-2.55 (3H, m), 2.60-2.85 (2H, m), 3.59 (2H, s), 3.78 (3H, s), 4.25-4.45 (1H, m), 7.20-7.35 (5H, m), 7.96 (1H, d, J=1.0 Hz), 8.16 (1H, d, J=6.7 Hz), 8.56 (1H, d, J=1.0 Hz).

The following compound was obtained in a similar manner to that of Preparation 439.

Preparation 792 ethyl (2E)-3-(5-{[(3R)-1-(cyclohexylmethyl)-2-oxo-3-pyrrolidinyl]amino}-2-pyrazinyl)acrylate $^1$H-NMR (300 MHz, CDCl$_3$) δ 0.88-1.06 (2H, m), 1.12-1.36 (3H, m), 1.33 (3H, t, J=7 Hz), 1.54-1.80 (5H, m), 1.87 (1H, m), 2.85 (1H, m), 3.16 (1H, dd, J=14, 7 Hz), 3.22 (1H, dd, J=14, 7 Hz), 3.30-3.50 (2H, m), 4.25 (2H, q, J=7 Hz), 4.47 (1H, m), 5.75 (1H, d, J=4 Hz), 6.72 (1H, d, J=15.5 Hz), 7.57 (1H, d, J=15.5 Hz), 8.01 (1H, d, J=1 Hz), 8.05 (1H, d, J=1 Hz); MS (ES+) m/z 373.

The following compound was obtained in a similar manner to that of Preparation 480.

Preparation 793 tert-butyl [(3R)-1-(2-quinolinylmethyl)-3-pyrrolidinyl]carbamate $^1$H-NMR (300 MHz, CDCl$_3$) δ 1.44 (9H, s), 1.64 (1H, m), 2.29 (1H, m), 2.48 (1H, m), 2.62 (1H, m), 2.78 (1H, dd, J=9.5, 6.5 Hz), 2.89 (1H, m), 3.95 (2H, s), 4.21 (1H, m), 4.96 (1H, br-d, J=8 Hz), 7.52 (1H, m), 7.56 (1H, d, J=8.5 Hz), 7.70 (1H, m), 7.81 (1H, dd, J=8, 1.5 Hz), 8.08 (1H, d, J=8 Hz), 8.13 (1H, d, J=8.5 Hz); MS (ES+) m/z 328.

The following compound was obtained in a similar manner to that of Preparation 336.

Preparation 794

(2E)-3-(5-{[(3R)-1-(2-methylbenzyl)-3-pyrrolidinyl]amino}-2-pyrazinyl)-N-(tetrahydro-2H-pyran-2-yloxy)acrylamide $^1$H-NMR (300 MHz, DMSO-d6) δ 1.42-1.78 (7H, m), 2.24 (1H, m), 2.32 (3H, s), 2.36-2.53 (2H, m), 2.66 (1H, m), 2.79 (1H, m), 3.52 (1H, m), 3.55 (2H, s), 3.95 (1H, m), 4.30 (1H, m), 4.89 (1H, m), 6.60 (1H, d, J=15 Hz), 7.09-7.18 (3H, m), 7.26 (1H, m), 7.37 (1H, d, J=15 Hz), 7.76 (1H, d, J=6.5 Hz), 7.97 (1H, s), 8.09 (1H, s), 11.18 (1H, s); MS (ES+) m/z 438.

The following compound was obtained in a similar manner to that of Preparation 450.

Preparation 795 tert-butyl [(3R)-1-(4-ethoxybenzyl)-3-pyrrolidinyl]carbamate $^1$H-NMR (300 MHz, CDCl$_3$) δ 1.41 (3H, t, J=7 Hz), 1.43 (3×3H, s), 1.61 (1H, m), 2.16-2.39 (2H, m), 2.48-2.67 (2H, m), 2.81 (1H, m), 3.56 (2H, s), 4.02 (2H, q, J=7 Hz), 4.18 (1H, m), 4.96 (1H, m), 6.84 (2×1H, d, J=8.5 Hz), 7.21 (2×1H, d, J=8.5 Hz); MS (ES+) m/z 321.

The following compound was obtained in a similar manner to that of Preparation 452.

Preparation 796

(3R}-1-(4-ethoxybenzyl)-3-pyrrolidinamine $^1$H-NMR (300 MHz, CDCl$_3$) δ 1.41 (3H, t, J=7 Hz), 1.44-1.58 (3H, m), 2.19 (1H, dddd, J=13, 8.5, 8, 6 Hz), 2.27 (1H, dd, J=9, 4.5 Hz), 2.46 (1H, ddd, J=8.5, 8.5, 6 Hz), 2.68 (1H, ddd, J=8.5, 8.5, 6 Hz), 2.71 (1H, dd, J=9, 5.5 Hz), 3.49 (1H, m), 3.51 (1H, d, J=12.5 Hz), 3.56 (1H, d, J=12.5 Hz), 4.02 (2H, q, J=7 Hz), 6.84 (2×1H, d, J=8.7 Hz), 7.21 (2×1H, d, J=8.7 Hz); MS (ES+) m/z 221.

The following compound was obtained in a similar manner to that of Preparation 439.

Preparation 797 ethyl (2E)-3-(5-{[(3R)-1-(4-ethoxybenzyl)-3-pyrrolidinyl]amino}-2-pyrazinyl)acrylate $^1$H-NMR (300 MHz, CDCl$_3$) δ 1.32 (3H, t, J=7 Hz), 1.41 (3H, t, J=7 Hz), 1.68 (1H, m), 2.28-2.44 (2H, m), 2.60-2.70 (2H, m), 2.88 (1H, m), 3.55 (1H, d, J=13 Hz), 3.59 (1H, d, J=13 Hz), 4.02 (2H, q, J=7 Hz), 4.25 (2H, q, J=7 Hz), 4.45 (1H, m), 5.24 (1H, d, J=7.5 Hz), 6.68 (1H, d, J=15.5 Hz), 6.85 (2×1H, d, J=8.5 Hz), 7.21 (2×1H, d, J=8.5 Hz), 7.56 (1H, d, J=15.5 Hz), 7.86 (1H, d, J=1 Hz), 8.04 (1H, d, J=1 Hz); MS (ES+) m/z 397.

The following compound was obtained in a similar manner to that of Preparation 336.

Preparation 798

(2E)-3-(5-{[(3R)-1-(4-ethoxybenzyl)-3-pyrrolidinyl]amino}-2-pyrazinyl)-N-(tetrahydro-2H-pyran-2-yloxy)acrylamide $^1$H-NMR (300 MHz, DMSO-d6) δ 1.31 (3H, t, J=7 Hz), 1.44-1.76 (7H, m), 2.21 (1H, m), 2.31-2.45 (2H, m), 2.63 (1H, m), 2.73 (1H, dd, J=9.5, 7 Hz), 3.33 (1H, m), 3.50 (2H, s), 3.53 (1H, m), 3.96 (1H, m), 3.98 (2H, q, J=7 Hz), 4.29 (1H, m), 4.89 (1H, m), 6.60 (1H, d, J=16 Hz), 6.85 (2×1H, d, J=8.5 Hz), 7.19 (2×1H, d, J=8.5 Hz), 7.37 (1H, d, J=15.5 Hz), 7.76 (1H, d, J=6.5 Hz), 7.96 (1H, s), 8.09 (1H, s), 11.09 (1H, s); MS (ES+) m/z 468.

The following compound was obtained in a similar manner to that of Preparation 380.

Preparation 799 tert-butyl (3R)-3-{[3-fluoro-5-(hydroxymethyl)-2-pyridinyl]amino}-1-pyrrolidinecarboxylate

MASS(API-ES); 312 (M+H)+

$^1$H-NMR (200 MHz), (DMSO-d6, δ): 1.30-1.50 (9H, m), 1.65-2.25 (2H, m), 3.05-3.70 (4H, m), 4.34 (2H, d, J=5.6 Hz), 4.30-4.50 (1H, m), 5.07 (1H, t, J=5.6 Hz), 6.68 (1H, d, J=6.1 Hz), 7.30 (1H, dd, J=1.7 Hz, J=12 Hz), 7.79 (1H, d, J=1.7 Hz).

The following compound was obtained in a similar manner to that of Preparation 405.

Preparation 800

(2E)-3-{6-{[(3R)-1-benzyl-3-pyrrolidinyl](tert-butoxycarbonyl)amino]-2-pyrazinyl)acrylic acid ¹H-NMR (300 MHz, CDCl₃) δ 1.48 (9H, s), 2.38-2.57 (2H, m), 3.22-3.47 (3H, m), 3.97 (1H, m), 4.10 (1H, d, J=12.5 Hz), 4.42 (1H, d, J=12.5 Hz), 5.20 (1H, m), 7.26 (1H, d, J=15.5 Hz), 7.36-7.45 (3H, m), 7.49 (1H, d, J=15.5 Hz), 7.49-7.58 (2H, m), 8.28 (1H, s), 8.60 (1H, s); MS (ES+) m/z 425.

The following compound was obtained in a similar manner to that of Preparation 414.

Preparation 801 tert-butyl [(3R)-1-benzyl-3-pyrrolidinyl](6-{(1E)-3-oxo-3-[(tetrahydro-2H-pyran-2-yloxy)amino]-1-propen-1-yl}-2-pyrazinyl)carbamate ¹H-NMR (300 MHz, DMSO-d6) δ 1.35 (9H, s), 1.44-1.76 (6H, m), 1.92-2.44 (3H, m), 2.62-2.75 (2H, m), 3.15-3.59 (4H, m), 3.96 (1H, m), 4.78 (1H, m), 4.95 (1H, m), 6.97 (1H, d, J=15.5 Hz), 7.04 (2×1H, d, J=7 Hz), 7.14-7.28 (3H, m), 7.61 (1H, d, J=15.5 Hz), 8.58 (1H, s), 8.71 (1H, s), 11.51 (1H, br-s); MS (ES+) m/z 524.

The following compound was obtained in a similar manner to that of Preparation 439.

Preparation 802 ethyl (2E)-3-(2-{[(3R)-1-(2-phenylethyl)-3-pyrrolidinyl]amino}-5-pyrimidinyl)acrylate ¹H-NMR (300 MHz, CDCl₃) δ 1.33 (3H, t, J=7 Hz), 1.72 (1H, m), 2.30-2.48 (2H, m), 2.64-2.86 (6H, m), 2.95 (1H, m), 4.25 (2H, q, J=7 Hz), 4.56 (1H, m), 5.73 (1H, d, J=7 Hz), 6.30 (1H, d, J=16 Hz), 7.14-7.34 (5H, m), 7.49 (1H, d, J=16 Hz), 8.45 (2×1H, s); MS (ES+) m/z 367.

The following compounds were obtained in a similar manner to that of Preparation 336.

Preparation 803

(2Z)-3-(5-{[(3R)-1-benzyl-3-pyrrolidinyl]amino}-2-pyrazinyl)-2-fluoro-N-(tetrahydro-2H-pyran-2-yloxy)acrylamide

MASS(API-ES); 442 (M+H)+,

¹H-NMR (200 MHz), (CDCl₃, δ): 1.50-2.00 (7H, m), 2.30-2.60 (2H, m), 2.70-3.10 (3H, m), 3.30-3.70 (1H, m), 3.72 (2H, s), 3.95-4.20 (1H, m), 4.40-4.60 (1H, m), 5.00-5.10 (1H, m), 6.89 (1H, d, J=39 Hz), 7.20-7.45 (5H, m), 7.89 (1H, d, J=1.3 Hz), 8.35 (1H, d, J=1.3 Hz).

(2E)-3-(5-{[(3R)-1-benzyl-3-pyrrolidinyl]amino}-2-pyrazinyl)-2-fluoro-N-(tetrahydro-2H-pyran-2-yloxy)acrylamide

MASS(API-ES); 442 (M+H)+,

¹H-NMR (200 MHz), (CDCl₃, δ): 1.50-2.00 (7H, m), 2.10-2.55 (2H, m), 2.65-2.85 (2H, m), 2.90-3.10 (1H, m), 3.60-3.80 (1H, m), 3.71 (2H, s), 3.95-4.15 (1H, m), 4.40-4.60 (1H, m), 5.07 (1H, s), 5.69 (1H, d, J=7.7 Hz), 6.60 (1H, d, J=25 Hz), 7.20-7.43 (5H, m), 7.77 (1H, d, J=1.0 Hz), 8.04 (1H, d, J=1.0 Hz).

The following compound was obtained in a similar manner to that of Preparation 311.

Preparation 804 ethyl (2E)-3-(5-fluoro-6-{[(3R)-1-(2-phenylethyl)-3-pyrrolidinyl]amino}-3-pyridinyl)acrylate

MASS(API-ES); 384 (M+H)+,

¹H-NMR (400 MHz), (DMSO-d6, δ): 1.23 (3H, t, J=7.0 Hz), 1.70-1.90 (1H, m), 2.00-2.25 (1H, m), 2.30-2.83 (7H, m), 2.85-2.95 (1H, m), 4.16 (2H, q, J=7.0 Hz), 4.35-4.55 (1H, m), 6.43 (1H, d, J=16 Hz), 7.00-7.30 (6H, m), 7.55 (1H, dd, J=2.0 Hz, J=16 Hz), 7.85 (1H, dd, J=1.8 Hz, J=13 Hz), 8.11 (1H, d, J=1.8 Hz).

The following compound was obtained in a similar manner to that of Preparation 390.

Preparation 805

(2E)-3-[5-fluoro-6-({(3R)-1-[2-(1H-pyrazol-1-yl)ethyl]-3-pyrrolidinyl}amino)-3-pyridinyl]acrylic acid

MASS(API-ES); 346 (M+H)+.

The following compound was obtained in a similar manner to that of Preparation 397.

Preparation 806

(2E)-3-[5-fluoro-6-({(3R)-1-[2-(1H-pyrazol-1-yl)ethyl]-3-pyrrolidinyl}amino)-3-pyridinyl]-N-(tetrahydro-2H-pyran-2-yloxy)acrylamide

MASS(API-ES); 445 (M+H)+,

¹H-NMR (200 MHz), (DMSO-d6, δ): 1.40-1.88 (7H, m), 2.00-2.25 (1H, m), 2.38-2.95 (6H, m), 3.43-3.62 (1H, m), 3.83-4.05 (1H, m), 4.20 (1H, t, J=6.6 Hz), 4.32-4.55 (1H, m), 4.88 (1H, s), 6.20 (1H, t, J=1.7 Hz), 6.26 (1H, d, J=16 Hz), 7.10 (1H, d, J=6.2 Hz), 7.39 (1H, d, J=16 Hz), 7.40 (1H, d, J=1.7 Hz), 7.57 (1H, d, J=12 Hz), 7.74 (1H, d, J=1.7 Hz), 8.04 (1H, s).

Preparation 807

To a stirred solution of 5-bromo-2-chloropyrimidine (500 mg) in DMF (5 mL) was added ethyl acrylate (1.41 mL), palladium(II) acetate (29 mg), tris(2-methylphenyl)phosphine (118 mg), and N,N-diisopropylethylamine (1.35 mL). The mixture was stirred at 100° C. for 4 hours. The resulting mixture was allowed to cool to ambient temperature, poured into brine, and extracted with ethyl acetate. The organic phase was washed with brine, dried over Na₂SO₄, and concentrated in vacuo. The residue was purified by silica gel column chromatography eluting with a mixture of hexane and ethyl acetate (90:10 v/v) to give ethyl (2E)-3-(2-chloro-5-pyrimidinyl)acrylate (494 mg) as a yellow powder.

¹H-NMR (300 MHz, CDCl₃) δ 1.35 (3H, t, J=7 Hz), 4.30 (2H, q, J=7 Hz), 6.59 (1H, d, J=16 Hz), 7.58 (1H, d, J=16 Hz), 8.76 (2×1H, s); MS ( ) m/z not detected.

The following compound was obtained in a similar manner to that of Preparation 439.

Preparation 808 ethyl (2E)-3-(5-{[(3R)-1-(1-phenylethyl)-3-pyrrolidinyl]amino}-2-pyrazinyl)acrylate ¹H-NMR (300 MHz, CDCl₃) δ 1.32 (1.5H, t, J=7 Hz), 1.33 (1.5H, t, J=7 Hz), 1.39 (1.5H, d, J=6.6 Hz), 1.41 (1.5H, d, J=6.6 Hz), 1.56-1.80 (1H, m), 2.26-2.40 (2H, m), 2.46 (0.5H, dd, J=10, 3 Hz), 2.56-2.72 (1.5H, m), 2.79 (0.5H, dd, J=10, 3 Hz), 3.04 (1H, m), 3.26 (1H, q, J=6.6 Hz), 4.24 (1H, q, J=7 Hz), 4.25 (1H, q, J=7 Hz), 4.42 (1H, m), 5.18 (0.5H, d, J=7.5 Hz), 5.25 (0.5H, d, J=7.5 Hz), 6.67 (0.5H, d, J=15.5 Hz), 6.69 (0.5H, d, J=15.5 Hz), 7.20-7.37 (5H, m), 7.55 (0.5H, d, J=15.5 Hz), 7.57 (0.5H, d, J=15.5 Hz), 7.86 (0.5H, d, J=1 Hz), 7.90 (0.5H, d, J=1 Hz), 8.03 (0.5H, d, J=1 Hz), 8.06 (0.5H, d, J=1 Hz); MS (ES+) m/z 367.

The following compound was obtained in a similar manner to that of Preparation 390.

Preparation 809

(2E)-3-(6-{[(3R)-1-(2,6-difluorobenzyl)-3-pyrrolidinyl]amino}-5-fluoro-3-pyridinyl)acrylic acid

MASS(API-ES); 378 (M+H)+, $^1$H-NMR (200 MHz), (DMSO-d6, δ): 1.60-2.25 (2H, m), 2.30-2.70 (3H, m), 2.80-3.00 (1H, m), 3.69 (2H, s), 4.30-4.55 (1H, m), 6.31 (1H, d, J=16 Hz), 7.00-7.44 (4H, m), 7.45 (1H, d, J=16 Hz), 7.80 (1H, d, J=13 Hz), 8.05 (1H, s).

The following compound was obtained in a similar manner to that of Preparation 198.

Preparation 810 ethyl (2E)-3-(5-chloro-6-{[1-(2-pyridinylmethyl)-4-piperidinyl]amino}-3-pyridinyl)acrylate $^1$H NMR (DMSO-d6, δ): 1.24(3H, t, J=7.1 Hz), 1.55-1.89 (4H, m), 2.05-2.17(2H, m), 2.81-2.87(2H, m), 3.59(2H, s), 3.90-4.10(1H, m), 4.16(2H, q, J=7.1 Hz), 6.47(1H, d, J=15.9 Hz), 6.65(1H, d, J=8.0 Hz), 7.23-7.29(1H, m), 7.43(1H, d, J=7.8 Hz), 7.50(1H, d, J=16.0 Hz), 7.73-7.81(1H, m), 8.10 (1H, d, J=1.9 Hz), 8.27(1H, d, J=1.9 Hz), 8.49(1H, d, J=4.1 Hz), Mass (APCI): 401(M+H)+.

The following compound was obtained in a similar manner to that of Preparation 850.

Preparation 811 ethyl (2E)-3-(5-chloro-6-{[1-(4-pyridinylmethyl)-4-piperidinyl]amino}-3-pyridinyl)acrylate $^1$H NMR (DMSO-d6, δ): 1.24(3H, t, J=7.1 Hz), 1.60-1.84 (4H, m), 2.03-2.13(2H, m), 2.78-2.83(2H, m), 3.51(2H, s), 3.91-4.10(1H, m), 4.16(2H, q, J=7.1 Hz), 6.47(1H, d, J=15.9 Hz), 6.64(1H, d, J=7.9 Hz), 7.32(2H, d, J=5.8 Hz), 7.50(1H, d, J=15.9 Hz), 8.10(1H, d, J=1.9 Hz), 8.27(1H, d, J=1.9 Hz), 7.51(1H, d, J=5.8 Hz), Mass (APCI): 401(M+H)+.

The following compounds were obtained in a similar manner to that of Preparation 62.

Preparation 812

(2E)-3-(5-chloro-6-{[1-(2-pyridinylmethyl)-4-piperidinyl]amino}-3-pyridinyl)-N-(tetrahydro-2H-pyran-2-yloxy)acrylamide $^1$H NMR (DMSO-d6, δ): 1.50-1.84(10H, m), 2.08-2.18(2H, m), 2.81-2.87(2H, m), 8.49-8.54(1H, m), 8.60(2H, s), 3.93-4.08(2H, m), 4.88(1H, brs), 6.30(1H, d, J=15.9 Hz), 6.53(1H, d, J=7.9 Hz), 7.23-7.29(1H, m), 7.38(1H, d, J=15.9 Hz), 7.43(1H, d, J=7.9 Hz), 7.23-7.84(2H, m), 8.20(1H, s), 8.49 (1H, d, J=4.2 Hz), 11.07(1H, brs), Mass (APCI): 472(M+H)+.

Preparation 813

(2E)-3-(5-chloro-6-{[1-(2-chlorobenzyl)-4-piperidinyl]amino}-3-pyridinyl)-N-(tetrahydro-2H-pyran-2-yloxy)acrylamide $^1$H NMR (DMSO-d6, δ): 1.45-1.90(10H, m), 2.10-2.20(2H, m), 2.82-2.89(2H, m), 3.49-3.60(1H, m), 3.57(2H, s), 3.80-4.10(2H, m), 4.89(1H, brs), 6.30(1H, d, J=15.9 Hz), 6.53(1H, d, J=7.9 Hz), 7.27-7.50(5H, m), 7.84(1H, s), 8.21(1H, s), 11.07(1H, brs), Mass (APCI): 505(M+H)+.

The following compound was obtained in a similar manner to that of Preparation 366.

Preparation 814 ethyl (2E)-3-{4-[(3R)-3-pyrrolidinylamino]phenyl}acrylate hydrochloride $^1$H-NMR (300 MHz, DMSO-d6) δ 1.24 (3H, t, J=7 Hz), 1.89 (1H, m), 2.21 (1H, m), 3.04 (1H, m), 3.16-3.50 (4H, m), 4.14 (2H, q, J=7 Hz), 6.30 (1H, d, J=16 Hz), 6.62 (2H, d, J=8.5 Hz), 7.49 (2H, d, J=8.5 Hz), 7.50 (1H, d, J=8.5 Hz), 9.20-9.38 (2H, br).

The following compound was obtained in a similar manner to that of Preparation 678.

Preparation 815 ethyl (2E)-3-(4-{[(3R)-1-(cyclohexylmethyl)-3-pyrrolidinyl]amino}phenyl)acrylate $^1$H-NMR (300 MHz, CDCl$_3$) δ 0.80-0.97 (2H, m), 1.10-1.31 (3H, m), 1.32 (3H, t, J=7 Hz), 1.44 (1H, m), 1.58-1.84 (4H, m), 2.18-2.42 (4H, m), 2.56 (1H, dd, J=9.5, 3 Hz), 2.68 (1H, dd, J=9.5, 6.5 Hz), 2.78 (1H, m), 4.01 (1H, m), 4.24 (2H, q, J=7 Hz), 4.30 (1H, m), 6.21 (1H, d, J=15.8 Hz), 6.56 (2×1H, d, J=8.5 Hz), 7.36 (2H, d, J=8.5 Hz), 7.59 (1H, d, J=15.8 Hz); MS (ES+) m/z 357.

The following compound was obtained in a similar manner to that of Preparation 434.

Preparation 816 ethyl (2E)-3-(4-{[(3R)-1-(cyclohexylcarbonyl)-3-pyrrolidinyl]amino}phenyl)acrylate $^1$H-NMR (300 MHz, CDCl$_3$) δ 1.10-2.12 (11H, m), 1.33 (3H, t, J=7 Hz), 2.18-2.42 (2H, m), 3.42 (1H, m), 3.55-3.70 (2H, m), 3.84° (1H, m), 4.06 (1H, m), 4.18 (1H, m), 4.24 (1H, q, J=7 Hz), 4.25 (1H, q, J=7 Hz), 6.23 (0.5H, d, J=15.8 Hz), 6.24 (0.5H, d, J=15.5 Hz), 6.58 (1H, d, J=7.7 Hz), 6.59 (1H, d, J=7.7 Hz), 7.38 (1H, d, J=7.7 Hz), 7.40 (1H, d, J=7.7 Hz), 7.59 (0.5H, d, J=15.8 Hz), 7.60 (0.5H, d, J=15.8 Hz); MS (ES+) m/z 371.

The following compound was obtained in a similar manner to that of Preparation 198.

Preparation 817 ethyl (2E)-3-(5-chloro-6-{[1-(cyclohexylmethyl)-4-piperidinyl]amino}-3-pyridinyl)acrylate $^1$H NMR (DMSO-d6, δ): 0.78-0.90 (2H, m), 1.14-1.36 (3H, m), 1.23 (3H, t, J=7.4 Hz), 1.41-2.08 (13H, m), 2.77-2.83

(2H, m), 3.92-4.01 (1H, m), 4.15 (2H, q, J=7.4 Hz), 6.48 (1H, d, J=15.9 Hz), 6.59 (1H, d, J=7.8 Hz), 7.50 (1H, d, J=15.9 Hz), 8.09 (1H, d, J=1.9 Hz), 8.27 (1H, d, J=1.9 Hz),

Mass (ESI): 406(M+H)+.

The following compound was obtained in a similar manner to that of Preparation 405.

Preparation 818

(2E)-3-(4-{[(3R)-1-(cyclohexylcarbonyl)-3-pyrrolidinyl]amino}phenyl)acrylic acid $^1$H-NMR (300 MHz, CDCl$_3$) δ 1.16-2.43 (13H, m), 3.36-3.70 (3H, m), 3.83 (1H, m), 4.04-4.24 (1H, m), 6.24 (0.5H, d, J=15.8 Hz), 6.26 (0.5H, d, J=15.8 Hz), 6.59 (1H, d, J=8 Hz), 6.61 (1H, d, J=8 Hz), 7.40 (1H, d, J=8 Hz), 7.43 (1H, d, J=8 Hz), 7.68 (0.5H, d, J=15.8 Hz), 7.69 (0.5H, d, J=15.8 Hz); MS (ES+) m/z 343.

The following compound was obtained in a similar manner to that of Preparation 414.

Preparation 819

(2E)-3-(4-{[(3R)-1-(cyclohexylcarbonyl)-3-pyrrolidinyl]amino}phenyl)-N-(tetrahydro-2H-pyran-2-yloxy)acrylamide $^1$H-NMR (300 MHz, DMSO-d6) δ 1.06-2.44 (19H, m), 3.17-3.66 (4H, m), 3.78-4.13 (3H, m), 4.87 (1H, m), 6.19 (1H, br), 6.40 (1H, m), 6.61 (1H, d, J=8.5 Hz), 6.64 (1H, d, J=8.5 Hz), 7.28-7.41 (3H, m), 10.99 (1H, s); MS ( ) m/z not detected.

The following compounds were obtained in a similar manner to that of Preparation 62.

Preparation 820

(2E)-3-(5-chloro-6-{[1-(3-fluorobenzyl)-4-piperidinyl]amino}-3-pyridinyl)-N-(tetrahydro-2H-pyran-2-yloxy)acrylamide $^1$H NMR (DMSO-d6): δ 1.50-1.90 (11H, m), 2.05-2.11 (2H, m), 2.73-2.78 (2H, m), 3.49 (2H, s), 3.95-4.05 (2H, m), 4.89 (1H, s), 6.30 (1H, d, J=15.9 Hz), 6.52 (1H, d, J=7.8 Hz), 7.02-7.16 (3H, m), 7.32-7.42 (2H, m), 7.84 (1H, s), 8.20 (1H, s), 11.07 (1H, brs), Mass (ESI): 489(M+H)+.

Preparation 821

(2E)-3-(5-chloro-6-{[1-(3-methyl-2-buten-1-yl)-4-piperidinyl]amino}-3-pyridinyl)-N-(tetrahydro-2H-pyran-2-yloxy)acrylamide $^1$H NMR (DMSO-d6): δ 1.53-1.85 (18H, m), 1.93-2.20 (2H, m), 2.87-3.07 (4H, m), 3.49-0.355 (1H, m), 3.80-4.10 (2H, m), 4.87 (1H, s), 5.17-5.24 (1H, m), 6.31 (1H, d, J=15.9 Hz), 6.55 (1H, d, J=7.8 Hz), 7.35 (1H, d, J=15.9 Hz), 7.84 (1H, s), 8.20 (1H, s), 11.08 (1H, brs), Mass (ESI): 449(M+H)+.

Preparation 822

(2E)-3-(5-chloro-6-{[1-(cyclohexylmethyl)-4-piperidinyl]amino}-3-pyridinyl)-N-(tetrahydro-2H-pyran-2-yloxy)acrylamide $^1$H NMR (DMSO-d6, δ): 0.78-0.90 (2H, m), 1.14-1.30 (3H, m), 1.46-2.08 (20H, m), 2.78-2.83 (2H, m), 3.49-3.55 (1H, m), 3.80-4.05 (2H, m), 4.88 (1H, s), 6.30 (1H, d, J=15.9 Hz), 6.49 (1H, d, J=7.8 Hz), 7.35 (1H, d, J=15.9 Hz), 7.83 (1H, s), 8.20 (1H, s), 11.07 (1H, brs).

Mass (ESI) 477(M+H)+.

The following compound was obtained in a similar manner to that of Preparation 370.

Preparation 823 ethyl 6-[(4-methylphenyl)amino]nicotinate $^1$H-NMR (300 MHz, CDCl$_3$) δ 1.38 (3H, t, J=7 Hz), 2.36 (3H, s), 4.35 (2H, q, J=7 Hz), 6.75 (1H, d, J=9 Hz), 6.89 (1H, br-s), 7.15-7.26 (4H, m), 8.03 (1H, dd, J=9, 2.5 Hz), 8.82 (1H, d, J=2.5 Hz); MS (ES+) m/z 257.

The following compound was obtained in a similar manner to that of Preparation 361.

Preparation 824

{6-[(4-methylphenyl)amino]-3-pyridinyl}methanol $^1$H-NMR (300 MHz, CDCl$_3$) δ 2.33 (3H, s), 4.58 (2H, s), 6.54 (1H, br-s), 6.82 (1H, d, J=8.5 Hz), 7.11-7.22 (4H, m), 7.52 (1H, dd, J=8.5, 2.5+Hz), 8.14 (1H, d, J=2.5 Hz); MS (ES+) m/z 215.

The following compound was obtained in a similar manner to that of Preparation 382.

Preparation 825

6-[(4-methylphenyl)amino]nicotinaldehyde $^1$H-NMR (300 MHz, CDCl$_3$) δ 2.37 (3H, s), 6.79 (1H, d, J=8.5 Hz), 7.15 (1H, br-s), 7.18-7.30 (4H, m), 7.94 (1H, dd, J=8.5, 2 Hz), 8.60 (1H, d, J=2 Hz), 9.83 (1H, s); MS (ES+) m/z 213.

The following compound was obtained in a similar manner to that of Preparation 683.

Preparation 826

(2E)-3-{6-[(4-methylphenyl)amino]-3-pyridinyl}acrylic acid $^1$H-NMR (300 MHz, DMSO-d6) δ 2.25 (3H, s), 6.35 (1H, d, J=16 Hz), 6.81 (1H, d, J=8.5 Hz), 7.10 (2×1H, d, J=8.5 Hz), 7.51 (1H, d, J=16 Hz), 7.58 (2H, d, J=8.5 Hz), 7.93 (1H, dd, J=8.5, 2 Hz), 8.35 (1H, d, J=2 Hz), 9.33 (1H, s); MS (ES+) m/z 255.

The following compound was obtained in a similar manner to that of Preparation 414.

Preparation 827

(2E)-3-{6-[(4-methylphenyl)amino]-3-pyridinyl}-N-(tetrahydro-2H-pyran-2-yloxy)acrylamide $^1$H-NMR (300 MHz, DMSO-d6) δ 1.45-1.78 (6H, m), 2.25 (3H, s), 3.53 (1H, m), 3.96 (1H, m), 4.89 (1H, m), 6.32 (1H, d, J=16 Hz), 6.83 (1H, d, J=8.8 Hz), 7.10 (2H, d, J=8.5 Hz), 7.42 (1H, d, J=16 Hz), 7.57 (2H, d, J=8.5 Hz), 7.76 (1H, br-d, J=8.8 Hz), 8.30 (1H, d, J=1.5 Hz), 9.29 (1H, s), 11.13 (1H, br-s); MS (ES+) m/z 354.

The following compound was obtained in a similar manner to that of Preparation 674.

Preparation 828 ethyl 6-[(2-ethoxyphenyl)amino]nicotinate

¹H-NMR (300 MHz, CDCl₃) δ 1.39 (3H, t, J=7 Hz), 1.46 (3H, t, J=7 Hz), 4.12 (2H, q, J=7 Hz), 4.36 (2H, q, J=7 Hz), 6.84 (1H, d, J=8.8 Hz), 6.89-7.06 (3H, m), 7.28 (1H, s), 8.03 (1H, dd, J=7.5, 2 Hz), 8.07 (1H, dd, J=8.8, 2.2 Hz), 8.89 (1H, d, J=2.2 Hz); MS (ES+) m/z 287.

The following compound was obtained in a similar manner to that of Preparation 361.

Preparation 829

{6-[(2-ethoxyphenyl)amino]-3-pyridinyl)methanol

¹H-NMR (300 MHz, CDCl₃) δ 1.45 (3H, t, J=7 Hz), 1.71 (1H, br), 4.11 (2H, q, J=7 Hz), 4.60 (2H, s), 6.86-6.99 (4H, m), 7.05 (1H, s), 7.56 (1H, dd, J=8.5, 2.5 Hz), 7.97 (1H, m), 8.20 (1H, d, J=2.5 Hz);

MS (ES+) m/z 245.

The following compound was obtained in a similar manner to that of Preparation 414.

Preparation 830

(2E)-3-{6-[(2-ethoxyphenyl)amino]-3-pyridinyl}-N-(tetrahydro-2H-pyran-2-yloxy)acrylamide ¹H-NMR (300 MHz, DMSO-d6) δ 1.35 (3H, t, J=7 Hz), 1.46-1.78 (6H, m), 3.53 (1H, m), 3.96 (1H, m), 4.10 (2H, q, J=7 Hz), 4.89 (1H, m), 6.33 (1H, d, J=16 Hz), 6.87-7.07 (4H, m), 7.42 (1H, d, J=16 Hz), 7.77 (1H, m), 8.08 (1H, dd, J=8, 1 Hz), 8.29 (1H, d, J=2 Hz), 8.37 (1H, s), 11.13 (1H, s); MS (ES+) m/z 384.

The following compound was obtained in a similar manner to that of Preparation 382.

Preparation 831

6-[(2-ethoxyphenyl)amino]nicotinaldehyde

¹H-NMR (300 MHz, CDCl₃) δ 1.46 (3H, t, J=7 Hz), 4.13 (2H, q, J=7 Hz), 6.88 (1H, d, J=8.8 Hz), 6.91-7.11 (3H, m), 7.43 (1H, s), 7.97 (1H, dd, J=8.8, 2.2 Hz), 8.09 (1H, dd, J=7.7, 1.8 Hz), 8.66 (1H, d, J=2.2 Hz), 9.86 (1H, s); MS (ES+) m/z 243.

The following compound was obtained in a similar manner to that of Preparation 683.

Preparation 832

(2E)-3-{6-[(2-ethoxyphenyl)amino]-3-pyridinyl}acrylic acid

¹H-NMR (300 MHz, DMSO-d6) δ 1.35 (3H, t, J=7 Hz), 4.10 (2H, q, J=7 Hz), 6.37 (1H, d, J=16 Hz), 6.86-7.07 (4H, m), 7.50 (1H, d, J=16 Hz), 7.93 (1H, dd, J=8.8, 2.2 Hz), 8.09 (1H, dd, J=8, 1.4 Hz), 8.33 (1H, d, J=2.2 Hz), 8.42 (1H, s); MS (ES+) m/z 285.

The following compound was obtained in a similar manner to that of Preparation 405.

Preparation 833

(2E)-3-(4-{[(3R)-1-(cyclohexylmethyl)-3-pyrrolidinyl]amino}phenyl)acrylic acid

¹H-NMR (300 MHz, DMSO-d6) δ 0.82-1.03 (2H, m), 1.04-1.32 (3H, m), 1.54-2.02 (7H, m), 2.24-2.46 (1H, m), 2.83-3.45 (5H, m), 3.56-4.34 (2H, m), 6.21 (1H, d, J=16 Hz), 6.61 (2H, d, J=8.5 Hz), 6.69 (1H, m), 7.46 (2H, d, J=8.5 Hz), 7.46 (1H, d, J=16 Hz), 10.29 (1H, br), 12.00 (1H, s); MS (ES+) m/z 329.

The following compound was obtained in a similar manner to that of Preparation 363.

Preparation 834 ethyl (2E)-3-(6-{[(3R)-1-(cyclohexylmethyl)-3-piperidinyl]amino}-3-pyridinyl)acrylate ¹H-NMR (300 MHz, CDCl₃) δ 0.78-0.96 (2H, m), 1.06-1.40 (5H, m), 1.40-1.84 (11H, m), 2.00-2.25 (3H, m), 2.38-2.64 (3H, m), 3.96 (1H, br peak), 4.25 (2H, q, J=7.1 Hz), 5.49 (1H, br peak), 6.21 (1H, d, J=15.9 Hz), 6.39 (1H, d, J=8.8 Hz), 7.57 (1H, d, J=15.9 Hz), 7.61 (1H, dd, J=8.7, 2.4 Hz), 8.19 (1H, d, J=2.2 Hz).

The following compound was obtained in a similar manner to that of Preparation 414.

Preparation 835

(2E)-3-(4-{[(3R)-1-(cyclohexylmethyl)-3-pyrrolidinyl]amino}phenyl)-N-(tetrahydro-2H-pyran-2-yloxy)acrylamide ¹H-NMR (300 MHz, DMSO-d6) δ 0.74-0.91 (2H, m), 1.04-1.30 (3H, m), 1.40 (1H, m), 1.46-1.81 (12H, m), 2.11-2.29 (3H, m), 2.33 (1H, dd, J=9, 4.5 Hz), 2.42 (1H, m), 2.56 (1H, m), 2.75 (1H, dd, J=9, 7 Hz), 3.53 (1H, m), 3.82-4.01 (2H, m), 4.87 (1H, m), 6.16 (1H, br-d, J=16 Hz), 6.29 (1H, d, J=6.5 Hz), 6.56 (2H, d, J=8.8 Hz), 7.26-7.38 (3H, m), 10.97 (1H, s); MS (ES+) m/z 428.

The following compound was obtained in a similar manner to that of Preparation 361.

Preparation 836

[5-chloro-6-(2,3-dihydro-1H-inden-1-ylamino)-3-pyridinyl]methanol

¹H-NMR (300 MHz, CDCl₃) δ 1.62 (1H, t, J=4 Hz), 1.88 (1H, m), 2.72 (1H, m), 2.84-3.10 (2H, m), 4.57 (2H, d, J=4 Hz), 5.25 (1H, br-d, J=8 Hz), 5.70 (1H, ddd, J=8, 7.5, 7.5 Hz), 7.17-7.37 (4H, m), 7.57 (1H, d, J=2 Hz), 8.05 (1H, d, J=2 Hz); MS (ES+) m/z 275.

The following compound was obtained in a similar manner to that of Preparation 382.

Preparation 837

5-chloro-6-(2,3-dihydro-1H-inden-1-ylamino)nicotinaldehyde

¹H-NMR (300 MHz, CDCl₃) δ 1.94 (H, m), 2.74 (1H, m), 2.85-3.13 (2H, m), 5.76-5.92 (2H, m), 7.18-7.38 (4H, m), 7.98 (1H, d, J=2 Hz), 8.51 (1H, d, J=2 Hz), 9.80 (1H, s); MS (ES+) m/z 273.

The following compound was obtained in a similar manner to that of Preparation 683.

Preparation 838

(2E)-3-[5-chloro-6-(2,3-dihydro-1H-inden-1-ylamino)-3-pyridinyl]acrylic acid

¹H-NMR (300 MHz, CDCl₃) δ 1.92 (1H, m), 2.74 (1H, m), 2.86-3.12 (2H, m), 5.58 (1H, d, J=8 Hz), 5.76 (1H, ddd, J=8, 7.5, 7.5 Hz), 6.26 (1H, d, J=15.7 Hz), 7.19-7.40 (4H, m), 7.66 (1H, d, J=15.7 Hz), 7.73 (1H, d, J=1.8 Hz), 8.22 (1H, d, J=1.8 Hz); MS (ES+) m/z 315.

The following compound was obtained in a similar manner to that of Preparation 414.

Preparation 839

(2E)-3-[5-chloro-6-(2,3-dihydro-1H-inden-1-ylamino)-3-pyridinyl]-N-(tetrahydro-2H-pyran-2-yloxy)acrylamide $^1$H-NMR (300 MHz, DMSO-d6) δ 1.44-1.76 (1H, m), 2.08 (1H, m), 2.76-3.15 (3H, m), 3.53 (1H, m), 3.95 (1H, m), 4.90 (1H, m), 5.78 (1H, ddd, J=8, 7.5, 7.5 Hz), 6.35 (1H, d, J=16 Hz), 7.06 (1H, d, J=8.5 Hz), 7.13-7.32 (5H, m), 7.40 (1H, d, J=16 Hz), 7.90 (1H, s), 8.26 (1H, s), 11.11 (1H, br-s); MS (ES+) m/z 414.

The following compound was obtained in a similar manner to that of Preparation 390.

Preparation 840

(2E)-3-(4-{[(3R)-1-benzyl-3-pyrrolidinyl]amino}-3-fluorophenyl)acrylic acid

MASS(API-ES); 341 (M+H)+.

$^1$H-NMR (200 MHz), (DMSO-d6, δ): 1.55-1.86 (1H, m), 2.07-2.73 (4H, m), 2.77-2.93 (1H, m), 3.57, 3.64 (2H, ABq, J=13 Hz), 3.90-4.10 (1H, m), 5.99 (1H, d, J=5.2 Hz), 6.26 (1H, d, J=16 Hz), 6.67 (1H, t, J=8.8 Hz), 7.10-7.37 (7H, m), 7.43 (1H, d, J=16 Hz).

The following compound was obtained in a similar manner to that of Preparation 397.

Preparation 841

(2E)-3-(4-{[(3R)-1-benzyl-3-pyrrolidinyl]amino}-3-fluorophenyl)-N-(tetrahydro-2H-pyran-2-yloxy)acrylamide

MASS(API-ES); 440 (M+H)+, $^1$H-NMR (200 MHz), (DMSO-d6, δ): 1.39-1.89 (7H, m), 2.07-2.33 (1H, m), 2.36-2.70 (3H, m), 2.75-2.93 (1H, m), 3.44-3.70 (3H, m), 3.83-4.12 (2H, m), 4.88 (1H, s), 5.90 (1H, d, J=5.3 Hz), 6.23 (1H, d, J=16 Hz), 6.69 (1H, t, J=8.9 Hz), 7.11-7.44 (8H, m).

The following compound was obtained in a similar manner to that of Preparation 198.

Preparation 842 ethyl (2E)-3-(5-chloro-6-{[1-(3-fluorobenzyl)-4-piperidinyl]amino}-3-pyridinyl}acrylate $^1$H NMR (DMSO-d6, δ): 1.23(3H, t, J=7.1 Hz), 1.58-1.83 (4H, m), 2.00-2.11(2H, m), 2.78-2.84(2H, m), 3.50(2H, s), 3.96-4.05(1H, m), 4.15(2H, q, J=7.1 Hz), 6.47(1H, d, J=15.9 Hz), 6.63(1H, d, J=8.0 Hz), 7.02-7.16(3H, m), 7.32-7.42(1H, m), 7.50(1H, d, J=15.9 Hz), 8.10(1H, d, J=1.9 Hz), 8.27(1H, d, J=1.9 Hz), Mass (APCI): 418(M+H)+.

The following compounds were obtained in a similar manner to that of Preparation 62.

Preparation 843

(2E)-3-(5-chloro-6-{[1-(3-chlorobenzyl)-4-piperidinyl]amino}-3-pyridinyl)-N-(tetrahydro-2H-pyran-2-yloxy)acrylamide $^1$H NMR (DMSO-d6, δ): 1.45-1.90(10H, m), 1.99-2.11(2H, m), 2.78-2.83(2H, m), 3.40-3.60(1H, m), 3.55(2H, s), 3.90-4.10(2H, m), 4.89(1H, brs), 6.30(1H, d, J=15.9 Hz), 6.52(1H, d, J=7.9 Hz), 7.25-7.41(5H, m), 7.84(1H, s), 8.20(1H, s), 11.07(1H, brs), Mass (APCI): 505(M+H)+.

Preparation 844

(2E)-3-(5-chloro-6-{[1-(2-fluorobenzyl)-4-piperidinyl]amino}-3-pyridinyl)-N-(tetrahydro-2H-pyran-2-yloxy)acrylamide $^1$H NMR (DMSO-d6, δ): 1.53-1.69(8H, m), 1.79-1.81(2H, m), 2.05-2.12(2H, m), 2.81-2.83(2H, m), 3.50-3.60(1H, m), 3.52(2H, s), 3.92-3.98(2H, m), 4.88(1H, s), 6.30(1H, d, J=15.7 Hz), 6.53(1H, d, J=7.9 Hz), 7.14-7.20(2H, m), 7.31-7.43(3H, m), 7.83(1H, s), 8.17(1H, s), 11.07(1H, s), Mass (APCI): 489(M+H)+.

The following compound was obtained in a similar manner to that of Preparation 198.

Preparation 845 ethyl (2E)-3-(5-chloro-6-{(1-(3-methyl-2-buten-1-yl)-4-piperidinyl]amino}-3-pyridinyl)acrylate $^1$H NMR (DMSO-d6, δ): 1.25 (3H, t, J=7.4 Hz), 1.61-1.81 (4H, m), 1.61 (3H, s), 1.70 (3H, s), 1.91-2.01 (2H, m), 2.81-2.89 (4H, m), 3.87-4.02 (1H, m), 4.16 (2H, q, J=7.4 Hz), 5.15-5.22 (1H, m), 6.47 (1H, d, J=15.9 Hz), 6.62 (1H, d, J=7.9 Hz), 7.50 (1H, d, J=15.9 Hz), 8.10 (1H, d, J=1.9 Hz), 8.27 (1H, d, J=1.9 Hz), Mass (ESI): 378(M+H)+.

The following compound was obtained in a similar manner to that of Preparation 414.

Preparation 846

(2E)-3-(5-chloro-6-{[2-(1-pyrrolidinylmethyl)phenyl]amino}-3-pyridinyl)-N-(tetrahydro-2H-pyran-2-yloxy)acrylamide $^1$H-NMR (300 MHz, CDCl$_3$) δ 1.50-1.95 (10H, m), 2.50-2.62 (4H, m), 3.67 (1H, m), 3.71 (2H, s), 3.97 (1H, m), 5.00 (1H, m), 6.30 (1H, br), 6.97 (1H, ddd, J=7.5, 7.5, 1 Hz), 7.15 (1H, dd, J=7.5, 1 Hz), 7.31 (1H, dd, J=7.5, 7.5 Hz), 7.64 (1H, d, J=15.5 Hz), 7.74 (1H, d, J=2 Hz), 8.24 (1H, d, J=2 Hz), 8.34 (1H, d, J=7.5 Hz), 8.36 (1H, br), 10.95 (1H, s);

MS ( ) m/z not detected.

The following compound was obtained in a similar manner to that of Preparation 62.

Preparation 847

(2E)-3-(5-chloro-6-{[1-(3-pyridinylmethyl)-4-piperidinyl]amino}-3-pyridinyl)-N-(tetrahydro-2H-pyran-2-yloxy)acrylamide $^1$H NMR (DMSO-d6, δ): 1.53-1.84(10H, m), 1.99-2.11(2H, m), 2.78-2.84(2H, m), 3.45-3.55(1H, m), 3.50(2H, s), 3.85-

4.10(2H, m), 4.88(1H, brs), 6.30(1H, d, J=15.9 Hz), 6.52(1H, d, J=7.9 Hz), 7.32-7.39(2H, m), 7.68-7.72(1H, m), 7.84(1H, s), 8.20(1H, s), 8.45-8.50(2H, m), 11.07(1H, brs), Mass (APCI): 472(M+H)+.

The following compound was obtained in a similar manner to that of Preparation 198.

Preparation 848 ethyl (2E)-3-(5-chloro-6-{[1-(2-fluorobenzyl)-4-piperidinyl]amino}-3-pyridinyl}acrylate $^1$H NMR (DMSO-d6, δ): 1.24(3H, t, J=7.1 Hz), 1.61-1.78 (4H, m), 2.03-2.13(2H, m), 2.80-2.86(2H, m), 3.53(2H, s), 3.93-4.05(1H, m), 4.15(2H, q, J=7.1 Hz), 6.47(1H, d, J=15.9 Hz), 6.62(1H, d, J=8.0 Hz), 7.15-7.44(4H, m), 7.50(1H, d, J=15.9 Hz), 8.09(1H, d, J=1.9 Hz), 8.27(1H, d, J=1.9 Hz), Mass (APCI) 418(M+H)+.

The following compound was obtained in a similar manner to that of Preparation 62.

Preparation 849

(2E)-3-(5-chloro-6-{[1-(4-pyridinylmethyl)-4-piperidinyl]amino}-3-pyridinyl)-N-(tetrahydro-2H-pyran-2-yloxy)acrylamide $^1$H NMR (DMSO-d6, δ): 1.53-1.85(10H, m), 2.03-2.14(2H, m), 2.77-2.83(2H, m), 3.50-3.54(1H, m), 3.51(2H, s), 3.90-4.10(2H, m), 4.88(1H, brs), 6.31(1H, d, J=15.3 Hz), 6.53(1H, d, J=7.9 Hz), 7.31(2H, d, J=5.9 Hz), 7.35(1H, d, J=15.9 Hz), 7.84(1H, s), 8.20(1H, s), 8.51(2H, d, J=5.9 Hz), 11.07(1H, brs), Mass (APCI): 472(M+H)+.

The following compound was obtained in a similar manner to that of Preparation 198.

Preparation 850 ethyl (2E)-3-(5-chloro-6-{[1-(3-pyridinylmethyl)-4-piperidinyl]amino}-3-pyridinyl)acrylate $^1$H NMR (DMSO-d6, δ): 1.24(3H, t, J=7.1 Hz), 1.55-1.83 (4H, m), 2.01-2.11(2H, m), 2.77-2.84(2H, m), 3.50(2H, s), 3.90-4.05(1H, m), 4.16(2H, q, J=7.1 Hz), 6.47(1H, d, J=15.9 Hz), 6.63(1H, d, J=7.9 Hz), 7.33-7.39(1H, m), 7.50(1H, d, J=15.9 Hz), 7.68-7.73(1H, m), 8.09(1H, d, J=1.9 Hz), 8.27 (1H, d, J=1.9 Hz), 8.45-8.50(2H, m), Mass (APCI): 401(M+H)+.

The following compound was obtained in a similar manner to that of Preparation 683.

Preparation 851

(2E)-3-(5-chloro-6-{[2-(1-pyrrolidinylmethyl)phenyl]amino}-3-pyridinyl)acrylic acid $^1$H-NMR (300 MHz, DMSO-d6) δ 1.72-1.86 (4H, m), 2.44-2.58 (4H, m), 3.73 (2H, s), 6.52 (1H, d, J=16 Hz), 6.98 (1H, dd, J=7.5, 7.5 Hz), 7.23 (1H, d, J=7.5 Hz), 7.29 (1H, dd, J=7.5, 7.5 Hz), 7.52 (1H, d, J=7.5 Hz), 8.28 (1H, d, J=2 Hz), 8.33 (1H, d, J=7.5 Hz), 8.39 (1H, d, J=2 Hz), 10.97 (1H, s); MS (ES+) m/z 358.

The following compound was obtained in a similar manner to that of Preparation 361.

Preparation 852

(5-chloro-6-{[2-(1-pyrrolidinylmethyl)phenyl]amino}-3-pyridinyl)methanol $^1$H-NMR (300 MHz, CDCl$_3$) 1.77-1.88 (4H, m), 2.50-2.60 (4H, m), 3.70 (2H, s), 4.59 (2H, s), 6.92 (1H, ddd, J=7.5, 7.5, 1.5 Hz), 7.14 (1H, dd, J=7.5, 1.5 Hz), 7.30 (1H, m), 7.64 (1H, d, J=2 Hz), 8.07 (1H, d, J=2' Hz), 8.32 (1H, d, J=7.5 Hz), 10.56 (1H, s); MS (ES+) m/z 318.

The following compound was obtained in a similar manner to that of Preparation 382.

Preparation 853

5-chloro-6-{[2-(1-pyrrolidinylmethyl)phenyl]amino}nicotinaldehyde $^1$H-NMR (300 MHz, CDCl$_3$) δ 1.76"1.91 (4H, m), 2.49-2.62 (4H, m), 3.74 (2H, s), 7.04 (1H, ddd, J=7.5, 7.5, 1.5 Hz), 7.18 (1H, d, J=7.5 Hz), 7.35 (1H, ddd, J=7.5, 7.5, 1.5 Hz), 8.03 (1H, d, J=2 Hz), 8.38 (1H, d, J=7.5 Hz), 8.52 (1H, d, J=2 Hz), 9.82 (1H, s), 11.39 (1H, br-s); MS (ES+) m/z 316.

The following compound was obtained in a similar manner to that of Preparation 714.

Preparation 854 ethyl (2E)-3-(4-{[(3R)-1-benzyl-3-pyrrolidinyl]amino}-3-fluorophenyl)acrylate

MASS(API-ES); 369 (M+H)+

$^1$H-NMR (200 MHz), (DMSO-d6, δ): 1.23 (3H, t, J=7.1 Hz), 1.63-1.87 (1H, m), 2.08-2.33 (1H, m), 2.37-2.70 (3H, m), 2.75-2.90 (1H, m), 3.55, 3.62 (2H, ABq, J=13 Hz), 3.88-4.11 (1H, m), 4.15 (2H, q, J=7.1 Hz), 6.02 (1H, d, J=5.1 Hz), 6.34 (1H, d, J=16 Hz), 6.67 (1H, t, J=8.8 Hz), 7.16-7.37 (6H, m), 7.41-7.59 (2H, m).

The following compound was obtained in a similar manner to that of Preparation 380.

Preparation 855

(4-{[(3R)-1-benzyl-3-pyrrolidinyl]amino}-3-fluorophenyl)methanol

MASS(API-ES); 301 (M+H)+, $^1$H-NMR (200 MHz), (DMSO-d6, δ): 1.52-1.86 (1H, m), 2.05-2.31 (1H, m), 2.32-2.69 (3H, m), 2.71-2.88 (1H, m), 3.46-3.68 (2H, m), 3.81-4.05 (1H, m), 4.32 (2H, d, J=5.6 Hz), 4.98 (1H, t, J=5.6 Hz), 5.15 (1H, d, J=5.7 Hz), 6.62 (1H, t, J=8.7 Hz), 6.84-7.00 (2H, m), 7.15-7.40 (5H, m).

The following compounds were obtained in a similar manner to that of Preparation 379.

Preparation 856 methyl 4-{[(3R)-1-benzyl-3-pyrrolidinyl]amino}-3-fluorobenzoate

MASS(API-ES); 329 (M+H)+

$^1$H-NMR (200 MHz), (DMSO-d6, δ): 1.64-1.94 (1H, m), 2.06-2.35 (1H, m), 2.38-2.95 (4H, m), 3.55, 3.63 (2H, ABq, J=13 Hz), 3.76 (3H, s), 3.92-4.14 (1H, m), 6.30 (1H, d, J=6.8

Hz), 6.74 (1H, t, J=8.7 Hz) 7.16-7.38 (5H, m), 7.49 (1H, dd, J=1.9 Hz, J=13 Hz), 7.60 (1H, dd, J=1.9 Hz, J=8.7 Hz).

The following compounds were obtained in a similar manner to that of Preparation 703.

Preparation 857 tert-butyl (3R)-3-({4 [(1E)-3-ethoxy-3-oxo-1-propen-1-yl phenyl]amino}-1-pyrrolidinecarboxylate $^1$H-NMR (300 MHz; CDCl$_3$) δ 1.33 (3H, t, J=7 Hz), 1.47 (9H, s), 1.92 (1H, m), 2.20 (1H, m), 3.26 (1H, m), 3.38-3.86 (2H, m), 3.71 (1H, m), 4.00-4.12 (2H, m), 4.24 (2H, q, J=7 Hz), 6.23 (1H, d J=16 Hz), 6.57 (2H, d, J=8.5 Hz), 7.38 (2H, d, J=8.5 Hz), 7.60 (1H, d, J=16 Hz).

Preparation 858 ethyl (2E)-3-{4-[(6-methyl-2-pyridinyl)amino] phenyl}acrylate $^1$H-NMR (300 MHz, CDCl$_3$) δ 1.34 (3H, t, J=7 Hz), 2.47 (3H, s), 4.26 (2H, q, J=7 Hz), 6.34 (1H, d, J=15.7 Hz), 6.64 (1H, s), 6.68 (1H, d, J=7.5 Hz), 6.76 (1H, d, J=7.5 Hz), 7.37 (2H, d, J=9 Hz), 7.45 (1H, dd, J=7.5, 7.5 Hz), 7.48 (2H, d, J=9-Hz), 7.64 (1H, d, J=15.7 Hz); MS (ES+) m/z 283.

Preparation 859

To a stirred solution of ethyl (2E)-3-(2-{[(3R)-1-(cyclohexylmethyl)-3-pyrrolidinyl]amino}-5-pyrimidinyl)acrylate 25 (384 mg) in acetonitrile (5 mL) was added di-tert-butyl dicarbonate (468 mg) and 4-dimethylaminopyridine (26 mg), and the mixture was stirred at 80° C. for 18 hours. Additional di-tert-butyl dicarbonate (1.0 g) and 4-dimethylaminopyridine (50 mg) was added and the mixture was stirred at 80° C. for 24 hours. The solvent was evaporated in vacuo and the residue was purified by silica gel column chromatography (chloroform/methanol=90/10 v/v) to give ethyl (2E)-3-(2-{(tert-butoxycarbonyl)[(3R)-1-(cyclohexylmethyl)-3-pyrrolidinyl]amino}-5-pyrimidinyl)acrylate (330 mg) as a tan solid.

$^1$H-NMR (300 MHz, CDCl$_3$) δ 0.66-0.86 (2H, m), 1.04-1.72 (9H, m), 1.35 (3×3H, t, J=7 Hz), 1.46 (9H, s), 2.06-2.30 (4H, m), 2.54 (2H, t, J=7 Hz), 2.70 (1H, dd, J=9, 7 Hz), 2.84 (1H, dd, J=9, 8 Hz), 4.29 (2H, q, J=7 Hz), 4.96 (1H, m), 6.54 (1H, d, J=16 Hz), 7.59 (1H, d, J=16 Hz), 8.80 (2×1H, s); MS (ES+) M/z 459.

Preparation 860

To a solution of ethyl (2E)-3-[5-chloro-6-(4-piperidinylamino)-3-pyridinyl]acrylate dihydrochloride (500 mg) in DMF (5 ml) was added 1-chloro-3-(chloromethyl)benzene (0.173 ml) and N,N-diisopropylethylamine (0.91 ml), the mixture was stirred at 70° C. for 7 hour. The mixed solution was poured into a mixture of water (30 ml) and AcOEt (30 ml). The organic layer was separated, washed with water twice and brine, dried over sodium sulfate and concentrated in vacuo. The residue was purified by silica gel column chromatography eluted with 5% MeOH in dichloromethane to give ethyl (2E)-3-(5-chloro-6-{[1-(3-chlorobenzyl)-4-piperidinyl]amino}-3-pyridinyl)acrylate (261 mg, 46%).

$^1$H NMR (DMSO-d6, δ): 1.23(3H, t, J=7.1 Hz), 1.62-1.83 (2H, m), 1.99-2.11(2H, m), 2.78-2.83(2H, m), 3.48(2H, s), 3.90-4.10(1H, m), 4.15(2H, q, J=7.1 Hz), 6.47(1H, d, J=15.9 Hz), 6.62(1H, d, J=7.9 Hz), 7.25-7.40(4H, m), 7.50(1H, d, J=15.9 Hz), 8.09(1H, d, J=1.9 Hz), 8.27(1H, d, J=1.9 Hz).

Mass (APCI): 434(M+H)+.

The following compound was obtained in a similar manner to that of Preparation 860.

Preparation 861 ethyl (2E)-3-(5-chloro-6-{[1-(2-chlorobenzyl)-4-piperidinyl]amino}-3-pyridinyl}acrylate $^1$H NMR (DMSO-d6, δ): 1.24(3H, t, J=7.1 Hz), 1.59-1.84 (4H, m), 2.09-2.20(2H, m), 2.52-2.88(2H, m), 3.56(2H, s), 3.90-4.15(1H, m), 4.15(2H, q, J=7.1 Hz), 6.47(1H, d, J=15.9 Hz), 6.65(1H, d, J=7.9 Hz), 7.24-7.55(4H, m), 7.50(1H, d, J=15.9 Hz), 8.10(1H, d, J=1.9 Hz), 8.28(1H, d, J=1.9 Hz).

Mass (APCI): 434(M+H)+.

Preparation 862

To a solution of ethyl (2E)-3-(5-chloro-6-{[1-(4-pyridinylmethyl)-4-piperidinyl]amino}-3-pyridinyl)acrylate (308 mg) in THF (3 ml) and MeOH (3 ml) was added 1N NaOHaq (2.3 ml), the mixture was stirred at 80° C. for 1 hour. The pH of the mixture was adjusted to ca.4.5 with 1N HClaq. The solution was evaporated under reduced pressure to give crude (2E)-3-(5-chloro-6-{[1-(4-pyridinylmethyl)-4-piperidinyl]amino}-3-pyridinyl)acrylic acid (469 mg, 164%)

$^1$H NMR (DMSO-d6, δ): 1.59-1.87(4H, m), 2.03-2.14(2H, m), 2.77-2.83(2H, m), 3.51(2H, s), 3.94-4.03(1H, m), 6.38 (1H, d, J=15.7 Hz), 6.48(1H, d, J=7.9 Hz), 7.31(1H, d, J=15.7 Hz), 7.32(2H, d, J=5.9 Hz), 7.98(1H, d, J=2.0 Hz), 8.19(1H, d, J=2.0 Hz), 8.51(2H, d, J=5.9 Hz),

Mass (APCI): 373(M+H)+.

The following compounds were obtained in a similar manner to that of Preparation 862.

Preparation 863

(2E)-3-(5-chloro-6-{[1-(2-pyridinylmethyl)-4-piperidinyl]amino}-3-pyridinyl)acrylic acid $^1$H NMR (DMSO-d6, δ): 1.58-1.85(4H, m), 2.07-2.18(2H, m), 2.81-2.86(2H, m), 3.59(2H, s), 3.87-4.02(1H, m), 6.34 (1H, d, J=15.7 Hz), 6.39(1H, d, J=7.3 Hz), 7.21(1H, d, J=15.7 Hz), 7.23-7.29(1H, m), 7.43(1H, d, J=7.8 Hz), 7.73-7.82(1H, m), 7.92(1H, d, J=2.0 Hz), 8.15(1H, d, J=2.0 Hz), 8.48-8.50 (1H, m), Mass (APCI): 373(M+H)+.

Preparation 864

(2E)-3-(5-chloro-6-{[1-(2-fluorobenzyl)-4-piperidinyl]amino}-3-pyridinyl)acrylic acid $^1$H NMR (DMSO-d6, δ): 1.80-2.10 (4H, m), 2.60-3.20 (4H, m), 3.16 (2H, s), 6.40 (1H, d, J=15.9 Hz), 6.79 (1H, brs), 7.23-7.71 (5H, m), 8.07 (1H, d, J=1.9 Hz), 8.25 (1H, d, J=1.9 Hz), Mass (ESI): 390(M+H)+.

Preparation 865

(2E)-3-(5-chloro-6-{[1-(3-pyridinylmethyl)-4-piperidinyl]amino}-3-pyridinyl)acrylic acid $^1$H NMR (DMSO-d6, δ): 1.55-1.86(4H, m), 2.01-2.11(2H, m), 2.78-2.83(2H, m), 3.50(2H, s), 3.88-4.02(1H, m), 6.38 (1H, d, J=15.7 Hz), 8.44(1H, d, J=7.9 Hz), 7.28(1H, d, J=15.7 Hz), 7.35-7.39(1H, m), 7.69-7.73(1H, m), 7.95(1H, d, J=2.0 Hz), 8.18(1H, d, J=2.0 Hz), 8.45-8.50(2H, m), Mass (APCI): 373(M+H)+.

Preparation 866

(2E)-3-(5-chloro-6-{[1-(3-chlorobenzyl)-4-piperidinyl]amino}-3-pyridinyl)acrylic acid $^1$H NMR (DMSO-d6, δ): 1.57-1.89(4H, m), 2.01-2.11(2H, m), 2.78-2.83(2H, m), 3.48(2H, s), 3.85-4.10(1H, m), 6.37 (1H, d, J=15.9 Hz), 6.51(1H, 6, J=7.9 Hz), 7.11-7.40(5H, m), 8.21(1H, d, J=1.9 Hz), 8.62(1H, d, J=1.9 Hz), Mass (APCI): 406(M+H)+.

Preparation 867

(2E)-3-(5-chloro-6-{[1-(3-fluorobenzyl)-4-piperidinyl]amino}-3-pyridinyl)acrylic acid $^1$H NMR (DMSO-d6, δ): 1.23-1.43 (2H, m), 1.64-1.67 (2H, m), 1.95-2.06 (2H, m), 2.73-2.79 (2H, m), 3.16 (2H, s), 3.65-3.75 (1H, m), 5.58 (1H, d, J=15.9 Hz), 6.85 (1H, d, J=15.9 Hz), 7.01-7.17 (4H, m), 7.30-7.41 (1H, m), 7.44 (1H, d, J=1.9 Hz), Mass (ESI): 390(M+H)+.

Preparation 868

(2E)-3-(5-chloro-6-{[1-(cyclohexylmethyl)-4-piperidinyl]amino}-3-pyridinyl)acrylic acid Mass (APCI): 378(M+H)+.

Preparation 869

(2E)-3-(5-chloro-6-{[1-(3-methyl-2-buten-1-yl)-4-piperidinyl]amino}-3-pyridinyl)acrylic acid $^1$H NMR (DMSO-d6, δ): 1.56-1.90 (2H, m), 1.62 (3H, s), 1.70 (3H, s), 1.96-2.06 (2H, m), 2.83-2.93 (4H, m), 3.87-4.02 (1H, m), 5.16-5.23 (1H, m), 6.37 (1H, d, J=15.9 Hz), 6.55 (1H, d, J=7.9 Hz), 7.40 (1H, d, J=15.9 Hz), 8.03 (1H, d, J=1.9 Hz), 8.22 (1H, d, J=1.9 Hz), Mass (ESI): 350(M+H)+.

Preparation 870

(2E)-3-(5-chloro-6-{[1-(2-chlorobenzyl)-4-piperidinyl]amino}-3-pyridinyl)acrylic acid $^1$H NMR (DMSO-d6, δ): 1.59-1.91(4H, m), 2.10-2.20(2H, m), 2.82-2.88(2H, m), 3.57(2H, s), 3.97-4.06(1H, m), 6.38 (1H, d, J=15.9 Hz), 6.56(1H, d, J=7.9 Hz), 7.26-7.52(5H, m), 8.03(1H, d, J=1.9 Hz), 8.23(1H, d, J=1.9 Hz), Mass (APCI): 406(M+H)+.

Preparation 871

Palladium(II) acetate (25 mg) and 2,2'-bis(diphenylphosphino)-1,1'-binaphthalene (106 mg) in dioxane (10 mL) was stirred at ambient temperature for 15 minutes. To this suspension was added ethyl 5,6-dichloronicotinate (500 mg), 2-aminoindane (363 mg), and cesium carbonate (1.1 g), and the mixture was heated at 100° C. for 8 hours. The resulting mixture was allowed to cool to ambient temperature, poured into water, and extracted with ethyl acetate. The organic phase was washed with brine, dried over anhydrous sodium sulfate and concentrated in vacuo. The residue was purified by silica gel column chromatography (hexane/ethyl acetate=10/1 v/v) to give ethyl 5-chloro-6-(2,3-dihydro-1H-inden-2-ylamino)nicotinate (420 mg) as a pale tan solid.

$^1$H-NMR (300 MHz, CDCl$_3$) δ 1.37 (3H, t, J=7 Hz), 2.86 (2H, dd, J=16, 5 Hz), 3.43 (2H, dd, J=16, 7 Hz), 4.27 (2H, q, J=7 Hz), 4.99 (1H, m), 5.59 (1H, br-d, J=3 Hz), 7.17-7.25 (4H, m), 8.02 (1H, d, J=2 Hz), 8.73 (1H, d, J=2 Hz); MS (ES+) m/z 317.

The following compounds were obtained in a similar manner to that of Preparation 871.

Preparation 872 ethyl 5-chloro-6-[(4-methylphenyl)amino]nicotinate $^1$H-NMR (300 MHz, CDCl$_3$) δ 1.38 (3H, t, J=7 Hz), 2.35 (3H, s), 4.35 (2H, q, J=7 Hz), 7.19 (2H, d, J=8.5 Hz), 7.20 (1H, s), 7.50 (2H, d, J=8.5 Hz), 8.14 (1H, d, J=2 Hz), 8.75 (1H, d, J=2 Hz); MS (ES+) m/z 291.

Preparation 873 ethyl 5-chloro-6-[(2-ethoxyphenyl)amino]nicotinate $^1$H-NMR (300 MHz, CDCl$_3$) δ 1.39 (3H, t, J=7 Hz), 1.51 (3H, t, J=7 Hz), 4.16 (2H, q, J=7 Hz), 4.36 (2H, q, J=7 Hz), 6.92 (1H, m), 6.98-7.05 (2H, m), 8.15 (1H, d, J=2 Hz), 8.27 (1H, br-s), 8.66 (1H, m), 8.82 (1H, d, J=2 Hz); MS (ES+) m/z 321.

Preparation 874 ethyl 5-chloro-6-(2,3-dihydro-1H-inden-1-ylamino)nicotinate $^1$H-NMR (300 MHz, CDCl$_3$) δ 1.38 (3H, t, J=7 Hz), 1.92 (1H, m), 2.74 (1H, m), 2.87-3.12 (2H, m), 4.35 (2H, q, J=7 Hz), 5.63 (1H, br-d, J=8 Hz), 5.80 (1H, ddd, J=8, 7.5, 7.5 Hz), 7.19-7.36 (4H, m), 8.06 (1H, d, J=2 Hz), 8.75 (1H, d, J=2 Hz); MS (ES+) m/z 317.

Preparation 875 ethyl 5-chloro-6-{[2-(1-pyrrolidinylmethyl)phenyl]amino}nicotinate $^1$H-NMR (300 MHz, CDCl$_3$) δ 1.39 (3H, t, J=7 Hz), 1.78-1.88 (4H, m), 2.51-2.62 (4H, m), 3.72 (2H, s), 4.36 (2H, q, J=7 Hz), 6.99 (1H, ddd, J=7.5, 7.5, 1.5 Hz), 7.16 (1H, dd, J=7.5, 1.5 Hz), 7.32 (1H, ddd, J=7.5, 7.5, 1.5 Hz), 8.12 (1H, d, J=2 Hz), 8.36 (1H, dd, J=7.5, 1.5 Hz), 8.76 (1H, d, J=2 Hz), 11.07 (1H, s); MS (ES+) m/z 360.

Preparation 876

A mixture of ethyl 1-(2-nitrobenzyl)pyrrolidine (1.90 g) and 10% palladium on carbon (200 mg) in methanol (40 mL) was hydrogenated at ambient temperature. After completion of the reaction, the catalyst in the reaction mixture was removed by filtration. The solvent was evaporated in vacuo. The residue was purified by silica gel column chromatography (chloroform/methanol=20/1 v/v) to give [2-(1-pyrrolidinylmethyl)phenyl]amine (1.65 g) as a pale yellow solid.

$^1$H-NMR (300 MHz, CDCl$_3$) δ 1.72-1.87 (4H, m), 2.46-2.62 (4H, m), 3.65 (2H, s), 6.61-6.72 (2H, m), 7.01 (1H, br-d, J=8 Hz), 7.09 (1H, br-dd, J=8, 8 Hz); MS (ES+) m/z 177.

Preparation 877

To a solution of 5,6-dichloronicotinic acid (7.0 g, 35 mmol) in DMF were added iodoethane (6.0 g, 38.5 mmol) and K₂CO₃ (5.8 g, 42 mmol) at ambient temperature and the mixture was stirred at 45° C. for 5 hrs. To the reaction mixture were added (3R)-1-benzyl-3-piperidinamine dihydrochloride (10.1 g, 38.5 mmol) and K₂CO₃ (16.9 g, 122 mmol) and the reaction mixture was stirred at 90° C. for 18 hrs. The reaction mixture was evaporated in vacuo and the residue was partitioned between water and EtOAc. The organic layer was separated, washed water and brine, dried over magnesium sulfate, and evaporated in vacuo. The residue was purified by silica gel column chromatography (EtOAc-hexane/1-4~1-3) to give ethyl 6-{[(3R)-1-benzyl-3-piperidinyl]amino}-5-chloronicotinate (6.75 g, 52%) as a powder.

$^1$H-NMR (300 MHz, CDCl₃) δ 1.36 (3H, t, J=7.1 Hz), 1.51-1.69 (2H, m), 1.69-1.88 (2H, m), 2.18-2.33 (1H, m), 2.41-2.54 (1H, m), 2.54-2.67 (1H, m), 2.67-2.79 (1H, m), 3.45 (1H, d, J=13 Hz), 3.61 (1H, d, J=13 Hz), 4.32 (2H, q, J=7.1 Hz), 6.24 (1H, br peak), 7.21-7.41 (5H, m), 8.00 (1H, d, J=2 Hz), 8.65 (1H, d, J=2 Hz); MS (ES+) m/z 374.

EXAMPLE 1

A solution of 10% HCl-MeOH solution (0.75 ml) was added to a mixture of (2E)-3-{6-[(1-benzyl-3-pyrrolidinyl)amino]-3-pyridyl}-N-(tetrahydro-2H-pyran-2-yloxy)acrylamide (170 mg) in MeOH 3 ml) and stirred at 15-25% for 2 hours. The reaction mixture was evaporated in vacuo and the residue was triturated with small amount MeOH and acetone and the precipitate was collected by filtration to give (2E)-3-{6-[(1-benzyl-3-pyrrolidinyl)amino]-3-pyridyl}-N-hydroxyacrylamide dihydrochloride (107 mg)

NMR (DMSO-d6, δ): 2.04-2.40 (2H, m), 3.18-3.83 (4H, m), 4.43-4.58 (2H, m), 4.80 (1H, m), 6.42 (1H, d, J=15.80 Hz), 7.04 (1H, d, J=9.20 Hz), 7.25 (1H, d, J=9.20H), 7.40-7.46 (4H, m), 7.65-7.70 (2H, m), 8.01-8.10 (1H, m), 8.18 (1H, s), 11043-11.78 (1H m)

The following compounds were obtained according to a similar manner to that of Example 1.

EXAMPLE 2

(2E)-3-{6-[(1-Benzyl-3-pyrrolidinyl)(methyl)amino]-3-pyridyl}-N-hydroxyacrylamide dihydrochloride NMR (DMSO-d6, δ): 2.09-2.40 (2H, m), 3.10 (3H, s), 3.10-3.28 (2H, m), 3.46-3.63 (2H, m), 4.41-4.49 (2H, m), 5.24-5.51 (1H, m), 6.38-6.50 (1H, m), 7.03-7.19 (1H, m), 7.38-7.47 (4H, m), 7.64-7.69 (2H, m), 7.98-8.07 (1H, m), 8.26 (1H, s)

EXAMPLE 3

(2E)-3-(6-{[(3R)-1-Benzyl-3-pyrrolidinyl]amino}-3-pyridyl)-N-hydroxyacrylamide dihydrochloride NMR (DMSO-d6, δ): 1.99-2.50 (2H, m), 3.25-3.83 (4H, m), 4.43, 4.55 (2H, ABq, J=5.38 Hz), 4.77 (1H, m), 6.36-6.45 (1H, m), 6.99 (0.5H, d, J=9.00 Hz), 7.19 (0.5H d, J=9.00 Hz), 7.74-7.46 (4H, m), 7.63-7.66 (2H, m), 7.98-8.06 (1H, m), 8.18 (1H, s)

EXAMPLE 4

(2E)-3-(6-{[(3S)-1-Benzyl-3-pyrrolidinyl]amino}-3-pyridyl)-N-hydroxyacrylamide dihydrochloride NMR (DMSO-d6, δ): 2.06-2.62 (2H, m), 3.26-3.83 (4H, m), 4.44, 4.56 (2H, ABq, J=5.48 Hz), 4.79 (1H, m), 6.42 (1H, d, J=15.72 Hz), 7.02 (0.5H, d, J=9.16 Hz), 7.22 (0.5H, d, J=9.16 Hz), 7.40-7.46 (4H, m), 7.64-7.70 (2H, m), 8.00-8.08 (1H, m), 8.18 (1H, s)

EXAMPLE 5

(2E)-3-(6-{[(3R)-1-Benzyl-3-pyrrolidinyl]amino}-5-chloro-3-pyridyl)-N-hydroxyacrylamide dihydrochloride NMR (DMSO-d6, δ): 1.91-2.16 (1H, m), 2.30-2.40 (1H, m), 3.08-3.68 (4H, m), 4.41 (2H, d, J=5.56 Hz), 4.70-4.89 (1H, m), 6.38 (1H, d, J=15.82 Hz), 7.34 (1H, d, J=15.82 Hz), 7.30-7.46 (3H, m), 7.62-7.66 (2H, m), 7.91 (1H, s), 8.21 (1H, s)

EXAMPLE 6

(2E)-3-(6-{[(3S)-1-Benzyl-3-pyrrolidinyl]amino}-5-chloro-3-pyridyl)-N-hydroxyacrylamide dihydrochloride NMR (DMSO-d6, δ): 1.95-2.16 (2H, m), 3.06-3.70 (4H, m), 4.41 (2H, d, J=5.50 Hz), 4.70-4.89 (1H, m), 6.39 (1H, d, J=15.82 Hz), 7.35 (1H, d, J=15.82 Hz), 7.39-7.51 (4H, m), 7.62-7.66 (2H, m), 7.91 (1H, s), 8.21 (1H, s)

EXAMPLE 7

(2E)-N-Hydroxy-3-(6-{[(3R)-1-(4-methoxybenzyl)-3-pyrrolidinyl]amino}-3-pyridyl)acrylamide dihydrochloride NMR (DMSO-d6, δ): 1.95-2.80 (2H, m), 3.10-3.90 (4H, m), 3.77 (3H, s), 4.30-4.49 (2H, m), 4.50-4.90 (1H, m), 6.40 (1H, dd, J=3.0 Hz, J=16 Hz), 6.90-7.21 (3H, m), 7.35-7.62 (3H, m), 7.95-8.08 (1H, m), 8.18 (1H, s), 8.70-10.40 (1H, m), 11.10-11.60 (1H, m)

MASS(API-ES); 369 (M+H)+Free

EXAMPLE 8

(2E)-3-(6-{[(3R)-1-(4-Fluorobenzyl)-3-pyrrolidinyl]amino}-3-pyridyl)-N-hydroxyacrylamide dihydrochloride NMR (DMSO-d6, δ): 1.95-2.90 (2H, m), 3.10-3.90 (4H, m), 4.40-4.90 (3H, m), 6.40 (1H, dd, J=2.5 Hz, J=16 Hz), 6.90-7.35 (3H, m), 7.42 (1H, dd, J=2.5 Hz, J=16 Hz), 7.60-7.80 (2H, m), 7.90-8.10 (1H, m), 8.18 (1H, s), 8.70-10.40 (1H, m), 11.30-11.80 (1H, m)

MASS(API-ES); 357 (M+H)+Free

EXAMPLE 9

(2E)-3-(6-{[(3R)-1-(4-Chlorobenzyl)-3-pyrrolidinyl]amino}-3-pyridyl)-N-hydroxyacrylamide dihydrochloride NMR (DMSO-d6, δ): 1.90-2.80 (2H, m), 3.10-3.90 (4H, m), 4.35-4.85 (3H, m), 6.40 (1H, dd, J=2.0 Hz, J=16 Hz), 6.95-7.25 (1H, m), 7.44 (1H, dd, J=2.0 Hz, J=16 Hz), 7.48-7.60 (2H, m), 7.64-7.80 (2H, m), 7.95-8.10 (1H, m), 8.18 (1H, s), 8.80-10.40 (1H, m), 11.40-11.80 (1H, m)

MASS(API-ES); 373 (M+H)+, 375 (M+H+2)+Free

EXAMPLE 10

(2E)-N-Hydroxy-3-(6-{[(3R)-1-(4-methylbenzyl)-3-pyrrolidinyl]amino}-3-pyridyl)acrylamide dihydrochloride MASS(API-ES); 353 (M+H)+Free NMR (DMSO-d6, δ): 1.95-2.75 (2H, m), 2.32 (3H, s), 3.10-3.90 (4H, m), 4.25-4.90 (3H, m), 6.40 (1H, dd, J=2.8 Hz, J=16 Hz), 6.95-7.30 (3H, m), 7.43 (1H, dd, J=2.5 Hz, J=16 Hz), 7.47-7.60 (2H, m), 7.95-8.10 (1H, m), 8.18 (1H, s), 8.80-10.30 (1H, m), 11.20-11.70 (1H, m)

EXAMPLE 11

(2E)-3-(6-{[(3R)-1-(Cyclopropylmethyl)-3-pyrrolidinyl]amino}-3-pyridyl)-N-hydroxyacrylamide dihydrochloride NMR (DMSO-d6, δ): 0.30-0.70 (4H, m), 1.00-1.30(1H, m), 1.95-2.80 (2H, m), 3.00-4.10 (6H, m), 4.55-4.90 (1H, m), 6.44 (1H, d, J=16 Hz), 7.05-7.30 (1H, m), 7.45 (1H, d, J=16 Hz), 8.07 (1H, d, J=9.3 Hz), 8.20 (1H, s), 9.20-10.60 (1H, m), 11.00-11.40 (1H, m)

MASS(API-ES); 303 (M+H)+Free

EXAMPLE 12

(2E)-3-(6-{[(3R)-1-Benzoyl-3-pyrrolidinyl]amino}-5-chloro-3-pyridyl)-N-hydroxyacrylamide hydrochloride NMR (DMSO-d6, δ): 1.90-2.40 (2H, m), 3.20-4.00 (4H, m), 4.40-4.80 (1H, m), 6.25-6.42 (1H, m), 7.04 (1H, br), 7.25-7.60 (6H, m), 7.85-8.00 (1H, m), 8.10-8.30 (1H, m)

MASS(API-ES); 387 (M+H)+Free, 389

EXAMPLE 13

(2E)-3-(5-Chloro-6-{[(3R)-1-(cyclopropylcarbonyl)-3-pyrrolidinyl]amino}-3-pyridyl)-N-hydroxyacrylamide hydrochloride NMR (DMSO-d6, δ): 0.60-0.80 (4H, m), 1.60-1.85 (1H, m), 1.90-2.40 (2H, m), 3.20-4.10 (4H, m), 4.45-5.00 (1H, m), 6.35 (1H, d, J=16 Hz), 7.01 (1H, br), 7.35 (1H, d, J=16 Hz), 7.91 (1H, s), 8.23 (1H, s)

MASS(API-ES); 351 (M+H)+Free

EXAMPLE 14

(2E)-3-{6-[(1-Benzoyl-4-piperidyl)amino]-3-pyridyl}-N-hydroxyacrylamide hydrochloride NMR (DMSO-d6, δ): 1.30-1.60(2H, m), 1.85-2.10(2H, m), 2.90-4.50(5H, m), 6.40(1H, d, J=16.0 Hz), 7.13(1H, d, J=9.0 Hz), 7.38-7.49(6H, m), 7.05(1H, d, J=9.0 Hz), 8.16(1H, s), 9.26(1H, brs)

EXAMPLE 15

(2E)-3-(6-{[1-(4-Fluorobenzoyl)-4-piperidyl]amino}-3-pyridyl)-N-hydroxyacrylamide hydrochloride NMR (DMSO-d6, δ): 1.45-1.60(2H, m), 1.95-2.10(2H, m), 3.00-4.60(5H, m), 6.39(1H, d, J=16.0 Hz), 7.13(1H, d, J=8.9 Hz), 7.25-7.53(5H, m), 8.06(1H, d, J=8.9 Hz), 8.17(1H, s)

Mass (ESI): 385(M+H)+

EXAMPLE 16

(2E)-N-Hydroxy-3-(6-{[1-(4-methylbenzoyl)-4-piperidyl]amino}-3-pyridyl)acrylamide hydrochloride NMR (DMSO-d6, δ): 1.40-1.60(2H, m), 1.85-2.10(2H, m), 2.34(3H, s), 3.00-4.50(5H, m), 6.39(1H, d, J=16.0 Hz), 7.10 (1H, d, J=8.9 Hz), 7.25(1H, d, J=8.8 Hz), 7.31(1H, d, J=8.8 Hz), 7.44(1H, d, J=16.0 Hz), 8.05(1H, d, J=8.9 Hz), 8.16(1H, s)

Mass (ESI): 381(M+H)+

EXAMPLE 17

(2E)-N-Hydroxy-3-(6-{[1-(4-methoxybenzoyl)-4-piperidyl]amino}-3-pyridyl)acrylamide hydrochloride NMR (DMSO-d6, δ): 1.30-1.60(2H, m), 1.95-2.10(2H, m), 3.15-3.80(4H, m), 3.79(3H, s), 3.90-4.15(2H, m), 6.38(1H, d, J=16.0 Hz), 6.99(2H, d, J=8.8 Hz), 7.10(1H, d, J=8.9 Hz), 7.38(2H, d, J=8.8 Hz), 7.44(1H, d, J=16.0 Hz), 8.04(1H, d, J=8.9 Hz), 8.17(1H, s)

Mass (ESI): 397(M+H)+

EXAMPLE 18

(2E)-N-Hydroxy-3-[6-({1-[4-(1H-pyrrol-1-yl)benzoyl]-4-piperidyl}amino-3-pyridyl]acrylamide hydrochloride NMR (DMSO-d6, δ): 1.35-1.60(2H, m), 1.85-2.15(2H, m), 3.00-4.50(5H, m), 6.28-6.30(2H, m), 6.40(1H, d, J=16.0 Hz), 7.15(1H, d, J=9.5 Hz), 7.42-7.53(5H, m), 7.67(2H, d, J=8.6 Hz), 8.07(1H, d, J=9.5 Hz), 8.17(1H, s), 9.30(1H, brs)

Mass (ESI): 432(M+H)+

EXAMPLE 19

N-(4-Chlorophenyl)-4-({5-[(1E)-3-(hydroxyamino)-3-oxo-1-propen-1-yl]-2-pyridyl}amino)-1-piperidinecarboxamide hydrochloride NMR (DMSO-d6, δ): 1.40-1.45(2H, m), 1.90-2.10(2H, m), 2.94-3.01(2H, m), 3.99(1H, brs), 4.10-4.15(2H, m), 6.37-6.40(1H, m), 7.00-7.14(1H, m), 7.27(2H, d, J=8.8 Hz), 7.43-7.53(3H, m), 8.03(1H, m), 8.18(1H, s), 8.76(1H, s), 10.81 (1H, brs)

Mass (ESI): 416(M+H)+

EXAMPLE 20

4-({5-[(1E)-3-(Hydroxyamino)-3-oxo-1-propen-1-yl]-2-pyridyl}amino)-N-(4-methylphenyl)-1-piperidinecarboxamide hydrochloride NMR (DMSO-d6, δ): 1.30-1.60(2H, m), 1.90-2.05(2H, m), 2.23(3H, s), 2.85-3.10(2H, m), 4.00-4.25(3H, m), 6.40(1H, d, J=15.4 Hz), 7.04(2H, d, J=8.8 Hz), 7.11(1H, brs), 7.34(2H, d, J=8.8 Hz), 7.45(1H, d, J=15.4 Hz), 8.04(1H, d, J=9.6 Hz), 8.17(1H, s), 8.51(1H, s)

Mass (ESI): 396(M+H)+

EXAMPLE 21

4-({5-[(1E)-3-(Hydroxyamino)-3-oxo-1-propen-1-yl]-2-pyridyl}amino)-N-(4-methoxyphenyl)-1-piperidinecarboxamide hydrochloride NMR (DMSO-d6, δ): 1.30-1.60(2H, m), 1.90-2.05(2H, m), 2.85-3.10(2H, m), 3.70(3H, s), 4.00-4.25(3H, m), 6.41(1H, d, J=15.4 Hz), 6.82(2H, d, J=8.8 Hz), 7.15(1H, d, J=9.4 Hz), 7.34(2H, d, J=8.8 Hz), 7.46(1H, d, J=15.4 Hz), 8.06(1H, d, J=9.4 Hz), 8.17(1H, s), 8.46(1H, s)

Mass (ESI): 412(M+H)+

EXAMPLE 22

(2E)-3-{6-[(1-Benzoyl-4-piperidyl)amino]-5-chloro-3-pyridyl}-N-hydroxyacrylamide hydrochloride NMR (DMSO-d6, δ): 1.50-2.10(6H, m), 2.80-3.00(2H, m), 6.33(1H, d, J=16.0 Hz), 7.25-7.60(6H, m), 7.92(1H, s), 8.20 (1H, s)

EXAMPLE 23

(2E)-3-(5-Chloro-6-{[1-(4-chlorobenzoyl)-4-piperidyl]amino}-3-pyridyl)-N-hydroxyacrylamide hydrochloride NMR (DMSO-d6, δ): 1.50-2.10(6H, m), 2.80-3.10(2H, m), 6.31(1H, d, J=16.0 Hz), 6.77(1H, brs), 7.34(1H, d, J=16.0 Hz), 7.42(2H, d, J=8.8 Hz), 7.54(2H, d, J=8.8 Hz), 7.91(1H, s), 8.19(1H, s)

EXAMPLE 24

(2E)-3-(5-Chloro-6-{[1-(3-chlorobenzoyl)-4-piperidyl]amino}-3-pyridyl)-N-hydroxyacrylamide hydrochloride $^1$H NMR (DMSO-d6, δ): 1.45-2.10(4H, m), 2.70-3.30(2H, m), 3.40-3.70(1H, m), 6.35(1H, d, J=16.0 Hz), 6.89(1H, brs), 7.31-7.57(5H, m), 7.95(1H, s), 8.20(1H, s)

EXAMPLE 25

(2E)-3-(5-Chloro-6-{[1-(2-chlorobenzoyl)-4-piperidyl]amino}-3-pyridyl]-N-hydroxyacrylamide hydrochloride NMR (DMSO-d6, δ): 1.45-2.05(4H, m), 2.80-3.40(3H, m), 4.10-4.30(1H, brs), 4.30-4.70(1H, m), 6.35(1H, d, J=16.0 Hz), 6.80-7.20(1H, m), 7.31-7.57(5H, m), 7.96(1H, s), 8.19 (1H, s)

EXAMPLE 26

(2E)-3-(5-Chloro-6-{[1-(4-phenoxybenzoyl)-4-piperidyl]amino}-3-pyridyl)-N-hydroxyacrylamide hydrochloride NMR (DMSO-d6, δ): 1.45-2.05(4H, m), 2.70-3.30(2H, m), 3.50-3.90(1H, m), 4.20-4.70(2H, m), 6.36(1H, d, J=16.0 Hz), 7.01-7.48(11H, m), 7.97(1H, s), 8.20(1H, s)

Mass (ESI): 493(M+H)+

EXAMPLE 27

4-({3-Chloro-5-[(1E)-3-(hydroxyamino)-3-oxo-1-propen-1-yl]-2-pyridyl}amino)-N-(4-chlorophenyl)-1-piperidinecarboxamide hydrochloride NMR (DMSO-d6, δ): 1.45-1.75(2H, m), 1.75-1.95(2H, m), 2.83-2.98(2H, m), 4.12-4.40(3H, m), 6.36(1H, d, J=15.8 Hz), 7.06(1H, brs), 7.28(2H, d, J=8.8 Hz), 7.3.6(1H, d, J=15.8 Hz), 7.53(2H, d, J=8.8 Hz), 7.58(1H, s), 8.21(1H, s), 8.76(1H, s)

Mass (ESII): 450(M+H)+

EXAMPLE 28

(2E)-3-(5-Chloro-6-{[1-(4-chlorobenzyl)-4-piperidyl]amino}-3-pyridyl)-N-hydroxyacrylamide dihydrochloride NMR (DMSO-d6, δ): 1.95-2.20(4H, m), 2.95-3.45(4H, m), 4.27(2H, m), 6.33(1H, brs), 7.03(1H, d, J=16.0 Hz), 7.34(1H, d, J=16.0 Hz), 7.54(1H, d, J=8.8 Hz), 7.71(1H, d, J=8.8 Hz), 7.90(1H, s), 8.18(1H, s), 11.04(1H, brs)

Mass (APCI): 406(M+H)+

EXAMPLE 29

A solution of 10% HCl-MeOH solution (0.5 ml) was added to a mixture of (2E)-3-{6-[(1-benzyl-4-piperidyl)amino]-3-pyridyl}-N-(tetrahydro-2H-pyran-2-yloxy)acrylamide (180 mg) in MeOH (5 ml) and stirred at 15-25° C. for 2 hours. The reaction mixture was evaporated in vacuo and the residue was triturated with small amount MeOH and acetone and the precipitate was collected by filtration to give (2E)-3-{6-[(1-benzyl-4-piperidyl)amino]-3-pyridyl}-N-hydroxyacrylamide dihydrochloride (120 mg)

$^1$H-NMR(DMSO-d6): δ 1.90-2.30 (4H, m), 2.85-3.45 (4H, m), 4.32 (2H, s), 6.38 and 6.46 (1H, s), 7.08 (1H, d, J=18.8 Hz), 7.47 (5H, s), 7.58-7.72 (2H, m), 8.04 (1H, d, J=18.8 Hz), 8.13 (1H, s), 9.33 (1H, br.s), 11.2 (2H, br.s).

The following compounds were obtained according to a similar manner to that of Example 29.

EXAMPLE 30

4-({5-[(1E)-3-(Hydroxyamino)-3-oxo-1-propen-1-yl]-2-pyridyl}amino)-N-phenyl-1-piperidinecarboxamide hydrochloride NMR (DMSO-d6, δ): 1.39-1.55 (2H, m), 1.96-2.02 (2H, m), 2.93-3.05 (2H, m), 4.19-4.29 (3H, m), 6.43 (1H, d, J=15.82 Hz), 6.89-6.97 (1H, m), 7.15-7.27 (3H, m), 7.42-7.50 (3H, m), 8.08 (1H, d, J=9.56 Hz), 8.28 (1H, s), 8.63 (1H, s), 9.40 (1H, m)

EXAMPLE 31

(2E)-3-(6-{[1-(4-Chlorobenzoyl)-4-piperidyl]amino}-3-pyridyl)-N-hydroxyacrylamide hydrochloride NMR (DMSO-d6, δ): 1.91-2.18 (6H, m), 2.95-3.01 (2H, m), 4.33-4.35 (1H, m), 6.41 (1H, d, J=15.86 Hz), 7.08 (1H, d, J=9.38 Hz), 7.44 (1H, d, J=15.86 Hz), 7.54 (2H, d, J=8.42 Hz), 7.71 (2H, d, J=8.42 Hz), 8.03-8.14 (2H, m), 11.37 (1H, m)

EXAMPLE 32

(2E)-3-(6-{[(3R)-1-Benzyl-3-pyrrolidinyl]amino}-3-pyridyl)-N-hydroxyacrylamide dihydrochloride (860 mg) was dissolved into water (40 ml), and the solution was adjusted to ca. pH4.0 by addition of a few drops of aq NaHCO$_3$ solution. The aqueous solution was chromatographed with HP-20 (100 ml), washing with water and eluting with 75% aqueous MeOH. The elute was concentrated to ca. 10 ml in vacuo, and the resulting precipitate was collected by filtration. (2E)-3-(6-{[(3R)-1-benzyl-3-pyrrolidinyl]amino}-3-pyridyl)-N-hydroxyacrylamide (240 mg) was obtained as colorless powder.

NMR (DMSO-d6, δ): 1.50-1.80 (1H, m), 2.10-2.90 (5H, m), 3.45-3.70 (2H, m), 4.20-4.45 (1H, m), 6.16 (1H, d, J=16 Hz), 6.51 (1H, d, J=8.8 Hz), 7.10-7.40 (7H, m), 7.57 (1H, dd, J=1.5 Hz, J=8.8 Hz), 8.10 (1H, d, J=1.5 Hz), 8.91 (1H, br), 10.57 (1H, br)

MASS(API-ES); 339 (M+H)+

EXAMPLE 33

To a suspension of (2E)-3-(6-{[(3R)-1-(4-tert-butylbenzyl)-3-pyrrolidinyl]amino}-3-pyridyl)-N-(tetrahydro-2H-pyran-2-yloxy)acrylamide (270 mg) was suspended in methanol (1 mL) and to this suspension was added hydrogen chloride in methanol solution (10%, 3 mL). The mixture was stirred at ambient temperature for 15 minutes and concentrated in vacuo. The residual solid was triturated with acetonitrile to give (2E)-3-(6-{[(3R)-1-(4-tert-butylbenzyl)-3-pyrrolidinyl]amino}-3-pyridyl)-N-hydroxyacrylamide dihydrochloride (228 mg) as a pale tan solid.

NMR (DMSO-d6, δ): 1.29 (9H, s), 1.96-2.67 (2H, m), 3.12-4.02 (2H, m), 4.34-4.54 (4H, m), 4.54-4.84 (1H, m), 6.33-6.45 (1H, m), 6.90-7.21 (1H, m), 7.36-7.51 (3H, m), 7.54-7.63 (2H, m), 7.89-8.09 (1H, m), 8.18 (1H, s)

MS (ES+) m/z 395.32(free, M+1)

EXAMPLE 34

10% Metallic hydrogen chloride (1.4 mL) was added to the solution of (2E)-3-(2-{[1-(4-chlorobenzoyl)-3-pyrrolidinyl]amino}-1,3-thiazol-4-yl)-N-(tetrahydro-2H-pyran-2-yloxy)acrylamide (0.6 g) in MeOH (12 ml) and the mixture was stirred at ambient temperature for 3.5 hours. To the reaction mixture was added ethyl ether and isolated precipitate was collected by filtration to give (2E)-3-(2-{[1-(4-chlorobenzoyl)-3-pyrrolidinyl]amino}-1,3-thiazol-4-yl)-N-hydroxyacrylamide hydrochloride (0.42 g)

NMR(DMSO-d6, δ): 1.89-2.33(2H, m), 3.31-3.71(3H, m), 3.72-3.87(1H, m), 4.30-4.49(1H, m), 4.63 and 4.50(total 1H, each d, J=15.3 Hz), 7.06 and 7.11(total 1H, each s), 7.18 and 7.22(total 1H, each d, J=15.3 Hz), 7.45-7.66(4H, m), 8.91 (1H, br s)

(+)ESI-MS: 393(M+H)+

The following compounds were obtained according to a similar manner to that of Example 34.

EXAMPLE 35

(2E)-3-{2-[(1-Benzyl-4-piperidyl)amino]-1,3-thiazol-4-yl}-N-hydroxyacrylamide dihydrochloride ¹H-NMR(DMSO-d6): δ 1.30-1.84 (4H, m), 2.89-3.46 (4H, m), 3.82-4.15 (1H, m), 4.30 (2H, s), 6.52 (1H, d, J=15.4 Hz), 7.09 (1H, s), 7.21 (1H, d, J=15.4 Hz), 7.39-7.51 (3H, m), 7.59-7.72 (2H, m), 8.99 (1H, br.s), 11.21 (1H, s), (+)ESI-MS: 359 (M+1).

EXAMPLE 36

(2E)-3-(2-{[1-(4-Chlorobenzoyl)-4-piperidyl]amino}-1,3-thiazol-4-yl)-N-hydroxyacrylamide hydrochloride NMR(DMSO-d6, δ): 1.37-1.66(2H, m), 1.87-2.15(2H, m), 3.04-3.30(2H, m), 3.48-3.75(1H, m), 3.93-4.14(1H, m), 4.17-4.43(1H, m), 6.51(1H, d, J=15.5 Hz), 7.13(1H, s), 7.23(1H, d, J=15.5 Hz), 7.43(2H, d, J=8.5 Hz), 7.53(2H, d, J=8.5 Hz), 9.16(1H, br s)

(+)ESI-MS: 407(M+H)+

EXAMPLE 37

To a stirred solution of tert-butyl [(3R)-1-(diphenylmethyl)-3-pyrrolidinyl](5-{(1E)-3-oxo-3-[(tetrahydro-2H-pyran-2-yloxy)amino]-1-propen-1-yl}-2-pyridyl)carbamate (94 mg) in methanol (2 mL) was added hydrogen chloride methanol reagent 10 (0.5 mL, Tokyo Kasei), and the mixture was stirred at ambient temperature for 30 minutes. The solvent was evaporated to dryness and the residue was dissolved in the mixture of dioxane (3 ml) and methanol (1 ml). To this solution was added 4N-hydrogen chloride in dioxane (3 ml) and the mixture was stirred at ambient temperature for 3 hours. The solvent was evaporated to dryness and the residue was triturated with acetonitrile to give (2E)-3-(6-{[(3R)-1-(diphenylmethyl)-3-pyrrolidinyl]amino}-3-pyridyl)-N-hydroxyacrylamide dihydrochloride (63 mg) as a pale yellow powder.

NMR (CDCl₃, δ): 1.36 (3H, t, J=7 Hz), 1.42 (3×3H, s), 2.02-2.30 (2H, m), 2.42-2.61 (2H, m), 2.64 (1H, dd, J=9.5, 7 Hz), 2.78 (1H, dd, J=9.5, 8 Hz), 4.17 (1H, s), 4.29 (2H, q, J=7 Hz), 4.91 (1H, m), 6.49 (1H, d, J=16 Hz), 7.08-7.38 (11H, m), 7.69 (1H, d, J=16 Hz), 7.83 (1H, dd, J=8.5, 2 Hz), 8.57 (1H, d, J=2 Hz)

MS (ES+) m/z 528.

EXAMPLE 38

To a solution of (2E)-3-{6-[(1-benzyl-4-piperidyl)amino]-5-chloro-3-pyridyl}-N-(tetrahydro-2H-pyran-2-yloxy)acrylamide (168 mg) in EtOH (2 ml) was treated with 10% HCl in MeOH (1.76 ml) and was stirred at 25° C. for 1 hour. The precipitate was collected, washed with EtOH, dried under reduced pressure to give (2E)-3-{6-[(1-benzyl-4-piperidyl)amino]-5-chloro-3-pyridyl}-N-hydroxyacrylamide dihydrochloride (137 mg).

NMR (DMSO-d6, δ): 1.90-2.30(4H, m), 2.90-3.45(4H, m), 4.05-4.30(1H, m), 4.25-4.28(2H, m), 6.37(1H, d, J=16.0 Hz), 6.86(1H, brs), 7.16(1H, d, J=16.0 Hz), 7.44-7.69(5H, m), 8.04(1H, s), 8.19(1H, s)

Mass (ESI): 387(M+H)+

The following compounds were obtained according to a similar manner to that of Example 38.

EXAMPLE 39

(2E)-3-(5-Chloro-6-{[1-(4-fluorobenzyl)-4-piperidyl]amino}-3-pyridyl)-N-hydroxyacrylamide dihydrochloride NMR (DMSO-d6, δ): 1.90-2.30(4H, m), 2.90-3.45(4H, m), 4.05-4.30(1H, m), 4.25-4.28(2H, m), 6.37(1H, d, J=16.0 Hz), 6.86(1H, brs), 7.26-7.45(3H, m), 7.71-7.78(2H, m), 7.95(1H, s), 8.19(1H, s)

Mass (ESI): 405(M+H)+

EXAMPLE 40

(2E)-3-{6-[[1-(4-Chlorobenzoyl)-4-piperidyl](methyl)amino]-3-pyridyl}-N-hydroxyacrylamide hydrochloride NMR (DMSO-d6, δ): 1.50-2.00(4H, m), 2.80-3.30(2H, m), 3.07(3H, s), 4.50-4.80(1H, brs), 6.46(1H, d, J=16.0 Hz), 7.25-7.60(6H, m), 8.09(1H, d, J=8.8 Hz), 8.23(1H, s).

Mass (ESI): 415(M+H)+

EXAMPLE 41

To a solution of (2E)-3-(5-chloro-6-{[1-(4-methylbenzyl)-4-piperidyl]amino}-3-pyridyl)-N-(tetrahydro-2H-pyran-2- yloxy)acrylamide (470 mg) in EtOH (2 ml) was treated with 2N HCl in EtOH (2.42 ml) and was stirred at 25° C. for 1 hour. The precipitate was collected, washed with EtOH, dried under reduced pressure to give (2E)-3-(5-chloro-6-{[1-(4-methylbenzyl)-4-piperidyl]amino}-3-pyridyl)-N-hydroxyacrylamide dihydrochloride (308 mg).

NMR (DMSO-d6, δ): 1.90-2.20(4H, m), 2.34(3H, s), 2.90-2.45(4H, m), 4.10-4.25(1H, m), 4.20-4.23(2H, m), 6.39(1H, d, J=16.0 Hz), 7.26(1H, d, J=8.8 Hz), 7.35(1H, d, J=16.0 Hz), 7.54(1H, d, J=8.8 Hz), 7.95(1H, s), 8.18(1H, s), 11.08(1H, brs)

Mass (ESI): 403(M+H)+

The following compounds were obtained according to a similar manner to that of Example 41.

EXAMPLE 42

(2E)-3-(5-Chloro-6-{[1-(4-methoxybenzyl)-4-piperidyl]amino}-3-pyridyl)-N-hydroxyacrylamide dihydrochloride NMR (DMSO-d6, δ): 1.90-2.20(4H, m), 2.90-2.45(4H, m), 3.79(3H, s), 4.10-4.25(1H, m), 4.20-4.23(2H, m), 6.38(1H, d, J=16.0 Hz), 7.00(1H, d, J=8.8 Hz), 7.35(1H, d, J=16.0 Hz), 7.58(1H, d, J=8.8 Hz), 7.94(1H, s), 8.18(1H, s), 10.98(1H, brs)

Mass (ESI): 417(M+H)+

EXAMPLE 43

(2E)-3-{5-Chloro-6-[(1-isobutyl-4-piperidyl)amino]-3-pyridyl}-N-hydroxyacrylamide dihydrochloride NMR (DMSO-d6, δ): 1.00(6H, d, J=6.5 Hz), 2.0-2.30(5H, m), 2.80-3.17(4H, m), 3.20-3.30(1H, m), 3.40-3.60(1H, m), 4.10-4.30(1H, m), 6.40(1H, d, J=16.0 Hz), 7.35(1H, d, J=16.0 Hz), 7.95(1H, s), 8.20(1H, s), 10.26(1H, brs)

Mass (ESI): 353(M+H)+

EXAMPLE 44

(2E)-3-(5-Chloro-6-{[1-(cyclopropylmethyl)-4-piperidyl]amino}-3-pyridyl)-N-hydroxyacrylamide dihydrochloride NMR (DMSO-d6, δ): 0.36-0.42(2H, m), 0.59-0.68(2H, m), 1.05-1.30(1H, m), 1.90-2.25(4H, m), 2.80-3.20(4H, m), 3.40-3.70(2H, m), 4.10-4.40(1H, m), 6.41(1H, d, J=16.0 Hz), 7.36(1H, d, J=16.0 Hz), 7.98(1H, s), 8.20(1H, s), 10.86(1H, brs)

Mass (ESI): 351(M+H)+

EXAMPLE 45

(2E)-3-(5-Chloro-6-{[(3R)-1-(4-fluorobenzyl)-3-pyrrolidinyl]amino}-3-pyridyl)-N-hydroxyacrylamide dihydrochloride NMR (DMSO-d6, δ): 1.95-2.16(2H, m), 3.06-3.70(4H, m), 4.42(2H, d, J=5.5 Hz), 4.60-5.00(1H, m), 6.40(1H, d, J=16.0 Hz), 7.25-7.39(4H, m), 7.68-7.76(2H, m), 7.92(1H, s), 8.21(1H, s)

EXAMPLE 46

(2E)-3-(5-Chloro-6-{[(3R)-1-(4-methylbenzyl)-3-pyrrolidinyl]amino}-3-pyridyl)-N-hydroxyacrylamide dihydrochloride NMR (DMSO-d6, δ): 2.03-2.30(2H, m), 3.10-3.66(4H, m), 4.35(2H, d, J=5.5 Hz), 4.65-5.00(1H, m), 6.39(1H, d, J=16.0 Hz), 7.25(2H, d, J=8.8 Hz), 7.34(1H, d, J=16.0 Hz), 7.51(1H, d, J=8.8 Hz), 7.91(1H, s), 8.20(1H, s)

EXAMPLE 47

(2E)-3-(5-Chloro-6-{[(3R)-1-(4-methoxybenzyl)-3-pyrrolidinyl]amino}-3-pyridyl)-N-hydroxyacrylamide dihydrochloride NMR (DMSO-d6, δ): 1.95-2.30(2H, m), 3.07-3.70(4H, m), 3.48(3H, s), 4.33(2H, d, J=5.5 Hz), 4.60-5.00(1H, m), 6.40(1H, d, J=16.0 Hz), 6.99(2H, d, J=8.8 Hz), 7.15-7.40(1H, m), 7.34(1H, d, J=16.0 Hz), 7.53-7.89(2H, m), 7.92(1H, s), 8.21(1H, s)

EXAMPLE 48

To [(3R)-1-(3-methoxybenzyl)-3-pyrrolidinyl](5-{(1E)-3-oxo-3-[(tetrahydro-2H-pyran-2-yloxy)amino]-1-propen-1-yl}-2-pyridyl)carbamate (275 mg) was added 4N HCl in dioxane (1.4 mL) and stirred for 15 minutes at ambient temperature. To the reaction mixture was added MeOH (5 mL) and stirred for 15 minutes. The solvent was removed in vacuo and the residue was suspended in 4N HCl in dioxane (1.24 mL) and stirred for 0.5 hour. To the reaction mixture was added CH₃CN and the solvent was removed in vacuo. Obtained colorless solid was triturated with CH₃CN to give (2E)-N-hydroxy-3-(6-{[(3R)-1-(3-methoxybenzyl)-3-pyrrolidinyl]amino}-3-pyridyl)acrylamide dihydrochloride (211 mg) as colorless powder.

NMR (DMSO-d6, δ): 2.13 (1H, br), 2.34 (0.5H, br), 2.59 (0.5H, br), 3.22-3.83 (4H, br), 3.79 (3H, s), 4.41 (1H, m), 4.51 (1H, d), 4.61 (0.5H, br), 4.75 (0.5H, br), 6.39 (0.5H, d, J=16.1 Hz), 6.40 (0.5H, d, J=16.1 Hz), 6.99 (1.5H, m), 7.19 (1.5H, m), 7.33 (2H, m), 7.43 (0.5H, d, J=16.1 Hz), 7.44 (0.5H, d, J=16.1 Hz), 8.01 (1H, m), 8.18 (1H, s)

MS (ES+) m/z 369 (M+1)

The following compounds were obtained according to a similar manner to that of Example 48.

EXAMPLE 49

(2E)-N-Hydroxy-3-[6-({(3R)-1-[(2-phenyl-1,3-thiazol-4-yl)methyl]-3-pyrrolidinyl}amino)-3-pyridyl]acrylamide dihydrochloride NMR (DMSO-d6, δ): 0.97-2.62 (2H, m), 3.30-4.10 (5H, m), 4.55-4.73 (2H, m), 6.35 (1H, d, J=16 Hz), 6.88-7.01 (1H, m), 7.41 (1H, d, J=16 Hz), 7.48-7.57 (3H, m), 7.89-8.03 (4H, m), 8.16-8.23 (1H, m)

MS (ES+) m/z 422 (M+1)

EXAMPLE 50

(2E)-3-(6-{[(3R)-1-(4-Benzoylbenzyl)-3-pyrrolidinyl]amino}-3-pyridyl)-N-hydroxyacrylamide dihydrochloride NMR (DMSO-d6, δ): 2.02-4.73 (9H, m), 6.32 (1H, d, J=16 Hz), 7.40 (1H, d, J=16 Hz), 7.55-7.82 (11H, m), 8.18-8.21 (1H, m)

MS (ES+) m/z 443 (M+1).

EXAMPLE 51

(2E)-3-(6-{[(3R)-1-(2,3-Dihydro-1-benzofuran-5-ylmethyl)-3-pyrrolidinyl]amino}-3-pyridyl)-N-hydroxyacrylamide dihydrochloride NMR (DMSO-d6, δ): 1.95-2.41 (2H, m), 3.19 (2H, t, J=9 Hz), 3.24-4.69 (7H, m), 4.56 (2H, t, J=9 Hz), 6.29-6.39 (1H, m), 6.79-7.09 (2H, m), 7.29-7.50 (3H, m), 7.87-7.99 (1H, m), 8.17-8.21 (1H, s)

MS (ES+) m/z 381 (M+1)

EXAMPLE 52

(2E)-3-(6-{[(3R)-1-(1-Benzofuran-2-ylmethyl)-3-pyrrolidinyl]amino}-3-pyridyl)-N-hydroxyacrylamide NMR (DMSO-d6, δ): 1.61-4.44 (9H, m), 6.17 (1H, d, J=16 Hz), 6.52 (1H, d, J=8 Hz), 7.19-7.36 (4H, m), 7.52-7.64 (3H, m), 8.10-8.15 (1H, m)

MS (ES+) m/z 379 (M+1)

EXAMPLE 53

(2E)-3-(6-{[(3R)-1-(1-Benzofuran-5-ylmethyl)-3-pyrrolidinyl]amino}-3-pyridyl)-N-hydroxyacrylamide NMR (DMSO-d6, δ): 1.72-4.53 (9H, m), 6.20 (1H, d, J=16 Hz), 6.54 (1H, d, J=8 Hz), 6.95-8.16 (8H, m)

MS (ES+) m/z 379 (M+1)

EXAMPLE 54

(2E)-N-Hydroxy-3-(6-{[(3R)-1-(3-phenylpropyl)-3-pyrrolidinyl]amino}-3-pyridyl)acrylamide dihydrochloride NMR (DMSO-d6, δ): 2.00 (2H, m), 2.06 (1H, br), 2.30 (0.5H, br), 2.54 (0.5H, br), 2.66 (2H, t, J=8.0 Hz), 3.12-4.01 (6H; br), 4.58 (1H, br), 4.69 (1H, br), 6.38 (1H, d, J=16.1 Hz), 6.96 (0.5H, d, J=8.0 Hz), 7.04 (0.5H, d, J=9.2 Hz), 7.23 (3H, m), 7.31 (2H, m), 7.43 (1H, d, J=16.1 Hz), 7.99 (1H, m), 8.21 (1H, s)

MS (ES+) m/z 367 (M+1)

EXAMPLE 55

(2E)-3-[6-({(3R)-1-[4-(Dimethylamino)benzyl]-3-pyrrolidinyl}amino)-3-pyridyl]-N-hydroxyacrylamide trihydrochloride NMR (DMSO-d6, δ): 2.12 (1H, br), 2.37 (1H, br), 2.96 (6H, s), 3.18-4.00 (4H, br), 4.30 (1H, br), 4.40 (1H, d, J=5.5 Hz), 4.58 (0.5H, br), 4.72 (0.5H, br), 6.39 (0.5H, d, J=16.1 Hz), 6.40 (0.5H, d, J=16.1 Hz), 6.92 (2H, br), 7.01 (0.5H, d, J=8.1 Hz), 7.15 (0.5H, d, J=8.1 Hz), 7.43 (1H, m), 7.48 (2H, m), 8.03 (1H, m), 8.20 (1H, s)

MS (ES+) m/z 382 (M+1)

EXAMPLE 56

(2E)-N-Hydroxy-3-(6-{[(3R)-1-(2-methoxybenzyl)-3-pyrrolidinyl]amino}-3-pyridyl)acrylamide dihydrochloride NMR (DMSO-d6, δ): 2.11 (1H, br), 2.39 (1H, br), 3.11-3.71 (4H, br), 3.82 (1.5H, s), 3.87 (1.5H, s), 4.39 (1H, br), 4.45 (1H, br), 4.59 (0.5H, br), 4.71 (0.5H, br), 6.36 (1H, d, J=16.1 Hz), 6.93 (1H, m), 7.02 (1H, m), 7.12 (1H, dd, J=8.4, 4.5 Hz), 7.43 (2H, m), 7.57 (1H, m), 7.96 (1H, m), 8.18 (1H, s)

MS (ES+) m/z 369 (M+1)

EXAMPLE 57

To a solution of tert-butyl [(3R)-1-(3-fluorobenzyl)-3-pyrrolidinyl](5-{(1E)-3-oxo-3-[(tetrahydro-2H-pyran-2-yloxy)amino]-1-propen-1-yl}-2-pyridyl)carbamate [(251 g) in MeOH (37 mL) was added hydrogen chloride methanol reagent 10 (9.28 mL, Tokyo Kasei), and the mixture was stirred at ambient temperature for 1 hour. The solvent was removed in vacuo and the residue was dissolved in dioxane (12 mL). To the reaction mixture was added 4N HCl in dioxane and stirred for 1 hour at ambient temperature. To the reaction mixture was added CH₃CN and the solvent was removed in vacuo. Obtained colorless solid was triturated with CH₃CN to give (2E)-3-(6-{[(3R)-1-(3-fluorobenzyl)-3-pyrrolidinyl]amino}-3-pyridyl)-N-hydroxyacrylamide dihydrochloride (1.87 g) as colorless powder.

NMR (CDCl₃, δ): 2.08 (1H, m), 2.34 (1H, m), 3.23-3.81 (4H, m), 4.45 (1H, m), 4.54 (1H, d, J=5.5 Hz), 4.58 (0.5H, br), 4.69 (0.5H, br), 6.35 (0.5H, d, J=16.1 Hz), 3.36 (0.5H, d, J=16.1 Hz), 6.90 (0.5H, br), 7.03 (0.5H, br), 7.30 (1H, m), 7.41 (1H, m), 7.48-7.60 (3H, m), 7.95 (1H, m), 8.18 (1H, s),

MS (ES+) m/z 357 (M+1)

The following compounds were obtained according to a similar manner to that of Example 57.

EXAMPLE 58

(2E)-N-Hydroxy-3-[6-({(3R)-1-[4-(trifluoromethyl)benzyl]-3-pyrrolidinyl}amino)-3-pyridyl]acrylamide dihydrochloride NMR (DMSO-d6, δ): 1.98-2.76 (2H, m), 3.17-4.25 (4H, m), 4.50-4.79 (3H, m), 6.29-6.45 (1H, m), 6.87-7.18 (1H, m), 7.36-7.48 (1H, m), 7.81-8.08 (5H, m), 8.19 (1H, brs)

MS (ES+) m/z 407.33(free, M+1)

EXAMPLE 59

(2E)-N-Hydroxy-3-[6-({(3R)-1-[4-(trifluoromethoxy)benzyl]-3-pyrrolidinyl}amino)-3-pyridyl]acrylamide dihydrochloride NMR (DMSO-d6, δ): 1.92-2.80 (2H, m), 3.14-4.23 (4H, m), 0.43-4.78 (3H, m), 6.30-6.46 (1H, m), 6.86-7.16 (1H, m), 7.37-7.53 (3H, m), 7.76-7.86 (2H, m), 7.88-8.08 (1H, m), 8.19 (1H, s)

MS (ES+) m/z 423.25(free, M+1)

EXAMPLE 60

(2E)-3-(6-{[(3R)-1-(Cyclohexylmethyl)-3-pyrrolidinyl]amino}-3-pyridyl)-N-hydroxyacrylamide dihydrochloride NMR (DMSO-d6, δ): 0.77-1.34 (5H, m), 1.52-1.91 (6H, m), 1.97-2.62 (4H, m), 3.00-4.09 (4H, m), 4.51-4.76 (1H, m), 6.36 (1H, d, J=15.8 Hz), 6.88-7.10 (1H, m), 7.43 (1H, d, J=15.8 Hz), 7.91-8.01 (1H, m), 8.20 (1H, s)

MS (ES+) m/z 345.41(free, M+1)

EXAMPLE 61

(2E)-3-(6-{[(3R)-1-(1-Cyclohexen-1-ylmethyl)-3-pyrrolidinyl]amino}-3-pyridyl)-N-hydroxyacrylamide dihydrochloride NMR (DMSO-d6, δ): 1.45-1.66 (4H, m), 1.90-2.20 (5H, m), 2.30-2.63 (1H, m), 2.99-3.90 (6H, m), 4.52-4.81 (1H, m), 5.94-6.04 (1H, m), 6.38 (1H, d, J=15.8 Hz), 6.93-7.17 (1H, m), 7.43 (1H, d, J=15.8 Hz), 7.91-8.09 (1H, m), 8.21 (1H, brs)

MS (ES+) m/z 343.50(free, M+1)

EXAMPLE 62

(2E)-3-(6-{[(3R)-1-(2-Fluorobenzyl)-3-pyrrolidinyl]amino}-3-pyridyl)-N-hydroxyacrylamide dihydrochloride NMR (DMSO-d6, δ): 2.12 (1H, br), 2.37 (1H, br), 2.60 (1H, br), 3.25 (1H, br), 3.45 (1H, br), 3.66 (1H, br), 3.91 (1H, br), 4.50 (1H, br), 4.56 (1H, d, J=5.1 Hz), 4.59 (0.5H, br), 4.70 (0.5H, br), 6.35 (1H, d, J=16.1 Hz), 6.91 (0.5H, br), 6.98 (0.5H, br), 7.30 (1H, d, J=7.3 Hz), 7.35 (1H, d, J=9.1 Hz), 7.41 (1H, d, J=16.1 Hz), 7.52 (1H, m), 7.78 (1H, m), 7.94 (1H, m), 8.19 (1H, s)

MS (ES+) m/z 357 (M+1)

EXAMPLE 63

(2E)-N-Hydroxy-3-(6-{[(3R)-1-(2-quinolinylmethyl)-3-pyrrolidinyl]amino}-3-pyridyl)acrylamide trihydrochloride NMR (DMSO-d6, δ): 2.21 (1H, br), 2.51 (1H, br), 3.61 (2H, br), 3.76 (1H, br), 3.95 (1H, br), 4.72 (1H, br), 4.93 (2H, s), 6.38 (1H, d, J=15.8 Hz), 7.08 (1H, d, J=9.5 Hz), 7.43 (1H, d, J=15.8 Hz), 7.69 (1H, m), 7.71 (1H, d, J=8.4 Hz), 7.84 (1H, m), 8.04 (2H, m), 8.20 (1H, s), 8.50 (1H, d, J=8.1 Hz)

MS (ES+) m/z 390 (M+1)

EXAMPLE 64

(2E)-N-Hydroxy-3-(6-{[(3R)-1-(3-quinolinylmethyl)-3-pyrrolidinyl]amino}-3-pyridyl)acrylamide trihydrochloride NMR (DMSO-d6, δ): 2.10 (1H, br), 2.63 (1H, br), 3.35 (1H, br), 3.49 (1H, br), 3.69 (1H, br), 3.90 (1H, br), 4.58 (1H, br), 4.72 (1H, br), 4.80 (1H, br), 6.35 (1H, d, J=16.1 Hz), 6.91 (0.5H, br), 7.03 (0.5H, br), 7.41 (1H, d, J=16.1 Hz), 7.76 (1H, t, J=7.7 Hz), 7.93 (2H, m), 8.08 (1H, d, J=7.7 Hz), 8.14 (1H, d, J=8.1 Hz), 8.19 (1H, s), 8.79 (1H, d, J=6.6 Hz), 9.23 (1H, d, J=8.1 Hz)

MS (ES+) m/z 390 (M+1)

EXAMPLE 65

(2E)-N-Hydroxy-3-[6-({(3R)-1-[(5-methyl-2-thienyl)methyl]-3-pyrrolidinyl}amino)-3-pyridyl]acrylamide dihydrochloride NMR (DMSO-d6, δ): 2.07 (1H, br), 2.31 (1H, br), 2.45 (3H, s), 3.23 (1H, br), 3.37 (1H, br), 3.52 (1H, br), 3.81 (1H, br), 4.56 (1H, d, J=4.4 Hz), 4.57 (0.5H, br), 4.64 (1H, d, J=5.1 Hz), 4.67 (0.5H, br), 6.35 (1H, d, J=16.1 Hz), 6.80 (1H, br), 6.90 (0.5H, br), 6.98 (0.5H, br), 7.19 (1H, m), 7.42 (1H, d, J=16.1 Hz), 7.93 (1H, m), 8.19 (1H, s)

MS (ES+) m/z 359 (M+1)

EXAMPLE 66

(2E)-N-Hydroxy-3-[6-({(3R)-1-[(5-methyl-2-furyl)methyl]-3-pyrrolidinyl}amino-3-pyridyl]acrylamide dihydrochloride NMR (DMSO-d6, δ): 2.09 (2H, br.), 2.26 (1.5H, s), 2.29 (1.5H, s), 3.26 (1H, br.), 3.53 (2H, br.), 3.86 (1H, br.), 4.44 (1H, s), 4.53 (1H, s), 4.64 (1H, br.d), 6.15 (1H, m), 6.39 (1H, d, J=15.8 Hz), 6.60 (1H, s), 7.04 (1H, m), 7.43 (1H, d, J=15.4 Hz), 8.00 (1H, br.), 8.20 (1H, s)

MS (ES+) m/z 343 (M+1)

EXAMPLE 67

(2E)-3-{6-[((3R)-1-{(2E)-3-[4-(Dimethylamino)phenyl]-2-propen-1-yl}-3-pyrrolidinyl)amino]-3-pyridyl}-N-hydroxyacrylamide trihydrochloride NMR (DMSO-d6, δ): 2.23 (2H, br.), 3.00 (6H, s), 3.07 (1H, br.), 3.43 (2H, br.), 3.71 (1H, br.), 3.97 (1H, br.), 4.07 (1H, br.), 4.65 (0.5H, br.), 4.77 (0.5H, br.), 6.27 (1H, br.), 6.42 (1H, d, J=15.8 Hz), 6.80 (1H, d, J=15.4 Hz), 7.09 (2H, br.), 7.22 (1H, d, J=8.4 Hz), 7.44 (3H, m), 8.07 (1H, m), 8.19 (1H, s)

MS (ES+) m/z 408 (M+1)

EXAMPLE 68

(2E)-3-(6-{[(3R)-1-(2,2-Dimethylpropyl)-3-pyrrolidinyl]amino}-3-pyridyl)-N-hydroxyacrylamide dihydrochloride NMR (DMSO-d6, δ): 1.06 (4.5H, s), 1.07 (4.5H, s), 2.08 (1H, m), 2.45 (1H, m), 3.16 (1H, m), 3.25 (1H, m), 3.39-3.92 (4H, br), 4.12 (1H, m), 4.59 (0.5H, br), 4.71 (0.5H, br), 6.35 (1H, d, J=16.1 Hz), 6.94 (1H, br.d), 7.42 (1H, d, J=16.1 Hz), 7.94 (1H, br.d), 8.21 (1H, br)

MS (ES+) m/z 319 (M+1)

EXAMPLE 69

To a solution of (2E)-3-(4-{[(3R)-1-(4-chlorobenzoyl)-3-pyrrolidinyl]amino}phenyl)-N-(tetrahydro-2H-pyran-2-yloxy) acrylamide (76 mg) in MeOH (1.3 mL) was added hydrogen chloride methanol reagent 10 (0.32 mL, Tokyo Kasei), and the mixture was stirred at ambient temperature for 1 hour. To the reaction mixture was added CH₃CN and the solvent was removed in vacuo. Obtained colorless solid was triturated with CH₃CN to give (2E)-3-(4-{[(3R)-1-(4-chlorobenzoyl)-3-pyrrolidinyl]amino}phenyl)-N-hydroxyacrylamide hydrochloride (64.1 mg) as colorless powder.

NMR (DMSO-d6, δ): 1.89 (1H, m), 2.18 (1H, m), 3.24 (0.5H, m), 3.45 (0.5H, m), 3.59 (1H, m), 3.67 (1H, m), 3.78 (1H, m), 4.03 (0.5H, m), 4.12 (0.5H, m), 6.15 (0.5H, d, J=15.8 Hz), 6.20 (0.5H, d, J=15.8 Hz), 6.59 (1H, d, J=8.4 Hz), 6.70 (1H, d, J=8.8 Hz), 7.26-7.36 (3H, m), 7.47-7.59 (5H, m)

EXAMPLE 70

To a solution of (2E)-3-(6-{[(3R)-1-(4-chlorobenzoyl)-3-pyrrolidinyl]amino}-3-pyridyl)-N-(tetrahydro-2H-pyran-2-yloxy)acrylamide (1.89 g) in MeOH (32 mL) was added hydrogen chloride methanol reagent 10 (8.0 mL, Tokyo Kasei), and the mixture was stirred at ambient temperature for 0.5 hour. The reaction mixture was diluted with AcOEt and the precipitate was collected with filtration to give (2E)-3-(6-{[(3R)-1-(4-chlorobenzoyl)-3-pyrrolidinyl]amino}-3-pyridyl)-N-hydroxyacrylamide hydrochloride (1.18 g) as colorless powder.

NMR (DMSO-d6, δ): 2.02 (1H, br), 2.25 (1H, br), 3.34-3.64 (4H, br), 3.85 (1H, m), 4.40 (0.5H, br), 4.50 (0.5H, br), 6.35 (0.5H, d, J=16.1 Hz), 6.37 (0.5H, d, J=16.1 Hz), 6.98 (0.5H, m), 7.06 (0.5H, m), 7.38-7.60 (5H, m), 8.01 (1H, m), 8.14 (0.5H, s), 8.23 (0.5H, s)

MS (ES+) m/z 387 (M+1)

The following compounds were obtained according to a similar manner to that of Example 70.

EXAMPLE 71

(2E)-3-(6-{[(3S)-1-(4-Chlorobenzoyl)-3-pyrrolidinyl] amino}-3-pyridyl)-N-hydroxyacrylamide hydrochloride NMR (DMSO-d6, δ): 2.02 (1H, br), 2.25 (1H, br), 3.34-3.64 (4H, br), 3.85 (1H, m), 4.40 (0.5H, br), 4.50 (0.5H, br), 6.35 (0.5H, d, J=16.1 Hz), 6.37 (0.5H, d, J=16.1 Hz), 6.98 (0.5H, m), 7.06 (0.5H, m), 7.38-7.60 (5H, m), 8.01 (1H, m), 8.14 (0.5H, s), 8.23 (0.5H, s)

MS (ES+) m/z 387 (M+1)

EXAMPLE 72

To a solution of (2E)-3-(4-{[(3R)-1-benzyl-3-pyrrolidinyl]amino}phenyl)-N-(tetrahydro-2H-pyran-2-yloxy)acrylamide (500 mg) in MeOH (5 mL) was added hydrogen chloride methanol reagent 10 (2.38 mL, Tokyo Kasei), and the mixture was stirred at ambient temperature for 1 hour. To the reaction mixture was added CH$_3$CN and the solvent was removed in vacuo. Obtained colorless solid was triturated with CH$_3$CN to give (2E)-3-(4-{[(3R)-1-benzyl-3-pyrrolidinyl]amino}phenyl)-N-hydroxyacrylamide hydrochloride (257.4 mg) as colorless powder.

NMR (DMSO-d6, δ): 1.94 (1H, m), 2.01 (0.5H, m), 2.29 (0.5H, m), 3.00 (0.5H, m), 3.19 (1.5H, m), 3.29-3.53 (2.5H, m), 3.73 (0.5H, m), 4.18 (0.5H, m), 4.31 (0.5H, m), 4.40 (1H, d, J=5.9 Hz), 4.44 (1H, d, J=5.9 Hz), 6.20 (1H, d, J=16.1 Hz), 6.61 (1H, d, J=8.8 Hz), 6.63 (1H, d, J=8.8 Hz), 7.33 (2H, m), 7.44 (3H, m), 7.64 (2H, m)

MS (ES+) m/z 338 (M+1)

EXAMPLE 73

To a solution of (2E)-3-(6-{[(3R)-1-benzyl-3-pyrrolidinyl] amino}-5-methyl-3-pyridyl)-N-(tetrahydro-2H-pyran-2-yloxy)acrylamide (306 mg) in MeOH (5.6 mL) was added hydrogen chloride methanol reagent 10 (1.4 mL, Tokyo Kasei), and the mixture was stirred at ambient temperature for 2 hours. To the reaction mixture was added Men and the solvent was removed in vacuo. Obtained colorless solid was triturated with Men to give (2E)-3-(6-{[(3R)-1-benzyl-3-pyrrolidinyl]amino}-5-methyl-3-pyridyl)-N-hydroxyacrylamide dihydrochloride (202.1 mg) as colorless powder.

NMR (DMSO-d6, δ): 2.16 (1H, m), 2.28 (3H, s), 2.65 (1H, m), 3.22 (1H, m), 3.48 (2H, m), 3.58 (1H, m), 4.44 (1H, d, J=5.8 Hz), 4.49 (1H, d, J=5.8 Hz), 4.98 (1H, br), 6.39 (1H, d, J=16.1 Hz), 7.41 (1H, d, J=16.1 Hz), 7.45 (3H, m), 7.63 (2H, m), 7.88 (1H, be), 8.09 (1H, s)

MS (ES+) m/z 353 (M+1)

EXAMPLE 74

To a solution of (2E)-3-(5-{[(3R)-1-(4-chlorobenzyl)-3-pyrrolidinyl]amino}-2-pyrazinyl)-N-(tetrahydro-2H-pyran-2-yloxy)acrylamide (1.43 g) in methanol (16 mL) was added hydrogen chloride in methanol (6.24 mL). After stirring at room temperature for 1 hour, the reaction mixture was evaporated in vacuo and triturated with ethyl acetate to give (2E)-3-(5-{[(3R)-1-(4-chlorobenzyl)-3-pyrrolidinyl]amino}-2-pyrazinyl)-N-hydroxyacrylamide dihydrochloride (1.40 g).

$^1$H-NMR (300 MHz, DMSO-d6) d 1.93-2.38 (2H, m), 3.00-3.79 (4H, m), 4.37-4.63 (3H, m), 6.63 (1H, d, J=15 Hz), 7.39 (1H, d, J=15 Hz), 7.52 (2H, d, J=8 Hz), 7.67 (2H, d, J=8 Hz), 8.00-8.16 (2H, m)

MS (ES+) m/z 374 (M+1)

The following compounds were obtained in a similar manner to that of Example 74.

EXAMPLE 75

(2E)-3-(5-{[(3R)-1-(Cyclohexylmethyl)-3-piperidinyl] amino}-2-pyrazinyl)-N-hydroxyacrylamide dihydrochloride $^1$H-NMR (300 MHz, DMSO-d6) δ 0.81-1.03 (2H, m), 1.04-1.35 (3H, m), 1.35-2.20 (10H, m), 2.56-2.76 (1H, m), 2.76-3.13 (3H, m), 3.16-3.65 (2H, m), 4.03-4.75 (1H, m), 6.63 (1H, d, J=15.0 Hz), 7.40 (1H, d, J=15.0 Hz), 7.76-7.89 (0.6H, m), 8.03 (1H, s), 8.05-8.35 (0.4H, m), 8.15 (1H, s), 9.80-10.02 (1H, br.s)

MS (ES+) m/z 360(M+1, free)

EXAMPLE 76

(2E)-3-(5-{[(3R)-1-Benzyl-3-piperidinyl]amino}-2-pyrazinyl)-N-hydroxyacrylamide dihydrochloride $^1$H-NMR (300 MHz, DMSO-d6) δ 1.31-1.53 (1H, m), 1.74-2.16 (3H, m), 2.56-2.78 (1H, m), 2.78-3.05 (1H, m), 3.23-3.40 (1H, m), 3.40-3.54 (1H, m), 4.20-4.45 (3H, m), 6.61 (1H, d, J=15 Hz), 7.36 (1H, d, J=15 Hz), 7.42-7.54 (3H, m), 7.54-7.70 (2H, m), 7.70-7.94 (1H, m), 8.00 (1H, s), 8.10 (1H, s)

MS (ES+) m/z 354

EXAMPLE 77

(2E)-3-(5-{[(3R)-1-Cyclohexyl-3-piperidinyl]amino}-2-pyrazinyl)-N-hydroxyacrylamide dihydrochloride $^1$H-NMR (300 MHz, CD$_3$OD)d 1.10-1.30 (1H, m), 1.30-1.77 (6H, m), 1.85-2.06 (3H, m), 2.06-2.30 (3H, m), 2.85 (1H, t, J=11 Hz), 2.99-3.15 (1H, m), 3.15-3.33 (2H, m), 3.45-3.58 (1H, m), 3.67-3.86 (1H, m), 4.28-4.44 (1H, m), 6.76 (1H, d, 3=15 Hz), 7.53 (1H, d, J=15 Hz), 8.11-8.24 (2H, m)

MS (ES+) m/z 346

EXAMPLE 78

(2E)-N-Hydroxy-3-(5-{[(3R)-1-(4-methylbenzyl)-3-piperidinyl]amino}-2-pyrazinyl)acrylamide dihydrochloride ¹H-NMR (300 MHz, DMSO-d6) δ 1.30-1.52 (1H, m), 1.70-2.15 (4H, m), 2.33 (3H, s), 2.54-2.71 (1H, m), 2.71-2.99 (1H, m), 3.21-3.36 (1H, m), 3.36-3.50 (1H, m), 4.23-4.44 (2H, m), 6.61 (1H, d, J=15 Hz), 7.10 (1H, s), 7.25 (2H, d, J=8 Hz), 7.30 (1H, s), 7.36 (1H, d, J=15 Hz), 7.41-7.55 (3H, m), 7.80 (1H, br peak), 7.93-8.06 (1H, m), 8.10 (1H, s)

MS (ES+) m/z 368

EXAMPLE 79

(2E)-3-(5-{[(3R)-1-(4-Chlorobenzyl)-3-piperidinyl]amino}-2-pyrazinyl)-N-hydroxyacrylamide dihydrochloride ¹H-NMR (300 MHz, DMSO-d6) δ 1.34-1.56 (1H, m), 1.70-2.11 (4H, m), 2.56-2.75 (1H, m), 2.75-2.93 (1H, m), 3.20-3.38 (1H, m), 3.38-3.55 (1H, m), 4.22-4.45 (2H, m), 6.62 (1H, d, J=15 Hz), 7.40 (1H, d, J=15 Hz), 7.49-7.58 (2H, m), 7.58-7.70 (2H, m), 7.70-7.82 (1H, m), 7.95-8.06 (1H, m), 8.11 (1H, s)

MS (ES+) m/z 388

EXAMPLE 80

(2E)-3-(5-{[(3R)-1-Cyclopentyl-3-piperidinyl]amino}-2-pyrazinyl)-N-hydroxyacrylamide dihydrochloride ¹H-NMR (300 MHz, DMSO-d6) δ 1.39-1.52 (3H, m), 1.52-2.04 (9H, m), 2.56-2.78 (1H, m), 2.78-3.10 (1H, m), 3.20-4.50 (4H, m), 6.63 (1H, d, J=15 Hz), 7.13 (1H, s), 7.30 (1H, s), 7.39 (1H, d, J=15 Hz), 7.47 (1H, s), 7.85 (1H, br peak), 7.98-8.10 (1H, m), 8.10-8.21 (1H, m)

MS (ES+) m/z 332

EXAMPLE 81

(2E)-3-(5-{[(3R)-1-(Cyclopentylmethyl)-3-piperidinyl]amino}-2-pyrazinyl)-N-hydroxyacrylamide dihydrochloride ¹H-NMR (300 MHz, DMSO-d6) δ 1.16-1.35 (2H, m), 1.35-1.69 (4H, m), 1.69-2.07 (5H, m), 2.18-2.36 (1H, m), 2.56-2.75 (1H, m), 2.75-2.96 (1H, m), 2.96-3.19 (2H, m), 3.19-4.20 (3H, m), 4.20-4.42 (1H, m), 6.63 (1H, d, J=15 Hz), 7.11 (1H, s), 7.28 (1H, s), 7.40 (1H, d, J=15 Hz), 7.45 (1H, s), 7.76-7.91 (1H, m), 8.01-8.11 (1H, m), 8.15 (1H, s)

MS (ES+) m/z 346

EXAMPLE 82

(2E)-3-(5-{[(R)-1-Benzyl-3-pyrrolidinyl]amino}-2-pyrazinyl)-N hydroxyacrylamide dihydrochloride ¹H-NMR (300 MHz, DMSO-d6) δ 1.95-2.36 (2H, m), 2.99-3.78 (4H, m), 4.33-4.62 (3H, m), 6.62 (1H, dd, J=2, 15 Hz), 7.38 (1H, d, J=15 Hz), 7.43-7.47 (3H, m), 7.59-7.65 (2H, m), 8.00-8.15 (2H, m)

MS (ES+) m/z 340 (M+1)

EXAMPLE 83

(2E)-N-Hydroxy-3-(5-{[(3R)-1-(4-methylbenzyl)-3-pyrrolidinyl]amino}-2-pyrazinyl)acrylamide dihydrochloride ¹H-NMR (300 MHz, DMSO-d6) δ 1.95-2.38 (2H, m), 2.32 (3H, s), 2.98-3.78 (4H, m), 4.31-4.61 (3H, m), 6.63 (1H, dd, J=2, 15 Hz), 7.22-7.28 (2H, m), 7.39 (1H, d, J=15 Hz), 7.46-7.52 (2H, m), 8.00-8.15 (2H, m)

MS (ES+) m/z 354 (M+1)

EXAMPLE 84

(2E)-3-(5-{[(3R)-1-(Cyclohexylmethyl)-3-pyrrolidinyl]amino}-2-pyrazinyl)-N-hydroxyacrylamide dihydrochloride ¹H-NMR (300 MHz, DMSO-d6) δ 0.85-1.03 (2H, m), 1.04-1.32 (3H, m), 1.54-1.77 (4H, m), 1.78-1.90 (2H, m), 2.04 (1H, m), 2.33 (1H, m), 2.92-3.85 (6H, m), 4.55 (1H, m), 6.63 (1H, d, J=15.3 Hz), 7.40 (1H, d, J=15.3 Hz), 8.05 (1H, d, J=8.4 Hz), 8.11-8.32 (3H, m), 10.44 (1H, br-s)

MS (ES+) m/z 346

EXAMPLE 85

To a stirred solution of (2E)-3-(5-{[(3R)-1-benzyl-3-pyrrolidinyl]amino}-2-pyrazinyl)-N-hydroxyacrylamide (300 mg) in 95% ethanol (3 mL) was added 4-methylbenzenesulfonic acid hydrate (168 mg) at ambient temperature. After stirring at the same temperature for one hour, additional 95% ethanol (1.5 mL) was added to the mixture. The precipitate was collected after two hours to afford (2E)-3-(5-{[(3R)-1-benzyl-3-pyrrolidinyl]amino}-2-pyrazinyl)-N-hydroxyacrylamide 4-methylbenzenesulfonate (253 mg) as a pale brown solid.

¹H-NMR (300 MHz, CD₃OD) δ 2.07-2.26 (1H, m), 2.36 (3H, s), 2.43-2.65 (1H, m), 3.24-3.49 (2H, m), 3.54-3.82 (2H, m), 4.38 (1H, d, J=12.8 Hz), 4.46 (1H, d, J=12.8 Hz), 4.51-4.65 (1H, m), 6.68 (1H, d, J=15.4 Hz), 7.22 (2H, d, J=8.1 Hz), 7.41-7.57 (6H, m), 7.70 (2H, d, J=8.1 Hz), 7.98 (1H, s), 8.05 (1H, s)

EXAMPLE 86

To a solution of (2E)-3-(5-{[(3R)-1-benzyl-3-pyrrolidinyl]amino}-2-pyrazinyl)-N-hydroxyacrylamide dihydrochloride (1.00 g) in water (10 mL) was added saturated NaHCO₃ at 4° C. (to pH 7-8). The mixture was extracted with CHCl₃ three times. The conbined organic layer was dried over Na₂SO₄, filtered, and evaporated in vacuo to give (2E)-3-(5-{[(3R)-1-benzyl-3-pyrrolidinyl]amino}-2-pyrazinyl)-N-hydroxyacrylamide (796 mg).

¹H-NMR (300 MHz, DMSO-d6) δ 1.58-1.72 (1H, m), 2.16-2.29 (1H, m), 2.36-2.48 (2H, m), 2.61-2.80 (2H, m), 3.58 (2H, s), 4.24-4.36 (1H, m), 6.56 (1H, d, J=15 Hz), 7.20-7.38 (6H, m), 7.73 (1H, d, J=7 Hz), 7.97 (1H, s), 8.07 (1H, s), 8.97 (1H, brs), 10.70 (1H, brs)

MS (ES+) m/z 340 (M+1)

The following compound was obtained in similar manners to those of Examples 74 and 86.

EXAMPLE 87

(2E)-N-Hydroxy-3-(5-{[(3R)-1-(4-methylbenzyl)-3-pyrrolidinyl]-amino}-2-pyrazinyl)acrylamide $^1$H-NMR (300 MHz, DMSO-d6) δ 1.55-1.72 (1H, m), 2.12-2.29 (1H, m), 2.27 (3H, s), 2.32-2.49 (2H, m), 2.57-2.78 (2H, m), 3.51 (1H, d, J=13.2 Hz), 3.55 (1H, d, J=13.2 Hz), 4.21-4.36 (1H, m), 6.56 (1H, d, J=15.0 Hz), 7.11 (2H, d, J=8.1 Hz), 7.19 (2H, d, J=8.1 Hz), 7.33 (1H, d, J=15.0 Hz), 7.71 (1H, d, J=6.2 Hz), 7.96 (1H, s), 8.06 (1H, s)

EXAMPLE 88

To a solution of (2E)-3-(5-{[(3R)-1-(2,3-dimethylbenzyl)-3-pyrrolidinyl]amino}-2-pyrazinyl)-N-(tetrahydro-2H-pyran-2-yloxy)acrylamide (46 mg) in ethanol (1 mL) was added 2N hydrogen chloride in ethanol (0.26 mL). After stirring at room temperature for 2 hours, the reaction mixture was evaporated in vacuo and triturated with ethyl acetate to give (2E)-3-(5-{[(3R)-1-(2,3-dimethylbenzyl)-3-pyrrolidinyl]amino}-2-pyrazinyl)-N-hydroxyacrylamide dihydrochloride (31 mg).

$^1$H-NMR (300 MHz, DMSO-d6) δ 1.94-2.39 (8H, m), 3.04-4.69 (7H, m), 6.63 (1H, dd, J 2, 16 Hz), 7.12-7.27 (2H, m), 7.36-7.46 (2H, m), 8.01-8.24 (2H, m).

MS (ES+) m/z 368 (M+1).

EXAMPLE 89

To a mixture of (2E)-3-(5-{[(3R)-1-(4-chlorobenzoyl)-3-pyrrolidinyl]amino}-2-pyrazinyl)-N-(tetrahydro-2H-pyran-2-yloxy)acrylamide (288 mg) and ethanol (2.9 mL) was added 2N hydrogen chloride in ethanol (1.53 mL). After stirring at room temperature for 2 hours, resulting precipitate was collected by filtration, and washed with ethanol to give (2E)-3-(5-{[(3R)-1-(4-chlorobenzoyl)-3-pyrrolidinyl]amino}-2-pyrazinyl)-N-hydroxyacrylamide hydrochloride (138 mg).

$^1$H-NMR (300 MHz, DMSO-d6) δ 1.86-2.29 (2H, m), 3.26-3.84 (4H, m), 4.32-4.51 (1H, m), 6.56-6.66 (1H, m), 7.31-7.61 (5H, m), 7.98-8.17 (2H, m).

MS (ES+) m/z 388 (M+1).

The following compounds were obtained in a similar manner to that of Example 89.

EXAMPLE 90

(2E)-3-(5-{[(3R)-1-(2-chlorobenzyl)-3-pyrrolidinyl]amino}-2-pyrazinyl)-N-hydroxyacrylamide dihydrochloride $^1$H-NMR (300 MHz, DMSO-d6) δ 1.94-2.45 (2H, m), 3.10-4.66 (7H, m), 6.63 (1H, d, J=16 Hz), 7.40 (1H, d, J=16 Hz), 7.45-7.63 (3H, m), 7.85-8.18 (4H, m), 11.1 (1H, brs).

MS (ES+) m/z 374 (M+1).

EXAMPLE 91

(2E)-3-(5-{[(3R)-1-(3-chlorobenzyl)-3-pyrrolidinyl]amino}-2-pyrazinyl)-N-hydroxyacrylamide dihydrochloride $^1$H-NMR (300 MHz, DMSO-d6) δ 1.94-2.36 (2H, m), 3.01-3.80 (4H, m), 4.39-4.62 (3H, m), 6.63 (1H, d, J=16 Hz), 7.39 (1H, d, J=16 Hz), 7.44-7.63 (3H, m), 7.77 (1H, s), 8.00-8.29 (3H, m), 11.4 (1H, brs).

MS (ES+) m/z 374 (M+1).

EXAMPLE 92

To a solution of tert-butyl [(3R)-1-(cyclopentylmethyl)-3-pyrrolidinyl](5-{(1E)-3-oxo-3-[(tetrahydro-2H-pyran-2-yloxy)amino]-1-propen-1-yl}-2-pyridinyl)carbamate (179 mg, 0.35 mmol) in MeOH (1 mL) was added hydrogen chloride methanol reagent 10 (3 mL, Tokyo Kasei), and the mixture was stirred at ambient temperature for 1 hr. The solvent was removed in vacuo and the residue was dissolved in dioxane (1 mL). To the reaction mixture was added 4N HCl in dioxane (4 mL) and stirred for 1 hr at ambient temperature. To the reaction mixture was added MeCN and the solvent was removed in vacuo. Obtained colorless solid was triturated with MeCN to give (2E)-3-(6-{[(3R)-1-(cyclopentylmethyl)-3-pyrrolidinyl]amino}-3-pyridinyl)-N-hydroxyacrylamide dihydrochloride (115 mg, 85%) as colorless powder.

$^1$H-NMR (300 MHz, DMSO-d6) δ 1.16-1.40 (2H, m), 1.40-1.72 (4H, m), 1.72-1.93 (2H, m), 1.93-2.53 (3H, m), 3.07-3.36 (3H, m), 3.36-4.09 (3H, m), 4.52-4.75 (1H, m), 6.36 (1H, d, J=15.7 Hz), 6.88-7.08 (1H, m), 7.43 (1H, d, J=15.8 Hz), 7.91-8.01 (1H, m), 8.12 (1H, s);

The following compounds were obtained in a similar manner to that of Example 92.

EXAMPLE 93

(2E)-3-(6-{[(3R)-1-(cycloheptylmethyl)-3-pyrrolidinyl]amino}-3-pyridinyl)-N-hydroxyacrylamide dihydrochloride $^1$H-NMR (300 MHz, DMSO-d6) δ 1.15-1.34 (2H, m), 1.34-1.71 (7H, m), 1.71-1.99 (3H, m), 1.99-2.19 (1H, m), 2.25-2.65 (1H, m), 3.02-3.24 (3H, m), 3.24-3.92 (3H, m), 3.92-4.11 (1H, m), 4.53-4.76 (1H, m), 6.36 (1H, d, J=15.8 Hz), 6.87-7.06 (1H, m), 7.43 (1H, d, J=15.8 Hz), 7.92-8.03 (1H, m), 8.20 (1H, s), 10.27 (1H, br peak); MS (ES+) m/z 359.

EXAMPLE 94

(2Z)-3-(6-{[(3R)-1-(cyclohexylmethyl)-3-pyrrolidinyl]amino}-3-pyridinyl)-2-fluoro-N-hydroxyacrylamide dihydrochloride $^1$H-NMR (300 MHz, DMSO-d6) δ 0.85-1.06 (2H, m), 1.06-1.35 (3H, m), 1.54-1.78 (4H, m), 1.78-1.95 (2H, m), 1.95-2.18 (1H, m), 2.25-2.65 (1H, m), 2.97-4.09 (6H, m), 4.52-4.76 (1H, m), 6.73-7.00 (2H, m), 7.08 (1H, s), 7.25 (1H, s), 7.42 (1H, s), 7.95 (1H, d, J=8.6 Hz), 8.25 (1H, s);

MS (ES+) m/z 363.

EXAMPLE 95

(2E)-3-(6-{[(3R)-1-(1-adamantylmethyl)-3-pyrrolidinyl]amino}-3-pyridinyl)-N-hydroxyacrylamide dihydrochloride $^1$H-NMR (300 MHz, DMSO-d6) δ 1.55-1.75 (16H, m), 1.90-2.03 (3H, m), 2.03-2.16 (1H, m), 2.95-4.20 (3H, m), 4.53-4.80 (1H, m), 6.38 (1H, d, J=15.4 Hz), 6.89-7.12 (1H, m), 7.44 (1H, d, J=15.4 Hz), 8.00 (1H, d, J=9.5 Hz), 8.21 (1H, s).

EXAMPLE 96

To the solution of (2E)-3-(5-{[(3R)-1-(2-phenylethyl)-3-piperidinyl]amino}-2-pyrazinyl)-N-(tetrahydro-2H-pyran-2-yloxy)acrylamide (3.2 g, 7.1 mmol) in EtOH (16 ml) was added 2M ethanlic hydrogen chloride (17.5 mL) and the mixture was stirred at ambient temperature for 3 hrs. To the reaction mixture was added IPE and isolated precipitate was collected by filtration to give (2E)-N-hydroxy-3-(5-{[(3R)-1-(2-phenylethyl)-3-piperidinyl]amino}-2-pyrazinyl)acrylamide dihydrochloride (2.3 g, 74%) as an amorphous powder.

¹H-NMR (300 MHz, DMSO-d6) δ 1.40-1.61 (1H, m), 1.74-2.21 (3H, m), 2.60-2.80 (1H, m), 2.80-3.01 (1H, m), 3.01-3.14 (2H, m), 3.21-3.38 (2H, m), 3.38-3.75 (2H, m), 4.23-4.42 (1H, m), 6.64 (1H, d, J=15.2 Hz), 7.20-7.48 (6H, m), 7.84 (1H, br peak), 8.00-8.12 (1H, m), 8.12-8.26 (1H, m); MS (ES+) m/z 368.

The following compounds were obtained in a similar manner to that of Example 96.

EXAMPLE 97

(2E)-3-(6-{[(3R)-1-benzyl-3-piperidinyl]amino}-3-pyridinyl)-N-hydroxyacrylamide dihydrochloride ¹H-NMR (300 MHz, DMSO-d6) δ 1.30-1.66 (1H, m), 1.66-2.17 (3H, m), 2.60-4.00 (4H, m), 4.16-4.60 (3H, m), 6.21-6.44 (1H, m), 6.55-7.10 (2H, m), 7.32-7.67 (6H, m), 7.79-8.01 (1H, m), 8.11-8.38 (1H, m); MS (ES+) m/z 353.

EXAMPLE 98

(2E)-3-(6-{[(3R)-1-(cyclohexylmethyl)-3-pyrrolidinyl]amino}-3-pyridinyl)-N-hydroxy-2-methylacrylamide dihydrochloride ¹H-NMR (300 MHz, DMSO-d6) δ 0.80-1.04 (2H, m), 1.04-1.32 (4H, m), 1.53-1.75 (5H, m), 1.75-1.90 (2H, m), 1.90-2.20 (4H, m), 2.20-2.65 (1H, m), 3.00-3.20 (3H, m), 3.94-4.10 (1H, m), 4.51-4.73 (1H, m), 6.87-7.04 (2H, m), 7.85 (1H, d, J=9.0 Hz), 8.03 (1H, s); MS (ES+) m/z 359.

EXAMPLE 99

(2E)-3-(6-{[(3S)-1-(cyclohexylmethyl)-3-piperidinyl]amino}-3-pyridinyl)-N-hydroxyacrylamide dihydrochloride ¹H-NMR (300 MHz, DMSO-d6) δ 0.86-1.05 (2H, m), 1.05-1.35 (3H, m), 1.35-2.15 (10H, m), 2.65-3.10 (3H, m), 3.20-4.00 (3H, m), 4.30-4.62 (1H, m), 6.37 (1H, d, J=16.1 Hz), 6.90-7.11 (1H, m), 7.35-7.51 (1H, m), 7.90-8.10 (1H, m), 8.15-8.30 (1H, m);

EXAMPLE 100

(2E)-3-(6-{[(3R)-1-cyclohexyl-3-piperidinyl]amino}-3-pyridinyl)-N-hydroxyacrylamide dihydrochloride ¹H-NMR (300 MHz, DMSO-d6) δ 1.00-1.69 (8H, m), 1.75-2.15 (7H, m), 2.58-3.90 (4H, m), 4.25-4.55 (1H, m), 6.26-6.41 (1H, m), 6.80-7.05 (1H, m), 7.35-7.50 (1H, m), 7.85-8.06 (1H, m), 8.21 (1H, s); MS (ES+) m/z 345.

EXAMPLE 101

(2E)-3-(6-{[(3R)-1-(4-chlorobenzyl)-3-piperidinyl]amino}-3-pyridinyl)-N-hydroxyacrylamide dihydrochloride ¹H-NMR (300 MHz, DMSO-d6) δ 1.31-1.66 (1H, m), 1.73-2.19 (3H, m), 2.64-3.09 (2H, m), 3.09-4.00 (2H, m), 4.20-4.65 (3H, m), 6.35 (1H, d, J=15.7 Hz), 6.85-7.10 (1H, m), 7.41 (1H, d, J=16.0 Hz), 7.55 (2H, d, J=8.2 Hz), 7.65 (2H, d, J=7.8 Hz), 7.89-8.11 (1H, m), 8.19 (1H, s);

MS (ES+) m/z 387.

EXAMPLE 102

(2E)-3-(6-{[(3R)-1-cyclopentyl-3-piperidinyl]amino}-3-pyridinyl)-N-hydroxyacrylamide dihydrochloride ¹H-NMR (300 MHz, DMSO-d6) δ 1.41-1.64 (3H, m), 1.64-2.18 (10H, m), 2.72-4.00 (4H, m), 4.21-4.60 (1H, m), 6.30-6.44 (1H, m), 6.94-7.11 (1H, m), 7.36-7.50 (1H, m), 7.94-8.08 (1H, m), 8.15-8.25 (1H, m);

MS (ES+) m/z 331.

EXAMPLE 103

(2E)-N-hydroxy-3-(6-{[(3R)-1-(4-methylbenzyl)-3-piperidinyl]amino}-3-pyridinyly acrylamide dihydrochloride ¹H-NMR (300 MHz, DMSO-d6) δ 1.31-1.65 (1H, m), 1.74-2.16 (4H, m), 2.33 (3H, s), 2.65-4.20 (3H, m), 4.20-4.70 (3H, m), 6.40 (1H, d, J=15.9 Hz), 6.91-7.16 (1H, m), 7.27 (2H, d, J=7.7 Hz), 7.35-7.59 (3H, m), 7.95-8.12 (1H, m), 8.20 (1H, br s).

EXAMPLE 104

(2Z)-2-fluoro-N-hydroxy-3-(6-{[(3R)-1-(4-methylbenzyl)-3-pyrrolidinyl]amino}-3-pyridinyl)acrylamide dihydrochloride ¹H-NMR (300 MHz, DMSO-d6) δ 1.90-2.20 (2H, m), 2.20-2.40 (4H, m), 2.40-3.86 (3H, m), 4.24-4.76 (3H, m), 6.70-7.10 (2H, m), 7.20-7.30 (2H, m), 7.45-7.55 (2H, m), 7.91-8.06 (1H, m), 8.24 (1H, s);

MS (ES+) m/z 371.

EXAMPLE 105

(2Z)-3-(6-{[(3R)-1-(4-chlorobenzyl)-3-pyrrolidinyl]amino}-3-pyridinyl)-2-fluoro-N-hydroxyacrylamide dihydrochloride ¹H-NMR (300 MHz, DMSO-d6) δ 1.93-2.21 (2H, m), 2.21-4.00 (4H, m), 4.34-4.80 (3H, m), 6.70-7.15 (2H, m), 7.53 (2H, d, J=8.2 Hz), 7.62-7.75 (2H, m), 8.00 (1H, t, J=9.9 Hz), 8.22 (1H, s);

MS (ES+) m/z 391.

EXAMPLE 106

(2E)-3-(6-{[(3R)-1-(cyclohexylcarbonyl)-3-piperidinyl]amino}-3-pyridinyl)-N-hydroxyacrylamide hydrochloride ¹H-NMR (300 MHz, DMSO-d6) δ 0.96-1.94 (12H, m), 1.94-2.14 (1H, m), 2.38-2.67 (1H, m), 2.94-4.15 (6H, m), 6.39 (1H, d, J=16.0 Hz), 6.95-7.20 (1H, m), 7.45 (1H, d, J=16.3 Hz), 7.92-8.14 (1H, m), 8.20 (1H, br s);

MS (ES+) m/z 373.

EXAMPLE 107

(2E)-3-(6-{[(3R)-1-(4-chlorobenzoyl)-3-piperidinyl]amino}-3-pyridinyl)-N-hydroxyacrylamide hydrochloride ¹H-NMR (300 MHz, DMSO-d6) δ 1.37-2.14 (5H, m), 3.04-4.20 (4H, m), 6.41 (1H, d, J=15.9 Hz), 6.95-7.95 (7H, m), 7.95-8.38 (1H, m);

MS (ES+) m/z 401.

EXAMPLE 108

(2E)-3-(6-{[(3R)-1-(cyclohexylmethyl)-3-piperidinyl]amino}-3-pyridinyl)-N-hydroxyacrylamide dihydrochloride $^1$H-NMR (300 MHz, DMSO-d6) δ 0.85-1.07 (2H, m), 1.07-1.36 (3H, m), 1.36-2.15 (10H, m), 2.65-3.10 (3H, m), 3.20-4.10 (3H, m), 4.30-4.65 (1H, m), 6.39 (1H, d, J=16.1 Hz), 6.94-7.12 (1H, m), 7.34-7.51 (1H, m), 7.91-8.09 (1H, m), 8.15-8.30 (1H, m).

EXAMPLE 109

(2E)-3-(5-{[(3R)-1-(3-chlorobenzyl)-3-piperidinyl]amino}-2-pyrazinyl)-N-hydroxyacrylamide dihydrochloride $^1$H-NMR (300 MHz, DMSO-d6) δ 1.34-1.54 (1H, m), 1.74-2.15 (4H, m), 2.59-3.23 (2H, m), 3.23-3.58 (2H, m), 4.21-4.46 (2H, m), 6.61 (1H, d, J=15.2 Hz), 7.38 (1H, d, J=15.2 Hz), 7.45-7.65 (3H, m), 7.70-7.84 (2H, m), 7.96-8.06 (1H, m), 8.06-8.16 (1H, m);

MS (ES+) m/z 388.

EXAMPLE 110

(2E)-3-(5-{[(3R)-1-(4-fluorobenzyl)-3-piperidinyl]amino}-2-pyrazinyl)-N-hydroxyacrylamide dihydrochloride $^1$H-NMR (300 MHz, DMSO-d6) δ 1.30-1.54 (1H, m), 1.70-2.15 (4H, m), 2.55-2.75 (1H, m), 2.75-2.94 (1H, m), 3.22-3.36 (1H, m), 3.36-3.53 (1H, m), 4.17-4.45 (2H, m), 6.62 (1H, d, J=15.2 Hz), 7.25-7.45 (3H, m), 7.65-7.85 (3H, m), 7.96-8.19 (2H, m);

MS (ES+) m/z 372.

EXAMPLE 111

(2E)-N-hydroxy-3-(5-{[(3R)-1-(2-thienylmethyl)-3-piperidinyl]amino}-2-pyrazinyl)acrylamide dihydrochloride $^1$H-NMR (300 MHz, DMSO-d6) δ 1.31-1.60 (1H, m), 1.72-2.19 (4H, m), 2.56-3.25 (2H, m), 3.25-3.58 (2H, m), 4.18-4.40 (1H, m), 4.52-4.65 (2H, m), 6.62 (1H, d, J=15.2 Hz), 7.09-7.19 (1H, m), 7.34-7.46 (2H, m), 7.65-7.88 (2H, m), 7.96-8.20 (2H, m);

MS (ES+) m/z 360.

EXAMPLE 112

(2E)-N-hydroxy-3-(5-{[(3R)-1-(2-pyridinylmethyl)-3-piperidinyl]amino}-2-pyrazinyl)acrylamide trihydrochloride $^1$H-NMR (300 MHz, DMSO-d6) δ 1.40-1.65 (1H, m), 1.80-2.05 (3H, m), 2.86-3.03 (1H, m), 3.03-3.20 (1H, m), 3.28-3.45 (1H, m), 3.45-3.57 (1H, m), 4.25-4.38 (1H, m), 4.51 (2H, s), 6.61 (1H, d, J=15.3 Hz), 7.40 (1H, d, J=15.2 Hz), 7.50 (1H, dd, J=7.0, 5.4 Hz), 7.66 (1H, d, J=7.7 Hz), 7.85 (1H, br peak), 7.90-7.98 (1H, m), 8.02 (1H, s), 8.10 (1H, s), 8.65 (1H, d, J=4.6 Hz);

MS (ES+) m/z 355.

EXAMPLE 113

(2E)-N-hydroxy-3-(5-{[(3R)-1-(4-pyridinylmethyl)-3-piperidinyl]amino}-2-pyrazinyl)acrylamide trihydrochloride $^1$H-NMR (300 MHz, DMSO-d6) δ 1.34-1.59 (1H, m), 1.74-2.19 (3H, m), 2.61-2.84 (1H, m), 2.84-3.01 (1H, m), 3.25-3.46 (1H, m), 3.46-3.60 (1H, m), 4.30-4.50 (1H, m), 4.50-4.70 (2H, m), 6.62 (1H, d, J=15.3 Hz), 7.39 (1H, d, J=15.2 Hz), 7.30 (1H, br peak), 8.01 (1H, s), 8.07-8.22 (3H, m), 8.94 (2H, d, J=5.9 Hz);

MS (ES+) m/z 355.

EXAMPLE 114

(2E)-N-hydroxy-3-(5-{[(3R)-1-(3-pyridinylmethyl)-3-piperidinyl]amino}-2-pyrazinyl)acrylamide trihydrochloride $^1$H-NMR (300 MHz, DMSO-d6) (1.35-2.15 (4H, m), 2.56-3.80 (4H, m), 4.45-4.70 (3H, m), 6.61 (1H, d, J=15.2 Hz), 7.39 (1H, d, J=15.2 Hz), 7.80 (1H, br peak), 7.90-7.98 (1H, m), 8.01 (1H, s), 8.13 (1H, s), 8.55-8.72 (1H, m), 8.90 (1H, d, J=5.0 Hz), 9.02-9.12 (1H, m), 11.59 (1H, br peak);

MS (ES+) m/z 355.

EXAMPLE 115

(2E)-N-hydroxy-3-(5-{[(3R)-1-(3-thienylmethyl)-3-piperidinyl]amino}-2-pyrazinyl)acrylamide dihydrochloride $^1$H-NMR (300 MHz, DMSO-d6) δ 1.31-1.54 (1H, m), 1.70-2.15 (3H, m), 2.54-3.21 (2H, m), 3.21-3.55 (2H, m), 4.20-4.43 (3H, m), 6.61 (1H, d, J=15.5 Hz), 7.30-7.45 (2H, m), 7.59-7.70 (1H, m), 7.70-85 (2H, m), 7.96-8.08 (1H, m), 8.08-8.17 (1H, m);

MS (ES+) m/z 360.

EXAMPLE 116

(2E)-3-(5-{[(3R)-1-(4-fluorobenzyl)-3-pyrrolidinyl]amino}-2-pyrazinyl)-N-hydroxyacrylamide dihydrochloride $^1$H-NMR (300 MHz, DMSO-d6) δ 1.87-2.16 (1H, m), 2.16-2.60 (1H, m), 2.96-3.11 (1H, m), 3.11-4.10 (3H, m), 4.32-4.51 (2H, m), 4.57 (1H, br peak), 6.63 (1H, d, J=15.2 Hz), 7.22 (2H, t-like, J=8.8 Hz), 7.39 (1H, d, J=15.2 Hz), 7.67 (2H, t-like, J=6.7 Hz), 7.90-8.16 (2H, m), 8.21 (1H, br peak); MS (ES+) m/z 358.

EXAMPLE 117

(2E)-3-(5-{[(3R)-1-(cycloheptylmethyl)-3-piperidinyl]amino}-2-pyrazinyl)-N-hydroxyacrylamide dihydrochloride $^1$H-NMR (300 MHz, DMSO-d6) δ 1.11-1.31 (2H, m), 1.31-1.69 (8H, m), 1.69-1.84 (2H, m), 1.84-2.06 (3H, m), 2.56-2.78 (1H, m), 2.78-3.09 (3H, m), 3.09-4.00 (4H, m), 4.30 (1H, br peak), 6.62 (1H, d, J=15.4 Hz), 7.40 (1H, d, J=15.4 Hz), 7.73-7.85 (1H, m), 7.98-8.10 (1H, m), 8.15 (1H, s), 9.52 (1H, br peak);

MS (ES+) m/z 374.

EXAMPLE 118

(2E)-3-(5-{[(3R)-1-cycloheptyl-3-piperidinyl]amino}-2-pyrazinyl)-N-hydroxyacrylamide dihydrochloride $^1$H-NMR (300 MHz, DMSO-d6) δ 1.30-2.25 (16H, m), 2.57-3.50 (5H, m), 4.24-4.40 (1H, m), 6.64 (1H, d, J=15.2 Hz), 7.40 (1H, d, J=15.2 Hz), 7.75 (1H, br peak), 7.98-8.10 (1H, m), 8.10-8.17 (1H, m);

MS (ES+) m/z 360.

EXAMPLE 119

(2E)-N-hydroxy-3-(5-{[(3R)-1-(2-phenylethyl)-3-pyrrolidinyl]amino}-2-pyrazinyl)acrylamide dihydrochloride $^1$H-NMR (300 MHz, DMSO-d6) δ 1.94-2.16 (1H, m), 2.16-2.70 (1H, m), 2.96-3.14 (2H, m), 3.14-4.10 (6H, m), 4.41-4.61 (1H, m), 6.64 (1H, d, J=15.2 Hz), 7.23-7.50 (5H, m), 8.05 (1H, s), 8.11-8.24 (1H, m);

MS (ES+) m/z 354.

EXAMPLE 120

(2E)-N-hydroxy-3-(5-{[(3R)-1-(2-pyrimidinyl)-3-piperidinyl]amino}-2-pyrazinyl)acrylamide dihydrochloride $^1$H-NMR (300 MHz, DMSO-d6) δ 1.45-1.72 (2H, m), 1.76-1.94 (1H, m), 1.94-2.10 (1H, m), 3.20-3.44 (2H, m), 3.88-4.04 (1H, m), 4.15-4.26 (1H, m), 4.42 (1H, dd, J=12.6, 3.4 Hz), 6.60 (1H, d, J=15.3 Hz), 6.68 (1H, t, J=4.8 Hz), 7.38 (1H, d, J=15.2 Hz), 7.80 (1H, br peak), 8.04 (1H, s), 8.13 (1H, s), 8.40 (1H, d, J=4.8 Hz);

MS (ES+) m/z 342.

EXAMPLE 121

(2E)-3-(5-{[(3R)-1-(2,3-dihydro-1H-inden-2-yl)-3-piperidinyl]amino}-2-pyrazinyl)-N-hydroxyacrylamide dihydrochloride $^1$H-NMR (300 MHz, DMSO-d6) δ 1.44-1.64 (1H, m), 1.76-2.20 (3H, m), 2.68-3.17 (2H, m), 3.17-3.41 (4H, m), 3.41-3.54 (1H, m), 3.54-3.65 (1H, m), 4.05-4.24 (1H, m), 4.24-4.41 (1H, m), 6.58-6.69 (1H, m), 7.14-7.31 (4H, m), 7.40 (1H, d, J=15.4 Hz), 7.99-8.11 (1H, m), 8.18 (1H, s);

MS (ES+) m/z 380.

EXAMPLE 122

(2Z)-3-(6-{[(3R)-1-cyclohexyl-3-pyrrolidinyl]amino}-3-pyridinyl)-2-fluoro-N-hydroxyacrylamide dihydrochloride $^1$H-NMR (300 MHz, DMSO-d6) δ 1.01-1.35 (3H, m), 1.35-1.54 (2H, m), 1.54-1.69 (1H, m), 1.72-1.89 (2H, m), 1.94-2.36 (4H, m), 3.02-4.10 (5H, m), 4.50-4.70 (1H, m), 6.75-7.07 (2H, m), 7.94-8.08 (1H, m), 8.26 (1H, s); MS (ES+) m/z 349.

EXAMPLE 123

To a solution of (2E)-3-(5-{[(3R)-1-cyclohexyl-3-pyrrolidinyl]amino}-2-pyrazinyl)-N-(tetrahydro-2H-pyran-2-yloxy)acrylamide (274 mg) in methanol (6.6 mL) was added hydrogen chloride in methanol (0.659 mL). After stirring at room temperature for 1 hour, the reaction mixture was evaporated in vacuo and triturated with ethyl acetate to give (2E)-3-(5-{[(3R)-1-cyclohexyl-3-pyrrolidinyl]amino}-2-pyrazinyl)-N-hydroxyacrylamide dihydrochloride (252 mg).

$^1$H-NMR (300 MHz, DMSO-d6) δ 1.01-4.59 (18H, m), 6.63 (1H, d, J=16 Hz), 7.40 (1H, d, J=16 Hz), 8.01-8.19 (2H, m).

MS (ES+) m/z 332 (M+1).

The following compounds were obtained in a similar manner to that of Example 123.

EXAMPLE 124

(2E)-3-(2-{[(3R)-1-benzyl-3-pyrrolidinyl]amino}-5-pyrimidinyl)-N-hydroxyacrylamide dihydrochloride $^1$H-NMR (300 MHz, DMSO-d6) δ 1.93-4.67 (9H, m), 6.37 (1H, d, J=16 Hz), 7.32 (1H, d, J=16 Hz), 7.41-7.65 (5H, m), 8.56 (2H, s).

MS (ES+) m/z 340 (M+1).

EXAMPLE 125

(2E)-3-(5-{[(3R)-1-benzyl-3-pyrrolidinyl]amino}-6-methyl-2-pyrazinyl)-N-hydroxyacrylamide dihydrochloride $^1$H-NMR (300 MHz, DMSO-d6) δ 2.01-4.83 (12H, m), 6.64 (1H, d, J=16 Hz), 7.18-7.27 (1H, m), 7.37 (1H, d, J=16 Hz), 7.42-7.51 (3H, m), 7.59-7.68 (2H, m), 8.03 (1H, s).

MS (ES+) m/z 354 (M+1).

EXAMPLE 126

(2E)-3-(6-{[(3R)-1-benzyl-3-pyrrolidinyl]amino}-3-pyridazinyl)-N-hydroxyacrylamide dihydrochloride $^1$H-NMR (300 MHz, DMSO-d6) δ 2.02-4.76 (9H, m), 6.74-6.83 (1H, m), 7.28-7.69 (7H, m), 7.84-7.97 (1H, m), 10.2 (1H, brs), 11.4 (1H, brs).

MS (ES+) m/z 340 (M+1).

EXAMPLE 127

(2E)-N-hydroxy-3-(6-{[(3R)-1-phenyl-3-pyrrolidinyl]amino}-3-pyridinyl)acrylamide dihydrochloride $^1$H-NMR (300 MHz, DMSO-d6) δ 2.04-2.16 (1H, m), 2.33-2.46 (1H, m), 3.29-4.65(5H, m), 6.42 (1H, d, J=16 Hz), 6.56-6.68 (3H, m), 7.12-7.24 (3H, m), 7.49 (1H, d, J=16 Hz), 8.06-8.13 (1H, m), 8.23 (1H, brs).

MS (ES+) m/z 323 (M−1).

EXAMPLE 128

(2E)-3-(6-{[(3R)-1-(cyclohexylmethyl)-3-pyrrolidinyl]amino}-3-pyridazinyl)-N-hydroxyacrylamide dihydrochloride $^1$H-NMR (300 MHz, DMSO-d6) δ 0.88-1.02 (2H, m), 1.09-4.79 (18H, m), 6.76-6.85 (1H, m), 7.35-7.56 (2H, m), 7.89-7.98 (1H, m), 10.6 (1H, brs).

MS (ES+) m/z 346 (M+1).

EXAMPLE 129

2M ethanolic hydrogen chloride (2.0 mL) was added to the solution of (2Z)-3-(5-chloro-6-{[(3R)-1-(cyclohexylmethyl)-3-piperidinyl]amino}-3-pyridinyl)-2-fluoro-N-(tetrahydro-2H-pyran-2-yloxy)acrylamide (0.5 g) in EtOH (5 ml) and the mixture was stirred at ambient temperature for 3 hrs. To the reaction mixture was added AcOEt and isolated precipitate was collected by filtration to give (2Z)-3-(5- chloro-6-{[(3R)-1-(cyclohexylmethyl)-3-piperidinyl]amino}-3-pyridinyl)-2-fluoro-N-hydroxyacrylamide dihydrochloride (0.28 g), (+)ESI-MS: 411(M+H)+.

The following compounds were obtained in a similar manner to that of Example 129.

EXAMPLE 130

(2E)-3-(2-{[(3R)-1-(cyclohexylmethyl)-3-pyrrolidinyl]amino}-1,3-thiazol-4-yl)-N-hydroxyacrylamide dihydrochloride $^1$H-NMR(DMSO-d6): δ 0.81-1.40(6H, m), 1.49-2.62(8H, m), 2.97-4.09(5H, m), 4.37-4.66(1H, m), 6.49-6.50(total 1H, each d, J=each 15.2 Hz), 7.09(1H, s), 7.20(1H, d, J=15.2 Hz), (+)ESI-MS: 351(M+H)+.

EXAMPLE 131

(2Z)-3-(6-{[(3R)-1-benzyl-3-piperidinyl]amino}-5-chloro-3-pyridinyl)-2-fluoro-N-hydroxyacrylamide dihydrochloride $^1$H-NMR(DMSO-d6): δ 1.48-2.09(4H, m), 2.66-3.42(4H, m), 4.31-4.47(2H, m), 4.62 and 4.75(total 1H, each s), 6.78 and 6.81(total 1H, each d, J=each 39.8 Hz), 6.94(1H, d, J=6.3 Hz), 7.43-7.50(3H, m), 7.62-7.74(2H, m), 7.88 and 7.90(total 1H, each d, J=each 1.9 Hz), 8.26 and 8.28(total 1H, each d, J=each 1.9 Hz), 11.34 and 11.66(total 1H, each s), (+)ESI-MS: 405(M+H)+.

EXAMPLE 132

(2Z)-3-(5-chloro-6-{[(3R)-1-cyclopentyl-3-piperidinyl]amino}-3-pyridinyl)-2-fluoro-N-hydroxyacrylamide dihydrochloride (+)ESI-MS: 383(M+H)+.

EXAMPLE 133

(2Z)-3-(5-chloro-6-{[(3R)-1-cyclohexyl-3-piperidinyl]amino}-3-pyridinyl)-2-fluoro-N-hydroxyacrylamide dihydrochloride (+)ESI-MS: 397(M+H)+.

EXAMPLE 134

(2Z)-3-(6-{[(3R)-1-benzyl-3-piperidinyl]amino}-3-pyridinyl)-2-fluoro-N-hydroxyacrylamide dihydrochloride (+)ESI-MS: 371(M+H)+.

EXAMPLE 135

(2Z)-3-(6-{[(3R)-1-(cyclohexylmethyl)-3-piperidinyl]amino}-3-pyridinyl)-2-fluoro-N-hydroxyacrylamide dihydrochloride $^1$H-NMR(DMSO-d6): δ 0.89-1.02(2H, m), 1.06-1.30(3H, m), 1.44-2.16(10H, m), 2.75-3.67(6H, m), 4.41 and 4.67(total 1H, each s), 6.87 and 6.89(total 1H, each d, J=each 39.2 Hz), 7.04-7.14(1H, m), 8.01-8.11(1H, m), 8.20-8.29(1H, m), (+)ESI-MS: 377(M+H)+.

EXAMPLE 136

(2Z)-3-(6-{[(3R)-1-cyclopentyl-3-piperidinyl]amino}-3-pyridinyl)-2-fluoro-N-hydroxyacrylamide dihydrochloride $^1$H-NMR(DMSO-d6): δ 1.45-2.15(12H, m), 2.79-3.09(2H, m), 3.34-3.66(3H, m), 4.31 and 4.67(total 1H, each s), 6.88 and 6.89(total 1H, each d, J=each 39.1 Hz), 7.07-7.15(1H, m), 8.04-8.13(1H, m), 8.20-8.30(1H, m), (+)ESI-MS: 349(M+H)+.

EXAMPLE 137

(2Z)-3-(6-{[(3R)-1-cyclohexyl-3-piperidinyl]amino}-3-pyridinyl)-2-fluoro-N-hydroxyacrylamide dihydrochloride $^1$H-NMR(DMSO-d6): δ 1.02-1.66(7H, m), 1.74-2.26(7H, m), 2.82-3.59(5H, m), 4.41 and 4.69(total 1H, each s), 6.89 and 6.90(total 1H, each d, J=each 39.0 Hz), 7.09-7.18(1H, m), 8.05-8.14(1H, m), 8.21 and 8.27(total 1H, each s)

(+)ESI-MS: 363(M+H)+.

EXAMPLE 138

A mixture of (2E)-3-(5-{[(3R)-1-benzyl-3-pyrrolidinyl]amino}-2-pyridinyl)-N-(tetrahydro-2H-pyran-2-yloxy)acrylamide (185 mg) and 2NHCl/EtOH (9 ml, 20 eq.) was stirred at room temperature for 3 hours. After then, IPE (50 ml) was added and stirred. Precipitate was filtered, washed with IPE, and dried to give 486 mg (95%) of (2E)-3-(5-{[(3R)-1-benzyl-3-pyrrolidinyl]amino}-2-pyridinyl)-N-hydroxyacrylamide dihydrochloride as a powder.

MASS (ESI+): m/z=339.13 (M+1).

$^1$HNMR (400 MHz, DMSO-d6): δ 1.90-2.10 (2H, m), 2.25-2.60 (2H, m), 3.10-3.40 (2H, m), 4.31 (1H, br.s), 4.42 (2H, d, J=6.0 Hz), 6.74 (1H, d, J=13.9 Hz), 7.44 (5H, s), 7.64 (2H, m), 7.80 (1H, m), 8.07 (d, 13.9 Hz).

EXAMPLE 139

To a solution of (2E)-3-(5-{[(3R)-1-(3-methoxybenzyl)-3-pyrrolidinyl]amino}-2-pyrazinyl)-N-(tetrahydro-2H-pyran-2-yloxy)acrylamide (240 mg) in ethanol (3.6 mL) was added 2N HCl-EtOH (10.1 mL), which was stirred at room temperature for 1 hour. To the resultant was added ethyl acetate (9.6 mL), which was stirred for 1 hour. The precipitate was filtered to give (2E)-N-hydroxy-3-(5-{[(3R)-1-(3-methoxybenzyl)-3-pyrrolidinyl]amino}-2-pyrazinyl)acrylamide dihydrochloride (223 mg) as a yellow powder.

$^1$H NMR (400 MHz, DMSO-d6) δ 1.94-2.58 (2H, m), 2.96-5.02 (10H, m), 6.63 (1H, dd, J=2.6, 15.2 Hz), 6.99 (1H, d, J=8.2 Hz), 7.15 (1H, d, J=6.4 Hz), 7.26-7.45 (3H, m), 8.00-8.34 (3H, m), 11.32 (1H, br);

MS (ES+) m/z 370 (M+1).

The following compounds were obtained in a similar manner to that of Example 139.

EXAMPLE 140

(2E)-3-(5-{[(3R)-1-(3-cyanobenzyl)-3-pyrrolidinyl]amino}-2-pyrazinyl)-N-hydroxyacrylamide dihydrochloride $^1$H NMR (DMSO-d6, 400 MHz) δ 1.19-2.40 (2H, m), 3.01-3.82 (4H, m), 3.95-5.05 (3H, m), 6.29 (1H, dd, J=2.5, 15.3

Hz), 7.39 (1H, d, J=15.3 Hz), 7.67 (1H, dt, J=1.8, 7.8 Hz), 7.93 (1H, d, J=7.9 Hz), 7.96-8.11 (3H, m), 8.11-8.38 (2H, m), 11.45-11.64 (1H, m);

MS (ES+) 365 (M+1).

EXAMPLE 141

(2E)-3-[5-({(3R)-1-[3-(acetylamino)benzyl]-3-pyrrolidinyl}amino)-2-pyrazinyl]-N-hydroxyacrylamide dihydrochloride ¹H NMR (DMSO-d6, 400 MHz) δ 1.92-2.39 (5H, m), 2.97-3.79 (4H, m), 3.81-4.68 (3H, m), 6.63 (1H, dd, J=2.9, 15.4 Hz), 7.23-7.45 (3H, m), 7.53 (1H, d, J=7.3 Hz), 7.85 (1H, d, J=9.0 Hz), 7.97-8.33 (3H, m), 10.18 (1H, s), 11.0.4 (1H, br);

MS (ES+) m/z 397 (M+1).

EXAMPLE 142

(2E)-3-[5-({(3R)-1-[3-(dimethylamino)benzyl]-3-pyrrolidinyl}amino)-2-pyrazinyl]-N-hydroxyacrylamide trihydrochloride ¹H NMR (DMSO-d6, 400 MHz) δ 1.92-2.84 (2H, m), 2.88-4.80 (13H, m), 6.65 (1H, d, J=15.3 Hz), 6.83-7.55 (5H, m), 7.94-8.36 (3H, m), 11.32 (1H, br);

MS (ES+) m/z 383 (M+1).

EXAMPLE 143

(2E)-N-hydroxy-3-(5-{[(3R)-1-{3-[(methylsulfonyl)amino]benzyl}-3-pyrrolidinyl]amino}-2-pyrazinyl)acrylamide dihydrochloride ¹H NMR (DMSO-d6, 400 MHz) δ 1.90-2.59 (2H, m), 3.08 (3H, s), 3.15-4.81 (7H, m), 6.63 (1H, dd, J=2.8, 15.2 Hz), 7.21 (1H, dd, J=2.0, 7.2 Hz), 7.32-7.47 (4H, m), 7.98-8.41 (3H, m), 9.9.8 (1H, s), 11.30 (1H, br); MS (ES+) m/z 433 (M+1).

EXAMPLE 144

(2E)-N-hydroxy-3-(5-{[(3R)-1-(2-methoxybenzyl)-3-pyrrolidinyl]amino}-2-pyrazinyl)acrylamide dihydrochloride ¹H NMR (DMSO-d6, 400 MHz) δ 1.94-2.43 (2H, m), 2.93-5.02 (10H, m), 6.60 (1H, dd, J=3.3, 15.3 Hz), 6.96-7.07 (1H, m), 7.11 (1H, t, J=9.0 Hz), 7.33-7.49 (2H, m), 7.50-7.61 (1H, m), 7.99-8.37 (3H, m), 10.72 (1H, br);

MS (ES+) m/z 369 (M+1).

EXAMPLE 145

(2E)-N-hydroxy-3-(5-{[(3R)-1-(2-hydroxybenzyl)-3-pyrrolidinyl]amino}-2-pyrazinyl)acrylamide dihydrochloride ¹H NMR (DMSO-d6, 400 MHz) δ 1.92-2.59 (2H, m), 3.01-4.73 (7H, m), 6.63 (1H, d, J=15.3 Hz), 6.81-6.93 (1H, m), 6.78 (1H, t, J=8.2 Hz), 7.26 (1H, t, J=7.5 Hz), 7.39 (1H, d, J=15.3 Hz), 7.42-7.51 (1H, m), 8.00-8.30 (2H, m), 10.22-10.69 (2H, m);

MS (ES+) m/z 356 (M+1).

EXAMPLE 146

(2E)-N-hydroxy-3-(5-{[(3R)-1-(3-hydroxybenzyl)-3-pyrrolidinyl]amino}-2-pyrazinyl)acrylamide dihydrochloride ¹H NMR (DMSO-d6, 400 MHz) δ 1.93-2.40 (2H, m), 2.99-3.80 (4H, m), 4.17-5.38 (3H, m), 6.63 (1H, dd, J=2.4, 15.2 Hz), 6.84 (1H, d, J=7.9 Hz), 6.93-7.08 (2H, m), 7.22 (1H, dt, J=2.1, 7.8 Hz), 7.38 (1H, d, J=15.3 Hz), 7.98-8.45 (3H, m), 11.16 (1H, br), MS (ES+) m/z 356 (M+1).

EXAMPLE 147

(2E)-N-hydroxy-3-(5-{[(3R)-1-(3-isopropoxybenzyl)-3-pyrrolidinyl]amino}-2-pyrazinyl)acrylamide dihydrochloride ¹H NMR (DMSO-d6, 400 MHz) δ 1.23-1.32 (6H, m), 1.94-2.56 (2H, m), 2.95-3.29 (4H, m), 3.86-4.84 (4H, m), 6.63 (1H, dd, J=2.9, 15.3 Hz), 6.95 (1H, dd, J=2.1, 8.1 Hz), 7.11 (1H, d, J=7.0 Hz), 7.21-7.49 (3H, m), 7.98-8.45 (3H, m), 11.35 (1H, br);

MS (ES+) m/z 398 (M+1).

EXAMPLE 148

A mixture of (2E)-3-(5-{[(3R)-1-(2-fluorobenzyl)-3-pyrrolidinyl]amino}-2-pyrazinyl)-N-(tetrahydro-2H-pyran-2-yloxy)acrylamide (600 mg) and 2N HCl/Ethanol (13.6 ml, 20 eq) was stirred at room temperature for 2 hours. After then, ethyl acetate (10 ml) and IPE (50 ml) was added and stirred. Precipitate was filtered, washed with IPE, and dried under reduced pressure to give 486 mg (83%) of (2E)-3-(5-{[(3R)-1-(2-fluorobenzyl)-3-pyrrolidinyl]amino}-2-pyrazinyl)-N-hydroxyacrylamide dihydrochloride as a powder.

MASS (ESI+): m/z=358.3(M+1).

¹HNMR (400 MHz, DMSOd6, δ): δ 1.96-2.37 (2H, m), 3.05-3.85 (4H, m), 4.47 (1H, d, J=5.5 Hz), 4.51 (1H, d, J=5.5 Hz), 4.59 (m, 1H), 6.63 (1H, dd, J=2.6 Hz and 15.1 Hz), 7.28-7.39 (2H, m), 7.39 (1H, d, J=15.1 Hz), 7.49-7.56 (1H, m), 7.72-7.79 (1H, m) 8.02 (1H, d, J=8.3 Hz), 8.14 (1H, s), 11.12 (1H, br.s).

EXAMPLE 149

A mixture of (2E)-3-(5-{[(3R)-1-(3-fluorobenzyl)-3-pyrrolidinyl]amino}-2-pyrazinyl)-N-(tetrahydro-2H-pyran-2-yloxy)acrylamide (700 mg) and 2N HCl/Ethanol (16.4 ml) was stirred for 2 hrs.

EtOAc (10 ml) and IPE (50 ml) was added and stirred. After 1 hr, precipitate was filtered and dried to give 565 mg of (2E)-3-(5-{[(3R)-1-(3-fluorobenzyl)-3-pyrrolidinyl]amino}-2-pyrazinyl)-N-hydroxyacrylamide dihydrochloride as a powder.

MASS (ESI+): m/z=358.3 (M+1).

¹HNMR (400 MHz, CDCl₃): δ 1.96-2.56 (2H, m), 3.03-3.80 (4H, m), 4.43 (1H, d, J=5.7 Hz), 4.49 (1H, d, J=5.7 Hz), 4.60 (m, 1H), 6.63 (1H, dd, J=2.2 Hz and 15.3 Hz), 7.25-7.32 (1H, m), 7.39 (1H, d, J=15.3 Hz), 7.46-7.54 (2H, m), 7.59 (1H, d, J=10.0 Hz), 8.03, 8.10 (1H, s), 8.14 (1H, s), 11.48-11.73 (1H, m).

EXAMPLE 150 i) To a solution of tert-butyl [(3R)-1-(2-ethylbutyl)-3-pyrrolidinyl](5-{(1E)-3-oxo-3-[(tetrahydro-2H-pyran-2-yloxy)amino]-1-propen-1-yl}-2-pyridinyl)carbamate (128 mg) in methanol (2.5 mL) was added hydrogen chloride in methanol (0.248 mL). After stirring at room temperature for 1 hour, the reaction mixture was evaporated in vacuo.

ii) To a mixture of above product and dioxane (2.5 mL) was added 4N hydrogen chloride in dioxane (1.02 mL). After stirring at room temperature for 2 hours, the reaction mixture was evaporated in vacuo and triturated with ethyl acetate to give (2E)-3-(6-{[(3R)-1-(2-ethylbutyl)-3-pyrrolidinyl]amino}-3-pyridinyl)-N-hydroxyacrylamide dihydrochloride (92.0 mg).

$^1$H-NMR (300 MHz, DMSO-d6) δ 0.85 (6H, t, J=7 Hz), 1.28-1.52 (4H, m), 1.58-1.72 (1H, m), 2.02-2.15 (1H, m), 2.32-2.67 (2H, m), 3.06-4.78 (6H, m), 6.37 (1H, d, J=16 Hz), 6.91-7.08 (1H, m), 7.43 (1H, d, J=16 Hz), 7.94-8.02 (1H, m), 8.21 (1H, brs), 10.4 (1H, brs).

MS (ES+) m/z 333 (M+1).

The following compounds were obtained in a similar manner to that of Example 150.

EXAMPLE 151

(2E)-3-(6-{[(3R)-1-(3,4-dimethylbenzyl)-3-pyrrolidinyl]amino}-3-pyridinyl)-N-hydroxyacrylamide $^1$H-NMR (300 MHz, DMSO-d6) δ 1.87-4.62 (15H, m), 6.23 (1H, d, J=16 Hz), 6.57 (1H, d, J=8 Hz), 7.15-7.69 (5H, m), 8.15 (1H, brs), 8.93 (1H, brs), 10.7 (1H, brs), 11.0 (1H, brs).

MS (ES+) m/z 367 (M+1).

EXAMPLE 152

(2E)-N-hydroxy-3-(6-{[(3R)-1-(2-phenoxyethyl)-3-pyrrolidinyl]amino}-3-pyridinyl)acrylamide dihydrochloride $^1$H-NMR (300 MHz, DMSO-d6) δ 2.01-4.75 (11H, m), 6.33-6.42 (1H, m), 6.96-7.07 (4H, m), 7.29-7.47 (3H, m), 7.92-8.01 (1H, m), 8.21 (1H, brs).

MS (ES+) m/z 3.69 (M+1).

EXAMPLE 153

(2E)-3-(6-{[(3R)-1-butyl-3-pyrrolidinyl]amino}-3-pyridinyl)-N-hydroxyacrylamide dihydrochloride $^1$H-NMR (300 MHz, DMSO-d6) δ 0.91 (3H, t, J=7 Hz), 1.26-1.40 (2H, m), 1.57-1.71 (2H, m), 1.95-4.73 (9H, m), 6.37 (1H, d, J=16 Hz), 6.90-7.07 (1H, m), 7.43 (1H, d, J=16 Hz), 7.93-8.02 (1H, m), 8.21 (1H, brs).

MS (ES+) m/z 305 (M+1).

EXAMPLE 154

(2E)-N-hydroxy-3-(6-{[(3R)-1-isobutyl-3-pyrrolidinyl]amino}-3-pyridinyl)acrylamide dihydrochloride $^1$H-NMR (300 MHz, DMSO-d6) δ 1.00 (6H, d, J=7 Hz), 1.95-2.15 (2H, m), 2.31-2.60 (2H, m), 3.02-4.76 (6H, m), 6.37 (1H, d, J=16 Hz), 6.90-7.08 (1H, m), 7.43 (1H, d, J=16 Hz), 7.93-8.02 (1H, m), 8.21 (1H, brs), 10.4 (1H, brs).

MS (ES+) m/z 305 (M+1).

EXAMPLE 155

To a solution of ethyl (2E)-3-(5-{[(3R)-1-(benzyloxy)-6-oxo-3-piperidinyl]amino}-2-pyrazinyl)acrylate (200 mg, 0.50 mmol) in methanol (5 mL) was added hydroxylamine hydrochloride (175 mg, 2.52 mmol) at ambient temperature under nitrogen. After cooling, 1M sodium methanolate in methanol (5 mL) was added dropwise to the mixture over 1 h, the reaction mixture was stirred at 0° C. for 2 hrs and at ambient temperature for 4 hrs. The reaction mixture was adjusted to PH 6.0 with 1 mol/L hydrochloric acid and evaporated in vacuo. The residue was dissolved in ethanol and the precipitate was removed by filtration. The solvent was evaporated in vacuo. The residue was purified by preparative HPLC (CH$_3$CN, 20% NH$_4$HCO$_3$/30%-90%, gradient) to give (2E)-3-(5-{[(3R)-1-(benzyloxy)-6-oxo-3-piperidinyl]amino}-2-pyrazinyl)-N-hydroxyacrylamide (15 mg, 8%) as a powder.

$^1$H-NMR (300 MHz, CD$_3$OD) δ 1.78-1.98 (1H, m), 1.98-2.15 (1H, m), 2.44-2.74 (2H, m), 3.40 (1H, dd, J=11.4, 5.9 Hz), 3.76 (1H, dd, J=11.4, 4.0 Hz), 4.31 (1H, br peak), 4.93 (2H, s), 6.66 (1H, d, J=15.4 Hz), 7.20-7.33 (3H, m), 7.33-7.43 (2H, m), 7.48 (1H, d, J=15.4 Hz), 7.94 (1H, s), 8.03 (1H, s);

MS (ES+) m/z 384.

The following compounds were obtained in a similar manner to that of Example 129.

EXAMPLE 156

(2E)-N-hydroxy-3-(5-{[(3R)-1-(phenylacetyl)-3-piperidinyl]amino}-2-pyrazinyl)acrylamide hydrochloride $^1$H-NMR (300 MHz, CD$_3$OD) δ 1.19-2.21 (4H, m), 3.12-3.49 (2H, m), 3.70-4.01 (4H, m), 4.24-4.35 (1H, m), 6.76-6.90 (1H, m), 7.09-7.41 (5H, m), 7.48-7.58 (1H, m), 8.01 (0.6H, br.s), 8.06 (0.4H, br.s), 8.18 (0.4H, br.s), 8.45 (0.6H, br.s).

EXAMPLE 157

(2E)-N-hydroxy-3-(5-{[(3R)-1-(3-methylbenzyl)-3-pyrrolidinyl]amino}-2-pyrazinyl)acrylamide dihydrochloride $^1$H-NMR (300 MHz, DMSO-d6) δ 1.90-2.15 (1H, m), 2.31 (1.5H, s), 2.33 (1.5H, s), 2.98-3.80 (5H, m), 4.30-4.66 (3H, m), 6.58-6.68 (1H, m), 7.21-7.46 (5H, m), 8.00-8.35 (3H, m);

MS (ES+) m/z 354(M+1, free).

EXAMPLE 158

(2E)-N-hydroxy-3-(6-{[(3R)-1-(2,2,6,6-tetramethyl-4-piperidinyl)-3-pyrrolidinyl]amino}-3-pyridinyl)acrylamide trihydrochloride $^1$H-NMR (300 MHz, DMSO-d6) δ 1.43 (3H, s), 1.49 (9H, s), 1.78-2.32 (6H, m), 3.04-4.85 (6H, m), 6.32-6.46 (1H, m), 6.86-7.27 (1H, m), 7.39-7.52 (1H, m), 7.91-8.12 (1H, m), 8.14-8.35 (2H, m), 9.51-9.78 (1H, m);

MS (ES+) m/z 388(M+1, free).

EXAMPLE 159

(2E)-N-hydroxy-3-(6-{[(3R)-1-(tetrahydro-2H-pyran-4-yl)-3-pyrrolidinyl]amino}-3-pyridinyl)acrylamide dihydrochloride $^1$H-NMR (300 MHz, DMSO-d6) δ 1.61-1.86 (2H, m), 1.87-2.41 (8H, m), 3.06-4.21 (5H, m), 4.49-4.73 (1H, m), 6.36 (1H, d, J=16.1 Hz), 6.84-7.09 (1H, m), 7.43 (1H, d, J=16.1 Hz), 7.89-8.05 (1H, m), 8.21 (1H, s);

MS (ES+) m/z 333(M+1, free).

EXAMPLE 160

(2E)-3-(5-chloro-6-{[(3R)-1-(cyclohexylmethyl)-3-piperidinyl]amino}-3-pyridinyl)-N-hydroxyacrylamide dihydrochloride $^1$H-NMR (300 MHz, DMSO-d6) δ 0.84-1.05 (2H, m), 1.07-1.34 (4H, m), 1.52-2.05 (9H, m), 2.67-3.10 (4H, m), 3.40-3.58 (2H, m), 6.35 (1H, d, J=15.8 Hz), 6.87 (1H, br.d, J=6.6 Hz), 7.36 (1H, d, J=15.8 Hz), 7.90 (1H, br.s), 8.22 (1H, br.s);

MS (ES+) m/z 393(free, M+1).

EXAMPLE 161

A solution of 2N HCl-EtOH solution (1.2 ml) was added to a mixture of (2E)-3-{2-[(1-benzyl-3-pyrrolidinyl)amino]-4-methyl-5-pyrimidinyl}-N-(tetrahydro-2H-pyran-2-yloxy) acrylamide (200 mg) in EtOH (5 ml) and stirred at 20-25° C. for 2 hours. IPE (30 ml) was added to a reaction mixture and the resultant mixture was stirred at ambient temperature for 20 minutes. The precipitate was collected by filtration to give (2E)-3-(2-[(1-benzyl-3-pyrrolidinyl)amino]-4-methyl-5-pyrimidinyl)-N-hydroxyacrylamide dihydrochloride (90 mg).

$^1$H-NMR (DMSO-d6): δ 1.70-20.7 (1H, m), 2.10-2.42 (1H, m), 2.42 (3H, s), 3.10-3.77 (4H, m), 4.42 (2H, s), 4.57-4.70 (1H, m), 6.34 (1H, d J=15.80 Hz), 7.39-7.46 (4H, m), 7.62-7.65 (2H, m), 8.49 (1H, s), 11.40-11.58 (1H, m).

The following compounds were obtained in a similar manner to that of Example 161.

EXAMPLE 162

(2E)-3-{2-[(1-benzyl-4-piperidinyl)amino]-4-methyl-5-pyrimidinyl}-N-hydroxyacrylamide dihydrochloride $^1$H-NMR (DMSO-d6): δ 1.86-2.13 (4H, m), 2.46 (3H, s), 2.78-3.49 (4H, m), 4.03 (1H, m), 4.29 (2H, d J=4.42 Hz), 6.37 (1H, d J=15.82 Hz), 7.41 (1H, d J=15.82 Hz), 7.44-7.47 (3H, m), 7.65-7.68 (2H, m), 8.15-8.25 (1H, m), 8.50 & 8.53 (total 1H, each s).

EXAMPLE 163

(2E)-N-hydroxy-3-(4-methyl-2-{[(3R)-1-(4-methylbenzyl)-3-pyrrolidinyl]amino}-5-pyrimidinyl)acrylamide dihydrochloride $^1$H-NMR (DMSO-d6): δ 1.80-2.46 (2H, m), 2.32 (3H, s), 2.49 (3H, s), 3.04-3.74 (4H, m), 4.35 (2H, s), 4.55-4.68 (1H, m), 6.33 (1H, d J=15.78 Hz), 7.25 (2H d J=7.12 Hz), 7.39-7.62 (3H, m), 8.48 (1H, s).

EXAMPLE 164

(2E)-3-(2-{[(3R)-1-(cyclohexylmethyl)-3-pyrrolidinyl]amino}-4-methyl-5-pyrimidinyl)-N-hydroxyacrylamide dihydrochloride $^1$H-NMR (DMSO-d6): δ 0.90-1.26 (6H, m), 1.65-2.09 (6H, m), 2.10-2.30 (1H, m), 2.43 (3H, s), 2.98-3.88 (5H, m), 3.88-3.91 (1H, m), 4.59-4.70 (1H, m), 6.34 (1H, d J=15.78 Hz), 7.43 (1H, d J=15.78 Hz), 8.01-8.10 (1H, m), 8.49 (1H, s), 10.54-10.64 (1H, m).

EXAMPLE 165

A solution of tert-butyl (3R)-3-[(5-{(1E)-3-oxo-3-[(tetrahydro-2H-pyran-2-yloxy)amino]-1-propen-1-yl}-2-pyridinyl)amino]-1-pyrrolidinecarboxylate (450 mg) and pyridinium p-toluenesulfonate (261 mg) in EtOH (10 ml) was stirred at 55-60° C. for 9 hours. The reaction mixture was evaporated in vacuo and the residue was dissolved in a mixture of AcOEt and H$_2$O and adjusted to was adjusted to PH10 with aq.K$_2$CO$_3$ solution. The aqueous solution was adjusted to PH6.5 with aq.HCl solution and extracted with AcOEt. The extract was washed with brine and dried over MgSO$_4$. The solvent was evaporated in vacuo and the residue was washed with IPE to give tert-butyl (3R)-3-({5-[(1E)-3-(hydroxyamino)-3-oxo-1-propen-1-yl]-2-pyridinyl}amino)-1-pyrrolidinecarboxylate (118 mg).

$^1$H-NMR (DMSO-d6): δ 1.39 (9H, s), 1.69-1.84 (1H, m), 1.99-2.12 (1H, m), 3.09-3.14 (1H, m), 3.34-3.43 (2H, m), 3.52-3.66 (1H, m), 4.01-4.05 (1H, m), 6.19 (1H, d J=15.88 Hz), 6.50 (1H, d J=8.38 Hz), 7.26 (1H, d J=6.62 Hz), 7.34 (1H, d J=15.88 Hz), 7.61 (1H, d J=8.38 Hz), 8.16 (1H, s), 8.91 (1H, s), 10.59 (1H, s).

EXAMPLE 166

A solution of 2N HCl-EtOH solution (2.3 ml) was added to a mixture of (2E)-3-(5-chloro-6-{[(3R)-1-(3-methylbenzyl)-3-pyrrolidinyl]amino}-3-pyridinyl)-N-(tetrahydro-2H-pyran-2-yloxy)acrylamide (440 mg) in EtOH (5 ml) and stirred at 20-25° C. for 2 hours.

IPE (20 ml) was added to a reaction mixture and the resultant mixture was stirred at ambient temperature for 20 minutes. The precipitate was collected by filtration to give (2E)-3-(5-chloro-6-{[(3R)-1-(3-methylbenzyl)-3-pyrrolidinyl]amino}-3-pyridinyl)$_7$N-hydroxyacrylamide dihydrochloride (375 mg).

$^1$H-NMR (DMSO-d6): 1.92-2.25 (2H, m), 2.32 (3H, s), 307-3.67 (4H, m), 4.35 (2H, d J=5.30 Hz), 4.71 & 4.90 (total 1H, each br, s), 6.39 (1H, d J=15.80 Hz), 7.22-7.45 (5H, m), 7.83 (1H, s), 8.21 (1H, s).

The following compounds were obtained in a similar manner to that of Example 166.

EXAMPLE 167

(2E)-3-(5-chloro-6-{[(3R)-1-(cyclobutylmethyl)-3-pyrrolidinyl]amino}-3-pyridinyl)-N-hydroxyacrylamide dihydrochloride $^1$H-NMR (DMSO-d6): δ 1.78-2.09 (8H, m), 2.73 (1H, m), 304-3.80 (6H, m), 4.46-4.52 (1H, m), 6.29 (1H, d J=15.60 Hz), 7.16-7.20 (1H, m), 7.24 (1H, d J=15.60 Hz), 7.91 (1H, s), 8.23 (1H, s).

EXAMPLE 168

(2E)-3-[5-chloro-6-(cyclopentylamino)-3-pyridinyl]-N-hydroxyacrylamide hydrochloride $^1$H-NMR (DMSO-d6): 1.37-1.73 (6H, m), 1.92-2.09 (2H, m), 4.33-4.39 (1H, m), 6.40 (1H, d J=15.80 Hz), 7.37 (1H, d J=15.80 Hz), 8.03 (1H, s), 8.19 (1H, s).

EXAMPLE 169

(2E)-3-{6-[(4-tert-butylcyclohexyl)amino]-5-chloro-3-pyridinyl}-N-hydroxyacrylamide hydrochloride $^1$H-NMR (DMSO-d6): δ 0.97 (9H, s), 0.97-1.45 (6H, m), 1.45-1.96 (3H, m), 3.84-3.89 & 4.21 (total 1H, each m), 6.36 & 6.37 (total 1H, each d J=15.66 Hz), 7.36 (1H, d J=15.66 Hz), 7.96 & 8.02 (total 1H, each s), 8.17 & 8.21 (total 1H, each s).

EXAMPLE 170

(2E)-3-(5-chloro-6-{[(3R)-1-(cyclohexylmethyl)-3-pyrrolidinyl]amino}-3-pyridinyl)-N-hydroxyacrylamide dihydrochloride $^1$H-NMR (DMSO-d6): δ 0.91-1.27 (6H, m), 1.65-1.89 (5H, m), 2.09-2.10 (1H, m), 2.98-3.91 (6H, m), 4.79-4.91 (1H, m), 6.37 (1H, d J=15.78 Hz), 7.35 (1H, d J=15.78 Hz), 7.91 (1H, s), 8.22 (1H, s), 10.64 (1H, br.s).

EXAMPLE 171

(2E)-3-(5-chloro-6-{[(3R)-1-(3-methyl-2-buten-1-yl)-3-pyrrolidinyl]amino}-3-pyridinyl) N-hydroxyacrylamide dihydrochloride $^1$H-NMR (DMSO-d6): δ 1.71 (3H, s), 1.77 (3H, s), 1.81-2.14 (2H, m), 3.02-3.66 (4H, m), 3.75-3.81 (2H, m), 4.68 (1H, m), 5.30-5.34 (1H, m), 6.36 (1H, d J=15.68 Hz), 7.05-7.15 (1H, m), 7.35 (1H, d J=15.68 Hz), 7.91 (1H, s), 8.24 (1H, s).

EXAMPLE 172

(2E)-3-(5-chloro-6-{[(3R)-1-(3-fluorobenzyl)-3-pyrrolidinyl]amino}-3-pyridinyl)-N-hydroxyacrylamide dihydrochloride $^1$H-NMR (DMSO-d6): δ 1.71-2.52 (2H, m), 3.06-4.71 (4H, m), 4.44 (2H, d J=5.58 Hz), 4.70-4.89 (1H, m), 6.37 (1H, d J=15.80 Hz), 7.23-7.90 (5H, m), 7.94 (1H, d J=1.88 Hz), 8.21 (1H, d J=1.88 Hz).

EXAMPLE 173

(2E)-3-[5-chloro-6-({(3R)-1-[(4-methylphenyl)sulfonyl]-3-pyrrolidinyl}amino)-3-pyridinyl]-N-hydroxyacrylamide hydrochloride $^1$H-NMR (DMSO-d6): δ 1.95-2.09 (2H, m), 2.39 (3H, s), 3.11-3.45 (3H, m), 3.44-3.53 (1H, m), 4.30-4.36 (1H, m), 6.35 (1H, d J=15.76 Hz), 7.34 (1H, d J=15.76 Hz), 7.37 (2H, d J=8.16 Hz), 7.64 (2H, d J=8.16 Hz), 7.86 (1H, d J=1.36 Hz), 8.18 (1H; d J=1.36 Hz).

EXAMPLE 174

(2E)-3-(5-chloro-6-{[(3R)-1-(cyclohexylcarbonyl)-3-pyrrolidinyl]amino}-3-pyridinyl)-N-hydroxyacrylamide hydrochloride $^1$H-NMR (DMSO-d6): δ 1.24-1.33 (6H, m), 1.66-2.52 (5H, m), 3.26-3.88 (4H, m), 4.51-4.67 (1H, m), 6.38 (1H, d J=15.68 Hz), 7.36 (1H, d J=15.68 Hz), 7.94 (1H, s), 8.23 (1H, s).

EXAMPLE 175

(2E)-N-hydroxy-3-[6-({(3R)-1-[(4-methylphenyl)sulfonyl]-3-pyrrolidinyl}amino)-3-pyridinyl]acrylamide hydrochloride $^1$H-NMR (DMSO-d6): δ 1.85-1.91 (1H, m), 2.07-2.14 (1H, m), 2.38 (3H, s), 3.12-3.49 (4H, m), 4.33 (1H, br.s), 6.41 (1H, d J=15.82 Hz), 6.92 (1H, d J=9.18 Hz), 7.38 (2H, d J=8.24 Hz), 7.44 (1H, d J=15.82 Hz), 7.67 (2H, d J=8.24 Hz), 8.02 (1H, d J=9.18 Hz), 8.15 (1H, s), 9.10 (1H, m).

EXAMPLE 176

(2E)-N-hydroxy-3-(6-{[(3R)-1-(1-piperidinylcarbonyl)-3-pyrrolidinyl]amino}-3-pyridinyl)acrylamide hydrochloride $^1$H-NMR (DMSO-d6): δ 1.50 (6H, br.s), 1.89-1.92 (1H, m), 2.18-2.22 (1H, m), 3.14 (4H, br.s), 3.14-3.54 (3H, m), 3.64-3.73 (1H, m), 4.76 (1H, br.s), 6.44 (1H, d J=15.84 Hz), 7.20 (1H, d J=9.36 Hz), 7.46 (1H, d J=15.84 Hz), 8.09 (1H, d J=9.36 Hz), 8.18 (1H, s), 9.61 (1H, m).

EXAMPLE 177

(2E)-3-(5-chloro-6-{([(3R)-1-(1-piperidinylcarbonyl)-3-pyrrolidinyl]amino}-3-pyridinyl)-N-hydroxyacrylamide hydrochloride $^1$H-NMR (DMSO-d6): δ 1.78 (6H, br.s), 1.82-2.10 (2H, m), 3.12 (4H, br.s), 3.30-3.43 (3H, m), 3.54-3.63 (1H, m), 4.47-4.54 (1H, m), 6.36 (1H, d J=15.76 Hz), 7.35 (1H, d J=15.76 Hz), 7.93 (1H, s), 8.21 (1H, s).

EXAMPLE 178

(2E)-3-(5-chloro-6-{[(3R)-1-(cyclopentylcarbonyl)-3-pyrrolidinyl]amino}-3-pyridinyl)-N-hydroxyacrylamide hydrochloride $^1$H-NMR (DMSO-d6): δ 1.51-1.76 (8H, m), 1.90-2.30 (2H, m), 2.70-2.88 (1H, m), 3.28-3.68 (3H, m), 3.88-3.90 (1H, m), 4.50-4.69 (1H, m), 6.36 (1H, d J=15.78 Hz), 7.35 (1H, d J=15.78 Hz), 7.92 (1H, s), 8.23 (1H, s).

EXAMPLE 179

(2E)-3-(5-chloro-6-{[(3R)-1-(cyclobutylcarbonyl)-3-pyrrolidinyl]amino}-3-pyridinyl)-N-hydroxyacrylamide hydrochloride $^1$H-NMR (DMSO-d6): δ 1.76-2.18 (9H, m), 3.26-3.68 (4H, m), 4.49-4.65 (1H, m), 6.35 (1H, d J=15.78 Hz), 7.35 (1H, d J=15.78 Hz), 7.90 (1H, s), 8.22 (1H, s).

EXAMPLE 180

(2E)-3-(5-chloro-6-{[(3R)-1-(2-pyridinylmethyl)-3-pyrrolidinyl]amino}-3-pyridinyl)-N-hydroxyacrylamide trihydrochloride $^1$H-NMR (DMSO-d6): δ 1.92-2.17 (1H, m), 2.18-2.35 (1H, m), 3.39-3.77 (4H, m), 4.66 (2H, s), 4.83 (1H, m), 6.41 (1H, d J=15.78 Hz), 7.54-7.60 (1H, m), 7.77-7.81 ( )1H, m), 7.92-7.09 (2H, m), 8.23 (1H, s), 8.70-8.73 (1H, m).

EXAMPLE 181

(2E)-3-(5-chloro-6-{[(3R)-1-(4-chlorobenzoyl)-3-pyrrolidinyl]amino}-3-pyridinyl)-N-hydroxyacrylamide hydrochloride $^1$H-NMR (DMSO-d6): δ 1.97-2.22 (2H, m), 3.39-3.85 (4H, m), 4.52-4.66 (1H, m), 6.28-6.40 (1H, m), 7.29-7.39 (1H, m), 7.40-7.69 (5H, m), 7.88-7.96 (1H, m), 8.16-8.25 (1H, m).

EXAMPLE 182

(2E)-3-(5-chloro-6-{[(3R)-1-(cyclopropylmethyl)-3-pyrrolidinyl]amino}-3-pyridinyl)-N-hydroxyacrylamide dihydrochloride $^1$H-NMR (DMSO-d6): δ 0.04-0.45 (2H, m), 0.56-0.65 (2H, m), 1.02-1.16 (1H, m), 2.08-2.13 (1H, m), 2.49-2.56 (1H, m), 2.02-3.93 (6H, m), 4.51-4.88 (1H, m), 6.39 (1H, d J=15.78 Hz), 7.35 (1H, d J=15.78 Hz), 7.91 (1H, s), 8.24 (1H, s), 11.12 (1H, br.s).

EXAMPLE 183

(2E)-3-(5-chloro-6-{[(3R)-1-(cyclopentylmethyl)-3-pyrrolidinyl]amino}-3-pyridinyl)-N-hydroxyacrylamide dihydrochloride $^1$H-NMR (DMSO-d6): δ 1.65-1.89 (5H, m), 2.06-2.13 (1H, m), 2.20-2.40 (1H, m), 2.98-3.92 (6H, m), 4.75-4.90 (1H, m), 6.37 (1H, d J=15.78 Hz), 7.35 (1H, d J=15.78 Hz), 7.91 (1H, s), 8.22 (1H, s).

EXAMPLE 184

(2E)-3-(5-chloro-6-{[(3R)-1-(2-pyrimidinyl)-3-pyrrolidinyl]amino}-3-pyridinyl)-N-hydroxyacrylamide dihydrochloride $^1$H-NMR (DMSO-d6): δ 2.18-2.39 (2H, m), 3.66-3.84 (3H, m), 3.95-4.04 (1H, m), 4.76-4.79 (1H, m), 6.39 (1H, d J=15.76 Hz), 6.92-6.98 (1H, m), 7.36 (1H, d J=15.76 Hz), 7.92 (1H, s), 8.26 (1H, s), 8.60-8.63 (2H, m).

EXAMPLE 185

(2E)-3-(5-chloro-6-{[(3R)-1-(4-fluorobenzoyl)-3-pyrrolidinyl]amino}-3-pyridinyl)-N-hydroxyacrylamide hydrochloride $^1$H-NMR (DMSO-d6): δ 2.09-2.22 (2H, m), 3.39-3.84 (4H, m), 4.55-4.67 (1H, m), 6.31 & 6.35 (total 1H, each d J=15.68 Hz), 7.00 (1H, m), 7.21-7.40 (3H, m), 7.56-7.63 (2H, m), 7.87 & 7.91 (total 1H, each s), 8.16 & 8.24 (total 1H, each s).

EXAMPLE 186

(2E)-3-(5-chloro-6-{[(3R)-1-(3-methylbenzoyl)-3-pyrrolidinyl]amino}-3-pyridinyl)-N-hydroxyacrylamide hydrochloride $^1$H-NMR (DMSO-d6): δ 2.09-2.32 (2H, m), 2.32 & 2.35 (total 3H, each s), 3.40-3.75 (4H, m), 4.53-4.66 (1H, m), 6.32 & 6.35 (total 1H, each d J=15.76 Hz), 6.98 (1H, m), 7.29-7.73 (5H, m), 7.88 & 7.92 (total 1H, each s), 8.15 & 8.24 (total 1H, each s).

EXAMPLE 187

(2E)-3-(5-chloro-6-{[(3R)-1-(3-chlorobenzoyl)-3-pyrrolidinyl]amino}-3-pyridinyl)-N-hydroxyacrylamide hydrochloride $^1$H-NMR (DMSO-d6): δ 2.03-2.23 (2H, m), 3.43-3.76 (4H, m), 4.53-4.67 (1H, m), 6.33 & 6.36 (total 1H, each d J=15.74 Hz), 7.05 (1H, m), 7.27 & 7.36 (total 1H, each d J=15.74 Hz), 7.45-7.58 (4H, m), 7.89 & 7.92 (total 1H, each s), 8.16 & 8.25 (total 1H, each s).

EXAMPLE 188

(2E)-3-(5-chloro-6-{[(3R)-1-(2-chlorobenzoyl)-3-pyrrolidinyl]amino}-3-pyridinyl)-N-hydroxyacrylamide hydrochloride $^1$H-NMR (DMSO-d6): δ 2.08-2.21 (2H, m), 3.15-3.22 (2H, m), 3.27-3.87 (2H, m), 4.55-4.65 (1H, m), 6.33 & 6.37 (total 1H, each d J=15.86 Hz), 6.93 (1H, m), 7.27-7.55 (5H, m), 7.88 & 7.93 (total 1H, each s), 8.15 & 8.25 (total 1H, each s).

EXAMPLE 189

To a stirred solution of tert-butyl (5-{(1E)-3-oxo-3-[(tetrahydro-2H-pyran-2-yloxy)amino]-1-propen-1-yl}-2-pyridinyl){(3R)-1-[(2,6,6-trimethyl-1-cyclohexen-1-yl)methyl]-3-pyrrolidinyl}carbamate (80 mg) in methanol (1 mL) was added 4N hydrogen chloride in methanol (3 mL) at ambient temperature and the mixture was stirred at the same temperature for fifteen minutes. The mixture was concentrated in vacuo and the mixture was dissolved in dioxane (1 mL). To this solution was added 4N hydrogen chloride in dioxane (3 mL) and the mixture was stirred at ambient temperature for two hours. The reaction mixture was concentrated in vacuo and the resulting solid was triturated with acetonitrile to give (2E)-N-hydroxy-3-[6-({(3R)-1-[(2,6,6-trimethyl-1-cyclohexen-1-yl)methyl]-3-pyrrolidinyl}amino)-3-pyridinyl]acrylamide dihydrochloride (40 mg) as a pale tan amorphous solid.

$^1$H-NMR (300 MHz, DMSO-d6) δ 1.10 (3H, s), 1.11 (3H, s), 1.35-1.49 (3H, m), 1.52-1.66 (3H, m), 1.73-1.86 (3H, m), 1.97-2.13 (2H, m), 3.09-4.22 (6H, m), 4.57-4.86 (1H, m), 6.39 (1H, d, J=16.1 Hz), 6.92-7.23 (1H, m), 7.39-7.54 (1H, m), 7.96-8.15 (1H, m), 8.16-8.27 (1H, m); MS (ES+) m/z 385(free, M+1).

The following compound was obtained in a similar manner to that of Example 189.

EXAMPLE 190

(2E)-N-hydroxy-3-(6-{[(3R)-1-(3,3,5,5-tetramethylcyclohexyl)-3-pyrrolidinyl]amino}-3-pyridinyl)acrylamide dihydrochloride $^1$H-NMR (300 MHz, DMSO-d6) δ 0.93 (3H, s), 0.95 (3H, s), 0.97-1.12 (2H, m), 1.01 (6H, s), 1.20-1.36 (4H, m), 1.73-1.92 (2H, m), 1.95-2.16 (2H, m), 2.18-2.36 (1H, m), 2.46-3.62 (2H, m), 4.50-4.74 (1H, m), 6.37 (1H, d, J=15.4 Hz), 6.88-7.15 (1H, m), 7.44 (1H, d, J=15.4 Hz), 7.92-8.06 (1H, m), 8.19-8.26 (1H, m); MS (ES+) m/z 387(M+1, free).

EXAMPLE 191

A solution of 2N HCl-EtOH solution (3.4 ml) was added to a mixture of (2Z)-3-(5-chloro-6-{[(3R)-1-cyclopentyl-3-pyrrolidinyl]amino}-3-pyridinyl)-2-fluoro-N-(tetrahydro-2H-pyran-2-yloxy)acrylamide (620 mg) in EtOH (5 ml) and stirred at 20-25° C. for 2 hours. IPE (20 ml) was added to a reaction mixture and the resultant mixture was stirred at ambient temperature for 20 minutes. The precipitate was collected by filtration to give (2Z)-3-(5-chloro-6-{[(3R)-1-cyclopentyl-3-pyrrolidinyl]amino}-3-pyridinyl)-2-fluoro-N-hydroxyacrylamide dihydrochloride (500 mg).

$^1$H-NMR (DMSO-d6): δ 1.52-1.55 (2H, m), 1.75-1.76 (4H, m), 1.97-2.09 (3H, m), 3.04-3.12 (1H, m), 3.20-3.81 (4H, m), 4.73.& 4.89 (total 1H, each m), 6.79 (1H, dd J=3.08 Hz, 39.72 Hz), 7.27 (1H, m), 7.90 (1H, d J=1.80 Hz), 8.30-8.32 (1H, m), 11.52 (1H, m).

The following compounds were obtained in a similar manner to that of Example 191.

EXAMPLE 192

(2Z)-3-(5-chloro-6-{[(3R)-1-cyclohexyl-3-pyrrolidinyl]amino}-3-pyridinyl)-2-fluoro-N-hydroxyacrylamide dihydrochloride $^1$H-NMR (DMSO-d6): δ 1.04-1.25 (3H, m), 1.45-1.48 (2H, m), 1.58-1.62 (1H, m), 1.78-1.80 (2H, m), 2.04-2.10 (3H, m), 2.20-2.51 (1H, m), 3.10-3.15 (2H, m), 3.26-3.46 (2H, m), 3.64 & 3.78 (total 1H, each m), 4.74 & 4.86 (total 1H, each m), 6.79 (1H, dd J=2.48 Hz, 39.72 Hz), 7.20-7.30 (1H, m), 7.90 (1H, d J=1.56 Hz), 8.30-8.32 (1H, m), 11.29-11.36 (1H, m).

EXAMPLE 193

(2Z)-3-(5-chloro-6-{[(3R)-1-(cyclohexylmethyl)-3-pyrrolidinyl]amino}-3-pyridinyl)-2-fluoro-N-hydroxyacrylamide dihydrochloride $^1$H-NMR (DMSO-d6): δ 0.93-0.96 (2H, m), 1.03-1.25 (3H, m), 1.60-1.73 (4H, m), 1.86-1.91 (2H, m), 2.05-2.10 (1H, m), 2.30-2.50 (1H, m), 2.99-3.11 (3H, m), 3.20-3.42 (1H, m), 3.52-3.60 (1H, m), 3.75 & 3.90-3.92 (total, 1H, each m), 4.77 & 4.91 (total 1H, each m), 6.79 (1H, dd J=1.80 Hz, 39.74 Hz), 7.21 & 7.41 (total 1H, each m), 7.90 (1H, d J=1.88 Hz), 8.30-8.32 (1H, m), 10.71-10.72 (1H, m).

EXAMPLE 194

(2Z)-3-(6-{[(3R)-1-benzyl-3-pyrrolidinyl]amino}-5-chloro-3-pyridinyl)-2-fluoro-N-hydroxyacrylamide dihydrochloride $^1$H-NMR (DMSO-d6): δ 2.05-2.07 (1H, m), 2.30-2.37 & 2.48-2.54 (total 1H, each m), 3.13-3.18 (1H, m), 3.32-3.68 (3H, m), 4.40 (2H, d J=5.64 Hz), 4.71 & 4.90 (total 1H, each m), 6.78 (1H, dd J=3.20 Hz, 39.70 Hz), 7.27 (1H, m), 7.44-7.48 (3H, m), 7.63-7.66 (2H, m), 7.89-7.91 (1H, m), 8.29 (1H, m), 11.56-11.57 (1H, m).

EXAMPLE 195

(2Z)-3-(6-{[(3R)-1-benzyl-3-pyrrolidinyl]amino}-3-pyridinyl)-2-fluoro-N-hydroxyacrylamide dihydrochloride $^1$H-NMR (DMSO-d6): δ 2.09-2.19 (1H, m), 2.32 & 2.62 (total 1H, each m), 3.24-3.47 (2H, m), 3.57-3.82 (2H, m), 4.44 & 4.55 (total 2H, each d J=5.68 Hz), 4.64 & 4.80 (total 1H, each m), 6.88 (1H, dd J=5.12 Hz, 39.08 Hz), 7.00 & 7.20 (total 1H, each d J=9.24 Hz), 7.44-7.47 (3H, m), 7.65-7.70 (2H, m), 8.03-8.09 (1H, m), 8.22 (1H, s), 11.52 & 11.65 (total 1H, each br, s).

EXAMPLE 196

A mixture of (2E)-3-(5-chloro-6-{[(3R)-1-({trans-4-[(dimethylamino)methyl]cyclohexyl}carbonyl)-3-pyrrolidinyl]amino}-3-pyridinyl)-N-(tetrahydro-2H-pyran-2-yloxy)acrylamide (530 mg) and 2N HCl/Ethanol (5 ml) was stirred for 3 hrs. EtOAc (10 ml) and IPE (50 ml) was added and stirred. After 1 hour, precipitate was filtered and dried to give 462 mg (89%) of (2E)-3-(5-chloro-6-{[(3R)-1-({trans-4-[(dimethylamino)methyl]cyclohexyl}carbonyl)-3-pyrrolidinyl]amino}-3-pyridinyl)-N-hydroxyacrylamide dihydrochloride.

MASS (ESI+): m/z=450.9 (M+1).

$^1$HNMR (400 MHz, DMSO-d6): δ 0.90-2.80 (14H, m), 2.51 (6H, b.s), 3.2-3.8 (4H, m), 4.52 and 4.66 (1H, br.s), 6.35 (1H, dd, J=4.9, 15.8 Hz), 6.84-6.98 (1H, m), 7.34 (1H, d, J=15.8 Hz), 7.89 (1H, dd, J=1.8, 4.4 Hz), 8.23 (1H, dd, J=1.8, 4.4 Hz).

EXAMPLE 197

A mixture of (2E)-3-(5-chloro-6-{[(3R)-1-(cyclohexylacetyl)-3-pyrrolidinyl]amino}-3-pyridinyl)-N-(tetrahydro-2H-pyran-2-yloxy)acrylamide (680 mg) and 2N HCl/Ethanol (13.8 ml) was stirred for 2 hrs. EtOAc (10 ml) and IPE (50 ml) was added and stirred. After 1 hr, precipitate was filtered and dried to give 387 mg (0.63%) of (2E)-3-(5-chloro-6-{[(3R)-1-(cyclohexylacetyl)-3-pyrrolidinyl]amino}-3-pyridinyl)-N-hydroxyacrylamide hydrochloride.

MASS (ESI+): m/z=408.1 (M+1);

$^1$HNMR (400 MHz, CDCl$_3$): δ 0.82-2.27 (15H, m), 3.20-3.80 (4H, m), 4.51 (1H, m), 4.61 (1H, m), 6.34 (1H, d, J=15.8 Hz), 7.34 (1H, d, J=15.8 Hz), 7.90 (1H, s), 8.23 (1H, s).

EXAMPLE 198

(2E)-3-(5-fluoro-6-{[(3R)-1-(2-octyn-1-yl)-3-pyrrolidinyl]amino}-3-pyridinyl)-N-hydroxyacrylamide bis(4-methylbenzenesulfonate) (salt)

To a solution of (2E)-3-(5-fluoro-6-{[(3R)-1-(2-octyn-1-yl)-3-pyrrolidinyl]amino}-3-pyridinyl)-N-(tetrahydro-2H-pyran-2-yloxy)acrylamide (155 mg) in methanol (3.5 ml) was added 4-methylbenzenesulfonic acid hydrate (122 mg) at 25° C. and then stirred at the same temperature for 1 hour. The mixture was concentrated under reduced pressure. The resulting residue was triturated with a mixed solvent of ethyl acetate, diisopropyl ether and methanol. Title compound (178 mg, 73%) was obtained as colorless powder.

MASS(API-ES); 375 (M+H)+Free $^1$H-NMR (200 MHz), (DMSO-d6, δ): 0.84 (3H, t, J=6.8 Hz), 1.20-1.50 (6H, m), 2.00-2.60 (4H, m), 2.29 (6H, s), 3.00-4.05 (4H, m), 4.10-4.20 (2H, m), 4.63 (1H, br), 6.32 (1H, d, J=16 Hz), 7.12 (4H, d, J=7.9 Hz), 7.39 (1H, d, J=16 Hz), 7.49 (4H, d, J=7.9 Hz), 7.70 (1H, d, J=13 Hz), 8.08 (1H, s), 10.30 (1H, br).

The following compound was obtained in a similar manner to that of Example 198.

EXAMPLE 199

(2E)-3-(5-fluoro-6-{[(3R)-1-(3-phenyl-2-propyn-1-yl)-3-pyrrolidinyl]amino}-3-pyridinyl)-N-hydroxyacrylamide bis (4-methylbenzenesulfonate) (salt)

MASS(API-ES); 381 (M+H)+Free, $^1$H-NMR (200 MHz), (DMSO-d6, δ): 2.00-2.65 (2H, m), 2.29 (6H, s), 3.10-4.20 (4H, m), 4.48 (2H, br), 4.69 (1H, br), 6.32 (1H, d, J=16 Hz), 7.12 (4H, d, J=7.8 Hz), 7.30-7.55 (11H, m), 7.60-7.80 (1H, m), 8.09 (1H, s), 10.51 (1H, br).

The following compounds were obtained in a similar manner to that of Example 41.

EXAMPLE 200

(2E)-3-(6-{[(3R)-1-acetyl-3-piperidinyl]amino}-5-chloro-3-pyridinyl)-N-hydroxyacrylamide hydrochloride

MASS(ESI); 339 (M+H)+.

EXAMPLE 201

(2E)-N-hydroxy-3-(5-{[(3R)-1-(1-phenylethyl)-3-pyrrolidinyl]amino}-2-pyrazinyl)acrylamide dihydrochloride $^1$H-NMR (300 MHz, DMSO-d6) δ 1.63 (1.5H, d, J=6 Hz), 1.65 (1.5H, d, J=6 Hz), 1.84-2.14 (1H, m), 2.30-2.53 (1H, m), 2.70-4.00 (4H, m), 4.32-4.68 (2H, m), 6.61 (0.5H, d, J=15 Hz), 6.65 (0.5H, d, J=15 Hz), 7.31-7.53 (4H, m), 7.61-7.73 (2H, m), 7.95-8.25 (3H, m), 11.63 (1H, br); MS (ES+) m/z 354.

EXAMPLE 202

(2E)-N-hydroxy-3-(5-{[2-(1-piperidinyl)phenyl]amino}-2-pyrazinyl)acrylamide dihydrochloride $^1$H-NMR (300 MHz, DMSO-d6) δ 1.59 (2H, m), 1.76-1.91 (4H, m), 3.16-3.30 (4H, m), 6.74 (1H, d, J=15.5 Hz), 7.21-7.38 (2H, m), 7.46 (1H, d, J=15.5 Hz), 7.54 (1H, m), 7.85 (1H, dd, J=7.5, 1.5 Hz), 8.26 (1H, s), 8.39 (1H, s); MS (ES+) m/z 340.

The following compound(s) was(were) obtained in a similar manner to that of Example 92.

EXAMPLE 203

(2E)-3-(2-{[(3R)-1-(cyclohexylmethyl)-3-pyrrolidinyl]amino}-5-pyrimidinyl)-N-hydroxyacrylamide dihydrochloride $^1$H-NMR (300 MHz, DMSO-d6) δ 0.85-1.32 (5H, m), 1.54-1.90 (6H, m), 2.05 (1H, m), 2.22-2.54 (1H, m), 2.93-3.30 (3H, m), 3.34-4.72 (7H, m), 6.40 (1H, d, J=16 Hz), 7.32 (1H, d, J=16 Hz), 8.06 (1H, m), 8.59 (2×1H, s), 10.41 (1H, m); MS (ES+) m/z 346.

The following compound was obtained in a similar manner to that of Example 89.

EXAMPLE 204

(2E)-3-(6-{[(3R)-1-benzyl-3-pyrrolidinyl]amino}-5-fluoro-3-pyridinyl)-N-hydroxyacrylamide dihydrochloride MASS(API-ES); 357 (M+H)+Free $^1$H-NMR (200 MHz), (DMSO-d6, δ): 1.90-2.60 (2H, m), 2.95-3.85 (4H, m), 4.35-4.50 (2H, m), 4.55-4.75 (1H, m), 4.77 (2H, br), 6.31 (1H, d, J=16 Hz), 7.30-7.80 (8H, m), 8.06 (1H, s), 11.31 (1H, br).

The following compounds were obtained in a similar manner to that of Example 89.

EXAMPLE 205

(2E)-3-(6-{[(3R)-1-(2,2-difluoro-2-phenylethyl)-3-pyrrolidinyl]amino}-5-fluoro-3-pyridinyl)-N-hydroxyacrylamide dihydrochloride MASS(API-ES); 407 (M+H)+Free $^1$H-NMR (200 MHz), (DMSO-d6, δ): 1.95-2.60 (2H, m), 3.15-4.20 (4H, m), 4.31 (2H, t, J=16 Hz), 4.50-4.85 (1H, m), 6.33 (1H, d, J=16 Hz), 7.39 (1H, d, J=16 Hz), 7.50-7.80 (7H, m), 8.08 (1H, s), 11.28(1H, br).

EXAMPLE 206

(2E)-3-(6-{[(3R)-1-(cyclohexylcarbonyl)-3-pyrrolidinyl]amino}-3-pyridinyl)-N-hydroxyacrylamide hydrochloride MASS(API-ES); 359 (M+H)+Free, $^1$H-NMR (200 MHz), (DMSO-d6, δ): 1.10-1.40 (5H, m), 1.55-1.80 (5H, m), 1.85-2.55 (3H, m), 3.25-3.95 (4H, m), 4.30-4.60 (1H, m), 6.40 (1H, d, J=16 Hz), 7.10 (1H, d, J=9.2 Hz), 7.45 (1H, d, J=16 Hz), 8.04 (1H, d, J=9.2 Hz), 8.20 (1H, s), 9.30 (1H, br), 10.90 (1H, br).

The following compound was obtained in a similar manner to that of Example 41.

EXAMPLE 207

(2E)-3-(6-{[1-(cyclohexylmethyl)-4-piperidinyl]amino}-3-pyridinyl)-N-hydroxyacrylamide dihydrochloride $^1$H-NMR (200 MHz, DMSO-d6): δ 1.85-1.40 (6H, m), 1.55-2.40 (12H, m), 2.75-3.15 (4H, m), 3.20-4.30 (6H, m), 6.43 (1H, d, J=15.8 Hz), 7.14 (1H, d, J=9.3 Hz), 7.43 (1H, d, J=15.8 Hz), 8.03-8.18 (2H, m), 10.28 (1H, brs), 10.29 (1H, brs).

The following compound was obtained in a similar manner to that of Example 89.

EXAMPLE 208

(2E)-3-(6-{[(3R)-1-benzoyl-3-pyrrolidinyl]amino}-3-pyridinyl)-N-hydroxyacrylamide hydrochloride MASS(API-ES); 353 (M+H)+Free $^1$H-NMR (200 MHz), (DMSO-d6, δ): 1.80-2.40 (2H, m), 3.30-3.95 (4H, m), 4.40-4.70 (1H, m), 6.40 (0.5H, d, J=16 Hz), 6.44 (0.5H, d, J=16 Hz), 7.12 (0.5H, d, J=9.2 Hz), 7.23 (0.5H, d, J=9.2 Hz), 7.30-7.70 (6H, m), 8.00-8.40 (2H, m), 9.48 (0.5H, br), 9.71 (0.5H, br), 10.90 (1H, br).

The following compound was obtained in a similar manner to that of Example 41.

EXAMPLE 209

(2E)-3-(6-{[1-(4-fluorobenzyl)-4-piperidinyl]amino}-3-pyridinyl)-N-hydroxyacrylamide dihydrochloride $^1$H NMR (DMSO-d6, δ): 1.72 (3H, s), 1.78 (3H, s), 2.90-3.30 (2H, m), 3.30-3.50 (2H, m), 3.55-3.80 (2H, m), 4.10-4.40 (1H, m), 5.37-5.44 (1H, m), 6.39 (1H, d, J=15.9 Hz), 7.35 (1H, d, J=15.9 Hz), 7.94 (1H, s), 8.19 (1H, s).

Mass (APCI): 371(M+H)+.

The following compound was obtained in a similar manner to that of EXAMPLE 129.

EXAMPLE 210

(2E)-3-[6-(2,3-dihydro-1H-inden-2-ylamino)-3-pyridinyl]-N-hydroxyacrylamide hydrochloride $^1$H-NMR (300 MHz, DMSO-d6) δ 2.95 (2H, dd, J=16.5, 5 Hz), 3.40 (2H, dd, J=16.5, 7 Hz), 4.64 (1H, m), 6.40 (1H, d, J=15.8 Hz), 7.05 (1H, d, J=10 Hz), 7.16-7.24 (2H, m), 7.25-7.33 (2H, m), 7.46 (1H, d, J=15.8 Hz), 8.04 (1H, d, J=10 Hz), 8.20 (1H, s), 9.38 (1H, br), 10.82 (1H, br); MS (ES+) m/z 296.

The following compounds were obtained in a similar manner to that of Example 41.

EXAMPLE 211

(2E)-3-(5-chloro-6-{[(3R)-1-cyclobutyl-3-pyrrolidinyl]amino}-3-pyridinyl)-N-hydroxyacrylamide dihydrochloride $^1$H-NMR (200 MHz, DMSO-d6) δ: 1.90-1.90 (2H, m), 2.00-2.40 (5H, m), 2.90-3.90 (5H, m), 4.69-4.86 (1H, m), 6.40 (1H, d, J=15.8 Hz), 7.22 (1H, brs), 7.50 (1H, d, J=15.8 Hz), 7.92 (1H, s), 8.23 (1H, s), 11.86 (1H, brs),

MASS(ESI); 337 (M+H)+.

EXAMPLE 212

(2E)-3-(5-chloro-6-{[(3R)-1-cyclopentyl-3-pyrrolidinyl]amino}-3-pyridinyl)-N-hydroxyacrylamide dihydrochloride $^1$H-NMR (200 MHz, DMSO-d6) δ: 1.40-1.60 (2H, m), 1.61-1.90 (4H, m), 1.91-2.20 (4H, m), 3.06-3.82 (4H, m), 4.73-4.88 (1H, m), 6.37 (1H, d, J=15.8 Hz), 7.18 (1H, brs), 7.35 (1H, d, J=15.8 Hz), 7.91 (1H, s), 8.23 (1H, s), 141.39 (1H, brs),

MASS(ESI); 351 (M+H)+.

The following compound was obtained in a similar manner to that of Example 129.

EXAMPLE 213

(2E)-N-hydroxy-3-{4-[(6-methyl-2-pyridinyl)amino]phenyl}acrylamide hydrochloride $^1$H-NMR (300 MHz, DMSO-d6) δ 2.50 (3H, s), 6.43 (1H, d, J=16 Hz), 6.88 (1H, d, J=7.5 Hz), 7.01 (1H, d, J=7.5 Hz), 7.45 (1H, d, J=16 Hz), 7.53 (2H, d, J=8.5 Hz), 7.59 (2H, d, J=8.5 Hz), 7.83 (1H, dd, J=7.5, 7.5 Hz), 10.12 (1H, br); MS (ES+) m/z 270.

The following compound was obtained in a similar manner to that of Example 41.

EXAMPLE 214

(2E)-3-{5-chloro-6-[(1-methyl-4-piperidinyl)amino]-3-pyridinyl}-N-hydroxyacrylamide dihydrochloride $^1$H-NMR (200 MHz, DMSO-d6) δ: 2.06 (4H, m), 2.71 (3H, d, J=4.6 Hz), 3.04-3.49 (4H, m), 4.09-4.40 (1H, m), 6.40 (1H, d, J=15.8 Hz), 7.35 (1H, d, J=15.8 Hz), 7.95 (1H, s), 8.20 (1H, s), 10.88 (1H, brs),

MASS(ESI); 311 (M+H)+.

The following compound was obtained in a similar manner to that of Example 129.

EXAMPLE 215

(2E)-3-(6-{[(1R,2R)-2-(benzyloxy)cyclopentyl]amino}-5-chloro-3-pyridinyl)-N-hydroxyacrylamide hydrochloride $^1$H-NMR (300 MHz, DMSO-d6) δ 1.48-1.78 (4H, m), 1.82-2.13 (2H, m), 4.00 (1H, m), 4.30-4.60 (1H, m), 4.54 (2H, s), 6.32 (1H, d, J=16 Hz), 6.86 (1H, br), 7.20-7.38 (6H, m), 7.88 (1H, s), 8.21 (1H, s); MS (ES+) m/z 388.

The following compound was obtained in a similar manner to that of Example 92.

EXAMPLE 216

(2E)-3-(6-{[(3R)-1-cycloheptyl-3-pyrrolidinyl]amino}-3-pyridinyl)-N-hydroxyacrylamide dihydrochloride $^1$H-NMR (300 MHz, DMSO-d6) δ 1.34-1.82 (10H, m), 1.94-2.16 (3H, m), 2.30 (1H, m), 3.08-4.20 (5H, m), 4.57 (1H, m), 4.66 (1H, m), 6.38 (1H, d, J=15.5 Hz), 7.00 (1H, m), 7.44 (1H, d, J=15.5 Hz), 7.98 (1H, m), 8.21 (1H, s), 10.26 (1H, br-s), 11.11 (1H, br); MS (ES+) m/z 345.

The following compounds were obtained in a similar manner to that of Example 41.

EXAMPLE 217

(2E)-3-(5-chloro-6-{[(3R)-1-cyclohexyl-3-piperidinyl]amino}-3-pyridinyl)-N-hydroxyacrylamide dihydrochloride $^1$H-NMR (200 MHz, DMSO-d6) δ: 1.09-1.62 (7H, m), 1.78-2.07 (7H, m), 2.84-3.46 (5H, m), 6.38 (1H, d, J=15.8 Hz), 6.77 (1H, d, J=7.6 Hz), 7.34 (1H, d, J=15.8 Hz), 7.90 (1H, s), 8.23 (1H, s), 10.44 (1H, brs).

MASS(ESI); 379 (M+H)+.

EXAMPLE 218

(2E)-3-(5-chloro-6-{[(3R)-1-cyclopentyl-3-piperidinyl]amino}-3-pyridinyl)-N-hydroxyacrylamide dihydrochloride $^1$H-NMR (200 MHz, DMSO-d6) δ: 1.56-1.99 (14H, m), 2.79-2.96 (1H, m), 3.32-3.54 (3H, m), 6.38 (1H, d, J=15.8. Hz), 6.84 (1H, d, J=7.6 Hz), 7.34 (1H, d, J=15.8 Hz), 7.90 (1H, s), 8.22 (1H, s), 10.71 (1H, brs),

MASS(ESI); 365 (M+H)+.

The following compound was obtained in a similar manner to that of Example 89.

EXAMPLE 219

(2E)-3-(5-{[(3R)-1-benzyl-3-pyrrolidinyl]amino}-2-pyrazinyl)-2-fluoro-N-hydroxyacrylamide dihydrochloride MASS(API-ES); 358 (M+H)+Free $^1$H-NMR (200 MHz), (DMSO-d6, δ): 1.90-2.60 (2H, m), 2.95-3.85 (4H, m), 4.35-4.70 (3H, m), 5.70 (2H, br), 6.69 (1H, d, J=25 Hz), 7.40-7.50 (3H, m), 7.60-7.70 (2H, m), 7.99 (0.5H, d, J=1.1 Hz), 8.06 (0.5H, d, J=1.1 Hz), 8.33 (1H, s), 11.43 (1H, br).

The following compounds were obtained in a similar manner to that of Example 129.

EXAMPLE 220

(2E)-3-(5-{[1-(cyclohexylmethyl)-2-oxo-3-pyrrolidinyl]amino}-2-pyrazinyl)-N-hydroxyacrylamide hydrochloride $^1$H-NMR (300 MHz, DMSO-d6) δ 0.78-0.97 (2H, m), 1.07-1.28 (3H, m), 1.51-1.74 (6H, m), 1.85 (1H, m), 2.44 (1H, m), 2.96-3.12 (2H, m), 3.25-3.40 (2H, m), 4.63 (1H, t, J=9 Hz), 6.61 (1H, d, J=15.5 Hz), 7.37 (1H, d, J=15.5 Hz), 7.90 (1H, br), 8.07 (1H, s), 8.08 (1H, s); MS (ES+) m/z 360.

EXAMPLE 221

N-[2-({3-chloro-5-[(1E)-3-(hydroxyamino)-3-oxo-1-propen-1-yl]-2-pyridinyl}amino)phenyl]cyclohexanecarboxamide hydrochloride $^1$H-NMR (300 MHz, DMSO-d6) δ 1.13-1.54 (5H, m), 1.64 (1H, m), 1.69-1.86 (4H, m), 2.42 (1H, m), 6.37 (1H, d, J=16 Hz), 7.14 (1H, ddd, J=7.5, 7.5, 1.5 Hz), 7.21-7.30 (2H, m), 7.36 (1H, d, J=16 Hz), 7.78 (1H, d, J=7.5 Hz), 8.02 (1H, d, J=1 Hz), 8.20 (1H, d, J=1 Hz), 8.32 (1H, s), 9.95 (1H, s); MS (ES+) m/z 415.

EXAMPLE 222

N-[2-({4-[(1E)-3-(hydroxyamino)-3-oxo-1-propen-1-yl]phenyl}amino)phenyl]cyclohexanecarboxamide hydrochloride $^1$H-NMR (300 MHz, DMSO-d6) δ 1.07-1.43 (5H, m), 1.55-1.78 (5H, m), 2.34 (1H, m), 6.23 (1H, d, J=16 Hz), 6.81 (2H, d, J=8 Hz), 7.05 (1H, dd, J=7.5, 7.5 Hz), 7.12 (1H, dd, J=7.5, 7.5 Hz), 7.28 (1H, d, J=7.5 Hz), 7.34 (1H, d, J=16 Hz), 7.37 (2H, d, J=8 Hz), 7.59 (1H, d, J=7.5 Hz), 7.72 (1H, br), 9.25 (1H, s), 10.60 (1H, br); MS (ES+) m/z 380.

EXAMPLE 223

N-[3-({3-chloro-5-[(1E)-3-(hydroxyamino)-3-oxo-1-propen-1-yl]-2-pyridinyl}amino)phenyl]cyclohexanecarboxamide hydrochloride $^1$H-NMR (300 MHz, DMSO-d6) δ 1.12-1.49 (5H, m), 1.59-1.84 (5H, m), 2.34 (1H, m), 6.40 (1H, d, J=16 Hz), 7.16-7.34 (3H, m), 7.39 (1H, d, J=16 Hz), 7.95 (1H, s), 8.03 (1H, s), 8.27 (1H, s), 8.65 (1H, s), 9.81 (1H, s); MS (ES+) m/z 415.

The following compound was obtained in a similar manner to that of Example 89.

EXAMPLE 224 cyclopentyl (3R)-3-({3-chloro-5-[(1E)-3-(hydroxyamino)-3-oxo-1-propen-1-yl]-2-pyridinyl}amino)-1-pyrrolidinecarboxylate $^1$H-NMR (200 MHz, DMSO-d6) δ: 1.40-1.90 (8H, m), 1.90-2.25 (4H, m), 3.24-3.54 (3H, m), 3.57-3.66 (1H, m), 4.54 (1H, m), 4.99 (1H, brs), 6.23 (1H, d, J=15.8 Hz), 6.91 (1H, brs), 7.34 (1H, d, J=15.8 Hz), 7.89 (1H, s), 8.22 (1H, s),

MASS(ESI); 395 (M+H)+.

The following compound was obtained in a similar manner to that of Example 41.

EXAMPLE 225

(2E)-3-(6-{[(3R)-1-benzyl-3-piperidinyl]amino}-5-chloro-3-pyridinyl)-N-hydroxyacrylamide dihydrochloride $^1$H-NMR (200 MHz, DMSO-d6) δ: 1.52-2.00 (4H, m), 2.73-2.92 (2H, m), 2.24-3.59 (2H, m), 4.34 (2H, d, J=3.8 Hz), 4.58 (1H, brs), 6.37 (1H, d, J=15.8 Hz), 6.86 (1H, brs), 7.34 (1H, d, J=15.8 Hz), 7.45-7.48 (3H, m), 7.61-7.72 (2H, m), 7.88 (1H, s), 8.18 (1H, s), 11.15-11.52 (1H, brs),

MASS(ESI); 387 (M+H)+.

The following compound was obtained in a similar manner, to that of Example 89.

EXAMPLE 226

(2E)-3-(6-{[(3R)-1-(cyclohexylmethyl)-3-pyrrolidinyl]amino}-5-fluoro-3-pyridinyl)-N-hydroxyacrylamide dihydrochloride MASS(API-ES); 363 (M+H)+Free $^1$H-NMR (200 MHz), (DMSO-d6, δ): 0.80-1.40 (5H, m), 1.55-1.90 (6H, m), 1.95-2.60 (2H, m), 2.90-4.10 (6H, m), 4.55-4.80 (1H, m), 4.82 (2H, br), 6.33 (1H, d, J=16 Hz), 7.39 (1H, d, J=16 Hz), 7.60 (1H, br), 7.69 (1H, d, J=12 Hz), 8.07 (1H, s), 10.53 (1H, br).

The following compounds were obtained in a similar manner to that of Example 41.

EXAMPLE 227

(2E)-3-(5-chloro-6-{[(3R)-1-(cyclopropylmethyl)-3-piperidinyl]amino}-3-pyridinyl)-N-hydroxyacrylamide dihydrochloride $^1$H-NMR (200 MHz, DMSO-d6) δ: 1.58-1.77 (7H, m), 1.98-2.13 (2H, m), 3.24-3.66 (4H, m), 4.54 (1H, m), 4.97 (1H, m), 6.34 (1H, d, J=15.8 Hz), 6.92 (1H, brs), 7.34 (1H, d, J=15.8 Hz), 7.89 (1H, s), 8.23 (1H, s),

MASS(ESI); 351 (M+H)+.

EXAMPLE 228

(2E)-3-(5-chloro-6-{[(3R)-1-(cyclohexylcarbonyl)-3-piperidinyl]amino}-3-pyridinyl)-N-hydroxyacrylamide hydrochloride $^1$H-NMR (200 MHz, DMSO-d6) δ: 1.02-1.91 (14H, m), 2.62-3.07 (3H, m), 3.80-4.25 (3H, m), 6.38 (1H, d, J=15.8 Hz), 6.69 (1H, brs), 7.36 (1H, d, J=15.8 Hz), 7.93 (1H, s), 8.19 (1H, s),

MASS(ESI); 407 (M+H)+.

The following compound was obtained in a similar manner to that of Example 89.

EXAMPLE 229

(2E)-3-(6-{[(3R)-1-(cyclohexylcarbonyl)-3-pyrrolidinyl]amino}-5-fluoro-3-pyridinyl)-N-hydroxyacrylamide hydrochloride MASS(API-ES); 377 (M+H)+Free, $^1$H-NMR (200 MHz), (DMSO-d6, δ): 1.10-1.45 (5H, m), 1.55-1.80 (5H, m), 1.90-2.60 (2H, m), 3.20-3.90 (4H, m), 4.40-4.70 (1H, m), 5.40 (1H, br), 6.33 (1H, d, J=16 Hz), 7.40 (1H, d, J=16 Hz), 7.75 (1H, d, J=13 Hz), 7.80 (1H, br), 8.08 (1H, s).

The following compound was obtained in a similar manner to that of Example 92.

EXAMPLE 230

(2E)-3-(6-{[(3R)-1-cyclopentyl-3-pyrrolidinyl]amino}-3-pyridinyl)-N-hydroxyacrylamide dihydrochloride $^1$H-NMR (300 MHz, DMSO-d6) δ 1.43-1.62 (2H, m), 1.64-1.84 (4H, m), 1.90-2.16 (3H, m), 2.29 (1H, m), 3.10-4.05 (5H, m), 4.58 (1H, m), 4.70 (1H, m), 6.38 (1H, d, J=16 Hz), 7.02 (1H, m), 7.44 (1H, d, J=16 Hz), 8.00 (1H, m), 8.21 (1H, s), 10.26 (1H, s), 11.16-11.44 (1H, br); MS (ES+) m/z 317.

The following compound was obtained in a similar manner to that of Example 129.

EXAMPLE 231

(2E)-N-hydroxy-3-(5-{[(3R)-1-(2-methylbenzyl)-3-pyrrolidinyl]amino}-2-pyrazinyl)acrylamide dihydrochloride $^1$H-NMR (300 MHz, CD$_3$OD) δ 2.10-2.32 (1H, m), 2.40-2.75 (1H, m), 2.47 (1.7H, s), 2.49 (1.3H, s), 3.23-3.45 (1H, m), 3.48-3.72 (2H, m), 3.84 (0.6H, m), 4.00 (0.4H, m), 4.48-4.74 (3H, m), 6.73 (1H, d, J=15.5 Hz), 6.74 (1H, d, J=15.5 Hz), 7.26-7.42 (3H, m), 7.44-7.58 (2H, m), 8.05-8.18 (3H, m); MS (ES+) m/z 354.

The following compounds were obtained in a similar manner to that of Example 89.

EXAMPLE 232

(2E)-3-(4-{[(3R)-1-benzyl-3-pyrrolidinyl]amino}-3-fluorophenyl)-N-hydroxyacrylamide dihydrochloride MASS(API-ES); 356 (M+H)+Free $^1$H-NMR (200 MHz), (DMSO-d6, δ): 1.90-2.70 (2H, m), 3.00-3.90 (4H, m), 4.00-4.50 (3H, m), 6.26 (1H, d, J=16 Hz), 6.60-6.90 (1H, m), 7.20-7.39 (3H, m), 7.40-7.50 (3H, m), 7.58-7.70 (2H, m), 11.10-11.50 (1H, m).

EXAMPLE 233

(2E)-3-(6-{[(3R)-1-(2,6-difluorobenzyl)-3-pyrrolidinyl]amino}-5-fluoro-3-pyridinyl)-N-hydroxyacrylamide dihydrochloride MASS(API-ES); 393 (M+H)+Free, $^1$H-NMR (200 MHz), (DMSO-d6, δ): 1.95-2.70 (2H, m), 3.10-4.00 (4H, m), 4.40-4.90 (3H, m), 6.31 (1H, d, J=16 Hz), 7.20-7.80 (6H, m), 8.07 (1H, s), 11.22 (1H, br).

EXAMPLE 234

(2E)-3-(5-fluoro-6-{[(3R)-1-(1,3-thiazol-2-ylmethyl)-3-pyrrolidinyl]amino}-3-pyridinyl)-N-hydroxyacrylamide dihydrochloride MASS(API-ES); 364 (M+H)+Free, $^1$H-NMR (200 MHz), (DMSO-d6, δ): 2.00-2.60 (2H, m), 3.10-4.00 (4H, m), 4.55-5.00 (3H, m), 6.34 (1H, d, J=16 Hz), 7.38 (1H, d, J=16 Hz), 7.56 (1H, br), 7.69 (1H, d, J=13 Hz), 7.90-8.00 (2H, m), 8.07 (1H, s), 11.58 (1H, br).

EXAMPLE 235

(2E)-3-(5-fluoro-6-{[(3R)-1-(2-phenylethyl)-3-pyrrolidinyl]amino}-3-pyridinyl)-N-hydroxyacrylamide dihydrochloride MASS(API-ES); 371 (M+H)+Free, $^1$H-NMR (200 MHz), (DMSO-d6, δ): 1.95-2.60 (2H, m), 3.00-4.40 (8H, m), 4.50-4.90 (1H, m), 6.32 (1H, d, J=16 Hz), 7.20-7.50 (6H, m), 7.52 (1H, br), 7.69 (1H, d, J=12 Hz), 8.06 (0.5H, s), 8.09 (0.5H, s), 11.00-11.30 (1H, m).

EXAMPLE 236

(2E)-3-(5-fluoro-6-{[(3R)-1-(1-piperidinylacetyl)-3-pyrrolidinyl]amino}-3-pyridinyl)-N-hydroxyacrylamide dihydrochloride MASS(API-ES); 392 (M+H)+Free, $^1$H-NMR (200 MHz), (DMSO-d6, δ): 1.20-1.90 (6H, m), 1.95-2.55 (2H, m), 2.85-3.10 (2H, m), 3.30-4.35 (8H, m), 4.40-4.75 (1H, m), 6.35 (1H, d, J=16 Hz), 7.39 (1H, d, J=16 Hz), 7.58 (1H, br), 7.69 (1H, d, J=13 Hz), 8.08 (1H, s), 9.65 (1H, br).

EXAMPLE 237

(2E)-3-[6-({(3R)-1-[(3-chloro-4-pyridinyl)methyl]-3-pyrrolidinyl}amino)-5-fluoro-3-pyridinyl]-N-hydroxyacrylamide trihydrochloride MASS(API-ES); 392 (M+H)+Free, $^1$H-NMR (200 MHz), (DMSO-d6, δ): 2.00-2.70 (2H, m), 3.10-4.05 (4H, m), 4.60-5.00 (3H, m), 6.35 (1H, d, J=16 Hz), 7.38 (1H, d, J=16 Hz), 7.72 (1H, d, J=12 Hz), 7.75 (1H, br), 8.00-8.10 (2H, m), 8.66 (1H, d, J=5.0 Hz), 8.79 (1H, s), 11.80-12.10 (1H, m).

The following compound was obtained in a similar manner to that of Example 129.

EXAMPLE 238

(2E)-N-hydroxy-3-(5-{[(3R)-1-(2-quinolinylmethyl)-3-pyrrolidinyl]amino}-2-pyrazinyl)acrylamide trihydrochloride $^1$H-NMR (300 MHz, DMSO-d6) δ 2.12 (1H, m), 2.44 (1H, m), 3.35-4.00 (4H, m), 4.59 (1H, m), 4.87 (2H, s), 6.64 (1H, d, J=15 Hz), 7.38 (1H, d, J=15 Hz), 7.65-7.76 (2H, m), 7.84 (1H, ddd, J=7, 7, 1.5 Hz), 8.02-8.38 (6H, m), 8.50 (1H, d, J=8.5 Hz), 11.16 (1H, br-s); MS (ES+) m/z 391.

The following compound was obtained in a similar manner to that of Example 92.

EXAMPLE 239

(2E)-3-(6-{[(3R)-1-cyclohexyl-3-pyrrolidinyl]amino}-3-pyridinyl)-N-hydroxyacrylamide dihydrochloride $^1$H-NMR (300 MHz, DMSO-d6) δ 1.02-1.52 (6H, m), 1.60 (1H, m), 1.73-1.86 (2H, m), 1.94-2.14 (2H, m), 2.27 (1H, m), 3.04-4.05 (5H, m), 4.58 (1H, m), 6.34 (1H, d, J=16 Hz), 6.90 (1H, m), 7.42 (1H, d, J=16 Hz), 8.21 (1H, s); MS (ES+) m/z 331.

The following compound was obtained in a similar manner to that of Example 89.

EXAMPLE 240

(2E)-3-(6-{[(3R)-1-(1,3-benzothiazol-2-ylmethyl)-3-pyrrolidinyl]amino}-5-fluoro-3-pyridinyl)-N-hydroxyacrylamide dihydrochloride MASS(API-ES); 414 (M+H)+Free, ¹H-NMR (400 MHz), (DMSO-d6, δ): 2.00-2.65 (2H, m), 3.20-4.10 (4H, m), 4.60-5.10 (3H, m), 6.32 (1H, d, J=16 Hz), 7.38 (1H, d, J=16 Hz), 7.50-7.75 (4H, m), 8.00-8.30 (3H, m), 11.50-11.90 (1H, m).

The following compounds were obtained in a similar manner to that of Example 41.

EXAMPLE 241

(2E)-3-(6-{[(3R)-1-(2-chlorobenzyl)-3-piperidinyl]amino}-3-pyridinyl)-N-hydroxyacrylamide dihydrochloride ¹H-NMR (400 MHz, DMSO-d6) δ: 1.52 (1H, brs), 1.93-2.06 (3H, m), 2.92-3.55 (4H, m), 4.34 (1H, brs), 4.50 (2H, s), 6.39 (1H, d, J=15.8 Hz), 7.04 (1H, brs), 7.39-7.52 (3H, m), 7.57-7.60 (1H, m), 7.97-8.02 (2H, m), 8.19 (1H, brs), 10.95 (1H, brs),

MASS(ESI); 387 (M+H)+.

EXAMPLE 242

(2E)-3-(6-{[(3R)-1-(3-chlorobenzyl)-3-piperidinyl]amino}-3-pyridinyl)-N-hydroxyacrylamide dihydrochloride ¹H-NMR (400 MHz, DMSO-d6) δ: 1.46 (1H, brs), 1.81-2.08 (3H, m), 2.89-3.52 (4H, m), 4.34 (1H, brs), 4.39-4.42 (1H, m), 6.42 (1H, d, J=15.8 Hz), 7.08-7.10 (1H, m), 7.42 (1H, d, J=15.8 Hz), 7.47-7.55 (3H, m), 7.62 (1H, d, J=6.8 Hz), 7.79 (1H, s), 8.06 (1H, brs), 8.20 (1H, s), 11.08-11.22 (1H, m),

MASS(ESI); 387 (M+H)+.

EXAMPLE 243

(2E)-3-(6-{[(3R)-1-acetyl-3-piperidinyl]amino}-5-fluoro-3-pyridinyl)-N-hydroxyacrylamide hydrochloride

MASS(ESI); 323 (M+H)+.

The following compounds were obtained in a similar manner to that of Example 129.

EXAMPLE 244

(2E)-3-(5-{[(3R)-1-(2,3-dihydro-1H-inden-2-yl)-3-pyrrolidinyl]amino}-2-pyrazinyl)-N-hydroxyacrylamide dihydrochloride ¹H-NMR (300 MHz, DMSO-d6) δ 2.00-2.40 (2H, m), 3.04-4.27 (9H, m), 4.52 (0.5H, m), 4.60 (0.5H, m), 6.64 (1H, d, J=15 Hz), 7.18-7.32 (5H, m), 7.40 (1H, d, J=15 Hz), 8.04 (0.5H, s), 8.06 (0.5H, s), 8.17 (1H, s), 11.63 (1H, br); MS (ES+) m/z 366.

EXAMPLE 245

(2E)-3-{6-[(2-benzylphenyl)amino]-5-chloro-3-pyridinyl}-N-hydroxyacrylamide hydrochloride ¹H-NMR (300 MHz, DMSO-d6) δ 3.93 (2H, s), 6.35 (1H, d, J=16 Hz), 7.07-7.32 (9H, m), 7.33 (1H, d, J=16 Hz), 7.45 (1H, d, J=8 Hz), 7.98 (1H, d, J=1.5 Hz), 8.09 (1H, d, J=1.5 Hz), 8.31 (1H, s); MS (ES+) m/z 380.

EXAMPLE 246

(2E)-3-(5-{[(3R)-1-(4-ethoxybenzyl)-3-pyrrolidinyl]amino}-2-pyrazinyl)-N-hydroxyacrylamide dihydrochloride ¹H-NMR (300 MHz, DMSO-d6) δ 1.32 (3H, t, J=7 Hz), 2.00 (1H, m), 2.21-2.53 (1H, m), 2.96-3.80 (4H, m), 4.03 (2H, q, J=7 Hz), 4.33 (2H, m), 4.44 (0.5H, m), 4.55 (0.5H, m), 6.62 (0.5H, d, J=15.5 Hz), 6.63 (0.5H, d, J=15.5 Hz), 6.97 (1H, d, J=9 Hz), 6.98 (1H, d, J=9 Hz), 7.38 (1H, d, J=15.5 Hz), 7.49 (1H, d, J=9 Hz), 7.50 (1H, d, J=9 Hz), 7.98 (0.5H, br), 8.02 (0.5H, s), 8.04 (0.5H, s), 8.14 (1H, s), 8.16 (0.5H, br), 10.87 (1H, br); MS (ES+) m/z 384.

The following compounds were obtained in a similar manner to that of Example 92.

EXAMPLE 247

(2E)-3-(6-{[(3R)-1-benzyl-3-pyrrolidinyl]amino}-2-pyrazinyl)-N-hydroxyacrylamide dihydrochloride ¹H-NMR (300 MHz, DMSO-d6) δ 1.92-2.17 (1H, m), 2.24-2.58 (1H, m), 3.05 (0.5H, m), 3.15-3.42 (2H, m), 3.51 (0.5H, m), 3.63 (0.5H, m), 3.95 (0.5H, m), 4.33-4.62 (3H, m), 7.01 (0.5H, d, J=15.5 Hz), 7.05 (0.5H, d, J=15.5 Hz), 7.33 (1H, d, J=15.5 Hz), 7.40-7.52 (3H, m), 7.60-7.71 (2H, m), 7.75 (0.5H, m), 7.92 (1H, s), 7.95 (0.5H, s), 7.96 (0.5H, m), 7.99 (0.5H, s), 11.18 (0.5H, br), 11.31 (0.5H, br); MS (ES+) m/z 340.

EXAMPLE 248

(2E)-N-hydroxy-3-(2-{[(3R)-1-(2-phenylethyl)-3-pyrrolidinyl]amino}-5-pyrimidinyl)acrylamide dihydrochloride ¹H-NMR (300 MHz, DMSO-d6) δ 1.95-2.16 (1H, m), 2.19-2.54 (1H, m), 2.96-4.00 (8H, m), 4.58 (1H, m), 6.40 (1H, d, J=16 Hz), 7.23-7.42 (7H, m), 7.99 (0.5H, br), 8.13 (0.5H, br), 8.58 (1H, s), 8.59 (1H, s), 10.89 (0.5H, br), 11.11 (0.5H, br); MS (ES+) m/z 354.

The following compounds were obtained in a similar manner to that of Example 89.

EXAMPLE 249

(2Z)-3-(5-{[(3R)-1-benzyl-3-pyrrolidinyl]amino}-2-pyrazinyl)-2-fluoro-N-hydroxyacrylamide dihydrochloride MASS(API-ES); 358 (M+H)+Free, ¹H-NMR (200 MHz), (DMSO-d6, δ): 1.90-2.60 (2H, m), 2.95-3.90 (4H, m), 4.35-4.70 (3H, m), 6.21 (2H, br), 6.70 (1H, d, J=39 Hz), 7.40-7.50 (3H, m), 7.60-7.70 (2H, m), 8.04 (0.5H, d, J=1.1 Hz), 8.10 (0.5H, d, J=1.1 Hz), 8.32 (1H, s), 11.46 (1H, br).

EXAMPLE 250

(2E)-3-(6-{[(3R)-1-(2,2-difluoroethyl)-3-pyrrolidinyl]amino}-5-fluoro-3-pyridinyl)-N-hydroxyacrylamide dihydrochloride MASS(API-ES); 331 (M+H)+Free, ¹H-NMR (200 MHz), (DMSO-d6, δ): 2.00-2.60 (2H, m), 3.05-4.10 (4H, m), 3.87 (2H, dt, J=3.8 Hz, J=13 Hz), 4.50-

4.90 (1H, m), 6.33 (1H, d, J=16 Hz), 6.57 (1H, tt, J=3.8 Hz, J=54 Hz), 7.39 (1H, d, J=16 Hz), 7.60 (1H, br), 7.69 (1H, d, J=13 Hz), 8.08 (1H, s).

EXAMPLE 251

(2E)-3-[5-fluoro-6-({(3R)-1-[2-(1H-pyrazol-1-yl)ethyl]-3-pyrrolidinyl}amino)-3-pyridinyl]-N-hydroxyacrylamide dihydrochloride MASS(API-ES); 361 (M+H)+Free, ¹H-NMR (200 MHz), (DMSO-d6, δ): 1.90-2.60 (2H, m), 2.85-3.90 (6H, m), 4.60 (2H, t, J=6.4 Hz), 4.65 (1H, br), 6.25-6.40 (2H, m), 7.38 (1H, d, J=16 Hz), 7.54 (1H, d, J=1.6 Hz), 7.69 (1H, d, J=13 Hz), 7.85 (1H, d, J=2.2 Hz), 8.06 (1H, s), 11.20-11.60 (1H, m).

The following compound was obtained in a similar manner to that of Example 129.

EXAMPLE 252

(2E)-3-(5-chloro-6-{[(1S,2R)-2-phenylcyclopropyl]amino}-3-pyridinyl)-N-hydroxyacrylamide hydrochloride ¹H-NMR (300 MHz, DMSO-d6) δ 1.26 (1H, m), 1.41 (1H, m), 2.12 (1H, m), 3.02 (1H, m), 6.34 (1H, d, J=16 Hz), 7.13-7.22 (3H, m), 7.24-7.38 (3H, m), 7.51 (1H, br), 7.92 (1H, s), 8.21 (1H, s); MS (ES−) m/z 328.

The following compound was obtained in a similar manner to that of Example 41.

EXAMPLE 253

(2E)-3-(5-chloro-6-{[(3R)-1-cyclohexyl-3-pyrrolidinyl]amino}-3-pyridinyl)-N-hydroxyacrylamide dihydrochloride ¹H-NMR (200 MHz, DMSO-d6) δ: 1.05-1.70 (6H, m), 1.77-1.82 (2H, m), 2.05-2.09 (3H, m), 3.00-3.78 (5H, m), 4.72-4.86 (1H, m), 5.75 (1H, d, J=15.8 Hz), 7.20 (1H, brs), 7.35 (1H, d, J=15.8 Hz), 7.91 (1H, s), 8.22 (1H, s), 11.32 (1H, brs).

The following compound was obtained in a similar manner to that of Example 89.

EXAMPLE 254 tert-butyl (3R)-3-({3-chloro-5-[(1E)-3-(hydroxyamino)-3-oxo-1-propen-1-yl]-2-pyridinyl}amino)-1-pyrrolidinecarboxylate ¹H-NMR (200 MHz, DMSO-d6) δ: 1.39 (9H, s), 1.91-2.12 (2H, m), 3.15-3.65 (4H, m), 4.53 (1H, brs), 6.33 (1H, d, J=15.8 Hz), 6.85 (1H, brs), 7.34 (1H, d, J=15.8 Hz), 7.88 (1H, s), 8.22 (1H, s).

MASS(ESI); 383 (M+H)+.

The following compounds were obtained in a similar manner to that of Example 41.

EXAMPLE 255

(2E)-3-(5-chloro-6-{[1-(3-fluorobenzyl)-4-piperidinyl]amino}-3-pyridinyl)-N-hydroxyacrylamide dihydrochloride ¹H NMR (DMSO-d6, δ): 2.00-2.20 (4H, m), 3.00-3.46 (4H, m), 4.10-4.20 (1H, m), 4.30-4.46 (2H, m), 6.39 (1H, d, J=15.9 Hz), 7.26-7.58 (4H, m), 7.66 (1H, d, J=8.3 Hz), 7.95 (1H, s), 8.18-8.22 (1H, m), Mass (APCI): 405(M+H)+.

EXAMPLE 256

(2E)-3-(5-chloro-6-{[1-(2-pyridinylmethyl)-4-piperidinyl]amino}-3-pyridinyl)-N-hydroxyacrylamide trihydrochloride ¹H NMR (DMSO-d6, δ): 2.05-2.10(4H, m), 3.17-3.25(2H, m), 3.41-4.78(2H, m), 4.15-4.25(1H, m), 4.51(2H, s), 6.37 (1H, d, J=15.8 Hz), 7.04(1H, brs), 7.34(1H, d, J=15.8 Hz), 7.56-7.59(1H, m), 7.83(1H, d, J=7.8 Hz), 7.93(1H, s), 8.02-8.06(1H, d), 8.19(1H, s), 8.73(1H, d, J=4.9 Hz), 10.97(1H, brs), Mass (APCI): 388(M+H)+.

EXAMPLE 257

(2E)-3-(5-chloro-6-{[1-(3-pyridinylmethyl)-4-piperidinyl]amino}-3-pyridinyl)-N-hydroxyacrylamide trihydrochloride ¹H NMR (DMSO-d6, δ): 2.00-2.30(4H, m), 3.05-3.45(2H, m), 3.45-3.50(2H, m), 4.15-4.35(1H, m), 4.57(2H, brs), 6.39 (1H, d, J=15.9 Hz), 7.23(1H, brs), 7.34(1H, d, J=15.9 Hz), 7.94(1H, s), 8.09-8.16(1H, m), 8.18(1H, s), 8.89(1H, d, J=7.9 Hz), 9.00(1H, d, J=5.4 Hz), 9.24(1H, s), 11.80(1H, brs), Mass (ESI): 388(M+H)+.

EXAMPLE 258

(2E)-3-(5-chloro-6-{[1-(4-pyridinylmethyl)-4-piperidinyl]amino}-3-pyridinyl)-N-hydroxyacrylamide trihydrochloride ¹H NMR (DMSO-d6, δ): 2.00-2.30(4H, m), 3.10-3.60(4H, m), 4.10-4.30(1H, m), 4.62(2H, brs), 6.37(1H, d, J=15.9 Hz), 7.17(1H, brs), 7.34(1H, d, J=15.9 Hz), 7.92(1H, s), 8.18(1H, s), 8.42(2H, m), 9.04(2H, d, J=5.8 Hz), 12.06(1H, brs), Mass (ESI): 388(M+H)+.

EXAMPLE 259

(2E)-3-(5-chloro-6-{[1-(3-chlorobenzyl)-4-piperidinyl]amino}-3-pyridinyl)-N-hydroxyacrylamide dihydrochloride ¹H NMR (DMSO-d6, δ): 2.00-2.25(4H, m), 2.90-3.20(2H, m), 3.20-3.40(2H, m), 4.10-4.30(1H, m), 4.29-4.44(2H, m), 6.38(1H, d, J=15.9 Hz), 7.35(1H, d, J=15.9 Hz), 7.49-7.67 (3H, m), 7.84(1H, s), 8.04(1H, s), 8.19(1H, s), 11.30(1H, brs), Mass (ESI): 421(M+H)+.

EXAMPLE 260

(2E)-3-(5-chloro-6-{[1-(2-chlorobenzyl)-4-piperidinyl]amino}-3-pyridinyl)-N-hydroxyacrylamide dihydrochloride ¹H NMR (DMSO-d6, δ): 2.00-2.25(4H, m), 3.10-3.50(4H, m), 4.10-4.30(1H, m), 4.42-4.56(2H, m), 6.38(1H, d, J=15.9 Hz), 7.35(1H, d, J=15.9 Hz), 7.46-7.62(3H, m), 7.93(1H, s), 8.04-8.09(1H, m), 8.19(1H, s), 11.20(1H, brs), Mass (ESI): 421(M+H)+.

EXAMPLE 261

(2E)-3-(5-chloro-6-{[1-(cyclohexylmethyl)-4-piperidinyl]amino}-3-pyridinyl)-N-hydroxyacrylamide dihydrochloride ¹H NMR (DMSO-d6, δ): 0.94-1.29 (7H, m), 1.65-1.92 (5H, m), 1.99-2.17 (3H, m), 2.86-3.04 (3H, m), 3.10-3.54 (3H, m), 4.19-4.31 (1H, m), 6.40 (1H, d, J=15.9 Hz), 7.35 (1H, d, J=15.9 Hz), 8.20 (1H, s), 8.30 (1H, s), 10.30 (1H, brs), Mass (APCI): 393(M+H)+.

EXAMPLE 262

(2E)-3-(5-chloro-6-{[1-(2-fluorobenzyl)-4-piperidinyl]amino}-3-pyridinyl)-N-hydroxyacrylamide dihydrochloride $^1$H NMR (DMSO-d6, δ): 2.05-2.20(4H, m), 3.08-3.18(2H, m), 3.41-3.44(2H, m), 4.15-4.20(1H, m), 4.32-4.46(2H, m), 6.38(1H, d, J=15.9 Hz), 7.30-7.37(3H, m), 7.52-7.56(1H, m), 7.86-7.89(1H, m), 7.93(1H, s), 8.19(1H, s), 11.22(1H, brs), Mass (APCI): 405(M+H)+.

EXAMPLE 263

(2E)-3-(5-chloro-6-{[1-(3-methyl-2-buten-1-yl)-4-piperidinyl]amino}-3-pyridinyl)-N-hydroxyacrylamide dihydrochloride $^1$H NMR (DMSO-d6, δ): 1.72 (3H, s), 1.78 (3H, s), 2.90-3.30 (2H, m), 3.30-3.50 (2H, m), 3.55-3.80 (2H, m), 4.10-4.40 (1H, m), 5.37-5.44 (1H, m), 6.39 (1H, d, J=15.9 Hz), 7.35 (1H, d, J=15.9 Hz), 7.94 (1H, s), 8.19 (1H, s), Mass (APCI): 365(M+H)+.

The following compounds were obtained in a similar manner to that of Example 129.

EXAMPLE 264

(2E)-3-(4-{[(3R)-1-(cyclohexylcarbonyl)-3-pyrrolidinyl]amino}phenyl)-N-hydroxyacrylamide $^1$H-NMR (300 MHz, DMSO-d6) δ 1.10-1.40 (5H, m), 1.54-1.95 (6H, m), 2.02-2.45 (2H, m), 3.25-4.15 (5H, m), 6.15 (1H, br-d, J=16 Hz), 6.34 (1H, m), 6.56-6.70 (2H, m), 7.26-7.40 (3H, m), 8.86 (1H, s), 10.53 (1H, s);

MS (ES+) m/z 358.

EXAMPLE 265

(2E)-N-hydroxy-3-{6-[(4-methylphenyl)amino]-3-pyridinyl}acrylamide hydrochloride $^1$H-NMR (300 MHz, DMSO-d6) δ 2.31 (3H, s), 6.38 (1H, d, J=16 Hz), 7.06 (1H, d, J=9 Hz), 7.22 (2H, d, J=8 Hz), 7.38-7.50 (3H, m), 8.00 (1H, br-d, J=8 Hz), 8.23 (1H, d, J=1.5 Hz), 10.27 (1H, br-s); MS (ES+) m/z 270.

EXAMPLE 266

(2E)-3-{6-[(2-ethoxyphenyl)amino]-3-pyridinyl}-N-hydroxyacrylamide hydrochloride $^1$H-NMR (300 MHz, DMSO-d6) δ 1.21 (3H, t, J=7 Hz), 4.10 (2H, q, J=7 Hz), 6.44 (1H, d, J=15.8 Hz), 7.03 (1H, dd, J=7.5, 7.5 Hz), 7.17 (1H, d, J=8 Hz), 7.21 (1H, d, J=9.5 Hz), 7.30 (1H, dd, J=7.5, 7.5 Hz), 7.46 (1H, d, 3=15.8 Hz), 7.53 (1H, br-d, J=7.5 Hz), 8.13 (1H, br-d, J=9.5 Hz), 8.21 (1H, d, J=1.5 Hz), 10.38 (1H, br), 10.82 (1H, br); MS (ES+) m/z 300.

EXAMPLE 267

(2E)-3-[5-chloro-6-(2,3-dihydro-1H-inden-1-ylamino)-3-pyridinyl]-N-hydroxyacrylamide hydrochloride $^1$H-NMR (300 MHz, DMSO-d6)δ 2.09 (1H, m), 2.77-3.06 (3H, m), 5.78 (1H, m), 6.35 (1H, d, J=16 Hz), 7.12-7.32 (5H, m), 7.37 (1H, d, J=16 Hz), 7.94 (1H, s), 8.24 (1H, s); MS (ES+) m/z 330.

The following compound was obtained in a similar manner to that of Example 96.

EXAMPLE 268

(2E)-3-(5-{[(3R)-1-(2-chlorobenzyl)-3-piperidinyl]amino}-2-pyrazinyl)-N-hydroxyacrylamide dihydrochloride $^1$H-NMR (300 MHz, DMSO-d6) δ 1.39-1.49 (1H, m), 1.70-2.06 (3H, m), 2.70-2.94 (1H, m), 2.94-3.21 (1H, m), 3.30-3.61 (2H, m), 4.21-4.41 (1H, m), 4.41-4.56 (2H, m), 6.62 (1H, d, J=15.2 Hz), 7.37 (1H, d, J=15.2 Hz), 7.44-7.55 (2H, m), 7.55-7.65 (1H, m), 7.72-7.87 (1H, m), 7.87-7.99 (1H, m), 7.99-8.06 (1H, m), 8.11 (1H, s); MS (ES+) m/z 388.

The following compound was obtained in a similar manner to that of Example 129.

EXAMPLE 269

(2E)-3-(4-{[(3R)-1-(cyclohexylmethyl)-3-pyrrolidinyl]amino}phenyl)-N-hydroxyacrylamide hydrochloride $^1$H-NMR (300 MHz, DMSO-d6) δ 0.84-1.03 (2H, m), 1.08-1.32 (3H, m), 1.54-1.76 (4H, m), 1.79-2.02 (3H, m), 2.22-2.50 (1H, m), 2.82-3.14 (3H, m), 3.40 (1H, m), 3.60 (1H, m), 3.87-4.40 (2H, m), 6.20 (1H, d, J=16 Hz), 6.62 (2H, d, J=8 Hz), 7.26-7.42 (3H, m), 10.46 (1H, s); MS (ES+) m/z 344.

The following compounds were obtained in a similar manner to that of Example 41.

EXAMPLE 270

(2E)-3-(6-{[(3R)-1-benzyl-3-piperidinyl]amino}-5-fluoro-3-pyridinyl)-N-hydroxyacrylamide dihydrochloride $^1$H-NMR (200 MHz, DMSO-d6) δ: 1.30-1.60 (1H, m), 1.70-1.98 (3H, m), 2.60-2.90 (2H, m), 3.25-3.50 (3H, m), 4.35 (2H, m), 6.34 (1H, d, J=16.1 Hz), 7.37 (1H, d, J=16.1 Hz), 7.41-7.47 (4H, m), 7.61-7.75 (3H, m), 8.03 (1H, s), 11.20 (1H, brs),

MASS(ESI); 371 (M+H)+.

EXAMPLE 271

(2E)-3-(6-{[(3R)-1-(cyclohexylmethyl)-3-piperidinyl]amino}-5-fluoro-3-pyridinyl)-N-hydroxyacrylamide dihydrochloride $^1$H-NMR (200 MHz, DMSO-d6) δ: 0.92-1.27 (5H, m), 1.52-2.02 (10H, m), 2.73-3.00 (3H, m), 3.20-3.57 (2H, m), 4.55-4.60 (2H, m), 6.34 (1H, d, J=16.1 Hz), 7.34-7.43 (2H, m), 7.64-7.76 (1H, m), 8.67 (1H, s), 10.11 (1H, brs),

MASS(ESI); 377 (M+H)+.

EXAMPLE 272

(2E)-3-(2-{[(3R)-1-benzyl-3-piperidinyl]amino}-5-pyrimidinyl)-N-hydroxyacrylamide dihydrochloride $^1$H-NMR (200 MHz, DMSO-d6) δ: 1.35-1.60 (1H, m), 1.70-2.00 (4H, m), 2.61-3.10 (2H, m), 3.20-3.67 (2H, m), 4.34 (2H, m), 6.39 (1H, d, J=16.0 Hz), 7.20 (1H, d, J=16.0 Hz), 7.44-7.47 (3H, m), 7.59-7.64 (2H, m), 8.15 (1H, d, J=8.0 Hz), 8.55 (2H, s), 11.07 (1H, brs),

MASS(ESI); 354 (M+H)+.

EXAMPLE 273

(2E)-3-(2-{[(3R)-1-(cyclohexylmethyl)-3-piperidinyl]amino}-5-pyrimidinyl)-N-hydroxyacrylamide dihydrochloride $^1$H-NMR (200 MHz, DMSO-d6) δ: 0.92-1.28 (5H, m), 1.64-2.10 (10H, m), 2.70-3.16 (3H, m), 3.32-3.57 (2H, m), 4.44 (2H, brs), 6.47 (1H, d, J=16.0 Hz), 7.33 (1H, d, J=16.0 Hz), 8.03 (1H, brs), 8.62 (2H, s), 10.40 (1H, brs),

MASS(ESI); 360 (M+H)+.

The following compound was obtained in a similar manner to that of Example 129.

EXAMPLE 274

(2E)-3-(5-chloro-6-{[2-(1-pyrrolidinylmethyl)phenyl]amino}-3'pyridinyl)-N-hydroxyacrylamide dihydrochloride $^1$H-NMR (300 MHz, DMSO-d6) δ 1.76-2.00 (4H, m), 2.96-3.13 (2H, m), 3.27-3.42 (2H, m), 4.23 (2H, br-s), 6.38 (1H, d, J=16 Hz), 7.30-7.52 (4H, m), 7.78 (1H, d, J=7.5 Hz), 8.02 (1H, s), 8.10 (1H, s), 8.81 (1H, s), 10.96 (1H, br-s); MS (ES+) m/z 373.

EXAMPLE 275

1N-NaOH (4.7 mL) was added to the solution of (2E)-N-hydroxy-3-(5-{[(3R)-1-(2-phenylethyl)-3-pyrrolidinyl]amino}-2-pyrazinyl)acrylamide dihydrochloride (1.0 g) in water (20 mL) under ice-cooling and the mixture was stirred at 5-10 deg for 5 hr. The isolated precipitate was collected by filtration to give (2E)-N-hydroxy-3-(5-{[(3R)-1-(2-phenylethyl)-3-pyrrolidinyl]amino}-2-pyrazinyl)acrylamide (0.71 g).

$^1$H-NMR(CD$_3$OD):d 1.77-1.89(1H, m), 2.33-2.46(1H, m), 2.71-2.91(6H,m), 2.94-3.04(1H, m), 3.10-3.17(1H, m), 4.43-4.52(1H, m), 6.64(1H, d, J=15.3 Hz), 7.16-7.32(5H, m), 7.45 (1H, d, J=15.3 Hz), 7.95(1H, s), 8.01(1H, s)

The following compounds can be obtained in a similar manner to that of Example 275.

EXAMPLE 276

(2E)-3-(6-{[(3R)-1-benzyl-3-pyrrolidinyl]amino}-3-pyridinyl)-N-hydroxyacrylamide

EXAMPLE 277

(2E)-3-(6-{[(3R)-1-(1-benzofuran-2-ylmethyl)-3-pyrrolidinyl]amino}-3-pyridinyl)-N-hydroxyacrylamide

EXAMPLE 278

(2E)-3-(6-{[(3R)-1-(1-benzofuran-5-ylmethyl)-3-pyrrolidinyl]amino}-3-pyridinyl)-N-hydroxyacrylamide

EXAMPLE 279

(2E)-3-(6-{[(3R)-1-(3,4-dimethylbenzyl)-3-pyrrolidinyl]amino}-3-pyridinyl)-N-hydroxyacrylamide

EXAMPLE 280

(2E)-3-(6-{[(3R)-1-(2,3-dimethylbenzyl)-3-pyrrolidinyl]amino}-3-pyridinyl)-N-hydroxyacrylamide

EXAMPLE 281

(2E)-3-(4-{[(3R)-1-(cyclohexylcarbonyl)-3-pyrrolidinyl]amino}phenyl)-N-hydroxyacrylamide

EXAMPLE 282

(2E)-3-(6-{[(3R)-1-(cyclohexylmethyl)-3-piperidinyl]amino}-3-pyridinyl)-N-hydroxyacrylamide

EXAMPLE 283 tert-butyl (3R)-3-({3-chloro-5-[(1E)-3-(hydroxyamino)-3-oxo-1-propen-1-yl]-2-pyridinyl}amino)-1-pyrrolidinecarboxylate

EXAMPLE 284

(2E)-3-(5-{[(3R)-1-benzyl-3-pyrrolidinyl]amino}-2-pyrazinyl)-N-hydroxyacrylamide

EXAMPLE 285 cyclopentyl (3R)-3-({3-chloro-5-[(1E)-3-(hydroxyamino)-3-oxo-1-propen-1-yl]-2-pyridinyl}amino)-1-pyrrolidinecarboxylate

EXAMPLE 286

(2E)-N-hydroxy-3-(5-{[(3R)-1-(4-methylbenzyl)-3-pyrrolidinyl]amino}-2-pyrazinyl)acrylamide

EXAMPLE 287

(2E)-3-(5-{[(3R)-1-(4-chlorobenzyl)-3-pyrrolidinyl]amino}-2-pyrazinyl)-N-hydroxyacrylamide

EXAMPLE 288

(2E)-3-(5-{[(3R)-1-(2-chlorobenzyl)-3-pyrrolidinyl]amino}-2-pyrazinyl)-N-hydroxyacrylamide

EXAMPLE 289

(2E)-3-(5-{[(3R)-1-(3-chlorobenzyl)-3-pyrrolidinyl]amino}-2-pyrazinyl)-N-hydroxyacrylamide

EXAMPLE 290

A solution of acetic acid (3.2 μL) in acetonitrile (29.2 μL) was added to the mixture of (2E)-N-hydroxy-3-(5-{[(3R)-1-(2-phenylethyl)-3-pyrrolidinyl]amino}-2-pyrazinyl)acrylamide (20 mg) in THF (0.1 mL) and acetonitrile (0.1 mL) and the mixture was stirred at ambient temperature for 5 minutes. To the mixture was added AcOEt (1.5 mL) and isolated precipitate was collected by filtration to give (2E)-N-hydroxy-3-(5-{[(3R)-1-(2-phenylethyl)-3-pyrrolidinyl]amino}-2-pyrazinyl)acrylamide acetate (18 mg).

¹H-NMR(DMSO-d6):d 1.59-1.70(1H, m), 1.91(3H, s), 2.15-2.27(1H, m), 2.43-2.53(2H, m), 2.60-2.66(2H, m), 2.70-2.77 (3H, m), 2.79-2.85(1H, m), 4.26-4.36(1H, m), 6.58(1H, d, J=15.2 Hz), 7.15-7.31(5H, m), 7.37(1H, d, J=15.2 Hz), 7.73 (1H, d, J=6.6 Hz), 7.98(1H, s), 8.10(1H, s), 10.71(1H, br-s)

The following compounds can be obtained in a similar manner to that of Example 290.

EXAMPLE 291

(2E)-3-(6-{[(3R)-1-benzyl-3-pyrrolidinyl]amino}-3-pyridinyl)-N-hydroxyacrylamide acetate

EXAMPLE 292

(2E)-3-(6-{[(3R)-1-(1-benzofuran-2-ylmethyl)-3-pyrrolidinyl]amino}-3-pyridinyl)-N-hydroxyacrylamide acetate

EXAMPLE 293

(2E)-3-(6-{[(3R)-1-(1-benzofuran-5-ylmethyl)-3-pyrrolidinyl]amino}-3-pyridinyl)-N-hydroxyacrylamide acetate

EXAMPLE 294

(2E)-3-(6-{[(3R)-1-(3,4-dimethylbenzyl)-3-pyrrolidinyl] amino}-3-pyridinyl)-N-hydroxyacrylamide acetate

EXAMPLE 295

(2E)-3-(6-{[(3R)-1-(2,3-dimethylbenzyl)-3-pyrrolidinyl] amino}-3-pyridinyl)-N-hydroxyacrylamide acetate

EXAMPLE 296

(2E)-3-(4-{[(3R)-1-(cyclohexylcarbonyl)-3-pyrrolidinyl] amino}phenyl)-N-hydroxyacrylamide acetate

EXAMPLE 297

(2E)-3-(6-{[(3R)-1-(cyclohexylmethyl)-3-piperidinyl] amino}-3-pyridinyl)-N-hydroxyacrylamide acetate

EXAMPLE 298 tert-butyl (3R)-3-({3-chloro-5-[(1E)-3-(hydroxyamino)-3-oxo-1-propen-1-yl]-2-pyridinyl}amino)-1-pyrrolidinecarboxylate acetate

EXAMPLE 299

(2E)-3-(5-{[(3R)-1-benzyl-3-pyrrolidinyl]amino}-2-pyrazinyl)-N-hydroxyacrylamide acetate

EXAMPLE 300 cyclopentyl (3R)-3-({3-chloro-5-[(1E)-3-(hydroxyamino)-3-oxo-1-propen-1-yl]-2-pyridinyl}amino)-1-pyrrolidinecarboxylate acetate

EXAMPLE 301

(2E)-N-hydroxy-3-(5-{[(3R)-1-(4-methylbenzyl)-3-pyrrolidinyl]amino}-2-pyrazinyl)acrylamide acetate

EXAMPLE 302

(2E)-3-(5-{[(3R)-1-(4-chlorobenzyl)-3-pyrrolidinyl] amino}-2-pyrazinyl)-N-hydroxyacrylamide acetate

EXAMPLE 303

(2E)-3-(5-{[(3R)-1-(2-chlorobenzyl)-3-pyrrolidinyl] amino}-2-pyrazinyl)-N-hydroxyacrylamide acetate

EXAMPLE 304

(2E)-3-(5-{[(3R)-1-(3-chlorobenzyl)-3-pyrrolidinyl] amino}-2-pyrazinyl)-N-hydroxyacrylamide acetate

What is claimed is:
1. A compound having the formula (I):

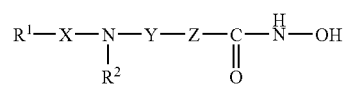

wherein
$R^1$ is hydrogen, lower alkyl, lower alkenyl, lower or higher alkynyl, cyclo(lower)alkyl, cyclo(higher)alkyl, cyclo (lower)alkyl(lower)alkyl, cyclo(higher)alkyl(lower) alkyl, cyclo(lower)alkenyl(lower)alkyl, aryl-fused cyclo(lower)alkyl, lower alkoxy, acyl, aryl, ar(lower) alkoxy, ar(lower)alkyl, heteroar(lower)alkyl, amino, heteroaryl, heterocyclyl or heterocyclyl(lower)alkyl, which may be substituted with one or more substituent(s) selected from the group consisting of lower alkyl, halogen, lower alkoxy, amino, hydroxy, cyano, aryl, aryloxy, acyl, cyclo(lower)alkyl, heteroaryl, halo(lower)alkyl and halo(lower)alkoxy,
$R^2$ is hydrogen or lower alkyl,
X is pyrrolidinylene or piperidinylene,
Y is pyrazinylene, pyrimidinylene, or pyridazinylene, which may be substituted with one or more substituent(s) selected from the group consisting of halogen and lower alkyl,
Z is lower alkenylene, which may be substituted with lower alkyl or halogen, or a salt thereof.
2. The compound or salt thereof of claim 1, wherein
$R^1$ is hydrogen, lower alkyl, lower alkenyl, lower or higher alkynyl, cyclo(lower)alkyl, cyclo(higber)alkyl, cyclo (lower)alkyl(lower)alkyl, cyclo(higher)alkyl(lower) alkyl, cyclo(lower)alkenyl(lower)alkyl, aryl-fused cyclo(lower)alkyl, lower alkoxy, acyl, aryl, ar(lower) alkoxy, ar(lower)alkyl, heteroar(lower)alkyl, amino, heteroaryl, heterocyclyl or heterocyclyl(lower)alkyl, which may be substituted with one or more substituent(s) selected from the group consisting of lower alkyl, halogen, lower alkoxy, amino, hydroxy, cyano, aryl, aryloxy, acyl, cyclo(lower)alkyl, heteroaryl, halo(lower)alkyl and halo(lower)alkoxy, and
Z is vinylene, which may be substituted with lower alkyl or halogen.

3. The compound or salt thereof of claim 2, wherein $R^1$ is lower alkyl, cyclo(lower)alkyl, cyclo(lower)alkyl(lower)alkyl, acyl, aryl, ar(lower)alkyl, heteroar(lower)alkyl, heteroaryl or heterocyclyl, which may be substituted with one or more substituent(s) selected from the group consisting of lower alkyl, halogen, lower alkoxy, amino, hydroxy, cyano, aryl, aryloxy, acyl, cyclo(lower)alkyl, heteroaryl, halo(lower)alkyl and halo(lower)alkoxy, $R^2$ is hydrogen, Z is vinylene, which may be substituted with methyl or fluorine.

4. The compound or salt thereof of claim 3, wherein $R^1$ is ar(lower)alkyl or heteroar(lower)alkyl optionally substituted with lower alkyl, halogen, lower alkoxy, amino, hydroxy, cyano, aryl, aryloxy, acyl, cyclo(lower)alkyl, heteroaryl, halo(lower)alkyl or halo(lower)alkoxy.

5. The compound or salt thereof of claim 4, wherein $R^1$ is ar(lower)alkyl or heteroar(lower)alkyl optionally substituted with lower alkyl, halogen, lower alkoxy, di(lower)alkylamino, lower alkanoylamino, lower alkylsulfonylamino, hydroxy, cyano, arylcarbonyl, cyclo(lower)alkyl, halo(lower)alkyl or halo(lower)alkoxy, and Z is vinylene.

6. The compound or salt thereof of claim 5, wherein Y is pyrazinylene.

7. A pharmaceutical composition, comprising a compound or salt thereof according to ef claim 1 and a pharmaceutically acceptable, substantially non-toxic carrier or excipient.

8. A method for treating cirrhosis, acute promyelocytic leukaemia (APL), an organ transplant rejection, or a protozoal infection , which comprises administering an effective amount of a compound or salt thereof according to claim 1 to a human being or an animal in need thereof.

9. A pharmaceutical composition, comprising a compound or salt thereof according to claim 2 and a pharmaceutically acceptable, substantially non-toxic carrier or excipient.

10. A pharmaceutical composition, comprising a compound or salt thereof according to claim 3 and a pharmaceutically acceptable, substantially non-toxic carner or excipient.

11. A pharmaceutical composition, comprising a compound or salt thereof according to claim 4 and a pharmaceutically acceptable, substantially non-toxic carrier or excipient.

12. A pharmaceutical composition, comprising a compound or salt thereof according to claim 5 and a pharmaceutically acceptable, substantially non-toxic carrier or excipient.

13. A pharmaceutical composition, comprising a compound or salt thereof according to claim 6 and a pharmaceutically acceptable, substantially non-toxic carrier or excipient.

14. A method for treating cirrhosis, acute promyelocytic leukaemia (APL), an organ transplant rejection, or a protozoal infection, which comprises administering an effective amount of a compound or salt thereof according to claim 2 to a human being or an animal in need thereof.

15. A method for treating cirrhosis, acute promyelocytic leukaemia (APL), an organ transplant rejection, or a protozoal infection, which comprises administering an effective amount of a compound or salt thereof according to claim 3 to a human being or an animal in need thereof.

16. A method for treating cirrhosis, acute promyclocytic leukaemia (APL), an organ transplant rejection, or a protozoal infection, which comprises administering an effective amount of a compound or salt thereof according to claim 4 to a human being or an animal in need thereof.

17. A method for treating cirrhosis, acute promyelocytic leukaemia (APL), an organ transplant rejection, or a protozoal infection, which comprises administering an effective amount of a compound or salt thereof according to claim 5 to a human being or an animal in need thereof.

18. A method for treating cirrhosis, acute promyelocytic leukaemia (APL), an organ transplant rejection, or a protozoal infection, which comprises administering an effective amount of a compound or salt thereof according to claim 6 to a human being or an animal in need thereof.

* * * * *

UNITED STATES PATENT AND TRADEMARK OFFICE
CERTIFICATE OF CORRECTION

| | | |
|---|---|---|
| PATENT NO. | : 7,465,731 B2 | Page 1 of 1 |
| APPLICATION NO. | : 11/199453 | |
| DATED | : December 16, 2008 | |
| INVENTOR(S) | : Ishibashi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 500 days.

Signed and Sealed this
Sixteenth Day of October, 2012

David J. Kappos
*Director of the United States Patent and Trademark Office*